United States Patent
Carswell et al.

(10) Patent No.: US 10,919,896 B2
(45) Date of Patent: Feb. 16, 2021

(54) PREPARATION AND USES OF PYRIMIDINONE DERIVATIVES

(71) Applicant: Cancer Research Technology Limited, London (GB)

(72) Inventors: Emma L. Carswell, Cambridge (GB); Mark David Charles, Cambridge (GB); Anne Cochi, Cambridge (GB); Benjamin J. Dugan, West Chester, PA (US); Chukuemeka Tennyson Ekwuru, Cambridge (GB); Fred Elustondo, Cambridge (GB); Katherine M. Fowler, Cambridge (GB); Frederic Georges Marie Leroux, Cambridge (GB); Nathaniel J. T. Monck, Cambridge (GB); Gregory R. Ott, West Chester, PA (US); Jonathan R. Roffey, Cambridge (GB); Gurwinder Sidhu, Cambridge (GB); Neil Tremayne, Cambridge (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 16/335,379

(22) PCT Filed: Sep. 22, 2017

(86) PCT No.: PCT/GB2017/052849
§ 371 (c)(1),
(2) Date: Mar. 21, 2019

(87) PCT Pub. No.: WO2018/055402
PCT Pub. Date: Mar. 29, 2018

(65) Prior Publication Data
US 2020/0123157 A1  Apr. 23, 2020

Related U.S. Application Data

(60) Provisional application No. 62/398,068, filed on Sep. 22, 2016.

(51) Int. Cl.
C07D 401/14 (2006.01)
C07D 487/02 (2006.01)
A61P 35/00 (2006.01)

(52) U.S. Cl.
CPC ............ *C07D 487/02* (2013.01); *A61P 35/00* (2018.01)

(58) Field of Classification Search
CPC .......................... A61K 31/506; C07D 401/14
USPC .......................................... 514/269; 544/319
See application file for complete search history.

(56) References Cited

FOREIGN PATENT DOCUMENTS

WO    WO-2011/130481 A1    10/2011

OTHER PUBLICATIONS

International Search Report and Written Opinion for International Application No. PCT/GB2017/052849 dated Nov. 3, 2017.
Montagnoli et al., "Targeting Cell Division Cycle 7 Kinase: A New Approach for Cancer Therapy," Clin Cancer Res, 16(18):4503-4508 (2010).

*Primary Examiner* — Jeffrey H Murray
(74) *Attorney, Agent, or Firm* — Foley Hoag LLP; David P. Halstead

(57) ABSTRACT

The present invention relates to compounds of formula (I), and salts and solvates thereof, that function as inhibitors of cell division cycle 7 (Cdc7) kinase enzyme activity:

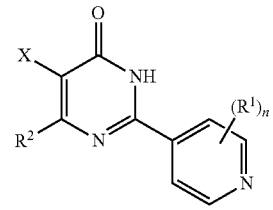

Formula I wherein X, $R^1$, $R^2$, and n are each as defined herein. The present invention also relates to processes for the preparation of these compounds, to pharmaceutical compositions comprising them, and to their use in the treatment of proliferative disorders, such as cancer, as well as other diseases or conditions in which Cdc7 kinase activity is implicated.

17 Claims, No Drawings

PREPARATION AND USES OF PYRIMIDINONE DERIVATIVES

RELATED APPLICATIONS

This application is a § 371 national-stage application based on Patent Cooperation Treaty Application serial number PCT/GB2017/052849, filed Sep. 22, 2017; which claims the benefit of priority to U.S. Provisional Application No. 62/398,068, filed on Sep. 22, 2016.

INTRODUCTION

This application relates to compounds of Formula I

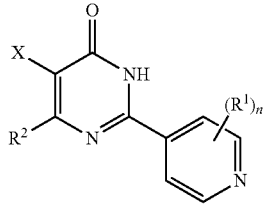

Formula I and/or a salt or solvate thereof, wherein X, $R^1$, $R^2$, and n are as defined herein.

The compounds of Formula I and their salts have Cdc7 inhibitory activity, and may be used to treat diseases or conditions mediated, at least in part, by Cdc7.

The present application further provides pharmaceutical compositions comprising a compound of Formula I and/or a pharmaceutically acceptable salt or solvate thereof and an pharmaceutically acceptable excipient.

In another aspect, the present application provides methods of treating a disease or condition mediated, at least in part, by Cdc7 in a subject in recognized need thereof comprising administering to the subject a compound of Formula I and/or a pharmaceutically acceptable salt or solvate thereof.

The section titles used herein are for indexing and search purposes only and should not be construed as limiting in any way.

BACKGROUND

Eukaryotic cells divide by a directed, highly regulated step-wise process known as the cell cycle. DNA replication is an essential part of cell cycle progression and tight regulation ensures that DNA is replicated accurately only once during S-phase. In mammalian cells DNA replication is initiated at multiple sites (origins of replication). Numerous pre-replication complexes (pre-RC) form at origins of replication along each DNA strand during G1 to ensure that the whole genome is completely replicated in S-phase. The inactive pre-RC consists of the heterohexamer helicase complex Minichromosome maintenance 2-7 (MCM2-7), Cell division cycle 6 (Cdc6) and Chromatin licensing and DNA replication factor 1 (Cdt1) (Donaldson et al., 1998; Masai et al., 2002). Cell division cycle 7 (Cdc7) is a Ser/Thr kinase, which together with its regulatory partner Dumbbell former 4 (Dbf4), forms the active S-phase kinase complex, Dbf4 dependent kinase (DDK) (Kumagai et al., 1999; Jiang et al., 1999; Duncker et al., 2003). DDK is essential in controlling the initiation of DNA replication in combination with Cdk/cyclins by activation or licensing of the pre-RC; this activation involves phosphorylation of MCM2 and MCM4 (Kim 2003, Bousset et al., 1998, Takeda et al., 2001; Bruck et al., 2009; Francis et al., 2009; Sheu et al., 2006; Sheu et al., 2010). Cdc7 phosphorylates MCM2 at various sites, including Ser53 and Ser40 exclusively (Charych et al., 2008; Tsuji et al., 2006; Montagnoli et al., 2006; Cho et al., 2006). The phosphorylation of the amino-terminus of MCM4 by Cdc7 is also essential for replication, but the exact phosphorylation sites are unknown (Masai et al., 2006; Pereverzeva et al., 2000).

Cdc7 depletion by siRNA inhibits phosphorylation of MCM2 in both non-transformed primary fibroblasts and cancer cell lines, however non-transformed primary fibroblast cells arrest in G1 whereas cancer cells apoptose (Rodriguez-Acebes et al., 2010; Kulkarni et al., 2009, Montagnoli et al., 2004). The lack of cell death in normal cells is believed to be due to the induction of a functioning G1 checkpoint which is deficient in cancer cell lines. Thus, when Cdc7 is depleted, cancer cells enter a defective S-phase and undergo apoptosis due to checkpoint dysfunction (Tudzarova et al., 2010; Im et al., 2008; Shreeram et al., 2002). Cdc7 depletion by siRNA in combination with hydroxyurea or etoposide treatment impairs hyper-phosphorylation of Mcm2 at specific Cdc7-dependent phosphorylation sites and drug-induced hyper-phosphorylation of chromatin-bound Mcm4. Indeed, sustained inhibition of Cdc7 in the presence of hydroxyurea or etoposide increases cell death supporting the notion that the Cdc7 kinase plays a role in maintaining cell viability during replication stress (Tenca et al., 2007).

In a panel of 62 cancer cell lines Cdc7 protein expression was found to be increased in ~50% human tumour cell lines examined, whereas, Cdc7 protein was very low or undetectable in normal tissues and cell lines. In addition most of the cancer cell lines with increased Cdc7 protein levels also had increased Dbf4 abundance and a high expression of Cdc7 protein was also detected in primary breast, colon, and lung tumours but not in the matched normal tissues (Bonte et al., 2008). Analysis of tumour samples from breast and ovarian cancers have shown a correlation between overexpression of Cdc7 and poor survival, tumour grade, genetic instability and aneuploidy (Rodriguez-Acebes et al., 2010; Kulkarni et al., 2009; Choschzick et al., 2010), supporting the importance of Cdc7 in regulating cellular proliferation. Moreover, Cdc7-Dbf4 is overexpressed in oral squamous cell carcinoma and expression is positively associated with poor clinical outcome and enhances resistance to the DNA-damaging cytotoxic agents such as hydroxyurea and camptothecin (Cheng et al., 2013).

The observation that siRNA mediated knockdown of Cdc7 results in apoptosis in multiple cancer cell lines but not in normal cells makes Cdc7 an attractive cancer target. Moreover, inhibition of Cdc7 catalytic activity has been demonstrated to result in apoptotic cell death in multiple cancer cell types and tumour growth inhibition in preclinical cancer models (Montagoli et al., 2008). Furthermore, inhibition of Cdc7 blocks DNA synthesis, prevents the activation of replication origins but does not impede replication fork progression and does not trigger a sustained DNA damage response (Montagoli et al., 2008). Taken together these studies suggest selective inhibition of Cdc7 to be a promising anticancer therapeutic.

SUMMARY OF THE INVENTION

In one aspect, the present invention provides a compound as defined herein, and/or a salt or solvate thereof.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the production of a Cdc7 inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of a Cdc7 inhibitory effect.

In another aspect, the present invention provides a method of inhibiting Cdc7 in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

Preferred, suitable, and optional features of any one particular aspect of the present invention are also preferred, suitable, and optional features of any other aspect.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I" and the more general term "compounds" refer to and includes any and all compounds described by and/or with reference to Formula I, as well as Formulae $Ia_1$ through If, inclusive. It should also be understood that the terms "compounds of Formula I" and the more general term "compounds" encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, either by themselves or in combination with additional agents.

The various hydrocarbon-containing moieties provided herein may be described using a prefix designating the minimum and maximum number of carbon atoms in the moiety, i.e. "$(C_a\text{-}C_b)$". For example, $(C_a\text{-}C_b)$alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, such as, for example, ±10% of the specified value. Accordingly, the phrase "about 50" should be understood as encompassing ±10% of the numerical value 50, or from 45 to 55, inclusive.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms, and can be substituted or unsubstituted. Representative examples include, but are not limited to, methylene (—$CH_2$—), the ethylene isomers (—$CH(CH_3)$— and —$CH_2CH_2$—), the propylene isomers (—$CH(CH_3)CH_2$—, —$CH(CH_2CH_3)$—, —$C(CH_3)_2$—, and —$CH_2CH_2CH_2$—), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl.

As used herein by themselves or in conjunction with another term or terms, "arylene" and "arylene group" refer to a phenylene (—$C_6H_4$—) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2$—). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydro-naphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2$—). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$ and —$CHFCH_2CF_3$. Haloalkyl groups can be substituted or unsubstituted.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4- tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca-2(7), 3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_4H_8NCH_2$—). Alkylheteroycloalkyl groups can be substituted or unsubstituted.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by itself or in conjunction with another term or terms, "pseudohalogen" refers to —OCN, —SCN, —CF$_3$, and —CN.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—CH$_3$), it can be optionally substituted by 1 to 3 $R^5$.

As used herein by themselves or in conjunction with another term or terms, "subject(s)" and "patient(s)", refer to mammals, including humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s) when used in conjunction with the phrase "optionally substituted" unless otherwise specified.

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I. It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

Compounds of the Invention

The following provides additional non-limiting details of the compounds suggested or disclosed herein, including compounds of the Formula I, subgenuses thereof (Formulae Ia$_1$, Ia$_2$ and Ib-If) and various species and/or embodiments of compounds of Formula I et seq., intermediates, and other compounds of interest.

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

It is also to be understood that certain compounds of the formula I may exist in solvated as well as unsolvated forms such as, for example, hydrated forms. It is to be understood that the invention encompasses all such solvated forms that possess antiproliferative activity.

It is also to be understood that certain compounds of the formula I may exhibit polymorphism, and that the invention encompasses all such forms that possess antiproliferative activity.

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

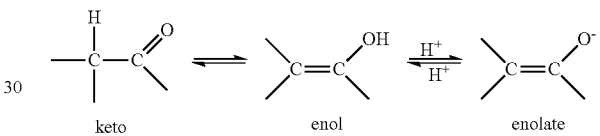

keto      enol      enolate

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

In one aspect, the present invention relates to compounds of formula (I) shown below:

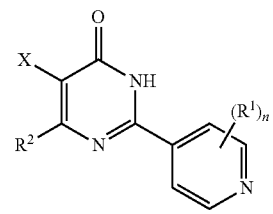

Formula I and/or a salt or solvate thereof wherein,
X is chosen from halogen, halo$C_1$-$C_6$alkyl, $NO_2$, —C(=O)NR$^5$R$^6$, —NHS(O)$_2$R$^6$, and CN;
Each R$^1$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^3$, —$C_0$-$C_6$alkylC(=O)$C_0$-$C_6$alkylNR$^3$C(=O)OR$^4$, —$C_0$-$C_6$alkylC(=O)$C_0$-$C_6$alkylOR$^3$, —$C_0$-$C_6$alkylC(=O)$C_0$-$C_6$alkylNR$^3$R$^4$, —$C_0$-$C_6$alkylC(=O)$C_0$-$C_6$alkylC(=O)$C_0$-$C_6$alkylC(=O)R$^3$, halo$C_1$-$C_6$alkyl, halogen, —$NO_2$, —$C_0$-$C_6$alkylNR$^3$R$^4$, —$C_0$-$C_6$alkylNR$^3$NR$^3$R$^4$, —$C_0$-

$C_6$alkylN=NR$^3$, —$C_0$-$C_6$alkylNR$_3$, $C_0$-$C_6$alkylOR$^4$, —$C_0$-$C_6$alkylNR$^3C_0$-$C_6$alkylC(=O)R$^4$, —$C_0$-$C_6$alkylNR$^3$C(=O)$C_0$-$C_6$alkylC(=O)R$^4$, —$C_0$-$C_6$alkylNR$^3C_0$-$C_6$alkylC(=O)OR$^4$, —$C_0$-$C_6$alkylNR$^3C_0$-$C_6$alkylC(=O)C(=O)OR$^4$, —$C_0$-$C_6$alkylNR$^3C_0$-$C_6$alkylC(=O)NR$^3$R$^4$, —$C_0$-$C_6$alkylNR$^3$C(=O)$C_0$-$C_6$alkylNR$^3$C(=O)R$^4$, —$C_0$-$C_6$alkylNR$^3$C(=O)$C_0$-$C_6$alkylNR$^3$C(=O)OR$^4$, —$C_0$-$C_6$alkylNR$^3$C(=O)$C_0$-$C_6$alkylC(=O)NR$^3$R$^4$, —$C_0$-$C_6$alkylNR$^3C_0$-$C_6$alkylS(=O)$_2$R$^4$, —$C_0$-$C_6$alkylNR$^3$S(=O)$_2C_0$-$C_6$alkylNR$^3$R$^4$, —$C_0$-$C_6$alkylOR$^3$, (=O), —$C_0$-$C_6$alkylOC(=O)$C_0$-$C_6$alkylR$^4$, —$C_0$-$C_6$alkylOC(=O)$C_0$-$C_6$alkylNR$^3$R$^4$, —$C_0$-$C_6$alkylOC(=O)$C_0$-$C_6$alkylOR$^4$, —$C_0$-$C_6$alkylOS(=O)R$^4$, —$C_0$-$C_6$alkylOS(=O)$_2$R$^4$, —$C_0$-$C_6$alkylOS(=O)$_2C_0$-$C_6$alkylOR$^4$, —$C_0$-$C_6$alkylOS(=O)$_2C_0$-$C_6$alkylNR$^3$R$^4$, —$C_0$-$C_6$alkylOP(=O)R$^3$R$^4$, —$C_0$-$C_6$alkylOP(=O)(NR$^3$R$^4$)(NR$^3$R$^4$), —$C_0$-$C_6$alkylOP(=O)(OR$^3$)(OR$^4$), —$C_0$-$C_6$alkylOP(=O)(SR$^3$)(SR$^4$), —$C_0$-$C_6$alkylP(=O)R$^3$R$^4$, —$C_0$-$C_6$alkylP(=O)(NR$^3$R$^4$)(NR$^3$R$^4$), —$C_0$-$C_6$alkylP(=O)(OR$^3$)(OR$^4$), —$C_0$-$C_6$alkylP(=O)(SR$^3$)(SR$^4$), —$C_0$-$C_6$alkylS(=O)$_p$R$^4$, —$C_0$-$C_6$alkylS(=O)$_2C_0$-$C_6$alkylNR$^3$R$^4$, —$C_0$-$C_6$alkylS(=O)$C_0$-$C_6$alkylNR$^3$R$^4$, and —$C_0$-$C_6$alkylSCN, wherein any of the foregoing is optionally substituted with one or more R$^5$; or
Any two R$^1$ on adjacent atoms may be taken together to form a 4 to 12 membered carbocyclic or heterocyclic ring system, wherein said ring system is optionally substituted with one or more R$^5$; R$^2$ is:
i) a group A-B-C wherein:
  A is a bond or is $C_1$-$C_{10}$alkyl;
  B is absent or is chosen from S(O)$_p$, NR$^3$, O, $C_2$-$C_{10}$alkenyl, and $C_2$-$C_{10}$alkynyl; and
  C is a 3 to 15 membered heterocycloalkyl or a 4 to 11 membered cycloalkyl either of which is optionally substituted with one or more R$^5$; or
ii) a group D-E-F wherein:
  D is chosen from NR$^3$ or O;
  E is a bond or is $C_1$-$C_{10}$alkyl; and
  F is a 3 to 15 membered heterocycloalkyl or an aryl, each of which is optionally substituted with one or more groups chosen from $C_1$-$C_{10}$alkyl, halogen, amino or alkoxy; R$^3$ and R$^4$ are each independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing, except for H, is optionally substituted with one or more R$^5$; or
R$^3$ and R$^4$ may be taken together to form a 3 to 15 membered carbocyclic or heterocyclic ring system, wherein said ring system is optionally substituted with one or more R$^5$;
Each R$^5$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^6$, —$C_0$-$C_6$alkylC(=O)$C_0$-$C_6$alkylOR$^6$, —$C_0$-$C_6$alkylC(=O)$C_0$-$C_6$alkylNR$^6$R$^6$, —$C_0$-$C_6$alkylC(=O)NR$^6$C(=O)OR$^6$, —$C_0$-$C_6$alkylC(=O)$C_0$-$C_6$alkylC(=O)R$^6$, halo$C_1$-$C_6$alkyl, halogen, —NO$_2$, —$C_0$-$C_6$alkylNR$^6$R$^6$, —$C_0$-$C_6$alkylNR$^6$NR$^6$R$^6$, —$C_0$-$C_6$alkylN=NR$^6$, —$C_0$-$C_6$alkylNR$^6$, $C_0$-$C_6$alkylOR$^6$, —$C_0$-$C_6$alkylNR$^6C_0$-$C_6$alkylC(=O)R$^6$, —$C_0$-$C_6$alkylNR$^6$C(=O)$C_0$-$C_6$alkylC(=O)R$^6$, —$C_0$-$C_6$alkylNR$^6C_0$-$C_6$alkylC(=O)OR$^6$, —$C_0$-$C_6$alkylNR$^6C_0$-$C_6$alkylC(=O)C(=O)OR$^6$, —$C_0$-$C_6$alkylNR$^6C_0$-$C_6$alkylC(=O)NR$^6$R$^6$, —$C_0$-$C_6$alkylNR$^6$C(=O)$C_0$-$C_6$alkylNR$^6$C(=O)R$^6$, —$C_0$-$C_6$alkylNR$^6$C(=O)$C_0$-$C_6$alkylNR$^6$C(=O)OR$^6$, —$C_0$-$C_6$alkylNR$^6$C(=O)$C_0$-$C_6$alkylC(=O)NR$^6$R$^6$, —$C_0$-$C_6$alkylNR$^6C_0$-$C_6$alkyl S(=O)$_2$R$^6$, —$C_0$-$C_6$alkylNR$^6$S(=O)$_2C_0$-$C_6$alkylNR$^6$R$^6$, —$C_0$-$C_6$alkylOR$^6$, (=O), —$C_0$-$C_6$alkylOC(=O)$C_0$-$C_6$alkylR$^6$, —$C_0$-$C_6$alkylOC(=O)$C_0$-$C_6$alkylNR$^6$R$^6$, —$C_0$-$C_6$alkylOC(=O)$C_0$-$C_6$alkylOR$^6$, —$C_0$-$C_6$alkylOS(=O)R$^6$, —$C_0$-$C_6$alkylOS(=O)$_2$R$^6$, —$C_0$-$C_6$alkylOS(=O)$_2C_0$-$C_6$alkylOR$^6$, —$C_0$-$C_6$alkylOS(=O)$_2C_0$-$C_6$alkylNR$^6$R$^6$, —$C_0$-$C_6$alkylOP(=O)R$^6$R$^6$, —$C_0$-$C_6$alkylOP(=O)(NR$^6$R$^6$)(NR$^6$R$^6$), —$C_0$-$C_6$alkylOP(=O)(OR$^6$)(OR$^6$), —$C_0$-$C_6$alkylOP(=O)(SR$^6$)(SR$^6$), —$C_0$-$C_6$alkylP(=O)R$^6$R$^6$, —$C_0$-$C_6$alkylP(=O)(NR$^6$R$^6$)(NR$^6$R$^6$), —$C_0$-$C_6$alkylP(=O)(OR$^6$)(OR$^6$), —$C_0$-$C_6$alkylP(=O)(SR$^6$)(SR$^6$), —$C_0$-$C_6$alkyl S(=O)$_p$R$^6$, —$C_0$-$C_6$alkylS(=O)$_2C_0$-$C_6$alkylNR$^6$R$^6$, —$C_0$-$C_6$alkylS(=O)$C_0$-$C_6$alkylNR$^6$R$^6$, and —$C_0$-$C_6$alkylSCN, wherein any of the foregoing is optionally substituted with one or more R$^7$; or together with carbon atom(s) to which they are attached, two R$^5$ groups may linked to form a fused aryl, heteroaryl, 3 to 6 membered heterocycloalkyl or a 3 to 6 membered cycloalkyl; Each R$^6$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing except for H is optionally substituted with one or more R$^7$; or
Two R$^6$ may be taken together to form a 3 to 15 membered carbocyclic or heterocyclic ring system, wherein said ring system is optionally substituted with one or more R$^7$;
Each R$^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^8$, —$C_0$-$C_6$alkylC(=O)$C_0$-$C_6$alkylOR$^8$, —$C_0$-$C_6$alkylC(=O)$C_0$-$C_6$alkylNR$^8$R$^8$, —$C_0$-$C_6$alkylC(=O)NR$^8$C(=O)OR$^8$, —$C_0$-$C_6$alkylC(=O)$C_0$-$C_6$alkylC(=O)R$^8$, halo$C_1$-$C_6$alkyl, halogen, —NO$_2$, —$C_0$-$C_6$alkylNR$^8$R$^8$, —$C_0$-$C_6$alkylNRNR$^8$R$^8$, —$C_0$-$C_6$alkylN=NR$^8$, —$C_0$-$C_6$alkylNR$^8C_0$-$C_6$alkylOR$^8$, —$C_0$-$C_6$alkylNR$^8C_0$-$C_6$alkylC(=O)R$^8$, —$C_0$-$C_6$alkylNR$^8$C(=O)$C_0$-$C_6$alkylC(=O)R$^8$, —$C_0$-$C_6$alkylNR$^8C_0$-$C_6$alkylC(=O)OR$^8$, —$C_0$-$C_6$alkylNR$^8C_0$-$C_6$alkylC(=O)C(=O)OR$^8$, —$C_0$-$C_6$alkylNR$^8C_0$-$C_6$alkylC(=O)NR$^8$R$^8$, —$C_0$-$C_6$alkylNR$^8$C(=O)$C_0$-$C_6$alkylNR$^8$C(=O)R$^8$, —$C_0$-$C_6$alkylNR$^8$C(=O)$C_0$-$C_6$alkylNR$^8$C(=O)OR$^8$, —$C_0$-$C_6$alkylNR$^8$C(=O)$C_0$-$C_6$alkylC(=O)NR$^8$R$^8$, —$C_0$-$C_6$alkylNR$^8C_0$-$C_6$alkylS(=O)$_2$R$^8$, —$C_0$-$C_6$alkylNR$^8$S(=O)$_2C_0$-$C_6$alkylNR$^8$R$^8$, —$C_0$-$C_6$alkylOR$^8$, (=O), —$C_0$-$C_6$alkylOC(=O)$C_0$-$C_6$alkylR$^8$, —$C_0$-$C_6$alkylOC(=O)$C_0$-$C_6$alkylNR$^8$R$^8$, —$C_0$-$C_6$alkylOC(=O)$C_0$-$C_6$alkylOR$^8$, —$C_0$-$C_6$alkylOS(=O)R$^8$, —$C_0$-$C_6$alkylOS(=O)$_2$R$^8$, —$C_0$-$C_6$alkylOS(=O)$_2C_0$-$C_6$alkylOR$^8$, —$C_0$-$C_6$alkylOS(=O)$_2C_0$-$C_6$alkylNR$^8$R$^8$, —$C_0$-$C_6$alkylOP(=O)R$^8$R$^8$, —$C_0$-$C_6$alkylOP(=O)(NR$^8$R$^8$)(NR$^8$R$^8$), —$C_0$-$C_6$alkylOP(=O)(OR$^8$)(OR$^8$), —$C_0$-$C_6$alkylOP(=O)(SR$^8$)(SR$^8$), —$C_0$-$C_6$alkylP(=O)R$^8$R$^8$, —$C_0$-$C_6$alkylP(=O)(NR$^8$R$^8$)(NR$^8$R$^8$), —$C_0$-$C_6$alkylP(=O)(OR$^8$)(OR$^8$), —$C_0$-$C_6$alkylP(=O)(SR$^8$)(SR$^8$), —$C_0$-$C_6$alkylS(=O)$_p$R$^8$, —$C_0$-$C_6$alkylS(=O)$_2C_0$-$C_6$alkylNR$^8$R$^8$, —$C_0$-$C_6$alkylS(=O)$C_0$-$C_6$alkylNR$^8$R$^8$, and —$C_0$-$C_6$alkylSCN;
Each R$^8$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, and $C_0$-$C_6$alkylheterocycloalkyl;
Each p is independently 0, 1 or 2; and
Each n is independently 0, 1, 2, 3 or 4,
with the proviso that the compound is not one of the following:

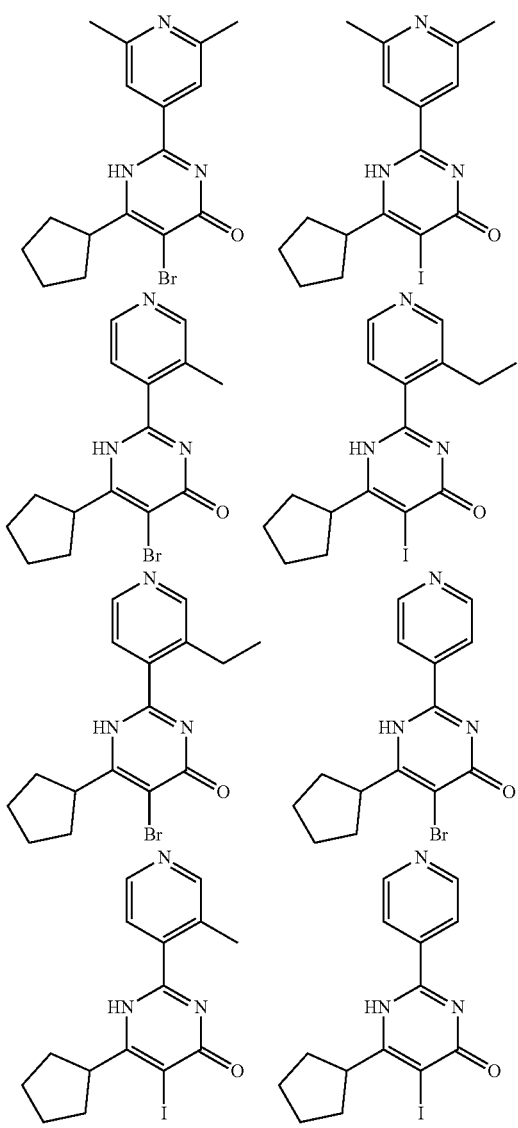

Particular compounds of the invention include, for example, compounds of the formula I, or salts and/or solvates thereof, wherein, unless otherwise stated, each of n, p, $R_1$, $R_2$, $R_3$, $R_4$, $R_5$, $R_6$, $R_7$, $R_8$, X and any associated substituent groups has any of the meanings defined hereinbefore or in any of paragraphs (1) to (64) hereinafter:—

(1) Each n is independently 0, 1, 2 or 3;
(2) Each n is independently 0, 1, or 2;
(3) n is 0 or 1;
(4) Each p is independently 1 or 2;
(5) p is 2;
(6) X is chosen from halogen, halo$C_1$-$C_6$alkyl, $NO_2$ and CN;
(7) X is chosen from halogen, halo$C_1$-$C_2$alkyl, and CN;
(8) X is chosen from halogen, $CF_3$, and CN;
(9) X is a halogen;
(10) X is chosen from chloro or fluoro;
(11) X is chloro;
(12) Each $R^1$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^3$, —$C_0$-$C_6$alkylC(=O)$C_0$-$C_6$alkylN$R^3$C(=O)O$R^4$, —$C_0$-$C_6$alkylC(=O)$C_0$-$C_6$alkylO$R^3$, —$C_0$-$C_6$alkylC(=O)$C_0$-$C_6$alkylN$R^3R^4$, —$C_0$-$C_6$alkylC(=O)$C_0$-$C_6$alkylC(=O)$R^3$, halo$C_1$-$C_6$alkyl, halogen, —$NO_2$, —$C_0$-$C_6$alkylN$R^3R^4$, —$C_0$-$C_6$alkylN$R^3$N$R^3R^4$, —$C_0$-$C_6$alkylN=N$R^3$, —$C_0$-$C_6$alkylN$R_3$, $C_0$-$C_6$alkylO$R^4$, —$C_0$-$C_6$alkylN$R^3$C(=O)$C_0$-$C_6$alkylC(=O)$R^4$, —$C_0$-$C_6$alkylN$R^3$C(=O)$C_0$-$C_6$alkylC(=O)$R^4$, —$C_0$-$C_6$alkylN$R^3$C(=O)$C_0$-$C_6$alkyl C(=O)O$R^4$, —$C_0$-$C_6$alkylN$R^3$C(=O)$C_0$-$C_6$alkylC(=O)C(=O)O$R^4$, —$C_0$-$C_6$alkylN$R^3$C(=O)$C_0$-$C_6$alkylC(=O)N$R^3R^4$, —$C_0$-$C_6$alkylN$R^3$C(=O)$C_0$-$C_6$alkylN$R^3$C(=O)$R^4$, —$C_0$-$C_6$alkylN$R^3$C(=O)$C_0$-$C_6$alkylN$R^3$C(=O)O$R^4$, —$C_0$-$C_6$alkylN$R^3$C(=O)$C_0$-$C_6$alkylC(=O)N$R^3R^4$, —$C_0$-$C_6$alkylN$R^3$C(=O)$C_0$-$C_6$alkylS(=O)$_2R^4$, —$C_0$-$C_6$alkylN$R^3$S(=O)$_2C_0$-$C_6$alkylN$R^3R^4$, —$C_0$-$C_6$alkylO$R^3$, (=O), —$C_0$-$C_6$alkylOC(=O)$C_0$-$C_6$alkyl$R^4$, —$C_0$-$C_6$alkylOC(=O)$C_0$-$C_6$alkylN$R^3R^4$, —$C_0$-$C_6$alkylOC(=O)$C_0$-$C_6$alkylO$R^4$, —$C_0$-$C_6$alkylOS(=O)$R^4$, —$C_0$-$C_6$alkylOS(=O)$_2R^4$, —$C_0$-$C_6$alkylOS(=O)$_2C_0$-$C_6$alkylO$R^4$, —$C_0$-$C_6$alkylOS(=O)$_2C_0$-$C_6$alkylN$R^3R^4$, —$C_0$-$C_6$alkylOP(=O)$R^3R^4$, —$C_0$-$C_6$alkylOP(=O)(N$R^3R^4$)(N$R^3R^4$), —$C_0$-$C_6$alkylOP(=O)(O$R^3$)(O$R^4$), —$C_0$-$C_6$alkylOP(=O)(S$R^3$)(S$R^4$), —$C_0$-$C_6$alkylP(=O)$R^3R^4$, —$C_0$-$C_6$alkylP(=O)(N$R^3R^4$)(N$R^3R^4$), —$C_0$-$C_6$alkylP(=O)($R^3$)(O$R^3$)(O$R^4$), —$C_0$-$C_6$alkylP(=O)(S$R^3$)(S$R^4$), —$C_0$-$C_6$alkylS(=O)$_pR^4$, —$C_0$-$C_6$alkylS(=O)$_2C_0$-$C_6$alkylN$R^3R^4$, —$C_0$-$C_6$alkylS(=O)$C_0$-$C_6$alkylN$R^3R^4$, and —$C_0$-$C_6$alkylSCN;

(13) Each $R^1$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^3$, —$C_0$-$C_6$alkylC(=O)$C_0$-$C_6$alkylN$R^3$C(=O)O$R^4$, —$C_0$-$C_6$alkylC(=O)$C_0$-$C_6$alkylO$R^3$, —$C_0$-$C_6$alkylC(=O)$C_0$-$C_6$alkylN$R^3R^4$, —$C_0$-$C_6$alkylC(=O)$C_0$-$C_6$alkylC(=O)$R^3$, halo$C_1$-$C_6$alkyl, halogen, —$NO_2$, —$C_0$-$C_6$alkylN$R^3R^4$, —$C_0$-$C_6$alkylN$R^3C_0$-$C_6$alkylO$R^4$, —$C_0$-$C_6$alkylN$R^3C_0$-$C_6$alkylC(=O)$R^4$, —$C_0$-$C_6$alkylN$R^3C_0$-$C_6$alkyl C(=O)O$R^4$—$C_0$-$C_6$alkylN$R^3C_0$-$C_6$alkylC(=O)N$R^3R^4$, —$C_0$-$C_6$alkylO$R^3$;

(14) Each $R^1$ is independently chosen from $C_1$-$C_6$alkyl, $C_2$-$C_6$alkenyl, $C_2$-$C_6$alkynyl, $C_0$-$C_2$alkylaryl, $C_0$-$C_2$alkylcycloalkyl, $C_0$-$C_2$alkylheterocycloalkyl, $C_0$-$C_2$alkylheteroaryl, —$C_0$-$C_2$alkylCN, —$C_0$-$C_2$alkylC(=O)$C_0$-$C_2$alkyl$R^3$, —$C_0$-$C_2$alkylC(=O)$C_0$-$C_2$alkylN$R^3$C(=O)O$R^4$, —$C_0$-$C_2$alkylC(=O)$C_0$-$C_2$alkylO$R^3$, —$C_0$-$C_2$alkylC(=O)$C_0$-$C_2$alkylN$R^3R^4$, —$C_0$-$C_2$alkylC(=O)$C_0$-$C_2$alkylC(=O)$R^3$, halo$C_1$-$C_4$alkyl, halogen, —$NO_2$, —$C_0$-$C_2$alkylN$R^3R^4$, —$C_0$-$C_2$alkylN$R_3C_0$-$C_2$alkylO$R^4$, —$C_0$-$C_2$alkylN$R^3C_0$-$C_2$alkylC(=O)$R^4$, —$C_0$-$C_2$alkylN$R^3C_0$-$C_2$alkyl C(=O)O$R^4$—$C_0$-$C_2$alkylN$R^3C_0$-$C_2$alkylC(=O)N$R^3R^4$, —$C_0$-$C_4$alkylO$R^3$;

(15) Each $R^1$ is independently chosen from $C_1$-$C_6$alkyl, $C_2$-$C_6$alkenyl, $C_2$-$C_6$alkynyl, $C_0$-$C_2$alkylaryl, $C_0$-$C_2$alkylcycloalkyl, $C_0$-$C_2$alkylheterocycloalkyl, $C_0$-$C_2$alkylheteroaryl, —CN, —C(=O)$C_0$-$C_2$alkyl$R^3$, —C(=O)$C_0$-$C_2$alkylO$R^3$, —C(=O)$C_0$-$C_2$alkylN$R^3R^4$, —C(=O)$C_0$-$C_2$alkylC(=O)$R^3$, halo$C_1$-$C_4$alkyl, halogen, —$NO_2$, —N$R^3R^4$, —N$R_3C_0$-

$C_2$alkylOR$^4$, —NR$^3C_0$-C$_2$alkylC(=O)R$^4$, —NR$^3C_0$-C$_2$alkyl C(=O)OR$^4$—NR$^3C_0$-C$_2$alkylC(=O)NR$^3$R$^4$, —C$_0$-C$_4$alkylOR$^3$;

(16) Each R$^1$ is independently chosen from C$_1$-C$_6$alkyl, C$_2$-C$_6$alkenyl, C$_2$-C$_6$alkynyl, aryl, cycloalkyl, heterocycloalkyl, heteroaryl, —CN, —C(=O)R$^3$, —C(=O)OR$^3$, —C(=O)NR$^3$R$^4$, haloC$_1$-C$_4$alkyl, halogen, —NO$_2$, —NR$^3$R$^4$, —NR$^3$C(=O)R$^4$, —NR$^3$C(=O)OR$^4$—NR$^3$C(=O)NR$^3$R$^4$, —C$_0$-C$_4$alkylOR$^3$;

(17) Each R$^1$ is independently chosen from C$_1$-C$_6$alkyl, C$_2$-C$_6$alkenyl, C$_2$-C$_6$alkynyl, aryl, cycloalkyl, heterocycloalkyl, heteroaryl, —CN, —C(=O)R$^3$, —C(=O)OR$^3$, —C(=O)NR$^3$R$^4$, haloC$_1$-C$_4$alkyl, halogen, —NO$_2$, —NR$^3$R$^4$, —NR$^3$C(=O)R$^4$, —NR$^3$C(=O)OR$^4$—NR$^3$C(=O)NR$^3$R$^4$, —C$_0$-C$_4$alkylOR$^3$;

(18) Each R$^1$ is independently chosen from C$_1$-C$_2$alkyl, —CN, haloC$_1$-C$_4$alkyl, halogen, —NO$_2$, —NR$^3$R$^4$, —C$_0$-C$_4$alkylOR$^3$;

(19) Each R$^1$ is independently chosen from C$_1$-C$_2$alkyl, —CN, haloC$_1$-C$_2$alkyl, halogen, —NO$_2$, —NR$^3$R$^4$, —C$_1$-C$_2$alkylOR$^3$;

(20) Each R$^1$ is independently chosen from haloC$_1$-C$_2$alkyl, halogen, —C$_1$-C$_2$alkylOR$^3$;

(21) Each R$^1$ is independently chosen from halogen, CF$_3$ or OH;

(22) Each R$^1$ is independently chosen from halogen (e.g. fluoro, chloro) or OH;

(23) R$^1$ is fluoro;

(24) R$^2$ is:
  i) a group A-B-C wherein:
    A is a bond or is C$_1$-C$_{10}$alkyl;
    B is absent or is chosen from S(O)$_p$, NR$^3$, O, C$_2$-C$_{10}$alkenyl, and C$_2$-C$_{10}$alkynyl; and
    C is a 3 to 15 membered heterocycloalkyl or a 4 to 11 membered cycloalkyl either of which is optionally substituted with one or more R$^5$; or
  ii) a group D-E-F wherein:
    D is chosen from NR$^3$ or O;
    E is a bond or is C$_1$-C$_4$alkyl; and
    F is a 6-membered heterocycloalkyl or phenyl, each of which is optionally substituted with one or more groups chosen from C$_1$-C$_2$alkyl, halogen or amino;

(25) R$^2$ is a group A-B-C wherein:
  A is a bond or is C$_1$-C$_{10}$alkyl;
  B is absent or is chosen from S(O)$_p$, NR$^3$, O, C$_2$-C$_{10}$alkenyl, and C$_2$-C$_{10}$alkynyl; and
  C is a 3 to 15 membered heterocycloalkyl or a 4 to 11 membered cycloalkyl either of which is optionally substituted with one or more R$^5$;

(26) R$^2$ is a group A-B-C wherein:
  A is a bond or is C$_1$-C$_{10}$alkyl;
  B is absent or is chosen from S(O)$_p$, NR$^3$ or O; and
  C is a 3 to 15 membered heterocycloalkyl or a 4 to 11 membered cycloalkyl either of which is optionally substituted with one or more R$^5$;

(27) R$^2$ is a group A-B-C wherein:
  A is a bond or is C$_1$-C$_{10}$alkyl;
  B is absent or is chosen from S, NR$^3$ or O; and
  C is a 3 to 12 membered heterocycloalkyl or a 6 to 11 membered cycloalkyl either of which is optionally substituted with one or more R$^5$;

(28) R$^2$ is a group A-B-C wherein:
  A is a bond or is C$_1$-C$_2$alkyl;
  B is absent or is chosen from S, NR$^3$ or O; and
  C is a 3 to 12 membered heterocycloalkyl or a 6 to 11 membered cycloalkyl either of which is optionally substituted with one or more R$^5$;

(29) R$^2$ is a 3 to 12 membered heterocycloalkyl or a 6 to 11 membered cycloalkyl either of which is optionally substituted with one or more R$^5$;

(30) R$^2$ is a 3 to 12 membered heterocycloalkyl optionally substituted with one or more R$^5$;

(31) R$^2$ is a 3 to 8 membered heterocycloalkyl optionally substituted with one or more R$^5$, wherein R$^5$ is selected from C$_1$-C$_4$alkyl, haloC$_1$-C$_4$alkyl or halogen;

(32) R$^2$ is a 4 to 8 membered heterocycloalkyl optionally substituted with one or more R$^5$, wherein R$^5$ is selected from C$_1$-C$_4$alkyl, haloC$_1$-C$_4$alkyl or halogen;

(33) R$^2$ is a 5 to 8 membered heterocycloalkyl optionally substituted with one or more R$^5$, wherein R$^5$ is selected from C$_1$-C$_4$alkyl, haloC$_1$-C$_4$alkyl or halogen;

(34) R$^2$ is a 6 to 8 membered heterocycloalkyl optionally substituted with one or more R$^5$, wherein R$^5$ is selected from C$_1$-C$_4$alkyl, haloC$_1$-C$_4$alkyl or halogen;

(35) R$^2$ is a 6 and 7 membered heterocycloalkyl optionally substituted with one or more R$^5$, wherein R$^5$ is selected from C$_1$-C$_4$alkyl, haloC$_1$-C$_4$alkyl or halogen;

(36) R$^3$ and R$^4$ are each independently chosen from H, C$_1$-C$_{10}$alkyl, C$_2$-C$_{10}$alkenyl, C$_2$-C$_{10}$alkynyl, haloC$_1$-C$_6$alkyl, C$_0$-C$_6$alkylaryl, C$_0$-C$_6$alkylcycloalkyl, C$_0$-C$_6$alkylheteroaryl, or C$_0$-C$_6$alkylheterocycloalkyl;

(37) R$^3$ and R$^4$ are each independently chosen from H, C$_1$-C$_6$alkyl, C$_2$-C$_6$alkenyl, C$_2$-C$_6$alkynyl, haloC$_1$-C$_6$alkyl, C$_0$-C$_2$alkylaryl, C$_0$-C$_2$alkylcycloalkyl, C$_0$-C$_2$alkylheteroaryl, or C$_0$-C$_2$alkylheterocycloalkyl;

(38) R$^3$ and R$^4$ are each independently chosen from H, C$_1$-C$_6$alkyl, C$_2$-C$_6$alkenyl, C$_2$-C$_6$alkynyl, haloC$_1$-C$_6$alkyl, aryl, cycloalkyl, heteroaryl, or heterocycloalkyl;

(39) R$^3$ and R$^4$ are each independently chosen from H, C$_1$-C$_6$alkyl or haloC$_1$-C$_4$alkyl;

(40) R$^3$ and R$^4$ are each independently chosen from H, or C$_1$-C$_4$alkyl;

(41) Each R$^5$ is independently chosen from C$_1$-C$_{10}$alkyl, C$_2$-C$_{10}$alkenyl, C$_2$-C$_{10}$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, —C$_0$-C$_6$alkylCN, —C$_0$-C$_6$alkylC(=O)C$_0$-C$_6$alkylR$^6$, —C$_0$-C$_6$alkylC(=O)C$_0$-C$_6$alkylOR$^6$, —C$_0$-C$_6$alkylC(=O)C$_0$-C$_6$alkylNR$^6$R$^6$, —C$_0$-C$_6$alkylC(=O)C$_0$-C$_6$alkylNR$^6$C(=O)OR$^6$, —C$_0$-C$_6$alkylC(=O)C$_0$-C$_6$alkylC(=O)R$^6$, haloC$_1$-C$_6$alkyl, halogen, —NO$_2$, —C$_0$-C$_6$alkylNR$^6$R$^6$, —C$_0$-C$_6$alkylNR$^6$NR$^6$R$^6$, —C$_0$-C$_6$alkylN=NR$^6$, —C$_0$-C$_6$alkylNR$^6$C$_0$-C$_6$alkylOR$^6$, —C$_0$-C$_6$alkylNR$^6$C$_0$-C$_6$alkylC(=O)R$^6$, —C$_0$-C$_6$alkylNR$^6$C(=O)C$_0$-C$_6$alkylC(=O)R$^6$, —C$_0$-C$_6$alkylNR$^6$C$_0$-C$_6$alkyl C(=O)OR$^6$, —C$_0$-C$_6$alkylNR$^6$C$_0$-C$_6$alkylC(=O)C(=O)OR$^6$, —C$_0$-C$_6$alkylNR$^6$C$_0$-C$_6$alkylC(=O)NR$^6$R$^6$, —C$_0$-C$_6$alkylNR$^6$C$_0$-C$_6$alkyl S(=O)$_2$R$^6$, —C$_0$-C$_6$alkylOR$^6$, —C$_0$-C$_6$alkylOC(=O)C$_0$-C$_6$alkylR$^6$, —C$_0$-C$_6$alkylOS(=O)$_2$R$^6$, —C$_0$-C$_6$alkylOP(=O)R$^6$R$^6$, —C$_0$-C$_6$alkylOP(=O)(NR$^6$R$^6$)(NR$^6$R$^6$), —C$_0$-C$_6$alkylOP(=O)(OR$^6$)(OR$^6$), —C$_0$-C$_6$alkylOP(=O)(SR$^6$)(SR$^6$), —C$_0$-C$_6$alkylP(=O)R$^6$R$^6$, —C$_0$-C$_6$alkylP(=O)(OR$^6$)(OR$^6$), —C$_0$-C$_6$alkylS(=O)$_p$R$^6$ and —C$_0$-C$_6$alkylS(=O)$_2$C$_0$-C$_6$alkylNR$^6$R$^6$, wherein any of the foregoing is optionally substituted with one or more R$^7$; or together with carbon atoms to which they are attached, two $R^5$ groups may be linked to form a fused aryl, heteroaryl, 3 to 6 membered heterocycloalkyl or a 3 to 6 membered cycloalkyl;

(42) Each $R^5$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^6$, —$C_0$-$C_6$alkylC(=O)$C_0$-$C_6$alkylO$R^6$, —$C_0$-$C_6$alkylC(=O)$C_0$-$C_6$alkylN$R^6R^6$, —$C_0$-$C_6$alkylC(=O)$C_0$-$C_6$alkylN$R^6$C(=O)O$R^6$, halo$C_1$-$C_6$alkyl, halogen, —$NO_2$, —$C_0$-$C_6$alkylN$R^6R^6$, —$C_0$-$C_6$alkylN$R^6C_0$-$C_6$alkylC(=O)$R^6$, —$C_0$-$C_6$alkylN$R^6$C(=O)$C_0$-$C_6$alkylC(=O)$R^6$, —$C_0$-$C_6$alkylN$R^6C_0$-$C_6$alkylS(=O)$_2R^6$, —$C_0$-$C_6$alkylO$R^6$ and —$C_0$-$C_6$alkylS(=O)$_pR^6$, wherein any of the foregoing is optionally substituted with one or more $R^7$; or
together with carbon atoms to which they are attached, two $R^5$ may be linked to form a fused aryl, heteroaryl, 3 to 6 membered heterocycloalkyl or a 3 to 6 membered cycloalkyl;

(43) Each $R^5$ is independently chosen from $C_1$-$C_6$alkyl, $C_2$-$C_6$alkenyl, $C_2$-$C_6$alkynyl, $C_0$-$C_2$alkylaryl, $C_0$-$C_2$alkylcycloalkyl, $C_0$-$C_2$alkylheterocycloalkyl, $C_0$-$C_2$alkylheteroaryl, —$C_0$-$C_4$alkylCN, —$C_0$-$C_2$alkylC(=O)$C_0$-$C_6$alkyl$R^6$, —$C_0$-$C_2$alkylC(=O)$C_0$-$C_6$alkylO$R^6$, —$C_0$-$C_2$alkylC(=O)$C_0$-$C_6$alkylN$R^6R^6$, —$C_0$-$C_4$alkylC(=O)$C_0$-$C_6$alkylN$R^6$C(=O)O$R^6$, halo$C_1$-$C_6$alkyl, halogen, —$NO_2$, —$C_0$-$C_4$alkylN$R^6R^6$, —$C_0$-$C_6$alkylN$R^6C_0$-$C_6$alkylC(=O)$R^6$, —$C_0$-$C_6$alkylN$R^6$C(=O)$C_0$-$C_6$alkylC(=O)$R^6$, —$C_0$-$C_6$alkylN$R^6C_0$-$C_6$alkylS(=O)$_2R^6$, —$C_0$-$C_6$alkylO$R^6$ and —$C_0$-$C_2$alkylS(=O)$_pR^6$, wherein any of the foregoing is optionally substituted with one or more $R^7$;

(44) Each $R^5$ is independently chosen from $C_1$-$C_6$alkyl, $C_2$-$C_6$alkenyl, $C_2$-$C_6$alkynyl, $C_0$-$C_2$alkylaryl, $C_0$-$C_2$alkylcycloalkyl, $C_0$-$C_2$alkylheterocycloalkyl, $C_0$-$C_2$alkylheteroaryl, —$C_0$-$C_4$alkylCN, —$C_0$-$C_2$alkylC(=O)$C_0$-$C_2$alkyl$R^6$, —$C_0$-$C_2$alkylC(=O)$C_0$-$C_2$alkylO$R^6$, —$C_0$-$C_2$alkylC(=O)$C_0$-$C_2$alkylN$R^6R^6$, —$C_0$-$C_4$alkylC(=O)$C_0$-$C_2$alkylN$R^6$C(=O)O$R^6$, halo$C_1$-$C_6$alkyl, halogen, —$NO_2$, —$C_0$-$C_4$alkylN$R^6R^6$, —$C_0$-$C_2$alkylN$R^6C_0$-$C_2$alkylC(=O)$R^6$, —$C_0$-$C_6$alkylO$R^6$ and —$C_0$-$C_2$alkylS(=O)$_pR^6$, wherein any of the foregoing is optionally substituted with one or more $R^7$;

(45) Each $R^5$ is independently chosen from $C_1$-$C_6$alkyl, $C_2$-$C_6$alkenyl, $C_2$-$C_6$alkynyl, $C_0$-$C_2$alkylaryl, $C_0$-$C_2$alkylcycloalkyl, $C_0$-$C_2$alkylheterocycloalkyl, $C_0$-$C_2$alkylheteroaryl, —$C_0$-$C_4$alkylCN, —C(=O)$C_0$-$C_2$alkyl$R^6$, —C(=O)O$R^6$, —$C_0$-$C_2$alkylC(=O)N$R^6R^6$, —$C_0$-$C_4$alkylC(=O)$C_0$-$C_2$alkylN$R^6$C(=O)O$R^6$, halo$C_1$-$C_6$alkyl, halogen, —$NO_2$, —$C_0$-$C_4$alkylN$R^6R^6$, —$C_0$-$C_2$alkylN$R^6$C(=O)$R^6$, —$C_0$-$C_6$alkylO$R^6$ and S(=O)$_pR^6$, wherein any of the foregoing is optionally substituted with one or more $R^7$;

(46) Each $R^5$ is independently chosen from $C_1$-$C_6$alkyl, $C_2$-$C_4$alkenyl, $C_2$-$C_4$alkynyl, $C_0$-$C_2$alkylphenyl $C_0$-$C_2$alkyl-3 to 6-membered cycloalkyl, $C_0$-$C_2$alkyl-5- or 6-membered heterocycloalkyl, $C_0$-$C_2$alkyl-5- or 6-membered heteroaryl, —$C_0$-$C_4$alkylCN, —C(=O)$C_0$-$C_2$alkyl$R^6$, —C(=O)O$R^6$, —$C_0$-$C_2$alkylC(=O)N$R^6R^6$, —$C_0$-$C_4$alkylC(=O)$C_0$-$C_2$alkylN$R^6$C(=O)O$R^6$, halo$C_1$-$C_4$alkyl, halogen, —$C_0$-$C_4$alkylN$R^6R^6$, —$C_0$-$C_2$alkylN$R^6$C(=O)$R^6$, —$C_0$-$C_4$alkylO$R^6$ and S(=O)$_pR^6$, wherein any of the foregoing is optionally substituted with one or more $R^7$;

(47) Each $R^5$ is selected from $C_1$-$C_4$alkyl, halo$C_1$-$C_4$alkyl or halogen;

(48) Each $R^6$ is independently chosen from H, $C_1$-$C_{10}$alkyl, halo$C_1$-$C_6$alkyl, $C_0$-$C_2$alkylaryl, $C_0$-$C_2$alkylcycloalkyl, $C_0$-$C_2$alkylheteroaryl, $C_0$-$C_2$alkylheterocycloalkyl, wherein any of the foregoing except for H is optionally substituted with one or more $R^7$; or
Two $R^6$ may be taken together to form a 3 to 6 membered carbocyclic or heterocyclic ring system, wherein said ring system is optionally substituted with one or more $R^7$;

(49) Each $R^6$ is independently chosen from H, $C_1$-$C_{10}$alkyl, halo$C_1$-$C_6$alkyl, $C_0$-$C_2$alkylaryl, $C_0$-$C_2$alkylcycloalkyl, $C_0$-$C_2$alkylheteroaryl, $C_0$-$C_2$alkylheterocycloalkyl, wherein any of the foregoing except for H is optionally substituted with one or more $R^7$;

(50) Each $R^6$ is independently chosen from H, $C_1$-$C_6$alkyl, halo$C_1$-$C_4$alkyl, $C_0$-$C_2$alkylaryl, $C_0$-$C_2$alkyl-5- or 6-membered cycloalkyl, $C_0$-$C_2$alkyl-5- or 6-membered heteroaryl, $C_0$-$C_2$alkyl-5- or 6-membered heterocycloalkyl, wherein any of the foregoing except for H is optionally substituted with one or more $R^7$;

(51) Each $R^6$ is independently chosen from H, $C_1$-$C_4$alkyl, halo$C_1$-$C_2$alkyl, $C_0$-$C_2$alkylaryl, $C_0$-$C_2$alkyl-5- or 6-membered cycloalkyl, $C_0$-$C_2$alkyl-5- or 6-membered heteroaryl, $C_0$-$C_2$alkyl-5- or 6-membered heterocycloalkyl, wherein any of the foregoing except for H is optionally substituted with one or more $R^7$;

(52) Each $R^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^8$, —$C_0$-$C_6$alkylC(=O)$C_0$-$C_6$alkylO$R^8$, —$C_0$-$C_6$alkylC(=O)$C_0$-$C_6$alkylN$R^8R^8$, $C_0$-$C_6$alkyl C(=O)$C_0$-$C_6$alkylN$R^8$C(=O)O$R^8$, —$C_0$-$C_6$alkyl C(=O)$C_0$-$C_6$alkylC(=O)$R^8$, halo$C_1$-$C_6$alkyl, halogen, —$NO_2$, —$C_0$-$C_6$alkylN$R^8R^8$, —$C_0$-$C_6$alkylN$R^8$N$R^8R^8$, —$C_0$-$C_6$alkylN=N$R^8$, —$C_0$-$C_6$alkylN$R^8C_0$-$C_6$alkylO$R^8$, —$C_0$-$C_6$alkylN$R^8C_0$-$C_6$alkylC(=O)$R^8$, —$C_0$-$C_6$alkylN$R^8$C(=O)$C_0$-$C_6$alkylC(=O)$R^8$, —$C_0$-$C_6$alkylN$R^8C_0$-$C_6$alkyl C(=O)O$R^8$, —$C_0$-$C_6$alkylN$R^8C_0$-$C_6$alkylC(=O)C(=O)O$R^8$, —$C_0$-$C_6$alkylN$R^8C_0$-$C_6$alkylC(=O)N$R^8R^8$, —$C_0$-$C_6$alkylN$R^8$C(=O)$C_0$-$C_6$alkylN$R^8$C(=O)$R^8$, —$C_0$-$C_6$alkylN$R^8$C(=O)$C_0$-$C_6$alkylN$R^8$C(=O)O$R^8$, —$C_0$-$C_6$alkylN$R^8C_0$-$C_6$alkylS(=O)$_2R^8$, —$C_0$-$C_6$alkylNRS(=O)$_2C_0$-$C_6$alkylN$R^8R^8$, —$C_0$-$C_6$alkylO$R^8$, —$C_0$-$C_6$alkylOC(=O)$C_0$-$C_6$alkyl$R^8$, —$C_0$-$C_6$alkylOC(=O)$C_0$-$C_6$alkylN$R^8R^8$, —$C_0$-$C_6$alkylOC(=O)$C_0$-$C_6$alkylO$R^8$, —$C_0$-$C_6$alkylOS(=O)$_2R^8$, —$C_0$-$C_6$alkylOS(=O)$_2C_0$-$C_6$alkylN$R^8R^8$, —$C_0$-$C_6$alkylOP(=O)$R^8R^8$, —$C_0$-$C_6$alkylOP(=O)(N$R^8R^8$)(N$R^8R^8$), —$C_0$-$C_6$alkylOP(=O)($R^8$)(OR)(OR), —$C_0$-$C_6$alkylP(=O)$R^8R^8$, —$C_0$-$C_6$alkylP(=O)(N$R^8R^8$)(N$R^8R^8$), —$C_0$-$C_6$alkylP(=O)(O$R^8$)(O$R^8$), —$C_0$-$C_6$alkyl S(=O)$_pR^8$, —$C_0$-$C_6$alkylS(=O)$_2C_0$-$C_6$alkylN$R^8R^8$ and —$C_0$-$C_6$alkylS(=O)$C_0$-$C_6$alkylN$R^8R^8$;

(53) Each $R^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-

$C_6$alkylC(=O)$C_0$-$C_6$alkylR$^8$, —$C_0$-$C_6$alkylC(=O)$C_0$-$C_6$alkylOR$^8$, —$C_0$-$C_6$alkylC(=O)$C_0$-$C_6$alkylNR$^8$R$^8$, —$C_0$-$C_6$alkylC(=O)$C_0$-$C_6$alkylNR$^8$C(=O)OR$^8$, —$C_0$-$C_6$alkylC(=O)$C_0$-$C_6$alkylC(=O)R$^8$, halo$C_1$-$C_6$alkyl, halogen, —NO$_2$, —$C_0$-$C_6$alkylNR$^8$R$^8$, —$C_0$-$C_6$alkylNR$^8$NR$^8$R$^8$, —$C_0$-$C_6$alkylNR$^8$$C_0$-$C_6$alkylC(=O)R$^8$, —$C_0$-$C_6$alkylNR$^8$C(=O)$C_0$-$C_6$alkylC(=O)R$^8$, —$C_0$-$C_6$alkylNR$^8$$C_0$-$C_6$alkyl C(=O)OR$^8$, —$C_0$-$C_6$alkylNR$^8$C(=O)$C_0$-$C_6$alkylNR$^8$C(=O)OR$^8$, —$C_0$-$C_6$alkylNR$^8$$C_0$-$C_6$alkyl S(=O)$_2$R$^8$, —$C_0$-$C_6$alkylNR$^8$(=O)$_2$$C_0$-$C_6$alkylNR$^8$R$^8$, —$C_0$-$C_6$alkylOR$^8$, $C_0$-$C_6$alkylS(=O)$_p$R$^8$, —$C_0$-$C_6$alkylS(=O)$_2$$C_0$-$C_6$alkylNR$^8$R$^8$ and —$C_0$-$C_6$alkylS(=O)$C_0$-$C_6$alkylNR$^8$R$^8$;

(54) Each R$^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^8$, —$C_0$-$C_6$alkylC(=O)$C_0$-$C_6$alkylOR$^8$, —$C_0$-$C_6$alkylC(=O)$C_0$-$C_6$alkylNR$^8$R$^8$, —$C_0$-$C_6$alkylC(=O)$C_0$-$C_6$alkylNR$^8$C(=O)OR$^8$, halo$C_1$-$C_6$alkyl, halogen, —$C_0$-$C_6$alkylNR$^8$R$^8$, —$C_0$-$C_6$alkylNR$^8$$C_0$-$C_6$alkylC(=O)R$^8$, —$C_0$-$C_6$alkylNR$^8$C(=O)R$^8$, —$C_0$-$C_6$alkylNR$^8$$C_0$-$C_6$alkyl C(=O)OR$^8$, —$C_0$-$C_6$alkylNR$^8$$C_0$-$C_6$alkyl S(=O)$_2$R$^8$, —$C_0$-$C_6$alkylOR$^8$, $C_0$-$C_6$alkylS(=O)$_p$R$^8$, —$C_0$-$C_6$alkylS(=O)$_2$$C_0$-$C_6$alkylNR$^8$R$^8$ and —$C_0$-$C_6$alkylS(=O)$C_0$-$C_6$alkylNR$^8$R$^8$;

(55) Each R$^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^8$, —$C_0$-$C_6$alkylC(=O)$C_0$-$C_6$alkylOR$^8$, halo$C_1$-$C_6$alkyl, halogen, —$C_0$-$C_6$alkylNR$^8$R$^8$, —$C_0$-$C_6$alkylNR$^8$$C_0$-$C_6$alkylC(=O)R$^8$, —$C_0$-$C_6$alkylNR$^8$$C_0$-$C_6$alkyl S(=O)$_2$R$^8$, —$C_0$-$C_6$alkylOR$^8$, $C_0$-$C_6$alkylS(=O)$_p$R$^8$ and —$C_0$-$C_6$alkylS(=O)$_2$$C_0$-$C_6$alkylNR$^8$R$^8$;

(56) Each R$^7$ is independently chosen from $C_1$-$C_{10}$alkyl, $C_2$-$C_6$alkenyl, $C_2$-$C_6$alkynyl, $C_0$-$C_2$alkylaryl, $C_0$-$C_2$alkylcycloalkyl, $C_0$-$C_2$alkylheterocycloalkyl, $C_0$-$C_2$alkylheteroaryl, —$C_0$-$C_4$alkylCN, —$C_0$-$C_2$alkylC(=O)$C_0$-$C_6$alkylR$^8$, —$C_0$-$C_2$alkylC(=O)$C_0$-$C_6$alkylOR$^8$, halo$C_1$-$C_6$alkyl, halogen, —$C_0$-$C_6$alkylNR$^8$R$^8$, —$C_0$-$C_2$alkylNR$^8$$C_0$-$C_6$alkylC(=O)R$^8$, —$C_0$-$C_2$alkylNR$^8$$C_0$-$C_6$alkyl S(=O)$_2$R$^8$, —$C_0$-$C_6$alkylOR$^8$, $C_0$-$C_2$alkylS(=O)$_p$R$^8$ and —$C_0$-$C_2$alkylS(=O)$_2$$C_0$-$C_6$alkylNR$^8$R$^8$;

(57) Each R$^7$ is independently chosen from $C_1$-$C_6$alkyl, aryl, cycloalkyl, heterocycloalkyl, heteroaryl, —$C_0$-$C_4$alkylCN, —$C_0$-$C_2$alkylC(=O)$C_0$-$C_2$alkylR$^8$, —$C_0$-$C_2$alkylC(=O)$C_0$-$C_6$alkylOR$^8$, halo$C_1$-$C_6$alkyl, halogen, —$C_0$-$C_6$alkylNR$^8$R$^8$, —$C_0$-$C_2$alkylNR$^8$$C_0$-$C_2$alkylC(=O)R$^8$, —$C_0$-$C_2$alkylNR$^8$$C_0$-$C_2$alkyl S(=O)$_2$R$^8$, —$C_0$-$C_6$alkylOR$^8$, $C_0$-$C_2$alkylS(=O)$_p$R$^8$ and —$C_0$-$C_2$alkylS(=O)$_2$$C_0$-$C_2$alkylNR$^8$R$^8$;

(58) Each R$^7$ is independently chosen from $C_1$-$C_6$alkyl, —$C_0$-$C_4$alkylCN, —$C_0$-$C_2$alkylC(=O)$C_0$-$C_2$alkylR$^8$, —$C_0$-$C_2$alkylC(=O)$C_0$-$C_2$alkylOR$^8$, halo$C_1$-$C_4$alkyl, halogen, —$C_0$-$C_6$alkylNR$^8$R$^8$, —$C_0$-$C_2$alkylNR$^8$$C_0$-$C_2$alkylC(=O)R$^8$, —$C_0$-$C_2$alkylNR$^8$$C_0$-$C_2$alkyl S(=O)$_2$R$^8$, —$C_0$-$C_4$alkylOR$^8$, $C_0$-$C_2$alkylS(=O)$_2$R$^8$ and —$C_0$-$C_2$alkylS(=O)$_2$$C_0$-$C_2$alkylNR$^8$R$^8$;

(59) Each R$^7$ is independently chosen from $C_1$-$C_6$alkyl, —$C_0$-$C_4$alkylCN, —C(=O)R$^8$, —C(=O)OR$^8$, halo$C_1$-$C_4$alkyl, halogen, —$C_0$-$C_4$alkylNR$^8$R$^8$, —NR$^8$C(=O)R$^8$, —NR$^8$S(=O)$_2$R$^8$, —$C_0$-$C_4$alkylOR$^8$, $C_0$-$C_2$alkylS(=O)$_2$R$^8$ and —S(=O)$_2$NR$^8$R$^8$;

(60) Each R$^8$ is independently chosen from H, $C_1$-$C_{10}$alkyl, $C_2$-$C_{10}$alkenyl, $C_2$-$C_{10}$alkynyl, halo$C_1$-$C_6$alkyl, aryl, cycloalkyl, heteroaryl, and heterocycloalkyl;

(61) Each R$^8$ is independently chosen from H, $C_1$-$C_6$alkyl, $C_2$-$C_6$alkenyl, $C_2$-$C_6$alkynyl, halo$C_1$-$C_4$alkyl, aryl, cycloalkyl, heteroaryl, and heterocycloalkyl;

(62) Each R$^8$ is independently chosen from H, $C_1$-$C_6$alkyl, $C_2$-$C_6$alkenyl, $C_2$-$C_6$alkynyl and halo$C_1$-$C_4$alkyl;

(63) Each R$^8$ is independently chosen from H, $C_1$-$C_6$alkyl and halo$C_1$-$C_4$alkyl;

(64) Each R$^8$ is independently chosen from H or $C_1$-$C_4$alkyl.

Suitably, a heterocyclylalkyl group as defined herein is a monocyclic, bicyclic or spiro heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclylalkyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably an aryl group is phenyl.

Suitably, X is as defined in any one of paragraphs (6) to (11) above. Most suitably, X is as defined in paragraph (11).

Suitably, $R_1$ is as defined in any one of paragraphs (12) to (23) above. More suitably, $R_1$ is as defined in any one of paragraphs (16) to (23). Most suitably, $R_1$ is as defined in paragraph (23).

Suitably, $R^2$ is as defined in any one of paragraphs (24) to (35) above. More suitably, $R^2$ is as defined in any one of paragraphs (29) to (35). Most suitably, $R^2$ is as defined in paragraph (35).

Suitably, $R^3$ and $R^4$ are defined as in any one of paragraphs (36) to (40) above. Most suitably, $R^3$ and $R^4$ are as defined in paragraph (40).

Suitably, $R^5$ is as defined in any one of paragraphs (41) to (47) above. More suitably, $R^5$ is as defined in any one of paragraphs (45) to (47). Most suitably, $R^5$ is as defined in paragraph (47).

Suitably, $R^6$ is as defined in any one of paragraphs (48) to (51) above. Most suitably, $R^6$ is as defined in paragraph (51).

Suitably, $R^7$ is as defined in any one of paragraphs (52) to (59) above. More suitably, $R^7$ is as defined in any one of paragraphs (54) to (59). Most suitably, $R^7$ is as defined in paragraph (59).

Suitably, $R_8$ is as defined in any one of paragraphs (60) to (64) above. Most suitably, $R_8$ is as defined in paragraph (64).

In one embodiment, X is as defined in any one of paragraphs (6), (7), (8), (9), (10) and (11), $R^1$ is as defined in paragraph (18) and $R^2$ is as defined in paragraph (27).

In another embodiment, X is as defined in any one of paragraphs (6), (7), (8), (9), (10) and (11), $R^1$ is as defined in paragraph (20) and $R^2$ is as defined in paragraph (33).

In another embodiment, X is as defined in any one of paragraphs (6), (7), (8), (9), (10) and (11), $R^1$ is as defined in paragraph (23) and $R^2$ is as defined in paragraph (35).

In one embodiment, X is as defined in paragraph (6), $R^1$ is as defined in paragraph (18) and $R^2$ is as defined in any one of paragraphs (24) to (35).

In one embodiment, X is as defined in paragraph (8), $R^1$ is as defined in paragraph (20) and $R^2$ is as defined in any one of paragraphs (24) to (35).

In one embodiment, X is as defined in paragraph (11), $R^1$ is as defined in paragraph (23) and $R^2$ is as defined in any one of paragraphs (24) to (35).

In one embodiment, X is as defined in paragraph (6), $R^1$ is as defined in any one of paragraphs (12) to (23) and $R^2$ is as defined paragraphs (29).

In one embodiment, X is as defined in paragraph (8), $R^1$ is as defined in any one of paragraphs (12) to (23) and $R^2$ is as defined in paragraphs (33).

In one embodiment, X is as defined in paragraph (11), $R^1$ is as defined in any one of paragraphs (12) to (23) and $R^2$ is as defined in paragraphs (35).

In a particular group of compounds of the invention, the compounds have the structural formula Ia$_1$ (a sub-definition of formula I) shown below:

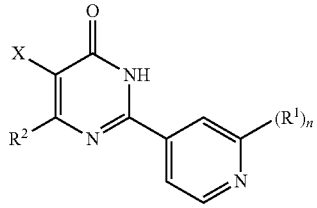

Formula Ia$_1$ wherein n, p, $R^1$, $R^2$ and X and any associated substituent groups each have any one of the meanings defined herein; or a salt, or solvate thereof.

In an embodiment of the compounds of formula Ia$_1$:
n is as defined in any one of paragraphs (1) to (3);
p is as defined in any one if paragraphs (4) to (5);
X is as defined in any one of paragraphs (6) to (11);
$R^1$ is as defined in any one of paragraphs (12) to (23);
$R^2$ is as defined in any one of paragraphs (24) to (35);
$R^3$ and $R^4$ are as defined in any one of paragraphs (36) to (40);
$R^5$ is as defined in any one of paragraphs (41) to (47) above;
$R^6$ is as defined in any one of paragraphs (48) to (51) above;
$R^7$ is as defined in any one of paragraphs (52) to (59) above; and
$R_8$ is as defined in any one of paragraphs (60) to (64) above.

In one embodiment, X is as defined in any one of paragraphs (6), (7), (8), (9), (10) and (11), $R^1$ is as defined in paragraph (18) and $R^2$ is as defined in paragraph (29).

In another embodiment, X is as defined in any one of paragraphs (6), (7), (8), (9), (10) and (11), $R^1$ is as defined in paragraph (20) and $R^2$ is as defined in paragraph (33).

In another embodiment, X is as defined in any one of paragraphs (6), (7), (8), (9), (10) and (11), $R^1$ is as defined in paragraph (23) and $R^2$ is as defined in paragraph (35).

In one embodiment, X is as defined in paragraph (6), $R^1$ is as defined in paragraph (18) and $R^2$ is as defined in any one of paragraphs (24) to (35).

In one embodiment, X is as defined in paragraph (8), $R^1$ is as defined in paragraph (20) and $R^2$ is as defined in any one of paragraphs (24) to (35).

In one embodiment, X is as defined in paragraph (11), $R^1$ is as defined in paragraph (23) and $R^2$ is as defined in any one of paragraphs (24) to (35).

In one embodiment, X is as defined in paragraph (6), $R^1$ is as defined in any one of paragraphs (12) to (23) and $R^2$ is as defined paragraphs (29).

In one embodiment, X is as defined in paragraph (8), $R^1$ is as defined in any one of paragraphs (12) to (23) and $R^2$ is as defined in paragraphs (33).

In one embodiment, X is as defined in paragraph (11), $R^1$ is as defined in any one of paragraphs (12) to (23) and $R^2$ is as defined in paragraphs (35).

In a particular group of compounds of the invention, the compounds have the structural formula Ia$_2$ (a sub-definition of formula I) shown below:

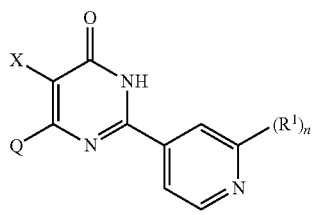

Formula Ia$_2$ wherein Q is selected from a group of the formula Q$_1$ or Q$_2$ as shown below:

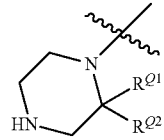

Q1

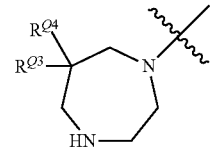

Q2 and wherein:
$R^{Q1}$, $R^{Q2}$, $R^{Q3}$ and $R^{Q4}$ are each independently selected from hydrogen, $C_1$-$C_4$alkyl, halo$C_1$-$C_4$alkyl or halogen; and
n, $R_1$, and X and any associated substituent groups each have any one of the meanings defined herein;
or a salt, or solvate thereof.

In an embodiment of the compounds of formula Ia$_2$:
$R^{Q1}$, $R^{Q2}$, $R^{Q3}$ and $R^{Q4}$ are each independently selected from hydrogen, $C_1$-$C_4$alkyl, halo$C_1$-$C_4$alkyl or halogen;
n is as defined in any one of paragraphs (1) to (3);
X is as defined in any one of paragraphs (6) to (11); and
$R^1$ is as defined in any one of paragraphs (12) to (23).

In an embodiment of the compounds of formula Ia$_2$:
$R^{Q1}$, $R^{Q2}$, $R^{Q3}$ and $R^{Q4}$ are each independently selected from hydrogen, $C_1$-$C_2$alkyl, halo$C_1$-$C_2$alkyl or halogen;
n is as defined in any one of paragraphs (2) to (3);
X is as defined in any one of paragraphs (8) to (11); and
$R^1$ is as defined in any one of paragraphs (15) to (23).

In an embodiment of the compounds of formula Ia$_2$:
$R^{Q1}$, $R^{Q2}$, $R^{Q3}$ and $R^{Q4}$ are each independently selected from hydrogen, $C_1$-$C_2$alkyl, $CF_3$, $CHF_2$, or fluoro;

n is as defined in paragraphs (3);
X is as defined in any one of paragraphs (10) to (11); and
R₁ is as defined in any one of paragraphs (20) to (23).
In an embodiment of the compounds of formula Ia₂:
R^{Q1}, R^{Q2}, R^{Q3} and R^{Q4} are each independently selected from hydrogen, $C_1$-$C_2$alkyl, halo$C_1$-$C_2$alkyl or halogen;
n is 1;
X is as defined in any one of paragraphs (8) to (11); and
$R^1$ is as defined in any one of paragraphs (20).
In an embodiment of the compounds of formula Ia₂:
R^{Q1}, R^{Q2}, R^{Q3} and R^{Q4} are each independently selected from hydrogen, $C_1$-$C_2$alkyl, halo$C_1$-$C_2$alkyl or halogen;
n is 1;
X is as defined in paragraph (11); and
R₁ is as defined in any one of paragraphs (20) to (23).
Particular compounds of the invention include, for example, compounds of Formulae Ia to If, shown herein below, wherein each of n, p, $R_1$, $R_2$, $R_3$, $R_4$, $R_5$, $R_6$, $R_7$, $R_8$, X and any associated substituent groups has any of the meanings defined in any of paragraphs (1) to (64) above or in any of the meanings defined in the Embodiments described hereinbelow.

In addition to the definitions of each substituent group defined hereinabove, the compounds of the present invention may be defined in terms of the following numbered Embodiments. When a higher numbered Embodiment refers back to multiple previous lower numbered Embodiments in the alternative and contains a new limitation not present in the lower numbered Embodiments, the higher numbered Embodiment is intended to be an express description of each and every one of the alternatives. For example, if Embodiment 2 refers back to Embodiment 1 and contains a limitation not present in Embodiment 1, Embodiment 3 refers back Embodiments 1 or 2 and contains a limitation(s) not present in Embodiments 1 or 2, and Embodiment 4 refers back to any of Embodiments 1-3 and contains a limitation(s) not present in Embodiments 1, 2, or 3, then Embodiment 4 is intended to be an explicit description of a genus having the limitations of Embodiments 1 and 4, an explicit description of a genus having the limitations of Embodiments 2 and 4 (i.e., 1, 2, and 4), and an explicit description of a genus having the limitations of Embodiments 3 and 4 (i.e., 1, 3, and 4, and 1, 2, 3 and 4). It should be noted in this regard that when a higher numbered Embodiment refers to a lower numbered Embodiment and contains limitations for a group (s) not present in the lower numbered Embodiment, the higher numbered Embodiment should be interpreted in context to ignore the group(s) missing from the lowered numbered Embodiment.

Embodiment 1

A compound of Formula I:

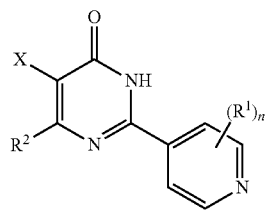

Formula I and/or a salt thereof wherein,
X is chosen from halogen, halo$C_1$-$C_6$alkyl, $NO_2$, —C(=O)$NR^8R^6$, —NHS(O)$_2R^6$, and CN;
Each $R^1$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^3$, —$C_0$-$C_6$alkylC(=O)$C_0$-$C_6$alkyl$NR^3$C(=O)$OR^4$, —$C_0$-$C_6$alkylC(=O)$C_0$-$C_6$alkyl$OR^3$, —$C_0$-$C_6$alkylC(=O)$C_0$-$C_6$alkyl$NR^3R^4$, —$C_0$-$C_6$alkylC(=O)$C_0$-$C_6$alkylC(=O)$R^3$, halo$C_1$-$C_6$alkyl, halogen, —$NO_2$, —$C_0$-$C_6$alkyl$NR^3R^4$, —$C_0$-$C_6$alkyl$NR^3NR^3R^4$, —$C_0$-$C_6$alkylN=$NR^3$, —$C_0$-$C_6$alkyl$NR^3C_0$-$C_6$alkyl$OR^4$, —$C_0$-$C_6$alkyl$NR^3C_0$-$C_6$alkylC(=O)$R^4$, —$C_0$-$C_6$alkyl$NR^3C(=O)C_0$-$C_6$alkylC(=O)$R^4$, —$C_0$-$C_6$alkyl$NR^3C_0$-$C_6$alkylC(=O)$OR^4$, —$C_0$-$C_6$alkyl$NR^3C_0$-$C_6$alkylC(=O)C(=O)$OR^4$, —$C_0$-$C_6$alkyl$NR^3C_0$-$C_6$alkylC(=O)$NR^3R^4$, —$C_0$-$C_6$alkyl$NR^3C(=O)C_0$-$C_6$alkyl$NR^3C(=O)R^4$, —$C_0$-$C_6$alkyl$NR^3C(=O)C_0$-$C_6$alkyl$NR^3C(=O)OR^4$, —$C_0$-$C_6$alkyl$NR^3C(=O)C_0$-$C_6$alkylC(=O)$NR^3R^4$, —$C_0$-$C_6$alkyl$NR^3C_0$-$C_6$alkylS(=O)$_2R^4$, —$C_0$-$C_6$alkyl$NR^3S(=O)_2C_0$-$C_6$alkyl$NR^3R^4$, —$C_0$-$C_6$alkyl$OR^3$, (=O), —$C_0$-$C_6$alkylOC(=O)$C_0$-$C_6$alkyl$R^4$, —$C_0$-$C_6$alkylOC(=O)$C_0$-$C_6$alkyl$NR^3R^4$, —$C_0$-$C_6$alkylOC(=O)$C_0$-$C_6$alkyl$OR^4$, —$C_0$-$C_6$alkylOS(=O)$R^4$, —$C_0$-$C_6$alkylOS(=O)$_2R^4$, —$C_0$-$C_6$alkylOS(=O)$_2C_0$-$C_6$alkyl$OR^4$, —$C_0$-$C_6$alkylOS(=O)$_2C_0$-$C_6$alkyl$NR^3R^4$, —$C_0$-$C_6$alkylOP(=O)$R^3R^4$, —$C_0$-$C_6$alkylOP(=O)($NR^3R^4$)($NR^3R^4$), —$C_0$-$C_6$alkylOP(=O)($OR^3$)($OR^4$), —$C_0$-$C_6$alkylOP(=O)($SR^3$)($SR^4$), —$C_0$-$C_6$alkylP(=O)$R^3R^4$, —$C_0$-$C_6$alkylP(=O)($NR^3R^4$)($NR^3R^4$), —$C_0$-$C_6$alkylP(=O)($R^3$)($OR^3$)($OR^4$), —$C_0$-$C_6$alkylP(=O)($SR^3$)($SR^4$), —$C_0$-$C_6$alkylS(=O)$_pR^4$, —$C_0$-$C_6$alkylS(=O)$_2C_0$-$C_6$alkyl$NR^3R^4$, —$C_0$-$C_6$alkylS(=O)$C_0$-$C_6$alkyl$NR^3R^4$, and —$C_0$-$C_6$alkylSCN, wherein any of the foregoing is optionally substituted with one or more $R^5$; or Any two $R^1$ on adjacent atoms may be taken together to form a 4 to 12 membered carbocyclic or heterocyclic ring system, wherein said ring system is optionally substituted with one or more $R^5$;
$R^2$ is a group A-B-C wherein:
A is a bond or is $C_1$-$C_{10}$alkyl;
B is absent or is chosen from S(O)$_p$, $NR^3$, O, $C_2$-$C_{10}$alkenyl, and $C_2$-$C_{10}$alkynyl; and
C is a 3 to 15 membered heterocycloalkyl or a 4 to 11 membered cycloalkyl either of which is optionally substituted with one or more $R^5$;
$R^3$ and $R^4$ are each independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing, except for H, is optionally substituted with one or more $R^5$; or
$R^3$ and $R^4$ may be taken together to form a 3 to 15 membered carbocyclic or heterocyclic ring system, wherein said ring system is optionally substituted with one or more $R^5$; Each $R^5$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^6$, —$C_0$-$C_6$alkylC(=O)$C_0$-$C_6$alkyl$OR^6$, —$C_0$-$C_6$alkylC(=O)$C_0$-$C_6$alkyl$NR^6R^6$, —$C_0$-$C_6$alkylC(=O)$C_0$-$C_6$alkyl$NR^6C(=O)OR^6$, —$C_0$-$C_6$alkylC(=O)$C_0$-

$C_6$alkylC(=O)$R^6$, halo$C_1$-$C_6$alkyl, halogen, —$NO_2$, —$C_0$-$C_6$alkylN$R^6R^6$, —$C_0$-$C_6$alkylN$R^6$N$R^6R^6$, —$C_0$-$C_6$alkylN=N$R^6$, —$C_0$-$C_6$alkylN$R^6C_0$-$C_6$alkylO$R^6$, —$C_0$-$C_6$alkylN$R^6C_0$-$C_6$alkylC(=O)$R^6$, —$C_0$-$C_6$alkylN$R^6$C(=O)$C_0$-$C_6$alkylC(=O)$R^6$, —$C_0$-$C_6$alkylN$R^6C_0$-$C_6$alkyl C(=O)O$R^6$, —$C_0$-$C_6$alkylN$R^6C_0$-$C_6$alkylC(=O)C(=O)O$R^6$, —$C_0$-$C_6$alkylN$R^6C_0$-$C_6$alkylC(=O)N$R^6R^6$, —$C_0$-$C_6$alkylN$R^6$C(=O)$C_0$-$C_6$alkylN$R^6$C(=O)$R^6$, —$C_0$-$C_6$alkylN$R^6$C(=O)$C_0$-$C_6$alkylN$R^6$C(=O)O$R^6$, —$C_0$-$C_6$alkylN$R^6$C(=O)$C_0$-$C_6$alkylC(=O)N$R^6R^6$, —$C_0$-$C_6$alkylN$R^6C_0$-$C_6$alkyl S(=O)$_2R^6$, —$C_0$-$C_6$alkylN$R^6$S(=O)$_2C_0$-$C_6$alkylN$R^6R^6$, —$C_0$-$C_6$alkylO$R^6$, (=O), —$C_0$-$C_6$alkylOC(=O)$C_0$-$C_6$alkyl$R^6$, —$C_0$-$C_6$alkylOC(=O)$C_0$-$C_6$alkylN$R^6R^6$, —$C_0$-$C_6$alkylOC(=O)$C_0$-$C_6$alkylO$R^6$, —$C_0$-$C_6$alkylOS(=O)$R^6$, —$C_0$-$C_6$alkylOS(=O)$_2R^6$, —$C_0$-$C_6$alkylOS(=O)$_2C_0$-$C_6$alkylO$R^6$, —$C_0$-$C_6$alkylOS(=O)$_2C_0$-$C_6$alkylN$R^6R^6$, —$C_0$-$C_6$alkylOP(=O)$R^6R^6$, —$C_0$-$C_6$alkylOP(=O)(N$R^6R^6$)(N$R^6R^6$), —$C_0$-$C_6$alkylOP(=O)(O$R^6$)(O$R^6$), —$C_0$-$C_6$alkylOP(=O)(S$R^6$)(S$R^6$), —$C_0$-$C_6$alkylP(=O)$R^6R^6$, —$C_0$-$C_6$alkylP(=O)(N$R^6R^6$)(N$R^6R^6$), —$C_0$-$C_6$alkylP(=O)($R^6$)(O$R^6$), —$C_0$-$C_6$alkylP(=O)(S$R^6$)(S$R^6$), —$C_0$-$C_6$alkylS(=O)$_pR^6$, —$C_0$-$C_6$alkylS(=O)$_2C_0$-$C_6$alkylN$R^6R^6$, —$C_0$-$C_6$alkylS(=O)$C_0$-$C_6$alkylN$R^6R^6$, and —$C_0$-$C_6$alkylSCN, wherein any of the foregoing is optionally substituted with one or more $R^7$;

Each $R^6$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing except for H is optionally substituted with one or more $R^7$; or Two $R^6$ may be taken together to form a 3 to 15 membered carbocyclic or heterocyclic ring system, wherein said ring system is optionally substituted with one or more $R^7$;

Each $R^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^8$, —$C_0$-$C_6$alkylC(=O)$C_0$-$C_6$alkylO$R^8$, —$C_0$-$C_6$alkylC(=O)$C_0$-$C_6$alkylN$R^8R^8$, —$C_0$-$C_6$alkylC(=O)$C_0$-$C_6$alkylN$R^8$C(=O)O$R^8$, —$C_0$-$C_6$alkylC(=O)$C_0$-$C_6$alkylC(=O)$R^8$, halo$C_1$-$C_6$alkyl, halogen, —$NO_2$, —$C_0$-$C_6$alkylN$R^8R^8$, —$C_0$-$C_6$alkylN$R^8$N$R^8R^8$, —$C_0$-$C_6$alkylN=N$R^8$, —$C_0$-$C_6$alkylN$R^8C_0$-$C_6$alkylO$R^8$, —$C_0$-$C_6$alkylN$R^8C_0$-$C_6$alkylC(=O)$R^8$, —$C_0$-$C_6$alkylN$R^8$C(=O)$C_0$-$C_6$alkylC(=O)$R^8$, —$C_0$-$C_6$alkylN$R_8C_0$-$C_6$alkyl C(=O)O$R^8$, —$C_0$-$C_6$alkylN$R^8C_0$-$C_6$alkylC(=O)C(=O)O$R^8$, —$C_0$-$C_6$alkylN$R^8C_0$-$C_6$alkylC(=O)N$R^8R^8$, —$C_0$-$C_6$alkylN$R^8$C(=O)$C_0$-$C_6$alkylN$R^8$C(=O)$R^8$, —$C_0$-$C_6$alkylN$R^8$C(=O)$C_0$-$C_6$alkylN$R^8$C(=O)O$R^8$, —$C_0$-$C_6$alkylN$R^8$C(=O)$C_0$-$C_6$alkylC(=O)N$R^8R^8$, —$C_0$-$C_6$alkylN$R^8C_0$-$C_6$alkyl S(=O)$_2R^8$, —$C_0$-$C_6$alkylN$R^8$S(=O)$_2C_0$-$C_6$alkylN$R^8R^8$, —$C_0$-$C_6$alkylO$R^8$, (=O), —$C_0$-$C_6$alkylOC(=O)$C_0$-$C_6$alkyl$R^8$, —$C_0$-$C_6$alkylOC(=O)$C_0$-$C_6$alkylN$R^8R^8$, —$C_0$-$C_6$alkylOC(=O)$C_0$-$C_6$alkylO$R^8$, —$C_0$-$C_6$alkylOS(=O)$R^8$, —$C_0$-$C_6$alkylOS(=O)$_2R^8$, —$C_0$-$C_6$alkylOS(=O)$_2C_0$-$C_6$alkylO$R^8$, —$C_0$-$C_6$alkylOS(=O)$_2C_0$-$C_6$alkylN$R^8R^8$, —$C_0$-$C_6$alkylOP(=O)$R^8R^8$, —$C_0$-$C_6$alkylOP(=O)(N$R^8R^8$)(N$R^8R^8$), —$C_0$-$C_6$alkylOP(=O)(O$R^8$)(O$R^8$), —$C_0$-$C_6$alkylOP(=O)(S$R^8$)(S$R^8$), —$C_0$-$C_6$alkylP(=O)$R^8R^8$, —$C_0$-$C_6$alkylP(=O)(N$R^8R^8$)(N$R^8R^8$), —$C_0$-$C_6$alkylP(=O)($R^8$)(OR)(OR), —$C_0$-$C_6$alkylP(=O)(S$R^8$)(S$R^8$), —$C_0$-$C_6$alkyl S(=O)$_pR^8$, —$C_0$-$C_6$alkyl S(=O)$_2C_0$-$C_6$alkylN$R^8R^8$, —$C_0$-$C_6$alkyl S(=O)$C_0$-$C_6$alkylN$R^8R^8$, and —$C_0$-$C_6$alkylSCN;

Each $R^8$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, and $C_0$-$C_6$alkylheterocycloalkyl;

Each p is independently 0, 1 or 2; and

Each n is independently 0, 1, 2, 3 or 4.

Embodiment 2

A compound according to embodiment 1 wherein X is halogen, halo$C_1$-$C_6$alkyl or CN.

Embodiment 3

A compound according to embodiments 1 or 2 wherein X is halo$C_1$-$C_6$alkyl.

Embodiment 4

A compound according to embodiment 1 or 2 wherein X is halogen.

Embodiment 5

A compound according to embodiment 1 or 2 wherein X is CN.

Embodiment 6

A compound according to any of the embodiments 1-5 wherein A is a bond.

Embodiment 7

A compound according to any of the embodiments 1-6 wherein B is absent.

Embodiment 8

A compound according to any of the embodiments 1-6 wherein B is chosen from S(O)$_p$, N$R^3$, and O.

Embodiment 9

A compound according to embodiment 1 wherein A is a bond and B is chosen from S(O)$_p$, N$R^3$, and O.

Embodiment 10

A compound according to embodiment 1 wherein A is a bond and B is absent.

Embodiment 11

A compound according to any of the embodiments 1-5 wherein A is $C_1$-$C_{10}$alkyl.

Embodiment 12

A compound according to embodiment 1 wherein A is $C_1$-$C_{10}$alkyl and B is absent.

Embodiment 13

A compound according to embodiment 1 wherein A is $C_1$-$C_{10}$alkyl and B is chosen from $S(O)_p$, $NR^3$, and O.

Embodiment 14

A compound according to embodiment 1 wherein X is halogen and A is a bond.

Embodiment 15

A compound according to embodiment 1 wherein X is halogen and A is $C_1$-$C_{10}$alkyl.

Embodiment 16

A compound according to embodiment 1 wherein X is halogen, A is a bond and B is absent.

Embodiment 17

A compound according to embodiment 1 wherein X is halogen, A is a bond and B is chosen from $S(O)_p$, $NR^3$, and O.

Embodiment 18

A compound according to embodiment 1 wherein X is halogen, A is $C_1$-$C_{10}$alkyl and B is absent.

Embodiment 19

A compound according to embodiment 1 wherein X is halogen, A is $C_1$-$C_{10}$alkyl and B is chosen from $S(O)_p$, $NR^3$, and O.

Embodiment 20

A compound according to embodiment 1 wherein X is halo$C_1$-$C_6$alkyl, A is a bond and B is chosen from $S(O)_p$, $NR^3$, and O.

Embodiment 21

A compound according to embodiment 1 wherein X is halo$C_1$-$C_6$alkyl, A is $C_1$-$C_{10}$alkyl and B is absent.

Embodiment 22

A compound according to embodiment 1 wherein X is halo$C_1$-$C_6$alkyl, A is $C_1$-$C_{10}$alkyl and B is chosen from $S(O)_p$, $NR^3$, and O.

Embodiment 23

A compound according to any of the preceding embodiments wherein at least one $R^5$ is chosen from $C_1$-$C_{10}$alkyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(═O)$C_0$-$C_6$alkyl$R^6$, —$C_0$-$C_6$alkylC(═O)$C_0$-$C_6$alkylOR^6$, —$C_0$-$C_6$alkylC(═O)$C_0$-$C_6$alkylNR^6R^6$, —$C_0$-$C_6$alkylC(═O)$C_0$-$C_6$alkylNR^6C(═O)OR^6$, halo$C_1$-$C_6$alkyl, halogen, —$C_0$-$C_6$alkylNR^6R^6$, —$C_0$-$C_6$alkylNR^6C_0$-$C_6$alkyl C(═O)OR^6$, —$C_0$-$C_6$alkylOR^6$, (═O), and —$C_0$-$C_6$alkylS(═O)_pR^6$, wherein any of the foregoing is optionally substituted with one or more $R^7$.

Embodiment 24

A compound according to any of the preceding embodiments wherein C is a heterocycloalkyl chosen from piperidinyl, piperzinyl, morpholinyl, azathianyl, tetrahydropyranyl, pyrrolidinyl, diazepanyl, furanyl, azepanyl, azetidinyl, diazaspiro[3.5]nonanyl, oxa-9-azabicyclo[3.3.1]nonanyl, 2-oxa-7-azaspiro[3.5]nonanyl, dihydropyranyl, octahydro-1H-pyrrolo[1,2-a][1,4]diazepinyl, hexahydropyrrolo[1,2-a]pyrazinyl, diazabicyclo[2.2.1]heptanyl, tetrahydropyridinyl, oxazepanyl, octahydrobenzo[b][1,4]oxazinyl, diazaspiro[4.5]decanyl, 3-oxa-9-azabicyclo[3.3.1]nonanyl, hexahydro-2H-pyrrolo[3,4-b][1,4]oxazinyl, diazaspiro[4.4]nonanyl, octahydropyrrolo[2,3-c]pyridinyl, hexahydro-1H-pyrrolo[3,4-c]pyrrolyl, octahydropyrrolo[3,2-c]pyridinyl, oxa-8-azabicyclo[3.2.1]octanyl, octahydropyrrolo[3,2-b]pyridinyl, octahydropyrrolo[3,2-c]pyridinyl, oxa-4,9-diazaspiro[5.5]undecanyl, azabicyclo[3.1.0]hexanyl, oxa-7-azaspiro[3.4]octanyl, diazaspiro[3.3]heptanyl, diazaspiro[4.5]decanyl, triazaspiro[4.5]decanyl, 1,4-dioxa-8-azaspiro[4.5]decanyl, octahydropyrrolo[3,4-c]pyridinyl, octahydropyrrolo[3,4-b]pyridinyl, hexahydro-2H-pyrrolo[3,4-b][1,4]oxazinyl, oxa-8-azaspiro[4.5]decanyl, hexahydro-1H-pyrrolo[3,2-b]pyrrolyl, diazaspiro[3.4]octanyl, hexahydro-2H-pyrrolo[3,2-c]pyridinyl, hexahydro-2H-pyrrolo[2,3-c]pyrrolyl, diazabicyclo[3.2.1]octanyl, octahydro-2H-naphthyridinyl, and dihydro-5H-[1,2,4]triazolo[4,3-a]pyrazinyl.

Embodiment 25

A compound of Formula Ia:

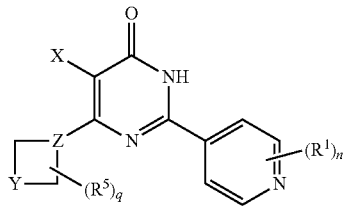

Formula Ia and/or a salt thereof, wherein:

X is chosen from halogen, halo$C_1$-$C_6$alkyl, $NO_2$, —C(═O)NR^8R^6$, —NHS(O)_2R^6$, and CN;

Each $R^1$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(═O)$C_0$-$C_6$alkylR^3$, —$C_0$-$C_6$alkylC(═O)$C_0$-$C_6$alkylNR^3C(═O)OR^4$, —$C_0$-$C_6$alkylC(═O)$C_0$-$C_6$alkylOR^3$, —$C_0$-$C_6$alkylC(═O)$C_0$-$C_6$alkylNR^3R^4$, —$C_0$-$C_6$alkylC(═O)$C_0$-$C_6$alkylC(═O)R^3$, halo$C_1$-$C_6$alkyl, halogen, —$NO_2$, —$C_0$-$C_6$alkylNR^3R^4$, —$C_0$-$C_6$alkylNR^3NR^3R^4$, —$C_0$-$C_6$alkylN═NR^3$, —$C_0$-$C_6$alkylNR^3C_0$-$C_6$alkylOR^4$, —$C_0$-$C_6$alkylNR^3C_0$-$C_6$alkylC(═O)R^4$, —$C_0$-$C_6$alkylNR^3C(═O)C_0$-$C_6$alkylC(═O)R^4$, —$C_0$-$C_6$alkylNR^3C_0$-$C_6$alkyl C(═O)OR^4$, —$C_0$-$C_6$alkylNR^3C_0$-$C_6$alkylC(═O)(═O)OR^4$, —$C_0$-$C_6$alkylNR^3C_0$-$C_6$alkylC(═O)NR^3R^4$, —$C_0$-$C_6$alkylNR^3C(═O)C_0$-$C_6$alkylNR^3C(═O)R^4$, —$C_0$-$C_6$alkylNR^3C(═O)C_0$-$C_6$alkylNR^3C(═O)OR^4$, —$C_0$-$C_6$alkylNR^3C(═O)C_0$-$C_6$alkylC(═O)NR^3R^4$, —$C_0$-$C_6$alkylNR^3C_0$-$C_6$alkylS(═O)_2R^4$, —$C_0$-$C_6$alkylNR^3S(═O)_2C_0$-$C_6$alkylNR^3R^4$, —$C_0$-

$C_6$alkylOR$^3$, (=O), —$C_0$-$C_6$alkylOC(=O)$C_0$-$C_6$alkylR$^4$, —$C_0$-$C_6$alkylOC(=O)$C_0$-$C_6$alkylNR$^3$R$^4$, —$C_0$-$C_6$alkylOC(=O)$C_0$-$C_6$alkylOR$^4$, —$C_0$-$C_6$alkylOS(=O)R$^4$, —$C_0$-$C_6$alkylOS(=O)$_2$R$^4$, —$C_0$-$C_6$alkylOS(=O)$_2$$C_0$-$C_6$alkylOR$^4$, —$C_0$-$C_6$alkylOS(=O)$_2$$C_0$-$C_6$alkylNR$^3$R$^4$, —$C_0$-$C_6$alkylOP(=O)R$^3$R$^4$, —$C_0$-$C_6$alkylOP(=O)(NR$^3$R$^4$)(NR$^3$R$^4$), —$C_0$-$C_6$alkylOP(=O)(OR$^3$)(OR$^4$), —$C_0$-$C_6$alkylOP(=O)(SR$^3$)(SR$^4$), —$C_0$-$C_6$alkylP(=O)R$^3$R$^4$, —$C_0$-$C_6$alkylP(=O)(NR$^3$R$^4$)(NR$^3$R$^4$), —$C_0$-$C_6$alkylP(=O)(R$^3$)(OR$^3$)(OR$^4$), —$C_0$-$C_6$alkylP(=O)(SR$^3$)(SR$^4$), —$C_0$-$C_6$alkyl S(=O)$_p$R$^4$, —$C_0$-$C_6$alkylS(=O)$_2$$C_0$-$C_6$alkylNR$^3$R$^4$, —$C_0$-$C_6$alkylS(=O)$C_0$-$C_6$alkylNR$^3$R$^4$, and —$C_0$-$C_6$alkylSCN, wherein any of the foregoing except for halogen and NO$_2$ is optionally substituted with one or more R$^5$; or Any two R$^1$ on adjacent atoms may be taken together to form a 4 to 12 membered carbocyclic or heterocyclic ring system, wherein said ring system is optionally substituted with one or more R$^5$;

Z is CR$^9$ or N;

Y is chosen from —(CH$_2$)$_m$—, —(CH$_2$)$_m$O(CH$_2$)$_m$—, —(CH$_2$)$_m$NR$^{10}$(CH$_2$)$_m$—, and —(CH$_2$)$_m$S(CH$_2$)$_m$;

R$^3$ and R$^4$ are each independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing, except for H, is optionally substituted with one or more R$^5$; or R$^3$ and R$^4$ may be taken together to form a 3 to 15 membered carbocyclic or heterocyclic ring system, wherein said ring system is optionally substituted with one or more R$^5$; Each R$^5$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^6$, —$C_0$-$C_6$alkylC(=O)$C_0$-$C_6$alkylOR$^6$, —$C_0$-$C_6$alkylC(=O)$C_0$-$C_6$alkylNR$^6$R$^6$, —$C_0$-$C_6$alkylC(=O)$C_0$-$C_6$alkylNR$^6$C(=O)OR$^6$, —$C_0$-$C_6$alkylC(=O)$C_0$-$C_6$alkylC(=O)R$^6$, halo$C_1$-$C_6$alkyl, halogen, —NO$_2$, —$C_0$-$C_6$alkylNR$^6$R$^6$, —$C_0$-$C_6$alkylNR$^6$NR$^6$R$^6$, —$C_0$-$C_6$alkylN=NR$^6$, —$C_0$-$C_6$alkylNR$^6$$C_0$-$C_6$alkylOR$^6$, —$C_0$-$C_6$alkylNR$^6$$C_0$-$C_6$alkylC(=O)R$^6$, —$C_0$-$C_6$alkylNR$^6$C(=O)$C_0$-$C_6$alkylR$^6$)R$^6$, —$C_0$-$C_6$alkylNR$^6$$C_0$-$C_6$alkyl C(=O)OR$^6$, —$C_0$-$C_6$alkylNR$^6$$C_0$-$C_6$alkylC(=O)C(=O)OR$^6$, —$C_0$-$C_6$alkylNR$^6$$C_0$-$C_6$alkylC(=O)NR$^6$R$^6$, —$C_0$-$C_6$alkylNR$^6$C(=O)$C_0$-$C_6$alkylNR$^6$C(=O)R$^6$, —$C_0$-$C_6$alkylNR$^6$C(=O)$C_0$-$C_6$alkylNR$^6$C(=O)OR$^6$, —$C_0$-$C_6$alkylNR$^6$C(=O)$C_0$-$C_6$alkylC(=O)NR$^6$R$^6$, —$C_0$-$C_6$alkylNR$^6$$C_0$-$C_6$alkyl S(=O)$_2$R$^6$, —$C_0$-$C_6$alkylNR$^6$S(=O)$_2$$C_0$-$C_6$alkylNR$^6$R$^6$, —$C_0$-$C_6$alkylOR$^6$, (=O), —$C_0$-$C_6$alkylOC(=O)$C_0$-$C_6$alkylR$^6$, —$C_0$-$C_6$alkylOC(=O)$C_0$-$C_6$alkylNR$^6$R$^6$, —$C_0$-$C_6$alkylOC(=O)$C_0$-$C_6$alkylOR$^6$, —$C_0$-$C_6$alkylOS(=O)R$^6$, —$C_0$-$C_6$alkylOS(=O)$_2$R$^6$, —$C_0$-$C_6$alkylOS(=O)$_2$$C_0$-$C_6$alkylOR$^6$, —$C_0$-$C_6$alkylOS(=O)$_2$$C_0$-$C_6$alkylNR$^6$R$^6$, —$C_0$-$C_6$alkylOP(=O)R$^6$R$^6$, —$C_0$-$C_6$alkylOP(=O)(NR$^6$R$^6$)(NR$^6$R$^6$), —$C_0$-$C_6$alkylOP(=O)(OR$^6$)(OR$^6$), —$C_0$-$C_6$alkylOP(=O)(SR$^6$)(SR$^6$), —$C_0$-$C_6$alkylP(=O)R$^6$R$^6$, —$C_0$-$C_6$alkylP(=O)(NR$^6$R$^6$)(NR$^6$R$^6$), —$C_0$-$C_6$alkylP(=O)(R$^6$)(OR$^6$), —$C_0$-$C_6$alkylP(=O)(SR$^6$)(SR$^6$), —$C_0$-$C_6$alkylS(=O)$_p$R$^6$, —$C_0$-$C_6$alkyl S(=O)$_2$$C_0$-$C_6$alkylNR$^6$R$^6$, —$C_0$-$C_6$alkyl S(=O)$C_0$-$C_6$alkylNR$^6$R$^6$, and —$C_0$-$C_6$alkylSCN, wherein any of the foregoing, except for halogen and NO$_2$, is optionally substituted with one or more R$^7$; or Any two R$^5$ or an R$^5$ and R$^{10}$ may be taken together to form a 4 to 12 membered carbocyclic or heterocyclic ring system, wherein said ring system is optionally substituted with one or more R$^7$;

Each R$^6$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing except for H is optionally substituted with one or more R$^7$; or Two R$^6$ may be taken together to form a 3 to 15 membered carbocyclic or heterocyclic ring system, wherein said ring system is optionally substituted with one or more R; Each R$^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^8$, —$C_0$-$C_6$alkylC(=O)$C_0$-$C_6$alkylOR$^8$, —$C_0$-$C_6$alkylC(=O)$C_0$-$C_6$alkylNR$^8$R$^8$, —$C_0$-$C_6$alkylC(=O)$C_0$-$C_6$alkylNR$^8$C(=O)OR$^8$, —$C_0$-$C_6$alkylC(=O)$C_0$-$C_6$alkylC(=O)R$^8$, halo$C_1$-$C_6$alkyl, halogen, —NO$_2$, —$C_0$-$C_6$alkylNR$^8$R$^8$, —$C_0$-$C_6$alkylNR$^8$NR$^8$R$^8$, —$C_0$-$C_6$alkylN=NR$^8$, —$C_0$-$C_6$alkylNR$^8$$C_0$-$C_6$alkylOR$^8$, —$C_0$-$C_6$alkylNR$^8$$C_0$-$C_6$alkylC(=O)R$^8$, —$C_0$-$C_6$alkylC(=O)R$^8$, —$C_0$-$C_6$alkylNR$^8$C(=O)$C_0$-$C_6$alkylC(=O)R$^8$, —$C_0$-$C_6$alkylNR$^8$$C_0$-$C_6$alkyl C(=O)OR$^8$, —$C_0$-$C_6$alkylNR$^8$$C_0$-$C_6$alkylC(=O)C(=O)OR$^8$, —$C_0$-$C_6$alkylNR$^8$$C_0$-$C_6$alkylC(=O)NR$^8$R$^8$, —$C_0$-$C_6$alkylNR$^8$C(=O)$C_0$-$C_6$alkylNR$^8$C(=O)R$^8$, —$C_0$-$C_6$alkylNR$^8$C(=O)$C_0$-$C_6$alkylNR$^8$C(=O)OR$^8$, —$C_0$-$C_6$alkylNR$^8$C(=O)$C_0$-$C_6$alkylC(=O)NR$^8$R$^8$, —$C_0$-$C_6$alkylNR$^8$$C_0$-$C_6$alkyl S(=O)$_2$R$^8$, —$C_0$-$C_6$alkylNR$^8$S(=O)$_2$$C_0$-$C_6$alkylNR$^8$R$^8$, —$C_0$-$C_6$alkylOR$^8$, (=O), —$C_0$-$C_6$alkylOC(=O)$C_0$-$C_6$alkylR$^8$, —$C_0$-$C_6$alkylOC(=O)$C_0$-$C_6$alkylNR$^8$R$^8$, —$C_0$-$C_6$alkylOC(=O)$C_0$-$C_6$alkylOR$^8$, —$C_0$-$C_6$alkylOS(=O)R$^8$, —$C_0$-$C_6$alkylOS(=O)$_2$R$^8$, —$C_0$-$C_6$alkylOS(=O)$_2$$C_0$-$C_6$alkylOR$^8$, —$C_0$-$C_6$alkylOS(=O)$_2$$C_0$-$C_6$alkylNR$^8$R$^8$, —$C_0$-$C_6$alkylOP(=O)R$^8$R$^8$, —$C_0$-$C_6$alkylOP(=O)(NR$^8$R$^8$)(NR$^8$R$^8$), —$C_0$-$C_6$alkylOP(=O)(OR$^8$)(OR$^8$), —$C_0$-$C_6$alkylOP(=O)(SR$^8$)(SR$^8$), —$C_0$-$C_6$alkylP(=O)R$^8$R$^8$, —$C_0$-$C_6$alkylP(=O)(NR$^8$R$^8$)(NR$^8$R$^8$), —$C_0$-$C_6$alkylP(=O)(R$^8$)(OR)(OR), —$C_0$-$C_6$alkylP(=O)(SR$^8$)(SR$^8$), —$C_0$-$C_6$alkyl S(=O)$_p$R$^8$, —$C_0$-$C_6$alkyl S(=O)$_2$$C_0$-$C_6$alkylNR$^8$R$^8$, —$C_0$-$C_6$alkyl S(=O)$C_0$-$C_6$alkylNR$^8$R$^8$, and —$C_0$-$C_6$alkylSCN;

Each R$^8$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, and $C_0$-$C_6$alkylheterocycloalkyl;

R$^9$ is chosen from H, $C_1$-$C_6$alkyl, and halogen;

R$^{10}$ is H, $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^8$, —$C_0$-$C_6$alkylC(=O)$C_0$-$C_6$alkylOR$^8$, —$C_0$-$C_6$alkylC(=O)$C_0$-$C_6$alkylNR$^8$R$^8$, —$C_0$-$C_6$alkylC(=O)$C_0$-$C_6$alkylNR$^8$C(=O)OR$^8$, —$C_0$-$C_6$alkylC(=O)$C_0$-$C_6$alkylC(=O)R$^8$, halo$C_1$-$C_6$alkyl, —$C_0$-$C_6$alkylNR$^8$R$^8$, —$C_0$-$C_6$alkylNR$^8$NR$^8$R$^8$, —$C_0$-$C_6$alkylN=NR$^8$, —$C_0$-$C_6$alkylNR$^8$$C_0$-$C_6$alkylOR$^8$, —$C_0$-$C_6$alkylNR$^8$$C_0$-$C_6$alkylC(=O)R$^8$, —$C_0$-$C_6$alkylNR$^8$C(=O)$C_0$-$C_6$alkylC(=O)R$^8$, —$C_0$-$C_6$alkylNR$^8$$C_0$-$C_6$alkyl C(=O)OR$^8$, —$C_0$-

$C_6$alkylNR$^8C_0$-$C_6$alkylC(=O)C(=O)OR$^8$, —$C_0$-$C_6$alkylNR$^8C_0$-$C_6$alkylC(=O)NR$^8R^8$, —$C_0$-$C_6$alkylNR$^8$C(=O)$C_0$-$C_6$alkylNR$^8$C(=O)R$^8$, —$C_0$-$C_6$alkylNR$^8$C(=O)$C_0$-$C_6$alkylNR$^8$C(=O)OR$^8$, —$C_0$-$C_6$alkylNR$^8$C(=O)$C_0$-$C_6$alkylC(=O)NR$^8R^8$, —$C_0$-$C_6$alkylNR$^8C_0$-$C_6$alkyl S(=O)$_2$R$^8$, —$C_0$-$C_6$alkylNR$^8$S(=O)$_2C_0$-$C_6$alkylNR$^8R^8$, —$C_0$-$C_6$alkylOR$^8$, (=O), —$C_0$-$C_6$alkylOC(=O)$C_0$-$C_6$alkylR$^8$, —$C_0$-$C_6$alkylOC(=O)$C_0$-$C_6$alkylNR$^8R^8$, —$C_0$-$C_6$alkylOC(=O)$C_0$-$C_6$alkylOR$^8$, —$C_0$-$C_6$alkylOS(=O)R$^8$, —$C_0$-$C_6$alkylOS(=O)$_2$R$^8$, —$C_0$-$C_6$alkylOS(=O)$_2C_0$-$C_6$alkylOR$^8$, —$C_0$-$C_6$alkylOS(=O)$_2C_0$-$C_6$alkylNR$^8R^8$, —$C_0$-$C_6$alkylOP(=O)R$^8R^8$, —$C_0$-$C_6$alkylOP(=O)(NR$^8R^8$)(NR$^8$), —$C_0$-$C_6$alkylOP(=O)(OR$^8$)(OR$^8$), —$C_0$-$C_6$alkylOP(=O)(SR$^8$)(SR$^8$), —$C_0$-$C_6$alkylP(=O)R$^8R^8$, —$C_0$-$C_6$alkylP(=O)(NR$^8R^8$)(NR$^8R^8$), —$C_0$-$C_6$alkylP(=O)(R$^8$)(OR)(OR$^8$), —$C_0$-$C_6$alkylP(=O)(SR$^8$)(SR$^8$), —$C_0$-$C_6$alkyl S(=O)$_p$R$^8$, —$C_0$-$C_6$alkyl S(=O)$_2C_0$-$C_6$alkylNR$^8R^8$, —$C_0$-$C_6$alkyl S(=O)$C_0$-$C_6$alkylNR$^8R^8$, and —$C_0$-$C_6$alkylSCN; wherein any of the foregoing, except for H, is optionally substituted with one or more R$^7$;
Each p is independently 0, 1 or 2;
Each n is independently 0, 1, 2, 3 or 4;
Each q is independently an integer between 0 and 8, inclusive; and
Each m is independently an integer between 1 and 5, inclusive.

Embodiment 26

A compound according to Embodiment 25 wherein X is halogen, halo$C_1$-$C_6$alkyl or CN.

Embodiment 27

A compound according to Embodiment 25 or 26 wherein X is halo$C_1$-$C_6$alkyl

Embodiment 28

A compound according to Embodiment 25 or 26 wherein X is halogen.

Embodiment 29

A compound according to Embodiment 25 or 26 wherein X is CN.

Embodiment 30

A compound according to any of Embodiments 25-29 wherein at least one R$^5$ is chosen from $C_1$-$C_{10}$alkyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^6$, —$C_0$-$C_6$alkylC(=O)$C_0$-$C_6$alkylOR$^6$, —$C_0$-$C_6$alkylC(=O)$C_0$-$C_6$alkylNR$^6R^6$, —$C_0$-$C_6$alkylC(=O)$C_0$-$C_6$alkylNR$^6$C(=O)OR$^6$, halo$C_1$-$C_6$alkyl, halogen, —$C_0$-$C_6$alkylNR$^6R^6$, —$C_0$-$C_6$alkylNR$^6C_0$-$C_6$alkyl C(=O)OR$^6$, —$C_0$-$C_6$alkylOR$^6$, (=O) and —$C_0$-$C_6$alkylS(=O)$_p$R$^6$.

Embodiment 31

A compound according to any of Embodiments 25-30 wherein n is 0, 1 or 2.

Embodiment 32

A compound according to any of the embodiments 25-31 wherein R$^1$ is chosen from $C_1$-$C_{10}$alkyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^3$, —$C_0$-$C_6$alkylC(=O)$C_0$-$C_6$alkylNR$^3$C(=O)OR$^4$, —$C_0$-$C_6$alkylC(=O)$C_0$-$C_6$alkylOR$^3$, —$C_0$-$C_6$alkylC(=O)$C_0$-$C_6$alkylNR$^3R^4$, halo$C_1$-$C_6$alkyl, halogen, —NO$_2$, —$C_0$-$C_6$alkylNR$^3R^4$, —$C_0$-$C_6$alkylNR$^3C_0$-$C_6$alkylOR$^4$, —$C_0$-$C_6$alkylNR$^3C_0$-$C_6$alkylC(=O)R$^4$, —$C_0$-$C_6$alkylNR$^3$C(=O)$C_0$-$C_6$alkylC(=O)R$^4$, —$C_0$-$C_6$alkylNR$^3C_0$-$C_6$alkyl C(=O)OR$^4$, —$C_0$-$C_6$alkylNR$^3C_0$-$C_6$alkylC(=O)NR$^3R^4$, —$C_0$-$C_6$alkylNR$^3$C(=O)$C_0$-$C_6$alkylNR$^3$C(=O)R$^4$, —$C_0$-$C_6$alkylNR$^3$C(=O)$C_0$-$C_6$alkylNR$^3$C(=O)OR$^4$, —$C_0$-$C_6$alkylNR$^3$C(=O)$C_0$-$C_6$alkylC(=O)NR$^3R^4$, —$C_0$-$C_6$alkylOR$^3$, (=O), —$C_0$-$C_6$alkylOC(=O)$C_0$-$C_6$alkylR$^4$, —$C_0$-$C_6$alkylOC(=O)$C_0$-$C_6$alkylNR$^3R^4$, —$C_0$-$C_6$alkylOC(=O)$C_0$-$C_6$alkylOR$^4$, —$C_0$-$C_6$alkylOS(=O)R$^4$, —$C_0$-$C_6$alkylOS(=O)$_2$R$^4$, —$C_0$-$C_6$alkylOS(=O)$_2C_0$-$C_6$alkylOR$^4$, —$C_0$-$C_6$alkylOS(=O)$_2C_0$-$C_6$alkylNR$^3R^4$, —$C_0$-$C_6$alkylOP(=O)R$^3R^4$, —$C_0$-$C_6$alkylOP(=O)(OR$^3$)(OR$^4$), —$C_0$-$C_6$alkylP(=O)R$^3R^4$, —$C_0$-$C_6$alkylP(=O)(OR$^3$)(OR$^4$), —$C_0$-$C_6$alkylS(=O)$_p$R$^4$, —$C_0$-$C_6$alkyl S(=O)$_2C_0$-$C_6$alkylNR$^3R^4$, —$C_0$-$C_6$alkylS(=O)$C_0$-$C_6$alkylNR$^3R^4$, and —$C_0$-$C_6$alkylSCN, wherein any of the foregoing is optionally substituted with one or more R$^5$.

Embodiment 33

A compound according to any of the embodiments 25-32 wherein R$^1$ is chosen from halo$C_1$-$C_6$alkyl, halogen, —$C_0$-$C_6$alkylOR$^3$, and (=O).

Embodiment 34

A compound that is of Formula Ib:

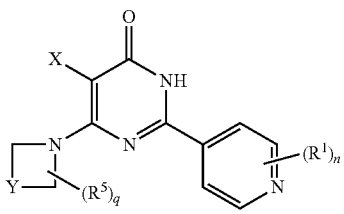

Formula Ib and/or a salt thereof, wherein:
X is chosen from halogen, halo$C_1$-$C_6$alkyl, NO$_2$, —C(=O)NR$^5R^6$, —NHS(O)$_2$R$^6$, and CN;
Each R$^1$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^3$, —$C_0$-$C_6$alkylC(=O)$C_0$-$C_6$alkylNR$^3$C(=O)OR$^4$, —$C_0$-$C_6$alkylC(=O)$C_0$-$C_6$alkylOR$^3$, —$C_0$-$C_6$alkylC(=O)$C_0$-$C_6$alkylNR$^3R^4$, —$C_0$-$C_6$alkylC(=O)$C_0$-$C_6$alkylC(=O)R$^3$, halo$C_1$-$C_6$alkyl, halogen, —NO$_2$, —$C_0$-$C_6$alkylNR$^3R^4$, —$C_0$-$C_6$alkylNR$^3$NR$^3R^4$, —$C_0$-$C_6$alkylN=NR$^3$, —$C_0$-$C_6$alkylNR$^3C_0$-$C_6$alkylOR$^4$, —$C_0$-$C_6$alkylNR$^3C_0$-$C_6$alkylC(=O)R$^4$, —$C_0$-$C_6$alkylNR$^3$C(=O)$C_0$-$C_6$alkylC(=O)R$^4$, —$C_0$-$C_6$alkylNR$^3C_0$-$C_6$alkyl C(=O)OR$^4$, —$C_0$-$C_6$alkylNR$^3C_0$-$C_6$alkylC(=O)C (=O)OR$^4$, —C$_0$-C$_6$alkylNR$^3$C$_0$-C$_6$alkylC(=O)NR$^3$R$^4$, —C$_0$-C$_6$alkylNR$^3$C(=O)C$_0$-C$_6$alkylNR$^3$C(=O)R$^4$, —C$_0$-C$_6$alkylNR$^3$C(=O)C$_0$-C$_6$alkylNR$^3$C(=O)OR$^4$, —C$_0$-C$_6$alkylNR$^3$C(=O)C$_0$-C$_6$alkylC(=O)NR$^3$R$^4$, —C$_0$-C$_6$alkylNR$^3$C$_0$-C$_6$alkylS(=O)$_2$R$^4$, —C$_0$-C$_6$alkylNR$^3$S(=O)$_2$C$_0$-C$_6$alkylNR$^3$R$^4$, —C$_0$-C$_6$alkylOR$^3$, (=O), —C$_0$-C$_6$alkylOC(=O)C$_0$-C$_6$alkylR$^4$, —C$_0$-C$_6$alkylOC(=O)C$_0$-C$_6$alkylNR$^3$R$^4$, —C$_0$-C$_6$alkylOC(=O)C$_0$-C$_6$alkylOR$^4$, —C$_0$-C$_6$alkylOS(=O)R$^4$, —C$_0$-C$_6$alkylOS(=O)$_2$R$^4$, —C$_0$-C$_6$alkylOS(=O)$_2$C$_0$-C$_6$alkylOR$^4$, —C$_0$-C$_6$alkylOS(=O)$_2$C$_0$-C$_6$alkylNR$^3$R$^4$, —C$_0$-C$_6$alkylOP(=O)R$^3$R$^4$, —C$_0$-C$_6$alkylOP(=O)(NR$^3$R$^4$)(NR$^3$R$^4$), —C$_0$-C$_6$alkylOP(=O)(OR$^3$)(OR$^4$), —C$_0$-C$_6$alkylOP(=O)(SR$^3$)(SR$^4$), —C$_0$-C$_6$alkylP(=O)R$^3$R$^4$, —C$_0$-C$_6$alkylP(=O)(NR$^3$R$^4$)(NR$^3$R$^4$), —C$_0$-C$_6$alkylP(=O)(R$^3$)(OR$^3$)(OR$^4$), —C$_0$-C$_6$alkylP(=O)(SR$^3$)(SR$^4$), —C$_0$-C$_6$alkyl S(=O)$_p$R$^4$, —C$_0$-C$_6$alkylS(=O)$_2$C$_0$-C$_6$alkylNR$^3$R$^4$, —C$_0$-C$_6$alkylS(=O)C$_0$-C$_6$alkylNR$^3$R$^4$, and —C$_0$-C$_6$alkylSCN, wherein any of the foregoing is optionally substituted with one or more R$^5$; or Any two R$^1$ on adjacent atoms may be taken together to form a 4 to 12 membered carbocyclic or heterocyclic ring system, wherein said ring system is optionally substituted with one or more R$^5$;

Y is chosen from —(CH$_2$)$_m$—, —(CH$_2$)$_m$O(CH$_2$)$_m$—, —(CH$_2$)$_m$NR$^{10}$(CH$_2$)$_m$—, and —(CH$_2$)$_m$S(CH$_2$)$_m$;

R$^3$ and R$^4$ are each independently chosen from H, C$_1$-C$_{10}$alkyl, C$_2$-C$_{10}$alkenyl, C$_2$-C$_{10}$alkynyl, haloC$_1$-C$_6$alkyl, C$_0$-C$_6$alkylaryl, C$_0$-C$_6$alkylcycloalkyl, C$_0$-C$_6$alkylheteroaryl, C$_0$-C$_6$alkylheterocycloalkyl, wherein any of the foregoing, except for H, is optionally substituted with one or more R$^5$; or R$^3$ and R$^4$ may be taken together to form a 3 to 15 membered carbocyclic or heterocyclic ring system, wherein said ring system is optionally substituted with one or more R$^5$;

Each R$^5$ is independently chosen from C$_1$-C$_{10}$alkyl, C$_2$-C$_{10}$alkenyl, C$_2$-C$_{10}$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, —C$_0$-C$_6$alkylCN, —C$_0$-C$_6$alkylC(=O)C$_0$-C$_6$alkylR$^6$, —C$_0$-C$_6$alkylC(=O)C$_0$-C$_6$alkylOR$^6$, —C$_0$-C$_6$alkylC(=O)C$_0$-C$_6$alkylNR$^6$R$^6$, —C$_0$-C$_6$alkylC(=O)C$_0$-C$_6$alkylNR$^6$C(=O)OR$^6$, —C$_0$-C$_6$alkylC(=O)C$_0$-C$_6$alkylC(=O)R$^6$, haloC$_1$-C$_6$alkyl, halogen, —NO$_2$, —C$_0$-C$_6$alkylNR$^6$R$^6$, —C$_0$-C$_6$alkylNR$^6$NR$^6$R$^6$, —C$_0$-C$_6$alkylN=NR$^6$, —C$_0$-C$_6$alkylNR$^6$C$_0$-C$_6$alkylOR$^6$, —C$_0$-C$_6$alkylNR$^6$C$_0$-C$_6$alkylC(=O)R$^6$, —C$_0$-C$_6$alkylNR$^6$C(=O)C$_0$-C$_6$alkylC(=O)R$^6$, —C$_0$-C$_6$alkylNR$^6$C$_0$-C$_6$alkylC(=O)OR$^6$, —C$_0$-C$_6$alkylNR$^6$C$_0$-C$_6$alkylC(=O)OR$^6$, —C$_0$-C$_6$alkylNR$^6$C$_0$-C$_6$alkylC(=O)NR$^6$R$^6$, —C$_0$-C$_6$alkylNR$^6$C(=O)C$_0$-C$_6$alkylNR$^6$C(=O)R$^6$, —C$_0$-C$_6$alkylNR$^6$C(=O)C$_0$-C$_6$alkylNR$^6$C(=O)OR$^6$, —C$_0$-C$_6$alkylNR$^6$C(=O)C$_0$-C$_6$alkylC(=O)NR$^6$R$^6$, —C$_0$-C$_6$alkylNR$^6$C$_0$-C$_6$alkyl S(=O)$_2$R$^6$, —C$_0$-C$_6$alkylNR$^6$S(=O)$_2$C$_0$-C$_6$alkylNR$^6$R$^6$, —C$_0$-C$_6$alkylOR$^6$, (=O), —C$_0$-C$_6$alkylOC(=O)C$_0$-C$_6$alkylR$^6$, —C$_0$-C$_6$alkylOC(=O)C$_0$-C$_6$alkylNR$^6$R$^6$, —C$_0$-C$_6$alkylOC(=O)C$_0$-C$_6$alkylOR$^6$, —C$_0$-C$_6$alkylOS(=O)R$^6$, —C$_0$-C$_6$alkylOS(=O)$_2$R$^6$, —C$_0$-C$_6$alkylOS(=O)$_2$C$_0$-C$_6$alkylOR$^6$, —C$_0$-C$_6$alkylOS(=O)$_2$C$_0$-C$_6$alkylNR$^6$R$^6$, —C$_0$-C$_6$alkylOP(=O)R$^6$R$^6$, —C$_0$-C$_6$alkylOP(=O)(NR$^6$R$^6$)(NR$^6$R$^6$), —C$_0$-C$_6$alkylOP(=O)(OR$^6$)(OR$^6$), —C$_0$-C$_6$alkylOP(=O)(SR$^6$)(SR$^6$), —C$_0$-C$_6$alkylP(=O)R$^6$R$^6$, —C$_0$-C$_6$alkylP(=O)(NR$^6$R$^6$)(NR$^6$R$^6$), —C$_0$-C$_6$alkylP(=O)(R$^6$)(OR$^6$), —C$_0$-C$_6$alkylP(=O)(S$^6$)(S$^6$), —C$_0$-C$_6$alkylS(=O)$_p$R$^6$, —C$_0$-C$_6$alkyl S(=O)$_2$C$_0$-C$_6$alkylNR$^6$R$^6$, —C$_0$-C$_6$alkyl S(=O)C$_0$-C$_6$alkylNR$^6$R$^6$, and —C$_0$-C$_6$alkylSCN, wherein any of the foregoing is optionally substituted with one or more R$^7$; or Any two R$^5$ or an R$^5$ and R$^{10}$ may be taken together to form a 4 to 12 membered carbocyclic or heterocyclic ring system, wherein said ring system is optionally substituted with one or more R$^7$;

Each R$^6$ is independently chosen from H, C$_1$-C$_{10}$alkyl, C$_2$-C$_{10}$alkenyl, C$_2$-C$_{10}$alkynyl, haloC$_1$-C$_6$alkyl, C$_0$-C$_6$alkylaryl, C$_0$-C$_6$alkylcycloalkyl, C$_0$-C$_6$alkylheteroaryl, C$_0$-C$_6$alkylheterocycloalkyl, wherein any of the foregoing except for H is optionally substituted with one or more R; or Two R$^6$ may be taken together to form a 3 to 15 membered carbocyclic or heterocyclic ring system, wherein said ring system is optionally substituted with one or more R$^7$;

Each R$^7$ is independently chosen from C$_1$-C$_{10}$alkyl, C$_2$-C$_{10}$alkenyl, C$_2$-C$_{10}$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, —C$_0$-C$_6$alkylCN, —C$_0$-C$_6$alkylC(=O)C$_0$-C$_6$alkylR$^8$, —C$_0$-C$_6$alkylC(=O)C$_0$-C$_6$alkylOR$^8$, —C$_0$-C$_6$alkylC(=O)C$_0$-C$_6$alkylNR$^8$R$^8$, —C$_0$-C$_6$alkylC(=O)C$_0$-C$_6$alkylNR$^8$C(=O)OR$^8$, —C$_0$-C$_6$alkylC(=O)C$_0$-C$_6$alkylC(=O)R$^8$, haloC$_1$-C$_6$alkyl, halogen, —NO$_2$, —C$_0$-C$_6$alkylNR$^8$R$^8$, —C$_0$-C$_6$alkylNR$^8$NR$^8$R$^8$, —C$_0$-C$_6$alkylN=NR$^8$, —C$_0$-C$_6$alkylNR$_8$C$_0$-C$_6$alkylOR$^8$, —C$_0$-C$_6$alkylNR$^8$C$_0$-C$_6$alkylC(=O)R$^8$, —C$_0$-C$_6$alkylNR$^8$C(=O)C$_0$-C$_6$alkylC(=O)R$^8$, —C$_0$-C$_6$alkylNR$^8$C$_0$-C$_6$alkylC(=O)OR$^8$, —C$_0$-C$_6$alkylNR$^8$C$_0$-C$_6$alkylC(=O)C(=O)OR$^8$, —C$_0$-C$_6$alkylNR$^8$C$_0$-C$_6$alkylC(=O)NR$^8$R$^8$, —C$_0$-C$_6$alkylNR$^8$C(=O)C$_0$-C$_6$alkylNR$^8$C(=O)R$^8$, —C$_0$-C$_6$alkylNR$^8$C(=O)C$_0$-C$_6$alkylNR$^8$C(=O)OR$^8$, —C$_0$-C$_6$alkylNR$^8$C(=O)C$_0$-C$_6$alkylC(=O)NR$^8$R$^8$, —C$_0$-C$_6$alkylNR$^8$C$_0$-C$_6$alkylS(=O)$_2$R$^8$, —C$_0$-C$_6$alkylNR$^8$S(=O)$_2$C$_0$-C$_6$alkylNR$^8$R$^8$, —C$_0$-C$_6$alkylOR$^8$, (=O), —C$_0$-C$_6$alkylOC(=O)C$_0$-C$_6$alkylR$^8$, —C$_0$-C$_6$alkylOC(=O)C$_0$-C$_6$alkylNR$^8$R$^8$, —C$_0$-C$_6$alkylOC(=O)C$_0$-C$_6$alkylOR$^8$, —C$_0$-C$_6$alkylOS(=O)R$^8$, —C$_0$-C$_6$alkylOS(=O)$_2$R$^8$, —C$_0$-C$_6$alkylOS(=O)$_2$C$_0$-C$_6$alkylOR$^8$, —C$_0$-C$_6$alkylOS(=O)$_2$C$_0$-C$_6$alkylNR$^8$R$^8$, —C$_0$-C$_6$alkylOP(=O)R$^8$R$^8$, —C$_0$-C$_6$alkylOP(=O)(NR$^8$R$^8$)(NR$^8$R$^8$), —C$_0$-C$_6$alkylOP(=O)(OR$^8$)(OR$^8$), —C$_0$-C$_6$alkylOP(=O)(SR$^8$)(SR$^8$), —C$_0$-C$_6$alkylP(=O)R$^8$R$^8$, —C$_0$-C$_6$alkylP(=O)(NR$^8$R$^8$)(NR$^8$R$^8$), —C$_0$-C$_6$alkylP(=O)(OR$^8$)(OR$^8$), —C$_0$-C$_6$alkylP(=O)(SR$^8$)(SR$^8$), —C$_0$-C$_6$alkylS(=O)$_p$R$^8$, —C$_0$-C$_6$alkylS(=O)$_2$C$_0$-C$_6$alkylNR$^8$R$^8$, —C$_0$-C$_6$alkylS(=O)C$_0$-C$_6$alkylNR$^8$R$^8$, and —C$_0$-C$_6$alkylSCN;

Each R$^8$ is independently chosen from H, C$_1$-C$_{10}$alkyl, C$_2$-C$_{10}$alkenyl, C$_2$-C$_{10}$alkynyl, haloC 1-C$_6$alkyl, C$_0$-C$_6$alkylaryl, C$_0$-C$_6$alkylcycloalkyl, C$_0$-C$_6$alkylheteroaryl, and C$_0$-C$_6$alkylheterocycloalkyl;

R$^{10}$ is H, C$_1$-C$_{10}$alkyl, C$_2$-C$_{10}$alkenyl, C$_2$-C$_{10}$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, —C$_0$-C$_6$alkylCN, —C$_0$-C$_6$alkylC(=O)C$_0$-C$_6$alkylR$^8$, —C$_0$-C$_6$alkylC(=O)C$_0$-C$_6$alkylOR$^8$, —C$_0$-C$_6$alkylC(=O)C$_0$-C$_6$alkylNR$^8$R$^8$, —C$_0$-C$_6$alkylC(=O)C$_0$-C$_6$alkylNR$^8$C(=O)OR$^8$, —C$_0$-C$_6$alkylC(=O)C$_0$-C$_6$alkylC(=O)R$^8$, haloC 1-C$_6$alkyl, —C$_0$-C$_6$alkylNR$^8$R$^8$, —C$_0$-C$_6$alkylNR$^8$NR$^8$R$^8$, —C$_0$-

C₆alkylN=NR⁸, —C₀-C₆alkylNR⁸C₀-C₆alkylOR⁸, —C₀-C₆alkylNR⁸C₀-C₆alkylC(=O)R⁸, —C₀-C₆alkylNR⁸C(=O)C₀-C₆alkylC(=O)R⁸, —C₀-C₆alkylNR⁸C₀-C₆alkyl C(=O)OR⁸, —C₀-C₆alkylNR⁸C₀-C₆alkylC(=O)C(=O)OR⁸, —C₀-C₆alkylNR⁸C₀-C₆alkylC(=O)NR⁸R⁸, —C₀-C₆alkylNR⁸C(=O)C₀-C₆alkylNR⁸C(=O)R⁸, —C₀-C₆alkylNR⁸C(=O)C₀-C₆alkylNR⁸C(=O)OR⁸, —C₀-C₆alkylNR⁸C(=O)C₀-C₆alkylC(=O)NR⁸R⁸, —C₀-C₆alkylNR⁸C₀-C₆alkylS(=O)₂R⁸, —C₀-C₆alkylNR⁸S(=O)₂C₀-C₆alkylNR⁸R⁸, —C₀-C₆alkylOR⁸, (=O), —C₀-C₆alkylOC(=O)C₀-C₆alkylR⁸, —C₀-C₆alkylOC(=O)C₀-C₆alkylNR⁸R⁸, —C₀-C₆alkylOC(=O)C₀-C₆alkylOR⁸, —C₀-C₆alkylOS(=O)R⁸, —C₀-C₆alkylOS(=O)₂R⁸, —C₀-C₆alkylOS(=O)₂C₀-C₆alkylOR⁸, —C₀-C₆alkylOS(=O)₂C₀-C₆alkylNR⁸R⁸, —C₀-C₆alkylOP(=O)R⁸R⁸, —C₀-C₆alkylOP(=O)(NR⁸R⁸)(NR⁸R⁸), —C₀-C₆alkylOP(=O)(OR⁸)(OR⁸), —C₀-C₆alkylOP(=O)(SR⁸)(SR⁸), —C₀-C₆alkylP(=O)R⁸R⁸, —C₀-C₆alkylP(=O)(NR⁸R⁸)(NR⁸R⁸), —C₀-C₆alkylP(=O)(R⁸)(OR)(OR), —C₀-C₆alkylP(=O)(SR⁸)(SR⁸), —C₀-C₆alkyl S(=O)ₚR⁸, —C₀-C₆alkyl S(=O)₂C₀-C₆alkylNR⁸R⁸, —C₀-C₆alkyl S(=O)C₀-C₆alkylNR⁸R⁸, and —C₀-C₆alkylSCN; wherein any of the foregoing, except for H, is optionally substituted with one or more R⁷;

Each p is independently 0, 1 or 2;

Each n is independently 0, 1, 2, 3 or 4;

Each q is independently an integer between 0 and 8, inclusive; and

Each m is independently an integer between 1 and 5, inclusive.

Embodiment 35

A compound according to Embodiment 34 wherein X is halogen or haloC 1-C₆alkyl.

Embodiment 36

A compound according to Embodiment 34 or 35 wherein X is haloC₁-C₆alkyl.

Embodiment 37

A compound according to Embodiment 34 or 35 wherein X is halogen.

Embodiment 38

A compound according to Embodiment 34 wherein X is CN.

Embodiment 39

A compound according to any of the preceding Embodiments 34-38 wherein at least one R⁵ is chosen from C₁-C₁₀alkyl, C₂-C₁₀alkynyl, C₀-C₆alkylaryl, C₀-C₆alkylcycloalkyl, C₀-C₆alkylheterocycloalkyl, C₀-C₆alkylheteroaryl, —C₀-C₆alkylCN, —C₀-C₆alkylC(=O)C₀-C₆alkylR⁶, —C₀-C₆alkylC(=O)C₀-C₆alkylOR⁶, —C₀-C₆alkylC(=O)C₀-C₆alkylNR⁶R⁶, —C₀-C₆alkylC(=O)C₀-C₆alkylNR⁶C(=O)OR⁶, haloC₁-C₆alkyl, halogen, —C₀-C₆alkylNR⁶R⁶, —C₀-C₆alkylNR⁶C₀-C₆alkyl C(=O)OR⁶, —C₀-C₆alkylOR⁶, (=O) and —C₀-C₆alkylS(=O)ₚR⁶.

Embodiment 40

A compound of Embodiment 34 that is of Formula Ic:

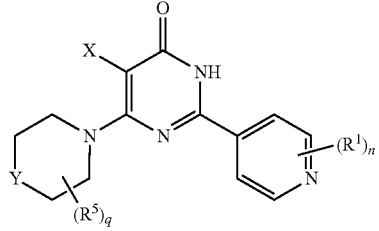

Formula Ic

Embodiment 41

A compound of Embodiment 25 that is of Formula Id:

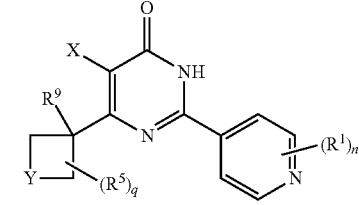

Formula Id and/or a salt thereof.

Embodiment 42

A compound of Embodiment 41 that is of Formula Ie:

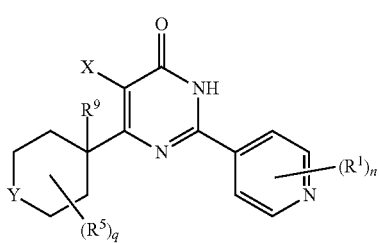

Formula Ie and/or a salt thereof.

Embodiment 43

A compound according to any of Embodiments 40, 41, or 42 wherein X is halogen or haloC₁-C₆alkyl.

Embodiment 44

A compound according to any of Embodiments 40, 41, 42, or 43 wherein X is haloC₁-C₆alkyl.

Embodiment 45

A compound according to any of Embodiments 40, 41, 42, or 43 wherein X is halogen.

Embodiment 46

A compound according to any of Embodiments 40, 41, or 42 wherein X is CN.

Embodiment 47

A compound according to any of the preceding Embodiments 40-46 wherein at least one $R^5$ is chosen from $C_1$-$C_{10}$alkyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^6$, —$C_0$-$C_6$alkylC(=O)$C_0$-$C_6$alkylOR$^6$, —$C_0$-$C_6$alkylC(=O)$C_0$-$C_6$alkylNR$^6$R$^6$, —$C_0$-$C_6$alkylC(=O)$C_0$-$C_6$alkylNR$^6$C(=O)OR$^6$, halo$C_1$-$C_6$alkyl, halogen, —$C_0$-$C_6$alkylNR$^6$R$^6$, —$C_0$-$C_6$alkylNR$^6$C_0$-$C_6$alkyl C(=O)OR$^6$, —$C_0$-$C_6$alkylOR$^6$, (=O) and —$C_0$-$C_6$alkylS(=O)$_p$R$^6$.

Embodiment 48

A compound of Formula If:

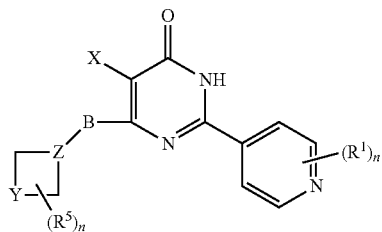

Formula If and/or a salt thereof, wherein:

X is chosen from halogen, halo$C_1$-$C_6$alkyl, $NO_2$, —C(=O)NR$^5$R$^6$, —NHS(O)$_2$R$^6$, and CN; Each $R^1$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^3$, —$C_0$-$C_6$alkylC(=O)$C_0$-$C_6$alkylNR$^3$C(=O)OR$^4$, —$C_0$-$C_6$alkylC(=O)$C_0$-$C_6$alkylOR$^3$, —$C_0$-$C_6$alkylC(=O)$C_0$-$C_6$alkylNR$^3$R$^4$, —$C_0$-$C_6$alkylC(=O)$C_0$-$C_6$alkylC(=O)R$^3$, halo$C_1$-$C_6$alkyl, halogen, —$NO_2$, —$C_0$-$C_6$alkylNR$^3$R$^4$, —$C_0$-$C_6$alkylNR$^3$NR$^3$R$^4$, —$C_0$-$C_6$alkylN=NR$^3$, —$C_0$-$C_6$alkylNR$^3$C_0$-$C_6$alkylOR$^4$, —$C_0$-$C_6$alkylNR$^3$C_0$-$C_6$alkylC(=O)R$^4$, —$C_0$-$C_6$alkylNR$^3$C(=O)$C_0$-$C_6$alkylC(=O)R$^4$, —$C_0$-$C_6$alkylNR$^3$C_0$-$C_6$alkyl C(=O)OR$^4$, —$C_0$-$C_6$alkylNR$^3$C_0$-$C_6$alkylC(=O)C(=O)OR$^4$, —$C_0$-$C_6$alkylNR$^3$C_0$-$C_6$alkylC(=O)NR$^3$R$^4$, —$C_0$-$C_6$alkylNR$^3$C(=O)$C_0$-$C_6$alkylNR$^3$C(=O)R$^4$, —$C_0$-$C_6$alkylNR$^3$C(=O)$C_0$-$C_6$alkylNR$^3$C(=O)OR$^4$, —$C_0$-$C_6$alkylNR$^3$C(=O)$C_0$-$C_6$alkylC(=O)NR$^3$R$^4$, —$C_0$-$C_6$alkylNR$^3$C_0$-$C_6$alkylS(=O)$_2$R$^4$, —$C_0$-$C_6$alkylNR$^3$S(=O)$_2$C_0$-$C_6$alkylNR$^3$R$^4$, —$C_0$-$C_6$alkylOR$^3$, (=O), —$C_0$-$C_6$alkylOC(=O)$C_0$-$C_6$alkylR$^4$, —$C_0$-$C_6$alkylOC(=O)$C_0$-$C_6$alkylNR$^3$R$^4$, —$C_0$-$C_6$alkylOC(=O)$C_0$-$C_6$alkylOR$^4$, —$C_0$-$C_6$alkylOS(=O)R$^4$, —$C_0$-$C_6$alkylOS(=O)$_2$R$^4$, —$C_0$-$C_6$alkylOS(=O)$_2$C_0$-$C_6$alkylOR$^4$, —$C_0$-$C_6$alkylOS(=O)$_2$C_0$-$C_6$alkylNR$^3$R$^4$, —$C_0$-$C_6$alkylOP(=O)R$^3$R$^4$, —$C_0$-$C_6$alkylOP(=O)(NR$^3$R$^4$)(NR$^3$R$^4$), —$C_0$-$C_6$alkylOP(=O)(OR$^3$)(OR$^4$), —$C_0$-$C_6$alkylOP(=O)(SR$^3$)(SR$^4$), —$C_0$-$C_6$alkylP(=O)R$^3$R$^4$, —$C_0$-$C_6$alkylP(=O)(R$^3$)(OR$^3$)(OR$^4$), —$C_0$-$C_6$alkylP(=O)(SR$^3$)(SR$^4$), —$C_0$-$C_6$alkylS(=O)$_p$R$^4$, —$C_0$-$C_6$alkylS(=O)$_2$C_0$-$C_6$alkylNR$^3$R$^4$, —$C_0$-$C_6$alkylS(=O)$C_0$-$C_6$alkylNR$^3$R$^4$, and —$C_0$-$C_6$alkylSCN, wherein any of the foregoing, except for halogen and $NO_2$, is optionally substituted with one or more $R^5$; or Any two $R^1$ on adjacent atoms may be taken together to form a 4 to 12 membered carbocyclic or heterocyclic ring system, wherein said ring system is optionally substituted with one or more $R^5$;

$R^3$ and $R^4$ are each independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing, except for H, is optionally substituted with one or more $R^5$; or $R^3$ and $R^4$ may be taken together to form a 3 to 15 membered carbocyclic or heterocyclic ring system, wherein said ring system is optionally substituted with one or more $R^5$;

B is chosen from S(O)$_p$, NR$^3$, O, $C_2$-$C_{10}$alkenyl, and $C_2$-$C_{10}$alkynyl;

Z is CR$^9$ or N;

Y is chosen from —(CH$_2$)$_m$—, —(CH$_2$)$_m$O(CH$_2$)$_m$—, —(CH$_2$)$_m$NR$^{10}$(CH$_2$)$_m$—, and —(CH$_2$)$_m$S(CH$_2$)$_m$;

$R^3$ and $R^4$ are each independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing, except for H, is optionally substituted with one or more $R^5$; or $R^3$ and $R^4$ may be taken together to form a 3 to 15 membered carbocyclic or heterocyclic ring system, wherein said ring system is optionally substituted with one or more $R^5$;

Each $R^5$ is independently chosen from $C_1$-$C_{10}$alkyl, $C_2$-$C_{10}$alkenyl, $C_{2-10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^6$, —$C_0$-$C_6$alkylC(=O)$C_0$-$C_6$alkylOR$^6$, —$C_0$-$C_6$alkylC(=O)$C_0$-$C_6$alkylNR$^6$R$^6$, —$C_0$-$C_6$alkylC(=O)$C_0$-$C_6$alkylNR$^6$C(=O)OR$^6$, —$C_0$-$C_6$alkylC(=O)$C_0$-$C_6$alkylC(=O)R$^6$, halo$C_1$-$C_6$alkyl, halogen, —$NO_2$, —$C_0$-$C_6$alkylNR$^6$R$^6$, —$C_0$-$C_6$alkylNR$^6$NR$^6$R$^6$, —$C_0$-$C_6$alkylN=NR$^6$, —$C_0$-$C_6$alkylNR$^6$C_0$-$C_6$alkylOR$^6$, —$C_0$-$C_6$alkylNR$^6$C_0$-$C_6$alkylC(=O)R$^6$, —$C_0$-$C_6$alkylNR$^6$C(=O)$C_0$-$C_6$alkylC(=O)R$^6$, —$C_0$-$C_6$alkylNR$^6$C_0$-$C_6$alkyl C(=O)OR$^6$, —$C_0$-$C_6$alkylNR$^6$C_0$-$C_6$alkylC(=O)C(=O)OR$^6$, —$C_0$-$C_6$alkylNR$^6$C_0$-$C_6$alkylC(=O)NR$^6$R$^6$, —$C_0$-$C_6$alkylNR$^6$C(=O)$C_0$-$C_6$alkylNR$^6$C(=O)R$^6$, —$C_0$-$C_6$alkylNR$^6$C(=O)$C_0$-$C_6$alkylNR$^6$C(=O)OR$^6$, —$C_0$-$C_6$alkylNR$^6$C(=O)$C_0$-$C_6$alkylC(=O)NR$^6$R$^6$, —$C_0$-$C_6$alkylNR$^6$C_0$-$C_6$alkylS(=O)$_2$R$^6$, —$C_0$-$C_6$alkylNR$^6$S(=O)$_2$C_0$-$C_6$alkylNR$^6$R$^6$, —$C_0$-$C_6$alkylOR$^6$, (=O), —$C_0$-$C_6$alkylOC(=O)$C_0$-$C_6$alkylR$^6$, —$C_0$-$C_6$alkylOC(=O)$C_0$-$C_6$alkylNR$^6$R$^6$, —$C_0$-$C_6$alkylOC(=O)$C_0$-$C_6$alkylOR$^6$, —$C_0$-$C_6$alkylOS(=O)R$^6$, —$C_0$-$C_6$alkylOS(=O)$_2$R$^6$, —$C_0$-$C_6$alkylOS(=O)$_2$C_0$-$C_6$alkylOR$^6$, —$C_0$-$C_6$alkylOS(=O)$_2$C_0$-$C_6$alkylNR$^6$R$^6$, —$C_0$-$C_6$alkylOP(=O)R$^6$R$^6$, —$C_0$-$C_6$alkylOP(=O)(NR$^6$R$^6$)(NR$^6$R$^6$), —$C_0$-$C_6$alkylOP(=O)(OR$^6$)(OR$^6$), —$C_0$-$C_6$alkylOP(=O)(SR$^6$)(SR$^6$), —$C_0$-$C_6$alkylP(=O)R$^6$R$^6$, —$C_0$-$C_6$alkylP(=O)(NR$^6$R$^6$)(NR$^6$R$^6$), —$C_0$-$C_6$alkylP(=O)(R$^6$)(OR$^6$), —$C_0$-$C_6$alkylP(=O)($SR^6$)($SR^6$), —$C_0$-$C_6$alkylS(=O)$_p R^6$, —$C_0$-$C_6$alkyl S(=O)$_2 C_0$-$C_6$alkylN$R^6 R^6$, —$C_0$-$C_6$alkyl S(=O)$C_0$-$C_6$alkylN$R^6 R^6$, and —$C_0$-$C_6$alkylSCN, wherein any of the foregoing, except for halogen and $NO_2$, is optionally substituted with one or more $R^7$; or Two $R^5$ or an $R^5$ and $R^{10}$ may be taken together to form a 4 to 12 membered carbocyclic or heterocyclic ring system, wherein said ring system is optionally substituted with one or more $R^7$;

Each $R^6$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing except for H is optionally substituted with one or more R; or Two $R^6$ may be taken together to form a 3 to 15 membered carbocyclic or heterocyclic ring system, wherein said ring system is optionally substituted with one or more $R^7$;

Each $R^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^8$, —$C_0$-$C_6$alkylC(=O)$C_0$-$C_6$alkylO$R^8$, —$C_0$-$C_6$alkylC(=O)$C_0$-$C_6$alkylN$R^8 R^8$, —$C_0$-$C_6$alkylC(=O)$C_0$-$C_6$alkylN$R^8$C(=O)O$R^8$, —$C_0$-$C_6$alkylC(=O)$C_0$-$C_6$alkylC(=O)$R^8$, halo$C_1$-$C_6$alkyl, halogen, —$NO_2$, —$C_0$-$C_6$alkylN$R^8 R^8$, —$C_0$-$C_6$alkylN$R^8$N$R^8 R^8$, —$C_0$-$C_6$alkylN=N$R^8$, —$C_0$-$C_6$alkylN$R^8 C_0$-$C_6$alkylO$R^8$, —$C_0$-$C_6$alkylN$R^8 C_0$-$C_6$alkylC(=O)$R^8$, —$C_0$-$C_6$alkylN$R^8 C(=O)C_0$-$C_6$alkylC(=O)$R^8$, —$C_0$-$C_6$alkylN$R^8 C_0$-$C_6$alkyl C(=O)O$R^8$, —$C_0$-$C_6$alkylN$R^8 C_0$-$C_6$alkylC(=O)C(=O)O$R^8$, —$C_0$-$C_6$alkylN$R^8 C_0$-$C_6$alkylC(=O)N$R^8 R^8$, —$C_0$-$C_6$alkylN$R^8 C(=O)C_0$-$C_6$alkylN$R^8 C(=O)R^8$, —$C_0$-$C_6$alkylN$R^8 C(=O)C_0$-$C_6$alkylN$R^8 C(=O)OR^8$, —$C_0$-$C_6$alkylN$R^8 C(=O)C_0$-$C_6$alkylC(=O)NR^8 R^8$, —$C_0$-$C_6$alkylN$R^8 C_0$-$C_6$alkyl S(=O)$_2 R^8$, —$C_0$-$C_6$alkylN$R^8$S(=O)$_2 C_0$-$C_6$alkylN$R^8 R^8$, —$C_0$-$C_6$alkylO$R^8$, (=O), —$C_0$-$C_6$alkylOC(=O)$C_0$-$C_6$alkyl$R^8$, —$C_0$-$C_6$alkylOC(=O)$C_0$-$C_6$alkylO$R^8$, —$C_0$-$C_6$alkylOC(=O)$C_0$-$C_6$alkylOR^8$, —$C_0$-$C_6$alkylOS(=O)$R^8$, —$C_0$-$C_6$alkylOS(=O)$_2 R^8$, —$C_0$-$C_6$alkylOS(=O)$_2 C_0$-$C_6$alkylO$R^8$, —$C_0$-$C_6$alkylOS(=O)$_2 C_0$-$C_6$alkylN$R^8 R^8$, —$C_0$-$C_6$alkylOP(=O)$R^8 R^8$, —$C_0$-$C_6$alkylOP(=O)(N$R^8 R^8$)(N$R^8 R^8$), —$C_0$-$C_6$alkylOP(=O)(O$R^8$)(O$R^8$), —$C_0$-$C_6$alkylOP(=O)(S$R^8$)(S$R^8$), —$C_0$-$C_6$alkylP(=O)$R^8 R^8$, —$C_0$-$C_6$alkylP(=O)(N$R^8 R^8$)(N$R^8 R^8$), —$C_0$-$C_6$alkylP(=O)($R^8$)(OR)(OR), —$C_0$-$C_6$alkylP(=O)(S$R^8$)(S$R^8$), —$C_0$-$C_6$alkyl S(=O)$_p R^8$, —$C_0$-$C_6$alkylS(=O)$_2 C_0$-$C_6$alkylN$R^8 R^8$, —$C_0$-$C_6$alkylS(=O)$C_0$-$C_6$alkylN$R^8 R^8$, and —$C_0$-$C_6$alkylSCN; wherein any of the foregoing, except for H, is optionally substituted with one or more $R^7$;

Each $R^8$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, and $C_0$-$C_6$alkylheterocycloalkyl;

$R^9$ is chosen from H, $C_{1-6}$alkyl, and halogen;

$R^{10}$ is H, $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^8$, —$C_0$-$C_6$alkylC(=O)$C_0$-$C_6$alkylO$R^8$, —$C_0$-$C_6$alkylC(=O)$C_0$-$C_6$alkylN$R^8 R^8$, —$C_0$-$C_6$alkylN$R^8$C(=O)O$R^8$, —$C_0$-$C_6$alkylC(=O)$C_0$-$C_6$alkylC(=O)$R^8$, halo$C_1$-$C_6$alkyl, —$C_0$-$C_6$alkylN$R^8 R^8$, —$C_0$-$C_6$alkylN$R^8$N$R^8 R^8$, —$C_0$-$C_6$alkylN=N$R^8$, —$C_0$-$C_6$alkylN$R^8 C_0$-$C_6$alkylO$R^8$, —$C_0$-$C_6$alkylN$R^8 C_0$-$C_6$alkylC(=O)$R^8$, —$C_0$-$C_6$alkylN$R^8 C_0$-$C_6$alkylC(=O)$R^8$, —$C_0$-$C_6$alkylN$R_8 C_0$-$C_6$alkyl C(=O)O$R^8$, —$C_0$-$C_6$alkylN$R^8 C_0$-$C_6$alkylC(=O)C(=O)O$R^8$, —$C_0$-$C_6$alkylN$R^8 C_0$-$C_6$alkylC(=O)N$R^8 R^8$, —$C_0$-$C_6$alkylN$R^8$C(=O)$C_0$-$C_6$alkylN$R^8$C(=O)$R^8$, —$C_0$-$C_6$alkylN$R^8$C(=O)$C_0$-$C_6$alkylN$R^8$C(=O)O$R^8$, —$C_0$-$C_6$alkylN$R^8$C(=O)$C_0$-$C_6$alkylC(=O)N$R^8 R^8$, —$C_0$-$C_6$alkylN$R^8 C_0$-$C_6$alkyl S(=O)$_2 R^8$, —$C_0$-$C_6$alkylN$R^8$S(=O)$_2 C_0$-$C_6$alkylN$R^8 R^8$, —$C_0$-$C_6$alkylO$R^8$, (=O), —$C_0$-$C_6$alkylOC(=O)$C_0$-$C_6$alkyl$R^8$, —$C_0$-$C_6$alkylOC(=O)$C_0$-$C_6$alkylN$R^8 R^8$, —$C_0$-$C_6$alkylOC(=O)$C_0$-$C_6$alkylO$R^8$, —$C_0$-$C_6$alkylOS(=O)$R^8$, —$C_0$-$C_6$alkylOS(=O)$_2 R^8$, —$C_0$-$C_6$alkylOS(=O)$_2 C_0$-$C_6$alkylO$R^8$, —$C_0$-$C_6$alkylOS(=O)$_2 C_0$-$C_6$alkylN$R^8 R^8$, —$C_0$-$C_6$alkylOP(=O)$R^8 R^8$, —$C_0$-$C_6$alkylOP(=O)(N$R^8 R^8$)(N$R^8 R^8$), —$C_0$-$C_6$alkylOP(=O)(O$R^8$)(O$R^8$), —$C_0$-$C_6$alkylOP(=O)(S$R^8$)(S$R^8$), —$C_0$-$C_6$alkylP(=O)$R^8 R^8$, —$C_0$-$C_6$alkylP(=O)(N$R^8 R^8$)(N$R^8 R^8$), —$C_0$-$C_6$alkylP(=O)($R^8$)(OR)(OR), —$C_0$-$C_6$alkylP(=O)(S$R^8$)(S$R^8$), —$C_0$-$C_6$alkyl S(=O)$_p R^8$, —$C_0$-$C_6$alkylS(=O)$_2 C_0$-$C_6$alkylN$R^8 R^8$, —$C_0$-$C_6$alkylS(=O)$C_0$-$C_6$alkylN$R^8 R^8$, and —$C_0$-$C_6$alkylSCN; wherein any of the foregoing, except for H, is optionally substituted with one or more $R^7$;

Each p is independently 0, 1 or 2;

Each n is independently 0, 1, 2, 3 or 4;

Each q is independently an integer between 0 and 8, inclusive; and

Each m is independently an integer between 1 and 5, inclusive.

Embodiment 49

A compound according to Embodiment 49 wherein B is chosen from S(O)$_p$, N$R^3$, and O.

Embodiment 50

A compound according to Embodiment 48 or 49 wherein B is S(O)$_p$.

Embodiment 51

A compound according to Embodiment 48 or 49 wherein B is N$R^3$.

Embodiment 52

A compound according to Embodiment 48 or 49 wherein B is O.

Embodiment 53

A compound according to any of Embodiments 48-52 wherein X is halogen or halo$C_1$-$C_6$alkyl.

Embodiment 54

A compound according to any of Embodiments 48-53 wherein X is halo$C_1$-$C_6$alkyl.

Embodiment 55

A compound according to any of Embodiments 48-53 wherein X is halogen.

Embodiment 56

A compound according to any of Embodiments 48-52 wherein X is CN.

Embodiment 57

A pharmaceutical composition comprising a compound according to any of the preceding Embodiments 1-57 and/or a salt thereof and a pharmaceutically acceptable excipient.

Embodiment 58

A method of treating a disease or condition mediated, at least in part, by Cdc7 comprising administering to a subject in recognized need thereof a compound according to any of the Embodiments 1-56 and/or a pharmaceutically acceptable salt thereof.

Particular compounds of the present invention include any of the compounds exemplified in the present application, or a pharmaceutically acceptable salt or solvate thereof, and, in particular, any of the following:

tert-butyl 4-[5-chloro-6-oxo-2-(4-pyridyl)-1H-pyrimidin-4-yl]piperidine-1-carboxylate;
5-chloro-4-(4-piperidyl)-2-(4-pyridyl)-1H-pyrimidin-6-one;
5-chloro-4-[1-(2-methylpropanoyl)-4-piperidyl]-2-(4-pyridyl)-1H-pyrimidin-6-one;
4-(1-acetyl-4-piperidyl)-5-chloro-2-(4-pyridyl)-1H-pyrimidin-6-one;
tert-butyl 4-[5-chloro-6-oxo-2-(4-pyridyl)-1H-pyrimidin-4-yl]piperazine-1-carboxylate;
4-(1-benzoyl-4-piperidyl)-5-chloro-2-(4-pyridyl)-1H-pyrimidin-6-one;
4-[5-chloro-6-oxo-2-(4-pyridyl)-1H-pyrimidin-4-yl]-N-isopropyl-piperidine-1-carboxamide;
4-[1-(benzenesulfonyl)-4-piperidyl]-5-chloro-2-(4-pyridyl)-1H-pyrimidin-6-one;
5-chloro-4-(1-methyl-4-piperidyl)-2-(4-pyridyl)-1H-pyrimidin-6-one;
5-chloro-4-(1-isobutyl-4-piperidyl)-2-(4-pyridyl)-1H-pyrimidin-6-one;
4-(4-acetylpiperazin-1-yl)-5-chloro-2-(4-pyridyl)-1H-pyrimidin-6-one;
5-chloro-4-(4-methylsulfonylpiperazin-1-yl)-2-(4-pyridyl)-1H-pyrimidin-6-one;
5-chloro-4-[4-[(3-chlorophenyl)methyl]piperazin-1-yl]-2-(4-pyridyl)-1H-pyrimidin-6-one;
5-chloro-4-(4-methylpiperazin-1-yl)-2-(4-pyridyl)-1H-pyrimidin-6-one;
5-chloro-4-(4-isobutylpiperazin-1-yl)-2-(4-pyridyl)-1H-pyrimidin-6-one;
5-chloro-4-(4-isopentylpiperazin-1-yl)-2-(4-pyridyl)-1H-pyrimidin-6-one;
5-chloro-4-[4-(cyclopentylmethyl)piperazin-1-yl]-2-(4-pyridyl)-1H-pyrimidin-6-one;
5-chloro-4-[4-(cyclohexylmethyl)piperazin-1-yl]-2-(4-pyridyl)-1H-pyrimidin-6-one;
5-chloro-4-(4-isopropylpiperazin-1-yl)-2-(4-pyridyl)-1H-pyrimidin-6-one;
5-chloro-2-(4-pyridyl)-4-tetrahydropyran-4-yl-1H-pyrimidin-6-one;
5-chloro-2-(4-pyridyl)-4-pyrrolidin-2-yl-1H-pyrimidin-6-one;
5-chloro-4-(1-piperidyl)-2-(4-pyridyl)-1H-pyrimidin-6-one;
5-chloro-4-morpholino-2-(4-pyridyl)-1H-pyrimidin-6-one;
5-chloro-4-(3-piperidyl)-2-(4-pyridyl)-1H-pyrimidin-6-one;
5-chloro-4-[1-(2,2-dimethylpropanoyl)-4-piperidyl]-2-(4-pyridyl)-1H-pyrimidin-6-one;
tert-butyl N-[2-[4-[5-chloro-6-oxo-2-(4-pyridyl)-1H-pyrimidin-4-yl]-1-piperidyl]-2-oxo-ethyl]carbamate;
5-chloro-4-[1-(pyridine-2-carbonyl)-4-piperidyl]-2-(4-pyridyl)-1H-pyrimidin-6-one;
4-[4-[5-chloro-6-oxo-2-(4-pyridyl)-1H-pyrimidin-4-yl]piperidine-1-carbonyl]benzonitrile;
5-chloro-4-[1-(pyridazine-4-carbonyl)-4-piperidyl]-2-(4-pyridyl)-1H-pyrimidin-6-one;
3-[4-[5-chloro-6-oxo-2-(4-pyridyl)-1H-pyrimidin-4-yl]piperidine-1-carbonyl]benzonitrile;
5-chloro-4-[1-(2-iodobenzoyl)-4-piperidyl]-2-(4-pyridyl)-1H-pyrimidin-6-one;
5-chloro-4-[1-(3-hydroxybenzoyl)-4-piperidyl]-2-(4-pyridyl)-1H-pyrimidin-6-one;
5-chloro-4-[1-(furan-2-carbonyl)-4-piperidyl]-2-(4-pyridyl)-1H-pyrimidin-6-one;
5-chloro-4-[1-(3-methyl-1H-pyrazole-5-carbonyl)-4-piperidyl]-2-(4-pyridyl)-1H-pyrimidin-6-one;
5-chloro-4-[1-[2-(1H-imidazol-4-yl)acetyl]-4-piperidyl]-2-(4-pyridyl)-1H-pyrimidin-6-one;
5-chloro-4-[1-(2,4-dimethylthiazole-5-carbonyl)-4-piperidyl]-2-(4-pyridyl)-1H-pyrimidin-6-one;
5-chloro-4-[1-(1-methylimidazole-4-carbonyl)-4-piperidyl]-2-(4-pyridyl)-1H-pyrimidin-6-one;
5-chloro-4-[1-(2,5-dimethylpyrazole-3-carbonyl)-4-piperidyl]-2-(4-pyridyl)-1H-pyrimidin-6-one;
5-chloro-2-(4-pyridyl)-4-[1-(thiazole-4-carbonyl)-4-piperidyl]-1H-pyrimidin-6-one;
5-chloro-4-[1-(1,5-dimethylpyrazole-3-carbonyl)-4-piperidyl]-2-(4-pyridyl)-1H-pyrimidin-6-one;
5-chloro-2-(4-pyridyl)-4-[1-(thiadiazole-4-carbonyl)-4-piperidyl]-1H-pyrimidin-6-one;
4-[1-(4-acetylbenzoyl)-4-piperidyl]-5-chloro-2-(4-pyridyl)-1H-pyrimidin-6-one;
3-[4-[5-chloro-6-oxo-2-(4-pyridyl)-1H-pyrimidin-4-yl]piperidine-1-carbonyl]-4-methoxy-benzenesulfonamide;
N-[4-[4-[5-chloro-6-oxo-2-(4-pyridyl)-1H-pyrimidin-4-yl]piperidine-1-carbonyl]phenyl]acetamide;
5-chloro-4-[1-(4-isopropoxybenzoyl)-4-piperidyl]-2-(4-pyridyl)-1H-pyrimidin-6-one;
tert-butyl N-[(1S)-2-[4-[5-chloro-6-oxo-2-(4-pyridyl)-1H-pyrimidin-4-yl]-1-piperidyl]-1-methyl-2-oxo-ethyl]carbamate;
N-[4-[4-[5-chloro-6-oxo-2-(4-pyridyl)-1H-pyrimidin-4-yl]piperidine-1-carbonyl]phenyl]-N-methyl-methanesulfonamide;
5-chloro-4-[1-(2-chlorobenzoyl)-4-piperidyl]-2-(4-pyridyl)-1H-pyrimidin-6-one;
5-chloro-4-[1-(4-methylthiazole-5-carbonyl)-4-piperidyl]-2-(4-pyridyl)-1H-pyrimidin-6-one;
5-chloro-4-[1-(1H-pyrazole-4-carbonyl)-4-piperidyl]-2-(4-pyridyl)-1H-pyrimidin-6-one;
5-chloro-4-[1-(5-methylisoxazole-3-carbonyl)-4-piperidyl]-2-(4-pyridyl)-1H-pyrimidin-6-one;
5-chloro-4-[1-(2,2-difluorocyclopropanecarbonyl)-4-piperidyl]-2-(4-pyridyl)-1H-pyrimidin-6-one;
tert-butyl N-[(1R)-2-[4-[5-chloro-6-oxo-2-(4-pyridyl)-1H-pyrimidin-4-yl]-1-piperidyl]-1-methyl-2-oxo-ethyl]carbamate;

5-chloro-4-[1-(3-methylbenzoyl)-4-piperidyl]-2-(4-pyridyl)-1H-pyrimidin-6-one;
5-chloro-4-[1-[4-(methylsulfonylmethyl)benzoyl]-4-piperidyl]-2-(4-pyridyl)-1H-pyrimidin-6-one;
5-chloro-2-(2-fluoro-4-pyridyl)-4-(1-isobutyl-4-piperidyl)-1H-pyrimidin-6-one;
5-chloro-2-(4-pyridyl)-4-pyrrolidin-3-yl-1H-pyrimidin-6-one;
5-chloro-4-(4-ethoxy-1-piperidyl)-2-(4-pyridyl)-1H-pyrimidin-6-one;
tert-butyl N-[1-[4-[5-chloro-6-oxo-2-(4-pyridyl)-1H-pyrimidin-4-yl]piperidine-1-carbonyl]butyl]carbamate;
4-[1-(2-aminopropanoyl)-4-piperidyl]-5-chloro-2-(4-pyridyl)-1H-pyrimidin-6-one;
5-chloro-2-(4-pyridyl)-4-tetrahydrofuran-3-yl-1H-pyrimidin-6-one;
5-chloro-2-(2-fluoro-4-pyridyl)-4-tetrahydropyran-4-yl-1H-pyrimidin-6-one;
5-chloro-4-(2-isopropyltetrahydropyran-4-yl)-2-(4-pyridyl)-1H-pyrimidin-6-one;
5-chloro-2-(4-pyridyl)-4-tetrahydropyran-2-yl-1H-pyrimidin-6-one;
5-chloro-4-(3,4-dimethylpiperazin-1-yl)-2-(4-pyridyl)-1H-pyrimidin-6-one;
5-chloro-4-[3-(dimethylamino)pyrrolidin-1-yl]-2-(4-pyridyl)-1H-pyrimidin-6-one;
5-chloro-2-(4-pyridyl)-4-pyrrolidin-1-yl-1H-pyrimidin-6-one;
5-bromo-4-(4-ethylpiperazin-1-yl)-2-(4-pyridyl)-1H-pyrimidin-6-one;
5-chloro-4-(2-phenylmorpholin-4-yl)-2-(4-pyridyl)-1H-pyrimidin-6-one;
5-chloro-4-(3-oxopiperazin-1-yl)-2-(4-pyridyl)-1H-pyrimidin-6-one;
5-chloro-2-(4-pyridyl)-4-tetrahydropyran-3-yl-1H-pyrimidin-6-one;
5-chloro-4-(2,6-dimethylmorpholin-4-yl)-2-(4-pyridyl)-1H-pyrimidin-6-one;
5-chloro-4-(2-isobutylmorpholin-4-yl)-2-(4-pyridyl)-1H-pyrimidin-6-one;
5-chloro-4-[2-(2-hydroxyethyl)morpholin-4-yl]-2-(4-pyridyl)-1H-pyrimidin-6-one;
5-chloro-4-(3-propylmorpholin-4-yl)-2-(4-pyridyl)-1H-pyrimidin-6-one;
4-[5-chloro-6-oxo-2-(4-pyridyl)-1H-pyrimidin-4-yl]morpholine-2-carboxamide;
4-[5-chloro-6-oxo-2-(4-pyridyl)-1H-pyrimidin-4-yl]-N,N-dimethyl-morpholine-2-carboxamide;
tert-butyl N-[[4-[5-chloro-6-oxo-2-(4-pyridyl)-1H-pyrimidin-4-yl]morpholin-2-yl]methyl]carbamate;
5-chloro-4-[2-(2-methoxyethyl)morpholin-4-yl]-2-(4-pyridyl)-1H-pyrimidin-6-one;
1-[5-chloro-6-oxo-2-(4-pyridyl)-1H-pyrimidin-4-yl]piperidine-4-carboxamide;
5-chloro-2-(4-pyridyl)-4-[3-(trifluoromethyl)piperazin-1-yl]-1H-pyrimidin-6-one;
5-chloro-2-(2-hydroxy-4-pyridyl)-4-tetrahydropyran-4-yl-1H-pyrimidin-6-one;
4-(4-benzyl-1-piperidyl)-5-chloro-2-(4-pyridyl)-1H-pyrimidin-6-one;
5-chloro-4-(3,5-dimethyl-1-piperidyl)-2-(4-pyridyl)-1H-pyrimidin-6-one;
5-chloro-4-(4-hydroxy-1-piperidyl)-2-(4-pyridyl)-1H-pyrimidin-6-one;
5-chloro-4-(3-methyl-1-piperidyl)-2-(4-pyridyl)-1H-pyrimidin-6-one;
5-chloro-4-(4-fluoro-1-piperidyl)-2-(4-pyridyl)-1H-pyrimidin-6-one;
5-fluoro-2-(4-pyridyl)-4-tetrahydropyran-4-yl-1H-pyrimidin-6-one;
5-fluoro-2-(2-fluoro-4-pyridyl)-4-tetrahydropyran-4-yl-1H-pyrimidin-6-one;
5-chloro-2-(4-pyridyl)-4-[3-(trifluoromethyl)-1-piperidyl]-1H-pyrimidin-6-one;
5-chloro-4-(3,5-dimethylpiperazin-1-yl)-2-(4-pyridyl)-1H-pyrimidin-6-one;
5-chloro-4-[4-(hydroxymethyl)-1-piperidyl]-2-(4-pyridyl)-1H-pyrimidin-6-one;
2-[4-[5-chloro-6-oxo-2-(4-pyridyl)-1H-pyrimidin-4-yl]piperazin-1l-yl]-N,N-dimethyl-acetamide;
5-chloro-4-[4-(3-fluorophenyl)piperazin-1l-yl]-2-(4-pyridyl)-1H-pyrimidin-6-one;
benzyl 4-[5-chloro-6-oxo-2-(4-pyridyl)-1H-pyrimidin-4-yl]piperazine-1-carboxylate;
5-chloro-4-[4-(3-methoxyphenyl)piperazin-1l-yl]-2-(4-pyridyl)-1H-pyrimidin-6-one;
4-(azepan-1l-yl)-5-chloro-2-(4-pyridyl)-1H-pyrimidin-6-one;
5-chloro-4-(1,4-diazepan-1-yl)-2-(4-pyridyl)-1H-pyrimidin-6-one;
5-chloro-2-(4-pyridyl)-4-[4-(3-pyridyl)piperazin-1l-yl]-1H-pyrimidin-6-one;
1-[5-chloro-6-oxo-2-(4-pyridyl)-1H-pyrimidin-4-yl]-1,4-diazepan-5-one;
5-bromo-2-(4-pyridyl)-4-tetrahydropyran-4-yl-1H-pyrimidin-6-one;
6-oxo-2-(4-pyridyl)-4-tetrahydropyran-4-yl-1H-pyrimidine-5-carbonitrile;
5-iodo-2-(4-pyridyl)-4-tetrahydropyran-4-yl-1H-pyrimidin-6-one;
(2R)—1-[5-chloro-6-oxo-2-(4-pyridyl)-1H-pyrimidin-4-yl]pyrrolidine-2-carboxamide;
4-[5-chloro-6-oxo-2-(4-pyridyl)-1H-pyrimidin-4-yl]-1,4-diazepane-1-carbaldehyde;
4-[(9aS)-1,3,4,5,7,8,9,9a-octahydropyrrolo[1,2-a][1,4]diazepin-2-yl]-5-chloro-2-(4-pyridyl)-1H-pyrimidin-6-one;
5-chloro-4-(3,6-dihydro-2H-pyran-4-yl)-2-(4-pyridyl)-1H-pyrimidin-6-one;
5-chloro-4-(2,2-dimethylmorpholin-4-yl)-2-(4-pyridyl)-1H-pyrimidin-6-one;
5-chloro-4-(4-methyl-1-piperidyl)-2-(4-pyridyl)-1H-pyrimidin-6-one;
5-chloro-4-[3-(hydroxymethyl)-1-piperidyl]-2-(4-pyridyl)-1H-pyrimidin-6-one;
5-chloro-4-[3-(hydroxymethyl)azetidin-1-yl]-2-(4-pyridyl)-1H-pyrimidin-6-one;
5-chloro-4-[4-(2-hydroxyethyl)piperazin-1-yl]-2-(4-pyridyl)-1H-pyrimidin-6-one;
5-chloro-4-(2-oxa-7-azaspiro[3.4]octan-7-yl)-2-(4-pyridyl)-1H-pyrimidin-6-one;
5-chloro-4-(4,4-difluoro-1-piperidyl)-2-(4-pyridyl)-1H-pyrimidin-6-one;
5-chloro-2-(4-pyridyl)-4-thiomorpholino-1H-pyrimidin-6-one;
5-chloro-4-[(3R)-3-(hydroxymethyl)piperazin-1-yl]-2-(4-pyridyl)-1H-pyrimidin-6-one;
5-chloro-4-[(3S)-3-methylpiperazin-1-yl]-2-(4-pyridyl)-1H-pyrimidin-6-one;
5-chloro-4-(3-fluoro-1-piperidyl)-2-(4-pyridyl)-1H-pyrimidin-6-one;
5-chloro-4-(3,3-difluoro-1-piperidyl)-2-(4-pyridyl)-1H-pyrimidin-6-one;

2-(4-pyridyl)-4-tetrahydropyran-4-yl-5-(trifluoromethyl)-1H-pyrimidin-6-one;
5-chloro-4-[(3R)-3-fluoropyrrolidin-1-yl]-2-(4-pyridyl)-1H-pyrimidin-6-one;
5-chloro-4-(6,6-difluoro-3-azabicyclo[3.1.0]hexan-3-yl)-2-(4-pyridyl)-1H-pyrimidin-6-one;
5-chloro-2-(4-pyridyl)-4-[3-(trifluoromethyl)pyrrolidin-1-yl]-1H-pyrimidin-6-one;
5-chloro-4-[4-(2-hydroxyethyl)-1,4-diazepan-1-yl]-2-(4-pyridyl)-1H-pyrimidin-6-one;
4-(4-tert-butyl-1,4-diazepan-1-yl)-5-chloro-2-(4-pyridyl)-1H-pyrimidin-6-one;
5-chloro-4-(3-hydroxypyrrolidin-1-yl)-2-(4-pyridyl)-1H-pyrimidin-6-one;
5-chloro-2-(4-pyridyl)-4-[(3R)-3-(trifluoromethyl)piperazin-1-yl]-1H-pyrimidin-6-one;
5-chloro-2-(4-pyridyl)-4-[(3S)-3-(trifluoromethyl)piperazin-1-yl]-1H-pyrimidin-6-one;
5-chloro-4-[(3R)-3-methylpiperazin-1-yl]-2-(4-pyridyl)-1H-pyrimidin-6-one;
5-chloro-4-piperazin-1-yl-2-(4-pyridyl)-1H-pyrimidin-6-one;
5-chloro-4-(4-methyltetrahydropyran-4-yl)-2-(4-pyridyl)-1H-pyrimidin-6-one;
5-chloro-2-(2-fluoro-4-pyridyl)-4-(4-methyltetrahydropyran-4-yl)-1H-pyrimidin-6-one;
4-[5-chloro-6-oxo-2-(4-pyridyl)-1H-pyrimidin-4-yl]-1,4-diazepan-2-one;
5-chloro-2-(4-pyridyl)-4-[4-(2,2,2-trifluoroethyl)-1,4-diazepan-1-yl]-1H-pyrimidin-6-one;
5-chloro-4-(4-propyl-1,4-diazepan-1-yl)-2-(4-pyridyl)-1H-pyrimidin-6-one;
5-chloro-2-(4-pyridyl)-4-[4-(2,2,2-trifluoroacetyl)-1,4-diazepan-1-yl]-1H-pyrimidin-6-one;
5-chloro-4-(4-methyl sulfonyl-1,4-diazepan-1-yl)-2-(4-pyridyl)-1H-pyrimidin-6-one;
5-chloro-2-(4-pyridyl)-4-[1-(2,2,2-trifluoroacetyl)-4-piperidyl]-1H-pyrimidin-6-one;
5-chloro-2-(4-pyridyl)-4-[4-(2,2,2-trifluoroacetyl)piperazin-1-yl]-1H-pyrimidin-6-one;
5-chloro-2-(4-pyridyl)-4-[4-(2,2,2-trifluoroethyl)piperazin-1-yl]-1H-pyrimidin-6-one;
5-chloro-4-[4-(2,2-difluoroethyl)piperazin-1-yl]-2-(4-pyridyl)-1H-pyrimidin-6-one;
2-[4-[5-chloro-6-oxo-2-(4-pyridyl)-1H-pyrimidin-4-yl]piperazin-1-yl]acetonitrile;
4-[(8aS)-7,7-difluoro-1,3,4,6,8,8a-hexahydropyrrolo[1,2-a]pyrazin-2-yl]-5-chloro-2-(4-pyridyl)-1H-pyrimidin-6-one;
5-chloro-4-(4-prop-2-ynylpiperazin-1-yl)-2-(4-pyridyl)-1H-pyrimidin-6-one;
5-chloro-2-(4-pyridyl)-4-[1-(2,2,2-trifluoroethyl)-4-piperidyl]-1H-pyrimidin-6-one;
5-chloro-4-(2-oxa-7-azaspiro[3.5]nonan-7-yl)-2-(4-pyridyl)-1H-pyrimidin-6-one;
5-chloro-2-(4-pyridyl)-4-[4-(2,2,3,3-tetrafluoropropyl)piperazin-1-yl]-1H-pyrimidin-6-one;
5-chloro-2-(2-fluoro-4-pyridyl)-4-(4-fluorotetrahydropyran-4-yl)-1H-pyrimidin-6-one;
5-chloro-4-[(3S)-3-methyl-4-(2,2,2-trifluoroacetyl)piperazin-1-yl]-2-(4-pyridyl)-1H-pyrimidin-6-one;
5-chloro-2-(2-fluoro-4-pyridyl)-4-morpholino-1H-pyrimidin-6-one;
5-chloro-4-(3-fluoro-3-piperidyl)-2-(4-pyridyl)-1H-pyrimidin-6-one;
1-[5-chloro-6-oxo-2-(4-pyridyl)-1H-pyrimidin-4-yl]piperidine-4-carbonitrile;
5-chloro-4-(3-oxa-9-azabicyclo[3.3.1]nonan-9-yl)-2-(4-pyridyl)-1H-pyrimidin-6-one;
4-(4-tert-butylpiperazin-1-yl)-5-chloro-2-(4-pyridyl)-1H-pyrimidin-6-one;
tert-butyl 4-[5-chloro-2-(2-fluoro-4-pyridyl)-6-oxo-1H-pyrimidin-4-yl]piperidine-1-carboxylate;
5-chloro-4-morpholin-2-yl-2-(4-pyridyl)-1H-pyrimidin-6-one;
5-chloro-2-(2-fluoro-4-pyridyl)-4-[(3R)-3-(trifluoromethyl)piperazin-1-yl]-1H-pyrimidin-6-one;
5-chloro-4-[(3S)-3,4-dimethylpiperazin-1-yl]-2-(4-pyridyl)-1H-pyrimidin-6-one;
5-chloro-4-[3-(1,1-difluoroethyl)piperazin-1-yl]-2-(4-pyridyl)-1H-pyrimidin-6-one;
5-chloro-4-[(3S)-3-isopropylpiperazin-1-yl]-2-(4-pyridyl)-1H-pyrimidin-6-one;
4-[(3S)-4-acetyl-3-methyl-piperazin-1-yl]-5-chloro-2-(4-pyridyl)-1H-pyrimidin-6-one;
5-chloro-4-(4-fluoro-4-piperidyl)-2-(4-pyridyl)-1H-pyrimidin-6-one;
tert-butyl 4-[5-chloro-6-oxo-2-(4-pyridyl)-1H-pyrimidin-4-yl]-4-fluoro-piperidine-1-carboxylate;
5-chloro-4-[(3S)-3-methyl-4-(2,2,2-trifluoroethyl)piperazin-1-yl]-2-(4-pyridyl)-1H-pyrimidin-6-one;
4-[(3S)-3-tert-butylpiperazin-1-yl]-5-chloro-2-(4-pyridyl)-1H-pyrimidin-6-one;
5-chloro-4-(5,8-diazaspiro[3.5]nonan-8-yl)-2-(4-pyridyl)-1H-pyrimidin-6-one;
5-chloro-2-(4-pyridyl)-4-[2-(trifluoromethyl)morpholin-4-yl]-1H-pyrimidin-6-one;
4-[(3S)-3-tert-butylpiperazin-1-yl]-5-chloro-2-(2-fluoro-4-pyridyl)-1H-pyrimidin-6-one;
5-chloro-4-[(1S,4S)-2,5-diazabicyclo[2.2.1]heptan-2-yl]-2-(4-pyridyl)-1H-pyrimidin-6-one;
5-chloro-2-(2-fluoro-4-pyridyl)-4-piperazin-1-yl-1H-pyrimidin-6-one;
O1-tert-butyl O2-methyl (2S)-4-[5-chloro-6-oxo-2-(4-pyridyl)-1H-pyrimidin-4-yl]piperazine-1,2-dicarboxylate;
methyl (2S)-4-[5-chloro-6-oxo-2-(4-pyridyl)-1H-pyrimidin-4-yl]piperazine-2-carboxylate;
4-[(3S)-3-benzylpiperazin-1-yl]-5-chloro-2-(4-pyridyl)-1H-pyrimidin-6-one;
4-[(3R)-3-benzylpiperazin-1-yl]-5-chloro-2-(4-pyridyl)-1H-pyrimidin-6-one;
5-chloro-4-[(2R,5R)-2,5-dimethylpiperazin-1-yl]-2-(4-pyridyl)-1H-pyrimidin-6-one;
5-chloro-2-(2-chloro-4-pyridyl)-4-tetrahydropyran-4-yl-1H-pyrimidin-6-one;
5-chloro-4-(3-hydroxy-1-piperidyl)-2-(4-pyridyl)-1H-pyrimidin-6-one;
5-chloro-4-[3-(4-chlorophenyl)piperazin-1-yl]-2-(4-pyridyl)-1H-pyrimidin-6-one;
5-chloro-4-[3-(4-methoxyphenyl)piperazin-1-yl]-2-(4-pyridyl)-1H-pyrimidin-6-one;
5-chloro-4-(3,3-difluoro-1-piperidyl)-2-(2-fluoro-4-pyridyl)-1H-pyrimidin-6-one;
5-chloro-2-(2-fluoro-4-pyridyl)-4-[(3S)-3-isopropylpiperazin-1-yl]-1H-pyrimidin-6-one;
5-chloro-2-(2-fluoro-4-pyridyl)-4-[(3S)-3-methylpiperazin-1-yl]-1H-pyrimidin-6-one;
5-chloro-4-[(2S,5S)-2,5-dimethylpiperazin-1-yl]-2-(4-pyridyl)-1H-pyrimidin-6-one;
5-chloro-4-[(2R,5 S)-2,5-dimethylpiperazin-1-yl]-2-(4-pyridyl)-1H-pyrimidin-6-one;
5-chloro-4-[(3R)-3-(2-hydroxyethyl)piperazin-1-yl]-2-(4-pyridyl)-1H-pyrimidin-6-one;

5-chloro-4-[(3S)-3-(2-hydroxyethyl)piperazin-1-yl]-2-(4-pyridyl)-1H-pyrimidin-6-one;
5-chloro-4-[(3S)-3-(1-hydroxy-1-methyl-ethyl)piperazin-1-yl]-2-(4-pyridyl)-1H-pyrimidin-6-one;
5-chloro-2-(4-pyridyl)-4-[3-(trifluoromethyl)-1-piperidyl]-1H-pyrimidin-6-one;
tert-butyl 4-[5-chloro-6-oxo-2-(4-pyridyl)-1H-pyrimidin-4-yl]-3,6-dihydro-2H-pyridine-1-carboxylate;
5-chloro-2-(2-fluoro-4-pyridyl)-4-(3-isopropylpiperazin-1-yl)-1H-pyrimidin-6-one;
5-chloro-2-(4-pyridyl)-4-[3-(2-thienyl)piperazin-1-yl]-1H-pyrimidin-6-one;
5-chloro-4-[3-(3-hydroxyphenyl)piperazin-1-yl]-2-(4-pyridyl)-1H-pyrimidin-6-one;
5-chloro-4-[3-(3-methoxyphenyl)piperazin-1-yl]-2-(4-pyridyl)-1H-pyrimidin-6-one;
5-chloro-4-(3,3-dimethylpiperazin-1-yl)-2-(4-pyridyl)-1H-pyrimidin-6-one;
5-chloro-4-tetrahydropyran-4-yl-2-[2-(trifluoromethyl)-4-pyridyl]-1H-pyrimidin-6-one;
4-[(3R)-3-(aminomethyl)-1-piperidyl]-5-chloro-2-(2-fluoro-4-pyridyl)-1H-pyrimidin-6-one;
4-[(3S)-3-(aminomethyl)-1-piperidyl]-5-chloro-2-(2-fluoro-4-pyridyl)-1H-pyrimidin-6-one;
5-chloro-4-[(3R)-3-(1,1-difluoroethyl)piperazin-1-yl]-2-(4-pyridyl)-1H-pyrimidin-6-one;
5-chloro-4-[(2R)-2-methylpiperazin-1-yl]-2-(4-pyridyl)-1H-pyrimidin-6-one;
5-fluoro-4-[(3S)-3-isopropylpiperazin-1-yl]-2-(4-pyridyl)-1H-pyrimidin-6-one;
4-[(3 S,8aS)-3-isobutyl-3,4,6,7,8,8a-hexahydro-1H-pyrrolo[1,2-a]pyrazin-2-yl]-5-chloro-2-(4-pyridyl)-1H-pyrimidin-6-one;
4-[(3S)-3-tert-butylpiperazin-1-yl]-5-fluoro-2-(4-pyridyl)-1H-pyrimidin-6-one;
5-chloro-4-(1,4-oxazepan-4-yl)-2-(4-pyridyl)-1H-pyrimidin-6-one;
5-chloro-4-[(3R)-3-(1,1-difluoroethyl)piperazin-1-yl]-2-(2-fluoro-4-pyridyl)-1H-pyrimidin-6-one;
4-[(3S)-3-amino-1-piperidyl]-5-chloro-2-(2-fluoro-4-pyridyl)-1H-pyrimidin-6-one;
4-[(3S)-3-(aminomethyl)pyrrolidin-1-yl]-5-chloro-2-(2-fluoro-4-pyridyl)-1H-pyrimidin-6-one;
4-[(3R)-3-amino-1-piperidyl]-5-chloro-2-(2-fluoro-4-pyridyl)-1H-pyrimidin-6-one;
4-[(3S)-3-aminopyrrolidin-1-yl]-5-chloro-2-(2-fluoro-4-pyridyl)-1H-pyrimidin-6-one;
4-(4-amino-1-piperidyl)-5-chloro-2-(2-fluoro-4-pyridyl)-1H-pyrimidin-6-one;
4-[(3S)-3-tert-butylpiperazin-1-yl]-5-fluoro-2-(2-fluoro-4-pyridyl)-1H-pyrimidin-6-one;
5-bromo-4-[(3S)-3-tert-butylpiperazin-1-yl]-2-(4-pyridyl)-1H-pyrimidin-6-one;
5-chloro-2-(2-fluoro-4-pyridyl)-4-[2-methylpiperazin-1-yl]-1H-pyrimidin-6-one;
5-chloro-2-(2-fluoro-4-pyridyl)-4-[(2S)-2-methylpiperazin-1-yl]-1H-pyrimidin-6-one;
5-chloro-2-(2-fluoro-4-pyridyl)-4-[(2R)-2-methylpiperazin-1-yl]-1H-pyrimidin-6-one;
5-bromo-4-[(3S)-3-isopropylpiperazin-1-yl]-2-(4-pyridyl)-1H-pyrimidin-6-one;
4-[(3S)-3-isopropylpiperazin-1-yl]-6-oxo-2-(4-pyridyl)-1H-pyrimidine-5-carbonitrile;
4-[(3S)-3-tert-butylpiperazin-1l-yl]-6-oxo-2-(4-pyridyl)-1H-pyrimidine-5-carbonitrile;
5-chloro-4-[(3S)-3-methylmorpholin-4-yl]-2-(4-pyridyl)-1H-pyrimidin-6-one;
5-chloro-4-(3-propylmorpholin-4-yl)-2-(4-pyridyl)-1H-pyrimidin-6-one;
5-chloro-4-(3-isobutylmorpholin-4-yl)-2-(4-pyridyl)-1H-pyrimidin-6-one;
5-chloro-4-[(2R)-2-methylpiperazin-1-yl]-2-(4-pyridyl)-1H-pyrimidin-6-one;
5-chloro-4-[(2 S)-2-ethylpiperazin-1-yl]-2-(4-pyridyl)-1H-pyrimidin-6-one;
5-chloro-4-[(2S)-2-isopropylpiperazin-1-yl]-2-(4-pyridyl)-1H-pyrimidin-6-one;
5-chloro-4-[(2R)-2-ethylpiperazin-1-yl]-2-(4-pyridyl)-1H-pyrimidin-6-one;
5-chloro-4-(3-phenylmorpholin-4-yl)-2-(4-pyridyl)-1H-pyrimidin-6-one;
4-[(3R)-3-aminopyrrolidin-1-yl]-5-chloro-2-(2-fluoro-4-pyridyl)-1H-pyrimidin-6-one;
4-(3-aminoazetidin-1l-yl)-5-chloro-2-(2-fluoro-4-pyridyl)-1H-pyrimidin-6-one;
5-chloro-2-(2-fluoro-4-pyridyl)-4-[(2S)-2-methylpiperazin-1-yl]-1H-pyrimidin-6-one;
5-chloro-2-(2-fluoro-4-pyridyl)-4-[(3R)-3-isopropylpiperazin-1-yl]-1H-pyrimidin-6-one;
5-chloro-2-(2-fluoro-4-pyridyl)-4-[(3R)-3-methylmorpholin-4-yl]-1H-pyrimidin-6-one;
5-chloro-2-(2-fluoro-4-pyridyl)-4-(4-piperidyloxy)-1H-pyrimidin-6-one;
4-[(3R)-3-aminoazepan-1l-yl]-5-chloro-2-(2-fluoro-4-pyridyl)-1H-pyrimidin-6-one;
5-chloro-2-(2-fluoro-4-pyridyl)-4-[[(3R)-3-piperidyl]oxy]-1H-pyrimidin-6-one;
5-chloro-2-(2-fluoro-4-pyridyl)-4-[[(3S)-3-piperidyl]oxy]-1H-pyrimidin-6-one;
5-chloro-2-(2-fluoro-4-pyridyl)-4-[(3R)-3-(1-hydroxy-1-methyl-ethyl)piperazin-1-yl]-1H-pyrimidin-6-one;
4-[(3S)-3-aminoazepan-1-yl]-5-chloro-2-(2-fluoro-4-pyridyl)-1H-pyrimidin-6-one;
4-[(4aS,8aS)-2,3,4a,5,6,7,8,8a-octahydrobenzo[b][1,4]oxazin-4-yl]-5-chloro-2-(2-fluoro-4-pyridyl)-1H-pyrimidin-6-one;
5-chloro-2-(2-fluoro-4-pyridyl)-4-[(3S)-3-methylmorpholin-4-yl]-1H-pyrimidin-6-one;
5-chloro-2-(2-fluoro-4-pyridyl)-4-(3-oxa-9-azabicyclo[3.3.1]nonan-9-yl)-1H-pyrimidin-6-one;
5-chloro-4-[(3,3-dimethyl-4-piperidyl)-methyl-amino]-2-(2-fluoro-4-pyridyl)-1H-pyrimidin-6-one;
5-chloro-4-[(3,3-dimethyl-4-piperidyl)amino]-2-(2-fluoro-4-pyridyl)-1H-pyrimidin-6-one;
5-chloro-4-[(3 S,5R)-3,5-dihydroxy-1-piperidyl]-2-(2-fluoro-4-pyridyl)-1H-pyrimidin-6-one;
5-chloro-2-(2-fluoro-4-pyridyl)-4-[3-(morpholinomethyl)pyrrolidin-1-yl]-1H-pyrimidin-6-one;
5-chloro-4-(2,6-diazaspiro[4.5]decan-2-yl)-2-(2-fluoro-4-pyridyl)-1H-pyrimidin-6-one;
5-chloro-2-(2-fluoro-4-pyridyl)-4-[(3R)-3-hydroxypyrrolidin-1-yl]-1H-pyrimidin-6-one;
5-chloro-2-(2-fluoro-4-pyridyl)-4-[(3S)-3-hydroxypyrrolidin-1-yl]-1H-pyrimidin-6-one;
4-(3,4a,5,6,7,7a-hexahydro-2H-pyrrolo[3,4-b][1,4]oxazin-4-yl)-5-chloro-2-(2-fluoro-4-pyridyl)-1H-pyrimidin-6-one;
5-chloro-4-(1,7-diazaspiro[4.4]nonan-7-yl)-2-(2-fluoro-4-pyridyl)-1H-pyrimidin-6-one;
5-chloro-4-(2,7-diazaspiro[4.4]nonan-2-yl)-2-(2-fluoro-4-pyridyl)-1H-pyrimidin-6-one;
4-[(3R)-3-(aminomethyl)pyrrolidin-1-yl]-5-chloro-2-(2-fluoro-4-pyridyl)-1H-pyrimidin-6-one;

5-chloro-4-(2,9-diazaspiro[4.5]decan-2-yl)-2-(2-fluoro-4-pyridyl)-1H-pyrimidin-6-one;
4-(2,3,3a,4,5,6,7,7a-octahydropyrrolo[2,3-c]pyridin-1-yl)-5-chloro-2-(2-fluoro-4-pyridyl)-1H-pyrimidin-6-one;
5-chloro-2-(2-fluoro-4-pyridyl)-4-(4-piperidylamino)-1H-pyrimidin-6-one;
5-chloro-2-(2-fluoro-4-pyridyl)-4-(6-hydroxy-1,4-diazepan-1-yl)-1H-pyrimidin-6-one;
1-[5-chloro-2-(2-fluoro-4-pyridyl)-6-oxo-1H-pyrimidin-4-yl]-1,4-diazepan-6-one;
5-chloro-2-(2-fluoro-4-pyridyl)-4-tetrahydropyran-4-ylsulfanyl-1H-pyrimidin-6-one;
5-chloro-2-(2-fluoro-4-pyridyl)-4-(3-oxa-8-azabicyclo[3.2.1]octan-8-yl)-1H-pyrimidin-6-one;
4-(2,3,3a,4,5,6,7,7a-octahydropyrrolo[3,2-b]pyridin-1-yl)-5-chloro-2-(2-fluoro-4-pyridyl)-1H-pyrimidin-6-one;
5-chloro-2-(2-fluoro-4-pyridyl)-4-(morpholin-3-ylmethylamino)-1H-pyrimidin-6-one;
4-(2,3,3a,4,5,6,7,7a-octahydropyrrolo[3,2-c]pyridin-1-yl)-5-chloro-2-(2-fluoro-4-pyridyl)-1H-pyrimidin-6-one;
4-(2,3,3a,4,6,6a-hexahydro-1H-pyrrolo[3,4-c]pyrrol-5-yl)-5-chloro-2-(2-fluoro-4-pyridyl)-1H-pyrimidin-6-one;
5-chloro-2-(2-fluoro-4-pyridyl)-4-(1-oxa-4,9-diazaspiro[5.5]undecan-4-yl)-1H-pyrimidin-6-one;
5-chloro-2-(2-fluoro-4-pyridyl)-4-(4-piperidylsulfanyl)-1H-pyrimidin-6-one;
5-chloro-4-(6,6-difluoro-1,4-diazepan-1-yl)-2-(2-fluoro-4-pyridyl)-1H-pyrimidin-6-one;
4-(azetidin-3-yloxy)-5-chloro-2-(2-fluoro-4-pyridyl)-1H-pyrimidin-6-one;
5-chloro-2-(2-fluoro-4-pyridyl)-4-(3-tetrahydropyran-4-ylpyrrolidin-1-yl)-1H-pyrimidin-6-one;
4-[(1R,3S)-3-aminocyclopentoxy]-5-chloro-2-(2-fluoro-4-pyridyl)-1H-pyrimidin-6-one;
5-chloro-2-(2-fluoro-4-pyridyl)-4-[(3R)-3-(methylamino)-1-piperidyl]-1H-pyrimidin-6-one;
5-chloro-2-(2-fluoro-4-pyridyl)-4-[(3S)-3-(methylamino)-1-piperidyl]-1H-pyrimidin-6-one;
5-chloro-4-(2,6-diazaspiro[3.3]heptan-2-yl)-2-(2-fluoro-4-pyridyl)-1H-pyrimidin-6-one;
5-chloro-2-(2-fluoro-4-pyridyl)-4-[methyl(tetrahydropyran-4-yl)amino]-1H-pyrimidin-6-one;
5-chloro-4-(2,8-diazaspiro[4.5]decan-2-yl)-2-(2-fluoro-4-pyridyl)-1H-pyrimidin-6-one;
1-[5-chloro-2-(2-fluoro-4-pyridyl)-6-oxo-1H-pyrimidin-4-yl]-N-methyl-piperidine-4-carboxamide;
N-[1-[5-chloro-2-(2-fluoro-4-pyridyl)-6-oxo-1H-pyrimidin-4-yl]-4-piperidyl]acetamide;
8-[5-chloro-2-(2-fluoro-4-pyridyl)-6-oxo-1H-pyrimidin-4-yl]-1,3,8-triazaspiro[4.5]decane-2,4-dione;
5-chloro-2-(2-fluoro-4-pyridyl)-4-(4-oxo-1-piperidyl)-1H-pyrimidin-6-one;
4-[(3R,4R)-3-amino-4-hydroxy-1-piperidyl]-5-chloro-2-(2-fluoro-4-pyridyl)-1H-pyrimidin-6-one;
5-chloro-4-(1,4-dioxa-8-azaspiro[4.5]decan-8-yl)-2-(2-fluoro-4-pyridyl)-1H-pyrimidin-6-one;
5-chloro-2-(2-fluoro-4-pyridyl)-4-(oxetan-3-yloxy)-1H-pyrimidin-6-one;
5-chloro-2-(2-fluoro-4-pyridyl)-4-[(3S)-tetrahydrofuran-3-yl]oxy-1H-pyrimidin-6-one;
5-chloro-2-(2-fluoro-4-pyridyl)-4-(morpholinomethyl)-1H-pyrimidin-6-one;
5-chloro-2-(2-fluoro-4-pyridyl)-4-(piperazin-1-ylmethyl)-1H-pyrimidin-6-one;
5-chloro-4-[(2 S,6R)-2,6-dimethylmorpholin-4-yl]-2-(2-fluoro-4-pyridyl)-1H-pyrimidin-6-one;
4-[(4a5,7a5)-3,4,4a,5,7,7a-hexahydro-2H-pyrrolo[3,4-b][1,4]oxazin-6-yl]-5-chloro-2-(2-fluoro-4-pyridyl)-1H-pyrimidin-6-one;
5-chloro-2-(2-fluoro-4-pyridyl)-4-(1-oxa-8-azaspiro[4.5]decan-8-yl)-1H-pyrimidin-6-one;
4-[5-chloro-2-(2-fluoro-4-pyridyl)-6-oxo-1H-pyrimidin-4-yl]piperazine-1-carboxamide;
4-[5-chloro-2-(2-fluoro-4-pyridyl)-6-oxo-1H-pyrimidin-4-yl]-N,N-dimethyl-piperazine-1-carboxamide;
5-chloro-4-(1,8-diazaspiro[4.5]decan-8-yl)-2-(2-fluoro-4-pyridyl)-1H-pyrimidin-6-one;
5-chloro-4-(2,8-diazaspiro[4.5]decan-8-yl)-2-(2-fluoro-4-pyridyl)-1H-pyrimidin-6-one;
4-(2,3,3a,5,6,6a-hexahydro-1H-pyrrolo[3,2-b]pyrrol-4-yl)-5-chloro-2-(2-fluoro-4-pyridyl)-1H-pyrimidin-6-one;
5-chloro-2-(2-fluoro-4-pyridyl)-4-(4-morpholino-1-piperidyl)-1H-pyrimidin-6-one;
5-chloro-2-(2-fluoro-4-pyridyl)-4-[2-(1-piperidylmethyl)morpholin-4-yl]-1H-pyrimidin-6-one;
1-[5-chloro-2-(2-fluoro-4-pyridyl)-6-oxo-1H-pyrimidin-4-yl]azepan-4-one;
5-chloro-4-(4,4-difluoroazepan-1-yl)-2-(2-fluoro-4-pyridyl)-1H-pyrimidin-6-one;
5-chloro-4-[(2R)-2-ethylmorpholin-4-yl]-2-(2-fluoro-4-pyridyl)-1H-pyrimidin-6-one;
5-chloro-4-(2,6-diazaspiro[3.4]octan-6-yl)-2-(2-fluoro-4-pyridyl)-1H-pyrimidin-6-one;
5-chloro-2-(2-fluoro-4-pyridyl)-4-[2-(morpholinomethyl)pyrrolidin-1-yl]-1H-pyrimidin-6-one;
(2R)-1-[5-chloro-2-(2-fluoro-4-pyridyl)-6-oxo-1H-pyrimidin-4-yl]pyrrolidine-2-carboxamide;
(2S)-1-[5-chloro-2-(2-fluoro-4-pyridyl)-6-oxo-1H-pyrimidin-4-yl]pyrrolidine-2-carboxamide;
(3R)-1-[5-chloro-2-(2-fluoro-4-pyridyl)-6-oxo-1H-pyrimidin-4-yl]pyrrolidine-3-carboxamide;
5-chloro-4-(1,9-diazaspiro[4.5]decan-9-yl)-2-(2-fluoro-4-pyridyl)-1H-pyrimidin-6-one;
(3S)-1-[5-chloro-2-(2-fluoro-4-pyridyl)-6-oxo-1H-pyrimidin-4-yl]pyrrolidine-3-carboxamide;
4-(3-amino-4-fluoro-1-piperidyl)-5-chloro-2-(2-fluoro-4-pyridyl)-1H-pyrimidin-6-one;
1-[5-chloro-2-(2-fluoro-4-pyridyl)-6-oxo-1H-pyrimidin-4-yl]-N-methyl-piperidine-3-carboxamide;
N-[1-[5-chloro-2-(2-fluoro-4-pyridyl)-6-oxo-1H-pyrimidin-4-yl]-4-piperidyl]-2-methyl-propanamide;
1-[5-chloro-2-(2-fluoro-4-pyridyl)-6-oxo-1H-pyrimidin-4-yl]-N-isopropyl-piperidine-4-carboxamide;
1-[5-chloro-2-(2-fluoro-4-pyridyl)-6-oxo-1H-pyrimidin-4-yl]-N-(2-hydroxyethyl)piperidine-4-carboxamide;
1-[5-chloro-2-(2-fluoro-4-pyridyl)-6-oxo-1H-pyrimidin-4-yl]-N-ethyl-piperidine-4-carboxamide;
5-chloro-4-[(3R)-3-ethylmorpholin-4-yl]-2-(2-fluoro-4-pyridyl)-1H-pyrimidin-6-one;
5-chloro-4-[(3S)-3-ethylmorpholin-4-yl]-2-(2-fluoro-4-pyridyl)-1H-pyrimidin-6-one;
5-chloro-2-(2-fluoro-4-pyridyl)-4-[(2R)-2-methylmorpholin-4-yl]-1H-pyrimidin-6-one;
5-chloro-2-(2-fluoro-4-pyridyl)-4-(1,4-oxazepan-4-yl)-1H-pyrimidin-6-one;
5-chloro-4-(2,7-diazaspiro[4.5]decan-7-yl)-2-(2-fluoro-4-pyridyl)-1H-pyrimidin-6-one;
5-chloro-4-(1,7-diazaspiro[4.4]nonan-1-yl)-2-(2-fluoro-4-pyridyl)-1H-pyrimidin-6-one;
5-chloro-4-(1,9-diazaspiro[4.5]decan-1-yl)-2-(2-fluoro-4-pyridyl)-1H-pyrimidin-6-one;

4-[(3aS,6aS)-3,3a,4,5,6,6a-hexahydro-2H-pyrrolo[2,3-c]pyrrol-1-yl]-5-chloro-2-(2-fluoro-4-pyridyl)-1H-pyrimidin-6-one;
5-chloro-4-(3,8-diazabicyclo[3.2.1]octan-8-yl)-2-(2-fluoro-4-pyridyl)-1H-pyrimidin-6-one;
5-chloro-4-(1,8-diazaspiro[4.5]decan-1-yl)-2-(2-fluoro-4-pyridyl)-1H-pyrimidin-6-one;
4-(3,4,4a, 5,6,7,8,8a-octahydro-2H-1,5-naphthyridin-1-yl)-5-chloro-2-(2-fluoro-4-pyridyl)-1H-pyrimidin-6-one;
5-chloro-2-(2-fluoro-4-pyridyl)-4-[4-(4-methylpiperazin-1-yl)-1-piperidyl]-1H-pyrimidin-6-one;
5-chloro-4-[ethyl(tetrahydropyran-4-yl)amino]-2-(2-fluoro-4-pyridyl)-1H-pyrimidin-6-one;
5-chloro-2-(2-fluoro-4-pyridyl)-4-[methyl-[(3S)-3-piperidyl]amino]-1H-pyrimidin-6-one;
5-chloro-2-(2-fluoro-4-pyridyl)-4-[methyl-[(3R)-3-piperidyl]amino]-1H-pyrimidin-6-one;
5-chloro-4-(3,3-dimethylmorpholin-4-yl)-2-(2-fluoro-4-pyridyl)-1H-pyrimidin-6-one;
5-chloro-4-(1,4-diazepan-1-yl)-2-(2-fluoro-4-pyridyl)-1H-pyrimidin-6-one;
5-chloro-2-(2-fluoro-4-pyridyl)-4-(6-hydroxy-1,4-oxazepan-4-yl)-1H-pyrimidin-6-one;
4-[5-chloro-2-(2-fluoro-4-pyridyl)-6-oxo-1H-pyrimidin-4-yl]-1,4-oxazepan-6-one;
5-chloro-4-(6,8-dihydro-5H-[1,2,4]triazolo[4,3-a]pyrazin-7-yl)-2-(2-fluoro-4-pyridyl)-1H-pyrimidin-6-one;
5-chloro-2-(2-fluoro-4-pyridyl)-4-(3-isopropyl-6,8-dihydro-5H-[1,2,4]triazolo[4,3-a]pyrazin-7-yl)-1H-pyrimidin-6-one;
4-[(3S)-3-anilino-1-piperidyl]-5-chloro-2-(2-fluoro-4-pyridyl)-1H-pyrimidin-6-one;
5-chloro-2-(2-fluoro-4-pyridyl)-4-[(3S)-3-(methylamino)pyrrolidin-1-yl]-1H-pyrimidin-6-one;
5-chloro-4-[(3S)-3-(dimethylamino)pyrrolidin-1l-yl]-2-(2-fluoro-4-pyridyl)-1H-pyrimidin-6-one;
4-[(3S)-3-amino-3-methyl-pyrrolidin-1-yl]-5-chloro-2-(2-fluoro-4-pyridyl)-1H-pyrimidin-6-one;
4-(1,2,3,3a,5,6,7,7a-octahydropyrrolo[3,2-b]pyridin-4-yl)-5-chloro-2-(2-fluoro-4-pyridyl)-1H-pyrimidin-6-one;
N-[(3S)-1-[5-chloro-2-(2-fluoro-4-pyridyl)-6-oxo-1H-pyrimidin-4-yl]pyrrolidin-3-yl]acetamide;
5-chloro-4-(2,5S-dimethylmorpholin-4-yl)-2-(2-fluoro-4-pyridyl)-1H-pyrimidin-6-one;
5-chloro-2-(2-fluoro-4-pyridyl)-4-(2-oxa-7-azaspiro[3.4]octan-7-yl)-1H-pyrimidin-6-one;
5-chloro-2-(4-pyridyl)-4-(2,2,6,6-tetrafluoromorpholin-4-yl)-1H-pyrimidin-6-one;
5-chloro-2-(2-fluoro-4-pyridyl)-4-[2-(phenoxymethyl)morpholin-4-yl]-1H-pyrimidin-6-one;
5-chloro-2-(2-fluoro-4-pyridyl)-4-pyrrolidin-1-yl-1H-pyrimidin-6-one;
5-chloro-2-(2-fluoro-4-pyridyl)-4-(1-piperidyl)-1H-pyrimidin-6-one;
5-chloro-2-(2-fluoro-4-pyridyl)-4-[(25)-2-methylpyrrolidin-1-yl]-1H-pyrimidin-6-one;
5-chloro-2-(2-fluoro-4-pyridyl)-4-[(2R)-2-methylpyrrolidin-1-yl]-1H-pyrimidin-6-one;
5-chloro-2-(2-fluoro-4-pyridyl)-4-[(2S)-2-methyl-1-piperidyl]-1H-pyrimidin-6-one;
5-chloro-2-(2-fluoro-4-pyridyl)-4-[(2R)-2-methyl-1-piperidyl]-1H-pyrimidin-6-one;
5-chloro-4-(6,6-difluoro-1,4-oxazepan-4-yl)-2-(2-fluoro-4-pyridyl)-1H-pyrimidin-6-one;
5-chloro-4-[(3R,5R)-3,5-dimethylmorpholin-4-yl]-2-(2-fluoro-4-pyridyl)-1H-pyrimidin-6-one;
5-chloro-4-[(3 S,5 S)-3,5-dimethylmorpholin-4-yl]-2-(2-fluoro-4-pyridyl)-1H-pyrimidin-6-one;
5-chloro-4-[(3 S,5R)-3,5-dimethylmorpholin-4-yl]-2-(2-fluoro-4-pyridyl)-1H-pyrimidin-6-one;
4-(4-aminophenoxy)-5-chloro-2-(2-fluoro-4-pyridyl)-1H-pyrimidin-6-one;
1-[5-chloro-2-(2-fluoro-4-pyridyl)-6-oxo-1H-pyrimidin-4-yl]-1,4-diazepan-5-one;
4-[benzyl(methyl)amino]-5-chloro-2-(2-fluoro-4-pyridyl)-1H-pyrimidin-6-one;
4-(benzylamino)-5-chloro-2-(2-fluoro-4-pyridyl)-1H-pyrimidin-6-one;
(2R)-1-[5-chloro-2-(2-fluoro-4-pyridyl)-6-oxo-1H-pyrimidin-4-yl]piperazine-2-carbonitrile;
(2S)-1-[5-chloro-2-(2-fluoro-4-pyridyl)-6-oxo-1H-pyrimidin-4-yl]piperazine-2-carbonitrile;
5-chloro-2-(2-fluoro-4-pyridyl)-4-[3-(trifluoromethyl)-6,8-dihydro-5H-[1,2,4]triazolo[4,3-a]pyrazin-7-yl]-1H-pyrimidin-6-one;
5-chloro-4-(1,9-dioxa-4-azaspiro[5.5]undecan-4-yl)-2-(2-fluoro-4-pyridyl)-1H-pyrimidin-6-one;
5-chloro-4-(1,4-diazabicyclo[3.2.2]nonan-4-yl)-2-(2-fluoro-4-pyridyl)-1H-pyrimidin-6-one;
5-chloro-2-(2-fluoro-4-pyridyl)-4-[(3R)-3-methoxy-1-piperidyl]-1H-pyrimidin-6-one;
5-chloro-2-(2-fluoro-4-pyridyl)-4-[(3S)-3-methoxy-1-piperidyl]-1H-pyrimidin-6-one;
5-chloro-4-(6,8-dihydro-5H-imidazo[1,5-a]pyrazin-7-yl)-2-(2-fluoro-4-pyridyl)-1H-pyrimidin-6-one;
4-benzyloxy-5-chloro-2-(2-fluoro-4-pyridyl)-1H-pyrimidin-6-one;
5-chloro-2-(2-fluoro-4-pyridyl)-4-[(3S)-3-(1-hydroxycyclopropyl)piperazin-1-yl]-1H-pyrimidin-6-one;
4-[(8aS)-7,7-difluoro-1,3,4,6,8,8a-hexahydropyrrolo[1,2-a]pyrazin-2-yl]-5-chloro-2-(2-fluoro-4-pyridyl)-1H-pyrimidin-6-one;
4-[(8aS)-3,4,6,7,8,8a-hexahydro-1H-pyrrolo[1,2-a]pyrazin-2-yl]-5-chloro-2-(2-fluoro-4-pyridyl)-1H-pyrimidin-6-one;
4-[(3 S,8aS)-3-isobutyl-3,4,6,7,8,8a-hexahydro-1H-pyrrolo[1,2-a]pyrazin-2-yl]-5-chloro-2-(2-fluoro-4-pyridyl)-1H-pyrimidin-6-one;
5-chloro-4-[4-(2,2-difluoroethyl)piperazin-1-yl]-2-(2-fluoro-4-pyridyl)-1H-pyrimidin-6-one;
5-chloro-2-(2-fluoro-4-pyridyl)-4-[4-(1H-1,2,4-triazol-3-yl)piperazin-1-yl]-1H-pyrimidin-6-one;
5-chloro-2-(2-fluoro-4-pyridyl)-4-[5-(trifluoromethyl)-1,4-diazepan-1-yl]-1H-pyrimidin-6-one;
5-chloro-4-(3,3-dimethylpiperazin-1-yl)-2-(2-fluoro-4-pyridyl)-1H-pyrimidin-6-one;
5-chloro-2-(2-fluoro-4-pyridyl)-4-(4-methyl-1,4-diazepan-1-yl)-1H-pyrimidin-6-one;
5-chloro-2-(2-fluoro-4-pyridyl)-4-(7-methyl-1,4-diazepan-1-yl)-1H-pyrimidin-6-one;
5-chloro-2-(2-fluoro-4-pyridyl)-4-[(2R)-2-methyl-1,4-diazepan-1-yl]-1H-pyrimidin-6-one;
5-chloro-4-(6,8-dihydro-5H-imidazo[1,2-a]pyrazin-7-yl)-2-(2-fluoro-4-pyridyl)-1H-pyrimidin-6-one;
5-chloro-2-(2-fluoro-4-pyridyl)-4-(5,6,8,9-tetrahydro-[1,2,4]triazolo[4,3-d][1,4]diazepin-7-yl)-1H-pyrimidin-6-one;
5-chloro-2-(2-fluoro-4-pyridyl)-4-[4-(2,2,2-trifluoroethyl)-1,4-diazepan-1-yl]-1H-pyrimidin-6-one;
5-chloro-2-(2-fluoro-4-pyridyl)-4-(3-methyl-1,4-oxazepan-4-yl)-1H-pyrimidin-6-one;
5-chloro-4-(2,2-dimethylmorpholin-4-yl)-2-(2-fluoro-4-pyridyl)-1H-pyrimidin-6-one;

5-chloro-4-(2,2-dimethyl-1,4-oxazepan-4-yl)-2-(2-fluoro-4-pyridyl)-1H-pyrimidin-6-one;
5-chloro-4-[5,8-dimethyl-3-(trifluoromethyl)-6,8-dihydro-5H-[1,2,4]triazolo[4,3-a]pyrazin-7-yl]-2-(2-fluoro-4-pyridyl)-1H-pyrimidin-6-one;
5-chloro-4-[(2R,5R)-2,5-dimethylmorpholin-4-yl]-2-(2-fluoro-4-pyridyl)-1H-pyrimidin-6-one;
5-chloro-4-(2,2-dimethylpiperazin-1-yl)-2-(2-fluoro-4-pyridyl)-1H-pyrimidin-6-one;
5-chloro-4-(2,4-dimethyl-1,4-diazepan-1-yl)-2-(2-fluoro-4-pyridyl)-1H-pyrimidin-6-one;
5-chloro-4-(2,3-dimethylmorpholin-4-yl)-2-(2-fluoro-4-pyridyl)-1H-pyrimidin-6-one;
5-chloro-2-(2-fluoro-4-pyridyl)-4-(5-methyl-1,4-diazepan-1-yl)-1H-pyrimidin-6-one;
5-chloro-4-(6-fluoro-6-methyl-1,4-diazepan-1-yl)-2-(2-fluoro-4-pyridyl)-1H-pyrimidin-6-one;
5-chloro-2-(2-fluoro-4-pyridyl)-4-[(2R,5 S)-2-methyl-5-(trifluoromethyl)piperazin-1-yl]-1H-pyrimidin-6-one;
2-[4-[5-chloro-2-(2-fluoro-4-pyridyl)-6-oxo-1H-pyrimidin-4-yl]-6,6-difluoro-1,4-diazepan-1-yl]acetamide;
5-chloro-2-(2-fluoro-4-pyridyl)-4-tetrahydropyran-4-yloxy-1H-pyrimidin-6-one;
2-[(2S)-4-[5-chloro-2-(2-fluoro-4-pyridyl)-6-oxo-1H-pyrimidin-4-yl]piperazin-2-yl]acetonitrile;
5-chloro-2-(2-fluoro-4-pyridyl)-4-[2-(trifluoromethyl)piperazin-1-yl]-1H-pyrimidin-6-one;
5-chloro-4-[2-(difluoromethyl)piperazin-1-yl]-2-(2-fluoro-4-pyridyl)-1H-pyrimidin-6-one;
5-chloro-4-(4,7-diazaspiro[2.5]octan-4-yl)-2-(2-fluoro-4-pyridyl)-1H-pyrimidin-6-one;
cis-5-chloro-2-(2-fluoro-4-pyridyl)-4-[2-methyl-5-(trifluoromethyl)piperazin-1-yl]-1H-pyrimidin-6-one;
cis-5-chloro-2-(2-fluoro-4-pyridyl)-4-[2-methyl-5-(trifluoromethyl)piperazin-1-yl]-1H-pyrimidin-6-one;
5-chloro-2-(2-fluoro-4-pyridyl)-4-[6-(trifluoromethyl)-1,4-diazepan-1-yl]-1H-pyrimidin-6-one;
5-chloro-4-(6-fluoro-1,4-diazepan-1-yl)-2-(2-fluoro-4-pyridyl)-1H-pyrimidin-6-one;
5-chloro-4-(6,6-difluoro-1,4-diazepan-1-yl)-2-(4-pyridyl)-1H-pyrimidin-6-one;
5-chloro-4-[2-(difluoromethyl)piperazin-1-yl]-2-(2-fluoro-4-pyridyl)-1H-pyrimidin-6-one;
5-chloro-4-[2R-(difluoromethyl)piperazin-1-yl]-2-(2-fluoro-4-pyridyl)-1H-pyrimidin-6-one;
5-chloro-4-[(2(S)-(difluoromethyl)piperazin-1-yl]-2-(2-fluoro-4-pyridyl)-1H-pyrimidin-6-one;
5-chloro-4-[(2(R)-(difluoromethyl)piperazin-1-yl]-2-(2-fluoro-4-pyridyl)-1H-pyrimidin-6-one;
5-chloro-4-[(2(S)-(difluoromethyl)piperazin-1-yl]-2-(2-fluoro-4-pyridyl)-1H-pyrimidin-6-one
5-chloro-2-(2-fluoro-4-pyridyl)-4-[2 S-(trifluoromethyl)piperazin-1-yl]-1H-pyrimidin-6-one;
5-chloro-2-(2-fluoro-4-pyridyl)-4-[2(R)-(trifluoromethyl)piperazin-1-yl]-1H-pyrimidin-6-one;
5-chloro-4-[6-fluoro-1,4-diazepan-1-yl]-2-(2-fluoro-4-pyridyl)-1H-pyrimidin-6-one;
5-chloro-4-[6R-fluoro-1,4-diazepan-1-yl]-2-(2-fluoro-4-pyridyl)-1H-pyrimidin-6-one;
5-chloro-4-[6S-fluoro-1,4-diazepan-1-yl]-2-(2-fluoro-4-pyridyl)-1H-pyrimidin-6-one;
5-chloro-2-(2-fluoro-4-pyridyl)-4-[6 S-(trifluoromethyl)-1,4-diazepan-1-yl]-1H-pyrimidin-6-one;
5-chloro-2-(2-fluoro-4-pyridyl)-4-[6R-(trifluoromethyl)-1,4-diazepan-1-yl]-1H-pyrimidin-6-one;
5-chloro-2-(4-pyridyl)-4-[2-(trifluoromethyl)piperazin-1-yl]-1H-pyrimidin-6-one;
5-chloro-2-(4-pyridyl)-4-[2R-(trifluoromethyl)piperazin-1-yl]-1H-pyrimidin-6-one;
5-chloro-2-(4-pyridyl)-4-[2S-(trifluoromethyl)piperazin-1-yl]-1H-pyrimidin-6-one;
5-chloro-2-(3-fluoro-4-pyridyl)-4-[(2R)-2-methylpiperazin-1-yl]-1H-pyrimidin-6-one;
5-chloro-4-[3-cyclopropylpiperazin-1-yl]-2-(2-fluoro-4-pyridyl)-1H-pyrimidin-6-one;
5-chloro-4-[3-cyclopropylpiperazin-1-yl]-2-(2-fluoro-4-pyridyl)-1H-pyrimidin-6-one;
5-chloro-4-(6,6-difluoro-1,4-diazepan-1-yl)-2-(3-fluoro-4-pyridyl)-1H-pyrimidin-6-one;
5-chloro-4-[2-(difluoromethyl)piperazin-1-yl]-2-(4-pyridyl)-1H-pyrimidin-6-one;
5-chloro-4-[2-(1,1-difluoroethyl)piperazin-1-yl]-2-(2-fluoro-4-pyridyl)-1H-pyrimidin-6-one;
5-chloro-4-[3-(1-fluoro-1-methyl-ethyl)piperazin-1-yl]-2-(2-fluoro-4-pyridyl)-1H-pyrimidin-6-one;
5-chloro-4-[3-(1-fluoro-1-methyl-ethyl)piperazin-1-yl]-2-(2-fluoro-4-pyridyl)-1H-pyrimidin-6-one;
5-chloro-2-(2-chloro-4-pyridyl)-4-(6,6-difluoro-1,4-diazepan-1-yl)-1H-pyrimidin-6-one; and
5-chloro-4-(6,6-difluoro-4-methyl-1,4-diazepan-1-yl)-2-(2-fluoro-4-pyridyl)-1H-pyrimidin-6-one.

In another embodiment, the compound of the invention, or a pharmaceutically acceptable salt or solvate thereof, is selected from a group consisting of the following:
tert-butyl 4-[5-chloro-6-oxo-2-(4-pyridyl)-1H-pyrimidin-4-yl]piperidine-1-carboxylate;
5-chloro-4-(4-piperidyl)-2-(4-pyridyl)-1H-pyrimidin-6-one;
5-bromo-2-(4-pyridyl)-4-tetrahydropyran-4-yl-1H-pyrimidin-6-one;
5-iodo-2-(4-pyridyl)-4-tetrahydropyran-4-yl-1H-pyrimidin-6-one;
5-fluoro-2-(4-pyridyl)-4-tetrahydropyran-4-yl-1H-pyrimidin-6-one;
5-chloro-2-(4-pyridyl)-4-tetrahydropyran-4-yl-1H-pyrimidin-6-one;
5-chloro-2-(4-pyridyl)-4-pyrrolidin-2-yl-1H-pyrimidin-6-one;
5-chloro-4-(3-piperidyl)-2-(4-pyridyl)-1H-pyrimidin-6-one;
5-chloro-4-(4-methyltetrahydropyran-4-yl)-2-(4-pyridyl)-1H-pyrimidin-6-one;
5-chloro-2-(2-fluoro-4-pyridyl)-4-(4-methyltetrahydropyran-4-yl)-1H-pyrimidin-6-one;
5-chloro-2-(4-pyridyl)-4-pyrrolidin-3-yl-1H-pyrimidin-6-one;
5-chloro-2-(4-pyridyl)-4-tetrahydrofuran-3-yl-1H-pyrimidin-6-one;
5-chloro-2-(2-fluoro-4-pyridyl)-4-tetrahydropyran-4-yl-1H-pyrimidin-6-one;
5-chloro-4-(isopropyltetrahydropyran-4-yl)-2-(4-pyridyl)-1H-pyrimidin-6-one;
5-chloro-2-(4-pyridyl)-4-tetrahydropyran-2-yl-1H-pyrimidin-6-one;
5-chloro-2-(4-pyridyl)-4-tetrahydropyran-3-yl-1H-pyrimidin-6-one;
5-fluoro-2-(2-fluoro-4-pyridyl)-4-tetrahydropyran-4-yl-1H-pyrimidin-6-one;
5-chloro-2-(2-fluoro-4-pyridyl)-4-(4-fluorotetrahydropyran-4-yl)-1H-pyrimidin-6-one;
5-chloro-4-(3-fluoro-3-piperidyl)-2-(4-pyridyl)-1H-pyrimidin-6-one;
5-chloro-4-morpholin-2-yl-2-(4-pyridyl)-1H-pyrimidin-6-one;
5-chloro-4-(4-fluoro-4-piperidyl)-2-(4-pyridyl)-1H-pyrimidin-6-one;

tert-butyl 4-[5-chloro-6-oxo-2-(4-pyridyl)-1H-pyrimidin-4-yl]-4-fluoro-piperidine-1-carboxylate;
5-chloro-2-(2-chloro-4-pyridyl)-4-tetrahydropyran-4-yl-1H-pyrimidin-6-one;
5-chloro-4-tetrahydropyran-4-yl-2-[2-(trifluoromethyl)-4-pyridyl]-1H-pyrimidin-6-one;
tert-butyl 4-[5-chloro-2-(2-fluoro-4-pyridyl)-6-oxo-1H-pyrimidin-4-yl]piperidine-1-carboxylate;
5-chloro-4-(1-piperidyl)-2-(4-pyridyl)-1H-pyrimidin-6-one;
5-chloro-4-(4-ethoxy-1-piperidyl)-2-(4-pyridyl)-1H-pyrimidin-6-one;
5-chloro-4-(3,4-dimethylpiperazin-1-yl)-2-(4-pyridyl)-1H-pyrimidin-6-one;
5-chloro-4-[3-(dimethylamino)pyrrolidin-1-yl]-2-(4-pyridyl)-1H-pyrimidin-6-one;
5-chloro-2-(4-pyridyl)-4-pyrrolidin-1-yl-1H-pyrimidin-6-one;
5-bromo-4-(4-ethylpiperazin-1-yl)-2-(4-pyridyl)-1H-pyrimidin-6-one;
tert-butyl 4-[5-chloro-6-oxo-2-(4-pyridyl)-1H-pyrimidin-4-yl]piperazine-1-carboxylate;
5-chloro-4-(3-oxopiperazin-1-yl)-2-(4-pyridyl)-1H-pyrimidin-6-one;
5-chloro-4-[1-(2-methylpropanoyl)-4-piperidyl]-2-(4-pyridyl)-1H-pyrimidin-6-one;
tert-butyl N-[2-[4-[5-chloro-6-oxo-2-(4-pyridyl)-1H-pyrimidin-4-yl]-1-piperidyl]-2-oxo-ethyl]carbamate;
4-[5-chloro-6-oxo-2-(4-pyridyl)-1H-pyrimidin-4-yl]-N-isopropyl-piperidine-1-carboxamide;
4-[1-(benzenesulfonyl)-4-piperidyl]-5-chloro-2-(4-pyridyl)-1H-pyrimidin-6-one;
5-chloro-2-(4-pyridyl)-4-[1-(2,2,2-trifluoroacetyl)-4-piperidyl]-1H-pyrimidin-6-one;
5-chloro-4-(1-isobutyl-4-piperidyl)-2-(4-pyridyl)-1H-pyrimidin-6-one;
4-(1-acetyl-4-piperidyl)-5-chloro-2-(4-pyridyl)-1H-pyrimidin-6-one;
4-(1-benzoyl-4-piperidyl)-5-chloro-2-(4-pyridyl)-1H-pyrimidin-6-one;
4-(4-acetylpiperazin-1-yl)-5-chloro-2-(4-pyridyl)-1H-pyrimidin-6-one;
5-chloro-4-(4-methylsulfonylpiperazin-1-yl)-2-(4-pyridyl)-1H-pyrimidin-6-one;
5-chloro-4-[1-(2,2-dimethylpropanoyl)-4-piperidyl]-2-(4-pyridyl)-1H-pyrimidin-6-one;
5-chloro-4-[1-(pyridine-2-carbonyl)-4-piperidyl]-2-(4-pyridyl)-1H-pyrimidin-6-one;
4-[4-[5-chloro-6-oxo-2-(4-pyridyl)-1H-pyrimidin-4-yl]piperidine-1-carbonyl]benzonitrile;
5-chloro-4-[1-(pyridazine-4-carbonyl)-4-piperidyl]-2-(4-pyridyl)-1H-pyrimidin-6-one;
3-[4-[5-chloro-6-oxo-2-(4-pyridyl)-1H-pyrimidin-4-yl]piperidine-1-carbonyl]benzonitrile;
5-chloro-4-[1-(2-iodobenzoyl)-4-piperidyl]-2-(4-pyridyl)-1H-pyrimidin-6-one;
5-chloro-4-[1-(3-hydroxybenzoyl)-4-piperidyl]-2-(4-pyridyl)-1H-pyrimidin-6-one;
5-chloro-4-[1-(furan-2-carbonyl)-4-piperidyl]-2-(4-pyridyl)-1H-pyrimidin-6-one;
5-chloro-4-[1-(3-methyl-1H-pyrazole-5-carbonyl)-4-piperidyl]-2-(4-pyridyl)-1H-pyrimidin-6-one;
5-chloro-4-[1-[2-(1H-imidazol-4-yl)acetyl]-4-piperidyl]-2-(4-pyridyl)-1H-pyrimidin-6-one;
5-chloro-4-[1-(2,4-dimethylthiazole-5-carbonyl)-4-piperidyl]-2-(4-pyridyl)-1H-pyrimidin-6-one;
5-chloro-4-[1-(1-methylimidazole-4-carbonyl)-4-piperidyl]-2-(4-pyridyl)-1H-pyrimidin-6-one;
5-chloro-4-[1-(2,5-dimethylpyrazole-3-carbonyl)-4-piperidyl]-2-(4-pyridyl)-1H-pyrimidin-6-one;
5-chloro-2-(4-pyridyl)-4-[1-(thiazole-4-carbonyl)-4-piperidyl]-1H-pyrimidin-6-one;
5-chloro-4-[1-(1,5-dimethylpyrazole-3-carbonyl)-4-piperidyl]-2-(4-pyridyl)-1H-pyrimidin-6-one;
5-chloro-2-(4-pyridyl)-4-[1-(thiadiazole-4-carbonyl)-4-piperidyl]-1H-pyrimidin-6-one;
4-[1-(4-acetylbenzoyl)-4-piperidyl]-5-chloro-2-(4-pyridyl)-1H-pyrimidin-6-one;
3-[4-[5-chloro-6-oxo-2-(4-pyridyl)-1H-pyrimidin-4-yl]piperidine-1-carbonyl]-4-methoxy-benzenesulfonamide;
N-[4-[4-[5-chloro-6-oxo-2-(4-pyridyl)-1H-pyrimidin-4-yl]piperidine-1-carbonyl]phenyl]acetamide;
5-chloro-4-[1-(4-isopropoxybenzoyl)-4-piperidyl]-2-(4-pyridyl)-1H-pyrimidin-6-one;
tert-butyl N-[(1S)-2-[4-[5-chloro-6-oxo-2-(4-pyridyl)-1H-pyrimidin-4-yl]-1-piperidyl]-1-methyl-2-oxo-ethyl]carbamate;
N-[4-[4-[5-chloro-6-oxo-2-(4-pyridyl)-1H-pyrimidin-4-yl]piperidine-1-carbonyl]phenyl]-N-methyl-methanesulfonamide;
5-chloro-4-[1-(2-chlorobenzoyl)-4-piperidyl]-2-(4-pyridyl)-1H-pyrimidin-6-one;
5-chloro-4-[1-(4-methylthiazole-5-carbonyl)-4-piperidyl]-2-(4-pyridyl)-1H-pyrimidin-6-one;
5-chloro-4-[1-(1H-pyrazole-4-carbonyl)-4-piperidyl]-2-(4-pyridyl)-1H-pyrimidin-6-one;
5-chloro-4-[1-(5-methylisoxazole-3-carbonyl)-4-piperidyl]-2-(4-pyridyl)-1H-pyrimidin-6-one;
5-chloro-4-[1-(2,2-difluorocyclopropanecarbonyl)-4-piperidyl]-2-(4-pyridyl)-1H-pyrimidin-6-one;
tert-butyl N-[(1R)-2-[4-[5-chloro-6-oxo-2-(4-pyridyl)-1H-pyrimidin-4-yl]-1-piperidyl]-1-methyl-2-oxo-ethyl]carbamate;
5-chloro-4-[1-(3-methylbenzoyl)-4-piperidyl]-2-(4-pyridyl)-1H-pyrimidin-6-one;
5-chloro-4-[1-[4-(methylsulfonylmethyl)benzoyl]-4-piperidyl]-2-(4-pyridyl)-1H-pyrimidin-6-one;
tert-butyl N-[1-[4-[5-chloro-6-oxo-2-(4-pyridyl)-1H-pyrimidin-4-yl]piperidine-1-carbonyl]butyl]carbamate;
4-[1-(2-aminopropanoyl)-4-piperidyl]-5-chloro-2-(4-pyridyl)-1H-pyrimidin-6-one;
5-chloro-2-(4-pyridyl)-4-[4-(2,2,2-trifluoroacetyl)piperazin-1-yl]-1H-pyrimidin-6-one;
5-chloro-4-[(3S)-3-methyl-4-(2,2,2-trifluoroacetyl)piperazin-1l-yl]-2-(4-pyridyl)-1H-pyrimidin-6-one;
4-[(3S)-4-acetyl-3-methyl-piperazin-1l-yl]-5-chloro-2-(4-pyridyl)-1H-pyrimidin-6-one;
5-chloro-4-(1-methyl-4-piperidyl)-2-(4-pyridyl)-1H-pyrimidin-6-one;
5-chloro-4-[[(3-chlorophenyl)methyl]piperazin-1l-yl]-2-(4-pyridyl)-1H-pyrimidin-6-one;
5-chloro-4-(4-methylpiperazin-1-yl)-2-(4-pyridyl)-1H-pyrimidin-6-one;
5-chloro-4-(4-isobutylpiperazin-1-yl)-2-(4-pyridyl)-1H-pyrimidin-6-one;
5-chloro-4-(4-isopentylpiperazin-1-yl)-2-(4-pyridyl)-1H-pyrimidin-6-one;
5-chloro-4-[4-(cyclopentylmethyl)piperazin-1-yl]-2-(4-pyridyl)-1H-pyrimidin-6-one;
5-chloro-4-(4-(cyclohexylmethyl)piperazin-1-yl]-2-(4-pyridyl)-1H-pyrimidin-6-one;
5-chloro-4-(4-isopropylpiperazin-1-yl)-2-(4-pyridyl)-1H-pyrimidin-6-one;
5-chloro-2-(2-fluoro-4-pyridyl)-4-(1-isobutyl-4-piperidyl)-1H-pyrimidin-6-one;

5-chloro-4-[(3S)-3,4-dimethylpiperazin-1-yl]-2-(4-pyridyl)-1H-pyrimidin-6-one;
5-chloro-4-morpholino-2-(4-pyridyl)-1H-pyrimidin-6-one;
5-chloro-4-(3,3-difluoro-1-piperidyl)-2-(2-fluoro-4-pyridyl)-1H-pyrimidin-6-one;
5-chloro-4-(2-phenylmorpholin-4-yl)-2-(4-pyridyl)-1H-pyrimidin-6-one;
5-chloro-4-(2,6-dimethylmorpholin-4-yl)-2-(4-pyridyl)-1H-pyrimidin-6-one;
5-chloro-4-(2-isobutylmorpholin-4-yl)-2-(4-pyridyl)-1H-pyrimidin-6-one;
5-chloro-4-[2-(2-hydroxyethyl)morpholin-4-yl]-2-(4-pyridyl)-1H-pyrimidin-6-one;
5-chloro-4-(3-propylmorpholin-4-yl)-2-(4-pyridyl)-1H-pyrimidin-6-one;
4-[5-chloro-6-oxo-2-(4-pyridyl)-1H-pyrimidin-4-yl]morpholine-2-carboxamide;
4-[5-chloro-6-oxo-2-(4-pyridyl)-1H-pyrimidin-4-yl]-N,N-dimethyl-morpholine-2-carboxamide;
tert-butyl N-[[4-[5-chloro-6-oxo-2-(4-pyridyl)-1H-pyrimidin-4-yl]morpholin-2-yl]methyl]carbamate;
5-chloro-4-[2-(2-methoxyethyl)morpholin-4-yl]-2-(4-pyridyl)-1H-pyrimidin-6-one;
1-[5-chloro-6-oxo-2-(4-pyridyl)-1H-pyrimidin-4-yl]piperidine-4-carboxamide;
5-chloro-2-(4-pyridyl)-4-[3-(trifluoromethyl)piperazin-1-yl]-1H-pyrimidin-6-one;
4-(4-benzyl-1-piperidyl)-5-chloro-2-(4-pyridyl)-1H-pyrimidin-6-one;
5-chloro-4-(3,5-dimethyl-1-piperidyl)-2-(4-pyridyl)-1H-pyrimidin-6-one;
5-chloro-4-(4-hydroxy-1-piperidyl)-2-(4-pyridyl)-1H-pyrimidin-6-one;
5-chloro-4-(3-methyl-1-piperidyl)-2-(4-pyridyl)-1H-pyrimidin-6-one;
5-chloro-4-(4-fluoro-1-piperidyl)-2-(4-pyridyl)-1H-pyrimidin-6-one;
5-chloro-2-(4-pyridyl)-4-[3-(trifluoromethyl)-1-piperidyl]-1H-pyrimidin-6-one;
5-chloro-4-(3,5-dimethylpiperazin-1-yl)-2-(4-pyridyl)-1H-pyrimidin-6-one;
5-chloro-4-[4-(hydroxymethyl)-1-piperidyl]-2-(4-pyridyl)-1H-pyrimidin-6-one;
2-[4-[5-chloro-6-oxo-2-(4-pyridyl)-1H-pyrimidin-4-yl]piperazin-1l-yl]-N,N-dimethyl-acetamide;
5-chloro-4-[4-(3-fluorophenyl)piperazin-1l-yl]-2-(4-pyridyl)-1H-pyrimidin-6-one;
benzyl 4-[5-chloro-6-oxo-2-(4-pyridyl)-1H-pyrimidin-4-yl]piperazine-1-carboxylate;
5-chloro-4-[4-(3-methoxyphenyl)piperazin-1l-yl]-2-(4-pyridyl)-1H-pyrimidin-6-one;
4-(azepan-1-yl)-5-chloro-2-(4-pyridyl)-1H-pyrimidin-6-one;
5-chloro-4-(1,4-diazepan-1-yl)-2-(4-pyridyl)-1H-pyrimidin-6-one;
5-chloro-2-(4-pyridyl)-4-[4-(3-pyridyl)piperazin-1l-yl]-1H-pyrimidin-6-one;
1-[5-chloro-6-oxo-2-(4-pyridyl)-1H-pyrimidin-4-yl]-1,4-diazepan-5-one;
(2R)-1-[5-chloro-6-oxo-2-(4-pyridyl)-1H-pyrimidin-4-yl]pyrrolidine-2-carboxamide;
4-[5-chloro-6-oxo-2-(4-pyridyl)-1H-pyrimidin-4-yl]-1,4-diazepane-1-carbaldehyde;
4-[(9aS)-1,3,4,5,7,8,9,9a-octahydropyrrolo[1,2-a][1,4]diazepin-2-yl]-5-chloro-2-(4-pyridyl)-1H-pyrimidin-6-one;
5-chloro-4-(2,2-dimethylmorpholin-4-yl)-2-(4-pyridyl)-1H-pyrimidin-6-one;
5-chloro-4-(4-methyl-1-piperidyl)-2-(4-pyridyl)-1H-pyrimidin-6-one;
5-chloro-4-[3-(hydroxymethyl)-1-piperidyl]-2-(4-pyridyl)-1H-pyrimidin-6-one;
5-chloro-4-[3-(hydroxymethyl)azetidin-1-yl]-2-(4-pyridyl)-1H-pyrimidin-6-one;
5-chloro-4-[4-(2-hydroxyethyl)piperazin-1-yl]-2-(4-pyridyl)-1H-pyrimidin-6-one;
5-chloro-4-(2-oxa-7-azaspiro[3.4]octan-7-yl)-2-(4-pyridyl)-1H-pyrimidin-6-one;
5-chloro-4-(4,4-difluoro-1-piperidyl)-2-(4-pyridyl)-1H-pyrimidin-6-one;
5-chloro-2-(4-pyridyl)-4-thiomorpholino-1H-pyrimidin-6-one;
5-chloro-4-[(3R)-3-(hydroxymethyl)piperazin-1-yl]-2-(4-pyridyl)-1H-pyrimidin-6-one;
5-chloro-4-[(3S)-3-methylpiperazin-1-yl]-2-(4-pyridyl)-1H-pyrimidin-6-one;
5-chloro-4-(3-fluoro-1-piperidyl)-2-(4-pyridyl)-1H-pyrimidin-6-one;
5-chloro-4-(3,3-difluoro-1-piperidyl)-2-(4-pyridyl)-1H-pyrimidin-6-one;
5-chloro-4-[(3R)-3-fluoropyrrolidin-1-yl]-2-(4-pyridyl)-1H-pyrimidin-6-one;
5-chloro-4-(6,6-difluoro-3-azabicyclo[3.1.0]hexan-3-yl)-2-(4-pyridyl)-1H-pyrimidin-6-one;
5-chloro-2-(4-pyridyl)-4-[3-(trifluoromethyl)pyrrolidin-1-yl]-1H-pyrimidin-6-one;
5-chloro-4-[4-(2-hydroxyethyl)-1,4-diazepan-1-yl]-2-(4-pyridyl)-1H-pyrimidin-6-one;
4-(4-tert-butyl-1,4-diazepan-1-yl)-5-chloro-2-(4-pyridyl)-1H-pyrimidin-6-one;
5-chloro-4-(3-hydroxypyrrolidin-1-yl)-2-(4-pyridyl)-1H-pyrimidin-6-one;
5-chloro-2-(4-pyridyl)-4-[(3S)-3-(trifluoromethyl)piperazin-1-yl]-1H-pyrimidin-6-one;
5-chloro-4-[(3R)-3-methylpiperazin-1-yl]-2-(4-pyridyl)-1H-pyrimidin-6-one;
4-[5-chloro-6-oxo-2-(4-pyridyl)-1H-pyrimidin-4-yl]-1,4-diazepan-2-one;
5-chloro-2-(4-pyridyl)-4-[4-(2,2,2-trifluoroethyl)-1,4-diazepan-1-yl]-1H-pyrimidin-6-one;
5-chloro-4-(4-propyl-1,4-diazepan-1-yl)-2-(4-pyridyl)-1H-pyrimidin-6-one;
5-chloro-2-(4-pyridyl)-4-[4-(2,2,2-trifluoroacetyl)-1,4-diazepan-1-yl]-1H-pyrimidin-6-one;
5-chloro-4-(4-methyl sulfonyl-1,4-diazepan-1-yl)-2-(4-pyridyl)-1H-pyrimidin-6-one;
5-chloro-2-(4-pyridyl)-4-[4-(2,2,2-trifluoroethyl)piperazin-1-yl]-1H-pyrimidin-6-one;
5-chloro-4-[4-(2,2-difluoroethyl)piperazin-1-yl]-2-(4-pyridyl)-1H-pyrimidin-6-one;
2-[4-[5-chloro-6-oxo-2-(4-pyridyl)-1H-pyrimidin-4-yl]piperazin-1-yl]acetonitrile;
4-[(8aS)-7,7-difluoro-1,3,4,6,8,8a-hexahydropyrrolo[1,2-a]pyrazin-2-yl]-5-chloro-2-(4-pyridyl)-1H-pyrimidin-6-one;
5-chloro-4-(prop-2-ynylpiperazin-1-yl)-2-(4-pyridyl)-1H-pyrimidin-6-one;
5-chloro-4-(2-oxa-7-azaspiro[3.5]nonan-7-yl)-2-(4-pyridyl)-1H-pyrimidin-6-one;
5-chloro-2-(4-pyridyl)-4-[4-(2,2,3,3-tetrafluoropropyl)piperazin-1-yl]-1H-pyrimidin-6-one;
1-[5-chloro-6-oxo-2-(4-pyridyl)-1H-pyrimidin-4-yl]piperidine-4-carbonitrile;
5-chloro-4-(3-oxa-9-azabicyclo[3.3.1]nonan-9-yl)-2-(4-pyridyl)-1H-pyrimidin-6-one;

4-(4-tert-butylpiperazin-1-yl)-5-chloro-2-(4-pyridyl)-1H-pyrimidin-6-one;
5-chloro-4-[3-(1,1-difluoroethyl)piperazin-1-yl]-2-(4-pyridyl)-1H-pyrimidin-6-one;
4-[(3S)-3-tert-butylpiperazin-1-yl]-5-chloro-2-(4-pyridyl)-1H-pyrimidin-6-one;
5-chloro-4-(5,8-diazaspiro[3.5]nonan-8-yl)-2-(4-pyridyl)-1H-pyrimidin-6-one;
5-chloro-2-(4-pyridyl)-4-[2-(trifluoromethyl)morpholin-4-yl]-1H-pyrimidin-6-one;
4-[(3S)-3-tert-butylpiperazin-1-yl]-5-chloro-2-(2-fluoro-4-pyridyl)-1H-pyrimidin-6-one;
5-chloro-4-[(1S,4S)-2,5-diazabicyclo[2.2.1]heptan-2-yl]-2-(4-pyridyl)-1H-pyrimidin-6-one;
O1-tert-butyl O2-methyl (2S)-4-[5-chloro-6-oxo-2-(4-pyridyl)-1H-pyrimidin-4-yl]piperazine-1,2-dicarboxylate;
methyl (2S)-4-[5-chloro-6-oxo-2-(4-pyridyl)-1H-pyrimidin-4-yl]piperazine-2-carboxylate;
4-[(3S)-3-benzylpiperazin-1l-yl]-5-chloro-2-(4-pyridyl)-1H-pyrimidin-6-one;
4-[(3R)-3-benzylpiperazin-1-yl]-5-chloro-2-(4-pyridyl)-1H-pyrimidin-6-one;
5-chloro-4-[(2R,5R)-2,5-dimethylpiperazin-1-yl]-2-(4-pyridyl)-1H-pyrimidin-6-one;
5-chloro-4-(3-hydroxy-1-piperidyl)-2-(4-pyridyl)-1H-pyrimidin-6-one;
5-chloro-4-[3-(4-chlorophenyl)piperazin-1-yl]-2-(4-pyridyl)-1H-pyrimidin-6-one;
5-chloro-4-[3-(4-methoxyphenyl)piperazin-1-yl]-2-(4-pyridyl)-1H-pyrimidin-6-one;
5-chloro-2-(2-fluoro-4-pyridyl)-4-[(3S)-3-isopropylpiperazin-1-yl]-1H-pyrimidin-6-one;
5-chloro-2-(2-fluoro-4-pyridyl)-4-[(3S)-3-methylpiperazin-1-yl]-1H-pyrimidin-6-one;
5-chloro-4-[(2S,5S)-2,5-dimethylpiperazin-1-yl]-2-(4-pyridyl)-1H-pyrimidin-6-one;
5-chloro-4-[(2R,5 S)-2,5-dimethylpiperazin-1-yl]-2-(4-pyridyl)-1H-pyrimidin-6-one;
5-chloro-4-[(3R)-3-(2-hydroxyethyl)piperazin-1-yl]-2-(4-pyridyl)-1H-pyrimidin-6-one;
5-chloro-4-[(3S)-3-(2-hydroxyethyl)piperazin-1-yl]-2-(4-pyridyl)-1H-pyrimidin-6-one;
5-chloro-2-(4-pyridyl)-4-[3-(trifluoromethyl)-1-piperidyl]-1H-pyrimidin-6-one;
5-chloro-2-(4-pyridyl)-4-[3-(2-thienyl)piperazin-1-yl]-1H-pyrimidin-6-one;
5-chloro-4-[3-(3-hydroxyphenyl)piperazin-1-yl]-2-(4-pyridyl)-1H-pyrimidin-6-one;
5-chloro-4-[3-(3-methoxyphenyl)piperazin-1-yl]-2-(4-pyridyl)-1H-pyrimidin-6-one;
5-chloro-2-(4-pyridyl)-4-[(3R)-3-(trifluoromethyl)piperazin-1-yl]-1H-pyrimidin-6-one;
5-chloro-4-[(3S)-3-methyl-4-(2,2,2-trifluoroethyl)piperazin-1-yl]-2-(4-pyridyl)-1H-pyrimidin-6-one;
5-chloro-2-(4-pyridyl)-4-[1-(2,2,2-trifluoroethyl)-4-piperidyl]-1H-pyrimidin-6-one;
4-[(3R)-3-aminoazepan-1l-yl]-5-chloro-2-(2-fluoro-4-pyridyl)-1H-pyrimidin-6-one;
5-chloro-2-(4-pyridyl)-4-[rac-(3 S,8aS)-3-isobutyl-3,4,6,7,8,8a-hexahydro-1H-pyrrolo[1,2-a]pyrazin-2-yl]-1H-pyrimidin-6-one;
4-[(3S)-3-tert-butylpiperazin-1-yl]-5-fluoro-2-(4-pyridyl)-1H-pyrimidin-6-one;
5-chloro-4-(1,4-oxazepan-4-yl)-2-(4-pyridyl)-1H-pyrimidin-6-one;
5-chloro-2-(2-fluoro-4-pyridyl)-4-[(3R)-3-(1-hydroxy-1-methyl-ethyl)piperazin-1-yl]-1H-pyrimidin-6-one;
4-[(3S)-3-aminoazepan-1-yl]-5-chloro-2-(2-fluoro-4-pyridyl)-1H-pyrimidin-6-one;
5-chloro-4-[(3 S,5R)-3,5-dihydroxy-1-piperidyl]-2-(2-fluoro-4-pyridyl)-1H-pyrimidin-6-one;
5-chloro-2-(2-fluoro-4-pyridyl)-4-(6-hydroxy-1,4-diazepan-1-yl)-1H-pyrimidin-6-one;
5-chloro-2-(2-fluoro-4-pyridyl)-4-tetrahydropyran-4-ylsulfanyl-1H-pyrimidin-6-one;
5-chloro-2-(2-fluoro-4-pyridyl)-4-(3-oxa-8-azabicyclo[3.2.1]octan-8-yl)-1H-pyrimidin-6-one;
5-chloro-2-(2-fluoro-4-pyridyl)-4-(4-piperidyl sulfanyl)-1H-pyrimidin-6-one;
4-(azetidin-3-yloxy)-5-chloro-2-(2-fluoro-4-pyridyl)-1H-pyrimidin-6-one;
4-[(1R,3S)-3-aminocyclopentoxy]-5-chloro-2-(2-fluoro-4-pyridyl)-1H-pyrimidin-6-one;
5-chloro-2-(2-fluoro-4-pyridyl)-4-[(3R)-3-(methylamino)-1-piperidyl]-1H-pyrimidin-6-one;
5-chloro-2-(2-fluoro-4-pyridyl)-4-[(3S)-3-(methylamino)-1-piperidyl]-1H-pyrimidin-6-one;
5-chloro-4-(2,6-diazaspiro[3.3]heptan-2-yl)-2-(2-fluoro-4-pyridyl)-1H-pyrimidin-6-one;
5-chloro-2-(2-fluoro-4-pyridyl)-4-(oxetan-3-yloxy)-1H-pyrimidin-6-one;
5-chloro-2-(2-fluoro-4-pyridyl)-4-[(3S)-tetrahydrofuran-3-yl]oxy-1H-pyrimidin-6-one;
5-chloro-4-[(2 S,6R)-2,6-dimethylmorpholin-4-yl]-2-(2-fluoro-4-pyridyl)-1H-pyrimidin-6-one;
5-chloro-2-(2-fluoro-4-pyridyl)-4-[2-(1-piperidylmethyl)morpholin-4-yl]-1H-pyrimidin-6-one;
1-[5-chloro-2-(2-fluoro-4-pyridyl)-6-oxo-1H-pyrimidin-4-yl]azepan-4-one;
5-chloro-4-(4,4-difluoroazepan-1-yl)-2-(2-fluoro-4-pyridyl)-1H-pyrimidin-6-one;
5-chloro-4-[(2R)-2-ethylmorpholin-4-yl]-2-(2-fluoro-4-pyridyl)-1H-pyrimidin-6-one;
5-chloro-4-(1,4-diazepan-1-yl)-2-(2-fluoro-4-pyridyl)-1H-pyrimidin-6-one;
5-chloro-2-(2-fluoro-4-pyridyl)-4-(6-hydroxy-1,4-oxazepan-4-yl)-1H-pyrimidin-6-one;
4-[5-chloro-2-(2-fluoro-4-pyridyl)-6-oxo-1H-pyrimidin-4-yl]-1,4-oxazepan-6-one;
4-[(3S)-3-anilino-1-piperidyl]-5-chloro-2-(2-fluoro-4-pyridyl)-1H-pyrimidin-6-one;
5-chloro-4-[(3,3-dimethyl-4-piperidyl)-methyl-amino]-2-(2-fluoro-4-pyridyl)-1H-pyrimidin-6-one;
5-chloro-4-[(3,3-dimethyl-4-piperidyl)amino]-2-(2-fluoro-4-pyridyl)-1H-pyrimidin-6-one;
5-chloro-2-(2-fluoro-4-pyridyl)-4-[3-(morpholinomethyl)pyrrolidin-1-yl]-1H-pyrimidin-6-one;
5-chloro-4-(2,6-diazaspiro[4.5]decan-2-yl)-2-(2-fluoro-4-pyridyl)-1H-pyrimidin-6-one;
5-chloro-2-(2-fluoro-4-pyridyl)-4-[(3R)-3-hydroxypyrrolidin-1-yl]-1H-pyrimidin-6-one;
5-chloro-2-(2-fluoro-4-pyridyl)-4-[(3S)-3-hydroxypyrrolidin-1-yl]-1H-pyrimidin-6-one;
4-(3,4a,5,6,7,7a-hexahydro-2H-pyrrolo[3,4-b][1,4]oxazin-4-yl)-5-chloro-2-(2-fluoro-4-pyridyl)-1H-pyrimidin-6-one;
5-chloro-4-(1,7-diazaspiro[4.4]nonan-7-yl)-2-(2-fluoro-4-pyridyl)-1H-pyrimidin-6-one;
5-chloro-4-(2,7-diazaspiro[4.4]nonan-2-yl)-2-(2-fluoro-4-pyridyl)-1H-pyrimidin-6-one;
4-[(3R)-3-(aminomethyl)pyrrolidin-1-yl]-5-chloro-2-(2-fluoro-4-pyridyl)-1H-pyrimidin-6-one;

5-chloro-4-(2,9-diazaspiro[4.5]decan-2-yl)-2-(2-fluoro-4-pyridyl)-1H-pyrimidin-6-one;
4-(2,3,3a,4,5,6,7,7a-octahydropyrrolo[2,3-c]pyridin-1-yl)-5-chloro-2-(2-fluoro-4-pyridyl)-1H-pyrimidin-6-one;
5-chloro-2-(2-fluoro-4-pyridyl)-4-(4-piperidylamino)-1H-pyrimidin-6-one
4-(2,3,3a,4,5,6,7,7a-octahydropyrrolo[3,2-b]pyridin-1-yl)-5-chloro-2-(2-fluoro-4-pyridyl)-1H-pyrimidin-6-one;
5-chloro-2-(2-fluoro-4-pyridyl)-4-(morpholin-3-ylmethylamino)-1H-pyrimidin-6-one;
4-(2,3,3a,4,5,6,7,7a-octahydropyrrolo[3,2-c]pyridin-1-yl)-5-chloro-2-(2-fluoro-4-pyridyl)-1H-pyrimidin-6-one;
4-(2,3,3a,4,6,6a-hexahydro-1H-pyrrolo[3,4-c]pyrrol-5-yl)-5-chloro-2-(2-fluoro-4-pyridyl)-1H-pyrimidin-6-one;
5-chloro-2-(2-fluoro-4-pyridyl)-4-(1-oxa-4,9-diazaspiro[5.5]undecan-4-yl)-1H-pyrimidin-6-one;
5-chloro-2-(2-fluoro-4-pyridyl)-4-(3-tetrahydropyran-4-ylpyrrolidin-1-yl)-1H-pyrimidin-6-one;
5-chloro-2-(2-fluoro-4-pyridyl)-4-[methyl(tetrahydropyran-4-yl)amino]-1H-pyrimidin-6-one;
5-chloro-4-(2,8-diazaspiro[4.5]decan-2-yl)-2-(2-fluoro-4-pyridyl)-1H-pyrimidin-6-one;
1-[5-chloro-2-(2-fluoro-4-pyridyl)-6-oxo-1H-pyrimidin-4-yl]-N-methyl-piperidine-4-carboxamide;
N-[1-[5-chloro-2-(2-fluoro-4-pyridyl)-6-oxo-1H-pyrimidin-4-yl]-4-piperidyl]acetamide;
8-[5-chloro-2-(2-fluoro-4-pyridyl)-6-oxo-1H-pyrimidin-4-yl]-1,3,8-triazaspiro[4.5]decane-2,4-dione;
5-chloro-2-(2-fluoro-4-pyridyl)-4-(4-oxo-1-piperidyl)-1H-pyrimidin-6-one;
4-[(3R,4R)-3-amino-4-hydroxy-1-piperidyl]-5-chloro-2-(2-fluoro-4-pyridyl)-1H-pyrimidin-6-one;
5-chloro-4-(1,4-dioxa-8-azaspiro[4.5]decan-8-yl)-2-(2-fluoro-4-pyridyl)-1H-pyrimidin-6-one;
4-[(4aS,7aS)-3,4,4a,5,7,7a-hexahydro-2H-pyrrolo[3,4-b][1,4]oxazin-6-yl]-5-chloro-2-(2-fluoro-4-pyridyl)-1H-pyrimidin-6-one;
5-chloro-2-(2-fluoro-4-pyridyl)-4-(1-oxa-8-azaspiro[4.5]decan-8-yl)-1H-pyrimidin-6-one;
4-[5-chloro-2-(2-fluoro-4-pyridyl)-6-oxo-1H-pyrimidin-4-yl]piperazine-1-carboxamide;
4-[5-chloro-2-(2-fluoro-4-pyridyl)-6-oxo-1H-pyrimidin-4-yl]-N,N-dimethyl-piperazine-1-carboxamide;
5-chloro-4-(1,8-diazaspiro[4.5]decan-8-yl)-2-(2-fluoro-4-pyridyl)-1H-pyrimidin-6-one;
5-chloro-4-(2,8-diazaspiro[4.5]decan-8-yl)-2-(2-fluoro-4-pyridyl)-1H-pyrimidin-6-one;
4-(2,3,3a,5,6,6a-hexahydro-1H-pyrrolo[3,2-b]pyrrol-4-yl)-5-chloro-2-(2-fluoro-4-pyridyl)-1H-pyrimidin-6-one;
5-chloro-2-(2-fluoro-4-pyridyl)-4-(4-morpholino-1-piperidyl)-1H-pyrimidin-6-one;
5-chloro-4-(2,6-diazaspiro[3.4]octan-6-yl)-2-(2-fluoro-4-pyridyl)-1H-pyrimidin-6-one;
5-chloro-2-(2-fluoro-4-pyridyl)-4-[2-(morpholinomethyl)pyrrolidin-1-yl]-1H-pyrimidin-6-one;
(2R)-1-[5-chloro-2-(2-fluoro-4-pyridyl)-6-oxo-1H-pyrimidin-4-yl]pyrrolidine-2-carboxamide;
(2S)-1-[5-chloro-2-(2-fluoro-4-pyridyl)-6-oxo-1H-pyrimidin-4-yl]pyrrolidine-2-carboxamide;
(3R)-1-[5-chloro-2-(2-fluoro-4-pyridyl)-6-oxo-1H-pyrimidin-4-yl]pyrrolidine-3-carboxamide;
5-chloro-4-(1,9-diazaspiro[4.5]decan-9-yl)-2-(2-fluoro-4-pyridyl)-1H-pyrimidin-6-one;
(3S)-1-[5-chloro-2-(2-fluoro-4-pyridyl)-6-oxo-1H-pyrimidin-4-yl]pyrrolidine-3-carboxamide;
4-(3-amino-4-fluoro-1-piperidyl)-5-chloro-2-(2-fluoro-4-pyridyl)-1H-pyrimidin-6-one;
1-[5-chloro-2-(2-fluoro-4-pyridyl)-6-oxo-1H-pyrimidin-4-yl]-N-methyl-piperidine-3-carboxamide;
N-[1-[5-chloro-2-(2-fluoro-4-pyridyl)-6-oxo-1H-pyrimidin-4-yl]-4-piperidyl]-2-methyl-propanamide;
1-[5-chloro-2-(2-fluoro-4-pyridyl)-6-oxo-1H-pyrimidin-4-yl]-N-isopropyl-piperidine-4-carboxamide;
1-[5-chloro-2-(2-fluoro-4-pyridyl)-6-oxo-1H-pyrimidin-4-yl]-N-(2-hydroxyethyl)piperidine-4-carboxamide;
1-[5-chloro-2-(2-fluoro-4-pyridyl)-6-oxo-1H-pyrimidin-4-yl]-N-ethyl-piperidine-4-carboxamide;
5-chloro-4-(2,7-diazaspiro[4.5]decan-7-yl)-2-(2-fluoro-4-pyridyl)-1H-pyrimidin-6-one;
5-chloro-4-(1,7-diazaspiro[4.4]nonan-1-yl)-2-(2-fluoro-4-pyridyl)-1H-pyrimidin-6-one;
5-chloro-4-(1,9-diazaspiro[4.5]decan-1-yl)-2-(2-fluoro-4-pyridyl)-1H-pyrimidin-6-one;
4-[(3aS,6aS)-3,3a,4,5,6,6a-hexahydro-2H-pyrrolo[2,3-c]pyrrol-1-yl]-5-chloro-2-(2-fluoro-4-pyridyl)-1H-pyrimidin-6-one;
5-chloro-4-(3,8-diazabicyclo[3.2.1]octan-8-yl)-2-(2-fluoro-4-pyridyl)-1H-pyrimidin-6-one;
5-chloro-4-(1,8-diazaspiro[4.5]decan-1-yl)-2-(2-fluoro-4-pyridyl)-1H-pyrimidin-6-one;
4-(3,4,4a,5,6,7,8,8a-octahydro-2H-1,5-naphthyridin-1-yl)-5-chloro-2-(2-fluoro-4-pyridyl)-1H-pyrimidin-6-one;
5-chloro-2-(2-fluoro-4-pyridyl)-4-[4-(4-methylpiperazin-1-yl)-1-piperidyl]-1H-pyrimidin-6-one;
5-chloro-4-[ethyl(tetrahydropyran-4-yl)amino]-2-(2-fluoro-4-pyridyl)-1H-pyrimidin-6-one;
5-chloro-2-(2-fluoro-4-pyridyl)-4-[methyl-[(3S)-3-piperidyl]amino]-1H-pyrimidin-6-one;
5-chloro-2-(2-fluoro-4-pyridyl)-4-[methyl-[(3R)-3-piperidyl]amino]-1H-pyrimidin-6-one;
5-chloro-4-(6,8-dihydro-5H-[1,2,4]triazolo[4,3-a]pyrazin-7-yl)-2-(2-fluoro-4-pyridyl)-1H-pyrimidin-6-one;
5-chloro-2-(2-fluoro-4-pyridyl)-4-(3-isopropyl-6,8-dihydro-5H-[1,2,4]triazolo[4,3-a]pyrazin-7-yl)-1H-pyrimidin-6-one;
5-chloro-2-(2-fluoro-4-pyridyl)-4-[(3S)-3-(methyl amino)pyrrolidin-1-yl]-1H-pyrimidin-6-one;
5-chloro-4-[(3S)-3-(dimethylamino)pyrrolidin-1-yl]-2-(2-fluoro-4-pyridyl)-1H-pyrimidin-6-one
4-[(3S)-3-amino-3-methyl-pyrrolidin-1-yl]-5-chloro-2-(2-fluoro-4-pyridyl)-1H-pyrimidin-6-one;
N-[(3S)-1-[5-chloro-2-(2-fluoro-4-pyridyl)-6-oxo-1H-pyrimidin-4-yl]pyrrolidin-3-yl]acetamide;
4-(1,2,3,3a,5,6,7,7a-octahydropyrrolo[3,2-b]pyridin-4-yl)-5-chloro-2-(2-fluoro-4-pyridyl)-1H-pyrimidin-6-one;
5-chloro-2-(2-fluoro-4-pyridyl)-4-pyrrolidin-1-yl-1H-pyrimidin-6-one;
5-chloro-2-(2-fluoro-4-pyridyl)-4-(1-piperidyl)-1H-pyrimidin-6-one;
5-chloro-2-(2-fluoro-4-pyridyl)-4-[(2S)-2-methylpyrrolidin-1-yl]-1H-pyrimidin-6-one;
5-chloro-2-(2-fluoro-4-pyridyl)-4-[(2R)-2-methylpyrrolidin-1-yl]-1H-pyrimidin-6-one;
5-chloro-2-(2-fluoro-4-pyridyl)-4-[(2S)-2-methyl-1-piperidyl]-1H-pyrimidin-6-one;
5-chloro-2-(2-fluoro-4-pyridyl)-4-[(2R)-2-methyl-1-piperidyl]-1H-pyrimidin-6-one;
5-chloro-2-(2-fluoro-4-pyridyl)-4-[(3R)-3-methoxy-1-piperidyl]-1H-pyrimidin-6-one;
5-chloro-2-(2-fluoro-4-pyridyl)-4-[(3S)-3-methoxy-1-piperidyl]-1H-pyrimidin-6-one;
5-chloro-2-(2-fluoro-4-pyridyl)-4-(2-oxa-7-azaspiro[3.4]octan-7-yl)-1H-pyrimidin-6-one;

5-chloro-2-(2-fluoro-4-pyridyl)-4-[2-(phenoxymethyl)morpholin-4-yl]-1H-pyrimidin-6-one;
5-chloro-4-(6,6-difluoro-1,4-oxazepan-4-yl)-2-(2-fluoro-4-pyridyl)-1H-pyrimidin-6-one;
4-(4-aminophenoxy)-5-chloro-2-(2-fluoro-4-pyridyl)-1H-pyrimidin-6-one;
1-[5-chloro-2-(2-fluoro-4-pyridyl)-6-oxo-1H-pyrimidin-4-yl]-1,4-diazepan-5-one;
4-[benzyl(methyl)amino]-5-chloro-2-(2-fluoro-4-pyridyl)-1H-pyrimidin-6-one;
4-(benzylamino)-5-chloro-2-(2-fluoro-4-pyridyl)-1H-pyrimidin-6-one;
5-chloro-2-(2-fluoro-4-pyridyl)-4-[3-(trifluoromethyl)-6,8-dihydro-5H-[1,2,4]triazolo[4,3-a]pyrazin-7-yl]-1H-pyrimidin-6-one;
5-chloro-4-(1,9-dioxa-4-azaspiro[5.5]undecan-4-yl)-2-(2-fluoro-4-pyridyl)-1H-pyrimidin-6-one;
5-chloro-4-(1,4-diazabicyclo[3.2.2]nonan-4-yl)-2-(2-fluoro-4-pyridyl)-1H-pyrimidin-6-one;
4-benzyloxy-5-chloro-2-(2-fluoro-4-pyridyl)-1H-pyrimidin-6-one;
5-chloro-2-(2-fluoro-4-pyridyl)-4-[4-(1H-1,2,4-triazol-3-yl)piperazin-1-yl]-1H-pyrimidin-6-one;
5-chloro-2-(2-fluoro-4-pyridyl)-4-[5-(trifluoromethyl)-1,4-diazepan-1-yl]-1H-pyrimidin-6-one;
5-chloro-4-(3,3-dimethylpiperazin-1-yl)-2-(2-fluoro-4-pyridyl)-1H-pyrimidin-6-one;
5-chloro-2-(2-fluoro-4-pyridyl)-4-(4-methyl-1,4-diazepan-1-yl)-1H-pyrimidin-6-one;
5-chloro-2-(2-fluoro-4-pyridyl)-4-[4-(2,2,2-trifluoroethyl)-1,4-diazepan-1-yl]-1H-pyrimidin-6-one;
5-chloro-4-(2,2-dimethylmorpholin-4-yl)-2-(2-fluoro-4-pyridyl)-1H-pyrimidin-6-one;
5-chloro-4-(2,2-dimethyl-1,4-oxazepan-4-yl)-2-(2-fluoro-4-pyridyl)-1H-pyrimidin-6-one;
5-chloro-4-(2,4-dimethyl-1,4-diazepan-1-yl)-2-(2-fluoro-4-pyridyl)-1H-pyrimidin-6-one;
5-chloro-2-(2-fluoro-4-pyridyl)-4-(5-methyl-1,4-diazepan-1-yl)-1H-pyrimidin-6-one;
5-chloro-4-(6-fluoro-6-methyl-1,4-diazepan-1-yl)-2-(2-fluoro-4-pyridyl)-1H-pyrimidin-6-one;
5-chloro-2-(2-fluoro-4-pyridyl)-4-tetrahydropyran-4-yloxy-1H-pyrimidin-6-one;
2-[(2 S)-4-[5-chloro-2-(2-fluoro-4-pyridyl)-6-oxo-1H-pyrimidin-4-yl]piperazin-2-yl]acetonitrile;
5-chloro-4-[(3R)-3-(1,1-difluoroethyl)piperazin-1-yl]-2-(4-pyridyl)-1H-pyrimidin-6-one;
5-fluoro-4-[(3S)-3-isopropylpiperazin-1-yl]-2-(4-pyridyl)-1H-pyrimidin-6-one;
5-chloro-4-[(3S)-3-isopropylpiperazin-1l-yl]-2-(4-pyridyl)-1H-pyrimidin-6-one;
5-chloro-2-(2-fluoro-4-pyridyl)-4-(3-isopropylpiperazin-1-yl)-1H-pyrimidin-6-one;
5-chloro-2-(2-fluoro-4-pyridyl)-4-[(3S)-3-(1-hydroxycyclopropyl)piperazin-1-yl]-1H-pyrimidin-6-one;
5-chloro-4-(6,6-difluoro-1,4-diazepan-1-yl)-2-(2-fluoro-4-pyridyl)-1H-pyrimidin-6-one;
5-chloro-2-(2-fluoro-4-pyridyl)-4-[2-(trifluoromethyl)piperazin-1-yl]-1H-pyrimidin-6-one;
5-chloro-2-(2-fluoro-4-pyridyl)-4-[(3R)-3-(trifluoromethyl)piperazin-1-yl]-1H-pyrimidin-6-one;
5-chloro-4-[(3R)-3-(1,1-difluoroethyl)piperazin-1-yl]-2-(2-fluoro-4-pyridyl)-1H-pyrimidin-6-one;
5-chloro-2-(2-fluoro-4-pyridyl)-4-morpholino-1H-pyrimidin-6-one;
4-[(3S)-3-amino-1-piperidyl]-5-chloro-2-(2-fluoro-4-pyridyl)-1H-pyrimidin-6-one;
4-[(3S)-3-(aminomethyl)pyrrolidin-1-yl]-5-chloro-2-(2-fluoro-4-pyridyl)-1H-pyrimidin-6-one;
5-chloro-2-(2-fluoro-4-pyridyl)-4-[rac-(3R)-3-amino-1-piperidyl]-1H-pyrimidin-6-one;
4-[(3S)-3-aminopyrrolidin-1l-yl]-5-chloro-2-(2-fluoro-4-pyridyl)-1H-pyrimidin-6-one;
4-(4-amino-1-piperidyl)-5-chloro-2-(2-fluoro-4-pyridyl)-1H-pyrimidin-6-one;
4-[(3S)-3-tert-butylpiperazin-1-yl]-5-fluoro-2-(2-fluoro-4-pyridyl)-1H-pyrimidin-6-one;
5-chloro-2-(2-fluoro-4-pyridyl)-4-[2-methylpiperazin-1-yl]-1H-pyrimidin-6-one;
5-chloro-2-(2-fluoro-4-pyridyl)-4-[rac-(2 S)-2-methylpiperazin-1-yl]-1H-pyrimidin-6-one;
5-chloro-2-(2-fluoro-4-pyridyl)-4-[rac-(2R)-2-methylpiperazin-1-yl]-1H-pyrimidin-6-one;
4-[(3R)-3-aminopyrrolidin-1-yl]-5-chloro-2-(2-fluoro-4-pyridyl)-1H-pyrimidin-6-one;
4-(3-aminoazetidin-1l-yl)-5-chloro-2-(2-fluoro-4-pyridyl)-1H-pyrimidin-6-one;
5-chloro-2-(2-fluoro-4-pyridyl)-4-[(2S)-2-methylpiperazin-1-yl]-1H-pyrimidin-6-one;
5-chloro-2-(2-fluoro-4-pyridyl)-4-[(3R)-3-isopropylpiperazin-1-yl]-1H-pyrimidin-6-one;
5-chloro-2-(2-fluoro-4-pyridyl)-4-[(3R)-3-methylmorpholin-4-yl]-1H-pyrimidin-6-one;
5-chloro-2-(2-fluoro-4-pyridyl)-4-(4-piperidyloxy)-1H-pyrimidin-6-one;
5-chloro-2-(2-fluoro-4-pyridyl)-4-[[(3R)-3-piperidyl]oxy]-1H-pyrimidin-6-one;
5-chloro-2-(2-fluoro-4-pyridyl)-4-[[(3S)-3-piperidyl]oxy]-1H-pyrimidin-6-one;
4-[(4aS,8aS)-2,3,4a,5,6,7,8,8a-octahydrobenzo[b][1,4]oxazin-4-yl]-5-chloro-2-(2-fluoro-4-pyridyl)-1H-pyrimidin-6-one;
5-chloro-2-(2-fluoro-4-pyridyl)-4-[(3S)-3-methylmorpholin-4-yl]-1H-pyrimidin-6-one;
5-chloro-2-(2-fluoro-4-pyridyl)-4-(3-oxa-9-azabicyclo[3.3.1]nonan-9-yl)-1H-pyrimidin-6-one;
5-chloro-4-[(3R)-3-ethylmorpholin-4-yl]-2-(2-fluoro-4-pyridyl)-1H-pyrimidin-6-one;
5-chloro-4-[(3S)-3-ethylmorpholin-4-yl]-2-(2-fluoro-4-pyridyl)-1H-pyrimidin-6-one;
5-chloro-2-(2-fluoro-4-pyridyl)-4-[(2R)-2-methylmorpholin-4-yl]-1H-pyrimidin-6-one;
5-chloro-2-(2-fluoro-4-pyridyl)-4-(1,4-oxazepan-4-yl)-1H-pyrimidin-6-one;
5-chloro-4-(3,3-dimethylmorpholin-4-yl)-2-(2-fluoro-4-pyridyl)-1H-pyrimidin-6-one;
5-chloro-4-(2,5-dimethylmorpholin-4-yl)-2-(2-fluoro-4-pyridyl)-1H-pyrimidin-6-one;
5-chloro-4-[(3R,5R)-3,5-dimethylmorpholin-4-yl]-2-(2-fluoro-4-pyridyl)-1H-pyrimidin-6-one;
5-chloro-4-[(3 S,5 S)-3,5-dimethylmorpholin-4-yl]-2-(2-fluoro-4-pyridyl)-1H-pyrimidin-6-one;
5-chloro-4-[(3 S,5R)-3,5-dimethylmorpholin-4-yl]-2-(2-fluoro-4-pyridyl)-1H-pyrimidin-6-one;
(2R)-1-[5-chloro-2-(2-fluoro-4-pyridyl)-6-oxo-1H-pyrimidin-4-yl]piperazine-2-carbonitrile;
(2S)-1-[5-chloro-2-(2-fluoro-4-pyridyl)-6-oxo-1H-pyrimidin-4-yl]piperazine-2-carbonitrile;
5-chloro-4-(6,8-dihydro-5H-imidazo[1,5-a]pyrazin-7-yl)-2-(2-fluoro-4-pyridyl)-1H-pyrimidin-6-one;
4-[(8aS)-7,7-difluoro-1,3,4,6,8,8a-hexahydropyrrolo[1,2-a]pyrazin-2-yl]-5-chloro-2-(2-fluoro-4-pyridyl)-1H-pyrimidin-6-one;

4-[(8aS)-3,4,6,7,8,8a-hexahydro-1H-pyrrolo[1,2-a]pyrazin-2-yl]-5-chloro-2-(2-fluoro-4-pyridyl)-1H-pyrimidin-6-one;
4-[(3 S, 8aS)-3-isobutyl-3,4,6,7,8,8a-hexahydro-1H-pyrrolo[1,2-a]pyrazin-2-yl]-5-chloro-2-(2-fluoro-4-pyridyl)-1H-pyrimidin-6-one;
5-chloro-4-[4-(2,2-difluoroethyl)piperazin-1-yl]-2-(2-fluoro-4-pyridyl)-1H-pyrimidin-6-one;
5-chloro-2-(2-fluoro-4-pyridyl)-4-(7-methyl-1,4-diazepan-1-yl)-1H-pyrimidin-6-one;
5-chloro-2-(2-fluoro-4-pyridyl)-4-[(2R)-2-methyl-1,4-diazepan-1-yl]-1H-pyrimidin-6-one;
5-chloro-4-(6,8-dihydro-5H-imidazo[1,2-a]pyrazin-7-yl)-2-(2-fluoro-4-pyridyl)-1H-pyrimidin-6-one;
5-chloro-2-(2-fluoro-4-pyridyl)-4-(5,6,8,9-tetrahydro-[1,2,4]triazolo[4,3-d][1,4]diazepin-7-yl)-1H-pyrimidin-6-one;
5-chloro-2-(2-fluoro-4-pyridyl)-4-(3-methyl-1,4-oxazepan-4-yl)-1H-pyrimidin-6-one;
5-chloro-4-[5,8-dimethyl-3-(trifluoromethyl)-6,8-dihydro-5H-[1,2,4]triazolo[4,3-a]pyrazin-7-yl]-2-(2-fluoro-4-pyridyl)-1H-pyrimidin-6-one;
5-chloro-4-[(2R,5R)-2,5-dimethylmorpholin-4-yl]-2-(2-fluoro-4-pyridyl)-1H-pyrimidin-6-one;
5-chloro-4-(2,2-dimethylpiperazin-1-yl)-2-(2-fluoro-4-pyridyl)-1H-pyrimidin-6-one;
5-chloro-4-(2,3-dimethylmorpholin-4-yl)-2-(2-fluoro-4-pyridyl)-1H-pyrimidin-6-one;
5-chloro-2-(2-fluoro-4-pyridyl)-4-piperazin-1-yl-1H-pyrimidin-6-one;
5-chloro-4-(3,3-dimethylpiperazin-1-yl)-2-(4-pyridyl)-1H-pyrimidin-6-one;
4-[(3R)-3-(aminomethyl)-1-piperidyl]-5-chloro-2-(2-fluoro-4-pyridyl)-1H-pyrimidin-6-one;
4-[(3S)-3-(aminomethyl)-1-piperidyl]-5-chloro-2-(2-fluoro-4-pyridyl)-1H-pyrimidin-6-one;
5-chloro-4-[(2R)-2-methylpiperazin-1-yl]-2-(4-pyridyl)-1H-pyrimidin-6-one;
5-chloro-4-[(3S)-3-methylmorpholin-4-yl]-2-(4-pyridyl)-1H-pyrimidin-6-one;
5-chloro-4-(3-propylmorpholin-4-yl)-2-(4-pyridyl)-1H-pyrimidin-6-one;
5-chloro-4-(3-isobutylmorpholin-4-yl)-2-(4-pyridyl)-1H-pyrimidin-6-one;
5-chloro-4-(2-methylpiperazin-1-yl)-2-(4-pyridyl)-1H-pyrimidin-6-one;
5-chloro-4-[(2 S)-2-ethylpiperazin-1-yl]-2-(4-pyridyl)-1H-pyrimidin-6-one;
5-chloro-2-(4-pyridyl)-4-[(2S)-2-isopropylpiperazin-1-yl]-1H-pyrimidin-6-one;
5-chloro-4-[(2R)-2-ethylpiperazin-1-yl]-2-(4-pyridyl)-1H-pyrimidin-6-one;
5-chloro-4-(3-phenylmorpholin-4-yl)-2-(4-pyridyl)-1H-pyrimidin-6-one;
5-chloro-4-(6-fluoro-1,4-diazepan-1-yl)-2-(2-fluoro-4-pyridyl)-1H-pyrimidin-6-one;
5-chloro-4-(6,6-difluoro-1,4-diazepan-1-yl)-2-(4-pyridyl)-1H-pyrimidin-6-one;
5-chloro-2-(2-fluoro-4-pyridyl)-4-[6-(trifluoromethyl)-1,4-diazepan-1-yl]-1H-pyrimidin-6-one;
5-chloro-4-[2-(difluoromethyl)piperazin-1-yl]-2-(2-fluoro-4-pyridyl)-1H-pyrimidin-6-one;
5-chloro-4-[2 S-(difluoromethyl)piperazin-1-yl]-2-(2-fluoro-4-pyridyl)-1H-pyrimidin-6-one;
5-chloro-4-[2R-(difluoromethyl)piperazin-1-yl]-2-(2-fluoro-4-pyridyl)-1H-pyrimidin-6-one;
5-chloro-4-(4,7-diazaspiro[2.5]octan-4-yl)-2-(2-fluoro-4-pyridyl)-1H-pyrimidin-6-one;
cis-5-chloro-2-(2-fluoro-4-pyridyl)-4-[2-methyl-5-(trifluoromethyl)piperazin-1-yl]-1H-pyrimidin-6-one;
5-chloro-4-[6-fluoro-1,4-diazepan-1-yl]-2-(2-fluoro-4-pyridyl)-1H-pyrimidin-6-one;
5-chloro-4-[6S-fluoro-1,4-diazepan-1-yl]-2-(2-fluoro-4-pyridyl)-1H-pyrimidin-6-one;
5-chloro-4-[6R-fluoro-1,4-diazepan-1-yl]-2-(2-fluoro-4-pyridyl)-1H-pyrimidin-6-one;
5-chloro-4-[3-(1-fluoro-1-methyl-ethyl)piperazin-1-yl]-2-(2-fluoro-4-pyridyl)-1H-pyrimidin-6-one;
5-chloro-4-[3 S-(1-fluoro-1-methyl-ethyl)piperazin-1-yl]-2-(2-fluoro-4-pyridyl)-1H-pyrimidin-6-one;
5-chloro-4-[3R-(1-fluoro-1-methyl-ethyl)piperazin-1-yl]-2-(2-fluoro-4-pyridyl)-1H-pyrimidin-6-one;
5-chloro-2-(2-fluoro-4-pyridyl)-4-[2-(trifluoromethyl)piperazin-1-yl]-1H-pyrimidin-6-one;
5-chloro-2-(2-fluoro-4-pyridyl)-4-[2 S-(trifluoromethyl)piperazin-1-yl]-1H-pyrimidin-6-one;
5-chloro-2-(2-fluoro-4-pyridyl)-4-[2R-(trifluoromethyl)piperazin-1-yl]-1H-pyrimidin-6-one;
5-chloro-2-(2-fluoro-4-pyridyl)-4-[6-(trifluoromethyl)-1,4-diazepan-1-yl]-1H-pyrimidin-6-one;
5-chloro-2-(2-fluoro-4-pyridyl)-4-[6 S-(trifluoromethyl)-1,4-diazepan-1-yl]-1H-pyrimidin-6-one;
5-chloro-2-(2-fluoro-4-pyridyl)-4-[6R-(trifluoromethyl)-1,4-diazepan-1-yl]-1H-pyrimidin-6-one;
5-chloro-2-(4-pyridyl)-4-[2-(trifluoromethyl)piperazin-1-yl]-1H-pyrimidin-6-one;
5-chloro-2-(4-pyridyl)-4-[2 S-(trifluoromethyl)piperazin-1-yl]-1H-pyrimidin-6-one;
5-chloro-2-(4-pyridyl)-4-[2R-(trifluoromethyl)piperazin-1-yl]-1H-pyrimidin-6-one;
5-chloro-4-[2-(difluoromethyl)piperazin-1-yl]-2-(2-fluoro-4-pyridyl)-1H-pyrimidin-6-one;
5-chloro-4-[2 S-(difluoromethyl)piperazin-1-yl]-2-(2-fluoro-4-pyridyl)-1H-pyrimidin-6-one;
5-chloro-4-[2R-(difluoromethyl)piperazin-1-yl]-2-(2-fluoro-4-pyridyl)-1H-pyrimidin-6-one;
5-chloro-4-[2-(difluoromethyl)piperazin-1-yl]-2-(4-pyridyl)-1H-pyrimidin-6-one;
5-chloro-4-[2R-(1,1-difluoroethyl)piperazin-1-yl]-2-(2-fluoro-4-pyridyl)-1H-pyrimidin-6-one;
5-chloro-4-[2S-(1,1-difluoroethyl)piperazin-1-yl]-2-(2-fluoro-4-pyridyl)-1H-pyrimidin-6-one;
5-chloro-4-[3-cyclopropylpiperazin-1-yl]-2-(2-fluoro-4-pyridyl)-1H-pyrimidin-6-one;
5-chloro-4-[3 S-cyclopropylpiperazin-1-yl]-2-(2-fluoro-4-pyridyl)-1H-pyrimidin-6-one;
5-chloro-4-[3R-cyclopropylpiperazin-1-yl]-2-(2-fluoro-4-pyridyl)-1H-pyrimidin-6-one;
cis-5-chloro-2-(2-fluoro-4-pyridyl)-4-[2-methyl-5-(trifluoromethyl)piperazin-1-yl]-1H-pyrimidin-6-one;
cis-5-chloro-2-(2-fluoro-4-pyridyl)-4-[2R-methyl-5 S-(trifluoromethyl)piperazin-1-yl]-1H-pyrimidin-6-one;
cis-5-chloro-2-(2-fluoro-4-pyridyl)-4-[2 S-methyl-5R-(trifluoromethyl)piperazin-1-yl]-1H-pyrimidin-6-one;
5-chloro-2-(2-fluoro-4-pyridyl)-4-(morpholinomethyl)-1H-pyrimidin-6-one;
5-chloro-2-(2-fluoro-4-pyridyl)-4-(piperazin-1-ylmethyl)-1H-pyrimidin-6-one;
5-chloro-4-(6,6-difluoro-1,4-diazepan-1-yl)-2-(3-fluoro-4-pyridyl)-1H-pyrimidin-6-one;
5-chloro-2-(3-fluoro-4-pyridyl)-4-[(2R)-2-methylpiperazin-1-yl]-1H-pyrimidin-6-one;
5-chloro-2-(2-chloro-4-pyridyl)-4-(6,6-difluoro-1,4-diazepan-1-yl)-1H-pyrimidin-6-one;

5-chloro-2-(2-hydroxy-4-pyridyl)-4-tetrahydropyran-4-yl-1H-pyrimidin-6-one;
6-oxo-2-(4-pyridyl)-4-tetrahydropyran-4-yl-1H-pyrimidine-5-carbonitrile;
5-chloro-4-(3,6-dihydro-2H-pyran-4-yl)-2-(4-pyridyl)-1H-pyrimidin-6-one;
tert-butyl 4-[5-chloro-6-oxo-2-(4-pyridyl)-1H-pyrimidin-4-yl]-3,6-dihydro-2H-pyridine-1-carboxylate;
2-(4-pyridyl)-4-tetrahydropyran-4-yl-5-(trifluoromethyl)-1H-pyrimidin-6-one;
5-chloro-4-[(3S)-3-(1-hydroxy-1-methyl-ethyl)piperazin-1-yl]-2-(4-pyridyl)-1H-pyrimidin-6-one;
5-bromo-4-[(3S)-3-isopropylpiperazin-1-yl]-2-(4-pyridyl)-1H-pyrimidin-6-one;
4-[(3S)-3-isopropylpiperazin-1-yl]-6-oxo-2-(4-pyridyl)-1H-pyrimidine-5-carbonitrile;
5-bromo-4-[(3S)-3-tert-butylpiperazin-1-yl]-2-(4-pyridyl)-1H-pyrimidin-6-one;
4-[(3S)-3-tert-butylpiperazin-1-yl]-6-oxo-2-(4-pyridyl)-1H-pyrimidine-5-carbonitrile;
1-[5-chloro-2-(2-fluoro-4-pyridyl)-6-oxo-1H-pyrimidin-4-yl]-1,4-diazepan-6-one;
5-chloro-2-(4-pyridyl)-4-(2,2,6,6-tetrafluoromorpholin-4-yl)-1H-pyrimidin-6-one;
2-[4-[5-chloro-2-(2-fluoro-4-pyridyl)-6-oxo-1H-pyrimidin-4-yl]-6,6-difluoro-1,4-diazepan-1-yl]acetamide;
5-chloro-4-(6,6-difluoro-4-methyl-1,4-diazepan-1-yl)-2-(2-fluoro-4-pyridyl)-1H-pyrimidin-6-one;
5-chloro-4-piperazin-1-yl-2-(4-pyridyl)-1H-pyrimidin-6-one.

Biological Activity

The Cdc7 enzyme and cell assays described in accompanying Example section may be used to measure the pharmacological effects of the compounds of the present invention.

Although the pharmacological properties of the compounds of formula I vary with structural change, as expected, the compounds of the invention were found to be active in these Cdc7 assays.

In general, the compounds of the invention demonstrate an $IC_{50}$ of 5 µM or less in the Cdc7 enzyme assay described herein, with preferred compounds of the invention demonstrating an $IC_{50}$ of 1 µM or less, more preferred compounds of the invention demonstrating an $IC_{50}$ of 500 nM or less and the most preferred compounds of the invention demonstrating an $IC_{50}$ of 200 nM or less.

In general, the compounds of the invention demonstrate an $IC_{50}$ of 10 µM or less in the Cdc7 cell assay described herein, with preferred compounds of the invention demonstrating an $IC_{50}$ of 5 µM or less, more preferred compounds of the invention demonstrating an $IC_{50}$ of 1 µM or less, and the most preferred compounds of the invention demonstrating an $IC_{50}$ of 500 nM or less.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The proviso recited in the compound definition above excludes certain compounds that are not novel, but the use of these compounds in any of the therapeutic methods or combination therapies defined herein is still encompassed by the present invention.

The present invention provides compounds that function as inhibitors of Cdc7.

The present invention therefore provides a method of inhibiting Cdc7 enzyme activity in vitro or in vivo, said method comprising contacting a cell with an effective amount of a compound, or a pharmaceutically acceptable salt, hydrate or solvate thereof, as defined herein.

The present invention also provides a method of treating a disease or disorder in which Cdc7 activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of Cdc7 enzyme activity.

The present invention provides a compound, or a pharmaceutically acceptable salt, hydrate or solvate thereof, as defined herein for use in the treatment of a disease or disorder in which Cdc7 activity is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of Cdc7 enzyme activity.

The present invention provides a use of a compound, or a pharmaceutically acceptable salt, hydrate or solvate thereof, as defined herein in the manufacture of a medicament for the treatment of a disease or disorder in which Cdc7 activity is implicated.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers (by virtue of their inhibition of Cdc7 enzyme activity).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrastemal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of antitumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

The following examples are provided solely to illustrate the present invention and are not intended to limit the scope of the invention, as described herein.

For convenience, the following common abbreviations are used herein:
Boc for tert-butyloxycarbonyl
DAST for diethylaminosulfur trifluoride
DBU for 1,8-diazabicyclo(5.4.0)undec-7-ene
DCE for 1,1-dichloroethane
DCM for dichloromethane
DEA for diethanolamine
DIPEA for N,N-diisopropylethylamine, Hünig's base
DMA for N,N-dimethylacetamide
DMAP for 4-(dimethylamino) pyridine
DMF for N,N-dimethylformamide
DMSO for dimethylsulfoxide.
h for hours
HATU for N-[(dimethylamino)-1H-1,2,3-triazolo-[4,5-b]pyridin-1-ylmethylene]-N-methylmethanaminium hexafluorophosphate N-oxide
HBTU for (1H-benzotriazol-1-yloxy)(dimethylamino)-N,N-dimethylmethaniminium hexafluorophosphate
HPLC for High Pressure Liquid Chromatography.
IPA for isopropyl alcohol
LCMS for Liquid Chromatography-Mass Spectrometry.
mCPBA for meta-chloroperoxybenzoic acid
MI for Molecular Ion
Min for minutes
MW for microwave
NBS for N-bromosuccinamide
NCS for N-chlorosuccinamide
NIS for N-iodosuccinamide
NMM for N-methylmorpholine
NMP for 1-methyl-2-pyrrolidinone
NMR for Nuclear Magnetic Resonance.
Pd(dppf)$_2$Cl$_2$ for [1,1'-bis(diphenylphosphino)ferrocene]dichloropalladium(II)
Pd(dba)$_2$ for bis(dibenzylideneacetone)palladium
RT for Retention Time.
SCX-2 for a silica-based sorbent with a chemically bonded propylsulfonic acid functional group
SFC for supercritical fluid chromatography
TBAF for tetra-n-butylammonium fluoride
TBDMS for tert-butyldimethylsilyl
TFAA for trifluoroacetic anhydride
TFA for trifluoroacetic acid
THF for tetrahydrofuran General Methods: NMR Proton NMR spectra were recorded using a Bruker AMX-300 NMR machine at 300 MHz, a Bruker AMX-400 NMR machine at 400 MHz or a Bruker Avance 500 machine at 500 MHz. Shifts were reported in ppm values relative to an internal standard of tetramethylsilane (TMS) or residual protic solvent. The following abbreviations were used to describe the splitting patterns: s (singlet), d (doublet), t (triplet), q (quartet), m (multiplet), dd (double-doublet), dt (double-triplet), br (broad).

General Methods: LCMS Methods
Method: LCMS6

Method LCMS6 employed Waters 515 pumps, a Waters 2525 mixer with valves directing to the different columns and a Waters 2487 diode array detector. The detection was performed at 254 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 2.5 minutes, these conditions were held for 0.65 min before the eluent level was returned to the starting conditions of 95% water:5% acetonitrile over 0.4 min. These conditions were held for 0.4 minutes to allow equilibration of the column before the next sample was injected. The run lasted 3.95 minutes in total.

Method: 1LCMS1

Method 1LCMS1 employed Waters 515 pumps, a Waters 2525 mixer with valves directing to the different columns and a Waters 2487 diode array detector. The detection was performed at 254 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and methanol contained 0.1% formic acid. The elution was started at 85% water: 15% methanol ramping up to 15% water:85% methanol over 4.5 minutes, these conditions were held for 1 minute before the eluent level was returned to the starting conditions of 85% water: 15% methanol over 6 seconds. These conditions were held for 1.4 minutes to allow equilibration of the column before the next sample was injected. The run lasted 7 minutes in total.

Method: 1LCMS5

Method 1LCMS5 employed Waters 515 pumps, a Waters 2525 mixer with valves directing to the different columns and a Waters 2998 diode array detector. The detection was performed between 210 nm and 400 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and methanol contained 0.1% formic acid. The elution was started at 85% water:15% methanol ramping up to 15% water:85% methanol over 4.5 minutes, these conditions were held for 1 min before the eluent level was returned to the starting conditions of 85% water:15% methanol over 6 seconds. These conditions were held for 1.4 minutes to allow equilibration of the column before the next sample was injected. The run lasted 7 minutes in total.

Method: 1LCMS6

Method 1LCMS6 employed Waters 515 pumps, a Waters 2525 mixer with valves directing to the different columns and a Waters 2998 diode array detector. The detection was performed between 210 nm and 400 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and methanol contained 0.1% formic acid. The elution was started at 85% water:15% methanol ramping up to 15% water:85% methanol over 3 minutes, these conditions were held for 2.5 min before the eluent level was returned to the starting conditions of 85% water:15% methanol over 6 seconds. These conditions were held for 1.4 minutes to allow equilibration of the column before the next sample was injected. The run lasted 7 minutes in total.

Method: 1LCMS12

Method 1LCMS12 employed Waters 515 pumps, a Waters 2525 mixer with valves directing to the different columns and a Waters 2998 diode array detector. The detection was performed between 210 nm and 400 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 5 minutes, these conditions were held for 0.5 min before the eluent level was returned to the starting conditions of 95% water:5% acetonitrile over 6 seconds. These conditions were held for 1.4 minutes to allow equilibration of the column before the next sample was injected. The run lasted 7 minutes in total.

Method. 1LCMS13

Method 1LCMS13 employed Waters 515 pumps, a Waters 2525 mixer with valves directing to the different columns and a Waters 2998 diode array detector. The detection was performed between 210 nm and 400 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 2.5 minutes, these conditions were held for 3 min before the eluent level was returned to the starting conditions of 95% water:5% acetonitrile over 18 seconds. These conditions were held for 1.2 minutes to allow equilibration of the column before the next sample was injected. The run lasted 7 minutes in total.

Method: 1LCMS15 Method 1LCMS15 employed Waters 515 pumps, a Waters 2525 mixer with valves directing to the different columns and a Waters 2996 diode array detector. The detection was performed between 210 nm and 650 nm. The mass spectrometer used was a Waters 3100 which detected masses between 100 and 700 g/mol. The column used was an XBridge, 5 micron pore size, C18, 50×4.60 mm. The injection volume was 10 µL of a solution at a maximum concentration of 1 mg/mL. The flow rate was 1.5 mL/min and the mobile phases of water pH 10 (35% ammonia solution (aq) 0.3 mL/L) and methanol (35% ammonia solution (aq) 0.3 mL/L). The elution was started at 85% water:15% methanol ramping up to 15% water:85% methanol over 4.5 minutes. These conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method: 2LCMS1

Method 2LCMS1 employed Waters 515 pumps, a Waters 2545 mixer with valves directing to the different columns and a Waters 2996 diode array detector. The detection was performed between 210 nm and 650 nm. The mass spectrometer was a Waters 3100 which detected masses between 100 and 700 g/mol. The column used was an XBridge, 5 micron pore size, C18, 50×4.60 mm. The injection volume was 10 µL at a maximum concentration of 1 mg/mL. The flow rate was 1.5 mL/min and the mobile phases of water pH 10 (35% ammonia solution (aq) 0.3 mL/L) and methanol (35% ammonia solution (aq) 0.3 mL/L). The elution was started at 85% water:15% methanol ramping up to 15% water:85% methanol over 4.5 minutes. These conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method: 4LCMS1

Method 4LCMS1 employed an Alliance e2695 liquid handler and SFO with a Waters 2998 diode array detector. The detection was done at 254 nm and an array between 210-600 nm. The mass spectrometer used was an Acquity SQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 5 minutes, these conditions were held for 0.5 min before the eluent level was returned to the starting conditions of 95% water:5% acetonitrile over 6 seconds. These conditions were held for 1.4 minutes to allow equilibration of the column before the next sample was injected. The run lasted 7 minutes in total.

Method: 4LCMS2

Method 4LCMS2 employed an Alliance e2695 liquid handler and SFO with a Waters 2998 diode array detector. The detection was done at 254 nm and an array between 210-600 nm. The mass spectrometer used was an Acquity SQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 10 minutes, these conditions were held for 0.5 min before the eluent level was returned to the starting conditions of 95% water:5% acetonitrile over 6 seconds. These conditions were held for 1.4 minutes to allow equilibration of the column before the next sample was injected. The run lasted 12 minutes in total.

Method: 4LCMS5

Method 4LCMS5 employed an Alliance e2695 liquid handler and SFO with a Waters 2998 diode array detector. The detection was done at 254 nm and an array between 210-600 nm. The mass spectrometer used was an Acquity SQ which detected masses between 100 and 700 g/mol. The column used was a SunFire, 5 micron pore size, C18 column of dimensions 50×4.60 mm. The injection volume was 10 μL at a maximum concentration of 1 mg/mL. The flow rate was 1.5 mL/min and the mobile phases of water and acetonitrile contained 0.1% formic acid. The elution was started at 95% water:5% acetonitrile and held at this for 2 min before ramping up to 50% water:50% acetonitrile over 3 minutes. This was then ramped up to 5% water:95% acetonitrile over 0.5 min. The eluent level was returned to the starting conditions of 95% water:5% acetonitrile over 6 seconds. These conditions were held for 1.4 min to allow equilibration of the column before the next sample was injected. The run lasted 7 minutes in total.

Method: 5LCMS1

Method 5LCMS1 employed Waters 515 pumps, a Waters 2525 mixer with valves directing to the different columns and a Waters 2998 diode array detector. The detection was performed at 254 nm and an array between 210-600 nm. The mass spectrometer used was a Waters 3100 which detected masses between 100 and 700 g/mol. The column used was a SunFire, 5 micron pore size, C18 column of dimensions 50×4.60 mm. The injection volume was 10 μL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 5 minutes, these conditions were held for 0.5 min before the eluent level was returned to the starting conditions of 95% water: 5% acetonitrile over 6 seconds. These conditions were held for 1.4 minutes to allow equilibration of the column before the next sample was injected. The run lasted 7 minutes in total.

Method: 5LCMS5

Method 5LCMS5 employed Waters 515 pumps, a Waters 2525 mixer with valves directing to the different columns and a Waters 2998 diode array detector. The detection was performed at 254 nm and an array between 210-600 nm. The mass spectrometer used was a Waters 3100 which detected masses between 100 and 700 g/mol. The column used was a SunFire, 5 micron pore size, C18 column of dimensions 50×4.60 mm. The injection volume was 10 μL at a maximum concentration of 1 mg/mL. The flow rate was 1.5 mL/min and the mobile phases of water and acetonitrile contained 0.1% formic acid. The elution was started at 95% water:5% acetonitrile and held at this for 2 min before ramping up to 50% water:50% acetonitrile over 3 minutes. This was then ramped up to 5% water:95% acetonitrile over 0.5 min. The eluent level was returned to the starting conditions of 95% water:5% acetonitrile over 6 seconds. These conditions were held for 1.4 min to allow equilibration of the column before the next sample was injected. The run lasted 7 minutes in total.

General Methods: Preparative HPLC

Samples purified by Mass Spectrometry directed High Performance Liquid Chromatography employed the following conditions.

Method A Method A employed Waters 515 pumps, a Waters 2525 mixer and a Waters 2487 UV detector (single wavelength 254 nm). The mass spectrometer was a Waters micromass ZQ and the column used was a Waters SunFire, 5 μm pore size, C18 of dimensions 50×19 mm. The injection volume was up to 500 μL of solution at a maximum concentration of 50 mg/mL. The mobile phase consisted of a mixture of water and acetonitrile containing 0.1% formic acid. The eluent flow rate was 25 mL/min using 95% water, 5% acetonitrile, changing linearly over 5.3 minutes to 95% acetonitrile, 5% water, and maintaining for 0.5 minutes. The eluent level was returned to the starting conditions of 95% water:5% acetonitrile over 30 seconds.

Method B

Method B employed Waters 515 pumps, a Waters 2545 mixer with valves directing to the different columns and a Waters 2996 diode array detector. The detection was performed between 210 nm and 650 nm. The mass spectrometer used was a Waters 3100 which detected masses between 100 and 700 g/mol. The column used was an XBridge, 5 micron pore size, C18, 50×19 mm. The injection volume was chosen by the user and can be up to 500 μL of the solution (max 50 mg/mL). The flow rate was 25 mL/min and the mobile phases of water pH 10 (35% ammonia solution (aq) 0.3 mL/L) and acetonitrile (35% ammonia solution (aq) 0.3 mL/L). The elution was started at 95% water:5% acetonitrile ramping up to 5% water:95% acetonitrile over 5.30 minutes. The eluent level was returned to the starting conditions of 95% water: 5% acetonitrile over 0.6 minutes. These conditions were held for 1.4 minutes to allow equilibration of the column before the next sample was injected. The run lasted 7 minutes in total.

Synthesis

Several methods for the chemical synthesis of 5,6-substituted-2-pyridin-4-yl-3H-pyrimidin-4-one compounds of the present application are described herein. These and/or other well known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

In one approach (Scheme 1), compounds of formula [F1-3] are prepared by the reaction of a 3-substituted β-ketopropyl ester compound of formula [F1-1] in a condensation reaction utilising a suitable substituted pyridine-4-carboximidamide derivative of general formula [F1-2] in a polar solvent such as methanol or THF in the presence of a base such as sodium methoxide or DBU.

The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Derivatives of general formula [F1-5] are prepared by the reaction of a halogenating agent such as NCS or NBS in a polar solvent such as DMF or THF and a base such as $Et_3N$ or DIPEA at ambient temperature. After reaction work up, typically by a liquid-liquid extraction, the reaction product was used crude in the next step or purified by flash column chromatography, reverse phase preparative HPLC or re-crystallisation.

Alternatively, compounds of formula [F1-5] are prepared by the reaction of a 2,3-disubstituted β-ketopropyl ester compound of formula [F1-4] in a condensation reaction utilising a suitable substituted pyridine-4-carboximidamide derivative of general formula [F1-2] in a polar solvent such as methanol or THF in the presence of a base such as sodium methoxide or DBU. The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation.

In cases where the substituent $R^2$ contained an amine protected by a standard amine protecting group such as a tert-butyloxycarbonyl (Boc), compounds of formula [F1-5] can be deprotected by a suitable deprotection reaction, for example reaction with an acid such as TFA in a suitable solvent such as DCM at ambient temperature. After reaction work up, typically by a liquid-liquid extraction or purification by acidic ion exchange catch-release the crude product can be purified by flash column chromatography, reverse phase preparative HPLC or re-crystallisation.

For example, synthesis of 5-chloro-6-piperidin-4-yl-2-pyridin-4-yl-3H-pyrimidin-4-one (2)

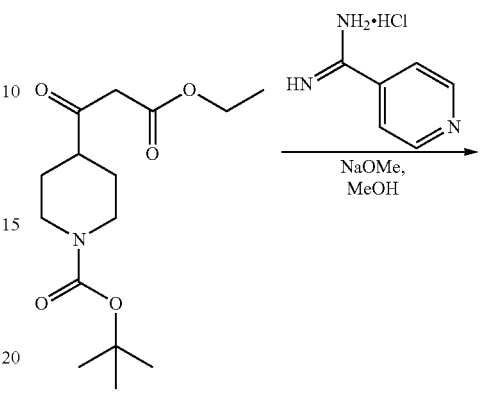

Scheme 1

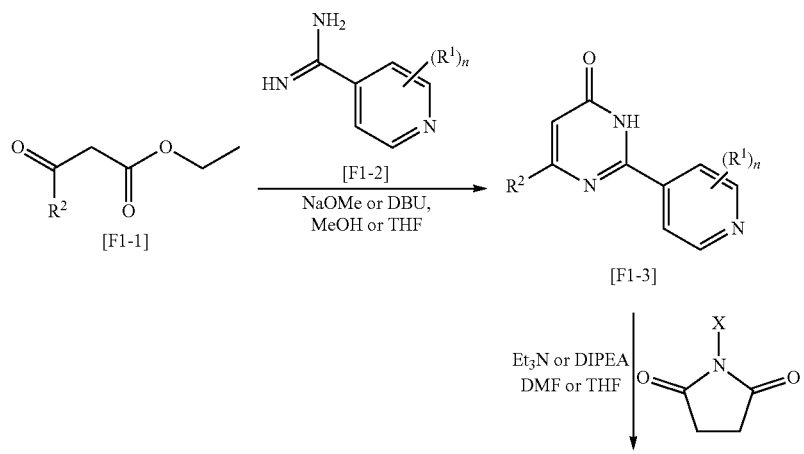

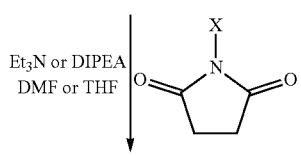

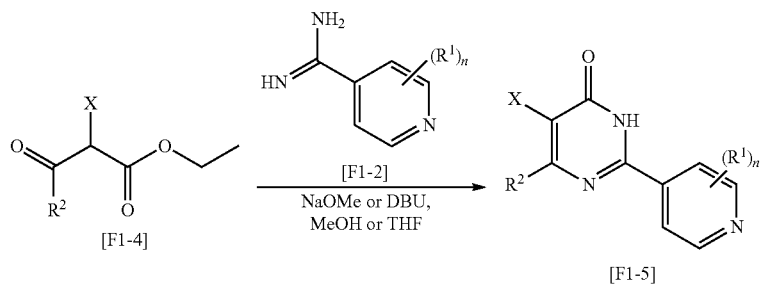

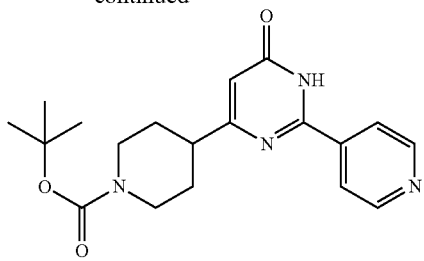

tert-Butyl 4-[6-oxo-2-(4-pyridyl)-1H-pyrimidin-4-yl]piperidine-1-carboxylate (1-001) Pyridine-4-carboximidamide hydrochloride (0.30 g, 2 mmol) was added to a round bottom flask and methanol (5 mL) and sodium methoxide (0.152 g, 4 mmol) were added. The mixture was allowed to stir at room temperature for 10 minutes then 4-(2-ethoxycarbonylacetyl)-piperidine-1-carboxylic acid tert-butyl ester (0.59 g, 2 mmol) was added and the reaction mixture was heated at 60° C. for 4 hours. The solvent was removed under reduced pressure and the residue was triturated with diisopropylether to provide a grey solid. This was dissolved in ethyl acetate (10 mL) and washed with water (10 mL) and brine (10 mL), dried (MgSO$_4$), filtered and evaporated under reduced pressure to give the title compound as an off-white solid (0.12 g, 17% yield). LCMS: RT: 3.08 min, MI 357, Method (4LCMS1).

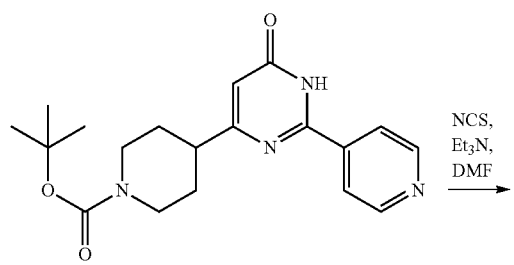

tert-Butyl 4-[5-chloro-6-oxo-2-(4-pyridyl)-1H-pyrimidin-4-yl]piperidine-1-carboxylate (1) tert-butyl 4-[6-oxo-2-(4-pyridyl)-1H-pyrimidin-4-yl]piperidine-1-carboxylate (1-001) (0.107 g, 0.3 mmol) was dissolved in DMF (2 mL) and triethylamine (0.084 mL, 0.6 mmol) added. The reaction mixture was treated with NCS (0.048 g, 0.36 mmol) and allowed to stir at room temperature for 30 minutes. The solvent was removed under reduced pressure and taken up in ethyl acetate (10 mL) and washed with water (10 mL). The organics were dried (MgSO$_4$), filtered and evaporated under reduced pressure to a brown gum. The residue was purified by HPLC (Method A) to yield the title compound as a white solid (0.05 g, 42% yield). LCMS: RT 3.70 min, MI 389/391, Method (4LCMS1); $^1$H NMR (400 MHz, d6-DMSO) δ 8.70 (2H, dd, J=1.6, 4.5 Hz), 7.98 (2H, dd, J=1.6, 4.5 Hz), 4.01 (2H, s), 3.18 (1H, m), 2.74 (2H, br), 1.66 (4H, m), 1.33 (9H, s).

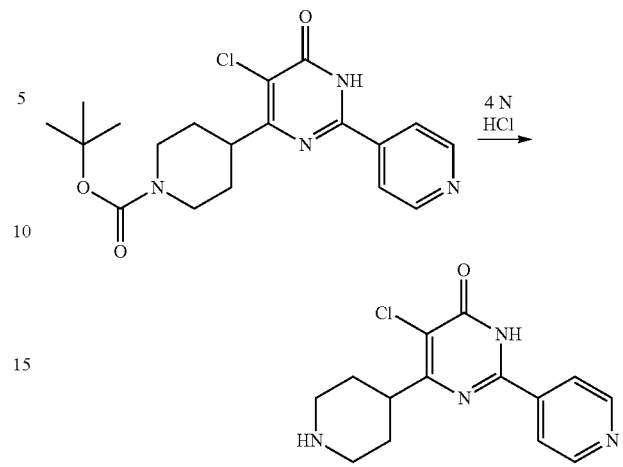

5-Chloro-6-piperidin-4-yl-2-pyridin-4-yl-3H-pyrimidin-4-one (2)

tert-Butyl 4-[5-chloro-6-oxo-2-(4-pyridyl)-1H-pyrimidin-4-yl]piperidine-1-carboxylate (1) (0.039 g, 0.1 mmol) was suspended in 4 N HCl in dioxane (5 mL) and allowed to stir at room temperature for 4 hours. The solvent was removed under reduced pressure to yield a white solid. This was dissolved in methanol and absorbed onto an SCX column. The column was washed with DCM (4 mL) and methanol (4 mL). The product was then eluted with 2 M ammonia in methanol to yield the title compound as a white solid (0.01 g, 33% yield). LCMS: RT 0.69 min, MI 291, Method (4LCMS1); $^1$H NMR (400 MHz, d6-DMSO) δ 8.61 (2H, dd, J=1.6, 4.5 Hz), 8.09 (2H, dd, J=1.6, 4.5 Hz), 3.36 (2H, m), 3.04 (2H, m), 2.68 (1H, m), 2.33 (1H, m), 2.03 (2H, m), 1.84 (2H, m).

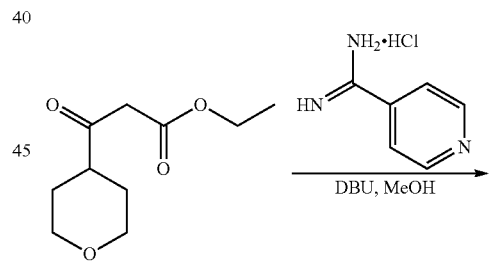

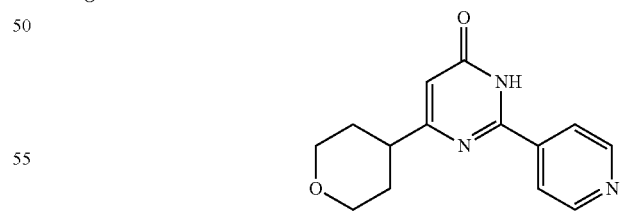

2-(4-pyridyl)-4-tetrahydropyran-4-yl-1H-pyrimidin-6-one (1-002)

Pyridine-4-carboximidamide hydrochloride (0.83 g, 5.26 mmol) was added to a round bottom flask and methanol (20 mL) and DBU (1.56 g, 5.26 mmol) were added. The mixture was allowed to stir at room temperature for 10 minutes then 3-oxo-3-(tetrahydro-pyran-4-yl)-propionic acid ethyl ester (1.0 g, 4.99 mmol) was added and the reaction mixture was heated at 75° C. for 24 hours. The reaction mixture was cooled and water (15 mL) was added, then the mixture was acidified to pH 5 by the addition of 2 N HCl and the precipitate was collected by filtration, washed with water and dried under reduced pressure to give the title compound as a pale yellow solid (1.02 g, 80% yield). LCMS: RT 2.6 min, MI 258, Method (4LCMS2); $^1$H NMR (400 MHz, d6-DMSO) δ 12.72 (1H, s), 8.77 (2H, m), 8.10 (2H, m), 6.36 (1H, s), 3.94 (4H, m), 2.78 (1H, m), 1.82 (4H, m).

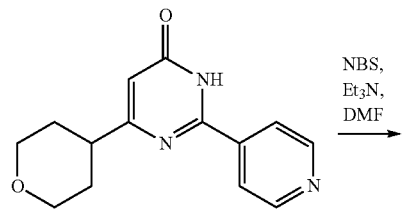

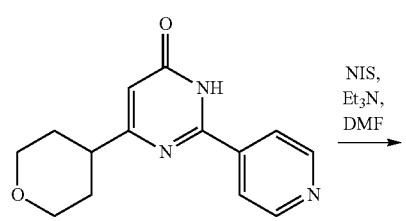

5-Bromo-2-(4-pyridyl)-4-tetrahydropyran-4-yl-1H-pyrimidin-6-one (3)

2-(4-Pyridyl)-4-tetrahydropyran-4-yl-1H-pyrimidin-6-one (1-002) (0.772 g, 3.0 mmol) was dissolved in DCM (10 mL) and triethylamine (0.84 mL, 6.0 mmol) added. The reaction mixture was treated with NBS (0.8 g, 4.5 mmol) and allowed to stir at room temperature for 30 minutes. The solvent was removed under reduced pressure and taken up in ethyl acetate (100 mL) and washed with water (100 mL). The organics were dried (MgSO$_4$), filtered and evaporated under reduced pressure to a brown gum. The residue was purified by HPLC (Method A) to yield the title compound as a white solid (0.95 g, 94% yield). LCMS: RT 2.69 min, MI 335/337 Method (4LCMS1); $^1$H NMR (400 MHz, d6-DMSO) δ 13.28 (1H, s), 8.64 (2H, dd, J=4.5, 1.7 Hz), 7.93 (2H, dd, J=4.5, 1.6 Hz), 3.82 (2H, dd, J=11.3, 3.5 Hz), 3.32 (2H, t, J=11.0 Hz), 3.21 (1H, m, partially obscured by water), 1.77 (2H, tt, J=12.4, 6.3 Hz), 1.49 (2H, d, J=10.9 Hz).

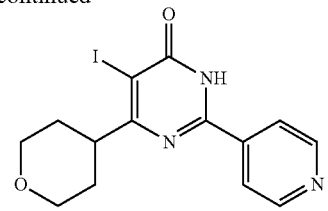

5-Iodo-2-(4-pyridyl)-4-tetrahydropyran-4-yl-1H-pyrimidin-6-one (4)

2-(4-Pyridyl)-4-tetrahydropyran-4-yl-1H-pyrimidin-6-one (1-002) (0.772 g, 3.0 mmol) was dissolved in DCM (10 mL) and triethylamine (0.84 mL, 6.0 mmol) added. The reaction mixture was treated with NIS (1.01 g, 4.5 mmol) and allowed to stir at room temperature for 30 minutes. The solvent was removed under reduced pressure and taken up in ethyl acetate (100 mL) and washed with water (100 mL). The organics were dried (MgSO$_4$), filtered and evaporated under reduced pressure to a brown gum. The residue was purified by HPLC (Method A) to yield the title compound as a white solid. LCMS: RT 2.85 min, MI 384, Method (4LCMS1); $^1$H NMR (400 MHz, d6-DMSO) δ 13.28 (1H, m), 8.77 (2H, dd, J=4.5, 1.6 Hz), 8.10 (2H, dd, J=4.5, 1.6 Hz), 3.98 (2H, m), 3.45 (2H, t, J=11.0 Hz), 3.28 (1H, m), 1.91 (2H, m), 1.64 (2H, m).

Synthesis of 5-fluoro-2-(4-pyridyl)-4-tetrahydropyran-4-yl-1H-pyrimidin-6-one (5)

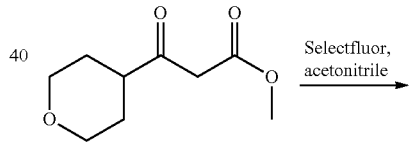

Synthesis of 2-fluoro-3-oxo-3-(tetrahydro-pyran-4-yl)-propionic acid methyl ester (1-003)

3-Oxo-3-(tetrahydro-pyran-4-yl)-propionic acid methyl ester (0.4 g, 2.0 mmol) was dissolved in acetonitrile and Selectfluor (0.78 g, 2.20 mmol) was added and the mixture was left to stir at room temperature for 2 days. The reaction mixture was evaporated under reduced pressure and the crude yellow oil was purified by column chromatography (3:7 EtOAc:cyclohexane) to give the title compound (0.38 g, 86% yield) as a colourless oil. $^1$H NMR (400 MHz, CDCl$_3$) δ 5.25 (1H, d), 4.32 (2H, m), 4.00 (2H, m), 3.45 (3H, s), 3.18 (1H, m), 1.75 (4H, m).

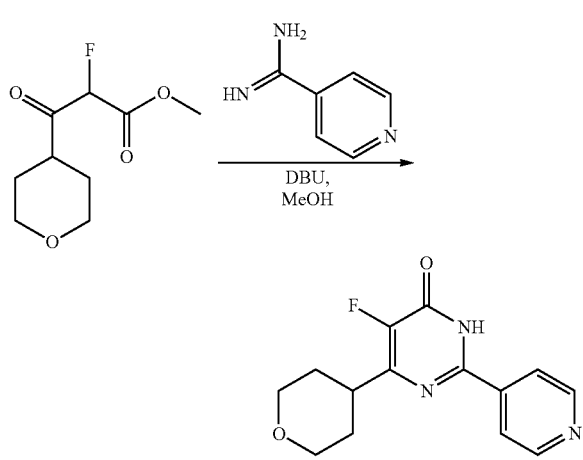

Synthesis of 5-fluoro-2-(4-pyridyl)-4-tetrahydropyran-4-yl-1H-pyrimidin-6-one (5)

2-fluoro-3-oxo-3-(tetrahydro-pyran-4-yl)-propionic acid methyl ester (1-003) (0.140 g, 0.640 mmol) was weighed into a round bottom flask and then methanol (5 mL) and DBU (0.300 g, 2.00 mmol) were added. The reaction mixture was treated with pyridine-4-carboxamidine (0.121 g, 1.00 mmol) and the resultant solution was heated at 50° C. for 2 hours. The solvent was removed under reduced pressure and the residue was dissolved in DCM (10 mL) and washed with saturated sodium citrate solution (10 mL). The organics were separated and evaporated under reduced pressure to yield a white solid. This was dissolved in DMSO and purified by HPLC (Method A) to afford a white solid. This was triturated with diethyl ether and filtered, washing with diethyl ether (5 mL) to afford the title compound (0.05 g, 28% yield) as a white solid. LCMS: RT 2.28 min, MI 276, Method (4LCMS1); $^1$H NMR (400 MHz, d6-DMSO) δ 13.46 (1H, s), 8.77 (2H, dd, J=4.5, 1.7 Hz), 8.03 (2H, d, J=6.1 Hz), 3.95 (2H, d, J=10.9 Hz), 3.48 (2H, t, J=11.0 Hz), 3.19 (1H, m), 1.93 (2H, d, J=8.5 Hz), 1.63 (2H, d, J=13.0 Hz).

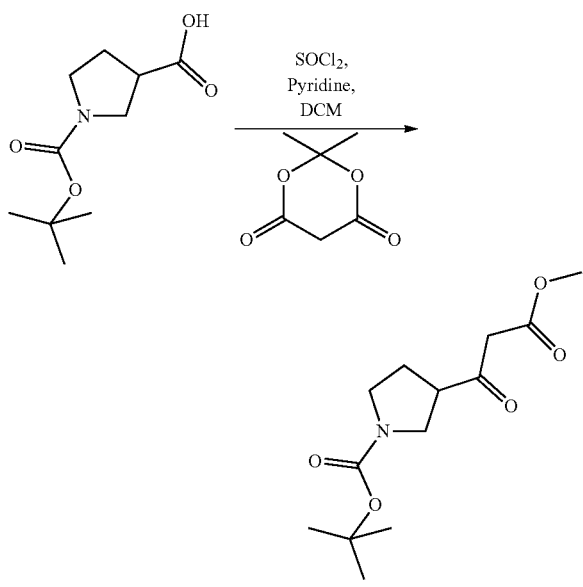

Synthesis of 3-(2-methoxycarbonyl-acetyl)-pyrrolidine-1-carboxylic acid tert-butyl ester (1-004)

Thionyl chloride (0.16 mL, 2.4 mmol) was added to a stirred solution of pyrrolidine-1,3-dicarboxylic acid 1-tert-butyl ester (0.43 g, 2.0 mmol), DMAP (0.61 g, 5.0 mmol) in DCM (4 mL). The mixture was left to stir at room temperature for 30 min then Meldrum's acid (0.58 g, 4.0 mmol) was added and the mixture was left to stir at room temperature for 1 hour. The reaction mixture was washed with a 2 N HCl (aq) solution and evaporated under reduced pressure. The residue was dissolved in methanol and heated to reflux for 6 h. Purification by column chromatography (0-10% DCM: MeOH) gave the title compound (0.27 g, 44% yield) which was used in the next step without further purification. $^1$H NMR (400 MHz, CDCl$_3$) δ 3.75 (3H, s), 3.46 (2H, s), 3.41 (3H, m), 3.36 (2H, m), 2.11 (2H, m), 1.52 (9H, s).

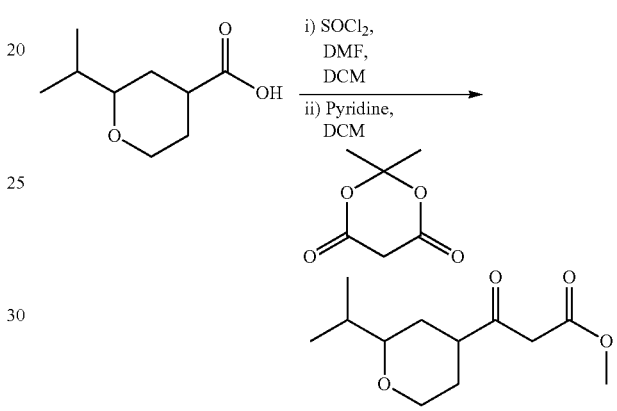

Synthesis of 3-(2-isopropyl-tetrahydro-pyran-4-yl)-3-oxo-propionic acid methyl ester (1-005)

Thionyl chloride (0.65 mL, 9.0 mmol) was added to a stirred solution of 2-isopropyl-tetrahydro-pyran-4-carboxylic acid (0.31 g, 1.8 mmol) in DCM (2 mL) and DMF (0.1 mL). The mixture was heated at reflux for three hours then evaporated under reduced pressure. DCM (4 mL) and pyridine (0.32 mL, 4 mmol) was added and the mixture stirred at room temperature for 5 min then Meldrum's acid (0.403 g, 3.6 mmol) was added and the mixture was left to stir at room temperature for 1 hour. The reaction mixture was washed with a 2 N HCl (aq) solution and evaporated under reduced pressure. The residue was dissolved in methanol and heated to reflux for 6 h. This was then concentrated under reduced pressure to give the title compound (0.110 g, 27% yield) which was used in the next step without further purification. $^1$H NMR (400 MHz, CDCl$_3$): as a mixture of diastereomers δ 4.48 (1H, m), 4.20 (1H, m), 3.75 (3H, s), 3.65 (2H, m), 3.40 (1H, m), 3.15 (1H, m), 2.60 (1H, m), 2.25 (1H, m), 1.80 (1H, m), 1.55 (1H, m), 1.20 (6H, m).

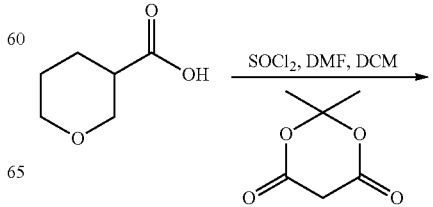

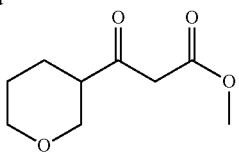

Synthesis of 3-Oxo-3-(tetrahydro-pyran-3-yl)-propionic acid methyl ester (1-006)

Thionyl chloride (0.17 mL, 2.4 mmol) was added to a stirred solution of tetrahydro-pyran-3-carboxylic acid (0.26 g, 2.0 mmol) in DCM (4 mL) and DMF (0.1 mL). The mixture was stirred at room temperature for 30 min then Meldrum's acid (0.576 g, 4.0 mmol) was added and the mixture was left to stir at room temperature for 1 hour. The reaction mixture was washed with a 2 N HCl (aq) solution and evaporated under reduced pressure. The residue was dissolved in methanol and heated to reflux for 6 h. The mixture was then concentrated under reduced pressure to give the title compound (0.27 g, 75% yield) which was used in the next step without further purification.

Synthesis of 3-(4-fluoro-tetrahydro-pyran-4-yl)-3-oxo-propionic acid ethyl ester (1-008)

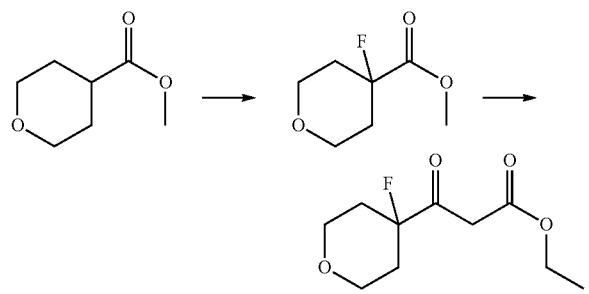

Synthesis of 4-fluoro-tetrahydro-pyran-4-carboxylic acid methyl ester (1-007)

A solution of diisopropylamine (2.95 mL, 21.0 mmol) in THF (25 mL) was cooled to −78° C. under a nitrogen atmosphere. n-Butyllithium (13.6 mL, 21.0 mmol of a 1.6 M solution in hexanes) was added over a 10 min period and the mixture was left to stir at −78° C. for 30 mins then the reaction mixture was warmed to room temperature then added dropwise over 10 min to a solution of tetrahydro-pyran-4-carboxylic acid methyl ester (2.83 g, 20.0 mmol) in THF (30 mL) at −78° C. keeping the temperature below −60° C. The reaction mixture was allowed to stir at −78° C. for 30 minutes and then warmed to 0° C. for 30 minutes before re-cooling to −78° C. A solution of N-fluorobenzenesulfonimide (6.30 g, 20.0 mmol) in THF (25 mL) was added dropwise over 5 minutes. The reaction mixture was allowed to stir at −78° C. for 2 hours and then the cooling bath was removed and allowed to warm to room temperature and stirred for a further 15 hours. The reaction mixture was concentrated under reduced pressure and then diluted with saturated ammonium chloride solution (100 mL). The aqueous was extracted with ethyl acetate (2×100 mL). The extracts were combined, dried (MgSO₄), filtered and evaporated under reduced pressure to give a brown oil that was purified by flash column chromatography (1:9 diethyl ether:cyclohexane to 1:1 diethyl ether:cyclohexane) to give the title compound (0.66 g, 20.3% yield) as a yellow liquid.

Synthesis of 3-(4-fluoro-tetrahydro-pyran-4-yl)-3-oxo-propionic acid ethyl ester (1-008)

Sodium hexamethyl disilazide (1.54 mL, 1.4 mmol of a 1M solution in THF) was cooled to −78° C. before the dropwise addition of ethyl acetate (0.135 mL, 1.5 mmol). The resultant mixture was allowed to stir for 30 minutes and then a solution of 4-fluoro-tetrahydro-pyran-4-carboxylic acid methyl ester (1-007) (0.227 g, 1.4 mmol) in THF (2 mL) was added dropwise at −78° C. The reaction mixture was allowed to stir at this temperature for 3 hours and then allowed to warm to room temperature and a saturated ammonium chloride solution (10 mL) was added. The reaction mixture was allowed to stir for 15 hours and then extracted with ethyl acetate (2×15 mL). The extracts were combined, washed with brine, dried with (MgSO₄), filtered and evaporated under reduced pressure to give the title compound (0.24 g, 77% yield) as a yellow oil which was used in the next step without further purification.

Synthesis of 3-(2-ethoxycarbonyl-acetyl)-3-fluoro-piperidine-1-carboxylic acid tert-butyl ester (1-010)

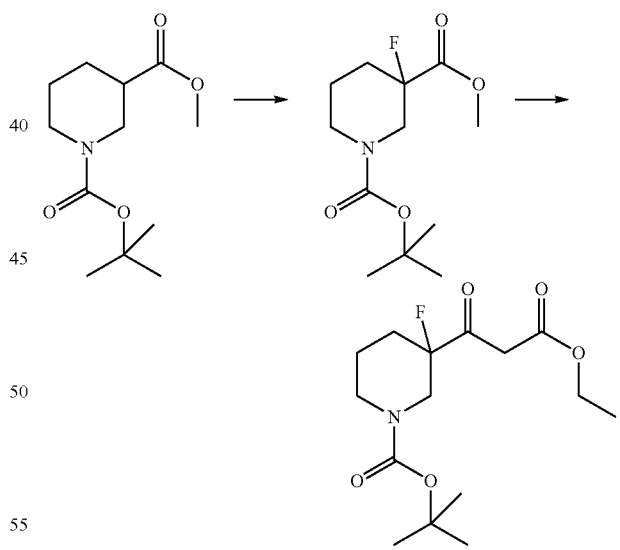

Synthesis of 3-fluoro-piperidine-1,3-dicarboxylic acid 1-tert-butyl ester 3-methyl ester (1-009)

This was synthesised according to the above procedure starting from piperidine-1,3-dicarboxylic acid 1-tert-butyl ester 3-ethyl ester, to give the title compound (0.33 g, 6% yield) which was used in the next step without further purification.

Synthesis of 3-(2-ethoxycarbonyl-acetyl)-3-fluoro-piperidine-1-carboxylic acid tert-butyl ester (1-010)

This was synthesised according to the above procedure starting from 3-fluoro-piperidine-1,3-dicarboxylic acid 1-tert-butyl ester 3-methyl ester (1-009), to give the title compound (0.38 g, 100% yield) which was used in the next step without further purification.

Synthesis of 4-(2-ethoxycarbonyl-acetyl)-4-fluoro-piperidine-1-carboxylic acid tert-butyl ester (1-012)

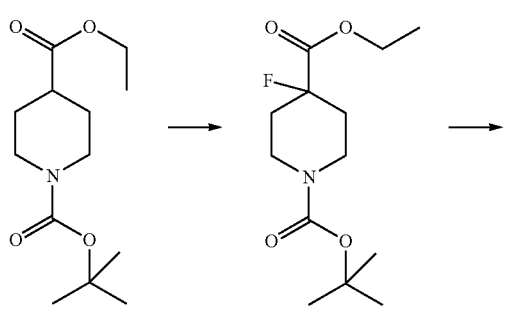

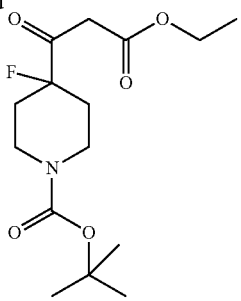

Synthesis of 4-fluoro-piperidine-1,4-dicarboxylic acid 1-tert-butyl ester 4-ethyl ester (1-011)

This was synthesised according to the above procedure starting from piperidine-1,4-dicarboxylic acid 1-tert-butyl ester 4-ethyl ester, to give the title compound (0.8 g, 94% yield) which was used in the next step without further purification.

Synthesis of 4-(2-ethoxycarbonyl-acetyl)-4-fluoro-piperidine-1-carboxylic acid tert-butyl ester (1-012)

This was synthesised according to the above procedure starting from piperidine-4-fluoro-piperidine-1,4-dicarboxylic acid 1-tert-butyl ester 4-ethyl ester (1-011), to give the title compound (0.74 g, 100% yield) which was used in the next step without further purification.

The following compounds were synthesised according to the general synthesis shown in scheme [1]:

| No | General formula of Starting Material | Product [F1-5] | Characterisation |
|---|---|---|---|
| 6 | F1-1 | (structure) | RT 2.62 min, MI 292, Method (4LCMS1) $^1$H NMR (400 MHz, CDCl$_3$) δ 8.80 (2H, m), 8.09 (2H, m), 3.99 (2H, m), 3.52 (2H, m), 3.45 (1H, m), 1.96 (2H, m), 1.62 (2H, m). |
| 7 | F1-1 | (structure) | MI 277, Method (4LCMS1) $^1$H NMR (400 MHz, MeOD) δ 8.80 (2H, m), 8.33 (2H, m), 5.60 (1H, m), 3.67 (1H, m), 3.52 (1H, m), 2.70 (1H, m), 2.25 (2H, m), 2.07 (1H, m). |
| 8 | F1-1 | (structure) ·HCl | $^1$H NMR (400 MHz, d6-DMSO) δ 9.08 (2H, d), 8.92 (2H, d), 3.75 (1H, m), 3.60 (3H, m), 3.20 (1H, m), 2.15 (2H, m), 2.0 (2H, m). |

-continued

| No | General formula of Starting Material | Product [F1-5] | Characterisation |
|---|---|---|---|
| 9 | F1-1 | (structure: 5-chloro-2-(pyridin-4-yl)-6-(4-methyltetrahydro-2H-pyran-4-yl)pyrimidin-4(3H)-one) | RT 2.97 min, MI 306, Method (4LCMS1)<br>$^1$H NMR (400 MHz, d6-DMSO) δ 13.55 (1H, s), 8.78 (2H, dd, J 4.5, 1.6 Hz), 8.05 (2H, dd, J = 4.5, 1.7 Hz), 3.73 (2H, m), 3.55 (2H, ddd, J = 11.5, 8.7, 2.8 Hz), 2.55 (2H, dd, J = 12.8, 8.6 Hz), 1.76 (2H, m), 1.43 (3H, s). |
| 10 | F1-1 | (structure: 5-chloro-2-(2-fluoropyridin-4-yl)-6-(4-methyltetrahydro-2H-pyran-4-yl)pyrimidin-4(3H)-one) | RT 3.73 min, MI 324, Method (5LCMS1)<br>$^1$H NMR (400 MHz, d6-DMSO) δ 13.68 (1H, br s), 8.45 (1H, d, J = 5.2 Hz), 8.02 (1H, d, J = 5.2 Hz), 7.80 (1H, s), 3.72 (2H, m), 3.54 (2H, m), 2.53 (2H, m), 1.77 (2H, m), 1.43 (3H, s). |
| 11 | F1-1 | (structure: 5-chloro-2-(pyridin-4-yl)-6-(pyrrolidin-3-yl)pyrimidin-4(3H)-one·HCl) | $^1$H NMR (400 MHz, CDCl$_3$) δ 9.02 (2H, d), 8.78 (2H, d), 4.25 (1H, m), 3.80 (1H, m), 3.70 (1H, m), 3.62 (1H, m), 3.50 (1H, m), 2.60 (1H, m), 2.23 (1H, m). |
| 12 | F1-1 | (structure: 5-chloro-2-(pyridin-4-yl)-6-(tetrahydrofuran-3-yl)pyrimidin-4(3H)-one) | RT 2.43 min, MI 278, Method (4LCMS1)<br>$^1$H NMR (400 MHz, CDCl$_3$) δ 8.80 (2H, d), 8.20 (2H, d), 4.25 (1H, t), 4.10 (1H, m), 4.05 (3H, m), 2.35 (2H, m). |
| 13 | F1-1 | (structure: 5-chloro-2-(2-fluoropyridin-4-yl)-6-(tetrahydro-2H-pyran-4-yl)pyrimidin-4(3H)-one) | RT 3.52 min, MI 310/312, Method (4LCMS1)<br>$^1$H NMR (400 MHz, d6-DMSO) 13.54 (1H, s), 8.46 (1H, d, J = 5.2 Hz), 8.07 (1H, d, J = 5.2 Hz), 7.85 (1H, s), 3.97 (2H, m), 3.48 (2H, m), 3.33 (1H, m), 1.93 (2H, m), 1.63 (2H, m). |
| 14 | F1-1 | (structure: 5-chloro-6-(2-isopropyltetrahydro-2H-pyran-4-yl)-2-(pyridin-4-yl)pyrimidin-4(3H)-one) | RT 3.81 min, MI 334, Method (4LCMS1)<br>$^1$H NMR (400 MHz, CDCl$_3$) δ 8.91 (2H, d), 8.15 (2H, d), 4.20 (1H, m), 3.60 (1H, m), 3.42 (1H, m), 3.18 (1H, m), 2.15 (1H, m), 1.62 (4H, m), 1.01 (3H, d), 0.95 (3H, d). |
| 15 | F1-1 | (structure: 5-chloro-2-(pyridin-4-yl)-6-(tetrahydro-2H-pyran-2-yl)pyrimidin-4(3H)-one) | RT 2.66 min, MI 292, Method (4LCMS1)<br>$^1$H NMR (400 MHz, CDCl$_3$) δ 8.88 (2H, m), 8.18 (2H, m), 4.89 (1H, d), 4.21 (1H, d), 3.68 (1H, t), 2.05 (2H, m), 1.75 (3H, m), 1.62 (1H, m). |

| No | General formula of Starting Material | Product [F1-5] | Characterisation |
|---|---|---|---|
| 16 | F1-1 | (5-chloro-2-(pyridin-4-yl)-6-(tetrahydro-2H-pyran-3-yl)pyrimidin-4(3H)-one) | RT 2.78 min, MI 291, Method (4LCMS1)<br>$^1$H NMR (400 MHz, d6-DMSO) δ 8.82 (2H, d), 8.05 (2H, d), 3.88 (2H, m), 3.58 (1H, t), 3.42 (2H, m), 1.85 (2H, m), 1.68 (2H, m). |
| 17 | F1-4 | (2-(2-fluoropyridin-4-yl)-5-fluoro-6-(tetrahydro-2H-pyran-4-yl)pyrimidin-4(3H)-one) | RT 3.27 min, MI 294, Method (4LCMS1)<br>$^1$H NMR (400 MHz, d6-DMSO) δ 13.52 (1H, s), 8.44 (1H, d, J = 5.2 Hz), 8.03 (1H, d, J = 5.2 Hz), 7.81 (1H, s), 3.95 (2H, m), 3.48 (2H, t, J = 10.9 Hz), 3.21 (1H, s), 1.93 (2H, dd, J = 12.8, 4.3 Hz), 1.63 (2H, d, J = 11.3 Hz). |
| 18 | F1-1 | (5-chloro-2-(2-fluoropyridin-4-yl)-6-(4-fluorotetrahydro-2H-pyran-4-yl)pyrimidin-4(3H)-one) | RT 3.69 min, MI 328/330, Method (5LCMS1)<br>$^1$H NMR (400 MHz, d6-DMSO) δ 13.69 (br s, 1H), 8.35 (d, J = 5.2 Hz, 1H), 7.94 (dt, J = 5.2, 1.6 Hz, 1H), 7.73 (t, J = 1.4 Hz, 1H), 3.78 (ddd, J = 11.4, 5.1, 2.1 Hz, 2H), 3.71-3.51 (m, 2H) 2.37-2.15 (m, 2H), 2.09-1.87 (m, 2H). |
| 19 | F1-1 | (5-chloro-6-(3-fluoropiperidin-3-yl)-2-(pyridin-4-yl)pyrimidin-4(3H)-one) | RT 0.6 min, MI 309, Method (4LCMS1)<br>$^1$H NMR (400 MHz, d6-DMSO) δ 8.20 (2H, d), 8.09 (2H d), 3.75 (1H, m), 3.62 (1H, m), 3.18 (2H, m), 3.05 (1H, m), 2.20 (1H, m), 1.82 (1H, m), 1.78 (1H, m). |
| 20 | F1-1 | (5-chloro-6-(morpholin-2-yl)-2-(pyridin-4-yl)pyrimidin-4(3H)-one) | MI 293, Method (4LCMS5)<br>$^1$H NMR (400 MHz, d6-DMSO) δ 9.35 (s, 1H), 8.79-8.67 (m, 2H), 8.14-7.92 (m, 2H), 5.06 (dd, J = 10.5, 2.5 Hz, 1H), 4.00 (dd, J = 12.6, 3.6 Hz, 1H), 3.97-3.77 (m, 1H), 3.47-3.35 (m, 1H), 3.34-3.26(m, 1H), 3.23-3.14 (m, 1H), 3.11-3.00 (m, 1H). |
| 21 | F1-1 | (5-chloro-6-(4-fluoropiperidin-4-yl)-2-(pyridin-4-yl)pyrimidin-4(3H)-one) | RT 1.25 min, MI 309, Method (4LCMS5)<br>$^1$H NMR (400 MHz, MeOD) δ 8.87-8.76 (m, 2H), 8.38-8.21 (m,2H), 3.61-3.35 (m, 4H), 2.81-2.50 (m, 4H). |

| No | General formula of Starting Material | Product [F1-5] | Characterisation |
|---|---|---|---|
| 22 | F1-1 | *(structure: 2-(pyridin-3-yl)-5-chloro-6-(4-(Boc)-4-fluoropiperidin-4-yl)-pyrimidin-4(3H)-one)* | RT 3.92 min, MI 409, Method (4LCMS1)<br>$^1$H NMR (400 MHz, MeOD) δ 8.84-8.61 (m, 2H), 8.12 (d, 2H), 4.19-3.98 (m, 2H), 3.31 (p, 2H), 2.50-2.14 (m, 4H), 1.49 (s, 9H). |
| 23 | F1-1 | *(structure: 2-(2-chloropyridin-4-yl)-5-chloro-6-(tetrahydropyran-4-yl)-pyrimidin-4(3H)-one)* | RT 3.27 min, MI 327, Method (1LCMS5)<br>$^1$H NMR (500 MHz, d6-DMSO) δ 8.62 (dd, J = 5.2, 0.6 Hz, 1H), 8.19-8.15 (m, 1H), 8.10 (d, J = 5.2 Hz, 1H), 3.97 (dd, J = 11.2, 3.9 Hz, 2H), 3.47 (t, J = 11.0 Hz, 2H), 3.39 - 3.28 (m, 1H), 1.92 (dd, J = 12.4, 4.0 Hz, 2H), 1.62 (d, J = 12.5 Hz, 2H). |
| 24 | F1-1 | *(structure: 2-(2-(trifluoromethyl)pyridin-4-yl)-5-chloro-6-(tetrahydropyran-4-yl)-pyrimidin-4(3H)-one)* | RT 4.60 min, MI 360, Method (1LCMS1)<br>$^1$H NMR (500 MHz, CDCl$_3$) δ 8.97 (d, J = 5.1 Hz, 1H), 8.65 (s, 1H), 8.45 (dd, J = 5.1, 1.5 Hz, 1H), 4.14 (dd, J = 11.2, 3.9 Hz, 2H), 3.61 (t, J = 11.1 Hz, 2H), 3.54-3.46 (m, 1H), 2.13 (dd, J = 12.8, 4.3 Hz, 2H), 1.73 (d, J = 10.8 Hz, 2H). |
| 25 | F1-1 | *(structure: 2-(2-fluoropyridin-4-yl)-5-chloro-6-(4-(Boc)-piperidin-4-yl)-pyrimidin-4(3H)-one)* | RT 4.68 min, MI 409, Method (4LCMS1) |

In one approach (Scheme 2), compounds of formula [F2-3] were prepared by the reaction of dimethyl malonate [F2-1] in a condensation reaction utilising a suitable substituted pyridine-4-carboximidamide derivative of general formula [F2-2] in a polar solvent such as methanol or THF in the presence of a base such as sodium methoxide, potassium-tert-butoxide or DBU. The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Derivatives of general formula [F2-4] were prepared by the reaction of a halogenating agent such as phosphorous oxychloride at high temperature. After reaction work up, typically by the addition of water followed by the addition of a base such as aqueous sodium hydroxide, the crude reaction mixture was purified by liquid-liquid extraction, and the reaction product was used crude in the next step or purified by flash column chromatography, reverse phase preparative chromatography or re-crystallisation. Derivatives of general formula [F2-6] are prepared in a nucleophilic aromatic substitution type reaction utilising a suitable amine of general formula [F2-5], and a base such as Et$_3$N or NaH in a polar solvent such as ethanol, butanol, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Compounds of general formula [F2-7] were prepared by reaction of 4-chloro-2-pyridin-4-yl-pyrimidine derivatives of general formula [F2-6] with aqueous base such as sodium hydroxide or potassium hydroxide at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Compounds of general formula [F2-8] were prepared by reaction of 2-pyridin-4-yl-3H-pyrimidin-4-one derivatives of general formula [F2-7] with a halogenating agent such as NCS or NBS in a polar solvent such as DMF or THF and a base such as Et₃N or DIPEA at ambient temperature. After reaction work up, typically by a liquid-liquid extraction, the reaction product was purified by flash column chromatography, reverse phase preparative HPLC or re-crystallisation.

hydrochloric acid. The mixture was cooled by the addition of ice and then neutralised by the addition of ammonium hydroxide solution (aq) (35% w/w) to give a clear, yellow solution. Concentrated hydrochloric acid was added until pH 6 was reached and the mixture was left to stand overnight.

Scheme 2

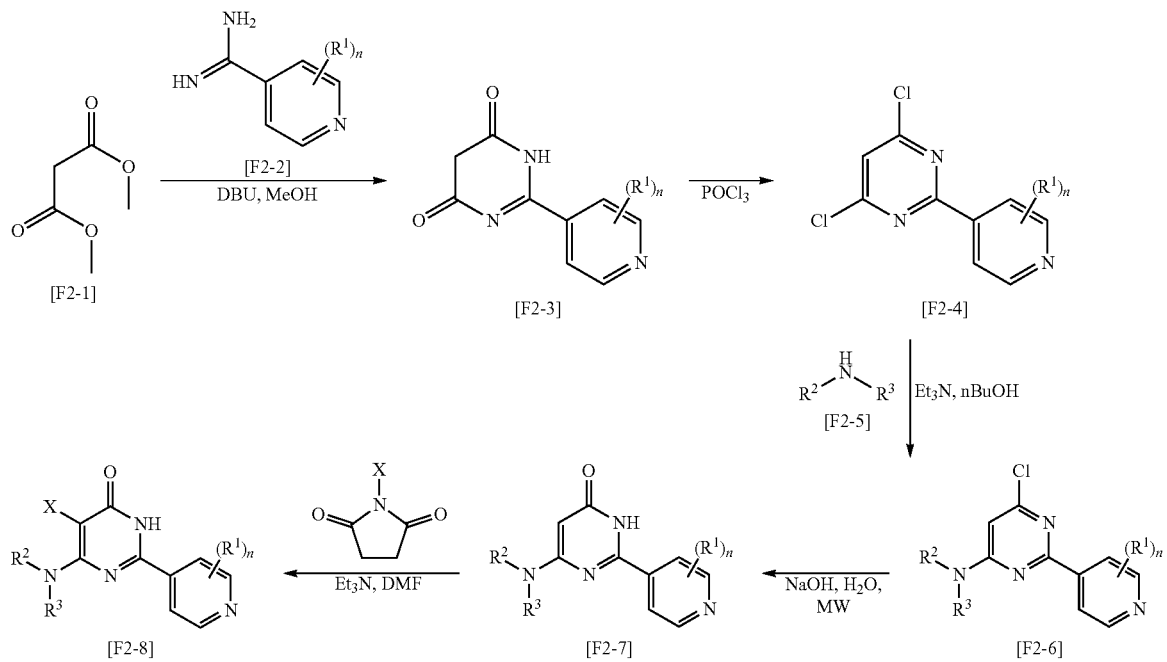

For example, synthesis of 5-chloro-4-(1-piperidyl)-2-(4-pyridyl)-1H-pyrimidin-6-one (26)

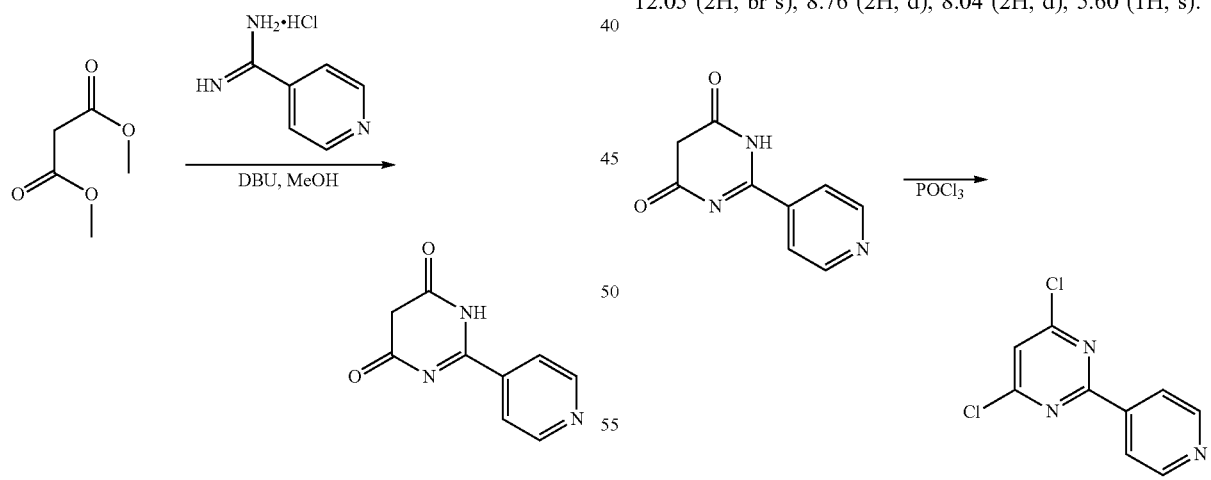

Synthesis of 2-(4-pyridyl)-1H-pyrimidine-4,6-dione (2-001)

To a stirred mixture of 4-amidinopyridine hydrochloride (10.0 g, 63.5 mmol) and dimethyl malonate (8.40 g, 63.5 mmol) in methanol (200 mL) was added DBU (38.6 g, 253 mmol) and the mixture was heated at reflux overnight. The resultant orange solution was evaporated under reduced pressure and the resultant gum was dissolved in 1 M The precipitate was collected by filtration to give the title compound (7.3 g, 61% yield). LCMS: RT 1.38 min, MI 190, Method (5LCMS1); ¹H NMR (400 MHz, d6-DMSO) δ 12.05 (2H, br s), 8.76 (2H, d), 8.04 (2H, d), 5.60 (1H, s).

Synthesis of 4,6-dichloro-2-pyridin-4-yl-pyrimidine (2-002)

To a stirred solution of phosphorus oxychloride (50 mL) was added 2-(4-pyridyl)-1H-pyrimidine-4,6-dione (2-001) (5.20 g, 27.5 mmol) and the mixture was heated at reflux overnight to give a black reaction mixture. The excess phosphoryl chloride was removed by evaporation under reduced pressure to give a black gum. Water was added dropwise, whilst stirring vigorously with a glass rod, to give a black solution which was neutralised with ammonium hydroxide solution (aq) (35% w/w). The resultant grey mixture was extracted with DCM and the extracts were combined, dried (MgSO₄), filtered and evaporated under reduced pressure to give the title compound (5.16 g, 83% yield) as a brown powder. LCMS: RT 3.57 min, MI 226, Method (5LCMS1); ¹H NMR (400 MHz, d6-DMSO) δ 8.82 (2H, d), 8.27 (2H, d), 7.41 (1H, s).

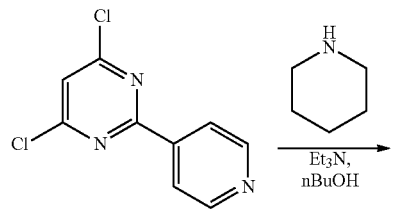

Synthesis of 4-chloro-6-piperidin-1-yl-2-pyridin-4-yl-pyrimidine (2-003)

A mixture of the 4,6-dichloro-2-pyridin-4-yl-pyrimidine (2-002) (1.00 g, 4.42 mmol), piperidine (0.40 g, 4.70 mmol), triethylamine (1.00 g, 10.0 mmol) and n-butanol (20 mL) was heated under microwave irradiation at 150° C. for 1 hr. The solvent was removed by evaporation under reduced pressure to give a brown gum which was washed with water and extracted with dichloromethane, dried (MgSO₄), filtered and evaporated under reduced pressure to give a brown semi-solid. Purification by column chromatography (0-50% EtOAc:cyclohexane) gave the title compound (0.4 g, 33% yield). LCMS: RT 3.65 min, MI 275, Method (5LCMS1); ¹H NMR (400 MHz, d6-DMSO) δ 8.73 (2H, m), 8.20 (2H, d), 6.49 (1H, s), 3.65 (4H, m), 1.68 (6H, m).

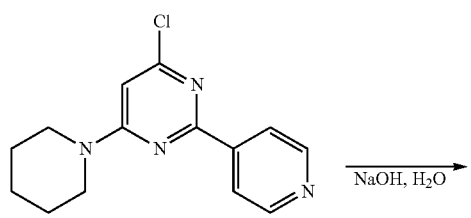

Synthesis of 6-piperidin-1-yl-2-pyridin-4-yl-3H-pyrimidin-4-one (2-004)

A suspension of 4-chloro-6-piperidin-1-yl-2-pyridin-4-yl-pyrimidine (2-003) (0.349 g, 1.27 mmol) in sodium hydroxide (0.250 g, 6.25 mmol) in water (20 mL) was heated under microwave irradiation at 150° C. for 1 h. The mixture was extracted with dichloromethane (3×20 mL) and the organic phase was collected and evaporated under reduced pressure and purified by preparative HPLC (Method A) to give the title compound (0.03 g, 9% yield). LCMS: RT 3.73 min, MI 275, Method (5LCMS1); ¹H NMR (400 MHz, CDCl₃) δ 8.82 (2H, d), 8.19 (2H, d), 5.53 (1H, s), 3.67 (4H, m), 1.69 (6H, m).

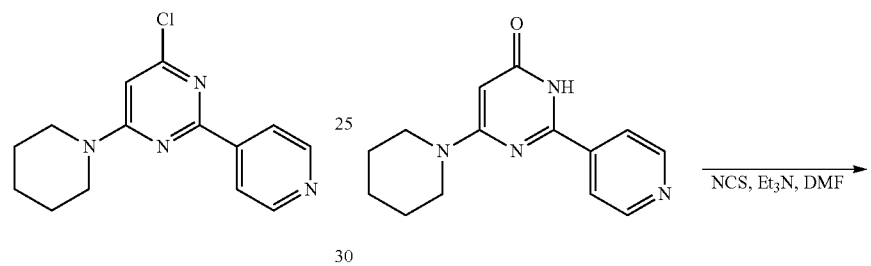

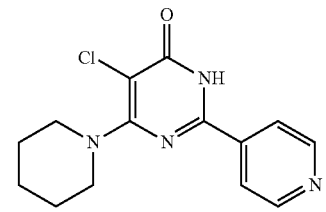

Synthesis of 5-chloro-4-(1-piperidyl)-2-(4-pyridyl)-1H-pyrimidin-6-one (26)

A mixture of 6-piperidin-1-yl-2-pyridin-4-yl-3H-pyrimidin-4-one (2-004) (0.027 g, 0.105 mmol) and triethylamine (0.037 g, 0.360 mmol) in DMF (10 mL) was stirred at room temperature and N-chlorosuccinamide (0.023 g, 0.172 mmol) was added. The mixture was left to stir overnight. The solvent was removed by evaporation under reduced pressure to give a brown residue which was loaded onto an SCX cartridge and washed with MeOH then the product eluted with 2 M ammonia/methanol. The ammonia/methanol eluent was concentrated under reduced pressure. Water (5 mL) was added, followed by a saturated solution of ammonium chloride (1 mL) and the mixture was stirred and then extracted with dichloromethane. The extracts were combined and evaporated under reduced pressure to give the title compound (0.018 g, 58% yield) LCMS: RT 3.25 min, MI 291, Method (5LCMS1); ¹H NMR (400 MHz, CDCl₃) δ 8.83 (2H, d), 8.21 (2H, d), 3.81 (4H, m), 1.74 (6H, m).

The following compounds were synthesised according to the general synthesis shown in scheme 2:

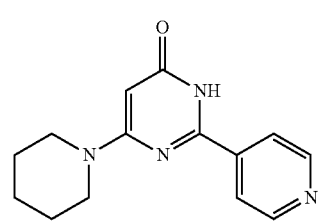

| No | Product [F2-8] | Characterisation |
|---|---|---|
| 27 | | RT 3.15 min, MI 335, Method (4LCMS1)<br>¹H NMR (400 MHz, MeOD) δ 8.70-8.76 (m, 2H), 8.02-8.05 (m, 2H), 4.18 (dt, 2H), 3.55-3.71 (m, 3H), 3.48 (ddd, 2H), 2.03 (ddd, 2H), 1.66 (ddt, 2H), 1.21 (t, 3H). |
| 28 | | RT 1.27 min, MI 320, Method (5LCMS1)<br>¹H NMR (400 MHz, d6-DMSO) δ 8.77 (2H, d), 8.04 (2H, d), 4.22 (2H, m), 3.24 (1H, m), 2.87 (2H, m), 2.52 (2H, m), 2.24 (3H, s), 1.07 (3H, d). |
| 29 | | RT 1.29 min, MI 320, Method (5LCMS1)<br>¹H NMR (400 MHz, d6-DMSO) δ 8.53 (2H, d), 7.81 (2H, d), 3.79 (2H, m), 3.60 (1H, m), 3.42 (1H, m), 2.60 (1H, m), 2.37 (6H, s), 1.90 (1H, m), 1.55 (1H, m). |
| 30 | | RT 2.81 min, MI 277 Method (5LCMS1)<br>¹H NMR (400 MHz, d6-DMSO) δ 8.76 (2H, d), 8.04 (2H, d), 3.82 (4H, m), 1.88 (4H, m). |
| 31 | | RT 1.35 min, MI 364, Method (5LCMS1)<br>¹H NMR (400 MHz, d6-DMSO) δ 8.77 (2H, d), 8.08 (2H, d), 3.69 (4H, m), 2.48 (6H, m), 1.08 (3H, t). |
| 32 | | RT 3.34 min, MI 392, Method (LCMS6) |
| 33 | | RT 2.63 min, MI 306, Method (1LCMS1) |

Scheme 3

In one approach (Scheme 3), compounds of general formula [F3-3] were prepared by the reaction of a compound of general formula [F3-1] with an acyl chloride of general formula [F3-2] in a polar aprotic solvent such as DMA, DMF or NMP in the presence of a tertiary amine base such as $Et_3N$, DIPEA or NMM to yield the N-acylated derivative of general formula [F3-3], Method A. After reaction work up, typically by a liquid-liquid extraction, the reaction product was used crude in the next step or purified by flash column chromatography, reverse phase preparative HPLC or re-crystallisation. In another approach compounds of general formula [F3-5] were prepared by the reaction of a compound of general formula [F3-1] with a carboxylic acid of general formula [F3-4] with a suitable coupling agent such as HBTU or HATU in a polar aprotic solvent such as DMA or DMF in the presence of a tertiary amine base such as $Et_3N$, DIPEA or NMM to yield the N-acylated derivative of general formula [F3-5], Method B. After reaction work up, typically by a liquid-liquid extraction, the reaction product was used crude in the next step or purified by flash column chromatography, reverse phase preparative HPLC or re-crystallisation. In another approach compounds of general formula [F3-7] were prepared by the reaction of a compound of general formula [F3-1] with an isocyanate of general formula [F3-6] in an aprotic solvent such as DCM, DMA or DMF at ambient or high temperature to yield the urea derivative of general formula [F3-7], Method C. After reaction work up, typically by a liquid-liquid extraction, the reaction product was used crude in the next step or purified by flash column chromatography, reverse phase preparative HPLC or re-crystallisation. In another approach compounds of general formula [F3-9] were prepared by the reaction of a compound of general formula [F3-1] with a sulfonyl chloride of general formula [F3-8] in a polar aprotic solvent such as DMA, DMF, NMP in the presence of an amine base such as $Et_3N$, DIPEA, NMM or pyridine at ambient or high temperature to yield the N-sulfonamide derivative of general formula [F3-9], Method D. After reaction work up, typically by a liquid-liquid extraction, the reaction product was used crude in the next step or purified by flash column chromatography, reverse phase preparative HPLC or re-crystallisation. In another approach compounds of general formula [F3-11] were prepared by the reaction of a compound of general formula [F3-1] with an acid anhydride of general formula [F3-10] in a solvent such as DCM at ambient or high temperature to yield the amide derivative of general formula [F3-11], Method E. After reaction work up, typically by a liquid-liquid extraction, the reaction product was used crude in the next step or purified by flash column chromatography, reverse phase preparative HPLC or re-crystallisation.

In another approach, compounds of formula [F3-13] were prepared by a reductive amination type reaction of an aldehyde or ketone derivative of general formula [F3-12] with an amine derivative of general formula [F3-1] with a reducing agent such as sodium borohydride, sodium triacetoxyborohydride or a supported borohydride reagent in acetic acid and a polar protic solvent such as MeOH or EtOH to yield the N-alkylated derivative of general formula [F3-13], Method F. After reaction work up, typically by a liquid-liquid extraction, the reaction product was used crude in the next step or purified by flash column chromatography, reverse phase preparative HPLC or re-crystallisation.

In cases where the substituent $R^2$ or $R^3$ contained an amine protected by a standard amine protecting group such as a tert-butyloxycarbonyl (Boc), compounds of formula [F3-3], [F3-5], [F3-7], [F3-9], [F3-11] can be deprotected by a suitable deprotection reaction, for example reaction with an acid such as TFA in a suitable solvent such as DCM at ambient temperature. After reaction work up, typically by a liquid-liquid extraction or purification by acidic ion exchange catch-release the crude product could be purified by flash column chromatography, reverse phase preparative HPLC or re-crystallisation.

Scheme 3

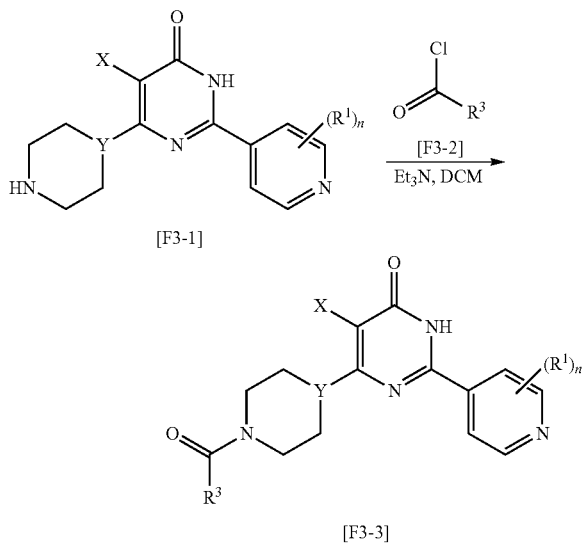

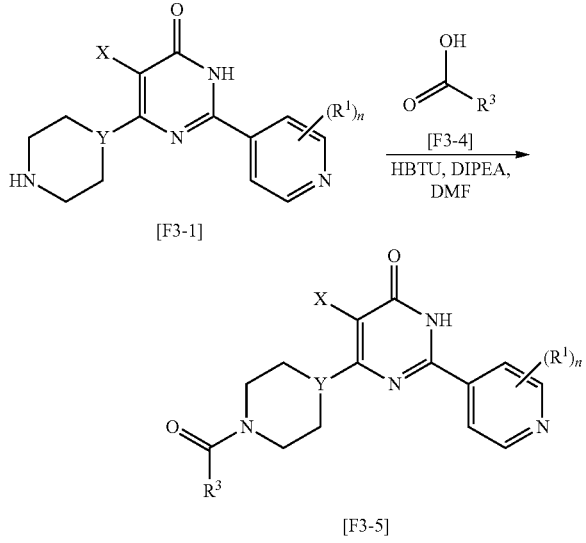

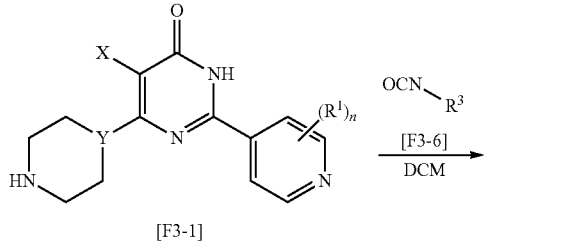

-continued

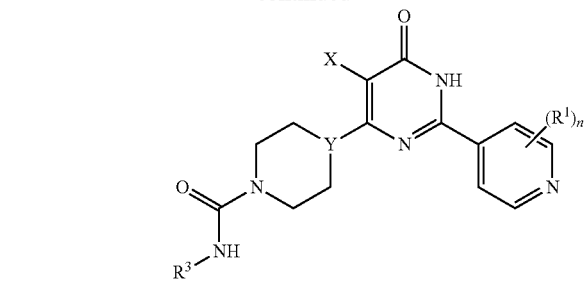

[F3-7]

Method D

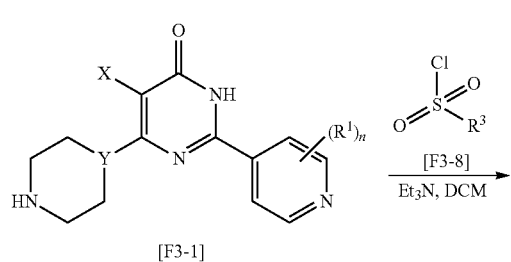

[F3-1]

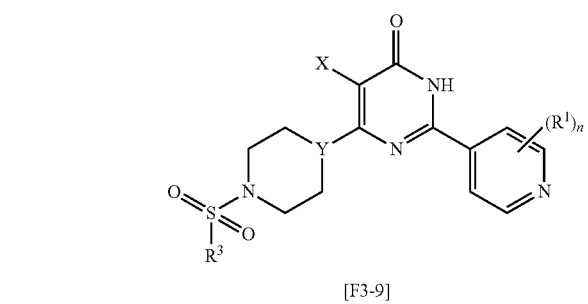

[F3-9]

Method E

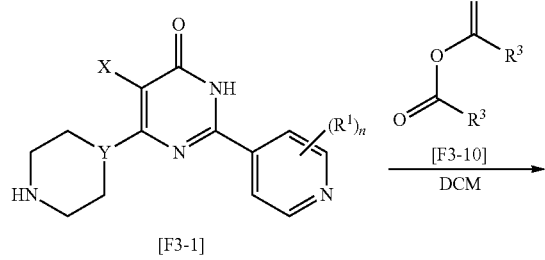

[F3-1]

-continued

Method F

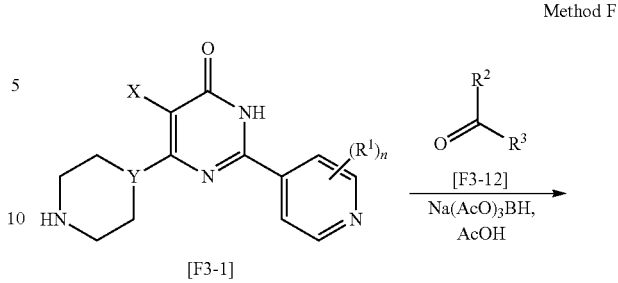

[F3-1]

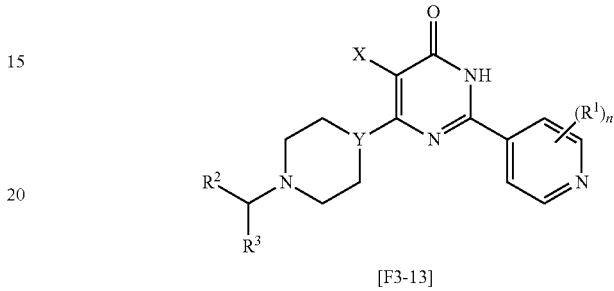

[F3-13]

For example synthesis of 5-chloro-4-[1-(2-methylpropanoyl)-4-piperidyl]-2-(4-pyridyl)-1H-pyrimidin-6-one (34), Method A

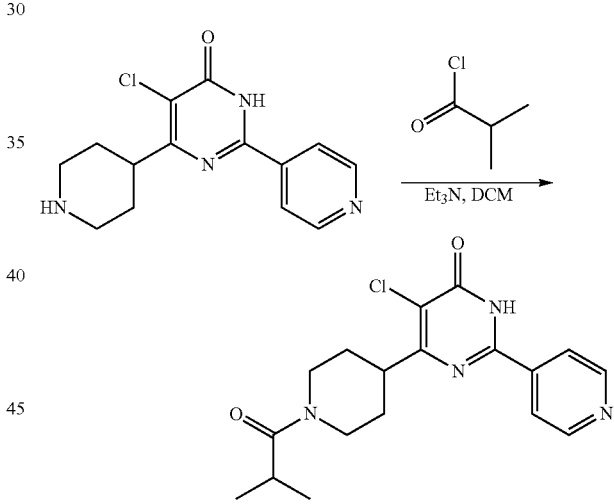

To a suspension of 5-chloro-6-piperidin-4-yl-2-pyridin-4-yl-3H-pyrimidin-4-one (2) (0.02 g, 0.07 mmol) in dichloromethane (5 mL) was added triethylamine (0.007 g, 0.07 mmol), followed by a solution of iso-propanoyl chloride (0.008 g, 0.075 mmol) in DCM (1 mL). The mixture was left to stir at room temperature overnight and the solvent was removed by evaporation under reduced pressure to give a solid which was purified by preparatory HPLC (Method A) to give the title compound (2.47 mg, 10% yield). LCMS: RT 2.66 min, MI 361, Method (LCMS6). $^1$H NMR (400 MHz, CDCl$_3$) δ 13.44 (s, 1H), 8.87 (d, 2H), 7.92-8.33 (m, 2H), 4.87 (d, 1H), 4.13 (d, 1H), 3.46 (tt, 1H), 3.23 (s, 1H), 2.88 (p, 1H), 2.72 (t, 1H), 1.80-2.00 (m, 4H), 1.18 (dd, 6H).

For example synthesis of tert-butyl-N-[2-[4-[5-chloro-6-oxo-2-(4-pyridyl)-1H-pyrimidin-4-yl]-1-piperidyl]-2-oxoethyl]carbamate (35), Method B

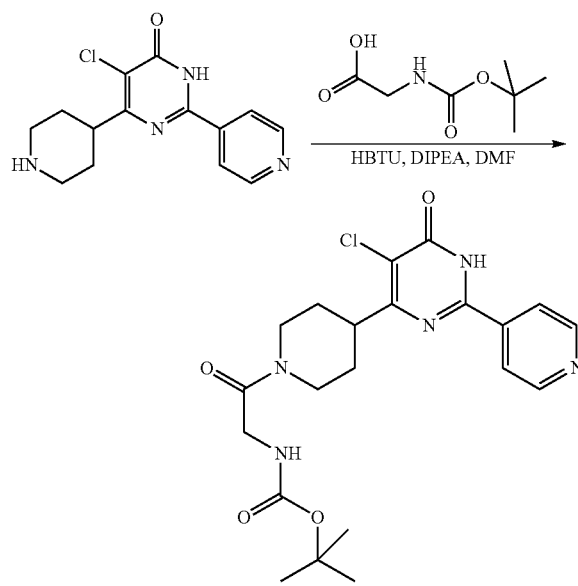

DIPEA (0.065 mL, 0.5 mmol) was added to a mixture of HBTU (0.056 g, 0.15 mmol) and N-(tert-butoxycarbonyl) glycine (0.19 g, 0.11 mmol) in DMF (1 mL). The mixture was stirred at room temperature for 5 min then a mixture of 5-chloro-6-piperidin-4-yl-2-pyridin-4-yl-3H-pyrimidin-4-one (2) (0.03 g, 0.10 mmol) in DMF (1 mL) was added and the mixture was left to stir at room temperature for 48 hours. The crude reaction mixture was purified by HPLC (Method A) to give the title compound (5.5 mg, 12% yield) LCMS: RT 4.43 min, MI 446, Method (1LCMS1).

For example synthesis of 4-[5-chloro-6-oxo-2-(4-pyridyl)-1-H-pyrimidin-4-yl]-N-isopropyl-piperidine-1-carboxamide (36), Method C

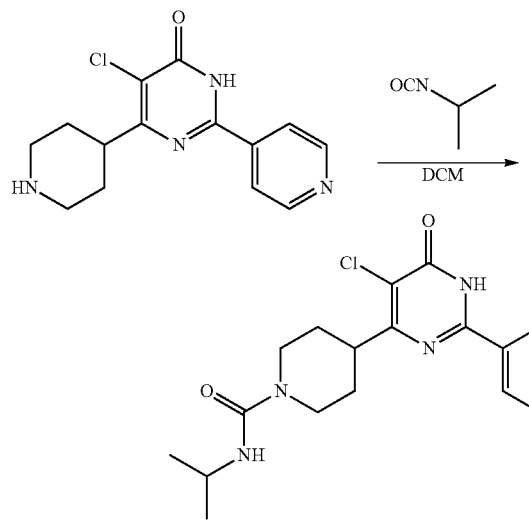

Isopropylisocyante (3 drops from a glass pipette) was added to a mixture of 5-chloro-4-(4-piperidyl)-2-(4-pyridyl)-1H-pyrimidin-6-one (2) (0.02 g, 0.062 mmol) in DCM (10 mL) and the mixture was left to stir at room temperature for 48 hours. The crude reaction mixture was purified by HPLC (Method A) to give the title compound (2.9 mg, 14% yield). LCMS: RT 2.53 min, MI 376, Method (1LCMS1). $^1$H NMR (400 MHz, MeOD) δ 8.70-8.83 (m, 1H), 8.04-8.20 (m, 1H), 4.16-4.29 (m, 2H), 3.96 (p, 1H), 3.46 (ddd, 1H), 2.96 (td, 2H), 1.75-2.12 (m, 4H), 1.20 (d, 6H).

For example synthesis of 4-[1-(benzenesulfonyl)-4-piperidyl]-5-chloro-2-(4-pyridyl)-1H-pyrimidin-6-one (37), Method D

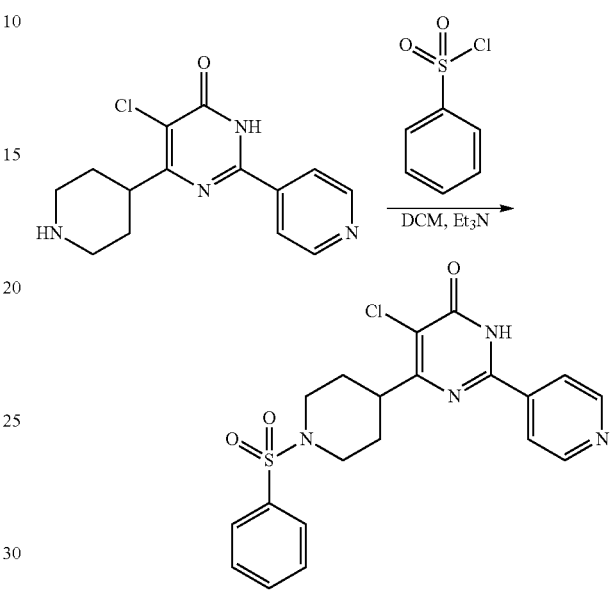

Triethylamine (0.013 mL, 0.092 mmol) was added to a mixture of 5-chloro-4-(4-piperidyl)-2-(4-pyridyl)-1H-pyrimidin-6-one (2) (0.02 g, 0.062 mmol) in DCM (10 mL) and the mixture was left to stir at room temperature for 5 minutes. A solution of benzenesulfonyl chloride (16.4 mg, 0.093 mmol) in DCM (2 mL) was added and the reaction mixture was left to stir at room temperature for 5 hours. The crude reaction mixture was purified by reverse phase preparative HPLC (Method A) to give the title compound (13.6 mg, 45% yield). LCMS: RT 3.49 min, MI 431, Method (4LCMS1).

For example synthesis of 5-chloro-2-(4-pyridyl)-4-[1-(2,2,2-trifluoroacetyl)-4-piperidyl]-1H-pyrimidin-6-one (38), Method E

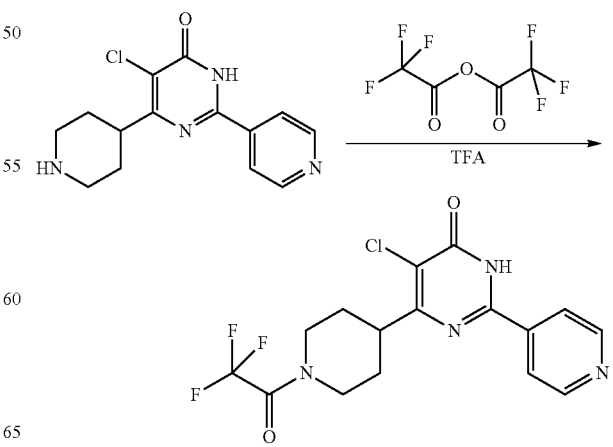

A mixture of 5-chloro-4-(4-piperidyl)-2-(4-pyridyl)-1H-pyrimidin-6-one (2) (0.05 g, 0.137 mmol) in TFA (5 mL) and TFAA (5 mL) was heated at 90° C. for 2 hours. The crude reaction mixture was purified by reverse phase preparative HPLC (Method A) to give the title compound (13.6 mg, 45% yield). RT 3.39 min, MI 387, Method (1LCMS1).

For example synthesis of 5-chloro-4-(1-isobutyl-4-piperidyl)-2-(4-pyridyl)-1H-pyrimidin-6-one (39): Method F

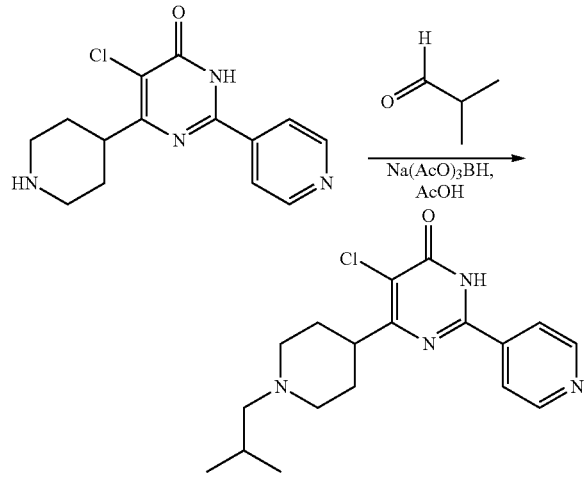

To a solution of 5-chloro-4-(4-piperidyl)-2-(4-pyridyl)-1H-pyrimidin-6-one (2) (0.01 g, 0.34 mmol) in glacial acetic acid (10 mL) was added isopropylcarboxaldehyde (0.5 mL, 0.7 mmol) and the mixture was left to stir at room temperature for 4 hours to give a clear, homogenous brown solution. Sodium triacetoxyborohydride (0.35 g, 1.65 mmol) was added and the mixture was left to stir at room temperature overnight. The solvent was removed by evaporation under reduced pressure to give a brown residue. The crude reaction mixture was loaded onto an SCX cartridge and washed with MeOH then the product was eluted with 2 M ammonia/methanol. The ammonia/methanol eluent was concentrated under reduced pressure and the crude product was purified by HPLC (Method A) to give the title compound (64 mg, 50% yield) as a brown solid. LCMS: RT 1.64 mins, MI 347, Method (5LCMS1); $^1$H NMR (400 MHz, MeOD) δ 8.57-8.46 (m, 2H), 8.21-8.12 (m, 2H), 3.68 (d, J=11.9 Hz, 2H), 3.44 (tt, J=11.6, 3.8 Hz, 1H), 3.09 (td, J=12.7, 12.2, 2.7 Hz, 2H), 2.98 (d, J=7.2 Hz, 2H), 2.39 (q, J=11.4 Hz, 2H), 2.27-2.13 (m, 1H), 2.06-1.97 (m, 2H), 1.06 (d, J=6.6 Hz, 6H).

The following compounds were synthesised according to the general synthesis shown in scheme [3]:

| No | Method | Product | Characterisation |
|----|--------|---------|------------------|
| 40 | A | | RT 2.17 min, MI 333, Method (LCMS6)<br>$^1$H NMR (400 MHz, MeOD) δ 8.72 (d, 2H), 8.08 (d, 2H), 4.53-4.72 (m, 2H), 3.45-3.56 (m, 2H), 2.79 (t, 2H), 2.15 (s, 3H), 1.77-1.95 (m, 3H). |
| 41 | A | | RT 2.90 min, MI 395, Method (4LCMS1) |
| 42 | A | | RT 0.65 min, MI 334, Method (4LCMS1)<br>$^1$H NMR (400 MHz, MeOD) δ 8.71-8.85 (m, 2H), 8.01-8.19 (m, 2H), 3.83-3.93 (m, 4H), 3.72-3.80 (m, 4H), 2.20 (s, 3H). |

-continued

| No | Method | Product | Characterisation |
|---|---|---|---|
| 43 | D | (structure) | RT 2.38 min, MI 370, Method (5LCMS1)<br>¹H NMR (400 MHz, d6-DMSO) δ 8.78 (2H, d), 8.09 (2H, d), 3.75 (4H, m), 3.35 (4H, m), 2.91 (3H, s). |
| 44 | A | (structure) | RT 4.73 min, MI 375, Method (1LCMS1)<br>¹H NMR (400 MHz, d6-DMSO) δ 8.77 (2H, m), 8.03 (2H, m), 4.44 (2H, m), 2.92 (2H, m), 1.75 (5H, m), 1.21 (9H, s). |
| 45 | B | (structure) | RT 3.58 min, MI 396, Method (4LCMS1)<br>¹H NMR (300 MHz, d6-DMSO) δ 13.51 (s, 1H), 8.78 (s, 2H), 8.59 (d, 1H), 8.06 (d, 2H), 7.93 (td, 1H), 7.58 (d, 1H), 7.51-7.43 (m, 1H), 4.63 (d, 1H), 3.77 (d, 1H), 3.27-3.12 (m, 2H), 3.02-2.86 (m, 1H), 1.95-1.61 (m, 4H). |
| 46 | B | (structure) | RT 4.04 min, MI 420, Method (1LCMS1)<br>¹H NMR (300 MHz, d6-DMSO) δ 13.51 (s, 1H), 8.85-8.69 (m, 2H), 8.13-8.01 (m, 2H), 7.93 (d, 2H), 7.62 (d, 2H), 4.60 (d, 1H), 3.54 (d, 1H), 3.33-3.11 (m, 2H, partially obscured by water), 3.06-2.86 (m, 1H), 1.95-1.52 (m, 4H). |
| 47 | B | (structure) | RT 2.96 min, MI 397, Method (1LCMS1)<br>¹H NMR (300 MHz, d6-DMSO) δ 13.51 (s, 1H), 9.40-9.26 (m, 2H), 8.91-8.68 (m, 2H), 8.15-8.03 (m, 2H), 7.81-7.73 (m, 1H), 4.62 (d, 1H), 3.56 (d, 1H), 3.37-3.20 (m, 2H, partially obscured by water), 3.08-2.90 (m, 1H), 1.97-1.63 (m, 4H). |
| 48 | B | (structure) | RT 4.05 min, MI 420, Method (1LCMS1)<br>¹H NMR (300 MHz, d6-DMSO) δ 13.51 (s, 1H), 8.78 (d, 2H), 8.08 (d, 2H), 7.92 (s, 2H), 7.77 (d, 1H), 7.66 (t, 1H), 4.62 (d, 1H), 3.59 (s, 1H), 3.40-3.18 (m, 2H, partially obscured by water), 3.04-2.84 (m, 1H), 1.93-1.59 (m, 4H). |

| No | Method | Product | Characterisation |
|---|---|---|---|
| 49 | B | 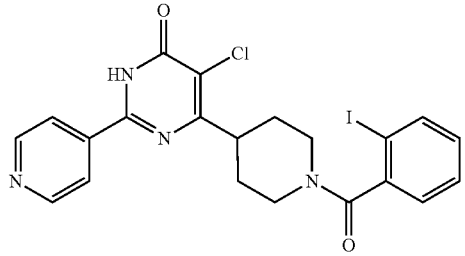 [SMILES: O=C(c1ccccc1I)N1CCC(c2nc(-c3ccncc3)[nH]c(=O)c2Cl)CC1] | RT 4.89 min, MI 521, Method (1LCMS1)<br>$^1$H NMR (300 MHz, d6-DMSO) δ 13.48 (s, 1H), 8.82-8.72 (m, 2H), 8.06 (dd, 2H), 7.94-7.83 (m, 1H), 7.53-7.41 (m, 1H), 7.38-7.21 (m, 1H), 7.16 (t, 1H), 4.72-4.57 (m, 1H), 3.26-3.06 (m, 2H), 2.93 (s, 1H), 2.17-1.58 (m, 5H). |
| 50 | B | 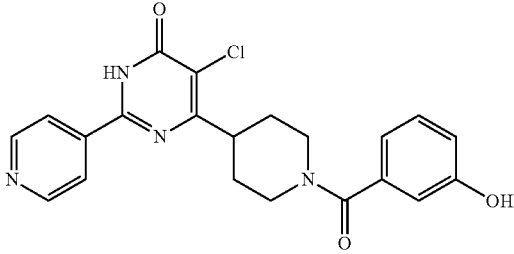 [SMILES: O=C(c1cccc(O)c1)N1CCC(c2nc(-c3ccncc3)[nH]c(=O)c2Cl)CC1] | RT 4.04 min, MI 411, Method (1LCMS1) |
| 51 | B | 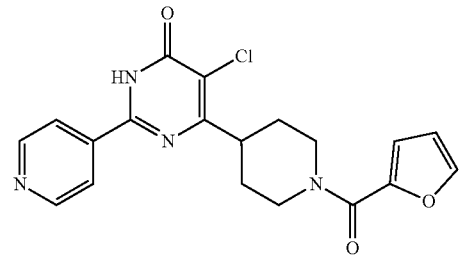 [SMILES: O=C(c1ccco1)N1CCC(c2nc(-c3ccncc3)[nH]c(=O)c2Cl)CC1] | RT 4.11 min, MI 385, Method (1LCMS1)<br>$^1$H NMR (300 MHz, d6-DMSO) δ 13.50 (s, 1H), 8.75 (d, 2H), 8.04 (d, 2H), 7.84 (s, 1H), 7.00 (d, 1H), 6.62 (s, 1H), 4.59-4.27 (m, 2H), 3.33 (m, 3H), 1.92-1.67 (m, 4H). |
| 52 | B | 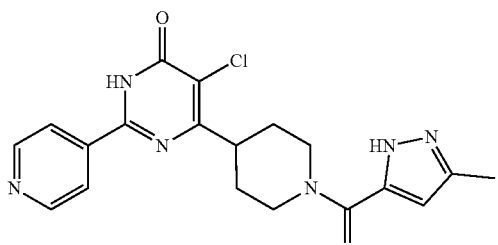 | RT 3.73 min, MI 399, Method (1LCMS1) |
| 53 | B | 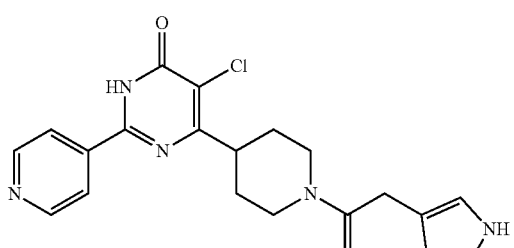 | RT 3.73 min, MI 399, Method (1LCMS1)<br>$^1$H NMR (300 MHz, d6-DMSO) δ 13.85 (s, 1H), 8.93 (s, 1H), 8.78 (d, 2H), 8.02 (d, 2H), 7.43 (s, 1H), 4.53 (d, 1H), 4.09 (d, 1H), 3.94 (d, 2H), 3.45-3.14 (m, 2H, partially obscured by water), 2.77 (t, 1H), 1.91-1.56 (m, 4H). |
| 54 | B | 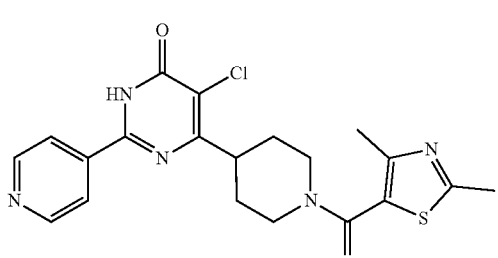 | RT 4.01 min, MI 430, Method (1LCMS1)<br>$^1$H NMR (300 MHz, d6-DMSO) δ 13.51 (s, 1H), 8.77 (d, 2H), 8.04 (d, 2H), 4.41-3.77 (m, 1H), 3.49-3.34 (m, 2H, partially obscured by water), 3.24-3.03 (m, 2H), 2.61 (s, 3H), 2.30 (s, 3H), 1.88-1.66 (m, 4H). |

-continued

| No | Method | Product | Characterisation |
|---|---|---|---|
| 55 | B | (structure) | RT 2.60 min, MI 399, Method (1LCMS1) |
| 56 | B | (structure) | RT 3.96 min, MI 413, Method (1LCMS1) |
| 57 | B | (structure) | RT 3.61 min, MI 402, Method (1LCMS1)<br>$^1$H NMR (300 MHz, d6-DMSO) δ 13.51 (s, 1H), 9.17 (d, 1H), 8.76 (d, 2H), 8.17 (d, 1H), 8.04 (d, 2H), 4.63 (d, 1H), 4.28 (d, 1H), 3.47-3.17 (m, 2H, partially obscured by water), 3.04-2.86 (m, 1H), 1.92-1.66 (m, 4H). |
| 58 | B | (structure) | RT 3.89 min, MI 413, Method (1LCMS1)<br>$^1$H NMR (300 MHz, d6-DMSO) δ 13.50 (s, 1H), 8.76 (d, 2H), 8.02 (d, 2H), 6.33 (s, 1H), 4.85 (d, 1H), 4.61 (d, 1H), 3.74 (s, 3H), 3.29-3.10 (m, 2H), 2.94-2.77 (m, 1H), 2.25 (s, 3H), 1.89-1.68 (m, 4H). |
| 59 | B | (structure) | RT 3.77 min, MI 403, Method (1LCMS1) |

-continued

| No | Method | Product | Characterisation |
|---|---|---|---|
| 60 | B | | RT 4.13 min, MI 437, Method (1LCMS1) |
| 61 | B | | RT 3.44 min, MI 504, Method (1LCMS1) |
| 62 | B | | RT 3.81 min, MI 452, Method (1LCMS1) |
| 63 | B | | RT 5.16 min, MI 453, Method (1LCMS1)<br>$^1$H NMR (300 MHz, d6-DMSO) δ 13.50 (s, 1H), 8.77 (d, 2H), 8.11-8.02 (m, 2H), 7.36 (d, 2H), 6.95 (d, 2H), 4.73-4.57 (m, 1H), 4.17-4.02 (m, 1H), 3.43-3.25 (m, 2H, partially obscured by water), 3.13-2.83 (m, 2H), 1.88-1.68 (m, 4H), 1.27 (d, 6H). |
| 64 | B | | RT 4.67 min, MI 462, Method (1LCMS1) |
| 65 | B | | RT 3.86 min, MI 502, Method (1LCMS1) |

| No | Method | Product | Characterisation |
|---|---|---|---|
| 66 | B | | RT 4.70 min, MI 429, Method (1LCMS1)<br>¹H NMR (300 MHz, d6-DMSO) δ 13.50 (s, 1H), 8.84-8.72 (m, 2H), 8.04 (ddd, 2H), 7.62-7.30 (m, 4H), 4.66 (d, 1H), 3.45-3.10 (m, 3H, partially obscured by water), 2.95 (ddd, 1H), 1.95-1.59 (m, 4H). |
| 67 | B | | RT 3.69 min, MI 416, Method (1LCMS1)<br>¹H NMR (300 MHz, D6-DMSO) δ 13.51 (s, 1H), 9.09 (s, 1H), 8.77 (d, 2H), 8.04 (d, 2H), 4.74-3.57 (m, 2H), 3.53-3.27 (m, 1H, partially obscured by water), 3.25-3.05 (m, 2H), 2.39 (s, 3H), 1.90-1.66 (m, 4H). |
| 68 | B | | RT 3.22 min, MI 385, Method (1LCMS1) |
| 69 | B | | RT 4.11 min, MI 400, Method (1LCMS1) |
| 70 | B | | RT 4.10 min, MI 395, Method (1LCMS1)<br>¹H NMR (300 MHz, d6-DMSO) δ 13.51 (s, 1H), 8.82-8.69 (m, 2H), 8.03 (ddd, 2H), 4.56-4.40 (m, 1H), 4.17 (t, 1H), 3.29-3.06 (m, 3H), 2.92-2.70 (m, 1H), 2.02-1.55 (m, 6H). |

-continued

| No | Method | Product | Characterisation |
|---|---|---|---|
| 71 | B | | RT 4.67 min, MI 462, Method (1LCMS1) |
| 72 | B | | RT 4.88 min, MI 409, Method (1LCMS1)<br>$^1$H NMR (300 MHz, d6-DMSO) δ 13.50 (s, 1H), 8.83-8.72 (m, 2H), 8.10-7.99 (m, 2H), 7.38-7.11 (m, 4H), 4.70-4.51 (m, 1H), 3.80-3.61 (m, 1H), 3.28-3.11 (m, 2H), 3.02-2.82 (m, 1H), 2.33 (s, 3H), 1.92-1.59 (m, 4H). |
| 73 | B | | RT 3.34 min, MI 487, Method (1LCMS1)<br>$^1$H NMR (300 MHz, d6-DMSO) δ 13.51 (s, 1H), 8.85-8.67 (m, 2H), 8.08 (d, 2H), 7.56-7.40 (m, 4H), 4.72-4.43 (m, 3H), 3.81-3.61 (m, 1H), 3.30-3.09 (m, 2H), 3.02-2.81 (m, 4H), 1.92-1.64 (m, 4H). |
| 74 | B | | RT 5.23 min, MI 490, Method (1LCMS1) |
| 75 | B | | RT 1.48 min, MI 362, Method (1LCMS1) |

| No | Method | Product | Characterisation |
|----|--------|---------|------------------|
| 76 | E | 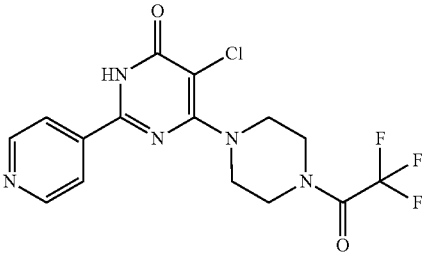 [SMILES: O=C(N1CCN(c2nc(-c3ccncc3)[nH]c(=O)c2Cl)CC1)C(F)(F)F] | RT 3.18 min, MI 388, Method (4LCMS1)<br>$^1$H NMR (400 MHz, d6-DMSO) δ 8.77 (d, J = 5.2 Hz, 2H), 8.07 (d, J = 5.3 Hz, 2H), 3.86-3.66 (m, 8H). |
| 77 | E | 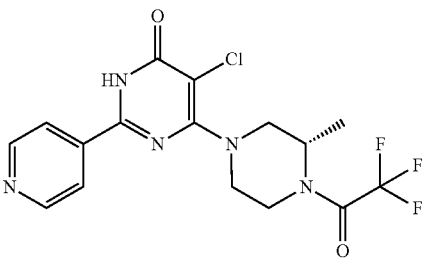 [SMILES: C[C@H]1CN(c2nc(-c3ccncc3)[nH]c(=O)c2Cl)CCN1C(=O)C(F)(F)F] | RT 4.73 min, MI 402/404, Method (1LCMS1) |
| 78 | A | 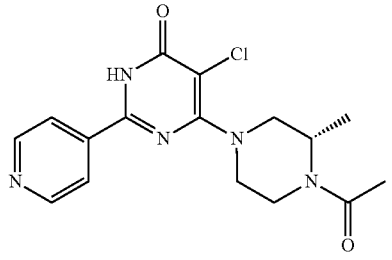 [SMILES: CC(=O)N1CCN(c2nc(-c3ccncc3)[nH]c(=O)c2Cl)C[C@@H]1C] | RT 3.42 min, MI 348/350, Method (1LCMS1)<br>$^1$H NMR (400 MHz, MeOD) δ 8.75 (2H, m), 8.09 (2H, m), 4.48 (2H, m), 4.34 (1H, m), 3.82 (1H, m), 3.62 (1H, m), 3.39 (1H, m), 3.29 (3H, s), 3.13 (1H, m), 2.16 (3H, d). |
| 79 | F | 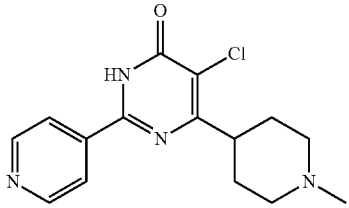 | RT 0.63 min, MI 305, Method (5LCMS5)<br>$^1$H NMR (400 MHz, MeOD) δ 8.61 (2H, m), 8.20 (2H, m), 3.58 (2H, m), 3.42 (1H, m), 3.18 (2H, m), 2.80 (3H, s), 2.25 (2H, m), 2.15 (2H, m). |
| 80 | F | 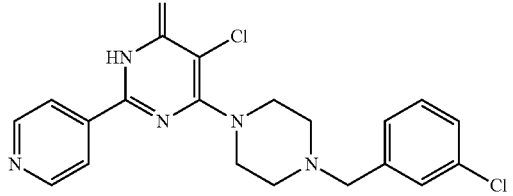 | RT 1.99 min, MI 416, Method (5LCMS1)<br>$^1$H NMR (400 MHz, Methanol-d$_4$) δ 8.76-8.68 (m, 2H), 8.03 (d, 2H), 7.42 (d, 1H), 7.37-7.26 (m, 3H), 3.86 (t, 4H), 3.61 (s, 2H), 2.71-2.58 (m, 4H). |
| 81 | F | 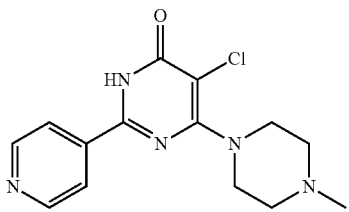 [SMILES: CC1CCN(c2nc(-c3ccncc3)[nH]c(=O)c2Cl)CC1] | RT 0.56 min, MI 306, Method (5LCMS5) |

| No | Method | Product | Characterisation |
|---|---|---|---|
| 82 | F | | RT 1.57 min, MI 348, Method (5LCMS1) |
| 83 | F | | RT 1.54 min, MI 362, Method (5LCMS1) |
| 84 | F | | RT 1.77 min, MI 374, Method (5LCMS1)<br>$^1$H NMR (400 MHz, d6-DMSO) δ 8.82-8.69 (m, 2H), 8.10-7.95 (m, 2H), 3.72-3.58 (m, 4H), 3.55-3.03 (m, 4H), 2.26-2.21 (m, 2H), 2.09 (dq, J = 14.4, 7.1 Hz, 1H), 1.75-1.64 (m, 2H), 1.61-1.44 (m, 4H), 1.25-1.14 (m, 2H). |
| 85 | F | | RT 1.92 min, MI 388, Method (5LCMS1)<br>$^1$H NMR (400 MHz, d6-DMSO) δ 8.75 (2H, m), 8.05 (2H, m), 3.25 (4H, m), 2.48 (4H, m), 2.18 (2H, m), 1.80 (2H, m), 1.62 (2H, m), 1.54 (2H, m), 1.20 (3H, m), 0.8 (2H, m). |
| 86 | F | | RT 1.57 min, MI 334, Method (5LCMS1)<br>$^1$H NMR (400 MHz, MeOD) δ 8.66 (2H, m), 8.14 (2H, m), 3.82 (4H, m), 3.13 (1H, m), 3.09 (4H, m), 1.29 (6H, d). |
| 87 | F | | RT 1.97 min, MI 365, Method (4LCMS1) |

| No | Method | Product | Characterisation |
|----|--------|---------|------------------|
| 88 | F | ![structure] | RT 0.64 min, MI 320/322, Method (1LCMS1)<br>¹H NMR (400 MHz, MeOD) δ 8.57 (2H, m), 8.03 (2H, m), 4.22 (2H, m), 3.31 (1H, m), 3.15 (1H, m), 3.08 (1H, m), 2.74 (2H, m), 2.58 (3H, s), 1.26 (3H, d). |

Scheme 4

In one approach (Scheme 4), compounds of general formula [F4-3] were prepared by the reaction of an α-halomalonate derivative of general formula [F4-2] in a condensation reaction utilising a suitable substituted pyridine-4-carboximidamide derivative of general formula [F4-1] in a polar solvent such as methanol or THF in the presence of a base such as sodium methoxide, potassium-tert-butoxide or DBU. The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Derivatives of general formula [F4-4] were prepared by the reaction of a 5-halo-2-pyridin-4-yl-1H-pyrimidine-4,6-dione derivative of general formula [F4-3] with a halogenating agent such as phosphorous oxychloride at high temperature. After reaction work up, typically by the addition of water followed by the addition of a base such as aqueous sodium hydroxide, the crude reaction mixture was purified by liquid-liquid extraction, and the reaction product was used crude in the next step or purified by flash column chromatography, reverse phase preparative HPLC or re-crystallisation. Derivatives of general formula [F4-5] were prepared by a hydrolysis reaction of a 4,5,6-halo-2-pyridin-4-yl-pyrimidine derivative of general formula [F4-4] with a mineral acid such as HCl or H₂SO₄ or an aqueous base such as NaOH at high temperature. After reaction work up, typically by a liquid-liquid extraction, the reaction product was used crude in the next step or purified by flash column chromatography, reverse phase preparative HPLC or re-crystallisation. Compounds of general formula [F4-7] were prepared by reaction of 5,6-dichloro-2-pyridin-4-yl-3H-pyrimidin-4-one derivatives of general formula [F4-5] in a nucleophilic aromatic substitution type reaction utilising a suitable amine of general formula [F4-6], and a base such as Et₃N or NaH, or a mineral acid such as HCl, in a polar solvent such as ethanol, butanol, dioxane, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. In cases where the substituent R² or R³ contained an amine protected by a standard amine protecting group such as a tert-butyloxycarbonyl (Boc), compounds of formula [F4-8] are prepared by a suitable deprotection reaction, for example reaction with an acid such as TFA in a suitable solvent such as DCM at ambient temperature, as exemplified in Scheme 1. After reaction work up, typically by a liquid-liquid extraction or purification by acidic ion exchange catch-release the crude product was purified by flash column chromatography, reverse phase preparative HPLC or re-crystallisation.

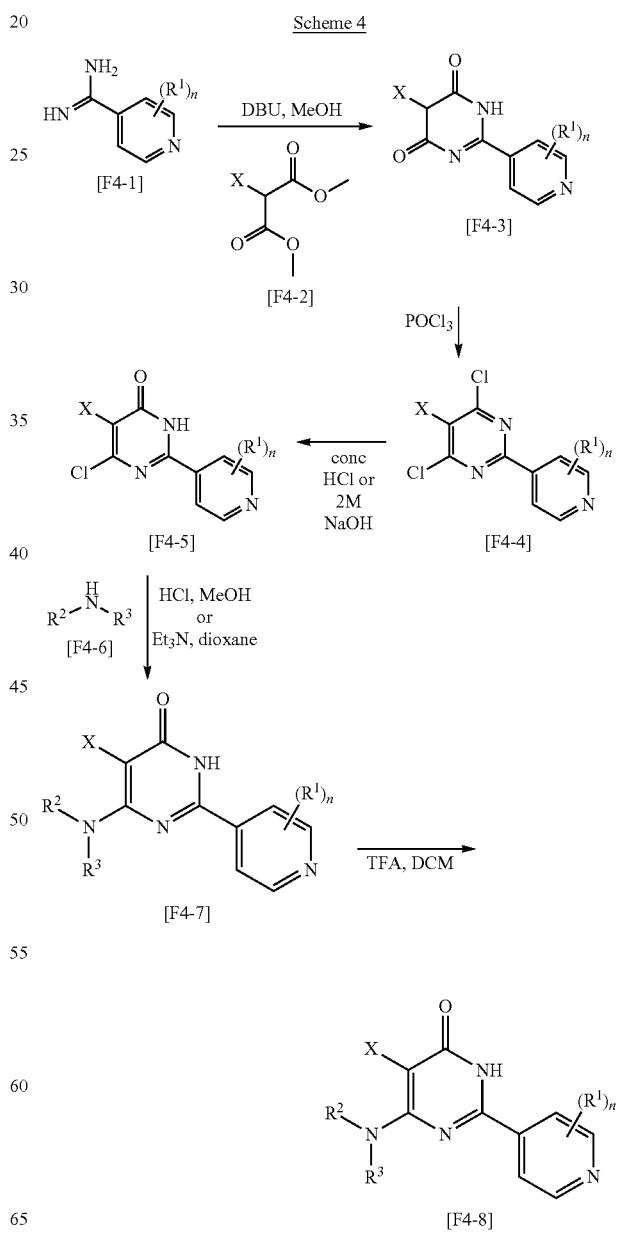

Scheme 4

For example synthesis of 5-chloro-4-morpholino-2-(4-pyridyl)-1H-pyrimidin-6-one (89)

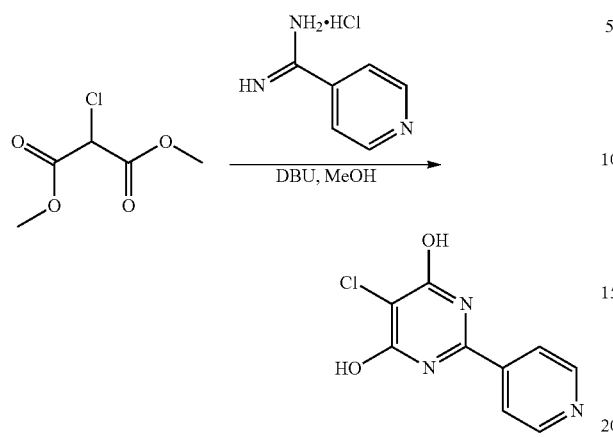

Synthesis of 5-chloro-2-pyridin-4-yl-1H-pyrimidine-4,6-dione (4-001)

A mixture of 4-amidinopyridine hydrochloride (15.76 g, 100 mmol), dimethyl chloromalonate (16.66 g, 100 mmol), DBU (60.08 g, 400 mmol) and MeOH (600 mL) was stirred at room temperature overnight. The crude reaction mixture was evaporated under reduced pressure to yield a brown oil. A 2 N HCl solution was cautiously added and the precipitate was collected by filtration, washed with water and dried in a vacuum oven to give the title compound (9.0 g, 40% yield) which was used in the next step without further purification. LCMS: RT 1.89 min, MI 223.99, Method (1LCMS5).

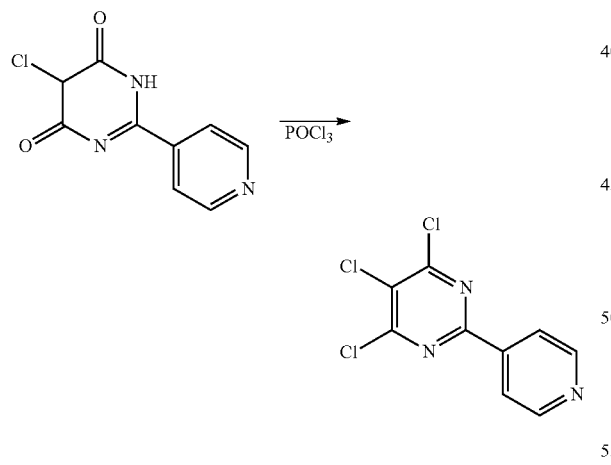

Synthesis of 4,5,6-trichloro-2-pyridin-4-yl-pyrimidine (4-002)

A mixture of 5-chloro-2-pyridin-4-yl-1H-pyrimidine-4,6-dione (4-001) (1.34 g, 6 mmol) in phosphorous oxychloride (10 mL) was heated at reflux overnight. The reaction mixture was cooled and evaporated under reduced pressure to give a brown oil. Chloroform was added, followed by the slow addition of ice, the mixture was left to stir for 10 min then the solution was neutralised by the addition of ammonium hydroxide. The mixture was extracted with CHCl₃ (2×100 mL), the extracts were combined, washed with brine, dried (MgSO₄), filtered and evaporated under reduced pressure to give the title compound (1.0 g, 64% yield) as an off-white solid which was used in the next step without further purification. LCMS: RT 5.82 min, MI 261.9, Method (1LCMS5).

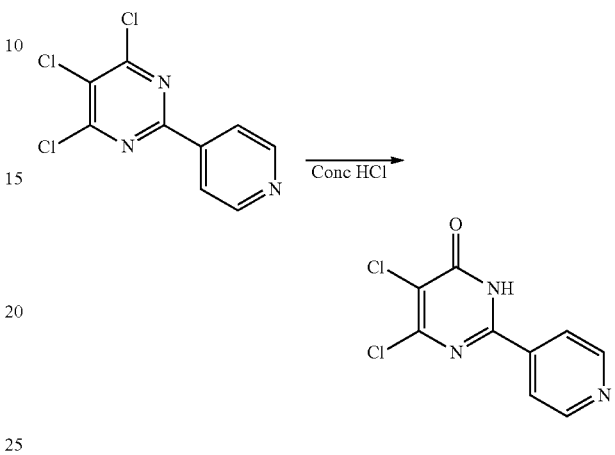

Synthesis of 5,6-dichloro-2-pyridin-4-yl-3H-pyrimidin-4-one (4-003)

A suspension of 4,5,6-trichloro-2-pyridin-4-yl-pyrimidine (4-002) (7.03 g, 27 mmol) in concentrated HCl (25 mL) was heated at reflux for 48 hours. The reaction mixture was cooled to 0° C. and the precipitate was collected by filtration, washed with water and dried in a vacuum oven to give the title compound (6.54 g, 58% yield) which was used in the next step without further purification. LCMS RT 4.31 min, MI 241.97 Method: (1LCMS5); $^1$H NMR (400 MHz, MeOD) δ 8.75 (2H, m), 8.12 (2H, m).

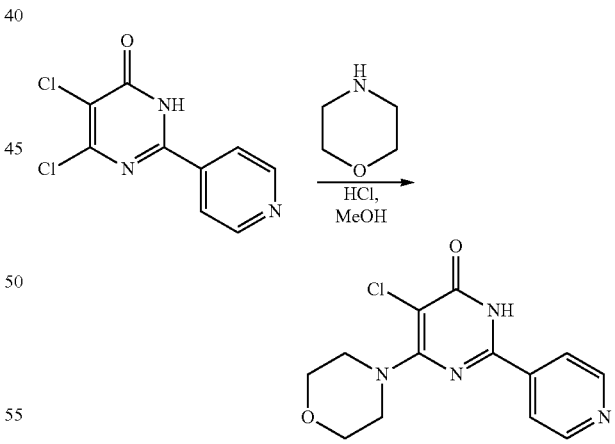

Synthesis of 5-chloro-4-morpholino-2-(4-pyridyl)-1H-pyrimidin-6-one (89)

To a suspension of 5,6-dichloro-2-pyridin-4-yl-3H-pyrimidin-4-one (4-003) (0.726 g, 3.0 mmol) and morpholine (0.52 g, 6 mmol) in methanol (20 mL) was added 12 drops of 1 N HCl and the mixture was heated under microwave irradiation at 150° C. for 30 minutes. The precipitate was collected by filtration, and dissolved in DCM (300 mL)

washed with water (50 mL), dried (MgSO₄), filtered and evaporated under reduced pressure to give the title compound (0.53 g, 60% yield). LCMS: RT 2.28 min, MI 293, Method (1LCMS1); ¹H NMR (400 MHz, CDCl₃) 13.60 (1H, s), 8.85 (2H, m), 8.19 (2H, m), 3.86 (8H, m).

For example, synthesis of 5-chloro-4-(3,3-difluoro-1-piperidyl)-2-(2-fluoro-4-pyridyl)-1H-pyrimidin-6-one (90)

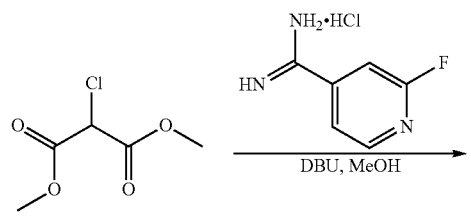

Synthesis of 5-chloro-2-(2-fluoro-pyridin-4-yl)-1H-pyrimidine-4,6-dione (4-004)

A mixture of 2-fluoro-4-amidinopyridine hydrochloride (5.7 g, 40.9 mmol), dimethyl chloromalonate (6.82 g, 40.98 mmol), DBU (24.4 mL, 163 mmol) and iPrOH (80 mL) was stirred at room temperature overnight. The crude reaction mixture was evaporated under reduced pressure to yield a brown oil. A 2 N HCl solution was cautiously added and the precipitate was collected by filtration, washed with water and dried in a vacuum oven to give the title compound (5.4 g, 55% yield). LCMS: RT 2.54 min, MI 242, Method (4LCMS1); ¹H NMR (400 MHz, d6-DMSO) δ 13.01 (2H, brs), 8.40 (1H, m), 8.0 (1H, m), 7.7 (1H, m).

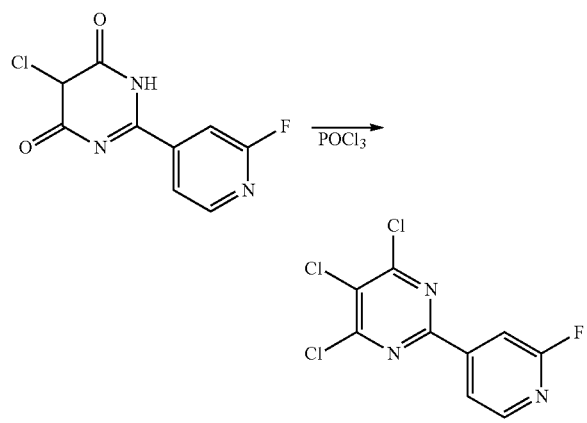

Synthesis of 4,5,6-trichloro-2-(2-fluoro-pyridin-4-yl)-pyrimidine (4-005)

A solution of 5-chloro-2-(2-fluoro-pyridin-4-yl)-1H-pyrimidine-4,6-dione (4-004) (13.73 g, 56.85 mmol) in toluene (300 mL) and diisopropylethylamine (29.38 g, 227 mmol) was cooled in an ice bath and phosphorous oxychloride (34.87 g, 227 mmol) was added portionwise, ensuring that the temperature did not rise above 10° C. The ice bath was removed and the reaction mixture was heated at 110° C. for 2 hours. The mixture was cooled to 10° C. whilst stirring and ice was added in small portions, ensuring that the temperature did not exceed 10° C. and the mixture cooled on further addition of ice/water (200 mL). The mixture was poured into a separating funnel and extracted with DCM (3×250 mL). The extracts were combined and washed with brine (200 mL), dried (MgSO₄), filtered and evaporated under reduced pressure to give a brown oil. Purification by column chromatography (1:9 EtOAc:cyclohexane) gave the title compound (6.6 g, 42% yield) as a pale yellow solid. LCMS: RT 5.46 min, MI 280, Method (4LCMS1); ¹H NMR (400 MHz, CDCl₃) δ 8.14 (m, 1H), 7.89 (m, 1H), 7.66 (s, 1H).

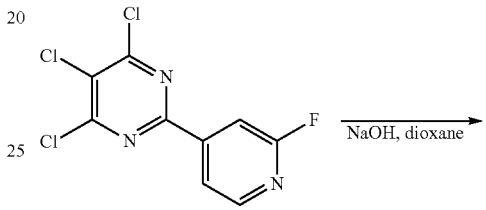

Synthesis of 5,6-dichloro-2-(2-fluoro-pyridin-4-yl)-pyrimidin-4-ol (4-006)

4,5,6-Trichloro-2-(2-fluoro-pyridin-4-yl)-pyrimidine (4-005) (3.18 g, 11.45 mmol) was dissolved in dioxane (30 mL) and a 2 N NaOH solution (30 mL) was added. The mixture was stirred at room temperature for 30 minutes. The reaction mixture was acidified by the addition of a 2 M HCl solution and the precipitate was collected by filtration, washed with water and dried in a vacuum oven. The crude reaction mixture was then purified by column chromatography to give the title compound (2.15 g, 72% yield) as a pale yellow solid. LCMS: RT 4.29 min, MI 260/262, Method (4LCMS1); ¹H NMR (400 MHz, d6-DMSO) δ 14.08 (1H, br s), 8.46 (1H, d), 7.98 (1H, m), 7.77 (1H, s).

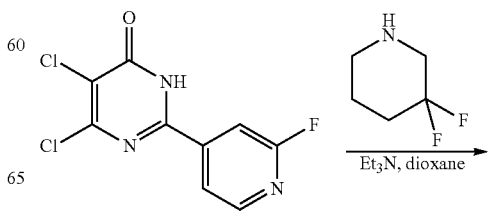

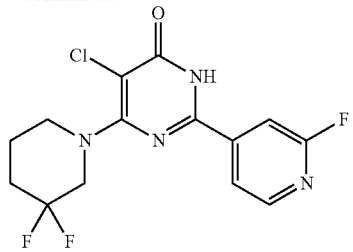

Synthesis of 5-chloro-4-(3,3-difluoro-1-piperidyl)-2-(2-fluoro-4-pyridyl)-1H-pyrimidin-6-one (90)

A mixture of 5,6-dichloro-2-(2-fluoro-pyridin-4-yl)-pyrimidin-4-ol (4-006) (0.13 g, 0.50 mmol), 3,3-difluoropiperidine hydrochloride (0.94 g, 0.60 mmol) and triethylamine (0.265 mL, 2.0 mmol) in 1,4-dioxane (4 mL) was heated to 150° C. in the microwave for 2 hours, then heated to 180° C. for 2 hours followed by 200° C. for 1.5 hours. The reaction mixture was then concentrated under vacuum and the residue dissolved in DCM and washed with water. The DCM layer was concentrated under vacuum and the residue purified by HPLC (Method A) then repurified by HPLC (Method B). The residue was then dissolved in DCM and washed with a saturated solution of sodium citrate to give the title compound (0.30 g, 56% yield). LCMS: RT 3.99 min, MI 345, Method (4LCMS1); $^1$H NMR (400 MHz, d6-DMSO) δ 13.10 (1H, br s), 8.45 (1H, d), 8.04 (1H, d), 7.83 (1H, s), 4.03 (2H, t), 3.70 (2H, m), 2.14 (2H, m), 1.87 (2H, m).

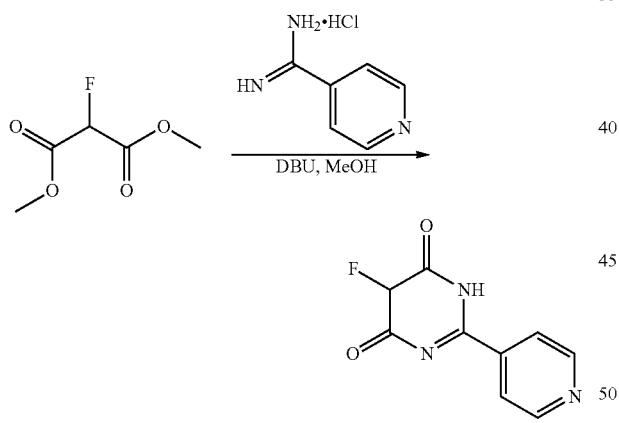

Synthesis of 5-fluoro-2-pyridin-4-yl-1H-pyrimidine-4,6-dione (4-007)

A mixture of 4-amidinopyridine hydrochloride (1.05 g, 6.662 mmol), dimethyl fluoromalonate (1 g, 6.662 mmol), DBU (3.35 mL, 22.4 mmol) and MeOH (50 mL) was stirred at room temperature overnight. The crude reaction mixture was evaporated under reduced pressure to yield a brown oil. A 2 N HCl solution was cautiously added and the precipitate was collected by filtration, washed with water and dried in a vacuum oven to give the title compound (1.03 g, 75% yield) which was used in the next step without further purification. LCMS: RT 1.44 min, MI 207, Method (1LCMS5).

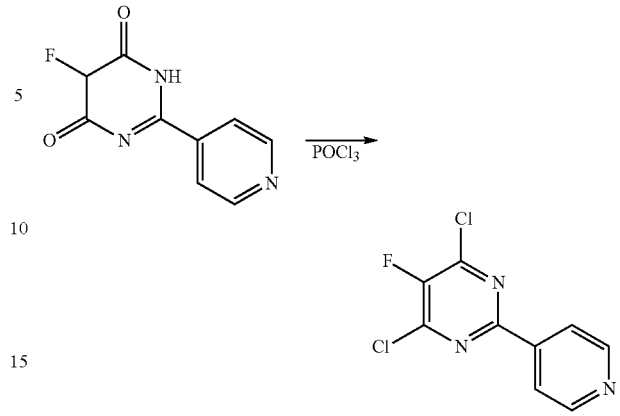

Synthesis of 4,6-dichloro-5-fluoro-2-pyridin-4-yl-pyrimidine (4-008)

A mixture of 5-fluoro-2-pyridin-4-yl-1H-pyrimidine-4,6-dione (4-007) (1.334 g, 4.99 mmol) in phosphorous oxychloride (10 mL) was heated at reflux overnight. The reaction mixture was cooled and evaporated under reduced pressure to give a brown oil. Chloroform was added, followed by the slow addition of ice. The mixture was left to stir for 10 min then the solution was neutralised by the addition of ammonium hydroxide. The mixture was extracted with CHCl$_3$ (2×100 mL), the extracts were combined, washed with brine, dried (MgSO$_4$), filtered and evaporated under reduced pressure to give the title compound (0.9 g, 44% yield) as an off-white solid which was used in the next step without further purification. LCMS: RT 5.17 min, MI 243, Method (1LCMS5).

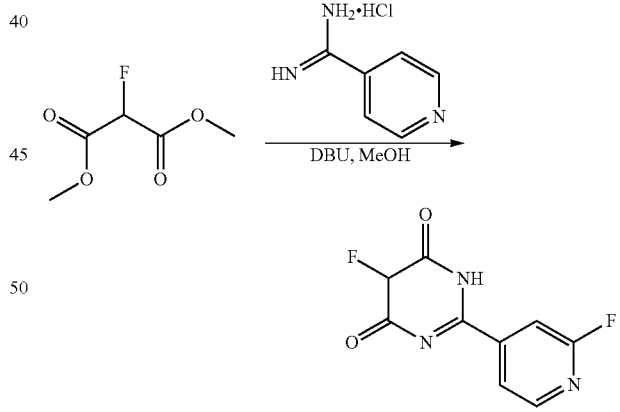

Synthesis of 5-fluoro-2-(2-fluoro-pyridin-4-yl)-1H-pyrimidine-4,6-dione (4-009)

A mixture of 2-fluoro-4-amidinopyridine hydrochloride (1.17 g, 6.662 mmol), dimethyl fluoromalonate (1 g, 6.662 mmol), DBU (3.35 mL, 22.4 mmol) and MeOH (50 mL) was stirred at room temperature overnight. The crude reaction mixture was evaporated under reduced pressure to yield a brown oil. A 2 N HCl solution was cautiously added and the precipitate was collected by filtration, washed with water and dried in a vacuum oven to give the title compound (0.992 g, 66% yield). LCMS: RT 2.91 min, MI 225, Method (4LCMS1).

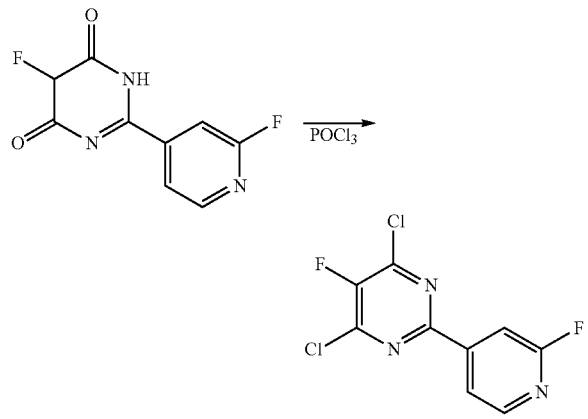

Synthesis of 4,6-dichloro-5-fluoro-2-(2-fluoro-pyridin-4-yl)-pyrimidine (4-010)

A solution of 5-fluoro-2-(2-fluoro-pyridin-4-yl)-1H-pyrimidine-4,6-dione (4-009) (0.993 g, 4.4 mmol) in toluene (10 mL) and phosphorous oxychloride (9 mL, 96.5 mmol) was heated at 110° C. for 18 hours. The mixture was cooled to 10° C. whilst stirring and ice was added in small portions, ensuring that the temperature did not exceed 10° C. and the mixture cooled on further addition of ice/water (200 mL). The mixture was poured into a separating funnel and extracted with DCM (3×250 mL). The extracts were combined and washed with brine (200 mL), dried (MgSO$_4$), filtered and evaporated under reduced pressure to give a brown oil. Purification by column chromatography (1:9 EtOAc:cyclohexane) gave the title compound (0.18 g, 16% yield) as a pale yellow solid. LCMS: RT 4.45 min, MI 261, Method (4LCMS1).

The following compounds were synthesised according to the general synthesis shown in scheme 4:

| No | Product | Characterisation |
|---|---|---|
| 91 | | RT 5.36 min, MI 369, Method (1LCMS1)<br>$^1$H NMR (400 MHz, d6-DMSO) δ 8.77 (2H, m), 8.02 (2H, m), 7.38 (5H, m), 4.63 (1H, d), 4.27 (2H, m), 4.05 (1H, t), 3.74 (1H, t), 3.08 (1H, m), 3.03 (1H, t). |
| 92 | | RT 4.6 min, MI 321, Method (1LCMS1)<br>$^1$H NMR (400 MHz, d6-DMSO) δ 8.78 (2H, d), 8.02 (2H, d), 4.20 (2H, d), 3.65 (2H, m), 2.60 (2H, t), 1.10 (6H, d). |
| 93 | | RT 5.55 min, MI 349, Method (1LCMS1)<br>$^1$H NMR (400 MHz, d6-DMSO) δ 8.75 (2H, d), 8.03 (2H, d), 4.18 (2H, t), 3.80 (1H, d), 3.58 (2H, m), 3.15 (1H, m), 2.75 (1H, m), 1.60 (1H, m), 1.38 (1H, m), 1.20 (1H, m), 0.85 (6H, m). |
| 94 | | RT 3.23 min, MI 337, Method (1LCMS1)<br>$^1$H NMR (400 MHz, d6-DMSO) δ 8.75 (2H, m), 8.02 (2H, m), 4.50 (1H, m), 4.40 (2H, dd), 3.82 (1H, d), 3.60 (3H, m), 3.15 (1H, t), 2.80 (1H, t), 1.58 (2H, d). |

-continued

| No | Product | Characterisation |
|---|---|---|
| 95 | | RT 4.87 min, MI 335, Method (1LCMS1)<br>¹H NMR (300 MHz, d6-DMSO) δ 12.85 (s, 1H), 8.75 (d, 2H), 8.01 (d, 2H), 4.46 (t, 1H), 3.95-3.40 (m, 5H), 1.89-1.62 (m, 3H), 1.31-1.17 (m, 2H), 0.85 (t, 3H). |
| 96 | | RT 2.93 min, MI 336, Method (1LCMS1)<br>¹H NMR (300 MHz, d6-DMSO) δ 8.76 (d, 2H), 8.02 (d, 2H), 7.36 (d, 2H), 4.41 (d, 1H), 4.13 (d, 1H), 3.99 (d, 2H), 3.68 (t, 1H), 3.26-2.93 (m, 2H). |
| 97 | | RT 3.26 min, MI 364, Method (1LCMS1)<br>¹H NMR (300 MHz, d6-DMSO) δ 8.88-8.66 (m, 2H), 8.14-7.91 (m, 2H), 4.37 (dd, 1H), 4.22 (dd, 2H), 3.94 (d, 1H), 3.78-3.64 (m, 1H), 3.29-3.13 (m, 2H), 3.02 (s, 3H), 2.81 (s, 3H). |
| 98 | | RT 4.67 min, MI 422, Method (1LCMS1)<br>¹H NMR (300 MHz, d6-DMSO) δ 12.96 (s, 1H), 8.81-8.67 (m, 2H), 8.03 (d, 2H), 7.03 (t, 1H), 4.21 (dd, 2H), 3.90 (d, 1H), 3.63-3.43 (m, 2H), 3.19-2.95 (m, 3H), 2.88-2.68 (m, 2H), 1.36 (s, 9H). |
| 99 | | RT 4.26 min, MI 351, Method (1LCMS1)<br>¹H NMR (400 MHz, d6-DMSO) δ 8.78 (2H, d), 8.02 (2H, d), 4.35 (1H, d), 4.20 (1H, d), 3.80 (1H, d), 3.58 (1H, m), 3.42 (2H, m), 3.23 (3H, s), 3.18 (2H, m), 2.80 (1H, m), 1.70 (2H, m). |
| 100 | | RT 2.95 min, MI 334, Method (1LCMS1) |
| 101 | | RT 3.0 min, MI 360, Method (1LCMS1)<br>¹H NMR (400 MHz, d6-DMSO) δ 8.71 (2H, d), 8.02 (2H, d), 4.10 (1H, d), 3.82 (1H, d), 3.55 (1H, m), 3.09 (2H, t), 2.91 (1H, m), 2.75 (1H, m) |

| No | Product | Characterisation |
|---|---|---|
| 102 | | RT 6.25 min, MI 381, Method (1LCMS1)<br>¹H NMR (300 MHz, d6-DMSO) δ 12.80 (s, 1H), 8.74 (d, 2H), 8.00 (d, 2H), 7.40-7.08 (m, 5H), 4.32 (d, 2H), 3.03-2.86 (m, 2H), 2.54 (d, 2H), 1.90-1.75 (m, 1H), 1.66 (d, 2H), 1.36-1.14 (m, 2H). |
| 103 | | RT 5.86 min, MI 319, Method (1LCMS1) |
| 104 | | RT 3.25 min, MI 307, Method (1LCMS1)<br>¹H NMR (300 MHz, d6-DMSO) δ 12.83 (s, 1H), 8.75 (d, 2H), 8.07-7.96 (m, 2H), 4.76 (d, 1H), 4.09-3.96 (m, 2H), 3.80-3.64 (m, 1H), 3.31-3.22 (m, 1H), 1.91-1.77 (m, 2H), 1.53-1.39 (m, 2H). |
| 105 | | RT 5.49 min, MI 305, Method (1LCMS1)<br>¹H NMR (400 MHz, d6-DMSO) δ 8.76 (2H, d), 8.02 (2H, d), 4.25 (2H, t), 2.94 (1H, t), 2.60 (1H, m), 1.69 (4H, m), 1.14 (1H, m), 0.90 (3H, d). |
| 106 | | RT 4.5 min, MI 309, Method (1LCMS1)<br>¹H NMR (400 MHz, MeOD) δ 8.76 (2H, d), 8.03 (2H, d), 4.90 (1H, brm), 3.73 (2H, m), 3.63 (2H, m), 2.01 (2H, m), 1.81 (2H, m). |
| 107 | | RT 5.41 min, MI 359, Method (1LCMS1)<br>¹H NMR (400 MHz, d6-DMSO) δ 8.77 (2H, d), 8.01 (2H, d), 4.43 (1H, d), 4.24 (1H, d), 3.11 (2H, t), 2.60 (1H, brm), 1.98 (1H, m), 1.79 (1H, m), 1.58 (2H, t). |

| No | Product | Characterisation |
|---|---|---|
| 108 | | RT 0.66 min, MI 320, Method (1LCMS1)<br>¹H NMR (400 MHz, d6-DMSO) δ 8.79 (2H, d), 8.06 (2H, d), 4.36 (2H, d), 3.39 (2H, m), 3.06 (2H, t), 1.29 (6H, d). |
| 109 | | RT 3.7 min, MI 321, Method (1LCMS1) |
| 110 | | RT 0.66 min, MI 377, Method (1LCMS1) |
| 111 | | RT 5.6 min, MI 386, Method (1LCMS1)<br>¹H NMR (400 MHz, d6-DMSO) δ 8.77 (2H, d), 8.05 (2H, d), 7.24 (1H, m), 6.81 (2H, m), 6.56 (1H, t), 3.82 (8H, m). |
| 112 | | RT 5.23 min, MI 426, Method (1LCMS1)<br>¹H NMR (400 MHz, d6-DMSO) δ 8.76 (2H, d), 8.04 (2H, d), 7.38 (5H, m), 5.10 (2H, s), 3.67 (4H, m), 3.54 (4H, m). |
| 113 | | RT 5.37 min, MI 398, Method (1LCMS1)<br>¹H NMR (400 MHz, d6-DMSO) δ 8.77 (2H, d), 8.05 (2H, d), 7.12 (1H, t), 6.58 (1H, d), 6.45 (1H, s), 6.30 (1H, d), 3.82 (4H, m), 3.71 (3H, s), 3.26 (4H, m). |

| No | Product | Characterisation |
|---|---|---|
| 114 | | RT 5.72 min, MI 305, Method (1LCMS1)<br>$^1$H NMR (400 MHz, d6-DMS0) δ 8.75 (2H, d), 8.01 (2H, d), 3.83 (4H, m), 1.78 (4H, m), 1.52 (4H, m). |
| 115 | | RT 3.55 min, MI 307, Method (1LCMS1)<br>$^1$H NMR (400 MHz, d6-DMSO) δ 8.74 (2H, d), 8.03 (2H, d), 4.78 (2H, m), 4.60 (2H, m), 3.80 (2H, m), 3.65 (2H, m), 1.93 (2H, m). |
| 116 | | RT 2.15 min, MI 369, Method (1LCMS1)<br>$^1$H NMR (400 MHz, d6-DMSO) δ 8.78 (2H, d), 8.35 (1H, d), 8.05 (3H, m), 7.43 (1H, m), 7.28 (1H, m), 3.85 (8H, m). |
| 117 | | RT 2.7 min, MI 320, Method (1LCMS1)<br>$^1$H NMR (300 MHz, d6-DMSO) δ 8.75 (d, 2H), 8.10-7.95 (m, 2H), 7.64 (t, 1H), 3.83-3.69 (m, 4H), 3.45-3.16 (m, 2H, partially obscured by water), 2.74-2.61 (m, 2H). |
| 118 | | RT 2.63 min, MI 320, Method (1LCMS1) |
| 119 | | RT 2.98 min, MI 334, Method (1LCMS1) |

-continued

| No | Product | Characterisation |
|---|---|---|
| 120 | (structure) | RT 6.65 min, MI 346, Method (1LCMS1) |
| 121 | (structure) | RT 4.33 min, MI 321, Method (1LCMS1)<br>¹H NMR (400 MHz, d6-DMSO) δ 8.76 (2H, m), 8.03 (2H, m), 3.75 (2H, m), 3.64 (2H, m), 3.53 (2H, m), 1.20 (6H, s). |
| 122 | (structure) | RT 5.5 min, MI 305, Method (1LCMS1)<br>¹H NMR (400 MHz, d6-DMSO) δ 8.76 (2H, d), 8.02 (2H, d), 4.35 (2H, d), 2.97 (2H, m), 1.73 (3H, m), 1.22 (2H, m), 0.94 (3H, d). |
| 123 | (structure) | RT 3.95 min, MI 321, Method (1LCMS1)<br>¹H NMR (400 MHz, d6-DMSO) δ 8.74 (2H, m), 8.03 (2H, m), 4.58 (1H, m), 4.37 (1H, d), 4.20 (1H, d), 3.32 (1H, m), 3.01 (1H, t), 2.75 (1H, t), 1.72 (3H, m), 1.58 (1H, m), 1.22 (1H, m). |
| 124 | (structure) | RT 3.01 min, MI 293, Method (1LCMS1)<br>¹H NMR (400 MHz, d6-DMSO) δ 8.75 (2H, d), 7.99 (2H, d), 4.85 (1H, t), 4.37 (2H, t), 4.11 (2H, m), 3.58 (2H, t). |
| 125 | (structure) | RT 0.62 min, MI 336, Method (1LCMS1)<br>¹H NMR (400 MHz, d6-DMSO) δ 8.64 (2H, d), 8.05 (2H, d), 3.56 (8H, m), 2.53 (2H, m), 2.43 (2H, m). |
| 126 | (structure) | RT 3.56 min, MI 319, Method (1LCMS1)<br>¹H NMR (400 MHz, d6-DMSO) δ 8.76 (2H, d), 8.04 (2H, d), 4.60 (2H, d), 4.50 (2H, d), 4.02 (2H, s), 3.81 (2H, t), 2.19 (2H, t). |

| No | Product | Characterisation |
|---|---|---|
| 127 | | RT 4.77 min, MI 327, Method (1LCMS1) |
| 128 | | RT 4.64 min, MI 308, Method (1LCMS1)<br>¹H NMR (300 MHz, d6-DMSO) δ 8.75 (d, 2H), 8.08-7.95 (m, 2H), 3.93-3.81 (m, 4H), 2.78-2.64 (m, 4H). |
| 129 | | RT 0.8 min, MI 322, Method (1LCMS1)<br>¹H NMR (400 MHz, MeOD) δ 8.67 (2H, d), 8.04 (2H, d), 4.11 (2H, m), 3.47 (2H, d), 3.06 (3H, m), 2.81 (2H, m). |
| 130 | | RT 1.76 min, MI 306, Method (1LCMS1) |
| 131 | | RT 4.5 min, MI 308, Method (1LCMS1)<br>¹H NMR (400 MHz, d6-DMSO) δ 8.77 (2H, d), 8.01 (2H, d), 4.90 (1H, m), 4.75 (1H, m), 4.31 (1H, s), 3.90 (1H, m), 3.75 (1H, m), 3.48 (1H, m), 1.90 (2H, m), 1.62 (1H, |
| 132 | | RT 4.7 min, MI 326, Method (1LCMS1)<br>¹H NMR (400 MHz, d6-DMSO) δ 8.73 (2H, d), 8.03 (2H, d), 3.95 (2H, t), 3.64 (2H, m), 2.15 (2H, m), 1.80 (2H, m). |
| 133 | | RT 3.96 min, MI 295, Method (1LCMS1)<br>¹H NMR (400 MHz, d6-DMSO) δ 8.75 (2H, d), 8.04 (2H, d), 5.40 (1H, d), 4.08-3.87 (4H, m), 2.22 (2H, m). |

-continued

| No | Product | Characterisation |
|---|---|---|
| 134 | (structure: 5-chloro-2-(pyridin-4-yl)-6-(3,3-difluorobicyclo[3.1.0]... pyrrolidinyl)pyrimidin-4(3H)-one) | RT 4.55 min, MI 325, Method (1LCMS1)<br>$^1$H NMR (400 MHz, d6-DMSO) δ 8.71 (2H, d), 8.03 (2H, d), 4.30 (2H, d), 4.06 (2H, d), 2.64 (2H, d). |
| 135 | (structure: 5-chloro-2-(pyridin-4-yl)-6-(3-(trifluoromethyl)pyrrolidin-1-yl)pyrimidin-4(3H)-one) | RT 4.98 min, MI 345, Method (1LCMS1)<br>$^1$H NMR (400 MHz, d6-DMSO) δ 8.76 (2H, d), 8.03 (2H, d), 4.09-3.84 (4H, m), 3.33 (1H, m), 2.25 (1H, m), 2.09 (1H, m). |
| 136 | (structure: 5-chloro-6-(4-(2-hydroxyethyl)-1,4-diazepan-1-yl)-2-(pyridin-4-yl)pyrimidin-4(3H)-one) | RT 0.6 min, MI 350, Method (1LCMS1)<br>$^1$H NMR (400 MHz, CDCl$_3$) δ 8.73 (2H, d), 8.06 (2H, d), 3.82 (4H, m), 3.48 (2H, m), 3.12 (1H, m), 2.86 (2H, m), 2.56 (2H, m), 2.48 (1H, t), 1.89 (2H, m). |
| 137 | (structure: 6-(4-tert-butyl-1,4-diazepan-1-yl)-5-chloro-2-(pyridin-4-yl)pyrimidin-4(3H)-one) | RT 1.45 min, MI 362, Method (1LCMS1)<br>$^1$H NMR (400 MHz, d6-DMSO) δ 8.66 (2H, d), 8.03 (2H, d), 3.76 (2H, m), 3.32 (2H, m), 3.03 (1H, m), 2.92 (1H, m), 2.75-2.50 (2H, m), 1.75 (2H, m), 1.02 (9H, s). |
| 138 | (structure: 5-chloro-6-(3-hydroxypyrrolidin-1-yl)-2-(pyridin-4-yl)pyrimidin-4(3H)-one) | RT 3.11 min, MI 293, Method (1LCMS1) |
| 139 | (structure: 5-chloro-2-(pyridin-4-yl)-6-(3-(trifluoromethyl)piperazin-1-yl)pyrimidin-4(3H)-one) | RT 2.03 min, MI 360, Method (4LCMS1)<br>$^1$H NMR (400 MHz, d6-DMSO) δ 8.75 (2H, m), 8.0 (2H, m), 4.25 (1H, d), 4.08 (1H, d), 3.57 (1H, m), 3.25 (2H, m), 3.0 (1H, d), 2.75 (1H, t). |
| 140 | (structure: 5-chloro-6-(3-methylpiperazin-1-yl)-2-(pyridin-4-yl)pyrimidin-4(3H)-one · HCl) | RT 1.6 min, MI 304/306, Method (2LCMS1) |

| No | Product | Characterisation |
|---|---|---|
| 141 | (5-chloro-2-(pyridin-4-yl)-6-(1,4-diazepan-1-yl with ketone)pyrimidin-4(3H)-one) | RT 2.54 min, MI 320, Method (1LCMS1)<br>$^1$H NMR (400 MHz, d6-DMSO) δ 8.71 (2H, d), 8.12 (2H, d), 7.55 (1H, s), 4.20 (2H, s), 3.86 (2H, m), 3.10 (2H, m), 1.91 (2H, m). |
| 142 | (5-chloro-2-(pyridin-4-yl)-6-(4-(2,2,2-trifluoroethyl)-1,4-diazepan-1-yl)pyrimidin-4(3H)-one) | RT 1.27 min, MI 388, Method (1LCMS1)<br>$^1$H NMR (400 MHz, d6-DMSO) δ 8.70 (2H, d), 8.06 (2H, d), 3.84 (2H, m), 3.34 (2H, m), 3.14 (1H, m), 3.02 (2H, m), 2.85 (1H, m), 2.81 (2H, m), 1.88 (2H, m). |
| 143 | (5-chloro-2-(pyridin-4-yl)-6-(4-propyl-1,4-diazepan-1-yl)pyrimidin-4(3H)-one) | RT 0.98 min, MI 348, Method (1LCMS1)<br>$^1$H NMR (400 MHz, d6-DMSO) δ 8.70 (2H, d), 8.03 (2H, d), 3.75 (2H, m), 3.33 (1H, m), 3.11 (1H, m), 2.75 (2H, m), 2.55 (2H, m), 2.35 (2H, m), 1.85 (2H, m), 1.41 (2H, m), 0.82 (3H, m). |
| 144 | (5-chloro-2-(pyridin-4-yl)-6-(4-(2,2,2-trifluoroacetyl)-1,4-diazepan-1-yl)pyrimidin-4(3H)-one) | $^1$H NMR (400 MHz, d6-DMSO) δ 8.61 (2H, d), 8.03 (2H, d), 3.98 (2H, m), 3.80 (2H, m), 3.25-3.15 (4H, m), 1.94 (2H, m). |
| 145 | (5-chloro-6-(4-(methylsulfonyl)-1,4-diazepan-1-yl)-2-(pyridin-4-yl)pyrimidin-4(3H)-one) | RT 3.38 min, MI 384, Method (1LCMS1)<br>$^1$H NMR (400 MHz, d6-DMSO) δ 8.76 (2H, d), 8.02 (2H, d), 3.99 (2H, d), 3.93 (2H, d), 3.47 (2H, d), 3.33 (3H, s), 3.30 (2H, m), 1.91 (2H, m). |
| 146 | (5-chloro-2-(pyridin-4-yl)-6-(4-(2,2,2-trifluoroethyl)piperazin-1-yl)pyrimidin-4(3H)-one) | RT 3.38 min, MI 374, Method (4LCMS1)<br>$^1$H NMR (400 MHz, d6-DMSO) δ 12.93 (1H, s), 8.78 (2H, d), 8.04 (2H, d), 3.71 (4H, m), 3.21 (2H, m), 2.51 (4H, m). |

| No | Product | Characterisation |
|---|---|---|
| 147 | 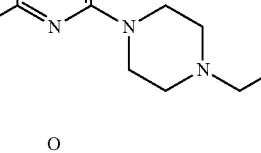 | RT 2.71 min, MI 356, Method (1LCMS5) |
| 148 | 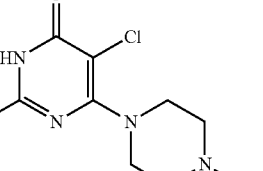 | RT 3.28 min, MI 331, Method (1LCMS5)<br>$^1$H NMR (400 MHz, d6-DMSO) δ 8.77 (2H, d), 8.04 (2H, d), 4.02 (2H, t), 3.66 (2H, m), 2.49 (2H, s), 2.11 (2H, m), 1.85 (2H, m). |
| 149 | 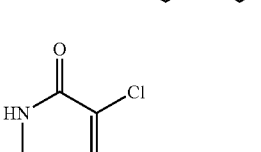 | RT 3.98 min, MI 368, Method (1LCMS5)<br>$^1$H NMR (400 MHz, d6-DMSO) δ 8.76 (2H, d), 8.02 (2H, d), 4.50 (1H, t), 4.37 (2H, d), 3.25 (2H, d), 2.97 (2H, t), 1.77 (2H, d), 1.72 (1H, m), 1.23 (2H, m). |
| 150 | 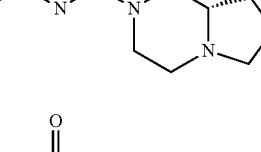 | RT 1.66 min, MI 330, Method (1LCMS5) |
| 151 | 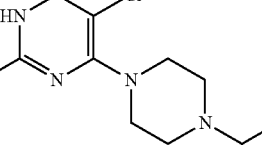 | RT 4.02 min, MI 333, Method (1LCMS1) |
| 152 | 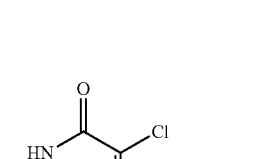 | RT 5.08 min, MI 406, Method (1LCMS1) |

| No | Characterisation |
|---|---|
| 153 | RT 3.7 min, MI 316, Method (1LCMS1)<br>¹H NMR (300 MHz, d6-DMSO) δ 12.93 (s, 1H), 8.81-8.68 (m, 2H), 8.08-7.95 (m, 2H), 3.97-3.80 (m, 2H), 3.52-3.37 (m, 2H), 3.21-3.07 (m, 1H), 2.08-1.92 (m, 2H), 1.91-1.69 (m, 2H). |
| 154 | RT 4.65 min, MI 331, Method (1LCMS1) |
| 155 | RT 1.02 min, MI 346, Method (1LCMS1) |
| 156 | RT 1.51 min, MI 356/358, Method (1LCMS1)<br>¹H NMR (400 MHz, d6-DMSO) δ 8.77 (2H, d), 8.02 (2H, d), 4.38 (1H, d), 4.17 (1H, d), 3.02-2.89 (4H, m), 2.71 (1H, m), 1.65 (3H, t). |
| 157 | RT 2.10 min, MI 348, Method (1LCMS5)<br>¹H NMR (400 MHz, d6-DMSO) δ 8.73 (2H, d), 8.02 (2H, d), 4.41 (1H, d), 4.25 (1H, d), 3.34 (1H, m), 3.15 (1H, m), 2.75-2.60 (3H, m), 0.97 (9H, s). |
| 158 | RT 1.43 min, MI 332, Method (1LCMS1) |

| No | Product | Characterisation |
|---|---|---|
| 159 | (structure) | RT 4.97 min, MI 361, Method (1LCMS5)<br>¹H NMR (500 MHz, d6-DMSO) δ 8.82-8.67 (m, 2H), 8.12-7.93 (m, 2H), 4.44-4.31 (m, 1H), 4.27 (d, 1H), 4.11 (d, 1H), 4.03 (d, 1H), 3.74 (td, 1H), 3.26-3.14 (m, 2H). |
| 160 | (structure) ·HCl | RT 2.07 min, MI 366/368, Method (5LCMS1)<br>¹H NMR (400 MHz, d6-DMSO) δ 13.18 (br s, 1H), 9.18-8.63 (m, 1H), 8.46 (d, J = 5.3 Hz, 1H), 8.05-7.99 (m, 1H), 7.82 (d, J = 1.5 Hz, 1H), 4.55 (d, J = 13.8 Hz, 1H), 4.42 (d, J = 14.1 Hz, 1H), 3.52-3.38 (m, 1H), 3.31 (s, 1H), 3.23-3.04 (m, 3H), 1.06 (s, 9H). |
| 161 | (structure) | ¹H NMR (400 MHz, d6-DMSO) δ 8.72 (2H, m), 8.02 (2H, m), 5.17 (1H, s), 4.39 (1H, s), 3.95 (1H, m), 3.56 (2H, m), 3.07 (2H, m), 2.08 (1H, d), 1.92 (1H, d). |
| 162 | (structure) | RT 4.90 min, MI 448/450, Method (1LCMS1) |
| 163 | (structure) ·HCl | RT 1.15 min, MI 350/352, Method (1LCMS1)<br>¹H NMR (300 MHz, d6-DMSO) δ 9.01 (d, J = 6.6 Hz, 2H), 8.85 (d, J = 6.7 Hz, 2H), 4.68-4.59 (m, 1H), 4.55 (dd, J = 9.3, 3.6 Hz, 1H), 4.36 (d, J = 14.6 Hz, 1H), 3.90 (s, 3H), 3.84-3.72 (m, 1H), 3.68-3.56 (m, 2H), 3.45-3.33 (m, 1H). |
| 164 | (structure) | RT 2.50 min, MI 382, Method (1LCMS5) |

| No | Product | Characterisation |
|---|---|---|
| 165 | | RT 2.47 min, MI 382, Method (1LCMS5)<br>¹H NMR (400 MHz, d6-DMSO) δ 8.66 (2H, d), 7.75 (2H, d), 7.39 (3H, m), 7.29 (2H, m), 4.30 (2H, dd), 3.40 (2H, m), 3.28 (1H, d), 3.03 (3H, m), 2.75 (1H, m). |
| 166 | | RT 1.41 min, MI 320, Method (1LCMS5)<br>¹H NMR (400 MHz, d6-DMSO) δ 8.62 (2H, d), 8.04 (2H, d), 4.34 (1H, m), 3.74 (1H, d), 3.03 (2H, m), 2.92 (2H, m), 1.28 (3H, d), 1.15 (3H, d). |
| 167 | | RT 3.12 min, MI 306, Method (1LCMS5)<br>¹H NMR (500 MHz, d6-DMSO) δ 8.82-8.69 (m, 2H), 8.09-7.95 (m, 2H), 4.93 (d, 1H), 4.18 (dd, 1H), 4.03 (d, 1H), 3.59 (dq, 1H), 3.19-3.04 (m, 1H), 2.97 (dd, 1H), 1.92 (dd, 1H), 1.88-1.72 (m, 1H), 1.59-1.30 (m, 2H). |
| 168 | | RT 2.78 min, MI 402, Method (1LCMS5)<br>¹H NMR (400 MHz, d6-DMSO) δ 8.75 (2H, d), 8.01 (2H, d), 7.52 (2H, d), 7.44 (2H, d), 4.34 (1H, d), 4.24 (1H, d), 3.98 (1H, d), 3.16 (2H, d), 2.98 (2H, m). |
| 169 | | RT 2.51 min, MI 398, Method (1LCMS5)<br>¹H NMR (400 MHz, d6-DMSO) δ 8.76 (2H, d), 8.01 (2H, d), 7.44 (2H, d), 6.99 (2H, d), 4.42 (1H, d), 4.60 (1H, d), 4.55 (1H, d), 3.76 (3H, s), 3.32 (2H, m), 3.20 (2H, m). |
| 170 | | RT 1.98 min, MI 352/354, Method (5LCMS1)<br>¹H NMR (400 MHz, d6-DMSO) δ 13.17 (s, 1H), 9.23 (br s, 1H), 9.05 (br s, 1H), 8.46 (d, J = 5.3 Hz, 1H), 8.03 (d, J = 5.3 Hz, 1H), 7.83 (s, 1H), 4.49-4.38 (m, 2H), 3.49-3.28 (m, 2H), 3.15-3.10 (m, 3H), 2.01-1.92 (m, 1H), 1.05 (dd, J = 10.7, 6.8 Hz, 6H).<br>·HCl |
| 171 | | RT 1.71 min, MI 324, Method (4LCMS1)<br>¹H NMR (400 MHz, d6-DMSO) δ 13.13 (br s, 1H), 9.23 (br s, 2H), 8.45 (d, J = 5.2 Hz, 1H), 8.12-8.00 (m, 1H), 7.85 (s, 1H), 4.29 (t, J = 13.1 Hz, 2H), 3.46-3.35 (m, 3H), 3.22 (dd, J = 14.1, 10.3 Hz, 1H), 3.18-3.09 (m, 1H), 1.29 (d, J = 6.5 Hz, 3H).<br>·HCl |

-continued

| No | Product | Characterisation |
|---|---|---|
| 172 | (structure) | RT 1.45 min, MI 320, Method (1LCMS5)<br>¹H NMR (400 MHz, d6-DMSO) δ 8.68 (2H, d), 8.02 (2H, d), 4.50 (1H, br s), 3.97 (1H, d), 3.16 (2H, m), 2.98 (2H, m), 1.35 (3H, d), 1.21 (3H, d). |
| 173 | (structure) | RT 1.02 min, MI 320, Method (1LCMS5) |
| 174 | (structure) | RT 0.64 min, MI 336, Method (1LCMS5) |
| 175 | (structure) | RT 0.59 min, MI 336, Method (1LCMS5) |
| 176 | (structure) | RT 4.16 min, MI 357/359, Method (1LCMS1) |
| 177 | (structure) | RT 2.20 min, MI 374, Method (1LCMS5)<br>¹H NMR (400 MHz, d6-DMSO) δ 8.78 (2H, d), 8.02 (2H, d), 7.45 (1H, d), 7.13 (1H, s), 7.02 (1H, d), 4.35 (1H, d), 4.25 (2H, d), 3.21 (1H, m), 3.16 (2H, m), 3.06 (1H, m). |
| 178 | (structure) | RT 2.16 min, MI 384, Method (1LCMS5)<br>¹H NMR (400 MHz, d6-DMSO) δ 8.78 (2H, d), 8.04 (2H, d), 7.22 (1H, t), 6.93 (2H, m), 6.64 (1H, d), 4.29 (1H, d), 4.23 (1H, d), 4.09 (1H, d), 3.22 (2H, m), 3.09 (2H, m). |

| No | Product | Characterisation |
|---|---|---|
| 179 | | RT 4.08 min, MI 398, Method (1LCMS5)<br>$^1$H NMR (500 MHz, d6-DMSO) δ 8.74 (dd, 2H), 8.06-7.95 (m, 2H), 7.28 (t, 1H), 7.08-6.97 (m, 2H), 6.86 (d, 1H), 4.28 (dd, 2H), 3.88 (d, 1H), 3.75 (s, 3H), 3.17-3.06 (m, 2H), 2.98-2.85 (m, 2H). |
| 180 | | RT 2.24 min, MI 360, Method (4LCMS1)<br>$^1$H NMR (400 MHz, CDCl$_3$) δ 8.91-8.80 (m, 2H), 8.18-8.10 (m, 2H), 4.58 (dt, 1H), 4.46-4.33 (m, 1H), 3.52 (dt, 1H), 3.43-3.15 (m, 3H), 3.00 (td, 1H). |

In one approach (Scheme 5), compounds of general formula [F5-2] were prepared by the reaction of an amide derivative of general formula [F5-1] in a reduction reaction in a polar solvent such as methanol or THF in the presence of a reducing agent such as diborane in THF. The reaction is suitably conducted at ambient temperature or at high temperature by heating thermally. After reaction work up, typically by a liquid-liquid extraction, the reaction product was purified by flash column chromatography, reverse phase preparative HPLC or re-crystallisation.

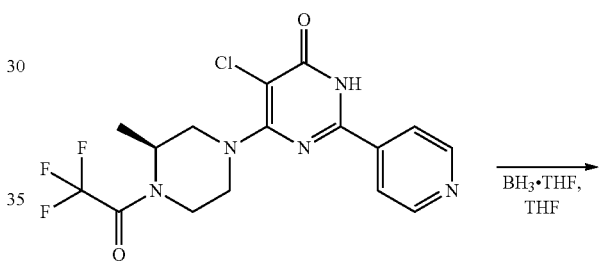

Scheme 5

For example synthesis of 5-chloro-4-[(3S)-3-methyl-4-(2,2,2-trifluoroethyl)piperazin-1-yl]-2-(4-pyridyl)-1H-pyrimidin-6-one (181)

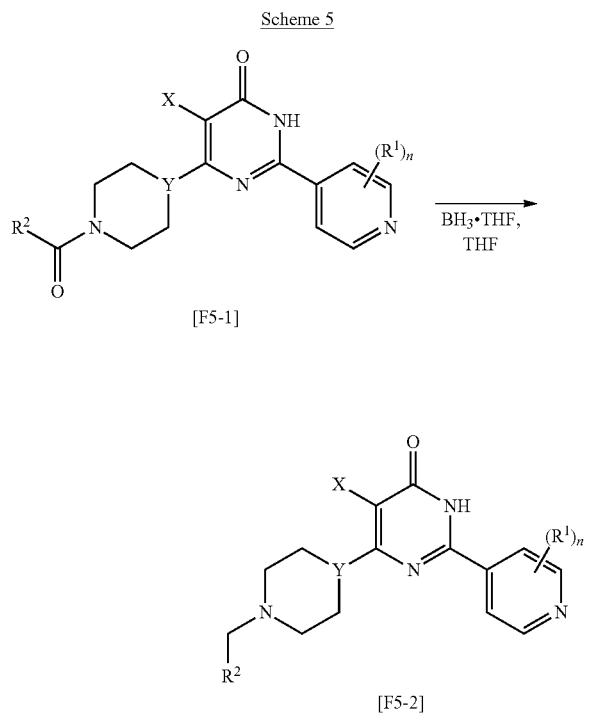

To a solution of 5-chloro-4-[(3S)-3-methyl-4-(2,2,2-trifluoroacetyl)piperazin-1-yl]-2-(4-pyridyl)-1H-pyrimidin-6-one (77) (0.1 g, 0.249 mmol) in dry THF (2.4 mL) at room temperature was added borane/THF complex (1 mL, 1.0 mmol, 1M solution in THF) and the mixture sealed and heated at 70° C. for 16 h. The reaction mixture was allowed to dry under a flow of nitrogen then taken into water (3 mL). Purification by HPLC (Method A) gave the title compound (31 mg, 32% yield) as an off-white powder. LCMS: RT 5.31 min, MI 388.07, Method (1LCMS1); $^1$H NMR (400 MHz, d6-DMSO) δ 8.73 (2H, d), 8.02 (2H, d), 4.18 (2H, d), 3.41 (1H, m), 3.29 (1H, m), 3.20 (1H, m), 3.09 (2H, m), 2.75 (2H, m), 1.17 (3H, d).

The following compound was synthesised according to the general synthesis shown in scheme [5]:

| No | Product [F5-2] | Characterisation |
|---|---|---|
| 182 | (structure shown) | RT 2.73 min, MI 373, Method (4LCMS1)<br>1H NMR (400 MHz, MeOD) δ 8.76-8.71 (m, 2H), 8.15-8.06 (m, 2H), 3.16-3.06 (m, 3H), 2.53 (dd, 2H), 2.10 (qd, 2H), 1.77 (d, 2H). |

In one approach (Scheme 6), compounds of general formula [F6-2] were prepared by the reaction of a 4,5,6-halo-2-pyridin-4-yl-pyrimidine derivative of general formula [F6-1] in a nucleophilic aromatic substitution type reaction with 4-methoxybenzyl alcohol, a base such as Et$_3$N or NaH in a polar solvent such as ethanol, butanol, THF, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Compounds of general formula [F6-4] were prepared by reaction of 4,5-halo-6-(4-methoxy-benzyloxy)-2-pyridin-4-yl-pyrimidine derivatives of general formula [F6-2] in a nucleophilic aromatic substitution type reaction utilising a suitable amine, thiol or alcohol of general formula [F6-3], and a base such as Et$_3$N or NaH in a polar solvent such as ethanol, butanol, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. 2-pyridin-4-yl-3H-pyrimidin-4-one derivatives of general formula [F6-5] were prepared from a (4-methoxy-benzyloxy)-2-pyridin-4-yl-pyrimidine derivative of general formula [F6-4] under acidic reaction conditions such as TFA or HCl in a suitable solvent such as DCM at ambient temperature. Under these reaction conditions compounds of general formula [F6-4] containing a Boc-protected nitrogen are deprotected. After reaction work up, typically by a liquid-liquid extraction or purification by acidic ion exchange catch-release the crude product was purified by flash column chromatography, reverse phase preparative HPLC or re-crystallisation.

Scheme 6

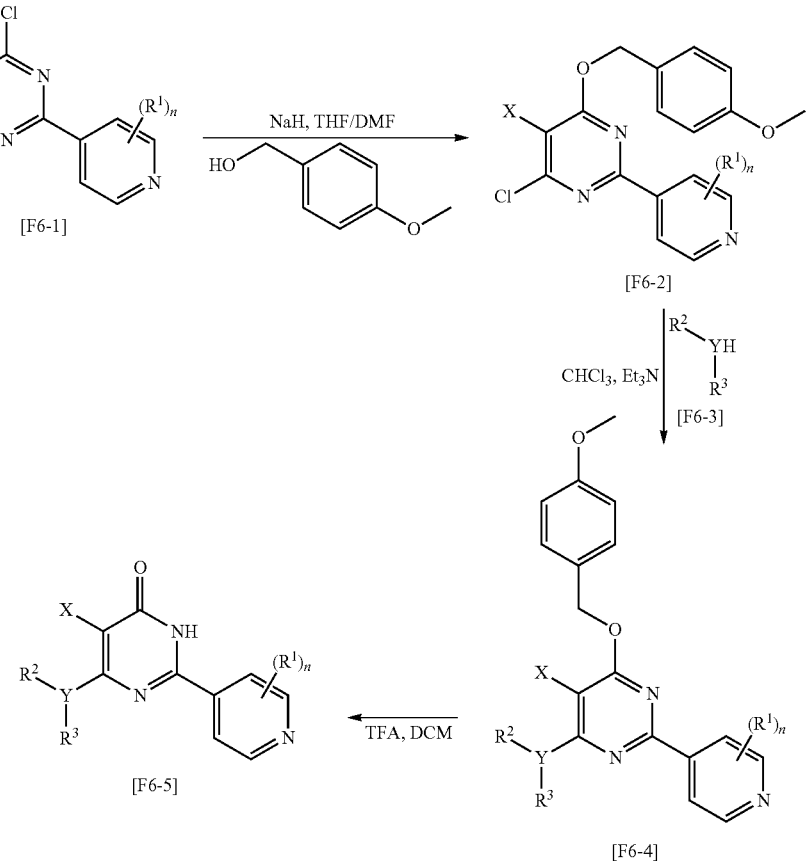

For example, synthesis of 4-[(3R)-3-aminoazepan-1-yl]-5-chloro-2-(2-fluoro-4-pyridyl)-1H-pyrimidin-6-one 2,2,2-trifluoroacetic acid (183)

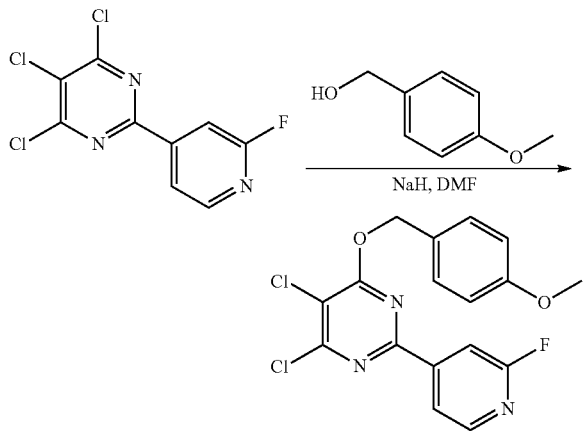

Synthesis of 4,5-dichloro-2-(2-fluoro-pyridin-4-yl)-6-(4-methoxy-benzyloxy)-pyrimidine (6-001)

To a solution of 4,5,6-trichloro-2-(2-fluoro-pyridin-4-yl)-pyrimidine (4-005, prepared in scheme 4) (2.5 g. 8.97 mmol) in DMF (35 mL) was added sodium hydride (0.54 g, 13.465 mmol) at 0° C. followed by a solution of 4-methoxybenzyl alcohol (1.24 g, 8.97 mmol) in DMF (5 mL). The mixture was then warmed to room temperature and left to stir overnight. Water (100 mL) was added and the mixture was extracted with ethyl acetate (2×150 mL), the organic layers were combined and washed with brine (100 mL), dried (MgSO$_4$), filtered and evaporated under reduced pressure. The crude reaction mixture was purified by column chromatography (0-80% EtOAc:cyclohexane) to give the title compound (1.73 g, 51% yield) as a white solid. LCMS: RT 3.93 min, MI 380/382/384, Method (1LCMS13).

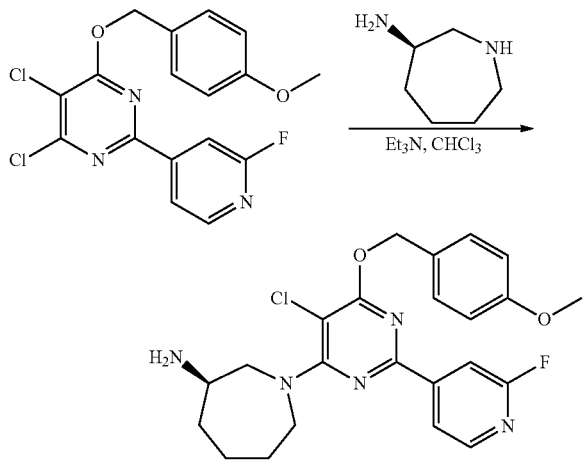

Synthesis of (R)-1-[5-chloro-2-(2-fluoro-pyridin-4-yl)-6-(4-methoxy-benzyloxy)-pyrimidin-4-yl]-azepan-3-ylamine (6-002)

To a solution of (R)-azepan-3-ylamine (0.07 g, 0.579 mmol) in chloroform (2 mL) was added triethylamine (0.11 mL, 0.789 mmol) and 4,5-dichloro-2-(2-fluoro-pyridin-4-yl)-6-(4-methoxy-benzyloxy)-pyrimidine (6-001) (0.2 g, 0.526 mmol) at 0° C. The mixture was then warmed to room temperature and left to stir overnight. The crude reaction mixture was purified by column chromatography (DCM 100% to DCM/MeOH 80/20) to give the title compound (0.23 g, 97% yield) as a white solid: LCMS: RT 2.26 min, MI 458.22, Method (1LCMS13).

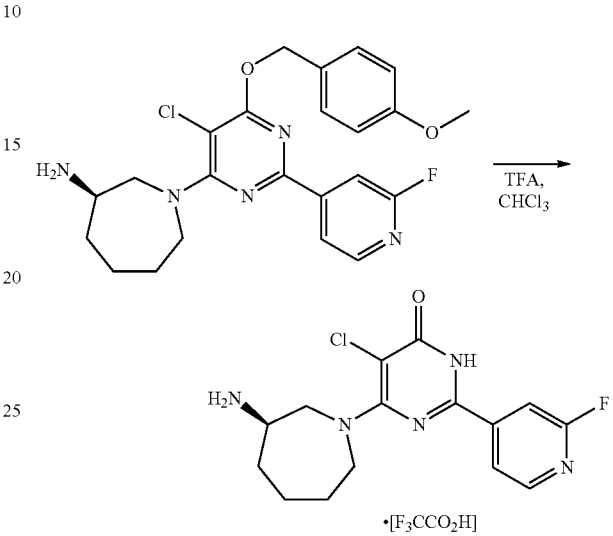

Synthesis of 4-[(3R)-3-aminoazepan-1-yl]-5-chloro-2-(2-fluoro-4-pyridyl)-1H-pyrimidin-6-one 2,2,2-trifluoroacetic acid (183)

To a solution of (R)-1-[5-chloro-2-(2-fluoro-pyridin-4-yl)-6-(4-methoxy-benzyloxy)-pyrimidin-4-yl]-azepan-3-ylamine (6-002) (0.23 g, 0.511 mmol) in chloroform (5 mL) was added TFA (0.39 mL, 5.11 mmol). The reaction mixture was left to stir at room temperature for 5 hours before a further amount of TFA (0.39 mL, 5.11 mmol) was added and the mixture was left to stir at room temperature overnight. The crude reaction mixture was evaporated under reduced pressure and the crude product was dissolved in the minimum quantity of DCM. Et$_2$O was added dropwise under vigorous stirring until no further precipitation occurred and the precipitate was collected by filtration, to give the title compound (0.179 g, 77.5% yield) as a pale yellow solid. LCMS: RT 2.01 min, MI 338.19, Method (1LCMS12); $^1$H NMR (600 MHz, d6-DMSO) 12.96 (brs, 1H), 8.44 (d, J=6 Hz, 1H), 8.06 (d, J=6 Hz, 1H), 7.94 (br s, 2H), 7.85 (s, 1H), 4.40 (m, 1H), 4.15 (m, 1H), 3.67-3.58 (m, 2H), 3.54 (m, 1H), 3.11 (m, 1H), 1.98-1.72 (m, 3H), 1.61 (m, 1H), 1.38 (m, 1H).

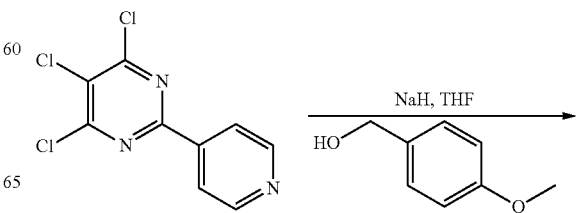

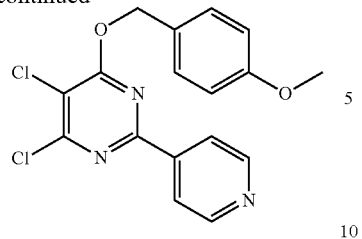

Synthesis of 4,5-dichloro-6-(4-methoxy-benzyloxy)-2-pyridin-4-yl-pyrimidine (6-003)

A mixture of 4,5,6-trichloro-2-pyridin-4-yl-pyrimidine (4-002, prepared in scheme 4) (9.65 g, 37.04 mmol) in dry THF (300 mL) was cooled to 0° C. Sodium hydride (2.22 g, 55.56 mmol, 60% oil suspension) was added and the mixture was left to stir for 5 min then a solution of 4-methoxybenzyl alcohol (5.37 g, 38.89 mmol) in dry THF (70 mL) was added dropwise, the reaction mixture was warmed to room temperature and left to stir for 5 days under a nitrogen atmosphere. The crude reaction mixture was poured into a saturated solution of ammonium chloride (100 mL) at 0° C. The mixture was then extracted with EtOAc (2×500 mL), the extracts were combined, dried (MgSO$_4$), filtered and evaporated under reduced pressure to give a dark brown residue. The crude reaction mixture was dissolved in DCM and isopropanol was added and the precipitate was collected by filtration and dried in a vacuum oven to give the title compound (8.18 g, 61% yield) which was used in the next step without further purification. LCMS: RT 6.16 min, MI 362.19, Method (1LCMS1); $^1$H NMR (400 MHz, CDCl$_3$) δ 8.80 (2H, d), 8.22 (2H, d), 7.45 (2H, d), 6.91 (2H, d), 5.58 (2H, s), 3.82 (3H, s).

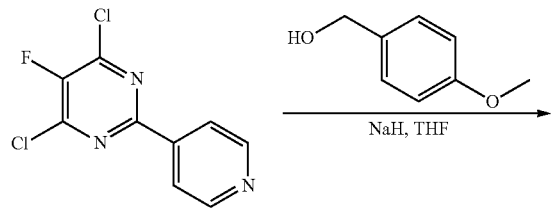

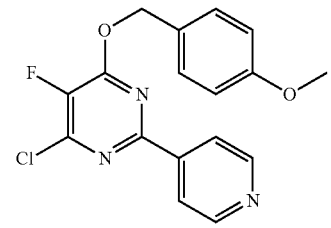

Synthesis of 4-chloro-5-fluoro-6-[(4-methoxyphenyl)methoxy]-2-(4-pyridyl)pyrimidine (6-004)

A mixture of 4,6-dichloro-5-fluoro-2-pyridin-4-yl-pyrimidine (4-008, prepared in scheme 4) (90.86 g, 3.5 mmol) in dry THF (30 mL) was cooled to 0° C. Sodium hydride (0.21 g, 5.262 mmol, 60% oil suspension) was added and the mixture was left to stir for 5 min then a solution of 4-methoxybenzyl alcohol (0.509 g, 3.684 mmol) in dry THF (10 mL) was added dropwise, the reaction mixture was warmed to room temperature and left to stir for 5 days under a nitrogen atmosphere. The crude reaction mixture was poured into an ice solution (100 mL) and the mixture was warmed to room temperature then extracted with DCM (2×100 mL), the extracts were combined, washed with brine, dried (MgSO$_4$), filtered and evaporated under reduced pressure. The crude reaction mixture was purified by column chromatography (cyclohexane 100% to EtOAc:cyclohexane 30/70) to give the title compound (0.67 g, 55% yield) as a red solid: LCMS: RT 4.72 min, MI 346, Method (1LCMS5).

The following compounds were synthesised according to the general synthesis shown in scheme [6]:

| No | Product [F6-5] | Characterisation |
|---|---|---|
| 184 | 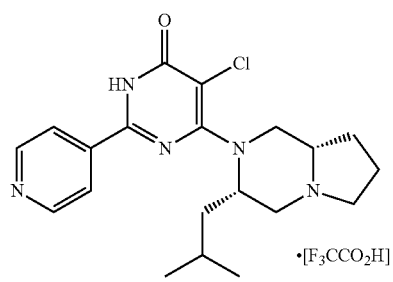 [SMILES: CC(C)C[C@H]1CN2CCC[C@H]2CN1c1nc(-c2ccncc2)[nH]c(=O)c1Cl] | RT 3.58 min, MI 388/390, Method (1LCMS1) |

-continued

| No | Product [F6-5] | Characterisation |
|---|---|---|
| 185 | (structure: 2-(pyridin-4-yl)-5-fluoro-6-[(3-tert-butyl)piperazin-1-yl]pyrimidin-4(3H)-one • [F₃CCO₂H]) | RT 2.63 min, MI 332, Method (1LCMS1)<br>¹H NMR (500 MHz, MeOD) δ 8.83 (d, 2H), 8.39 (d, 2H), 4.74 (d, 1H), 3.51-3.42 (m, 2H), 3.39-3.30 (m, 2H), 3.28-3.21 (m, 2H), 1.15 (s, 9H). |
| 186 | (structure: 2-(pyridin-4-yl)-5-chloro-6-(1,4-oxazepan-4-yl)pyrimidin-4(3H)-one • [F₃CCO₂H]) | RT 4.91 min, MI 307/309, Method (1LCMS1)<br>¹H NMR (500 MHz, MeOD) δ 8.83 (d, 2H), 8.35 (d, 2H), 4.07 (dt, 4H), 3.89 (t, 2H), 3.79 (t, 2H), 2.06 (p, 2H). |
| 187 | (structure: 2-(2-fluoropyridin-4-yl)-5-chloro-6-[(3-(2-hydroxy-2-methylpropyl))piperazin-1-yl]pyrimidin-4(3H)-one) | RT 1.91 min, MI 368, Method (1LCMS12)<br>¹H NMR (600 MHz, d6-DMSO) δ 8.33 (d, J = 6 Hz, 1H), 8.01 (d, J = 6 Hz, 1H), 7.75 (s, 1H), 4.98 (m, 1H), 4.25 (d, J = 18 Hz, 1H), 4.09 (d, J = 12 Hz, 1H), 3.16 (d, J = 6 Hz, 1H), 3.07 (t, J = 12 Hz, 1H), 2.93 (t, J = 12 Hz, 1H), 2.80 (t, J = 12 Hz, 1H), 1.23 (s, 3H), 1.18 (s, 3H). |
| 188 | (structure: 2-(2-fluoropyridin-4-yl)-5-chloro-6-[(3-amino)azepan-1-yl]pyrimidin-4(3H)-one) | RT 1.99 min, MI 338, Method (1LCMS12)<br>¹H NMR (600 MHz, d6-DMSO) δ 8.22 (d, J = 6 Hz, 1H), 7.99 (d, J = 6Hz, 1H), 7.69 (s, 1H), 4.22 (dd, J = 14.4 and 4.2 Hz, 1H), 3.97 (dt, J = 12 and 6 Hz, 1H), 3.57 (m, 1H), 3.41 (m, 1H), 1.90 (m, 1H), 1.82 (m, 1H), 1.76 (m, 1H), 1.67 (m, 1H), 1.61 (m, 1H), 1.39 (m, 1H), 1H under water peak. |
| 189 | (structure: 2-(2-fluoropyridin-4-yl)-5-chloro-6-[(3,5-dihydroxy)piperidin-1-yl]pyrimidin-4(3H)-one) | RT 2.52 min, MI 341, Method (1LCMS12)<br>¹H NMR (600 MHz, d6-DMSO) δ 12.94 (br s, 1H), 8.44 (d, J = 6 Hz, 1H), 8.02 (d, J= 6Hz, 1H), 7.80 (s, 1H), 5.09 (d, J = 4.8 Hz, 1H), 4.35 (dd, J = 12.6 and 4.8 Hz, 1H), 3.62-3.53 (m, 2H), 2.64-2.56 (m, 2H), 2.20 (m, 1H), 1.25 (q, J = 10.8 Hz, 1H). |
| 190 | (structure: 2-(2-fluoropyridin-4-yl)-5-chloro-6-[(6-hydroxy)-1,4-diazepan-1-yl]pyrimidin-4(3H)-one • [F₃CCO₂H]) | RT 1.82 min, MI 340, Method (1LCMS12)<br>¹H NMR (600 MHz, d6-DMSO) δ 8.45 (d, J = 4.8 Hz, 1H), 8.02 (d, J = 4.8 Hz, 1H), 7.82 (s, 1H), 5.85 (m, 1H), 4.29-4.20 (m, 2H), 4.13 (dd, J = 14.4 and 4.8 Hz, 1H), 3.84 (ddd, J = 15.6, 7.2 and 3 Hz, 1H), 3.79 (dd, J = 14.4 and 5.4 Hz, 1H), 3.44 (m, 1H), 3.20 (dd, J = 13.8 and 6.6 Hz, 1H), 1H under water peak. |

-continued

| No | Product [F6-5] | Characterisation |
|---|---|---|
| 191 | | RT 2.67 min, MI 342, Method (1LCMS13)<br>$^1$H NMR (600 MHz, d6-DMSO) δ 13.57 (br s, 1H), 8.48 (d, J = 5.4 Hz, 1H), 8.02 (d, J = 5.4Hz, 1H), 7.81 (s, 1H), 4.17 (dddd, J = 4.2, 4.2, 5.6 and 15 Hz, 1H), 3.87 (dt, J = 3.6 and 12 Hz, 2H), 3.56 (td, J = 2.4 and 12 Hz, 2H), 2.04 (m, 2H), 1.70 (m, 2H). |
| 192 | | RT 3.48 min, MI 337, Method (1LCMS12)<br>$^1$H NMR (600 MHz, d6-DMSO) δ 12.95 (br s, 1H), 8.42 (d, J = 5.4 Hz, 1H), 8.01 (d, J = 5.4 Hz, 1H), 7.81 (s, 1H), 4.91 (m, 2H), 3.74-3.70 (m, 2H), 3.65-3.60 (m, 2H), 2.00-1.87 (m, 4H). |
| 193 | •[F$_3$CCO$_2$H] | RT 2.01 min, MI 341, Method (1LCMS12)<br>$^1$H NMR (600 MHz, d6-DMSO) δ 8.75 (br s, 1H), 8.50 (br s, 1H), 8.47 (d, J = 4.8 Hz, 1H), 8.07 (d, J = 4.8 Hz, 1H), 7.86 (s, 1H), 4.21 (m, 1H), 3.33 (m, 2H), 3.19 (m, 2H), 2.25 (m, 2H), 1.83 (m, 2H). |
| 194 | •[F$_3$CCO$_2$H] | RT 1.70 min, MI 297, Method (1LCMS12)<br>$^1$H NMR (600 MHz, d6-DMSO) δ 9.08 (br s, 1H), 8.81 (br s, 1H), 8.47 (d, J = 4.8 Hz, 1H), 8.03 (d, J = 5.4 Hz, 1H), 7.81 (s, 1H), 5.60 (q, J = 6.6 Hz, 1H), 4.51 (m, 2H), 4.18 (m, 2H). |
| 195 | •[F$_3$CCO$_2$H] | RT 1.93 min, MI 325, Method (1LCMS12)<br>$^1$H NMR (600 MHz, d6-DMSO) δ 13.43 (br s, 1H), 8.46 (d, J = 5.4 Hz, 1H), 8.08 (d, J = 5.4 Hz, 1H), 7.96 (br s, 1H), 7.93 (br s, 1H), 7.85 (s, 1H), 5.52 (q, J = 7.2 Hz, 1H), 3.56 (m, 1H), 2.68 (q, J = 7.8 Hz, 1H), 2.14 (m, 1H), 2.07-1.95 (m, 2H), 1.83-1.74 (m, 2H). |
| 196 | | RT 1.89 min, MI 338.7, Method (1LCMS12)<br>$^1$H NMR (300 MHz, d6-DMSO) δ 13.05 (br s, 1H), 8.72 (br s, 1H), 8.45 (d, 1H), 8.04 (d, 1H), 7.83 (s, 1H), 4.36 (d, 1H), 4.07 (d, 1H), 3.29-3.11 (m, 3H), 2.65 (s, 3H), 2.22-2.09 (m, 1H), 1.92-1.77 (m, 1H), 1.70-1.49 (m, 2H). |
| 197 | | RT 1.82 min, MI 338.7, Method (1LCMS12)<br>$^1$H NMR (300 MHz, d6-DMSO) δ 8.39 (d, 1H), 7.98 (d, 1H), 7.76 (s, 1H), 4.27 (d, 1H), 4.00 (d, 1H), 3.41-3.14 (m, 3H), 2.62 (s, 3H), 2.22-2.02 (m, 1H), 1.92-1.73 (m, 1H), 1.72-1.49 (m, 2H). |

| No | Product [F6-5] | Characterisation |
|---|---|---|
| 198 | 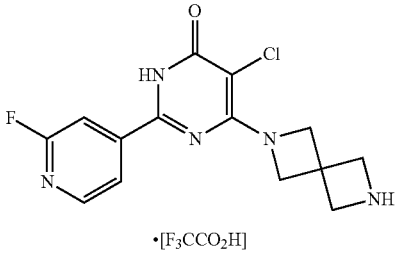 [SMILES: O=c1[nH]c(-c2ccnc(F)c2)nc(N2CC3(CNC3)C2)c1Cl]•[F₃CCO₂H] | RT 1.63 min, MI 322, Method (1LCMS12)<br>¹H NMR (600 MHz, d6-DMSO) δ 12.83 (br s, 1H), 8.53 (br s, 2H), 8.44 (d, J = 5.2 Hz, 1H), 7.97 (d, J = 4.6 Hz, 1H), 7.77 (s, 1H), 4.53 (m, 4H), 4.17 (m, 4H). |
| 199 | 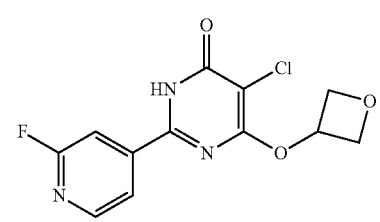 [SMILES: O=c1[nH]c(-c2ccnc(F)c2)nc(OC2COC2)c1Cl] | RT 1.93 min, MI 298, Method (1LCMS12)<br>¹H NMR (600 MHz, d6-DMSO) δ 8.48 (d, J = 4.8 Hz, 1H), 7.68 (d, J = 4.8 Hz, 1H), 7.55 (s, 1H), 5.20 (m, 1H), 4.51 (dd, J = 8.4 and 9.6 Hz, 1H), 4.22 (dd, J = 6.6 and 9.6 Hz, 1H), 3.78 (dd, J = 2.4 and 12.6 Hz, 1H), 3.64 (dd, J = 4 and 12.6 Hz, 1H). |
| 200 | 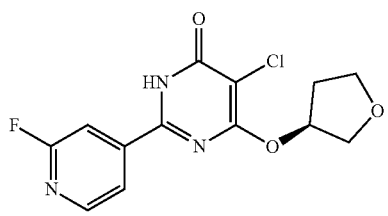 [SMILES: O=c1[nH]c(-c2ccnc(F)c2)nc(O[C@H]2CCOC2)c1Cl] | RT 3.34 min, MI 312, Method (1LCMS12)<br>¹H NMR (600 MHz, d6-DMSO) δ 8.41 (m, 1H), 8.06 (m, 1H), 7.81 (m, 1H), 5.71 (m, 1H), 3.98 (dd, J = 4.8 and 10.2 Hz, 1H), 3.90-3.80 (m, 2H), 3.77 (m, 1H), 2.30 (m, 1H), 2.06 (m, 1H). |
| 201 | 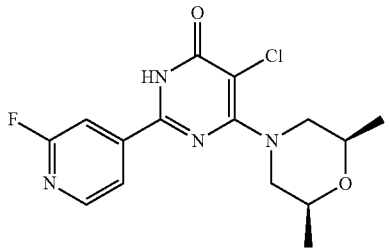 [SMILES: C[C@@H]1CN(c2nc(-c3ccnc(F)c3)[nH]c(=O)c2Cl)C[C@H](C)O1] | RT 3.75 min, MI 339, Method (1LCMS12)<br>¹H NMR (600 MHz, d6-DMSO) δ 8.43 (d, J = 6 Hz, 1H), 8.02 (d, J = 4.8 Hz, 1H), 7.81 (s, 1H), 4.23 (dapp, J = 13.2 Hz, 2H), 3.66 (m, 2H), 2.70 (dd, J = 10.8 and 13.2 Hz, 2H), 1.13 (d, J = 6 Hz, 6H). |
| 202 | 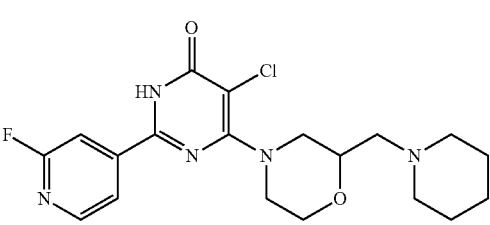•[F₃CCO₂H] | RT 2.12 min, MI 408, Method (1LCMS12)<br>¹H NMR (600 MHz, d6-DMSO) δ 13.14 (br s, 1H), 9.34 (br s, 1H), 8.45 (d, J = 5.4 Hz, 1H), 8.04 (d, J = 4.8 Hz, 1H), 7.84 (s, 1H), 4.25-4.18 (m, 2H), 4.04 (t, J = 9.6 Hz, 1H), 3.98 (d, J = 11.4 Hz, 1H), 3.76 (td, J = 1.8 and 11.4 Hz, 1H), 3.53-3.29 (m, 3H), 3.23-3.14 (m, 2H), 3.01-2.86 (m, 3H), 1.85-1.58 (m, 5H), 1.38 (m, 1H). |
| 203 | 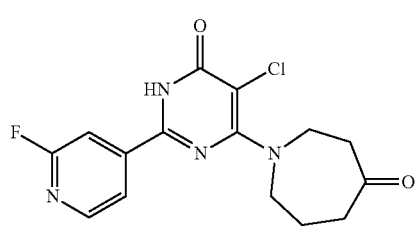 [SMILES: O=C1CCCN(c2nc(-c3ccnc(F)c3)[nH]c(=O)c2Cl)CC1] | RT 3.09 min, MI 337, Method (1LCMS12)<br>¹H NMR (600 MHz, d6-DMSO) δ 12.93 (br s, 1H), 8.43 (d, J = 4.8 Hz, 1H), 7.99 (d, J = 5.4 Hz, 1H), 7.78 (s, 1H), 4.15 (t, J = 6Hz, 2H), 3.99 (t, J = 5.4 Hz, 2H), 2.68 (t, J = 6 Hz, 4H), 1.88 (m, 2H). |

| No | Product [F6-5] | Characterisation |
| --- | --- | --- |
| 204 | 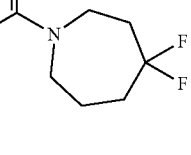 | RT 4.0 min, MI 359, Method (1LCMS12)<br>$^1$H NMR (600 MHz, d6-DMSO) δ 12.93 (br s, 1H), 8.44 (d, J = 5.4 Hz, 1H), 8.01 (d, J = 4.8 Hz, 1H), 7.79 (s, 1H), 3.86 (t, J = 6.6 Hz, 2H), 3.83 (m, 2H), 2.38 (m, 2H), 2.12 (m, 2H), 1.91 (m, 2H). |
| 205 | 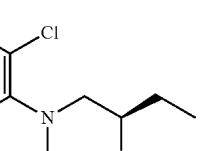 | RT 3.88 min, MI 339, Method (1LCMS12)<br>$^1$H NMR (600 MHz, d6-DMSO) δ 13.03 (br s, 1H), 8.44 (d, J = 4.8 Hz, 1H), 8.02 (d, J = 4.8 Hz, 1H), 7.81 (s, 1H), 4.25 (dt, J = 2.4 and 12.6 Hz, 1H), 4.19 (d, J = 13.8 Hz, 1H), 3.91 (d, J = 11.4 Hz, 1H), 3.57 (td, J = 2.4 and 11.4 Hz, 1H), 3.41 (m, 1H), 3.13 (ddd, J = 3, 11.4 and 13.2 Hz, 1H), 2.82 (dd, J = 10.2 and 13.2 Hz, 1H), 1.48 (qd, J = 7.2 and 7.2 Hz, 2H), 0.93 (t, J = 7.2 Hz, 3H). |
| 206 | 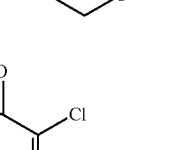·[F$_3$CCO$_2$H] | RT 1.77 min, MI 324, Method (1LCMS12)<br>$^1$H NMR (600 MHz, d6-DMSO) δ 12.97 (br s, 1H), 8.91 (br s, 2H), 8.45 (d, J = 4.2 Hz, 1H), 8.02 (d, J = 4.8 Hz, 1H), 7.81 (s, 1H), 4.03 (t, J = 5.0 Hz, 2H), 3.90 (t, J = 6.0 Hz, 2H), 3.37 (m, 2H), 3.22 (m, 2H), 2.12 (q, J = 6.0 Hz, 2H). |
| 207 | 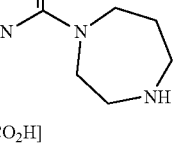 | RT 2.61 min, MI 341, Method (1LCMS12)<br>$^1$H NMR (600 MHz, d6-DMSO) δ 12.93 (br s, 1H), 8.44 (d, J = 5 Hz, 1H), 8.01 (d, J = 5 Hz, 1H), 7.80 (s, 1H), 5.12 (br s, 1H), 4.40 (dd, J = 5 and 14 Hz, 1H), 4.33 (dt, J = 4 and 14 Hz, 1H), 4.00 (m, 1H), 3.88 (dt, J = 4 and 12 Hz, 1H), 3.71 (m, 1H), 3.65 (dd, J = 4 and 13 Hz, 1H), 3.62-3.55 (m, 2H), 3.39 (dd, J = 8.5 and 14 Hz, 1H). |
| 208 | 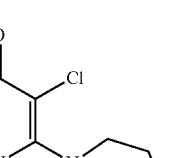 | RT 3.13 min, MI 339, Method (1LCMS12)<br>$^1$H NMR (600 MHz, d6-DMSO) δ 13.18 (br s, 1H), 8.43 (d, J = 5.26 Hz, 1H), 7.90 (d, J = 5.26 Hz, 1H), 7.66 (s, 1H), 4.29 (m, 2H), 4.21 (m, 2H), 4.10 (m, 2H), 3.87 (t, J = 4.60 Hz, 2H). |
| 209 | 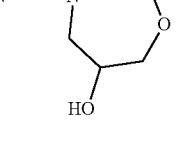 | RT 4.20 min, MI 400, Method (1LCMS12)<br>$^1$H NMR (600 MHz, d6-DMSO) δ 8.44 (1H, d, J = 5.0 Hz), 7.94 (1H, br s), 7.75 (1H, s), 7.02 (2H, t, J = 7.4 Hz), 6.65 (2H, d, J = 7.6 Hz), 6.52 (1H, t, J = 6.8 Hz), 4.48 (1H, d, J = 12.8 Hz), 4.25 (1H, d, J = 13.2 Hz), 3.46-3.40 (1H, br m), 3.16-3.11 (1H, m), 2.83-2.79 (1H, m), 2.04-2.02 (1H, br m), 1.86-1.83 (1H, m), 1.66-1.59 (1H, m), 1.54-1.47 (1H, m). |

-continued

| No | Product [F6-5] | Characterisation |
|---|---|---|
| 210 | (structure) | MI 366.3<br>¹H NMR (400 MHz, CDCl₃) δ 8.44 (d, J = 5.3 Hz, 1H), 8.03 (d, J = 5.0 Hz, 1H), 7.82 (s, 1H), 4.75 (dd, J = 12.3, 3.8 Hz, 1H), 3.36-3.28 (m, 1H), 3.20 (s, 3H), 2.90-2.80 (m, 1H), 2.70-2.62 (m, 1H), 2.59-2.51 (m, 1H), 2.18-2.07 (m, 2H), 1.69-1.64 (m, 2H), 1.21 (s, 3H), 0.82 (s, 3H). |
| 211 | (structure) | MI 352.2<br>¹H NMR (400 MHz, d6-DMSO) δ 8.70-8.35 (m, 1H), 8.33 (d, J = 5.3 Hz, 1H), 8.06 (d, J = 5.0 Hz, 1H), 7.79 (s, 1H), 5.66 (d, J = 9.3 Hz, 1H), 4.41-4.23 (m, 1H), 3.25-3.09 (m, 2H), 2.98-2.71 (m, 3H), 1.97-1.78 (m, 1H), 1.76-1.63 (m, 1H), 1.02 (s, 3H), 0.87 (s, 3H). |
| 212 | (structure) •[F₃CCO₂H] | MI 394.3<br>¹H NMR (400 MHz, d6-DMSO) δ 12.60 (br s, 1H), 8.41 (d, J = 5.2 Hz, 1H), 8.02-7.98 (m, 1H), 7.78 (s, 1H), 3.95-3.74 (m, 3H), 3.61-3.49 (m, 5H), 2.52-2.37 (m, 7H), 2.06-1.97 (m, 1H), 1.68-1.57 (m, 1H). |
| 213 | (structure) •[F₃CCO₂H] | MI 364.2<br>¹H NMR (400 MHz, d6-DMSO) δ 12.90 (br s, 1H), 8.83-8.87 (m, 2H), 8.45 (d, J = 5.2 Hz, 1H), 8.05 (d, J = 4.8 Hz, 1H), 7.84 (s, 1H), 4.19 (d, J = 12.8 Hz, 1H), 4.11-4.03 (m, 1H), 4.00-3.92 (m, 1H), 3.86 (d, J = 12.7 Hz, 1H), 3.20-3.14 (m, 2H), 2.35-2.27 (m, 1H), 2.19-2.10 (m, 1H), 1.88-1.60 (m, 6H). |
| 214 | (structure) | MI 311.2<br>¹H NMR (400 MHz, d6-DMSO) δ 12.71 (br s, 1H), 8.42 (d, J = 5.2 Hz, 1H), 8.03-8.00 (m, 1H), 7.80 (s, 1H), 5.00 (d, J = 3.3 Hz, 1H), 4.37-4.31 (m, 1H), 3.95-3.82 (m, 3H), 3.69 (d, J = 11.8 Hz, 1H), 1.98-1.81 (m, 2H). |
| 215 | (structure) | MI 311.2<br>¹H NMR (400 MHz, d6-DMSO) δ 12.71 (br s, 1H), 8.42 (d, J = 5.2 Hz, 1H), 8.03-8.00 (m, 1H), 7.80 (s, 1H), 5.00 (d, J = 3.2 Hz, 1H), 4.37-4.31 (m, 1H), 3.95-3.82 (m, 3H), 3.69 (d, 11.8 Hz, 1H), 1.98-1.81 (m, 2H). |

| No | Product [F6-5] | Characterisation |
|---|---|---|
| 216 | 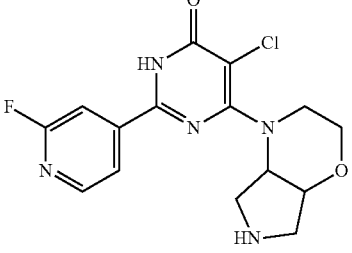 •[F₃CCO₂H] | MI 352.2<br>¹H NMR (400 MHz, d6-DMSO) δ 13.16 (s, 1H), 9.33 (br s, 1H), 8.92 (br s, 1H), 8.45 (d, J = 5.3 Hz, 1H), 8.05 (d, J = 5.3 Hz, 1H), 7.85 (s, 1H), 4.89-4.82 (m, 1H), 4.22-4.17 (m, 2H), 3.99-3.94 (m, 1H), 3.72-3.65 (m, 1H), 3.62-3.52 (m, 1H), 3.48-3.24 (m, 4H). |
| 217 | 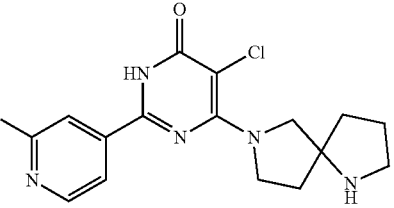 •[F₃CCO₂H] | MI 350.02<br>¹H NMR (400 MHz, d6-DMSO) δ 13.00 (br s, 1H), 8.97 (br s, 1H), 8.85 (br s, 1H), 8.45 (d, J = 5.1 Hz, 1H), 8.04 (d, J = 5.1 Hz, 1H), 7.83 (s, 1H), 4.19 (d, J = 12.4 Hz, 1H), 4.07-3.95 (m, 2H), 3.90 (d, J = 12.6 Hz, 1H), 3.54-3.24 (m, 2H), 2.35-2.27 (m, 1H), 2.24-1.98 (m, 5H). |
| 218 | 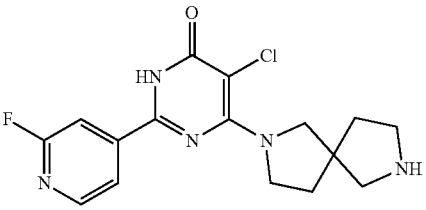 •[F₃CCO₂H] | MI 350.02<br>¹H NMR (400 MHz, d6-DMSO) δ 12.82 (br s, 1H), 8.84 (br s, 2H), 8.43 (d, J = 5.2 Hz, 1H), 8.04-8.01 (m, 1H), 7.81 (s, 1H), 3.95-3.78 (m, 4H), 3.45-3.11 (m, 4H), 2.05-1.89 (m, 4H). |
| 219 | 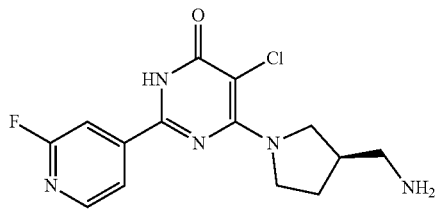 •[F₃CCO₂H] | MI 323.99<br>¹H NMR (400 MHz, d6-DMSO) δ 12.81 (br s, 1H), 8.43 (d, J = 5.1 Hz, 1H), 8.04-8.01 (m, 1H), 7.85-7.75 (m, 4H), 4.03-3.90 (m, 2H), 3.87-3.78 (m, 1H), 3.62-3.56 (m, 1H), 2.99-2.91 (m, 1H), 2.52-2.40 (m, 2H), 2.14-2.06 (m, 1H), 1.76-1.65 (m, 1H). |
| 220 | 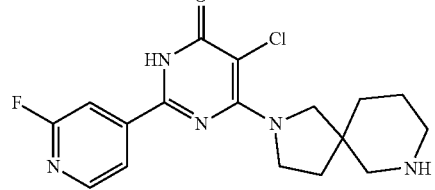 •[F₃CCO₂H] | MI 364.04<br>¹H NMR (400 MHz, d6-DMSO) δ 12.82 (br s, 1H), 8.50 (br s, 2H), 8.44 (d, J = 5.3 Hz, 1H), 8.05-8.01 (m, 1H), 7.82 (s, 1H), 3.98-3.86 (m, 2H), 3.83 (d, J = 11.7 Hz, 1H), 3.69 (d, J = 11.7 Hz, 1H), 3.15-2.98 (m, 4H), 2.01-1.93 (m, 1H), 1.86-1.55 (m, 5H). |

| No | Product [F6-5] | Characterisation |
|---|---|---|
| 221 | 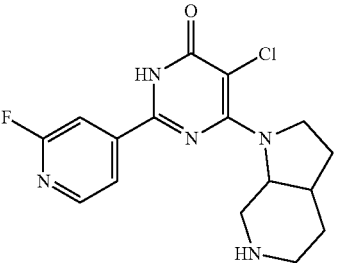<br>•[F₃CCO₂H] | MI 350.02<br>¹H NMR (400 MHz, d6-DMSO) δ 12.90 (br s, 1H), 8.62-8.38 (m, 3H), 8.03 (d, J = 5.2 Hz, 1H), 7.81 (s, 1H), 4.72-4.66 (m, 1H), 4.15-4.07 (m, 1H), 3.84-3.76 (m, 1H), 3.45-3.03 (m, 4H), 2.52-2.42 (m, 1H), 2.08-1.89 (m, 3H), 1.84-1.74 (m, 1H). |
| 222 | 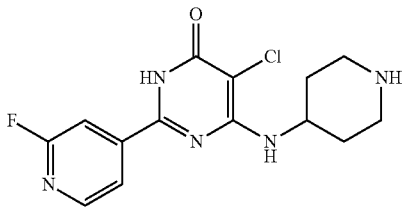<br>•[F₃CCO₂H] | MI 323.98<br>¹H NMR (400 MHz, d6-DMSO) δ 12.81 (br s, 1H), 8.71-8.54 (m, 1H), 8.43 (d, J = 5.3 Hz, 1H), 8.33-8.15 (m, 1H), 8.07 (d, J = 5.3 Hz, 1H), 7.86 (s, 1H), 7.18-6.99 (m, 1H), 4.46-4.29 (m, 1H), 3.47-3.27 (m, 1H, coincident with water), 3.19-3.01 (m, 3H), 2.11-1.93 (m, 2H), 1.89-1.73 (m, 2H). |
| 223 | 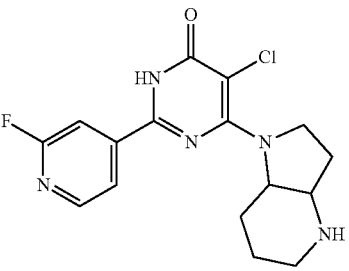<br>•[F₃CCO₂H] | MI 350.01<br>¹H NMR (400 MHz, d6-DMSO) δ 12.96 (br s, 1H), 9.08 (br s, 1H), 8.52-8.40 (m, 2H), 7.98 (d, J = 5.0 Hz, 1H), 7.76 (s, 1H), 4.66-4.60 (m, 1H), 4.29-4.20 (m, 1H), 3.94-3.86 (m, 1H), 3.72-3.64 (m, 1H), 3.20-2.96 (m, 2H), 2.22-2.12 (m, 2H), 2.05-1.92 (m, 2H), 1.67-1.57 (m, 2H). |
| 224 | 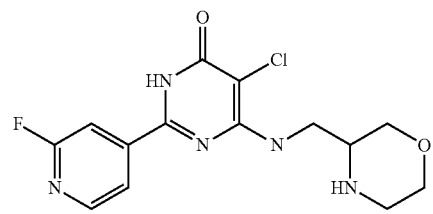<br>•[F₃CCO₂H] | MI 339.99<br>¹H NMR (400 MHz, d6-DMSO) δ 12.86 (br s, 1H), 9.03 (br s, 1H), 8.74 (br s, 1H), 8.44 (d, J = 5.2 Hz, 1H), 8.09 (d, J = 5.1 Hz, 1H), 7.89 (s, 1H), 7.33 (br s, 1H), 3.98-3.93 (m, 1H), 3.90-3.84 (m, 1H), 3.76-3.48 (m, 5H), 3.33-3.27 (m, 1H), 3.16-3.06 (m, 1H). |
| 225 | 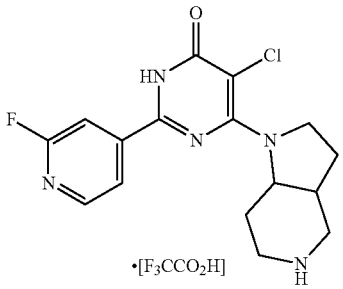 [SMILES: O=c1[nH]c(-c2ccnc(F)c2)nc(N2CCC3CNCCC32)c1Cl]<br>•[F₃CCO₂H] | MI 350.03<br>¹H NMR (400 MHz, d6-DMSO) δ 12.87 (br s, 1H), 8.58 (br s, 1H), 8.43 (d, J = 5.2 Hz, 1H), 8.35 (br s, 1H), 8.01 (d, J = 5.0 Hz, 1H), 7.79 (s, 1H), 4.69-4.63 (m, 1H), 4.17-4.09 (m, 1H), 3.78-3.70 (m, 1H), 3.35-3.25 (m, 2H), 3.19-3.00 (m, 3H), 2.20-1.84 (m, 4H). |

| No | Product [F6-5] | Characterisation |
|---|---|---|
| 226 | 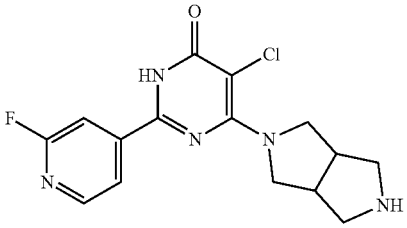 •[F₃CCO₂H] | MI 336.02<br>¹H NMR (400 MHz, d6-DMSO) δ 12.87 (br s, 1H), 8.86 (br s, 2H), 8.44 (d, J = 5.2 Hz, 1H), 8.02 (d, J = 5.0 Hz, 1H), 7.81 (s, 1H), 4.01 (dd, J = 12.0, 7.3 Hz, 2H), 3.90 (dd, J = 12.0, 3.5 Hz, 2H), 3.48-3.02 (m, 6H). |
| 227 | 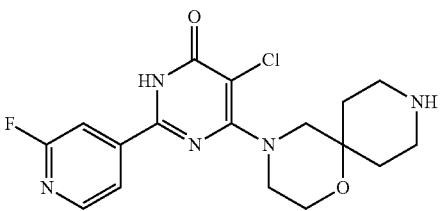 •[F₃CCO₂H] | MI 380.03<br>¹H NMR (400 MHz, d6-DMSO) δ 13.05 (br s, 1H), 8.55-8.38 (m, 2H), 8.31-8.14 (m, 1H), 8.03 (d, J = 5.3 Hz, 1H), 7.82 (s, 1H), 3.84-3.65 (m, 6H), 3.25-3.11 (m, 2H), 3.04-2.87 (m, 2H), 2.13-1.98 (m, 2H), 1.78-1.59 (m, 2H). |
| 228 | 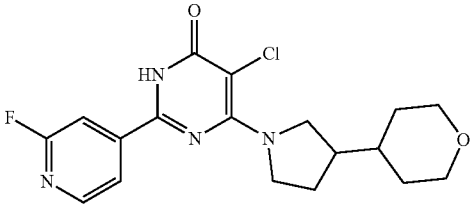 [SMILES: O=c1[nH]c(-c2ccnc(F)c2)nc(N2CCC(C3CCOCC3)C2)c1Cl] | MI 379.05<br>¹H NMR (400 MHz, d6-DMSO) δ 12.71 (br s, 1H), 8.41 (d, J = 5.3 Hz, 1H), 8.01 (d, J = 5.2 Hz, 1H), 7.80 (s, 1H), 3.99-3.71 (m, 5H), 3.50-3.43 (m, 1H), 3.33-3.25 (m, 2H), 2.10-2.02 (m, 1H), 1.99-1.86 (m, 1H), 1.68-1.43 (m, 4H), 1.35-1.20 (m, 2H). |
| 229 | 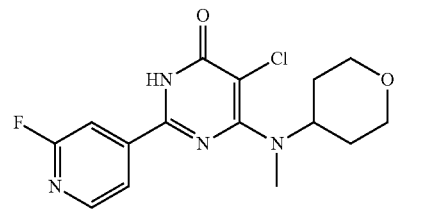 [SMILES: CN(c1nc(-c2ccnc(F)c2)[nH]c(=O)c1Cl)C1CCOCC1] | MI 339.00<br>¹H NMR (400 MHz, d6-DMSO) δ 12.84 (br s, 1H), 8.43 (d, J = 5.2 Hz, 1H), 7.99 (d, J = 5.1 Hz, 1H), 7.78 (s, 1H), 4.45-4.35 (m, 1H), 3.95 (dd, J = 11.1, 4.2 Hz, 2H), 3.47-3.39 (m, 2H), 3.03 (s, 3H), 1.95-1.83 (m, 2H), 1.71-1.65 (m, 2H). |
| 230 | 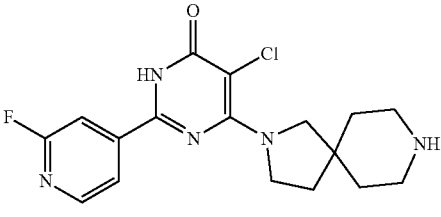 •[F₃CCO₂H] | MI 364.04<br>¹H NMR (400 MHz, d6-DMSO) δ 12.80 (br s, 1H), 8.43 (d, J = 5.3 Hz, 1H), 8.37 (br s, 2H), 8.03 (d, J = 5.2 Hz, 1H), 7.82 (s, 1H), 3.93-3.87 (m, 2H), 3.71 (s, 2H), 3.12 (s, 4H), 1.90-1.85 (m, 2H), 1.78-1.65 (m, 4H). |
| 231 | 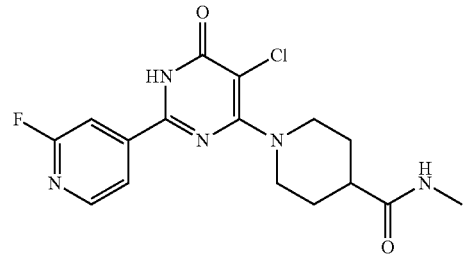 [SMILES: CNC(=O)C1CCN(c2nc(-c3ccnc(F)c3)[nH]c(=O)c2Cl)CC1] | MI 366.03<br>¹H NMR (400 MHz, d6-DMSO) δ 12.88 (br s, 1H), 8.43 (d, J = 5.3 Hz, 1H), 8.01 (d, J = 5.3 Hz, 1H), 7.83-7.73 (m, 2H), 4.34 (d, J = 13.3 Hz, 2H), 3.09-2.99 (m, 2H), 2.57 (d, J = 4.5 Hz, 3H), 2.46-2.33 (m, 1H), 1.84-1.73 (m, 2H), 1.71-1.58 (m, 2H). |

-continued

| No | Product [F6-5] | Characterisation |
|---|---|---|
| 232 | | MI 366.03<br>$^1$H NMR (400 MHz, d6-DMSO) δ 12.93 (br s, 1H), 8.43 (d, J = 5.3 Hz, 1H), 8.02 (d, J = 5.3 Hz, 1H), 7.84 (d, J = 7.5 Hz, 1H), 7.80 (s, 1H), 4.28-4.19 (m, 2H), 3.90-3.79 (m, 1H), 3.21-3.11 (m, 2H), 1.90-1.82 (m, 2H), 1.79 (s, 3H), 1.52-1.39 (m, 2H). |
| 233 | | MI 393.01<br>$^1$H NMR (400 MHz, d6-DMSO) δ 12.96 (br s, 1H), 10.74 (s, 1H), 8.62 (s, 1H), 8.44 (d, J = 5.3 Hz, 1H), 8.02 (d, J = 5.0 Hz, 1H), 7.81 (s, 1H), 4.26-4.14 (m, 2H), 3.52-3.40 (m, 2H), 2.02-1.87 (m, 2H), 1.75-1.62 (m, 2H). |
| 234 | | MI 322.97<br>$^1$H NMR (400 MHz, d6-DMSO) δ 13.03 (br. s, 1H), 8.44 (d, J = 5.3 Hz, 1H), 8.03 (d, J = 5.3 Hz, 1H), 7.83 (s, 1H), 4.00 (t, J = 6.0 Hz, 4H), 2.57-2.51 (m, 4H). |
| 235 | ·[F$_3$CCO$_2$H] | MI 339.97<br>$^1$H NMR (400 MHz, d6-DMSO) δ 13.05 (br s, 1H), 8.45 (d, J = 5.3 Hz, 1H), 8.16-8.08 (m, 1H), 8.07-8.02 (m, 1H), 7.83 (s, 1H), 5.57 (d, J = 5.0 Hz, 1H), 4.53-4.39 (m, 1H), 4.32-4.20 (m, 1H), 3.73-3.56 (m, 2H), 3.00 (d, J = 7.3 Hz, 4H), 2.07-1.93 (m, 1H), 1.64-1.43 (m, 1H). |
| 236 | | MI 367.01<br>$^1$H NMR (400 MHz, d6-DMSO) δ 12.97 (s, 1H), 8.43 (d, J = 5.3 Hz, 1H), 8.01 (d, J = 5.0 Hz, 1H), 7.80 (s, 1H), 3.93 (s, 4H), 3.77-3.70 (m, 4H), 1.78-1.72 (m, 4H). |
| 237 | | MI 351.97<br>$^1$H NMR (400 MHz, d6-DMSO) δ 8.38-8.44 (m, 1H), 7.99-8.03 (m, 1H), 7.76-7.83 (m, 1H), 3.91-4.01 (m, 2H), 3.86 (d, J = 10.5 Hz, 1H), 3.52-3.63 (m, 2H), 3.40-3.49 (m, 2H), 2.73-2.89 (m, 3H). |

-continued

| No | Product [F6-5] | Characterisation |
|---|---|---|
| 238 | 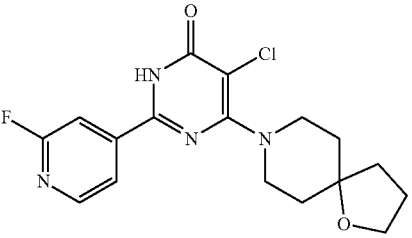 | MI 365.0<br>$^1$H NMR (400 MHz, d6-DMSO) δ 12.87 (br s, 1H), 8.42 (d, J = 5.3 Hz, 1H), 8.01 (d, J = 5.1 Hz, 1H), 7.79 (s, 1H), 3.86 (dt, J = 13.2, 4.6 Hz, 2H), 3.76 (t, J = 6.7 Hz, 2H), 3.50-3.62 (m, 2H), 1.82-2.03 (m, 2H), 1.48-1.76 (m, 6H). |
| 239 | 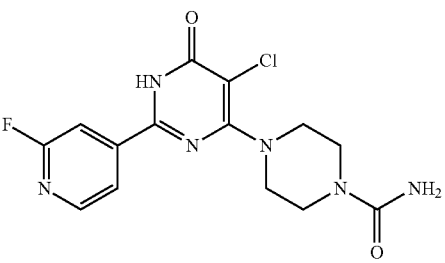 [SMILES: NC(=O)N1CCN(c2nc(-c3ccnc(F)c3)[nH]c(=O)c2Cl)CC1] | MI 353.0<br>$^1$H NMR (400 MHz, d6-DMSO) δ 12.98 (br s, 1H), 8.45 (d, J = 5.3 Hz, 1H), 8.04 (d, J = 5.3 Hz, 1H), 7.83 (s, 1H), 6.07 (br s, 2H), 3.59-3.42 (m, 8H). |
| 240 | 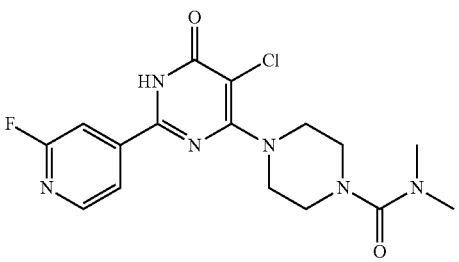 [SMILES: CN(C)C(=O)N1CCN(c2nc(-c3ccnc(F)c3)[nH]c(=O)c2Cl)CC1] | MI 381.0<br>$^1$H NMR (400 MHz, d6-DMSO) δ 8.43 (d, J = 5.3 Hz, 1H), 8.03 (d, J = 5.3 Hz, 1H), 7.82 (s, 1H), 3.49-3.91 (m, 4H), 3.09-3.32 (m, 4H), 2.78 (s, 6H). |
| 241 | 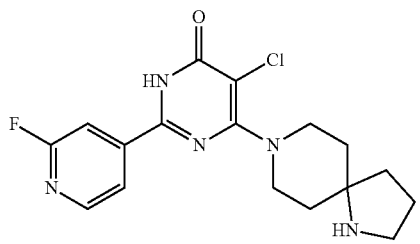<br>•[F$_3$CCO$_2$H] | MI 364.02<br>$^1$H NMR (400 MHz, d6-DMSO) δ 13.03 (br s, 1H), 8.73 (br s, 1H), 8.45 (d, J = 5.3 Hz, 1H), 8.02 (d, J = 5.3 Hz, 1H), 7.82 (s, 1H), 4.72-4.17 (m, 1H), 4.10-3.98 (m, 2H), 3.50-3.37 (m, 2H), 3.32-3.22 (m, 2H), 2.07-1.85 (m, 8H). |
| 242 | 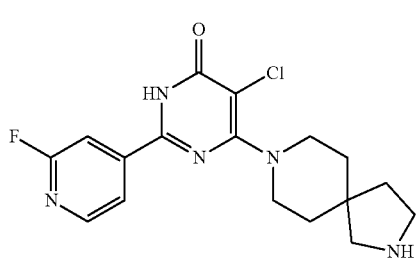<br>•[F$_3$CCO$_2$H] | MI 364.04<br>$^1$H NMR (400 MHz, d6-DMSO) δ 12.93 (br s, 1H), 8.80 (br s, 1H), 8.44 (d, J = 5.3 Hz, 1H), 8.01 (d, J = 5.3 Hz, 1H), 7.80 (s, 1H), 4.01-3.41 (m, 5H), 3.34-3.22 (m, 2H), 3.11-3.01 (m, 2H), 1.88 (t, J = 7.5 Hz, 2H), 1.74-1.60 (m, 4H). |

-continued

| No | Product [F6-5] | Characterisation |
|---|---|---|
| 243 | 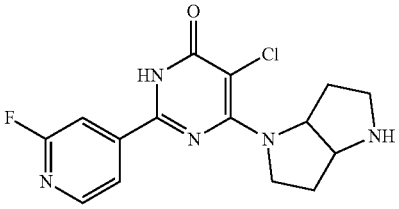·[F₃CCO₂H] | MI 335.98<br>¹H NMR (400 MHz, d6-DMSO) δ 12.65-13.10 (m, 1H), 8.74-9.33 (m, 2H), 8.44 (d, J = 5.3 Hz, 1H), 8.02 (d, J = 5.0 Hz, 1H), 7.81 (s, 1H), 5.13-5.25 (m, 1H), 4.31 (br s, 1H), 4.00-4.14 (m, 1H), 3.88-4.00 (m, 1H), 3.23-3.30 (m, 1H), 3.04-3.19 (m, 1H), 2.16-2.31 (m, 3H), 2.00-2.11 (m, 1H). |
| 244 | 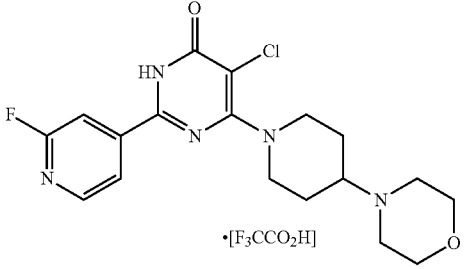 [SMILES: O=c1[nH]c(-c2ccnc(F)c2)nc(N2CCC(N3CCOCC3)CC2)c1Cl]·[F₃CCO₂H] | MI 394.04<br>¹H NMR (400 MHz, d6-DMSO) δ 12.89-13.21 (m, 1H), 9.71 (br s, 1H), 8.45 (d, J = 5.3 Hz, 1H), 8.03 (d, J = 5.0 Hz, 1H), 7.82 (s, 1H), 4.49 (d, J = 13.3 Hz, 2H), 4.02 (d, J = 11.5 Hz, 2H), 3.66 (t, J = 11.9 Hz, 2H), 3.44-3.56 (m, 3H), 2.98-3.19 (m, 4H), 2.19 (d, J = 11.3 Hz, 2H), 1.62-1.77 (m, 2H). |
| 245 | 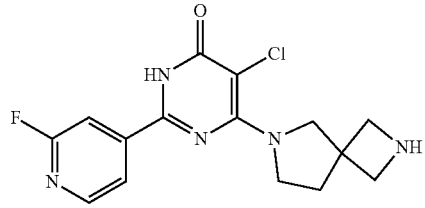·[F₃CCO₂H] | MI 335.98<br>¹H NMR (400 MHz, d6-DMSO) δ 12.71-12.97 (m, 1H), 8.49-8.86 (m, 2H), 8.44 (d, J = 5.3 Hz, 1H), 8.02 (d, J = 5.0 Hz, 1H), 7.80 (s, 1H), 4.04 (s, 4H), 3.88-3.96 (m, 2H), 3.85 (t, J = 6.9 Hz, 2H), 2.18 (t, J = 6.9 Hz, 2H). |
| 246 | 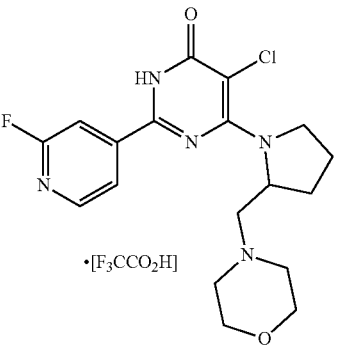 [SMILES: O=c1[nH]c(-c2ccnc(F)c2)nc(N2CCCC2CN2CCOCC2)c1Cl]·[F₃CCO₂H] | MI 394.05<br>¹H NMR (400 MHz, d6-DMSO) δ 12.74-13.18 (m, 1H), 9.36 (br s, 1H), 8.45 (d, J = 5.3 Hz, 1H), 7.98 (d, J = 5.0 Hz, 1H), 7.80 (s, 1H), 5.10 (br s, 1H), 3.95-4.05 (m, 1H), 3.76-3.93 (m, 2H), 3.61-3.75 (m, 3H), 3.43-3.57 (m, 2H), 2.94-3.40 (m, 4H), 1.98-2.20 (m, 2H), 1.81-1.97 (m, 2H). |
| 247 | 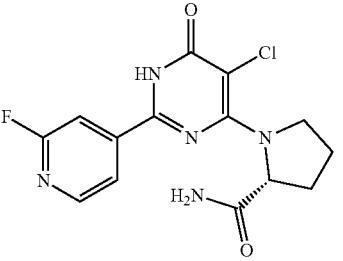 [SMILES: NC(=O)[C@H]1CCCN1c1nc(-c2ccnc(F)c2)[nH]c(=O)c1Cl] | MI 337.96<br>¹H NMR (400 MHz, d6-DMSO) δ 12.18-12.92 (m, 1H), 8.40 (d, J = 5.3 Hz, 1H), 8.04 (d, J = 5.3 Hz, 1H), 7.82 (s, 1H), 7.52 (s, 1H), 6.99 (s, 1H), 4.59-4.74 (m, 1H), 3.90-4.10 (m, 2H), 2.09-2.24 (m, 1H), 1.78-2.04 (m, 3H). |

| No | Product [F6-5] | Characterisation |
|---|---|---|
| 248 | 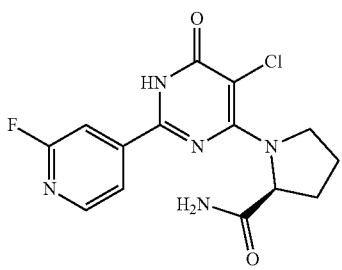 [SMILES: NC(=O)[C@@H]1CCCN1c1nc(-c2ccnc(F)c2)[nH]c(=O)c1Cl] | MI 337.96<br>$^1$H NMR (400 MHz, d6-DMSO) δ 12.09-12.97 (m, 1H), 8.40 (d, J = 5.3 Hz, 1H), 8.04 (d, J = 5.3 Hz, 1H), 7.83 (s, 1H), 7.52 (s, 1H), 7.00 (s, 1H), 4.60-4.72 (m, 1H), 3.88-4.12 (m, 2H), 2.10-2.23 (m, 1H), 1.75-2.03 (m, 3H). |
| 249 | 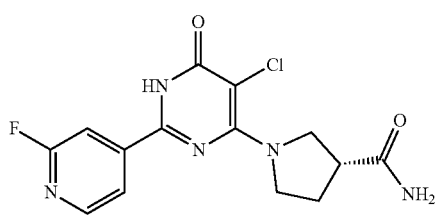 [SMILES: NC(=O)[C@@H]1CCN(c2nc(-c3ccnc(F)c3)[nH]c(=O)c2Cl)C1] | MI 338.00<br>$^1$H NMR (400 MHz, d6-DMSO) δ 12.09-12.95 (m, 1H), 8.42 (d, J = 5.3 Hz, 1H), 8.01 (d, J = 5.3 Hz, 1H), 7.80 (s, 1H), 7.51 (br s, 1H), 7.01 (br s, 1H), 3.75-4.02 (m, 4H), 2.97 (quin, J = 7.5 Hz, 1H), 1.95-2.18 (m, 2H). |
| 250 | 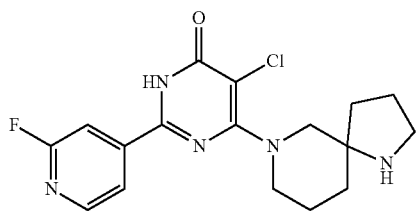 | MI 364.03<br>$^1$H NMR (400 MHz, d6-DMSO) δ 13.11 (br s, 1H), 8.74 (br s, 1H), 8.52 (br s, 1H), 8.46 (d, J = 5.3 Hz, 1H), 8.03 (d, J = 5.0 Hz, 1H), 7.83 (s, 1H), 3.56-3.88 (m, 3H), 3.19-3.52 (m, 3H), 1.69-2.06 (m, 8H). |
| 251 | 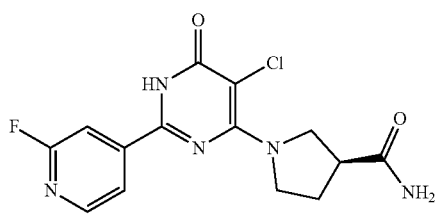 [SMILES: NC(=O)[C@H]1CCN(c2nc(-c3ccnc(F)c3)[nH]c(=O)c2Cl)C1] | MI 337.98<br>$^1$H NMR (400 MHz, d6-DMSO) δ 12.77 (br s, 1H), 8.42 (d, J = 5.3 Hz, 1H), 8.01 (d, J = 5.3 Hz, 1H), 7.80 (s, 1H), 7.51 (br s, 1H), 7.01 (br s, 1H), 3.76-4.03 (m, 4H), 2.97 (quin, J = 7.6 Hz, 1H), 1.93-2.19 (m, 2H). |
| 252 | 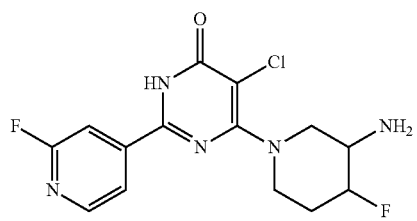 | MI 341.9<br>$^1$H NMR (400 MHz, d6-DMSO) δ 13.06 (br s, 1H), 8.45 (d, J = 5.0 Hz, 1H), 8.37 (br s, 1H), 8.06 (d, J = 5.5 Hz, 1H), 7.85 (s, 1H), 4.70-5.22 (m, 2H), 4.07-4.57 (m, 2H), 3.27-3.75 (m, 3H), 3.00-3.23 (m, 1H), 1.71-2.31 (m, 2H): 1:1 mix of cis and trans diastereomers |
| 253 | 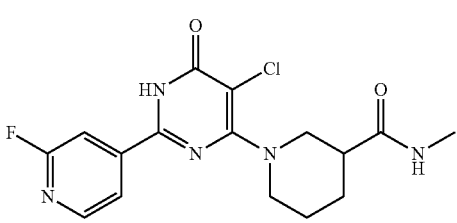 [SMILES: CNC(=O)C1CCCN(c2nc(-c3ccnc(F)c3)[nH]c(=O)c2Cl)C1] | MI 366.02<br>$^1$H NMR (400 MHz, d6-DMSO) δ 12.92 (br s, 1H), 8.43 (d, J = 5.0 Hz, 1H), 8.00 (d, J = 5.0 Hz, 1H), 7.75-7.88 (m, 2H), 4.22-4.35 (m, 2H), 2.92-3.12 (m, 2H), 2.58 (d, J = 4.5 Hz, 3H), 2.38-2.47 (m, 1H), 1.72-1.94 (m, 2H), 1.48-1.72 (m, 2H). |

| No | Product [F6-5] | Characterisation |
|---|---|---|
| 254 | | ¹H NMR (400 MHz, d6-DMSO) δ 12.93 (br s, 1H), 8.44 (d, J = 5.0 Hz, 1H), 8.02 (d, J = 4.8 Hz, 1H), 7.81 (s, 1H), 7.68 (d, J = 7.5 Hz, 1H), 4.25 (d, J = 13.6 Hz, 2H), 3.77-3.90 (m, 1H), 3.15 (t, J = 11.7 Hz, 2H), 2.26-2.38 (m, 1H), 1.78-1.88 (m, 2H), 1.40-1.54 (m, 2H), 0.99 (d, J = 7.0 Hz, 6H). |
| 255 | | MI 394.06<br>¹H NMR (400 MHz, d6-DMSO) δ 12.90 (br s, 1H), 8.43 (d, J = 5.3 Hz, 1H), 8.01 (d, J = 5.0 Hz, 1H), 7.80 (s, 1H), 7.68 (d, J = 7.5 Hz, 1H), 4.35 (d, J = 13.1 Hz, 2H), 3.75-3.87 (m, 1H), 3.02 (t, J = 11.4 Hz, 2H), 2.29-2.42 (m, 1H), 1.56-1.81 (m, 4H), 1.04 (d, J = 6.5 Hz, 6H). |
| 256 | | MI 396.03<br>¹H NMR (400 MHz, d6-DMSO) δ 12.91 (br s, 1H), 8.43 (d, J = 5.0 Hz, 1H), 8.01 (d, J = 5.3 Hz, 1H), 7.75-7.88 (m, 2H), 4.34 (d, J = 13.1 Hz, 2H), 3.82 (br s, 1H), 3.38 (t, J = 6.1 Hz, 2H), 2.96-3.16 (m, 4H), 2.36-2.48 (m, 1H), 1.55-1.85 (m, 4H). |
| 257 | | MI 380.3<br>¹H NMR (400 MHz, d6-DMSO) δ 12.89 (br s, 1H), 8.43 (d, J = 5.3 Hz, 1H), 8.01 (d, J = 5.0 Hz, 1H), 7.75-7.86 (m, 2H), 4.35 (d, J = 13.3 Hz, 2H), 2.96-3.11 (m, 4H), 2.29-2.45 (m, 1H), 1.56-1.82 (m, 4H), 1.00 (t, J = 7.3 Hz, 3H). |
| 258 | •[F₃CCO₂H] | MI 364.03<br>¹H NMR (400 MHz, d6-DMSO) δ 12.98 (br s, 1H), 8.75 (br s, 2H), 8.44 (d, J = 5.3 Hz, 1H), 8.03 (d, J = 5.0 Hz, 1H), 7.82 (s, 1H), 3.44-3.70 (m, 4H), 3.25 (d, J = 2.5 Hz, 2H), 3.13 (d, J = 12.0 Hz, 1H), 2.91-3.00 (m, 1H), 1.87-2.00 (m, 1H), 1.58-1.78 (m, 5H). |
| 259 | •[F₃CCO₂H] | MI 349.99<br>¹H NMR (400 MHz, d6-DMSO) δ 12.87-13.04 (m, 1H), 8.93-9.07 (m, 1H), 8.77-8.92 (m, 1H), 8.42 (s, 1H), 7.77 (br s, 1H), 7.60 (s, 1H), 3.94 (d, J = 9.8 Hz, 2H), 3.82 (br s, 1H), 3.37-3.46 (m, 1H), 3.12 (d, J = 11.0 Hz, 1H), 2.82 (br s, 1H), 2.53-2.58 (m, 1H), 2.05-2.13 (m, 1H), 1.83-2.02 (m, 4H). |

| No | Product [F6-5] | Characterisation |
|---|---|---|
| 260 | 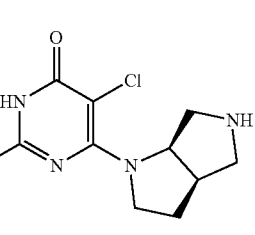 •[F₃CCO₂H] | MI 364.00<br>¹H NMR (400 MHz, d6-DMSO) δ 12.87 (br s, 1H), 8.85 (br s, 1H), 8.47 (d, J = 5.3 Hz, 1H), 8.20 (br s, 1H), 7.89 (br s, 1H), 7.68 (s, 1H), 4.23 (br s, 1H), 4.02-4.11 (m, 1H), 3.71 (br. s, 1H), 3.19 (d, J = 12.3 Hz, 1H), 2.85 (br s, 1H), 2.68-2.76 (m, 1H), 2.34-2.38 (m, 1H), 1.54-2.04 (m, 7H). |
| 261 | 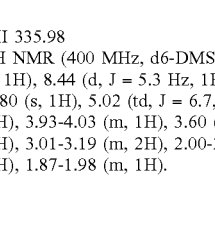 •[F₃CCO₂H] | MI 335.98<br>¹H NMR (400 MHz, d6-DMSO) δ 12.94 (br s, 1H), 8.88 (br s, 1H), 8.44 (d, J = 5.3 Hz, 1H), 8.02 (d, J = 5.3 Hz, 1H), 7.80 (s, 1H), 5.02 (td, J = 6.7, 2.5 Hz, 1H), 4.04-4.19 (m, 1H), 3.93-4.03 (m, 1H), 3.60 (br s, 1H), 3.42 (d, J = 9.3 Hz, 2H), 3.01-3.19 (m, 2H), 2.00-2.16 (m, 1H), 1.87-1.98 (m, 1H), 1.87-1.98 (m, 1H). |
| 262 | 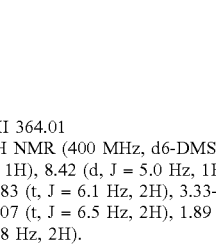 •[F₃CCO₂H] | MI 335.96<br>¹H NMR (400 MHz, d6-DMSO) δ 12.44-13.38 (m, 1H), 9.09 (br s, 1H), 8.73 (br s, 1H), 8.45 (d, J = 5.3 Hz, 1H), 8.04 (d, J = 5.0 Hz, 1H), 7.83 (s, 1H), 5.08 (br s, 2H), 3.26 (d, J = 8.8 Hz, 4H), 1.99-2.14 (m, 4H). |
| 263 | 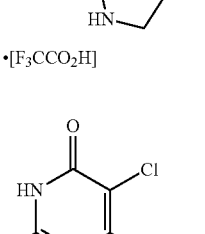 •[F₃CCO₂H] | MI 364.01<br>¹H NMR (400 MHz, d6-DMSO) δ 12.79 (br s, 1H), 8.66 (br s, 1H), 8.42 (d, J = 5.0 Hz, 1H), 7.94 (br s, 2H), 7.72 (s, 1H), 3.83 (t, J = 6.1 Hz, 2H), 3.33-3.38 (m, 2H), 3.05 (br s, 4H), 2.07 (t, J = 6.5 Hz, 2H), 1.89 (t, J = 6.5 Hz, 2H), 1.68 (d, J = 9.8 Hz, 2H). |
| 264 | 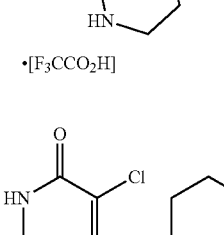 •[F₃CCO₂H] | MI 364.02<br>¹H NMR (400 MHz, d6-DMSO) δ 13.03 (br s, 1H), 8.78-8.94 (m, 1H), 8.59-8.75 (m, 1H), 8.46 (d, J = 5.3 Hz, 1H), 8.03 (d, J = 5.3 Hz, 1H), 7.81 (s, 1H), 4.49-4.60 (m, 1H), 4.00 (d, J = 14.3 Hz, 1H), 3.56-3.68 (m, 1H), 2.92-3.19 (m, 3H), 2.11-2.29 (m, 2H), 1.57-1.95 (m, 6H). |

-continued

| No | Product [F6-5] | Characterisation |
|---|---|---|
| 265 | 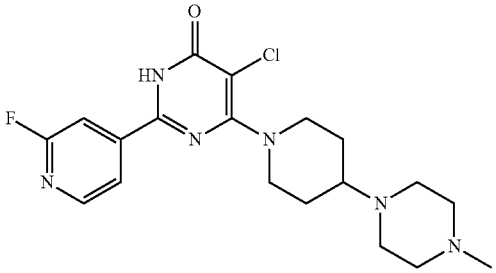 •[F₃CCO₂H] | MI 407<br>¹H NMR (400 MHz, d6-DMSO) δ 12.98 (br s, 1H), 8.44 (d, J = 5.3 Hz, 1H), 8.02 (d, J = 5.3 Hz, 1H), 7.81 (s, 1H), 4.42 (d, J = 12.8 Hz, 2H), 3.16-3.58 (m, 5H), 3.03 (s, 5H), 2.76 (br s, 4H), 1.99 (br s, 2H), 1.57 (d, J = 11.0 Hz, 2H). |
| 266 | 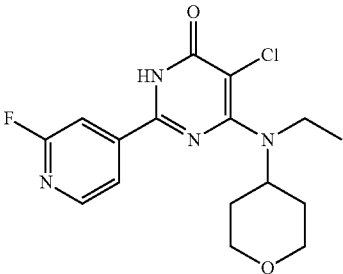 [SMILES: CCN(c1nc(-c2ccnc(F)c2)[nH]c(=O)c1Cl)C1CCOCC1] | MI 353.02<br>¹H NMR (400 MHz, d6-DMSO) δ 12.86 (br s, 1H), 8.44 (d, J = 5.3 Hz, 1H), 7.98 (d, J = 5.0 Hz, 1H), 7.77 (s, 1H), 4.36-4.47 (m, 1H), 3.94 (dd, J = 11.2, 4.1 Hz, 2H), 3.61 (q, J = 6.9 Hz, 2H), 3.40 (t, J = 11.0 Hz, 2H), 1.84-1.99 (m, 2H), 1.64-1.74 (m, 2H), 1.12 (t, J = 6.9 Hz, 3H). |
| 267 | 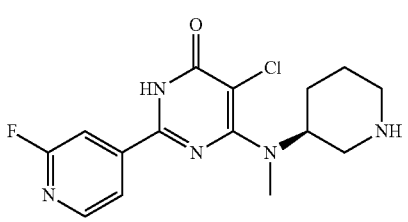 •[F₃CCO₂H] | MI 337.98<br>¹H NMR (400 MHz, d6-DMSO) δ 12.95 (br s, 1H), 8.80 (br s, 1H), 8.70 (br s, 1H), 8.45 (d, J = 5.3 Hz, 1H), 8.06 (d, J = 4.8 Hz, 1H), 7.85 (s, 1H), 4.43-4.59 (m, 1H), 3.22-3.42 (m, 2H), 3.11-3.22 (m, 1H), 3.07 (s, 3H), 2.76-2.93 (m, 1H), 1.83-2.01 (m, 3H), 1.67-1.83 (m, 1H). |
| 268 | 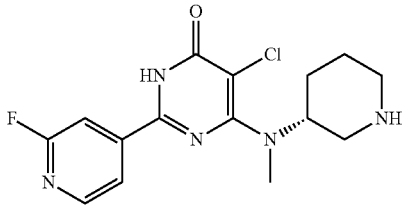 •[F₃CCO₂H] | MI 337.99<br>¹H NMR (400 MHz, d6-DMSO) δ 12.97 (br s, 1H), 8.80 (br s, 1H), 8.70 (br s, 1H), 8.45 (d, J = 5.3 Hz, 1H), 8.06 (d, J = 5.3 Hz, 1H), 7.85 (s, 1H), 4.44-4.57 (m, 1H), 3.23-3.39 (m, 2H), 3.17 (br s, 1H), 3.07 (s, 3H), 2.84 (br s, 1H), 1.83-1.99 (m, 3H), 1.66-1.83 (m, 1H). |
| 269 | 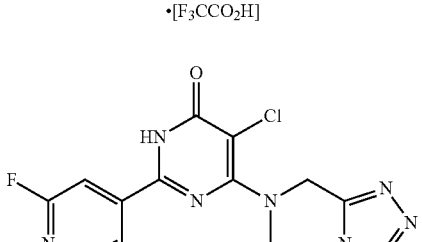 | RT 2.32 min, MI 347, Method (1LCMS12)<br>¹H NMR (600 MHz, d6-DMSO) δ 13.19 (s, 1H), 8.52 (s, 1H), 8.44 (d, 1H), 8.04 (dt, 1H), 7.84 (d, 1H), 5.00 (s, 2H), 4.23 (t, 2H), 4.08 (t, 2H). |

| No | Product [F6-5] | Characterisation |
|---|---|---|
| 270 | (structure) | RT 2.62 min, MI 390, Method (1LCMS12)<br>$^1$H NMR (600 MHz, Methanol-d$_4$) δ 8.36 (d, 1H), 7.96 (d, 1H), 7.73 (s, 1H), 5.06 (s, 2H), 4.21 (s, 4H), 3.15 (p, 1H), 1.37 (d, 6H). |
| 271 | (structure) ·[F$_3$CCO$_2$H] | MI 323.49<br>$^1$H NMR (400 MHz, d6-DMSO) δ 12.90 (br s, 1H), 8.70 (br s, 2H), 8.45 (d, J = 5.3 Hz, 1H), 8.03 (d, J = 5.3 Hz, 1H), 7.82 (s, 1H), 3.96-4.13 (m, 3H), 3.77-3.94 (m, 2H), 2.66 (br s, 3H), 2.24-2.32 (m, 1H), 2.07-2.19 (m, 1H). |
| 272 | (structure) ·[F$_3$CCO$_2$H] | MI 337.49<br>$^1$H NMR (400 MHz, d6-DMSO) δ 12.87 (br s, 1H), 9.86 (br s, 1H), 8.44 (d, J = 5.3 Hz, 1H), 8.05 (d, J = 5.3 Hz, 1H), 7.85 (s, 1H), 3.80-4.24 (m, 5H), 2.88 (s, 6H), 2.34-2.45 (m, 1H), 2.08-2.21 (m, 1H). |
| 273 | (structure) ·[F$_3$CCO$_2$H] | MI 323.49<br>$^1$H NMR (400 MHz, d6-DMSO) δ 12.90 (br s, 1H), 8.45 (d, J = 5.3 Hz, 1H), 8.10 (br s, 2H), 8.02 (d, J = 5.3 Hz, 1H), 7.81 (s, 1H), 3.94-4.14 (m, 3H), 3.74-3.86 (m, 1H), 2.02-2.22 (m, 2H), 1.45 (s, 3H). |
| 274 | (structure) | MI 351.50<br>$^1$H NMR (400 MHz, d6-DMSO) δ 12.82 (br s, 1H), 8.43 (d, J = 5.5 Hz, 1H), 8.14 (d, J = 6.8 Hz, 1H), 8.02 (br s, 1H), 7.80 (s, 1H), 4.20-4.32 (m, 1H), 3.82-4.04 (m, 3H), 3.63-3.70 (m, 1H), 2.01-2.14 (m, 1H), 1.77-1.90 (m, 4H). |
| 275 | (structure) ·[F$_3$CCO$_2$H] | MI 349.51<br>$^1$H NMR (400 MHz, d6-DMSO) δ 13.14 (br s, 1H), 8.88 (br s, 1H), 8.77 (br s, 1H), 8.45 (d, J = 5.3 Hz, 1H), 8.02 (d, J = 5.3 Hz, 1H), 7.80 (s, 1H), 4.66-4.79 (m, 1H), 3.65-3.83 (m, 2H), 3.18-3.33 (m, 3H), 2.14-2.32 (m, 2H), 1.67-2.00 (m, 3H), 1.51-1.63 (m, 1H). |

| No | Product [F6-5] | Characterisation |
|---|---|---|
| 276 | | MI 295.08<br>$^1$H NMR (400 MHz, d6-DMSO) δ 12.73 (br s, 1H), 8.41 (d, J = 5.5 Hz, 1H), 8.01 (d, J = 5.0 Hz, 1H), 7.80 (s, 1H), 3.73-3.86 (m, 4H), 1.82-1.95 (m, 4H). |
| 277 | | MI 309.11<br>$^1$H NMR (400 MHz, d6-DMSO) δ 12.87 (br. s, 1H), 8.43 (d, J = 5.3 Hz, 1H), 8.01 (d, J = 5.3 Hz, 1H), 7.79 (s, 1H), 3.59-3.69 (m, 4H), 1.64 (br. s, 6H). |
| 278 | | MI 309.13<br>$^1$H NMR (400 MHz, d6-DMSO) δ 12.43-13.05 (m, 1H), 8.43 (d, J = 5.0 Hz, 1H), 7.96-8.04 (m, 1H), 7.78 (s, 1H), 4.51-4.70 (m, 1H), 3.92-4.01 (m, 1H), 3.65-3.77 (m, 1H), 1.89-2.15 (m, 2H), 1.73-1.88 (m, 1H), 1.53-1.68 (m, 1H), 1.24 (d, J = 6.0 Hz, 3H). |
| 279 | | MI 309.13<br>$^1$H NMR (400 MHz, d6-DMSO) δ 12.75 (br. s, 1H), 8.43 (d, J = 5.3 Hz, 1H), 8.00 (d, J = 5.0 Hz, 1H), 7.78 (s, 1H), 4.54-4.69 (m, 1H), 3.89-4.04 (m, 1H), 3.66-3.79 (m, 1H), 1.91-2.15 (m, 2H), 1.73-1.89 (m, 1H), 1.54-1.68 (m, 1H), 1.24 (d, J = 6.0 Hz, 3H). |
| 280 | | MI 323.15<br>$^1$H NMR (400 MHz, d6-DMSO) δ 12.86 (br. s, 1H), 8.43 (d, J = 5.3 Hz, 1H), 8.00 (d, J = 5.0 Hz, 1H), 7.78 (s, 1H), 4.52-4.66 (m, 1H), 3.97-4.09 (m, 1H), 3.14-3.25 (m, 1H), 1.48-1.80 (m, 6H), 1.30 (d, J = 6.8 Hz, 3H). |
| 281 | | MI 323.15<br>$^1$H NMR (400 MHz, d6-DMSO) δ 12.86 (br. s, 1H), 8.43 (d, J = 5.3 Hz, 1H), 8.00 (d, J = 5.0 Hz, 1H), 7.78 (s, 1H), 4.50-4.68 (m, 1H), 3.96-4.11 (m, 1H), 3.14-3.26 (m, 1H), 1.47-1.81 (m, 6H), 1.30 (d, J = 6.8 Hz, 3H). |
| 282 | | MI 339.16<br>$^1$H NMR (400 MHz, d6-DMSO) δ 12.90 (br. s, 1H), 8.43 (d, J = 5.0 Hz, 1H), 7.97-8.04 (m, 1H), 7.80 (s, 1H), 4.10 (d, J = 11.3 Hz, 1H), 3.81-3.92 (m, 1H), 3.24-3.44 (m, 6H), 1.77-2.05 (m, 2H), 1.41-1.64 (m, 2H). |

| No | Product [F6-5] | Characterisation |
|---|---|---|
| 283 | | MI 339.16<br>$^1$H NMR (400 MHz, d6-DMSO) δ 12.90 (br. s, 1H), 8.43 (d, J = 5.3 Hz, 1H), 8.01 (d, J = 5.3 Hz, 1H), 7.80 (s, 1H), 4.10 (d, J = 11.0 Hz, 1H), 3.86 (dd, J = 13.1, 4.3 Hz, 1H), 3.24-3.42 (m, 6H), 1.76-2.10 (m, 2H), 1.42-1.61 (m, 2H). |
| 284 | | RT 3.10 min, MI 337.73, Method (1LCMS12)<br>$^1$H NMR (600 MHz, d6-DMSO) δ 12.81 (s, 1H), 8.42 (d, 1H), 8.03 (d, 2H), 7.82 (s, 1H), 4.61 (d, 2H), 4.50 (d, 2H), 4.04 (s, 2H), 3.81 (t, 2H), 2.18 (t, 2H). |
| 285 | | RT 2.91 min, MI 417, Method (1LCMS13)<br>$^1$H NMR (600 MHz, d6-DMSO) δ 8.43 (1H, d, J = 5.2 Hz), 8.02 (1H, br d, J = 4.5 Hz), 7.83 (1H, s), 7.31-7.28 (2H, m), 6.98-6.93 (3H, m), 4.37 (1H, d, J = 13.1 Hz), 4.21 (1H, d, J = 13.0 Hz), 4.09 (2H, d, J = 5.5 Hz), 3.97-3.95 (1H, br m), 3.93-3.90 (1H, br m), 3.68-3.63 (1H, m), 3.24-3.19 (1H, m), 3.12-3.08 (1H, m). |
| 286 | | RT 3.61 min, MI 361.72, Method (1LCMS12)<br>$^1$H NMR (500 MHz, d6-DMSO) δ 13.09 (s, 1H), 8.43 (d, 1H), 8.01 (d, 1H), 7.81 (s, 1H), 4.48 (t, 2H), 3.86-4.04 (m, 6H). |
| 287 | | RT 2.45 min, MI 333.65, Method (1LCMS12)<br>$^1$H NMR (600 MHz, d6-DMSO) δ 8.40 (d, J = 5.2 Hz, 1H), 7.75 (d, J = 5.2 Hz, 1H), 7.52 (s, 1H), 7.18 (d, J = 8.0 Hz, 2H), 7.02 (m, 2H). |
| 288 | | RT 2.48 min, MI 338.75, Method (1LCMS12)<br>$^1$H NMR (600 MHz, d6-DMSO) δ 13.02 (br s, 1H), 8.44 (d, J = 5.1 Hz, 1H), 8.03 (d, J = 4.9 Hz, 1H), 7.82 (s, 1H), 7.66 (t, J = 5.6 Hz, 1H), 3.84-3.75 (m, 4H), 3.32 (dd, J = 5.5 and 8.9 Hz, 2H), 2.69 (t, J = 5.5 Hz, 2H). |
| 289 | | RT 4.28 min, MI 345.73, Method (1LCMS12)<br>$^1$H NMR (600 MHz, d6-DMSO) δ 12.93 (br s, 1H), 8.40 (d, J = 5.2 Hz, 1H), 7.97 (d, J = 4.6 Hz, 1H), 7.74 (s, 1H), 7.36 (t, J = 7.5 Hz, 2H), 7.32 (d, J = 7.1 Hz, 2H), 7.27 (t, J = 7.5 Hz, 1H), 4.91 (s, 2H), 3.19 (s, 3H). |

-continued

| No | Product [F6-5] | Characterisation |
|---|---|---|
| 290 | 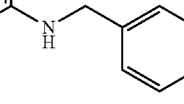 | RT 3.88 min, MI 331.70, Method (1LCMS12)<br>$^1$H NMR (600 MHz, d6-DMSO) δ 12.81 (br s, 1H), 8.40 (d, J = 5.5 Hz, 1H), 7.96 (d, J = 4.8 Hz, 1H), 7.84 (br s, 1H), 7.72 (s, 1H), 7.36 (d, J = 7.3 Hz, 2H), 7.31 (t, J = 7.3 Hz, 2H), 7.22 (t, J = 7.3 Hz, 1H), 4.70 (d, J = 6.6 Hz, 2H). |
| 291 |  | RT 3.19 min, MI 416.7, Method (1LCMS12)<br>$^1$H NMR (500 MHz, d6-DMSO) δ 13.20 (s, 1H), 8.43 (d, 1H), 8.02 (d, 1H), 7.83 (s, 1H), 5.09 (s, 2H), 4.32 (t, 2H), 4.15 (t, 2H). |
| 292 | 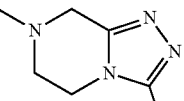 | RT 3.30 min, MI 381.8, Method (1LCMS12)<br>$^1$H NMR (600 MHz, d6-DMSO) δ 12.98 (s, 1H), 8.44 (d, 1H), 8.02 (d, 1H), 7.82 (s, 1H), 3.78 (t, 2H), 3.68 (t, 2H), 3.53-3.64 (m, 6H), 1.74 (d, 2H), 1.57-1.65 (m, 2H). |
| 293 | 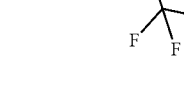<br>•[F$_3$CCO$_2$H] | RT 1.85 min, MI 350.8, Method (1LCMS12)<br>$^1$H NMR (500 MHz, d6-DMSO) δ 8.43 (d, 1H), 8.02 (dt, 1H), 7.82 (d, 1H), 4.71-4.79 (m, 1H), 4.04 (t, 2H), 3.47 (t, 2H), 3.35-3.44 (m, 2H), 3.25-3.35 (m, 2H), 2.16-2.27 (m, 2H), 2.04-2.16 (m, 2H). |
| 294 | 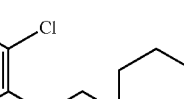 | RT 4.43 min, MI 332.68, Method (1LCMS12)<br>$^1$H NMR (600 MHz, d6-DMSO) δ 8.45 (d, J = 5.5 Hz, 1H), 8.10 (d, J = 5.5 Hz, 1H), 7.87 (s, 1H), 7.50 (d, J = 7.7 Hz, 2H), 7.41 (t, J = 7.7 Hz, 2H), 7.35 (t, J = 7.7 Hz, 1H), 5.62 (s, 2H). |
| 295 | 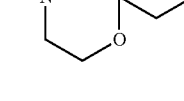 | RT 2.50 min, MI 377.12, Method (1LCMS12)<br>$^1$H NMR (600 MHz, d6-DMSO) δ 8.44 (d, J = 5.6 Hz, 1H), 8.21 (s, 1H), 8.05 (d, J = 5.6 Hz, 1H), 7.83 (s, 1H), 7.51 (s, 1H), 3.77 (t, J = 4.5 Hz, 4H), 3.46 (m, 2H), 3.42 (m, 2H). |

| No | Product [F6-5] | Characterisation |
|---|---|---|
| 296 | 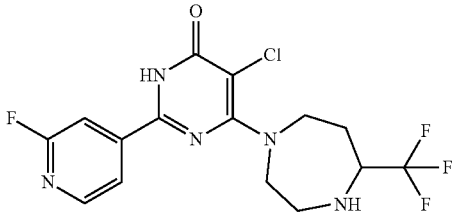 [SMILES: O=c1[nH]c(-c2ccnc(F)c2)nc(N2CCNC(C(F)(F)F)CC2)c1Cl] | RT 2.09 min, MI 392, Method (1LCMS13)<br>¹H NMR (600 MHz, d6-DMSO) δ 12.80 (1H, br s), 8.44 (1H, d, J = 5.2 Hz), 7.99 (1H, d, J = 5.2 Hz), 7.78 (1H, s), 4.14-4.09 (1H, m), 4.04-4.00 (1H, m), 3.93-3.89 (1H, m), 3.80-3.75 (1H, m), 3.39 (1H, br s), 3.09-3.05 (1H, m), 2.83-2.81 (1H, m), 2.18-2.13 (1H, m), 1.82-1.76 (1H, m). |
| 297 | 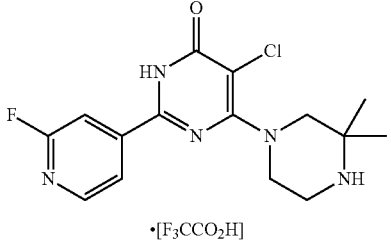 [SMILES: CC1(C)CN(c2nc(-c3ccnc(F)c3)[nH]c(=O)c2Cl)CCN1] | RT 1.89 min, MI 338.35, Method (1LCMS12)<br>¹H NMR (600 MHz, d6-DMSO) δ 13.17 (brs, 1H), 9.15 (br s, 2H), 8.45 (d, J = 5.5 Hz, 1H), 8.05 (d, J = 5.5 Hz, 1H), 7.85 (s, 1H), 3.82 (m, 2H), 3.70 (m, 2H), 3.30 (m, 2H), 1.37 (s, 6H). |
| 298 | 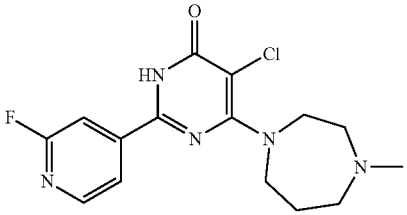 | RT 1.85 min, MI 338.21, Method (1LCMS12)<br>¹H NMR (600 MHz, d6-DMSO) δ 13.00 (br s, 1H), 9.68 (br s, 1H), 8.45 (d, J = 5.1 Hz, 1H), 8.02 (d, J = 4.7 Hz, 1H), 7.82 (s, 1H), 4.24 (dd, J = 4.6 and 16.0 Hz, 1H), 3.97 (dt, J = 4.3 and 13.5 Hz, 1H), 3.83-3.71 (m, 2H), 3.66 (dm, J = 13.4 Hz, 1H), 3.47 (dm, J = 13.5 Hz, 1H), 3.39 (m, 1H), 3.24 (m, 1H), 2.84 (d, J = 3.5 Hz, 3H), 2.19 (m, 2H). |
| 299 | 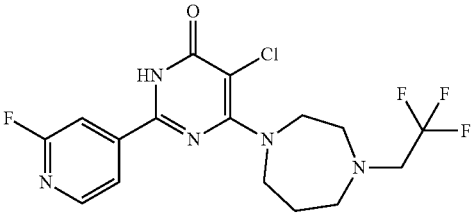 | RT 4.11 min, MI 406.38, Method (1LCMS12)<br>¹H NMR (600 MHz, d6-DMSO) δ 12.87 (br s, 1H), 8.43 (d, J = 5.1 Hz, 1H), 8.00 (d, J = 4.9 Hz, 1H), 7.79 (s, 1H), 7.09 (br s, 1H), 3.90 (t, J = 5.3 Hz, 2H), 3.85 (t, J = 6.0 Hz, 2H), 3.46 (m, 2H), 3.11 (m, 2H), 2.92 (m, 2H), 1.94 (m, 2H). |
| 300 | 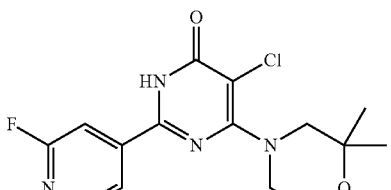 | RT 3.59 min, MI 339.13, Method (1LCMS12)<br>¹H NMR (600 MHz, d6-DMSO) δ 12.97 (br s, 1H), 8.41 (d, J = 51 Hz, 1H), 8.03 (d, J = 4.6 Hz, 1H), 7.80 (s, 1H), 3.75 (t, 4.9 Hz, 2H), 3.58 (m, 2H), 3.48 (m, 2H), 1.21 (s, 6H). |
| 301 | 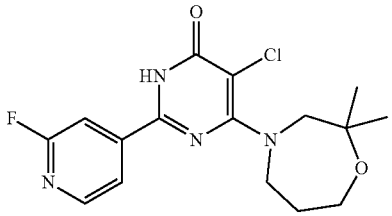 [SMILES: CC1(C)CN(c2nc(-c3ccnc(F)c3)[nH]c(=O)c2Cl)CCCO1] | RT 3.53 min, MI 353.11, Method (1LCMS12)<br>¹H NMR (600 MHz, d6-DMSO) δ 12.85 (br s, 1H), 8.43 (d, J = 5.1 Hz, 1H), 8.01 (d, J = 4.5 Hz, 1H), 7.81 (s, 1H), 4.03 (m, 2H), 3.73 (m, 4H), 1.93 (m, 2H), 1.05 (s, 6H). |

-continued

| No | Product [F6-5] | Characterisation |
|---|---|---|
| 302 | | RT 1.96 min, MI 352.39, Method (1LCMS12)<br>$^1$H NMR (600 MHz, d6-DMSO) δ 8.42 (d, J = 5.0 Hz, 1H), 7.99 (d, J = 5.0 Hz, 1H), 7.76 (s, 1H), 4.77 (tt, J = 5.8 and 12.1 Hz, 2H), 4.22 (dm, J = 15.2 Hz, 1H), 2.95 (dd, J = 5.5 and 14.4 Hz, 1H), 2.78 (dm, J = 12.1 Hz, 1H), 2.61 (m, 1H), 2.34 (s, 3H), 2.13-2.03 (m, 2H), 1.74 (m, 1H), 1.18 (d, J = 6.4 Hz, 3H). |
| 303 | | RT 1.90 min, MI 338.26, Method (1LCMS12)<br>$^1$H NMR (600 MHz, d6-DMSO) δ 8.39 (d, J = 5.2 Hz, 1H), 7.99 (d, J = 5.0 Hz, 1H), 7.76 (s, 1H), 4.07-3.97 (m, 2H), 3.87 (ddd, J = 3.0, 9.1 and 14.6 Hz, 1H), 3.67 (ddd, J = 3.7, 9.6 and 13.9 Hz, 1H), 3.47 (dt, J = 3.6 and 13.9 Hz, 1H), 3.44-3.37 (m, 2H, partially obscured by water), 2.10-1.96 (m, 2H), 1.25 (d, J = 6.6 Hz, 3H). |
| 304 | •[F$_3$CCO$_2$H] | RT 1.94 min, MI 356.2, Method (1LCMS12)<br>$^1$H NMR (600 MHz, d6-DMS0) δ 8.45 (d, 1H), 8.03 (d, 1H), 7.83 (s, 1H), 4.84 (t, 1H), 4.20-4.30 (m, 1H), 3.75-3.89 (m, 2H), 3.44-3.61 (m, 4H), 1.47 (d, 3H). |
| 305 | | RT 9.97 min, MI 326.04, Method (1LCMS1)<br>$^1$H NMR (600 MHz, d6-DMS0) δ 13.39 (br s, 1H), 8.44 (d, J = 5.2 Hz, 1H), 8.06 (d, J = 5.1 Hz, 1H), 7.83 (s, 1H), 5.45 (m, 1H), 3.86 (dt, J = 4.3 and 10.2 Hz, 2H), 3.58 (dt, J = 2.2 and 10.5 Hz, 2H), 2.05 (m, 2H), 1.71 (ddd, J = 3.8, 8.5 and 21.3 Hz, 2H). |
| 306 | | RT 1.92 min, MI 349, Method (1LCMS12)<br>$^1$H NMR (600 MHz, d6-DMSO) δ 8.44 (d, J = 5.2 Hz, 1H), 8.05 (d, J = 5.3 Hz, 1H), 7.84 (s, 1H), 4.34 (d, J = 13.4 Hz, 1H), 4.24 (d, J = 13.9 Hz, 1H), 3.51 (brs, 1H), 3.31-3.13 (m, 3H), 3.04 (br s, 1H), 2.93 (br s, 2H). |
| 307 | •[F$_3$CCO$_2$H] | RT 1.96 min, MI 356/358, Method (1LCMS1)<br>$^1$H NMR (400 MHz, d6-DMSO) δ 8.84 (2H, d), 8.32 (2H, d), 4.77 (1H, d), 4.61 (1H, d), 4.14 (1H, m), 3.56 (1H, d), 3.42 (3H, m), 1.87 (3H, t). |

| No | Product [F6-5] | Characterisation |
|---|---|---|
| 308 | 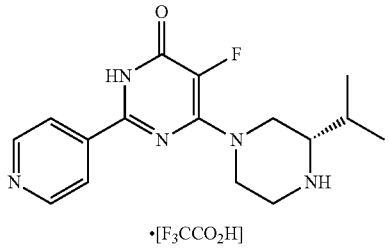 [SMILES: CC(C)[C@H]1CN(c2nc(-c3ccncc3)[nH]c(=O)c2F)CCN1] •[F₃CCO₂H] | RT 1.08 min, MI 318, Method (1LCMS1)<br>¹H NMR (400 MHz, d6-DMSO) δ 8.82 (2H, d), 8.30 (2H, d), 4.75 (1H, d), 4.68 (1H, d), 3.42 (2H, m), 3.30 (1H, m), 3.21 (2H, m), 2.0 (1H, m), 1.15 (6H, d). |
| 309 | 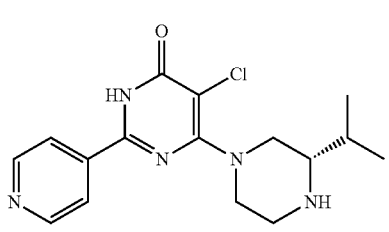 •HCl | RT 1.71 min, MI 334/336, Method (1LCMS1) |
| 310 | 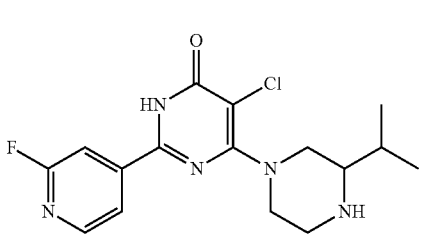 •HCl | RT 1.98 min, MI 352/354, Method (5LCMS1)<br>¹H NMR (400 MHz, d6-DMSO) δ 13.18 (s, 1H), 9.13 (s, 1H), 8.98 (s, 1H), 8.47 (d, J = 5.3 Hz, 1H), 8.03 (dd, J = 5.1, 1.8 Hz, 1H), 7.83 (d, J = 1.4 Hz, 1H), 4.44 (dd, J = 31.4, 12.7 Hz, 2H), 3.49-3.30 (m, 2H), 3.21-3.07 (m, 3H), 1.94 (dt, J = 12.0, 6.0 Hz, 1H), 1.05 (dd, J = 10.2, 6.8 Hz, 6H). |
| 311 | 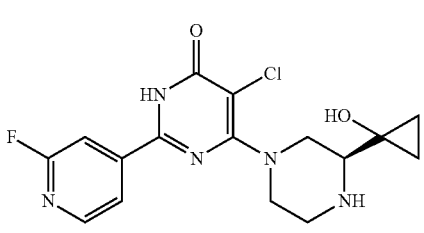 •[F₃CCO₂H] | RT 1.77 min, MI 366.19, Method (1LCMS12)<br>¹H NMR (600 MHz, d6-DMSO) δ 13.20 (br s, 1H), 9.23 (br s, 1H), 8.91 (br s, 1H), 8.47 (d, J = 5.0 Hz, 1H), 8.02 (d, J = 4.9 Hz, 1H), 7.81 (s, 1H), 6.14 (s, 1H), 4.41 (d, J = 13.8 Hz, 2H), 3.44-3.27 (m, 3H, partially obscured by water), 3.15 (m, 1H), 2.92 (t, J = 9.0 Hz, 1H), 0.86-0.77 (m, 2H), 0.77-0.67 (m, 2H). |

In one approach (Scheme 7), compounds of general formula [F7-3] were prepared by the reaction of a 4,5,6-trihalo-2-pyridin-4-yl-pyrimidine derivative of general formula [F7-1] in a nucleophilic aromatic substitution type reaction utilising a suitable amine, thiol or alcohol of general formula [F7-2], and a base such as Et₃N or NaH in a polar solvent such as ethanol, 1,4-dioxane, DMA or DMF at high temperature either by heating thermally or using a microwave reactor. Alternatively, a base such as nBuLi can be used in a polar solvent such as THF at low temperatures. After reaction work up, typically by a liquid-liquid extraction, the reaction product was used crude in the next step or purified by flash column chromatography, reverse phase preparative HPLC or re-crystallisation. 5-Halo-(2-pyridin-4-y)-3H-pyrimidin-4-one derivatives of general formula [F7-4] were prepared by a hydrolysis reaction of 4,5-halo-2-(pyridin-4-yl)-pyrimidine derivatives of general formula [F7-3] with an aqueous base such as NaOH or KOH at high temperature either by heating thermally or using a microwave reactor. After reaction work up, typically by a liquid-liquid extraction or purification by acidic ion exchange catch-release the crude product was purified by flash column chromatography, reverse phase preparative HPLC or re-crystallisation. In cases where the substituent R² or R³ contained an amine protected by a standard amine protecting group such as a tert-butyloxycarbonyl (Boc), compounds of formula [F7-4] are prepared by a suitable deprotection reaction, for example reaction with an acid such as TFA in a suitable solvent such as DCM at ambient temperature, as exemplified in Scheme 1. After reaction work up, typically by a liquid-liquid extraction or purification by acidic ion exchange catch-release the crude product was purified by flash column chromatography, reverse phase preparative HPLC or re-crystallisation.

Scheme 7

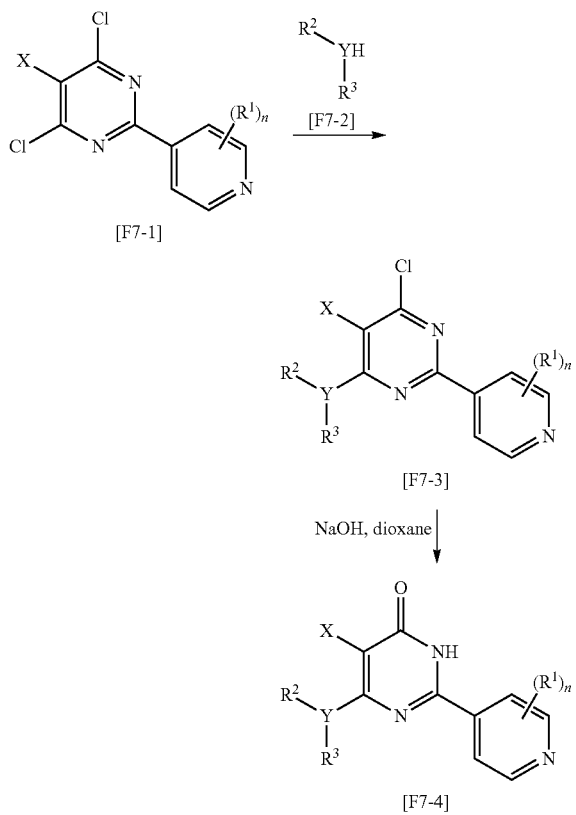

For example, synthesis of 5-chloro-4-(6,6-difluoro-1,4-diazepan-1-yl)-2-(2-fluoro-4-pyridyl)-1H-pyrimidin-6-one hydrochloride (312)

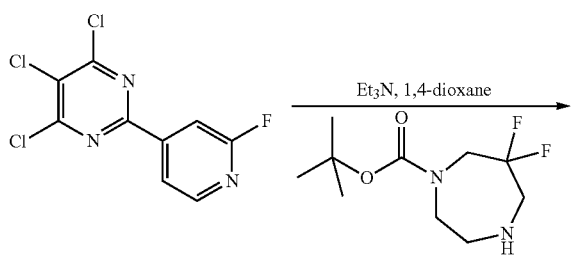

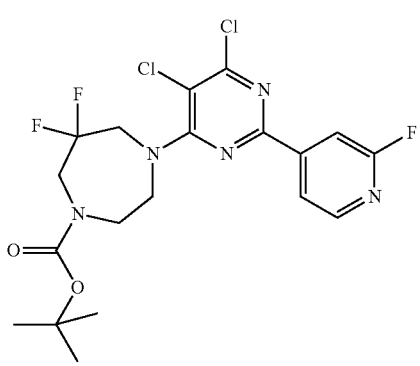

Synthesis of tert-butyl 4-[5,6-dichloro-2-(2-fluoro-4-pyridyl)pyrimidin-4-yl]-6,6-difluoro-1,4-diazepane-1-carboxylate (7-001)

tert-Butyl 6,6-difluoro-1,4-diazepane-1-carboxylate (4.84 g, 20.47 mmol), 4,5,6-trichloro-2-(2-fluoro-4-pyridyl)pyrimidine (4-005, prepared in Scheme 4) (4.75 g, 17.06 mmol) and triethylamine (3.57 mL, 25.58 mmol) were combined in 1,4-dioxane (50 mL) and the mixture was heated to reflux for 3 hours. The reaction mixture was evaporated under reduced pressure and the residue adsorbed onto silica gel then purified by flash chromatography on silica gel (eluting with cyclohexane to 30% ethyl acetate in cyclohexane) to give the title compound as a white solid (6.5 g, 80% yield). LCMS: RT 5.89 min, MI 478, Method (4LCMS1); $^1$H NMR (400 MHz, CDCl$_3$) δ 8.37-8.31 (m, 1H), 8.05 (dt, J=5.2, 1.6 Hz, 1H), 7.79 (s, 1H), 4.46 (t, J=12.1 Hz, 2H), 4.01-3.76 (m, 6H), 1.49 (s, 9H).

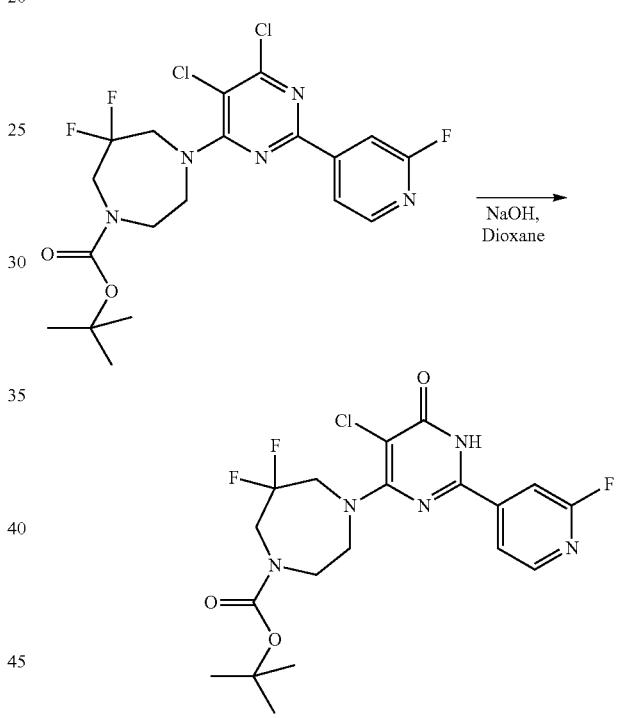

Synthesis of tert-butyl 4-[5-chloro-2-(2-fluoro-4-pyridyl)-6-oxo-1H-pyrimidin-4-yl]-6,6-difluoro-1,4-diazepane-1-carboxylate (7-002)

To a solution of tert-butyl 4-[5,6-dichloro-2-(2-fluoro-4-pyridyl)pyrimidin-4-yl]-6,6-difluoro-1,4-diazepane-1-carboxylate (7-001) (8.34 g, 17.43 mmol) in 1,4-dioxane (100 mL) was added 2 M aqueous NaOH solution (104.6 mL, 209.2 mmol). The reaction mixture was heated to reflux for 90 minutes before allowing to cool to room temperature. 2 M HCl solution was added until a pH 8 was obtained and the mixture was then extracted with DCM/IPA (4/1) (4×50 mL). The combined organic phase was dried (MgSO$_4$), filtered and concentrated under reduced pressure. The residue was purified by flash chromatography on silica gel (eluting with cyclohexane to 50% ethyl acetate in cyclohexane) to afford a white solid. The solid was then triturated with ether and collected by filtration to give the title compound as a white solid (2.9 g, 36.2% yield). LCMS: RT 4.41 min, MI 460, Method (4LCMS1); ¹H NMR (400 MHz, d6-DMSO) δ 12.89 (br s, 1H), 8.44 (d, J=5.2 Hz, 1H), 8.02 (d, J=5.2 Hz, 1H), 7.82 (s, 1H), 4.40 (t, J=12.5 Hz, 2H), 3.99-3.67 (m, 6H), 1.37 (s, 9H).

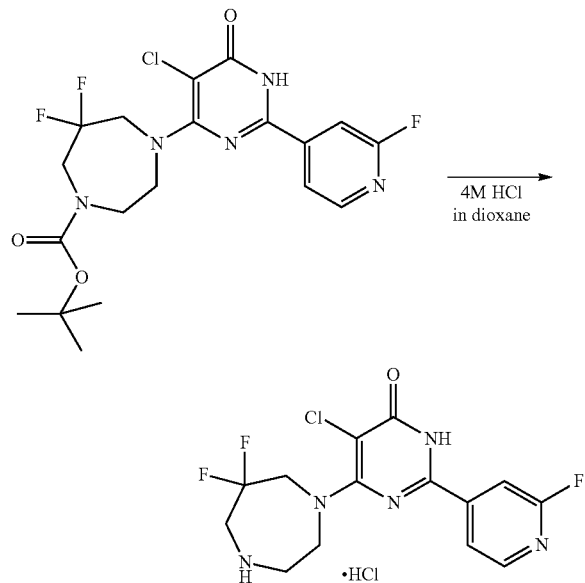 [SMILES: CC(C)(C)OC(=O)N1CCN(c2nc(-c3ccnc(F)c3)[nH]c(=O)c2Cl)CC(F)(F)C1 ; O=c1[nH]c(-c2ccnc(F)c2)nc(N2CCNCC(F)(F)C2)c1Cl ; Cl]

Synthesis of 5-chloro-4-(6,6-difluoro-1,4-diazepan-1-yl)-2-(2-fluoro-4-pyridyl)-1H-pyrimidin-6-one hydrochloride (312)

tert-Butyl 4-[5-chloro-2-(2-fluoro-4-pyridyl)-6-oxo-1H-pyrimidin-4-yl]-6,6-difluoro-1,4-diazepane-1-carboxylate (7-002) (3.4 g, 7.39 mmol) was stirred at room temperature in a 4 M solution of HCl in 1,4-dioxane (36.97 mL, 147.9 mmol) for 4 hours. The resulting white precipitate was collected by filtration and washed with ether. The solid was then transferred to a round bottomed flask and evaporated under reduced pressure. The solid was triturated with ether then dried under vacuum at 40° C. to give the title compound as a white solid (2.9 g, 98.9% yield). LCMS: RT 1.84 min, MI 360, Method (4LCMS1); ¹H NMR (400 MHz, d6-DMSO) δ 9.90 (br s, 2H), 8.46 (d, J=5.2 Hz, 1H), 8.04 (dt, J=5.3, 1.6 Hz, 1H), 7.85 (d, J=1.4 Hz, 1H), 4.59 (t, J=13.2 Hz, 2H), 4.11 (t, J=5.2 Hz, 2H), 3.78 (t, J=12.8 Hz, 2H), 3.49 (t, J=5.3 Hz, 2H).

For example, synthesis of 5-chloro-2-(2-fluoro-4-pyridyl)-4-[2-(trifluoromethyl)piperazin-1-yl]-1H-pyrimidin-6-one hydrochloride (313)

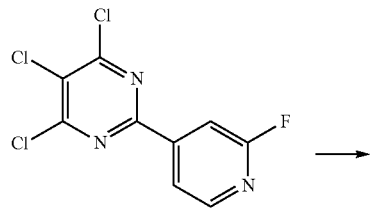

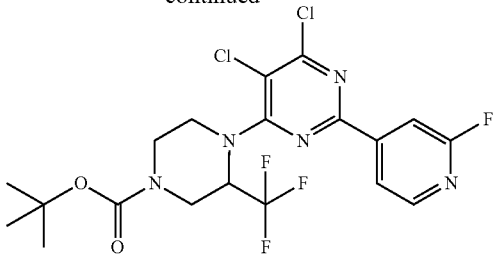

Synthesis of tert-butyl 4-[5,6-dichloro-2-(2-fluoro-4-pyridyl)pyrimidin-4-yl]-3-(trifluoromethyl)piperazine-1-carboxylate (7-003)

A solution of tert-butyl 3-(trifluoromethyl)piperazine-1-carboxylate (2.74 g, 10.7 mmol) in THF (40 mL) was prepared and cooled to −78° C. n-Butyllithium (4.45 mL of a 2.5 M solution in hexane, 11.1 mmol) was added drop-wise and the reaction mixture stirred at −78° C. for 5 min, 0° C. for 10 min then cooled back to −78° C. A solution of 4,5,6-trichloro-2-(2-fluoro-4-pyridyl)pyrimidine (4-005, prepared in Scheme 4) (2.00 g, 7.18 mmol) in THF (20 mL) was prepared and cooled to −78° C. then added to the solution of tert-butyl 3-(trifluoromethyl)piperazine-1-carboxylate and n-Butyllithium. The reaction mixture was allowed to warm to room temperature and stirred overnight (dry-ice/acetone bath removed after 1 h). The reaction mixture was quenched with water (50 mL) and diluted with EtOAc (100 mL). The organic phase was separated and washed with water (50 mL) and brine (50 mL). The organic phase was dried over Na₂SO₄, filtered and concentrated by rotary evaporation. The residue was purified by column chromatography on silica gel, eluting with cyclohexane containing 0-15% EtOAc. The appropriate fractions were combined and concentrated to give the title compound (2.42 g, 68% yield) as an off-white solid. LCMS: RT 6.06 min, MI 496/498, Method (4LCMS1); ¹H NMR (400 MHz, CDCl₃) δ 8.36 (br d, J=5.2 Hz, 1H), 8.05 (br dt, J=5.3, 1.6 Hz, 1H), 7.79 (s, 1H), 5.25 (br s, 1H), 4.63-4.59 (br m, 1H), 4.37-4.15 (br m, 1H), 3.99 (br d, J=13.2 Hz, 1H), 3.77 (t, J=13.0 Hz, 1H), 3.46-3.34 (br m, 1H), 3.09-2.95 (br m, 1H), 1.50 (s, 9H).

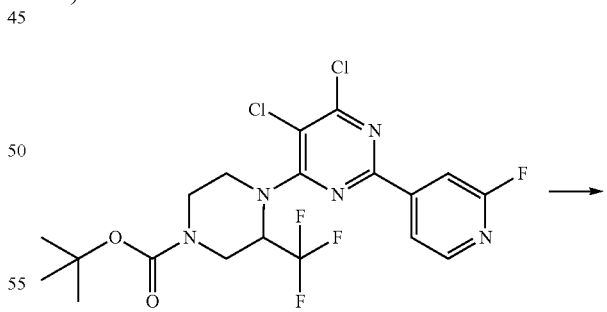

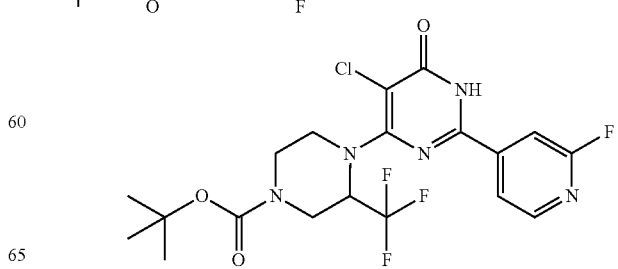

Synthesis of tert-butyl 4-[5-chloro-2-(2-fluoro-4-pyridyl)-6-oxo-1H-pyrimidin-4-yl]-3-(trifluoromethyl)piperazine-1-carboxylate (7-004)

To a solution of tert-butyl 4-[5,6-dichloro-2-(2-fluoro-4-pyridyl)pyrimidin-4-yl]-3-(trifluoromethyl)piperazine-1-carboxylate (7-003) (2.42 g, 4.87 mmol) in 1,4-dioxane (50 mL) was added NaOH (29.2 mL of a 2 M aq solution, 58.4 mmol). The reaction mixture was refluxed for 1 h. The reaction mixture was cooled to room temperature and the mixture adjusted to approx. pH 10 by addition of 2 M HCl. The resulting solution was extracted with $CH_2Cl_2$:iso-propanol (9:1, 4×50 mL). The combined organic extracts were dried over $Na_2SO_4$, filtered and concentrated by rotary evaporation. The residue was purified by column chromatography on silica gel eluting with $CH_2Cl_2$ containing 0-10% MeOH. The appropriate fractions were combined and concentrated and the residue was partitioned between saturated disodium citrate (aq) (pH 5) and EtOAc. The organic phase washed again with saturated disodium citrate (aq), dried over $Na_2SO_4$, filtered and concentrated to give the title compound (1.44 g, 58% yield). LCMS: RT 4.64 min, MI 478, Method (4LCMS1); $^1$H NMR (400 MHz, $CDCl_3$) δ 13.88 (br s, 1H), 8.47 (d, J=5.3 Hz, 1H), 8.08 (dt, J=5.3, 1.5 Hz, 1H), 7.87 (s, 1H), 5.22 (br s, 1H), 4.67-4.57 (br m, 1H), 4.37-4.14 (m, 1H), 3.99 (d, J=13.4 Hz, 1H), 3.77 (t, J=12.8 Hz, 1H), 3.42-3.31 (br m, 1H), 3.12-2.92 (br m, 1H), 1.50 (s, 9H).

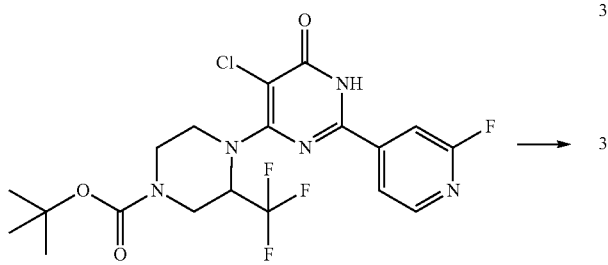

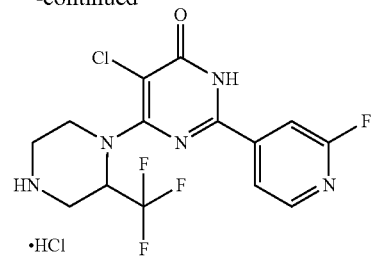

Synthesis of 5-chloro-2-(2-fluoro-4-pyridyl)-4-[2-(trifluoromethyl)piperazin-1-yl]-1H-pyrimidin-6-one hydrochloride (313)

tert-Butyl 4-[5-chloro-2-(2-fluoro-4-pyridyl)-6-oxo-1H-pyrimidin-4-yl]-3-(trifluoromethyl)piperazine-1-carboxylate (7-004) (0.35 g, 0.737 mmol) was stirred in hydrochloric acid (3.68 mL of a 4 M solution in 1,4-dioxane, 14.7 mmol) at room temperature for 4 h. The reaction mixture was concentrated by rotary evaporation and the residue was stored under vacuum overnight. The residue was stirred in hydrochloric acid (3.68 mL of a 4 M solution in 1,4-dioxane, 14.7 mmol) at room temperature for 2 h. The precipitate was filtered and washed with 1,4-dioxane (2 mL) then diethyl ether (10 mL). The precipitate was triturated in diethyl ether, filtered and dried under vacuum for 3 days to give the title compound (0.226 g, 74% yield). LCMS: RT 1.88 min, MI 378, Method (4LCMS1); $^1$H NMR (400 MHz, d6-DMSO) δ 8.46 (d, J=5.2 Hz, 1H), 8.13 (dt, J=5.3, 1.7 Hz, 1H), 7.98 (s, 1H), 5.80-5.71 (m, 1H), 4.11 (d, J=14.6 Hz, 1H), 3.75 (d, J=14.4 Hz, 1H), 3.64 (t, J=13.4 Hz, 1H), 3.47 (dd, J=14.4, 6.2 Hz, 1H), 3.29 (d, J=13.0 Hz, 1H), 3.03 (td, J=12.7, 3.9 Hz, 1H).

The following compounds were synthesised according to the general synthesis shown in scheme [7]:

| No | Product [F7-4] | Characterisation |
|---|---|---|
| 314 | | RT 2.70 min, MI 378, Method (4LCMS1)<br>$^1$H NMR (400 MHz, d6-DMSO) δ 8.45 (d, 1H), 8.00 (d, 1H), 7.79 (s, 1H), 4.25 (d, 1H), 4.05 (d, 1H), 3.62-3.48 (m, 1H), 3.25 (ddd, 2H), 3.00 (d, 1H), 2.82-2.71 (m, 1H). |
| 315 | | RT 2.11 min, MI 373.76, Method (1LCMS1)<br>$^1$H NMR (400 MHz, MeOD) δ 8.42 (1H, d), 7.91 (1H, d), 7.70 (1H, s), 4.62 (1H, d), 4.43 (1H, d), 3.60 (1H, m), 3.21 (1H, m), 2.75 (3H, m), 1.75 (3H, t). |

| No | Product [F7-4] | Characterisation |
|---|---|---|
| 316 | 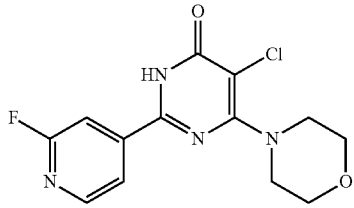 | RT 3.26 min, MI 311.13, Method (5LCMS1)<br>¹H NMR (400 MHz, d6-DMSO) δ 12.97 (s, 1H), 8.44 (s, 1H), 8.03 (s, 1H), 7.82 (s, 1H), 3.81-3.57 (m, 8H). |
| 317 | 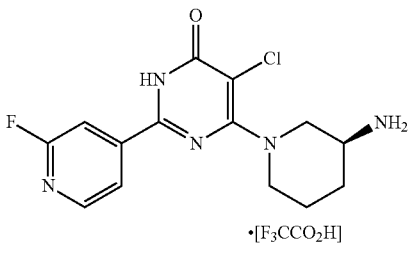 [SMILES: N[C@H]1CCCN(c2nc(-c3ccnc(F)c3)[nH]c(=O)c2Cl)C1]<br>•[F₃CCO₂H] | RT 1.93 min, MI 324, Method (1LCMS13)<br>¹H NMR (600 MHz, d6-DMSO) δ 13.07 (1H, br s), 8.46 (1H, d, J = 5.3 Hz), 8.05 (1H, d, J = 5.1 Hz), 7.98 (2H, br s),<br>7.84 (1H, s), 4.31-4.28 (1H, br m), 4.09-4.06 (1H, br m), 3.35 (1H, br s), 3.19-3.13 (2H, m), 2.04-2.03 (1H, br m), 1.83-1.81 (1H, br m), 1.62-1.56 (2H, br m). |
| 318 | 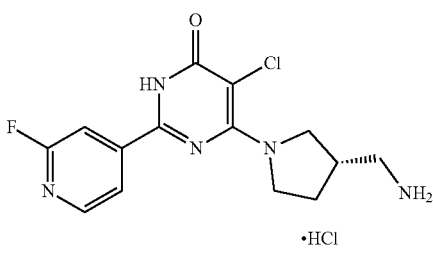 [SMILES: NC[C@@H]1CCN(c2nc(-c3ccnc(F)c3)[nH]c(=O)c2Cl)C1 ; Cl]<br>•HCl | RT 1.84 min, MI 324, Method (4LCMS1)<br>¹H NMR (400 MHz, MeOD) δ 8.37 (1H, m), 7.92 (1H, m), 7.71 (1H, m), 4.16 (2H, m), 3.72 (1H, m), 3.09 (1H, m), 2.55<br>(1H, m), 2.27 (1H, m), 1.78 (1H, m), 1.36 (1H, m), 0.92 (1H,<br>m). |
| 319 | 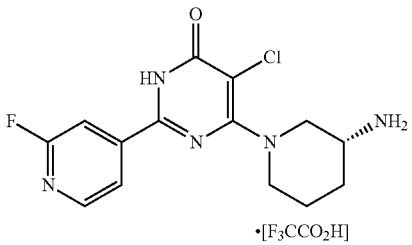 [SMILES: N[C@@H]1CCCN(c2nc(-c3ccnc(F)c3)[nH]c(=O)c2Cl)C1]<br>•[F₃CCO₂H] | RT 1.96 min, MI 324, Method (1LCMS13)<br>¹H NMR (600 MHz, d6-DMSO) δ 13.06 (1H, br s), 8.45 (1H, d, J = 5.3 Hz), 8.05 (1H, d, J = 5.1 Hz), 8.01 (2H, br s),<br>7.84 (1H, s), 4.31-4.29 (1H, br m), 4.09-4.07 (1H, br m), 3.35 (1H, br s), 3.19-3.13 (2H, m), 2.04-2.03 (1H, br m), 1.83-1.81 (1H, br m), 1.63-1.53 (2H, br m). |
| 320 | 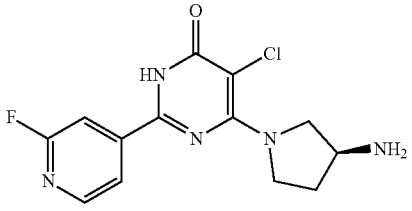<br>•HCl | RT 1.72 min, MI 310, Method (4LCMS1)<br>¹H NMR (400 MHz, d6-DMSO) δ 12.93 (br s, 1H), 8.51 (d, J = 5.2 Hz, 1H), 8.38 (br s, 3H), 8.10-8.05 (m, 1H), 7.86 (s, 1H), 4.17-3.89 (m, 5H), 2.31 (dq, J = 13.9, 7.5 Hz, 1H), 2.13 (tt, J = 12.9, 5.8 Hz, 1H). |
| 321 | 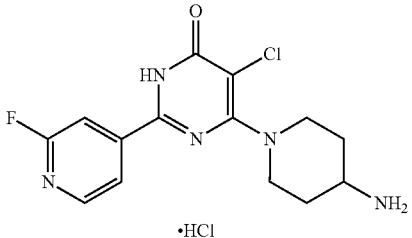 [SMILES: NC1CCN(c2nc(-c3ccnc(F)c3)[nH]c(=O)c2Cl)CC1 ; Cl]<br>•HCl | RT 1.81 min, MI 324, Method (4LCMS1) |

-continued

| No | Product [F7-4] | Characterisation |
|---|---|---|
| 322 | 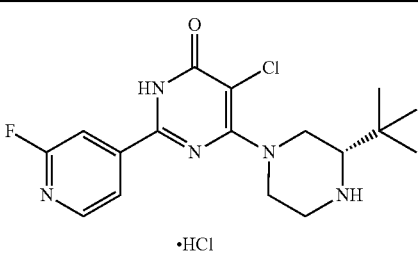·HCl | RT 1.52 min, MI 350, Method (5LCMS1)<br>$^1$H NMR (500 MHz, DMSO-d$_6$) δ 9.01 (br s, 1H), 8.71 (br s,<br>1H), 8.41 (d, J = 5.1 Hz, 1H), 7.98 (d, J = 4.5 Hz, 1H), 7.76<br>(s, 1H), 4.61 (s, 1H), 4.49 (d, J = 14.4 Hz, 1H), 3.30 (d, J = 12.4 Hz, 2H), 3.15 (d, J = 11.1 Hz, 3H), 1.05 (s, 9H). |
| 323 | 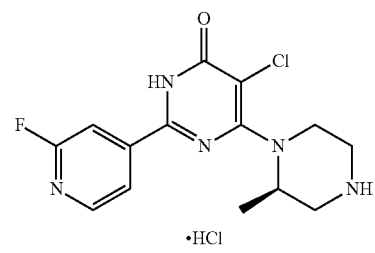 [SMILES: C[C@@H]1CNCCN1c1nc(-c2ccnc(F)c2)[nH]c(=O)c1Cl ; Cl]·HCl | RT 1.71 min, MI 324, Method (5LCMS1)<br>$^1$H NMR (400 MHz, d6-DMSO) δ 13.14 (br s, 1H), 9.67 (br<br>s, 1H), 9.26 (br s, 1H), 8.45 (d, J = 5.2 Hz, 1H), 8.12-7.96 (m, 1H), 7.83 (s, 1H), 4.64 (dt, J = 7.4, 3.5 Hz, 1H), 4.16 (d,<br>J = 14.7 Hz, 1H), 3.49 (ddd, J = 14.7, 11.8, 2.9 Hz, 1H), 3.28 (d, J = 12.4 Hz, 1H), 3.19 (s, 2H), 3.13-3.01 (m, 1H), 1.44 (d, J = 7.0 Hz, 3H). |
| 324 | 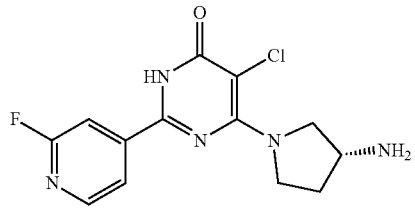·[F$_3$CCO$_2$H] | RT 1.87 min, MI 310, Method (1LCMS13)<br>$^1$H NMR (600 MHz, d6-DMSO) δ 12.92 (s, 1H), 8.45 (m, 1H), 8.05 (br s, 2H), 8.02 (m, 1H), 7.80 (s, 1H), 4.15-3.97 (m, 2H), 3.97-3.86 (m, 2H), 3.34-3.33 (m, 1H, obscured by water), 2.24 (m, 1H), 2.03 (m, 1H). |
| 325 | 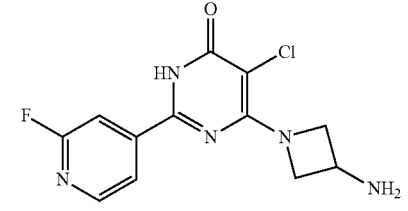·[F$_3$CCO$_2$H] | RT 1.53 min, MI 296, Method (1LCMS13)<br>$^1$H NMR (600 MHz, d6-DMSO) δ 12.88 (br s, 1H), 8.44 (m,<br>1H), 8.31 (br s, 2H), 8.00 (m, 1H), 7.80 (m, 1H), 4.60 (m, 2H), 4.31 (m, 2H), 4.09 (m, 1H). |
| 326 | 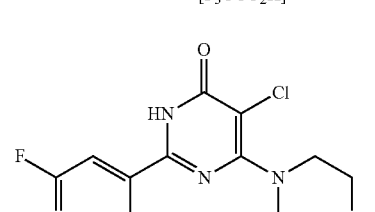·[F$_3$CCO$_2$H] | RT 1.66 min, MI 324, Method (1LCMS13)<br>$^1$H NMR (600 MHz, d6-DMSO) δ 13.21 (br s, 1H), 9.09 (br<br>s, 1H), 8.77 (br s, 1H), 8.45 (m, 1H), 8.04 (m, 1H), 7.83 (m,<br>1H), 4.65 (m, 1H), 4.17 (m, 1H), 3.59-3.04 (m, 5H), 1.40 (d,<br>J = 12 Hz, 3H). |
| 327 | 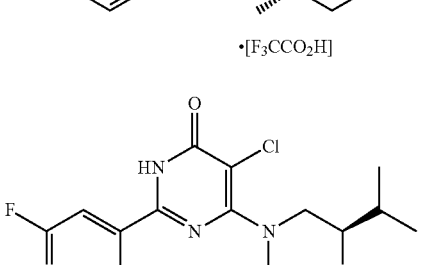·[F$_3$CCO$_2$H] | RT 1.74 min, MI 352, Method (1LCMS13)<br>$^1$H NMR (600 MHz, d6-DMSO) δ 13.21 (br s, 1H), 8.84 (br<br>s, 2H), 8.47 (m, 1H), 8.03 (m, 1H), 7.83 (m, 1H), 4.49 (d,<br>J = 18 Hz, 1H), 4.41 (d, J = 12 Hz, 1H), 3.42-3.31 (m, 2H, partially obscured by water), 3.21-3.16 (m, 2H), 3.09 (m,<br>1H), 1.90 (m, 1H), 1.03 (dd, J = 6 and 12 Hz, 6H). |

-continued

| No | Product [F7-4] | Characterisation |
|---|---|---|
| 328 | | RT 2.59 min, MI 325, Method (1LCMS13)<br>¹H NMR (600 MHz, d6-DMSO) δ 12.98 (br s, 1H), 8.43 (m, 1H), 8.02 (m, 1H), 7.81 (m, 1H), 4.47 (m, 1H), 3.96 (d, J = 12 Hz, 1H), 3.88 (d, J = 12 Hz, 1H), 3.69-3.61 (m, 2H), 3.54 (m, 1H), 3.45 (m, 1H), 1.32 (d, J = 6Hz, 3H). |
| 329 | | RT 1.88 min, MI 325, Method (1LCMS13)<br>¹H NMR (600 MHz, d6-DMSO) δ 13.49 (br s, 1H), 8.58 (br s, 1H), 8.45 (m, 1H), 8.40 (br s, 1H), 8.09 (m, 1H), 7.87 (m, 1H), 5.52 (m, 1H), 3.41-3.28 (m, 6H), 2.18 (m, 1H), 1.94 (m, 1H). |
| 330 | | RT 1.95 min, MI 325, Method (1LCMS13)<br>¹H NMR (600 MHz, d6-DMSO) δ 8.10 (d, J = 6 Hz, 1H), 7.83 (d, J = 6 Hz, 1H), 7.55 (s, 1H), 5.18 (m, 1H), 3.69 (m, 1H), 3.36 (m, 1H, partially obscured by water), 3.19 (m, 1H), 3.06 (m, 1H), 2.04 (m, 1H), 1.95 (m, 1H), 1.87 (m, 1H), 1.76 (m, 1H). |
| 331 | | RT 1.96 min, MI 325, Method (1LCMS13)<br>¹H NMR (600 MHz, d6-DMSO) δ 8.05 (m, 1H), 7.79 (m, 1H), 7.51 (s, 1H), 5.14 (m, 1H), 3.78 (m, 1H), 3.37-3.33 (m, 1H, partially obscured by water), 3.20 (m, 1H), 3.05 (m, 1H), 2.08 (m, 1H), 1.98-1.84 (m, 2H), 1.76 (m, 1H). |
| 332 | | RT 3.03 min, MI 365, Method (1LCMS13)<br>¹H NMR (600 MHz, d6-DMSO) δ 13.37 (br s, 1H), 8.46 (d, J = 6 Hz, 1H), 8.01 (d, J = 6 Hz, 1H), 7.79 (s, 1H), 3.87 (dt, J = 6 and 12 Hz, 1H), 3.73 (td, J = 6 and 12 Hz, 1H), 3.39 (d, J = 12 Hz, 1H), 3.32-3.30 (m, 1H, partially obscured by water), 3.19 (td, J = 2.4 and 10.2 Hz, 1H), 2.87 (td, J = 3 and 12 Hz, 1H), 2.10 (d, J = 12 Hz, 1H), 1.84 (d, J = 12 Hz, 1H), 1.71 (m, 1H), 1.59 (m, 1H), 1.47-1.28 (m, 3H), 0.98 (m, 1H). |
| 333 | | RT 2.44 min, MI 325, Method (1LCMS13)<br>¹H NMR (600 MHz, d6-DMSO) δ 12.97 (br s, 1H), 8.43 (d, J = 5.4 Hz, 1H), 8.02 (d, J = 4.8 Hz, 1H), 7.81 (s, 1H), 4.47 (dd, J = 6 and 12 Hz, 1H), 3.96 (d, J = 12 Hz, 1H), 3.88 (d, J = 12 Hz, 1H), 3.68-3.61 (m, 2H), 3.54 (td, J = 1.8 and 11.4 Hz, 1H), 3.44 (td, J = 3 and 13.8 Hz, 1H), 1.32 (d, J = 6.6 Hz, 3H). |

| No | Product [F7-4] | Characterisation |
|---|---|---|
| 334 | | RT 2.92 min, MI 351, Method (1LCMS13)<br><sup>1</sup>H NMR (600 MHz, d6-DMSO) δ 12.92 (br s, 1H), 8.42 (d, J = 5.4 Hz, 1H), 8.01 (d, J = 4.2 Hz, 1H), 7.80 (s, 1H), 4.50-<br>4.45 (m, 2H), 3.96 (m, 1H), 3.94 (m, 1H), 3.83 (m, 1H), 3.81<br>(m, 1H), 3.31 (m, 1H), 2.0-1.86 (m, 4H), 1.61 (q, J = 6 Hz, 1H). |
| 335 | | RT 3.74 min, MI 339, Method (1LCMS13)<br><sup>1</sup>H NMR (600 MHz, d6-DMSO) δ 12.95 (br s, 1H), 8.43 (d, J = 4.8 Hz, 1H), 8.01 (d, J = 4.8 Hz, 1H), 7.81 (s, 1H), 4.36 (t, J = 7.2 Hz, 1H), 3.94 (d, J = 12.6 Hz, 1H), 3.86 (d, J = 10.8 Hz, 1H), 3.79 (d, J = 12 Hz, 1H), 3.62 (dd, J = 3 and 12<br>Hz, 1H), 3.52-3.41 (m, 2H), 1.82 (m, 2H), 0.85 (t, J = 7.8 Hz, 3H). |
| 336 | | RT 3.72 min, MI 339, Method (1LCMS13)<br><sup>1</sup>H NMR (600 MHz, d6-DMSO) δ 12.95 (br s, 1H), 8.43 (d, J = 4.8 Hz, 1H), 8.01 (d, J = 5.4 Hz, 1H), 7.81 (s, 1H), 4.36 (m, 1H), 3.94 (d, J = 12.6 Hz, 1H), 3.86 (d, J = 10.8 Hz, 1H), 3.79 (d, J = 11.4 Hz, 1H), 3.62 (dd, J = 3 and 12 Hz, 1H), 3.52-3.41 (m, 2H), 1.81 (m, 2H), 0.85 (t, J = 7.8Hz, 3H). |
| 337 | | RT 3.46 min, MI 325, Method (1LCMS12)<br><sup>1</sup>H NMR (600 MHz, d6-DMSO) δ 13.00 (br s, 1H), 8.43 (d, J = 5.4 Hz, 1H), 8.02 (d, J = 4.8 Hz, 1H), 7.81 (s, 1H), 4.19 (m, 2H), 3.88 (dm, J = 11.4 Hz, 1H), 3.65-3.56 (m, 2H), 3.10 (ddd, J = 3, 12 and 13.8 Hz, 1H), 2.80 (dd, J = 10.2 and<br>13.2 Hz, 1H), 1.14 (d, J = 6 Hz, 3H). |
| 338 | | RT 3.23 min, MI 325, Method (1LCMS12)<br><sup>1</sup>H NMR (600 MHz, DMSO-d6) δ 12.88 (br s, 1H), 8.43 (d, J = 5.4 Hz, 1H), 8.00 (d, J = 4.8 Hz, 1H), 7.78 (s, 1H), 3.95 (t, J = 4.8 Hz, 2H), 3.92 (t, J = 6 Hz, 2H), 3.77 (t, J = 5.4 Hz,<br>2H), 3.68 (t, J = 5.4 Hz, 2H), 1.95 (q, J = 5.4 Hz, 2H). |
| 339 | | RT 3.80 min, MI 339, Method (1LCMS12)<br><sup>1</sup>H NMR (600 MHz, DMSO-d6) δ 13.20 (br s, 1H), 8.46 (d, J = 5.65 Hz, 1H), 7.94 (d, J = 4.54 Hz, 1H), 7.75 (s, 1H), 3.75 (t, J = 4.6 Hz, 2H), 3.36 (m, 2H), 3.31 (m, 1H), 3.29 (t,<br>J = 4.37 Hz, 1H), 1.43 (s, 6H). |

| No | Product [F7-4] | Characterisation |
|---|---|---|
| 340 | | RT 3.72 min, MI 339, Method (1LCMS12)<br>$^1$H NMR (600 MHz, DMSO-d6) δ 13.00 (br s, 1H), 8.44 (m,<br>1Hmaj and 1Hmin), 8.00 (m, 1Hmaj and 1Hmin), 7.80 (s,<br>1Hmaj and 1Hmin), 4.47 (m, 1Hmaj), 4.11 (m, 1Hmin), 4.03<br>(d, J = 13.5 Hz, 1Hmaj), 3.89 (dd, J = 3.4 and 11.4 Hz,<br>1Hmin), 3.83 (m, 1Hmaj), 3.67 (m, 1Hmaj and 1Hmin), 3.58<br>(m, 1Hmaj), 3.48 (d, J = 12.9 Hz, 1Hmin), 3.17 (m,<br>1Hmin),<br>3.05 (dd, J = 10.8 and 13.6 Hz, 1Hmaj), 2.93 (m, 1Hmin),<br>1.31 (d, J = 6.8 Hz, 3Hmaj), 1.17 (d, J = 6.3 Hz, 3Hmaj),<br>1.14 (d, J = 6.3 Hz, 3Hmin), 1.10 (d, J = 6.05 Hz, 3Hmin). |
| 341 | | RT 3.79 min, MI 339, Method (1LCMS12)<br>$^1$H NMR (600 MHz, DMSO-d6) δ 13.33 (s, 1H), 8.45 (d,<br>1H), 8.01 (d, 1H), 7.79 (s, 1H), 3.89 (m, 2H), 3.80 (dd,<br>2H),<br>3.43 (dd, 2H), 1.00 (d, 6H). |
| 342 | | RT 3.79 min, MI 339, Method (1LCMS12)<br>$^1$H NMR (600 MHz, DMSO-d6) δ 13.33 (s, 1H), 8.45 (d,<br>1H), 8.01 (d, 1H), 7.79 (s, 1H), 3.86-3.92 (m, 2H), 3.80<br>(dd, 2H), 3.43 (dd, 2H), 1.00 (d, 6H). |
| 343 | | RT 3.71 min, MI 339, Method (1LCMS12)<br>$^1$H NMR (600 MHz, DMSO-d6) δ 13.14 (br s, 1H), 8.44 (d,<br>J = 5.2 Hz, 1H), 8.03 (d, J = 5.2 Hz, 1H), 7.81 (s, 1H),<br>4.23-<br>4.03 (m, 2H), 3.69 (dd, J = 3.6 and 11.4 Hz, 2H), 3.59-3.52<br>(m, 2H), 1.16 (d, J = 5.8 Hz, 6H). |
| 344 | | RT 1.71 min, MI 335.7, Method (1LCMS12) |
| 345 | •[F$_3$CCO$_2$H] | RT 1.73 min, MI 335.7, Method (1LCMS12) |

| No | Product [F7-4] | Characterisation |
|---|---|---|
| 346 | | RT 1.88 min, MI 347.2, Method (1LCMS12)<br>¹H NMR (500 MHz, DMSO-d6) δ 9.09 (d, 1H), 8.44 (d, 1H), 8.04 (dt, 1H), 7.84 (d, 1H), 7.56 (d, 1H), 4.98 (s, 2H), 4.42 (t, 2H), 4.13 (t, 2H). |
| 347 | | RT 3.11 min, MI 386.40, Method (1LCMS12)<br>¹H NMR (600 MHz, DMSO-d6) δ 12.99 (br s, 1H), 8.44 (d, J = 5.1 Hz, 1H), 8.03 (d, J = 5.2 Hz, 1H), 7.82 (s, 1H), 4.40 (dt, J = 12.5 and 2.2 Hz, 1H), 4.33 (dm, J = 12.9 Hz, 1H), 3.43 (tm, J = 12.6 Hz, 1H), 3.33-3.30 (m, 1H, partially obscured by water), 3.13 (td, J = 12.5 and 3.2 Hz, 1H), 3.02 (dm, J = 10.7 Hz, 1H), 2.91 (dd, J = 13.2 and 10.3 Hz, 1H), 2.59 (dt, J = 17.4 and 10.7 Hz, 1H), 2.44-2.33 (m, 2H), 1.98 (m, 1H). |
| 348 | | RT 1.87 min, MI 350.26, Method (1LCMS12)<br>¹H NMR (600 MHz, DMSO-d6) δ 8.42 (d, J = 5.2 Hz, 1H), 8.02 (d, J = 5.3 Hz, 1H), 7.80 (s, 1H), 4.37 (d, J = 12.3 Hz, 1H), 4.28 (d, J = 13.0 Hz, 1H), 3.33-3.29 (m, 1H, partially obscured by water), 3.14-3.00 (m, 2H), 2.82 (t, J = 10.5 Hz, 1H), 2.29 (m, 1H), 2.20-2.00 (m, 2H), 1.83 (m, 1H), 1.79-1.62 (m, 2H), 1.38 (m, 1H). |
| 349 | | RT 2.30 min, MI 406.40, Method (1LCMS12)<br>¹H NMR (600 MHz, DMSO-d6) δ 8.44 (d, J = 4.8 Hz, 1H), 8.00 (d, J = 4.9 Hz, 1H), 7.79 (s, 1H), 4.75 (m, 1H), 4.10 (d, J = 11.7 Hz, 1H), 3.08 (t, J = 11.8 Hz, 1H), 3.04-2.94 (m, 2H), 2.31 (m, 1H), 2.01 (m, 1H), 1.90-1.57 (m, 5H), 1.57-1.44 (m, 2H), 1.39 (m, 1H), 0.87 (d, J = 6.3 Hz, 3H), 0.79 (d, J = 6.3 Hz, 3H). |
| 350 | | RT 2.50 min, MI 374.26, Method (1LCMS12)<br>¹H NMR (600 MHz, DMSO-d6) δ 12.96 (br s, 1H), 8.43 (d, J = 5.0 Hz, 1H), 8.02 (d, J = 4.6 Hz, 1H), 7.81 (s, 1H), 6.19 (tt, J = 4.3 and 55.6 Hz, 3H), 3.69 (t, J = 4.1 Hz, 3H), 2.80 (td, J = 4.5 and 15.6 Hz, 2H), 2.66 (t, J = 4.7 Hz, 3H). |
| 351 | ·[F₃CCO₂H] | RT 1.62 min, MI 338, Method (1LCMS13)<br>¹H NMR (600 MHz, d6-DMSO) δ 12.96 (1H, br s), 8.75 (1H, br s), 8.46 (1H, br s), 8.45 (1H, d, J = 5.1 Hz), 8.01 (1H, d, J = 5.1 Hz), 7.79 (1H, s), 4.78-4.75 (1H, m), 4.39 (1H, d, J = 16.5 Hz), 3.47-3.41 (2H, m), 3.37-3.34 (1H, m (overlapping with water signal), 3.27-3.24 (1H, br m), 3.02-2.78 (1H, br m), 2.34-2.29 (1H, m), 1.89-1.83 (1H, m), 1.28 (3H, d, J = 6.3 Hz). |

| No | Product [F7-4] | Characterisation |
|---|---|---|
| 352 | 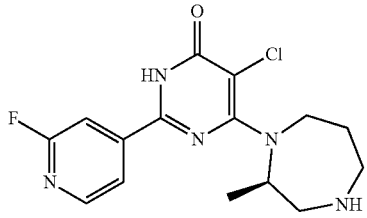 •[F₃CCO₂H] | RT 1.65 min, MI 338, Method (1LCMS13)<br>¹H NMR (600 MHz, d6-DMSO) δ 12.92 (1H, br s), 9.09 (1H, br s), 8.59 (1H, br s), 8.46 (1H, d, J = 5.2 Hz), 8.01 (1H, d, J = 5.1 Hz), 7.79 (1H, s), 4.96-4.92 (1H, m), 4.31 (1H, d, J = 15.4 Hz), 3.60 (1H, dd, J = 14.3, 6.0 Hz), 3.50-3.46 (1H, m), 3.32-3.30 (1H, m), 3.21-3.17 (1H, m), 3.01-2.96 (1H, m), 2.24-2.17 (1H, m), 2.01-1.98 (1H, m), 1.29 (3H, d, J = 6.3 Hz). |
| 353 | 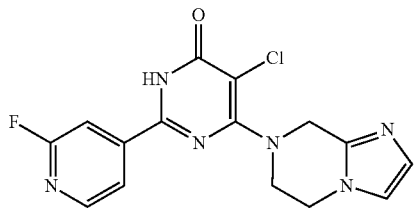 [SMILES: O=c1[nH]c(-c2ccnc(F)c2)nc(N2CCn3ccnc3C2)c1Cl] | RT 1.84 min, MI 347.3/349.3, Method (1LCMS12)<br>¹H NMR (600 MHz, DMSO-d6) δ 8.43 (d, 1H), 8.04 (d, 1H), 7.83 (s, 1H), 7.15 (d, 1H), 6.93 (d, 1H), 4.86 (s, 2H), 4.17 (t, 2H), 4.08 (t, 2H). |
| 354 | 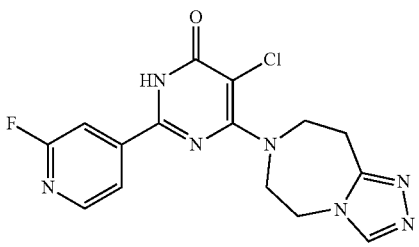 [SMILES: O=c1[nH]c(-c2ccnc(F)c2)nc(N2CCc3nncn3CC2)c1Cl] | RT 2.32 min, MI 362.3, Method (1LCMS12)<br>¹H NMR (600 MHz, DMSO-d6) δ 13.02 (s, 1H), 8.45 (d, 1H), 8.39 (s, 1H), 8.04 (dt, 1H), 7.83 (s, 1H), 4.31-4.39 (m, 2H), 4.03-4.11 (m, 2H), 3.94-4.03 (m, 2H), 3.22-3.27 (m, 2H). |
| 355 | 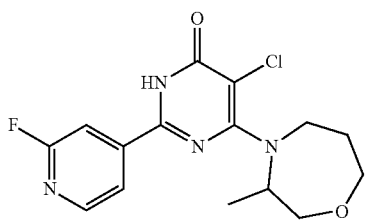 [SMILES: CC1COCCCN1c1nc(-c2ccnc(F)c2)[nH]c(=O)c1Cl] | RT 9.79 min, MI 339.13, Method (1LCMS1)<br>¹H NMR (600 MHz, d6-DMSO) δ 12.84 (br s, 1H), 8.42 (d, J = 5.1 Hz, 1H), 8.00 (d, J = 4.7 Hz, 1H), 7.77 (s, 1H), 4.72 (m, 1H), 4.23 (d, J = 15.4 Hz, 1H), 3.95 (dd, J = 5.1 and 13.4 Hz, 1H), 3.84 (dq, J = 3.0 and 12.0 Hz, 1H), 3.56 (td, J = 4.3 and 11.5 Hz, 1H), 3.50 (dd, J = 8.6 and 13.3 Hz, 1H), 3.47 (dd, J = 11.8 and 14.1 Hz, 1H), 2.09 (m, 1H), 1.83 (d, J = 15.2 Hz, 1H), 1.19 (d, J = 6.6 Hz, 3H). |
| 356 | 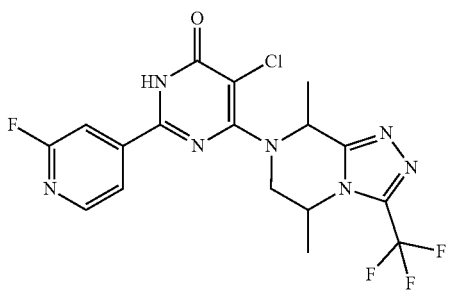 [SMILES: CC1c2nnc(C(F)(F)F)n2C(C)CN1c1nc(-c2ccnc(F)c2)[nH]c(=O)c1Cl] | RT 5.97 min, MI 444.3, Method (1LCMS15)<br>¹H NMR (600 MHz, DMSO-d6) δ 13.30 (s, 1H), 8.46 (d, 1H), 8.05 (dt, 1H), 7.84 (s, 1H), 5.62 (q, 1H), 4.72 (tt, 1H), 4.11 (dd, 1H), 3.65 (dd, 1H), 1.70 (d, 3H), 1.63 (d, 3H). |
| 357 | 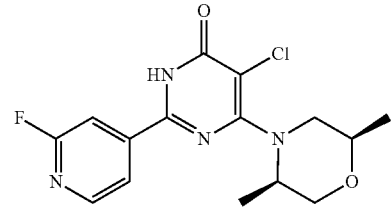 [SMILES: C[C@@H]1CN(c2nc(-c3ccnc(F)c3)[nH]c(=O)c2Cl)[C@H](C)CO1] | RT 10.33 min, MI 339.13, Method (1LCMS1)<br>¹H NMR (600 MHz, MeOD) δ 8.36 (d, J = 5.3 Hz, 1H), 7.95 (d, J = 5.3 Hz, 1H), 7.70 (s, 1H), 4.56 (q, J = 6.7 Hz, 1H), 4.13 (d, J = 13.6 Hz, 1H), 3.82 (dd, J = 3.0 and 11.1 Hz, 1H), 3.76 (d, J = 12.0 Hz, 1H), 3.70 (ddq, J = 2.5, 2.5 and 8.8 Hz, 1H), 3.15 (dd, 10.7 and 13.7 Hz, 1H), 1.42 (d, J = 7.1 Hz, 3H), 1.24 (d, J = 6.3 Hz, 3H). |

| No | Product [F7-4] | Characterisation |
|---|---|---|
| 358 | 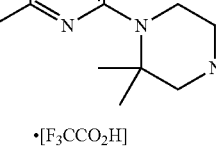 •[F₃CCO₂H] | RT 1.94 min, MI 338.16, Method (1LCMS12)<br>¹H NMR (600 MHz, DMSO-d6) δ 13.37 (br s, 1H), 8.91 (br s, 2H), 8.48 (d, J = 4.8 Hz, 1H), 7.98 (d, J = 4.8 Hz, 1H), 7.74 (s, 1H), 3.40 (t, J = 4.8 Hz, 2H), 3.22 (t, J = 4.8 Hz, 2H), 3.07 (m, 2H), 1.53 (s, 6H). |
| 359 | 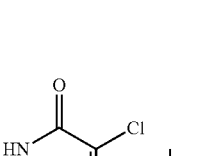 | RT 10.04 min, MI 339.13, Method (1LCMS1)<br>¹H NMR (600 MHz, CDCl₃) δ 13.04 (br s, 1H), 8.43 (d, J = 5.1 Hz, 1H), 8.02 (d, J = 5.0 Hz, 1H), 7.80 (s, 1H), 3.97 (m, 1H), 3.87 (m, 1H), 3.70-3.58 (m, 3H), 3.40 (m, 1H), 1.26 (d, J = 6.7 Hz, 3H), 1.24 (d, J = 6.7 Hz, 3H). |
| 360 | 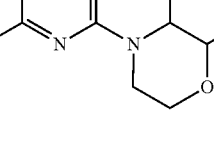 •[F₃CCO₂H] | RT 1.78 min, MI 310, Method (1LCMS12)<br>¹H NMR (600 MHz, d6-DMSO) δ 13.17 (br s, 1H), 8.84 (br S, 1H), 8.45 (1H, d, J = 5.2 Hz), 8.05 (1H, d, J = 5.2 Hz), 7.84 (1H, s), 3.85-3.83 (4H, m), 3.25-3.23 (4H, m). |
| 361 | 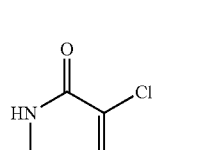 | RT 1.03 min, MI 320, Method (1LCMS5)<br>¹H NMR (400 MHz, d6-DMSO) δ 8.62 (2H, d), 8.09 (2H, d), 3.18 (2H, m), 3.02 (2H, m), 2.84 (2H, m), 1.09 (6H, s). |
| 362 | 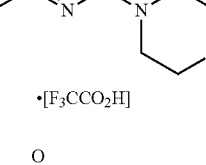 | RT 1.98 min, MI 338, Method (4LCMS1) |
| 363 | 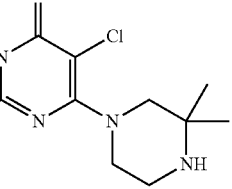 | RT 1.97 min, MI 338, Method (4LCMS1) |

| No | Product [F7-4] | Characterisation |
|----|----|----|
| 364 | 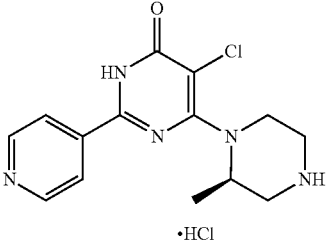 [SMILES: C[C@@H]1CNCCN1c1nc(-c2ccncc2)[nH]c(=O)c1Cl ; Cl] •HCl | RT 1.04 min, MI 306/308, Method (1LCMS1)<br>$^1$H NMR (500 MHz, d6-DMSO) δ 9.87 (s, 1H), 9.44 (s, 1H),<br>9.00-8.94 (m, 2H), 8.49-8.42 (m, 2H), 4.70-4.54 (m, 1H), 4.15 (d, 1H), 3.52 (t, 1H), 3.30-2.99 (m, 4H), 1.50-1.41 (m, 3H). |
| 365 | 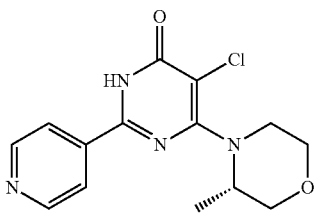 [SMILES: C[C@H]1COCCN1c1nc(-c2ccncc2)[nH]c(=O)c1Cl] | RT 0.91 min, MI 307/309, Method (1LCMS1)<br>$^1$H NMR (400 MHz, d6-DMSO) δ 8.82 (2H, d), 8.16 (2H, d), 4.67 (1H, m), 4.24 (1H, m), 4.0 (1H, d), 3.80 (2H, m), 3.69 (1H, m), 3.57 (1H, m), 1.54 (3H, d). |
| 366 | 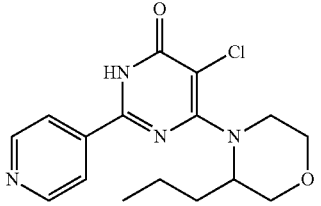 | RT 1.07 min, MI 335, Method (1LCMS1)<br>$^1$H NMR (400 MHz, d6-DMSO) δ 8.84 (2H, m), 8.16 (2H, d), 4.62 (1H, m), 4.15 (1H, m), 3.96 (1H, d), 3.87 (1H, d), 3.77 (1H, d), 3.64 (2H, m), 1.91 (2H, m), 1.36 (2H, m), 0.94 (3H, t). |
| 367 | 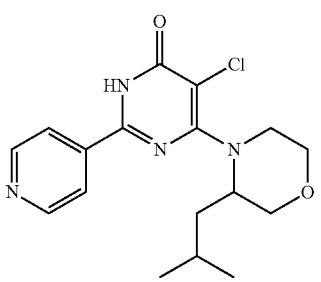 [SMILES: CC(C)CC1COCCN1c1nc(-c2ccncc2)[nH]c(=O)c1Cl] | RT 0.94 min, MI 349, Method (1LCMS1)<br>$^1$H NMR (400 MHz, d6-DMSO) δ 8.82 (2H, m), 8.16 (2H, d), 4.78 (1H, t), 4.09 (1H, d), 3.95 (1H, d), 3.86 (1H, d), 3.67 (1H, d), 3.49 (2H, m), 1.85 (1H, m), 1.61 (1H, m), 1.31 (1H, m), 0.95 (3H, d), 0.89 (3H, d). |
| 368 | 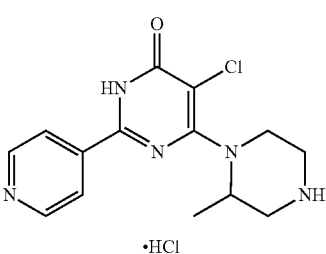 [SMILES: CC1CNCCN1c1nc(-c2ccncc2)[nH]c(=O)c1Cl ; Cl] •HCl | RT 0.64 min, MI 306, Method (1LCMS1)<br>$^1$H NMR (400 MHz, d6-DMSO) δ 8.98 (2H, d), 8.86 (2H, d), 4.31 (1H, d), 3.71 (1H, t), 3.46 (2H, m), 3.30 (3H, m), 1.51 (3H, d). |
| 369 | 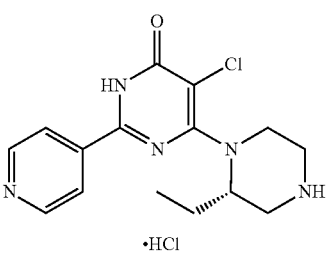 [SMILES: CC[C@H]1CNCCN1c1nc(-c2ccncc2)[nH]c(=O)c1Cl ; Cl] •HCl | RT 1.58 min, MI 320/322, Method (1LCMS1)<br>$^1$H NMR (400 MHz, MeOD) δ 8.98 (2H, d), 8.78 (2H, d), 4.73 (1H, m), 4.37 (1H, d), 3.66 (1H, t), 3.41 (1H, m), 3.31 (2H, m), 3.26 (1H, m), 2.06 (1H, m), 1.88 (1H, m), 1.0 (3H, d). |

-continued

| No | Product [F7-4] | Characterisation |
|---|---|---|
| 370 | | RT 2.03 min, MI 334/336, Method (1LCMS1)<br>¹H NMR (400 MHz, MeOD) δ 8.98 (2H, d), 8.67 (2H, d), 4.48 (2H, dd), 3.68 (2H, m), 3.41 (2H, m), 3.30 (1H, m), 2.44 (1H, m), 1.15 (3H, d), 0.96 (3H, d). |
| 371 | | RT 1.60 min, MI 320/322, Method (1LCMS1)<br>¹H NMR (400 MHz, MeOD) δ 8.95 (2H, m), 8.69 (2H, m), 4.68 (1H, m), 4.40 (1H, m), 3.68 (1H, m), 3.48 (2H, m), 3.40<br>(2H, m), 2.07 (1H, m), 1.93 (1H, m), 1.01 (3H, d). |
| 372 | | RT 3.81 min, MI 369/371, Method (1LCMS6)<br>¹H NMR (400 MHz, d6-DMSO) δ 8.68 (2H, d), 8.50 (1H, d), 7.86 (2H, d), 7.64 (1H, m), 7.48 (1H, m), 7.29 (1H, m), 7.18 (1H, m), 4.58 (1H, m), 3.99 (2H, m), 3.92 (2H, m), 3.70<br>(1H, m), 3.65 (1H, m). |
| 373 | | RT 1.66 min, MI 342, Method (4LCMS1).<br>¹H NMR (400 MHz, DMSO-d₆) δ 10.08 (br s, 1H), 9.21 (br s, 1H), 8.45 (d, J = 5.2 Hz, 1H), 8.03 (dt, J = 5.3, 1.7 Hz, 1H), 7.83 (s, 1H), 5.42-5.29 (m, 1H), 4.37 (td, J = 16.3, 4.7 Hz, 1H), 4.27-4.19 (m, 2H), 3.98 (ddd, J = 15.6, 7.2, 3.6 Hz, 1H), 3.61-3.27 (m, 4H). |
| 374 | | RT 0.68 min/0.99 min, MI 342, Method (4LCMS5)<br>¹H NMR (400 MHz, DMSO-d₆) δ 10.28 (br s, 2H), 8.94-8.93 (m, 2H), 8.33 (br s, 2H), 4.63 (t, J = 13.2 Hz, 2H), 4.14<br>(t, J = 5.2 Hz, 2H), 3.79 (t, J = 12.9 Hz, 2H), 3.51 (t, J = 5.3<br>Hz, 2H). |

| No | Product [F7-4] | Characterisation |
|---|---|---|
| 375 | 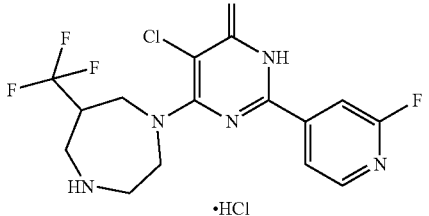 | RT 2.06 min, MI 392, Method (4LCMS1)<br>$^1$H NMR (400 MHz, DMSO-$d_6$) δ 8.46 (d, J = 5.2 Hz, 1H), 7.99 (dt, J = 5.4, 1.6 Hz, 1H), 7.78 (s, 1H), 4.45 (dd, J = 14.4, 4.1 Hz, 1H), 4.19 (ddd, J = 15.3, 8.0, 4.1 Hz, 1H), 4.03 (ddd, J = 15.4, 6.0, 3.9 Hz, 1H), 3.89 (dd, J = 14.4, 9.6 Hz, 1H), 3.53-3.31 (m, 5H). |
| 376 | 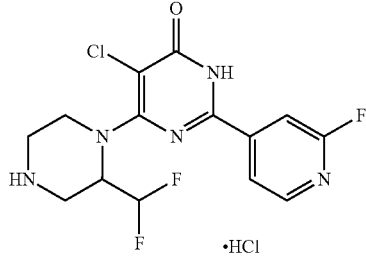 [SMILES: O=c1[nH]c(-c2ccnc(F)c2)nc(N2CCNCC2C(F)F)c1Cl ; Cl] | RT 1.67 min, MI 360, Method (4LCMS1)<br>$^1$H NMR (400 MHz, DMSO-$d_6$) δ 13.28 (s, 1H), 9.64 (s, 1H), 9.32 (s, 1H), 8.46 (d, J = 5.3 Hz, 1H), 8.08 (dt, J = 5.3, 1.7 Hz, 1H), 7.90 (d, J = 1.5 Hz, 1H), 6.75 (td, J = 55.1, 5.5 Hz, 1H), 5.11-5.05 (m, 1H), 4.18 (d, J = 14.8 Hz, 1H), 3.66-3.53 (m, 2H), 3.40-3.30 (m, 2H), 3.07 (br m, 1H). |
| 377 | 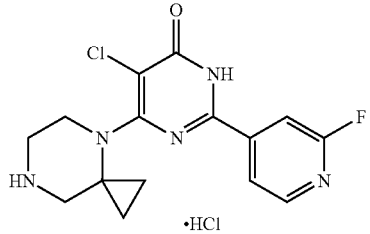 [SMILES: O=c1[nH]c(-c2ccnc(F)c2)nc(N2CCNCC23CC3)c1Cl ; Cl] | RT 1.70 min, 1.76 min (split peak) MI 336, Method (4LCMS1)<br>$^1$H NMR (400 MHz, DMSO-$d_6$) δ 13.15 (s, 1H), 9.30 (s, 2H), 8.46 (d, J = 5.2 Hz, 1H), 8.03 (d, J = 5.2 Hz, 1H), 7.81 (s, 1H), 3.94 (br s, 3H), 3.10 (br s, 3H), 1.10 (d, J = 6.7 Hz, 2H), 0.86 (s, 2H). |
| 378 | 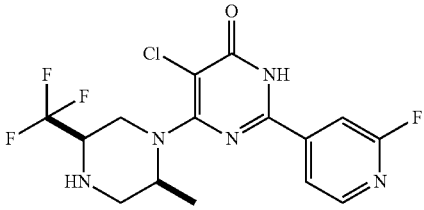 [SMILES: C[C@H]1CN[C@@H](C(F)(F)F)CN1c1nc(-c2ccnc(F)c2)[nH]c(=O)c1Cl] | RT 3.33 min, MI 392, Method (4LCMS1)<br>$^1$H NMR (400 MHz, DMSO-$d_6$) δ 8.31 (d, J = 5.2 Hz, 1H), 8.02-7.94 (m, 1H), 7.70 (s, 1H), 3.87 (dd, J = 13.4, 3.4 Hz, 1H), 3.62 (s, 1H), 3.23-3.07 (m, 2H), 2.94-2.63 (m, 2H), 1.26 (d, J = 6.7 Hz, 3H). |

In one approach (Scheme 8), compounds of general formula [F8-3] were prepared by the reaction of a 4,5,6-trihalo-2-pyridin-4-yl-pyrimidine derivative of general formula [F8-1] in a nucleophilic aromatic substitution type reaction utilising a suitable racemic amine of general formula [F8-2], and a base such as Et$_3$N or NaH in a polar solvent such as ethanol, 1,4-dioxane, DMA or DMF at high temperature either by heating thermally or using a microwave reactor. Alternatively, a base such as nBuLi can be used in a polar solvent such as THF at low temperatures. After reaction work up, typically by a liquid-liquid extraction, the reaction product was used crude in the next step or purified by flash column chromatography, reverse phase preparative HPLC or re-crystallisation. 5-Halo-(2-pyridin-4-y)-3H-pyrimidin-4-one derivatives of general formula [F8-4] were prepared by a hydrolysis reaction of 4,5-dihalo-2-(pyridin-4-yl)-pyrimidine derivatives of general formula [F8-3] with an aqueous base such as NaOH or KOH at high temperature either by heating thermally or using a microwave reactor. After reaction work up, typically by a liquid-liquid extraction or purification by acidic ion exchange catch-release the crude product was purified by flash column chromatography, reverse phase preparative HPLC or re-crystallisation. Racemic 5-halo-(2-pyridin-4-y)-3H-pyrimidin-4-one derivatives of general formula [F8-4] were separated by SFC to give single enantiomers of unknown absolute stereochemistry of general formula [F8-5] enantiomer 1 (first eluting) and [F8-5] enantiomer 2 (second eluting). Compounds of formula [F8-6] are prepared by a suitable deprotection reaction, for example reaction with an acid such as HCl in a suitable solvent such as 1,4-dioxane at ambient temperature. After reaction work up, typically by a liquid-liquid extraction or purification by acidic ion exchange catch-release the crude product can be purified by flash column chromatography, reverse phase preparative HPLC or re-crystallisation.

Scheme 8
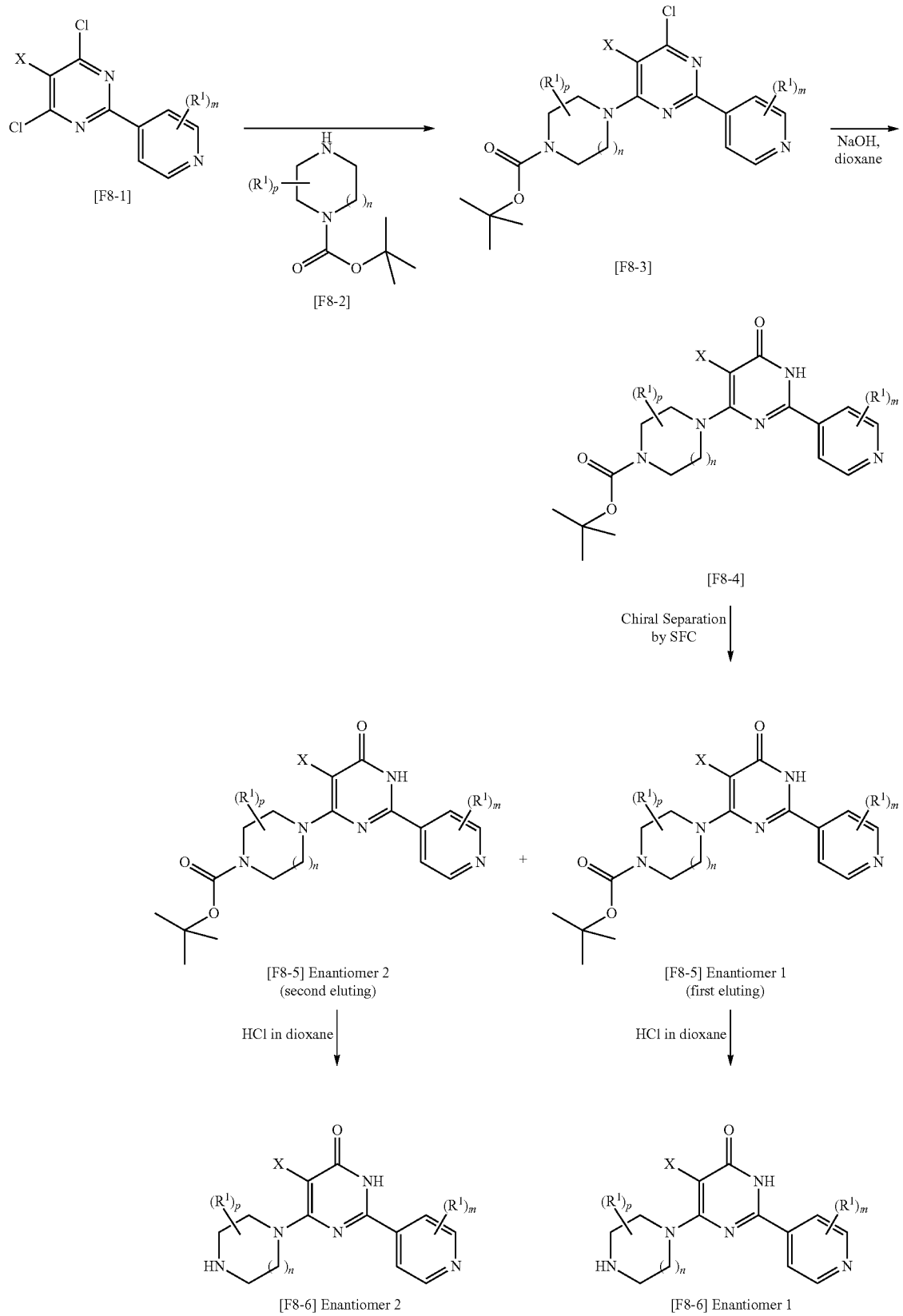

For example, synthesis of 5-chloro-4-(6-fluoro-1,4-diazepan-1-yl)-2-(2-fluoro-4-pyridyl)-1H-pyrimidin-6-one hydrochloride; enantiomer 1 (379) and enantiomer 2 (380).

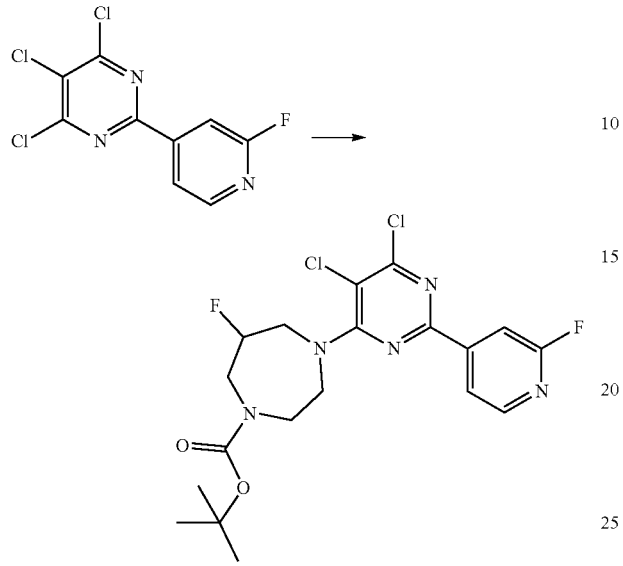

Synthesis of tert-butyl 4-[5,6-dichloro-2-(2-fluoro-4-pyridyl)pyrimidin-4-yl]-6-fluoro-1,4-diazepane-1-carboxylate (8-001)

A solution of 4,5,6-trichloro-2-(2-fluoro-4-pyridyl)pyrimidine (4-005, prepared in Scheme 4) (1.75 g, 6.28 mmol) and tert-butyl 6-fluoro-1,4-diazepane-1-carboxylate (1.44 g, 6.60 mmol) in 1,4-dioxane (30 mL) was prepared and triethylamine (1.05 mL, 7.54 mmol) was added. The reaction mixture was heated to 100° C. under microwave irradiation for 30 min. The reaction mixture was diluted with EtOAc (50 mL) and washed with water (20 mL) and brine (20 mL). The organic phase was dried over Na$_2$SO$_4$, filtered and concentrated by rotary evaporation. The residue was purified by column chromatography on silica gel, eluting with cyclohexane containing 0-25% EtOAc. The appropriate fractions were combined and concentrated to give the title compound (2.10 g, 72% yield) as a yellow foam. LCMS: RT 5.79 min, MI 460/462, Method (4LCMS1); $^1$H NMR (400 MHz, DMSO-d$_6$) δ 8.36-8.34 (m, 1H), 8.04 (dt, J=5.3, 1.6 Hz, 1H), 7.78 (s, 1H), 5.25-5.01 (m, 1H), 4.53-4.38 (m, 1H), 4.18-3.63 (m, 6H), 3.54-3.24 (m, 1H), 1.46 (s, 9H).

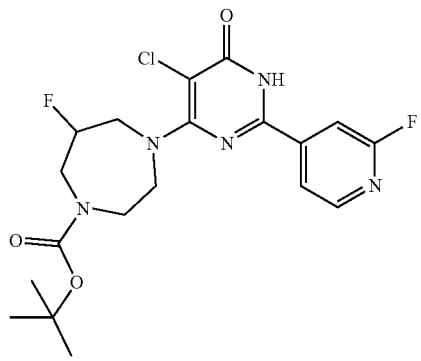

Synthesis of tert-butyl 4-[5-chloro-2-(2-fluoro-4-pyridyl)-6-oxo-1H-pyrimidin-4-yl]-6-fluoro-1,4-diazepane-1-carboxylate (8-002)

To a solution of tert-butyl 4-[5,6-dichloro-2-(2-fluoro-4-pyridyl)pyrimidin-4-yl]-6-fluoro-1,4-diazepane-1-carboxylate (8-001) (2.10 g, 4.55 mmol) in 1,4-dioxane (40 mL) was added NaOH (27.3 mL of a 2 M aq solution, 54.6 mmol). The reaction mixture was refluxed for 3.5 h then cooled to room temperature. The mixture was adjusted to pH 7-8 by addition of 2 M HCl (aq). The resulting solution was extracted with CH$_2$Cl$_2$:iso-propanol (9:1, 4×50 mL). The combined organic extracts were dried over Na$_2$SO$_4$, filtered and concentrated by rotary evaporation. The residue was purified by column chromatography on silica gel, eluting with CH$_2$Cl$_2$ containing 0-5% MeOH. The appropriate fractions were combined and concentrated to give the title compound (0.771 g, 38%). LCMS: RT 4.19 min, MI 442, Method (4LCMS1); $^1$H NMR (400 MHz, CDCl$_3$) δ 13.84 (s, 1H), 8.45 (d, J=5.3 Hz, 1H), 8.10 (dt, J=5.4, 1.5 Hz, 1H), 7.90 (s, 1H), 5.20-4.96 (m, 1H), 4.51-3.32 (m, 8H), 1.46 (s, 9H).

Chiral separation of tert-butyl 4-[5-chloro-2-(2-fluoro-4-pyridyl)-6-oxo-1H-pyrimidin-4-yl]-6-fluoro-1,4-diazepane-1-carboxylate

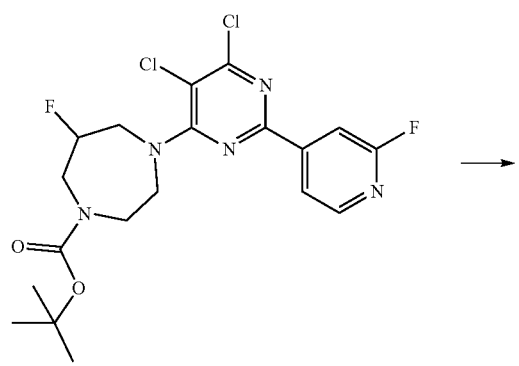

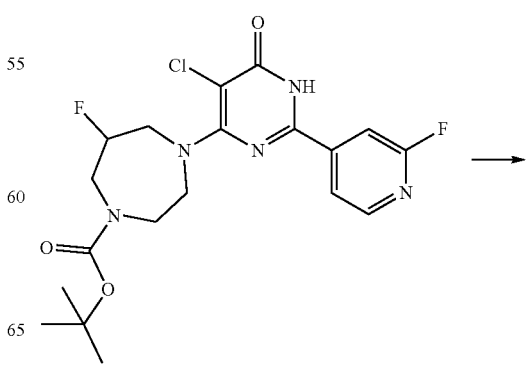

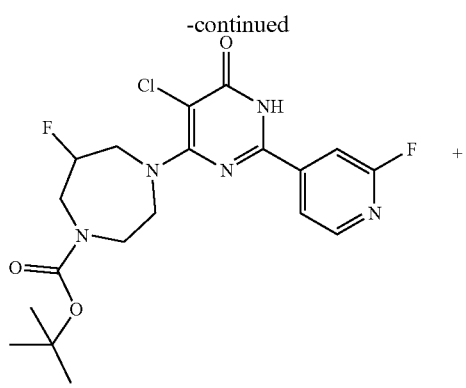

Enantiomer 1

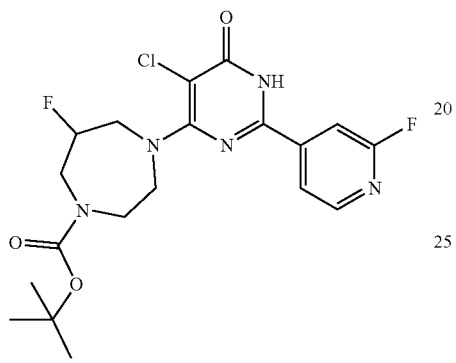

Enantiomer 2 tert-Butyl 4-[5-chloro-2-(2-fluoro-4-pyridyl)-6-oxo-1H-pyrimidin-4-yl]-6-fluoro-1,4-diazepane-1-carboxylate (8-002) (0.771 g, 1.74 mmol) was dissolved to 40 mg/mL in methanol and was then purified by SFC (Column=Lux C4 (21.2 mm×250 mm, 5 ☐m; Column temperature 40° C.; Flow rate=50 mL/min, BPR=100 BarG, Isocratic conditions 40:60 MeOH:CO₂). The appropriate fractions containing the first eluted isomer (enantiomer 1) were combined and concentrated to give tert-butyl 4-[5-chloro-2-(2-fluoro-4-pyridyl)-6-oxo-1H-pyrimidin-4-yl]-6-fluoro-1,4-diazepane-1-carboxylate, enantiomer 1 (8-003) (0.329 g, 43% yield) as a yellow solid in 100% ee (RT: 2.71 min; Column details: Lux C4 4.6 mm×250 mm, 5um; Column Temperature: 40° C.; Flow Rate: 4 mL/min; Isocratic Conditions: 40:60 MeOH:CO₂). LCMS: RT 4.13 min, MI 442, Method (5LCMS1); ¹H NMR (400 MHz, CDCl₃) δ 13.95 (s, 1H), 8.44 (d, J=5.3 Hz, 1H), 8.10 (dt, J=5.3, 1.5 Hz, 1H), 7.91 (s, 1H), 5.20-4.96 (m, 1H), 4.50-4.31 (m, 1H), 4.18-3.32 (m, 7H), 1.46 (s, 9H).

The appropriate fractions containing the second eluted isomer (enantiomer 2) were combined and concentrated. The residue was triturated in diethyl ether, filtered and dried under vacuum to give tert-butyl 4-[5-chloro-2-(2-fluoro-4-pyridyl)-6-oxo-1H-pyrimidin-4-yl]-6-fluoro-1,4-diazepane-1-carboxylate, enantiomer 2 (8-004) (0.245 g, 32% yield) as a yellow solid with 97.8% ee (RT: 3.01 min; Column details: Lux C4 4.6 mm×250 mm, 5 um; Column Temperature: 40° C.; Flow Rate: 4 mL/min; Isocratic Conditions: 40:60 MeOH:CO₂). LCMS: RT 4.12 min, MI 442, Method (5LCMS1); ¹H NMR (400 MHz, CDCl₃) δ 13.92 (s, 1H), 8.44 (d, J=5.3 Hz, 1H), 8.10 (dt, J=5.4, 1.5 Hz, 1H), 7.90 (d, J=1.5 Hz, 1H), 5.20-4.96 (m, 1H), 4.50-4.32 (m, 1H), 4.18-3.31 (m, 7H), 1.46 (s, 9H).

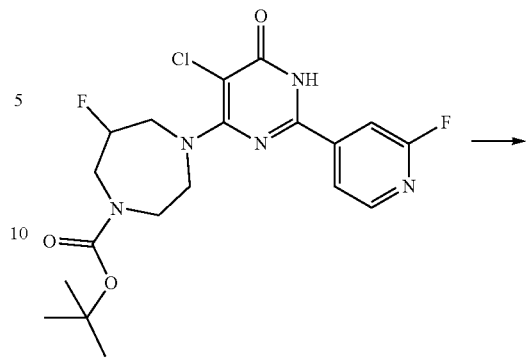

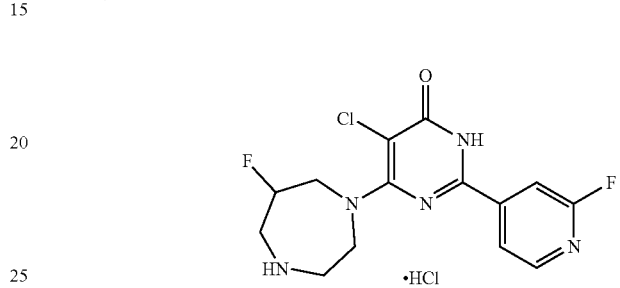

Synthesis of 5-chloro-4-(6-fluoro-1,4-diazepan-1-yl)-2-(2-fluoro-4-pyridyl)-1H-pyrimidin-6-one hydrochloride, enantiomer 1 (379)

tert-Butyl 4-[5-chloro-2-(2-fluoro-4-pyridyl)-6-oxo-1H-pyrimidin-4-yl]-6-fluoro-1,4-diazepane-1-carboxylate, enantiomer 1 (8-003) (0.31 g, 0.702 mmol) was stirred in HCl (3.51 mL of a 4 M solution in 1,4-dioxane, 14.0 mmol) at room temperature for 3 h. The reaction mixture was concentrated by rotary evaporation. The residue was triturated in diethyl ether, filtered, washed with diethyl ether and dried under vacuum at 40° C. for 7 days to the title compound (0.248 g, 93% yield) as a pale yellow solid. LCMS: RT 1.65 min, MI 342, Method (4LCMS1); ¹H NMR (400 MHz, DMSO-d₆) δ 8.46 (d, J=5.2 Hz, 1H), 8.03 (dt, J=5.3, 1.6 Hz, 1H), 7.83 (br s, 1H), 5.43-5.28 (m, 1H), 4.37 (td, J=16.3, 4.7 Hz, 1H), 4.26-4.15 (m, 2H), 4.01-3.95 (m, 1H), 3.59-3.46 (m, 3H), 3.33-3.27 (m, 1H).

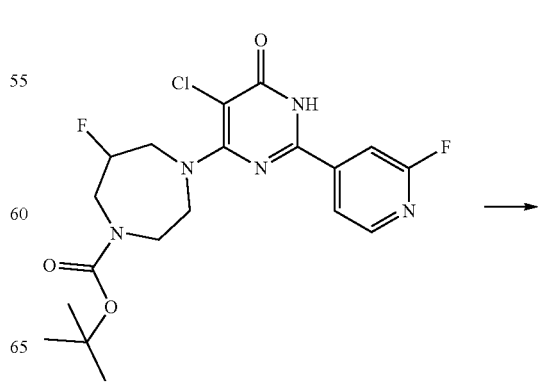

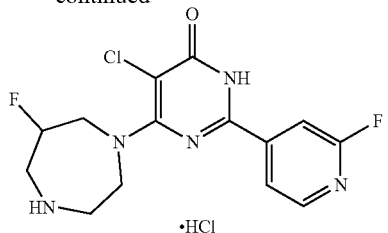

Synthesis of 5-chloro-4-(6-fluoro-1,4-diazepan-1-yl)-2-(2-fluoro-4-pyridyl)-1H-pyrimidin-6-one hydrochloride, enantiomer 2 (380)

tert-Butyl 4-[5-chloro-2-(2-fluoro-4-pyridyl)-6-oxo-1H-pyrimidin-4-yl]-6-fluoro-1,4-diazepane-1-carboxylate, enantiomer 2 (8-004) (0.31 g, 0.702 mmol) was stirred in HCl (2.77 mL of a 4 M solution in 1,4-dioxane, 11.1 mmol) at room temperature for 2 h. The reaction mixture was concentrated by rotary evaporation. The residue was triturated in diethyl ether, filtered, washed with diethyl ether and dried under vacuum at 40° C. for 7 days to give the title compound (0.193 g, 92% yield) as a pale yellow solid. LCMS: RT 1.66 min, MI 342, Method (4LCMS1); $^1$H NMR (400 MHz, DMSO-$d_6$) δ 8.46 (d, J=5.2 Hz, 1H), 8.03 (dt, J=5.3, 1.6 Hz, 1H), 7.83 (s, 1H), 5.43-5.28 (m, 1H), 4.37 (td, J=16.3, 4.7 Hz, 1H), 4.27-4.15 (m, 2H), 3.98 (ddd, J=15.7, 7.2, 3.6 Hz, 1H), 3.59-3.46 (m, 3H), 3.33-3.27 (m, 1H).

Synthesis of 5-chloro-4-[3-(1-fluoro-1-methyl-ethyl)piperazin-1-yl]-2-(2-fluoro-4-pyridyl)-1H-pyrimidin-6-one hydrochloride, enantiomer 1 (381) and enantiomer 2 (382)

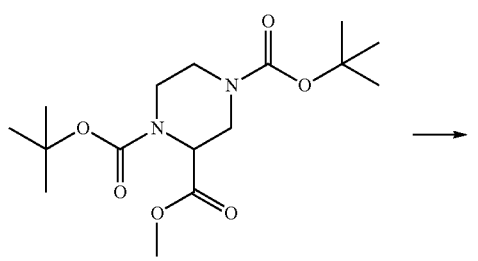

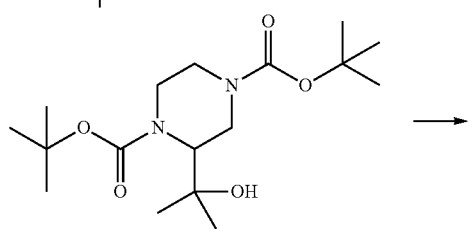

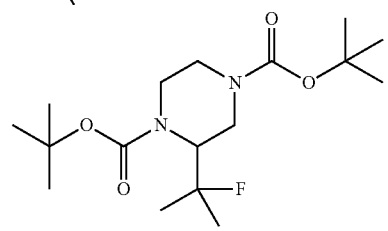

Synthesis of di-tert-butyl 2-(1-fluoro-1-methyl-ethyl)piperazine-1,4-dicarboxylate (8-005)

To a solution of O1,O4-di-tert-butyl O2-methyl piperazine-1,2,4-tricarboxylate (3.0 g, 8.71 mmol) in THF (60 mL) at −10° C. was added dropwise methyl magnesium bromide 3 M (18.5 mL, 55.5 mmol). The reaction was allowed to warm up slowly to room temperature and stirred overnight. The mixture was quenched by dropwise addition of saturated ammonium chloride solution. The reaction mixture was extracted with EtOAc, dried, and concentrated under vacuum then flash chromatographed over silica (loaded in DCM, eluting with cyclohexane to 30% ethyl acetate in cyclohexane), to afford the intermediate di-tert-butyl 2-(1-hydroxy-1-methyl-ethyl)piperazine-1,4-dicarboxylate (2.5 g, 83% yield). This was then dissolved in DCM (15 mL) and the mixture cooled to −20° C. under nitrogen and diethylaminosulfur trifluoride (1.15 mL, 8.71 mmol) was added dropwise. The mixture was stirred at −10° C. for 1 hour then gradually allowed to warm to ~10° C. over 1 hour. Saturated sodium bicarbonate was added dropwise then the mixture was partitioned between saturated sodium bicarbonate solution (20 mL) and DCM (20 mL). The organics were dried, concentrated under reduced pressure and the residue purified by flash chromatography on silica gel (eluting with cyclohexane to 20% ethyl acetate in cyclohexane) to afford the title compound (0.97 g, 38% yield) as a colourless oil. LCMS: RT 5.3 min, MI 347, Method (4LCMS1).

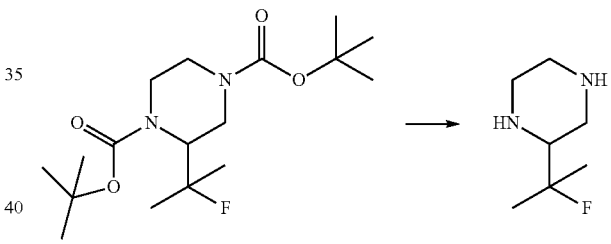

Synthesis of 2-(1-fluoro-1-methyl-ethyl)piperazine; 2,2,2-trifluoroacetic acid (8-006)

Di-tert-butyl 2-(1-fluoro-1-methyl-ethyl)piperazine-1,4-dicarboxylate (8-005) (0.97 g, 2.79 mmol) was dissolved in DCM (5 mL) and treated with TFA (2.0 mL, 2.79 mmol) and left to stir at room temperature overnight. The reaction mixture was then evaporated to give the title compound (0.4 g, 38% yield). LCMS: RT solvent front, MI 147, Method (4LCMS1); $^1$H NMR (400 MHz, DMSO-$d_6$) δ 3.78-3.64 (2H, m), 3.61-3.43 (2H, m), 3.40-3.12 (3H, m), 1.46 (6H, t).

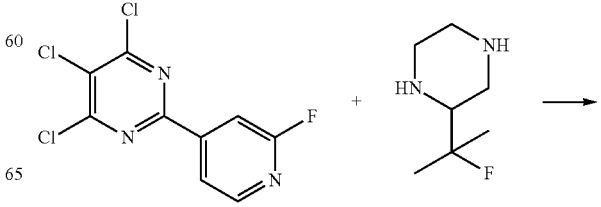

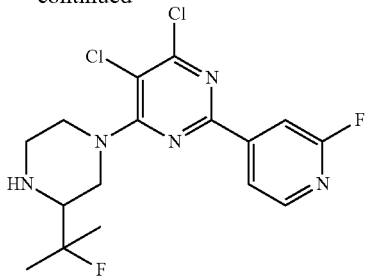

Synthesis of 4,5-dichloro-6-[3-(1-fluoro-1-methyl-ethyl)piperazin-1-yl]-2-(2-fluoro-4-pyridyl)pyrimidine (8-007)

4,5,6-Trichloro-2-(2-fluoro-4-pyridyl)pyrimidine (4-005) (0.3 g, 1.07 mmol), triethylamine (0.89 mL, 6.41 mmol) and 2-(1-fluoro-1-methyl-ethyl)piperazine; 2,2,2-trifluoroacetic acid (8-006) (0.4 g, 1.07 mmol) were stirred in 1,4-dioxane (6 mL) and the mixture was heated to reflux for 2 hours. The mixture was partitioned between water (20 mL) and ethyl acetate (20 mL), the organics were dried and concentrated under reduced pressure. The residue was purified by flash chromatography on silica gel, (eluting with cyclohexane to 50% ethyl acetate in cyclohexane) to give the title compound (0.133 g, 32% yield) as a yellow oil. LCMS: RT 2.69 min, MI 388/390, Method (4LCMS1); $^1$H NMR (400 MHz, DMSO-d6) δ 8.43 (1H, d), 8.07 (1H, d), 7.78 (1H, d), 4.58-4.29 (2H, m), 3.20-2.97 (2H, m), 2.94-2.67 (3H, m), 1.51-1.32 (6H, m).

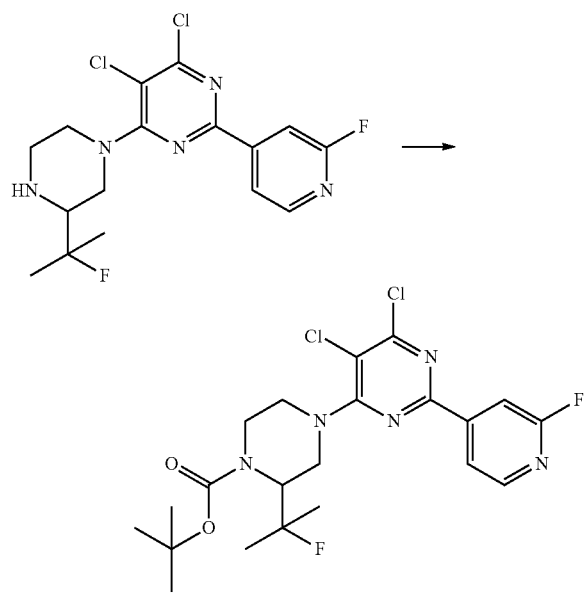

Synthesis of tert-butyl 4-[5,6-dichloro-2-(2-fluoro-4-pyridyl)pyrimidin-4-yl]-2-(1-fluoro-1-methyl-ethyl)piperazine-1-carboxylate (8-008)

4,5-Dichloro-6-[3-(1-fluoro-1-methyl-ethyl)piperazin-1-yl]-2-(2-fluoro-4-pyridyl)pyrimidine (8-007) (0.13 g, 0.343 mmol) was dissolved in DCM (2 mL) and treated with triethylamine (0.07 mL, 0.514 mmol) and di-tert-butyldicarbonate (0.08 g, 0.377 mmol). This was left to stir at room temperature for 3 days. The reaction mixture was then heated to 50° C. for 4 days. The reaction mixture was then allowed to return to room temperature and acidified to pH 5-6 through dropwise addition of aqueous HCl (2 M). This was extracted into DCM which was then passed down an SCX cartridge, eluting with DCM. This was then concentrated under reduced pressure to give the title compound (0.16 g, 96% yield). LCMS: RT 6.18 min, MI 488, Method (4LCMS1); $^1$H NMR (400 MHz, DMSO-d6) δ 8.44 (1H, d), 8.09 (1H, dt), 7.81 (1H, s), 4.55 (1H, s), 4.45-4.16 (2H, m), 4.03 (1H, d), 3.89 (1H, dd), 3.40 (2H, s), 1.48 (6H, s), 1.46-1.21 (9H, m).

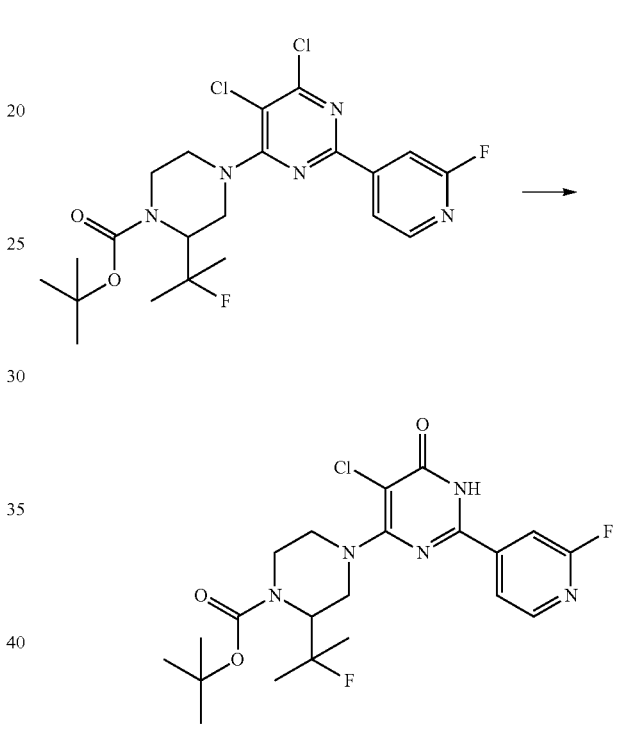

Synthesis of tert-butyl 4-[5-chloro-2-(2-fluoro-4-pyridyl)-6-oxo-1H-pyrimidin-4-yl]-2-(1-fluoro-1-methyl-ethyl)piperazine-1-carboxylate (8-009)

tert-butyl 4-[5,6-dichloro-2-(2-fluoro-4-pyridyl)pyrimidin-4-yl]-2-(1-fluoro-1-methyl-ethyl)piperazine-1-carboxylate (8-008) (0.16 g, 0.328 mmol) was treated with 1,4-dioxane (2 mL) and sodium hydroxide (1.97 mL, 3.93 mmol) and heated to 100° C. for 2 days. The reaction mixture was then allowed to return to room temperature and acidified to pH5 by the slow addition of aq 2 M HCl. This was then extracted into DCM (2×20 mL) and the combined organics concentrated under reduced pressure. The residue was purified by flash chromatography on silica gel (eluting with 0-50% ethyl acetate in cyclohexane) to give the title compound (0.06 g, 39% yield) as a yellow solid. LCMS: RT 4.6 min, MI 470, Method (4LCMS1); $^1$H NMR (400 MHz, DMSO-d$_6$) δ 12.96 (s, 1H), 8.45 (t, J=5.5 Hz, 1H), 8.01 (dt, J=5.3, 1.6 Hz, 1H), 7.81 (s, 1H), 4.37 (s, 1H), 4.20 (d, J=27.1 Hz, 3H), 4.05-3.75 (m, 3H), 1.48-1.22 (m, 15H).

257

Chiral separation of tert-butyl 4-[5-chloro-2-(2-fluoro-4-pyridyl)-6-oxo-1H-pyrimidin-4-yl]-2-(1-fluoro-1-methyl-ethyl)piperazine-1-carboxylate:

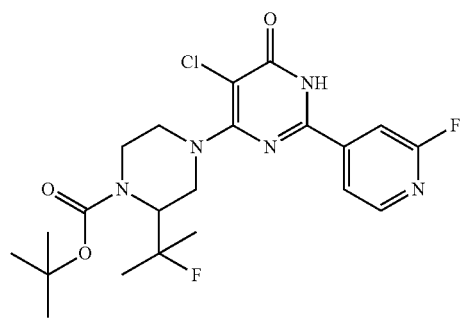

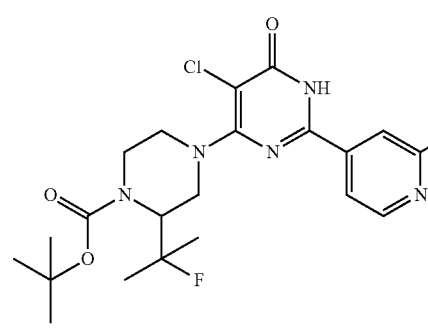

Enantiomer 1

Enantiomer 2 tert-butyl 4-[5-chloro-2-(2-fluoro-4-pyridyl)-6-oxo-1H-pyrimidin-4-yl]-2-(1-fluoro-1-methyl-ethyl)piperazine-1-carboxylate (8-009) (0.06 g, 0.127 mmol) was dissolved 12 mg/mL in ethanol and purified by SFC (Lux $C_1$ (21.2 mm×250 mm, 5 μm), 40° C., 20:80 EtOH:$CO_2$ (0.1% v/v $NH_3$). The first eluted isomer: enantiomer 1 (8-010) was collected (0.012 g, 7.8% yield) with 100% e.e. (RT: 3.7 min; Column details: Lux $C_1$ 4.6 mm×250 mm, 5 μm; Column Temperature: 40° C.; Flow Rate: 4 mL/min; Isocratic Conditions: 20:80 EtOH:$CO_2$ 0.1% v/v $NH_3$).

The second eluted isomer: enantiomer 2 (8-011) was collected (0.009 g, 5.8% yield) with 93% e.e. (RT: 4.37 min; Column details: Lux $C_1$ 4.6 mm×250 mm, 5 μm; Column Temperature: 40° C.; Flow Rate: 4 mL/min; Isocratic Conditions: 20:80 EtOH:$CO_2$ 0.1% v/v $NH_3$).

258

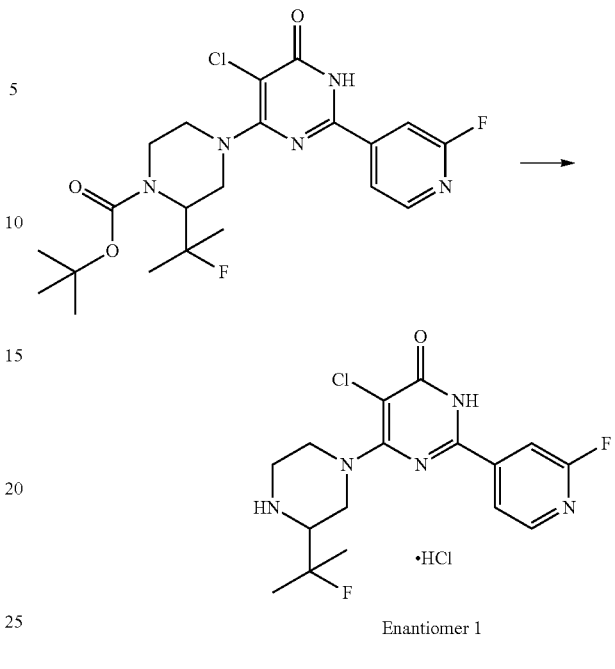

Enantiomer 1

Synthesis of 5-chloro-4-[3-(1-fluoro-1-methyl-ethyl)piperazin-1-yl]-2-(2-fluoro-4-pyridyl)-1H-pyrimidin-6-one hydrochloride, enantiomer 1 (381)

tert-butyl 4-[5-chloro-2-(2-fluoro-4-pyridyl)-6-oxo-1H-pyrimidin-4-yl]-2-(1-fluoro-1-methyl-ethyl)piperazine-1-carboxylate, enantiomer 1 (8-010) (0.01 g, 0.019 mmol) was dissolved in DCM (1 mL) and treated with 2 M HCl in diethyl ether (0.04 mL, 0.077 mmol) and left to stir at room temperature overnight. This was then treated with further 2 M HCl in diethyl ether (2.5 mL) and stirred for 24 hours. The reaction was then treated with a further 2 M HCl in diethyl ether (1 mL) and DCM (1 mL) and stirred for a further 24 hours. This was repeated for a total of 11 days. The reaction mixture was then dissolved in methanol and concentrated under reduced pressure. The residue was triturated in diethyl ether and dried under vacuum at 40° C. for four days to give the title compound (0.003 g, 27% yield). LCMS: RT 1.85 min, MI 370/372, Method (4LCMS1); $^1$H NMR (400 MHz, d6-DMSO) δ 8.46 (1H, d), 8.01 (1H, d), 7.83 (1H, s), 4.47 (2H, dd), 3.57 (2H, s), 3.38 (1H, d), 3.12 (2H, d), 1.51 (6H, dd).

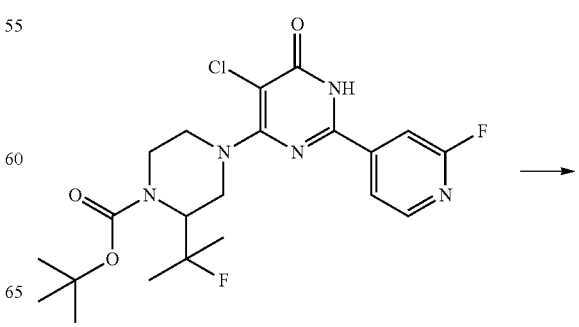

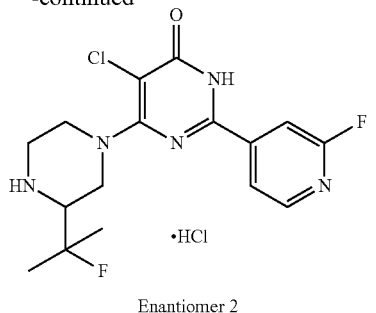

Enantiomer 2

Synthesis of 5-chloro-4-[3-(1-fluoro-1-methyl-ethyl)piperazin-1-yl]-2-(2-fluoro-4-pyridyl)-1H-pyrimidin-6-one hydrochloride, enantiomer 2 (382)

tert-butyl 4-[5-chloro-2-(2-fluoro-4-pyridyl)-6-oxo-1H-pyrimidin-4-yl]-2-(1-fluoro-1-methyl-ethyl)piperazine-1-carboxylate, enantiomer 2 (8-011) (0.01 g, 0.019 mmol) was dissolved in DCM (1 mL) and treated with 2 M HCl in diethyl ether (0.04 mL, 0.077 mmol) and left to stir at room temperature overnight. This was then treated with further 2 M HCl in diethyl ether (2.5 mL) and stirred for 24 hours. The reaction was then treated with a further 2 M HCl in diethyl ether (1 mL) and DCM (1 mL) and stirred for a further 24 hours. This was repeated for a total of 11 days. The reaction mixture was then dissolved in methanol and concentrated under reduced pressure. The residue was triturated in diethyl ether and dried under vacuum at 40° C. for four days to give the title compound (1.6 mg, 20.6% yield). LCMS: RT 1.86 min, MI 370/372, Method (4LCMS1); $^1$H NMR (400 MHz, d6-DMSO) δ 8.47 (1H, d), 8.04 (1H, dt), 7.84 (1H, s), 4.48 (2H, dd), 3.72-3.38 (2H, m), 3.24-3.00 (2H, m), 2.45 (1H, m), 1.53 (6H, dd).

The following compounds were synthesised according to the general synthesis shown in scheme 8:

| No | Product [F8-6] | Characterisation |
|---|---|---|
| 383 | Enantiomer 1 | RT 1.87 min, MI 377, Method (4LCMS1)<br>$^1$H NMR (400 MHz, DMSO-$d_6$) δ 8.46 (d, J = 5.2 Hz, 1H), 8.14 (dt, 5.3, 1.6 Hz, 1H), 7.99 (s, 1H), 5.80-5.71 (m, 1H), 4.11 (d, J = 14.4 Hz, 1H), 3.74 (d, J = 14.5 Hz, 1H), 3.64 (t, J = 13.2 Hz, 1H), 3.46 (dd, J = 14.6, 6.2 Hz, 1H), 3.29 (d, J = 12.9 Hz, 1H), 3.02 (td, J = 12.7, 3.9 Hz, 1H). |
| 384 | Enantiomer 2 | RT 1.86 min, MI 377, Method (4LCMS1)<br>$^1$H NMR (400 MHz, DMSO-$d_6$) δ 8.46 (d, J = 5.3 Hz, 1H), 8.14 (dt, J = 5.3, 1.6 Hz, 1H), 7.99 (s, 1H), 5.80-5.72 (m, 1H), 4.11 (d, J = 14.4 Hz, 1H), 3.73 (d, J = 14.4 Hz, 1H), 3.64 (t, J = 13.2 Hz, 1H), 3.46 (dd, 14.5, 6.2 Hz, 1H), 3.29 (d, J = 12.8 Hz, 1H), 3.01 (td, J = 12.7, 3.9 Hz, 1H). |
| 385 | Enantiomer 1 | RT 2.04 min, MI 392, Method (4LCMS1)<br>$^1$H NMR (400 MHz, DMSO-d6) δ 8.47 (d, J = 5.3 Hz, 1H), 7.99 (dt, J = 5.4, 1.6 Hz, 1H), 7.78 (s, 1H), 4.46 (dd, J = 14.5, 4.1 Hz, 1H), 4.18 (ddd, J = 12.6, 7.9, 4.1 Hz, 1H), 4.02 (dt, J = 15.2, 4.8 Hz, 1H), 3.88 (dd, J = 14.5, 9.5 Hz, 1H), 3.55-3.34 (m, 5H). |

| No | Product [F8-6] | Characterisation |
|---|---|---|
| 386 | 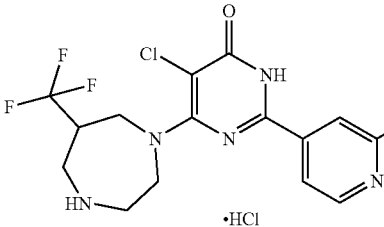 Enantiomer 2 | RT 2.03 min, MI 392, Method (4LCMS1)<br>$^1$H NMR (400 MHz, DMSO-d6) δ 8.47 (d, J = 5.2 Hz, 1H), 7.99 (dt, J = 5.4, 1.6 Hz, 1H), 7.78 (d, J = 1.6 Hz, 1H), 4.45 (dd, J = 14.4, 4.0 Hz, 1H), 4.19 (ddd, J = 15.3, 8.0, 4.1 Hz, 1H), 4.02 (ddd, J = 15.3, 6.2, 4.2 Hz, 1H), 3.88 (dd, J = 14.5, 9.6 Hz, 1H), 3.62-3.36 (m, 5H). |
| 387 | 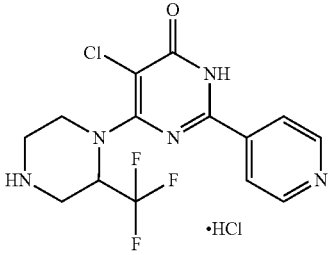 Enantiomer 1 | RT 1.56 min, MI 360, Method (4LCMS1)<br>$^1$H NMR (400 MHz, DMSO-d6) δ 10.21 (s, 1H), 8.97-8.78 (m, 2H), 8.61 (s, 1H), 8.38-8.13 (m, 2H), 5.73 (t, J = 7.9 Hz, 1H), 4.14 (d, J = 14.8 Hz, 1H), 3.76 (d, J = 14.4 Hz, 1H), 3.64 (t, J = 13.4 Hz, 1H), 3.55-3.43 (m, 1H), 3.31 (d, J = 12.7 Hz, 1H), 3.06 (s, 1H). |
| 388 | 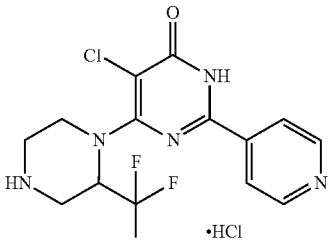 Enantiomer 2 | RT 1.55 min, MI 360, Method (4LCMS1)<br>$^1$H NMR (400 MHz, DMSO-d6) δ 13.39 (s, 1H), 10.22 (s, 1H), 8.99-8.76 (m, 2H), 8.61 (s, 1H), 8.37-8.09 (m, 2H), 5.72 (td, J = 9.6, 6.1 Hz, 1H), 4.14 (d, J = 14.1 Hz, 1H), 3.76 (d, J = 14.4 Hz, 1H), 3.64 (t, J = 13.5 Hz, 1H), 3.49 (s, 1H), 3.31 (d, J = 12.7 Hz, 1H), 3.05 (s, 1H). |
| 389 | 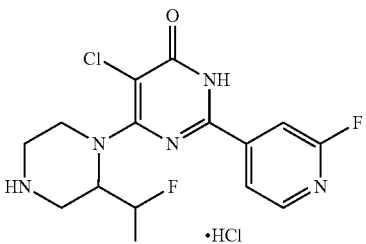 Enantiomer 1 | RT 1.68 min, MI 360, Method (4LCMS1)<br>$^1$H NMR (400 MHz, DMSO-d6) δ 13.30 (s, 1H), 9.54 (s, 1H), 9.16 (s, 1H), 8.46 (d, J = 5.3 Hz, 1H), 8.08 (dt, J = 5.3, 1.7 Hz, 1H), 7.91 (d, J = 1.6 Hz, 1H), 6.64 (dd, J = 55.0, 5.4 Hz, 1H), 5.26-4.91 (m, 1H), 4.18 (d, J = 14.8 Hz, 1H), 3.71-3.60 (m, 2H), 3.46-3.24 (m, 2H), 3.19-3.00 (m, 1H). |
| 390 | 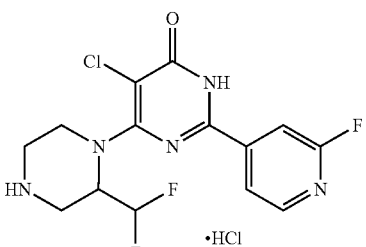 Enantiomer 2 | RT 1.68 min, MI 360, Method (4LCMS1)<br>$^1$H NMR (400 MHz, DMSO-d6) δ 13.30 (s, 1H), 9.54 (s, 1H), 9.17 (s, 1H), 8.46 (d, J = 5.2 Hz, 1H), 8.08 (dt, J = 5.3, 1.6 Hz, 1H), 7.91 (s, 1H), 6.71 (d, J = 5.4 Hz, 1H), 5.09 (dt, J = 13.1, 7.1 Hz, 1H), 4.18 (d, J = 14.8 Hz, 1H), 3.74-3.52 (m, 2H), 3.33 (d, J = 12.9 Hz, 2H), 3.08 (s, 1H). |

| No | Product [F8-6] | Characterisation |
|---|---|---|
| 391 | 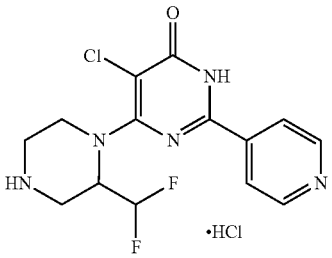<br>•HCl<br>Enantiomer 2 | RT 1.72 min, MI 342, Method (4LCMS1)<br>$^1$H NMR (400 MHz, DMSO-d$_6$) δ 9.68 (s, 1H), 9.36 (s, 1H),<br>8.86 (d, 2H), 8.23 (d, J = 5.1 Hz, 2H), 6.77 (t, J = 5.5 Hz, 1H), 5.08-5.00 (m, 1H), 4.54 (s, 1H), 4.18 (d, J = 14.6 Hz, 1H), 3.67 (t, J = 12.9 Hz, 1H), 3.42-3.29 (m, 2H), 3.08 (d, J = 12.5 Hz, 1H). |
| 392 | 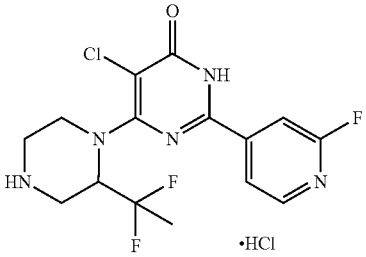<br>•HCl<br>Enantiomer 1 | RT 1.76 min, 1.92 min (split peak), MI 374/376, Method (4LCMS1)<br>$^1$H NMR (400 MHz, DMSO-d6) δ 13.24 (s, 1H), 10.21 (s, 1H), 8.45 (d, J = 5.3 Hz, 1H), 8.24 (dd, J = 1.5, 0.7 Hz, 1H),<br>8.11 (dt, J = 5.3, 1.6 Hz, 1H), 7.96 (d, J = 1.5 Hz, 1H), 5.23 (td, J = 16.1, 5.7 Hz, 1H), 4.08 (d, J = 14.5 Hz, 1H), 3.73 (d,<br>J = 14.1 Hz, 1H), 3.66-3.58 (m, 1H), 3.29 (dd, J = 34.5, 13.8 Hz, 2H), 2.98 (t, J = 12.5 Hz, 1H), 1.71 (t, J = 19.6 Hz, 3H). |
| 393 | 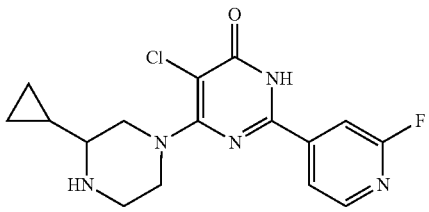<br>•HCl<br>Enantiomer 1 | RT 1.85 min, MI 350, Method (4LCMS1)<br>$^1$H NMR (400 MHz, DMSO-d6) δ 13.13 (s, 1H), 9.23 (s, 1H), 8.47 (d, J = 5.3 Hz, 1H), 8.02 (d, J = 5.3 Hz, 1H), 7.82<br>(s, 1H), 4.31 (t, J = 12.4 Hz, 2H), 3.34 (m, 3H), 3.07 (t, J = 12.8 Hz, 1H), 2.64 (td, J = 11.6, 9.7, 3.4 Hz, 1H), 1.03 (dd, J = 11.7, 6.1 Hz, 1H), 0.72-0.54 (m, 3H), 0.41 (dd, J = 7.6, 3.7 Hz, 1H). |
| 394 | 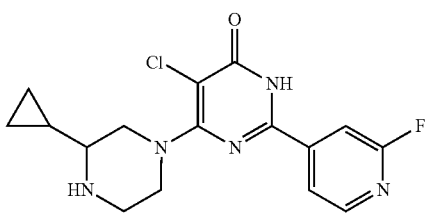<br>•HCl<br>Enantiomer 2 | RT 1.86 min, MI 350, Method (4LCMS1)<br>$^1$H NMR (400 MHz, DMSO-d$_6$) δ 13.11 (s, 1H), 9.27 (s, 1H), 8.46 (d, J = 5.3 Hz, 1H), 8.01 (d, J = 5.2 Hz, 1H), 7.81<br>(d, J = 1.5 Hz, 1H), 4.43-4.17 (m, 2H), 3.53-3.37 (m, 3H), 3.06 (t, J = 12.0 Hz, 1H), 2.70-2.58 (m, 1H), 1.06 (dt, J = 20.7, 6J Hz, 1H), 0.62 (dtd, J = 17.5, 9.9, 9.1, 5.5 Hz, 3H), 0.41 (dd, J = 9.7, 5.1 Hz, 1H). |

Synthesis of cis-5-chloro-2-(2-fluoro-4-pyridyl)-4-[2-methyl-5-(trifluoromethyl)piperazin-1-yl]-1H-pyrimidin-6-one hydrochloride, enantiomer 1 (395) and enantiomer 2 (396)

Chiral separation of racemic cis-5-chloro-2-(2-fluoro-4-pyridyl)-4-[2-methyl-5-(trifluoromethyl) piperazin-1-yl]-1H-pyrimidin-6-one (378)

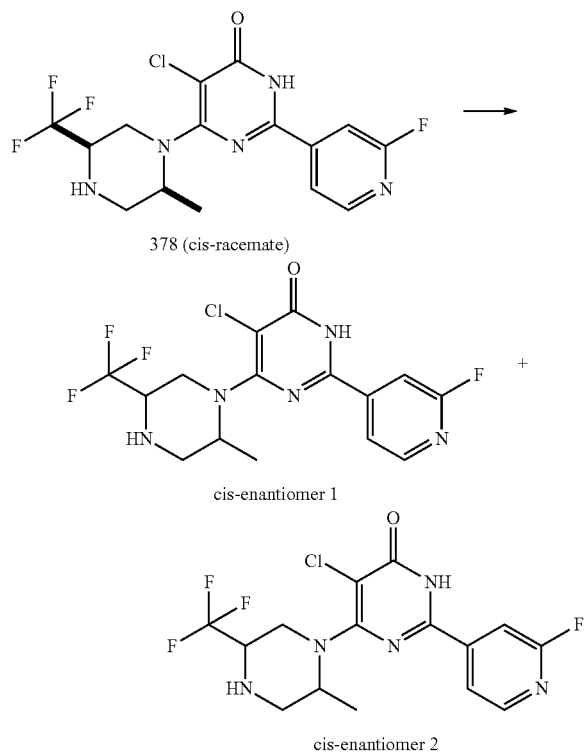

378 (cis-racemate)

cis-enantiomer 1 cis-enantiomer 2

Cis-5-chloro-2-(2-fluoro-4-pyridyl)-4-[2-methyl-5-(trifluoromethyl)piperazin-1-yl]-1H-pyrimidin-6-one (378, prepared in scheme 7) was dissolved to 20 mg/mL in methanol:DCM and was then purified by SFC (Column Details Amy-C 20 mm×250 mm, 5 μm, Column Temperature 40° C., Isocratic Conditions 20:80 MeOH:$CO_2$). Combined fractions of each isomer were then evaporated to near dryness using a rotary evaporator, transferred into final vessels with DCM, which was removed under a stream of nitrogen at 40° C. before being stored in a vacuum oven at 40° C. and 5 mbar for 2 hours to afford cis-5-chloro-2-(2-fluoro-4-pyridyl)-4-[2-methyl-5-(trifluoromethyl)piperazin-1-yl]-1H-pyrimidin-6-one, enantiomer 1 (first eluting) and enantiomer 2 (second eluting). The free base of each was then dissolved in dioxane (20 mL) with heating and then treated with 1 eq of 4 M HCl in dioxane. Each was then evaporated under reduced pressure and the residues triturated in MTBE. The resulting solids were dried under vacuum at 40° C. for 7 days to give:

Cis-5-chloro-2-(2-fluoro-4-pyridyl)-4-[2-methyl-5-(trifluoromethyl)piperazin-1-yl]-1H-pyrimidin-6-one hydrochloride, enantiomer 1 (395), (0.119 g). e.e. 97% (RT=1.51 min, Column Details Lux A1 4.6 mm×250 mm, 5 μm, Column Temperature 40° C., Isocratic Conditions 20:80 MeOH:$CO_2$ (0.1% v/v $NH_3$)). $^1$H NMR (400 MHz, DMSO-$d_6$) δ 8.26 (d, J=5.3 Hz, 1H), 7.79 (dt, J=5.4, 1.6 Hz, 1H), 7.59 (d, J=1.5 Hz, 1H), 4.34 (s, 1H), 4.15 (t, J=13.9 Hz, 1H), 3.56-3.25 (m, 1H), 3.24-3.12 (m, 1H), 3.05-2.88 (m, 2H), 1.24 (d, J=7.0 Hz, 3H).

Cis-5-chloro-2-(2-fluoro-4-pyridyl)-4-[2-methyl-5-(trifluoromethyl)piperazin-1-yl]-1H-pyrimidin-6-one hydrochloride, enantiomer 2 (396) (0.162 g). e.e. 96.2% (RT=1.94 min, Column Details Lux A1 4.6 mm×250 mm, 5 μm, Column Temperature 40° C., Isocratic Conditions 20:80 MeOH:$CO_2$ (0.1% v/v $NH_3$)). $^1$H NMR (400 MHz, DMSO-$d_6$) δ 13.01 (s, 1H), 8.26 (d, J=5.2 Hz, 1H), 7.79 (dt, J=5.3, 1.6 Hz, 1H), 7.60 (d, J=1.4 Hz, 1H), 4.35 (s, 1H), 4.24-4.08 (m, 2H), 3.28-3.10 (m, 1H), 2.96 (d, J=17.7 Hz, 2H), 1.25 (d, J=7.0 Hz, 3H).

In one approach (Scheme 9), compounds of general formula [F9-3] were prepared by the reaction of methyl 2,4-dichloro-3-oxo-butanoate [F9-1] in a condensation reaction utilising a suitable substituted pyridine-4-carboximidamide derivative of general formula [F9-2] in a polar solvent such as methanol or THF in the presence of a base such as sodium methoxide or potassium-tert-butoxide. The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. The 5-chloro-6-chloromethyl-2-(pyridin-4-yl)-3H-pyrimidin-4-one derivative of general formula [F9-3] was then reacted in a nucleophilic substitution type reaction utilising a suitable amine, thiol or alcohol of general formula [F9-4], and a base such as $Et_3N$ or NaH in a polar solvent such as ethanol, butanol, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. In cases where the substituent $R^2$ or $R^3$ contained an amine protected by a standard amine protecting group such as a tert-butyloxycarbonyl (Boc), compounds of formula [F9-5] are prepared by a suitable deprotection reaction, for example reaction with an acid such as TFA in a suitable solvent such as DCM at ambient temperature, as exemplified in Scheme 1. After reaction work up, typically by a liquid-liquid extraction or purification by acidic ion exchange catch-release the crude product was purified by flash column chromatography, reverse phase preparative HPLC or re-crystallisation.

Scheme 9

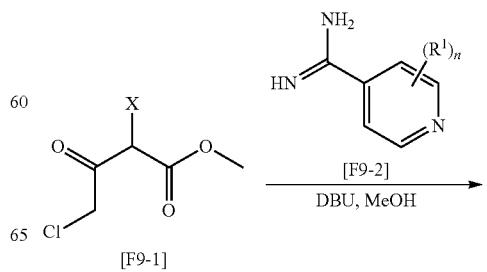

-continued

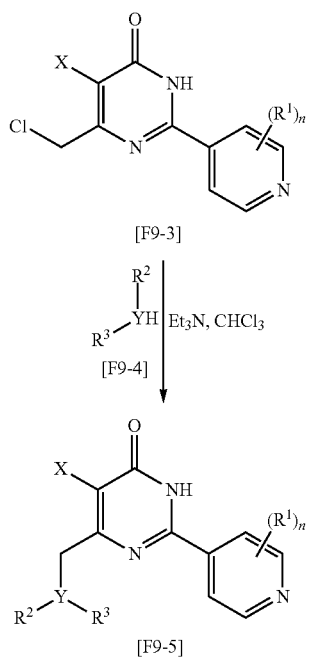

For example, synthesis of 5-chloro-2-(2-fluoro-4-pyridyl)-4-(morpholinomethyl)-1H-pyrimidin-6-one (397)

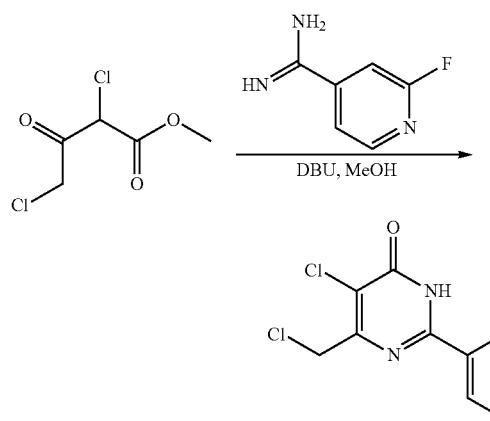

Synthesis of 5-chloro-6-chloromethyl-2-(2-fluoro-pyridin-4-yl)-3H-pyrimidin-4-one (9-001)

To a suspension of 2-fluoropyridine-4-carboxamidine hydrochloride (0.26 g, 1.45 mmol) in anhydrous methanol (7 mL) was added methyl 2,4-dichloro-3-oxo-butanoate (0.27 g, 1.45 mmol) followed by the dropwise addition of DBU (0.43 mL, 2.91 mmol). The reaction mixture was left to stir at room temperature overnight. The reaction mixture was evaporated under reduced pressure and the crude mixture was dissolved in 2 N HCl and the precipitate was collected by filtration to give the title compound (0.081 g, 20.3% yield) as a pink solid. LCMS: RT 2.56 min, MI 274.55, Method (1LCMS13).

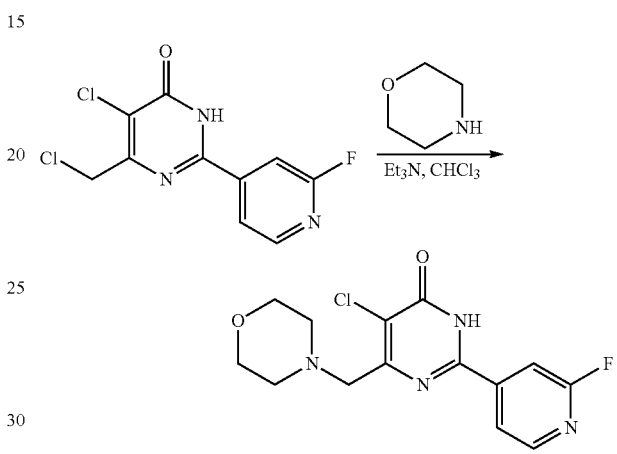

Synthesis of 5-chloro-2-(2-fluoro-4-pyridyl)-4-(morpholinomethyl)-1H-pyrimidin-6-one (397)

Morpholine (0.02 mL, 0.219 mmol) and Et$_3$N (0.03 mL, 0.219 mmol) were added to a solution of 5-chloro-6-chloromethyl-2-(2-fluoro-pyridin-4-yl)-3H-pyrimidin-4-one (9-001) (0.04 g, 0.146 mmol) in chloroform (3 mL) at 0° C. The reaction mixture was left to stir at room temperature overnight. The crude reaction mixture was purified by chromatography (DCM 100% to DCM/MeOH 80/20) to give the title compound (0.027 g, 57% yield) as a pale purple solid. LCMS: RT 1.67 min, MI 325.63, Method (1LCMS12); $^1$H NMR (400 MHz, d6-DMSO) δ 8.42 (d, J=5.4 Hz, 1H), 8.01 (d, J=4.8 Hz, 1H), 7.80 (s, 1H), 3.84-3.70 (m, 2H), 3.68-3.56 (m, 4H), 2.84-2.58 (m, 4H).

The following compounds were synthesised according to the general synthesis shown in scheme 9:

| No | Product [F9-5] | Characterisation |
|---|---|---|
| 398 | ![structure] •[F$_3$CO$_2$H] | RT 1.61 min, MI 324, Method (1LCMS12)<br>$^1$H NMR (600 MHz, DMS0-d6) δ 9.08 (br s, 1H), 8.74 (br s, 1H), 8.48 (d, J = 4.8 Hz, 1H), 8.04 (d, J = 5.4 Hz, 1H), 7.85 (s, 1H), 4.01 (m, 2H), 3.27-3.15 (m, 4H), 3.11-2.93 (m, 4H). |

In one approach (Scheme 10), compounds of general formula [F10-3] were prepared by the reaction of a 4,5,6-trichloro-2-iodo-pyrimidine derivative of general formula [F10-1] in a nucleophilic aromatic substitution type reaction utilising a suitable amine, thiol or alcohol of general formula [F10-2], and a base such as Et₃N or N,N-diisopropylethylamine in a polar solvent such as ethanol, 1,4-dioxane, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. 4,5-Dichloro-2-(pyridin-4-yl)-pyrimidine derivatives of general formula [F10-5] were prepared by a Suzuki-type coupling reaction with a suitable partner of general formula [F10-4] utilising a suitable catalyst such as bis(triphenylphosphine)palladium(II) dichloride or 1,1'-bis(diphenylphosphino)ferrocene]dichloropalladium(II), and a base such as sodium carbonate or potassium carbonate, in a polar solvent mixture such as 1,4-dioxane/water at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. 5-Chloro-(2-pyridin-4-yl)-3H-pyrimidin-4-one derivatives of general formula [F10-6] were prepared by a hydrolysis reaction of 4,5-dichloro-2-(pyridin-4-yl)-pyrimidine derivatives of general formula [F10-5] with an aqueous base such as NaOH or KOH at high temperature either by heating thermally or using a microwave reactor. After reaction work up, typically by a liquid-liquid extraction or purification by acidic ion exchange catch-release the crude product was purified by flash column chromatography, reverse phase preparative HPLC or re-crystallisation. In cases where the substituent R² or R³ contained an amine protected by a standard amine protecting group such as a tert-butyloxycarbonyl (Boc), compounds of formula [F10-6] are prepared by a suitable deprotection reaction, for example reaction with an acid such as TFA or HCl in a suitable solvent such as DCM at ambient temperature, as exemplified in Scheme 1. After reaction work up, typically by a liquid-liquid extraction or purification by acidic ion exchange catch-release the crude product was purified by flash column chromatography, reverse phase preparative HPLC or re-crystallisation.

Scheme 10

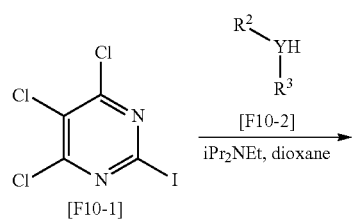

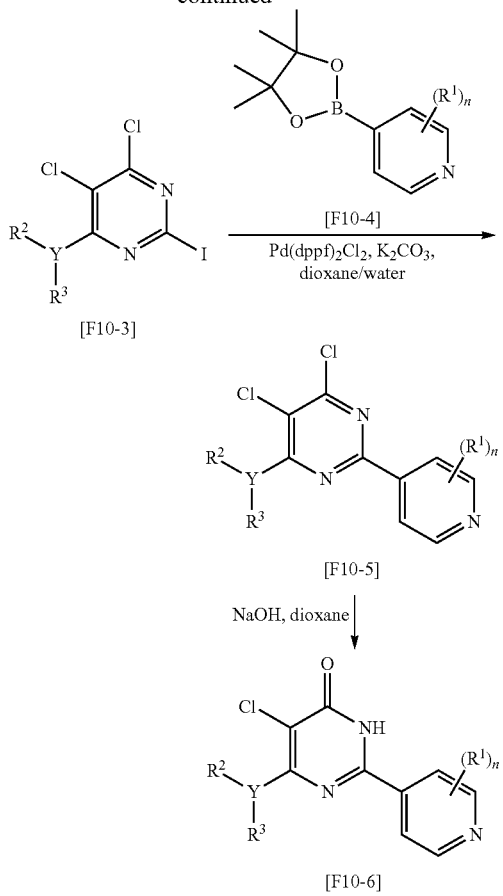

For example, synthesis of 5-chloro-4-(6,6-difluoro-1,4-diazepan-1-yl)-2-(3-fluoro-4-pyridyl)-1H-pyrimidin-6-one hydrochloride (399)

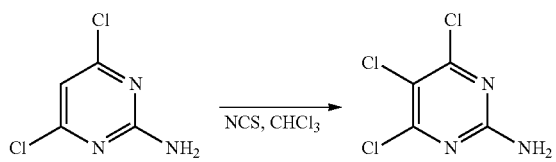 [SMILES: Nc1nc(Cl)cc(Cl)n1 ; Nc1nc(Cl)c(Cl)c(Cl)n1]

Synthesis of 4,5,6-trichloropyrimidin-2-amine (10-001)

A suspension of 2-amino-4,6-dichloropyrimidine (2.0 g, 12.20 mmol) in chloroform (30 mL) was prepared and N-chlorosuccinimide (1.71 g, 12.81 mmol) was added portionwise. The reaction mixture was refluxed for 2 h. The reaction mixture was cooled to room temperature, diluted with a saturated solution of NaHCO₃ then extracted with DCM and ethyl acetate. A precipitate formed which was removed by filtration. The combined organic extracts were dried and concentrated under reduced pressure. The crude residue was purified by column chromatography, eluting with 0-40% EtOAc in cyclohexane. The appropriate fractions were combined and concentrated to give the title compound (2.1 g, 86.8% yield). LCMS: RT 4.03 min, MI 199.8, Method (4LCMS1).

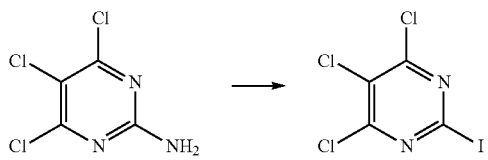 [SMILES: Nc1nc(Cl)c(Cl)c(Cl)n1 ; Clc1nc(I)nc(Cl)c1Cl]

Synthesis of 4,5,6-trichloro-2-iodo-pyrimidine (10-002)

4,5,6-trichloropyrimidin-2-amine (10-001) (5.0 g, 25.20 mmol) and di-iodomethane (20.3 mL, 251.96 mmol) were suspended in MeCN (25 mL). This was then treated with the dropwise addition tert-butyl nitrite (15.04 mL, 125.98 mmol). The reaction turned pale green and a gas was given off. The reaction mixture was heated to 80° C. for 2 hours before allowing to cool to room temperature and treating with saturated sodium bicarbonate solution (gas evolved). The reaction was then extracted into DCM (2×50 mL), the organics dried and concentrated under reduced pressure. The crude product was purified by flash chromatography on silica gel, eluting with cyclohexane containing 0-5% EtOAc. The appropriate fractions were combined and concentrated to give the title compound (4.13 g, 53% yield) as a white solid. LCMS: RT 4.98 min, MI 310, Method (4LCMS1).

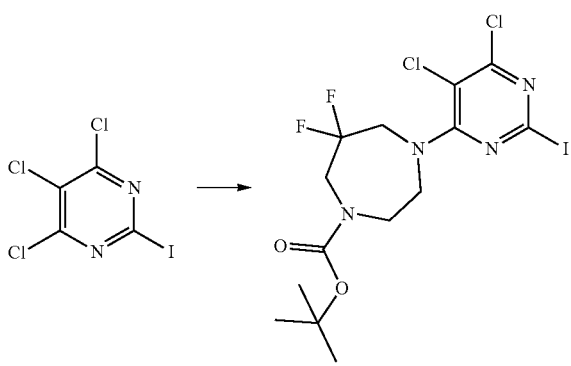 [SMILES: Clc1nc(I)nc(Cl)c1Cl ; CC(C)(C)OC(=O)N1CCN(c2nc(I)nc(Cl)c2Cl)CC(F)(F)C1]

Synthesis of tert-butyl 4-(5,6-dichloro-2-iodo-pyrimidin-4-yl)-6,6-difluoro-1,4-diazepane-1-carboxylate (10-003)

To a solution of 4,5,6-trichloro-2-iodo-pyrimidine (10-002) (0.5 g, 1.62 mmol) in 1,4-dioxane (5 mL) and N,N-diisopropylethylamine (0.56 mL, 3.23 mmol) was added tert-butyl 6,6-difluoro-1,4-diazepane-1-carboxylate (0.42 g, 1.778 mmol) as a solution in 1,4-dioxane (5 mL) and the reaction was allowed to stir at room temperature overnight. The reaction was concentrated and the residue was purified by column chromatography eluting with an EtOAc/hexane gradient (10-30% EtOAc). Fractions containing the product were combined and concentrated under reduced pressure to give the title compound (500 mg, 60.8% yield) as a colourless oil. LCMS: RT 5.70 min, MI 508/510, Method (4LCMS1). $^1$H NMR (400 MHz, DMSO-d6) δ 4.68-4.01 (m, 2H), 4.08-3.49 (m, 6H), 1.41 (s, 9H).

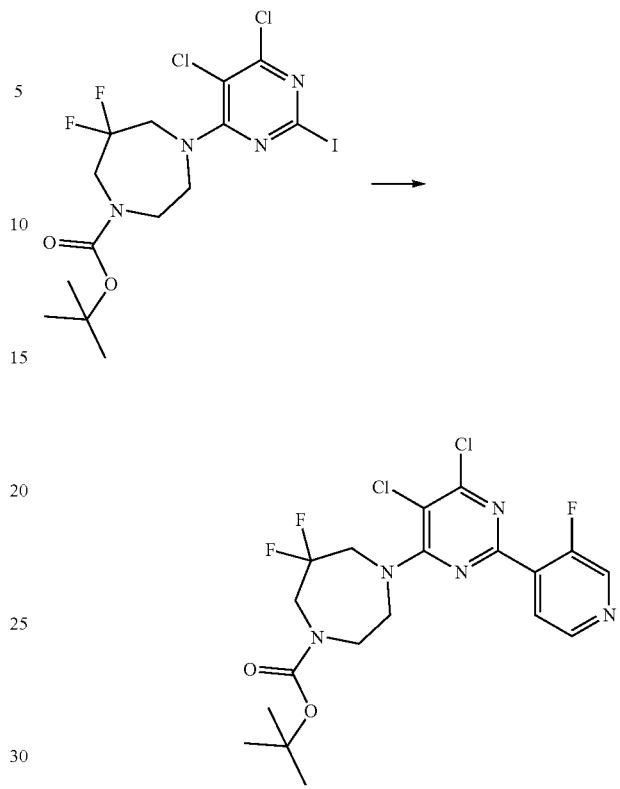

Synthesis of tert-butyl 4-[5,6-dichloro-2-(3-fluoro-4-pyridyl)pyrimidin-4-yl]-6,6-difluoro-1,4-diazepane-1-carboxylate (10-004)

tert-Butyl 4-(5,6-dichloro-2-iodo-pyrimidin-4-yl)-6,6-difluoro-1,4-diazepane-1-carboxylate (10-003) (0.50 g, 0.982 mmol), 3-fluoro-4-(4,4,5,5-tetramethyl-1,3,2-dioxaborolan-2-yl)pyridine (0.328 g, 1.473 mmol), 1,1'-bis(diphenylphosphino)ferrocene]dichloropalladium(II), complex with dichloromethane (80.2 mg, 0.098 mmol) and potassium carbonate (271 mg, 1.96 mmol) were weighed into a 2 neck round bottom flask. The flask was fitted with a reflux condenser, nitrogen inlet and suba seal and placed under nitrogen. In a separate vessel 1,4-dioxane (3 mL) and water (1 mL) were degassed for 5 minutes with nitrogen before being transferred to the solid reagents. The reaction mixture was then allowed to heat at 100° C. for 2 hours. The reaction mixture was evaporated under reduced pressure and the residue was partitioned between DCM (10 mL) and water (10 mL). The organics were dried (Na$_2$SO$_4$), filtered and evaporated to a brown residue. The residue was purified by flash column chromatography eluting a gradient from 100% cyclohexane to 30% ethyl acetate in cyclohexane. Fractions containing the product were combined and evaporated to give the title compound (0.290 g, 61.7% yield). LCMS: RT 5.55 min, MI 478/480, Method (4LCMS1); $^1$H NMR (400 MHz, DMSO-d6) δ 8.76 (d, J=3.0 Hz, 1H), 8.60 (dd, J=5.0, 0.8 Hz, 1H), 8.03 (dd, J=6.8, 5.0 Hz, 1H), 4.73-4.36 (m, 2H), 4.02 (d, J=7.7 Hz, 2H), 3.85 (d, J=13.5 Hz, 4H), 1.36 (s, 9H).

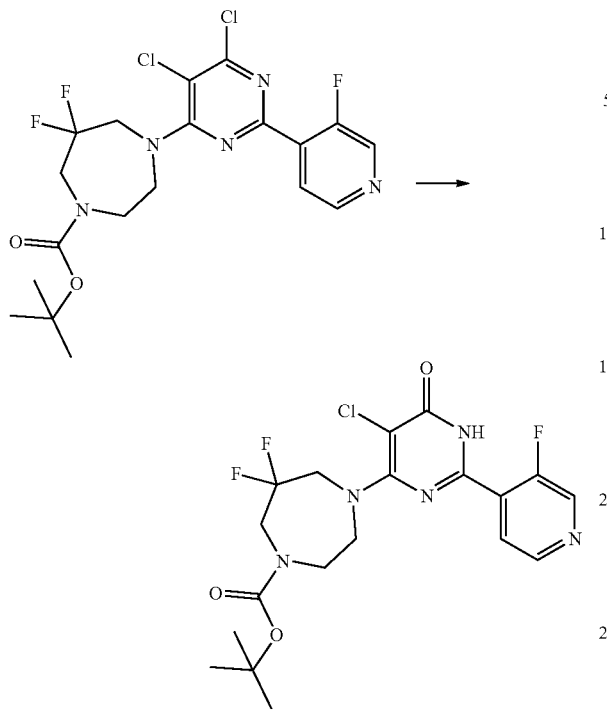

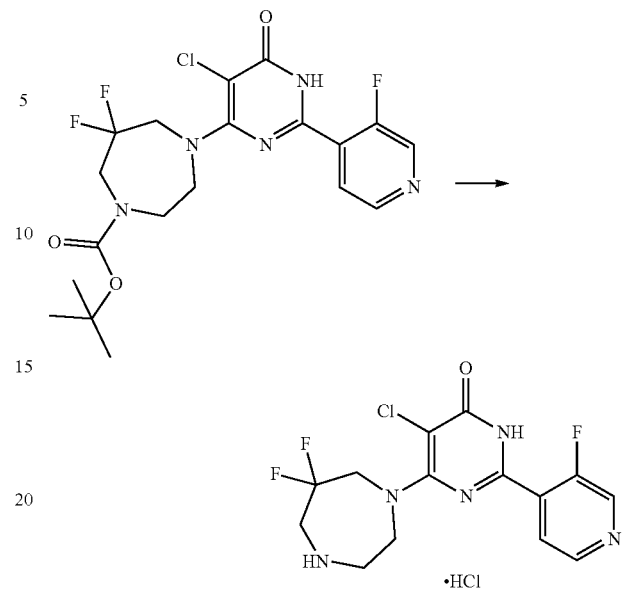

Synthesis of 5-chloro-4-(6,6-difluoro-1,4-diazepan-1-yl)-2-(3-fluoro-4-pyridyl)-1H-pyrimidin-6-one hydrochloride (399)

Synthesis of tert-butyl 4-[5-chloro-2-(3-fluoro-4-pyridyl)-6-oxo-1H-pyrimidin-4-yl]-6,6-difluoro-1,4-diazepane-1-carboxylate (10-005)

tert-butyl 4-[5,6-dichloro-2-(3-fluoro-4-pyridyl)pyrimidin-4-yl]-6,6-difluoro-1,4-diazepane-1-carboxylate (10-004) (290 mg, 0.606 mmol) was treated with sodium hydroxide (3.03 mL, 6.06 mmol) and 1,4-dioxane (6 mL) and heated to reflux for 4 hours. The reaction mixture was concentrated by reduced pressure to remove the 1,4-dioxane and the aqueous residue acidified to pH 4 using 1 M aqueous HCl solution and extracted into ethyl acetate (2×50 mL). The organic layer was dried ($Na_2SO_4$), filtered and then evaporated to a yellow oil. This was purified using flash chromatography on silica gel (eluting with EtOAc/hexane 0-95% EtOAc) to afford the title compound (0.170 g, 61% yield). LCMS: RT 4.06 min, MI 459/461, Method (4LCMS1); $^1$H NMR (400 MHz, $CDCl_3$) δ 11.09 (s, 1H), 9.33-8.30 (m, 2H), 7.98 (dd, J=6.5, 5.0 Hz, 1H), 4.36 (t, J=12.1 Hz, 2H), 4.05-3.68 (m, 6H), 1.49 (s, 9H).

tert-butyl 4-[5-chloro-2-(3-fluoro-4-pyridyl)-6-oxo-1H-pyrimidin-4-yl]-6,6-difluoro-1,4-diazepane-1-carboxylate (170 mg, 0.370 mmol) was dissolved in DCM (6 mL) and to this was added 2 M hydrochloric acid in diethyl ether (0.74 mL, 1.479 mmol) and the reaction was allowed to stir for 2 hours. The reaction was dosed with a further portion of 2 M hydrochloric acid in diethyl ether (0.74 mL, 1.479 mmol) and the reaction was stirred for a further 4 hours. The reaction was dosed a further two times with 2 M hydrochloric acid in diethyl ether (0.74 mL, 1.479 mmol) over 24 hours. Upon completion, the resulting yellow precipitate was filtered and dried to give the title compound (136 mg, 85% yield) as a yellow solid. LCMS: RT 1.70 min, MI 360, Method (4LCMS1); $^1$H NMR (400 MHz, DMSO-d6) δ 13.17 (s, 1H), 10.11 (s, 2H), 8.81 (d, J=2.1 Hz, 1H), 8.64 (dd, J=4.9, 0.9 Hz, 1H), 7.84 (t, J=5.6 Hz, 1H), 4.55 (t, J=13.2 Hz, 2H), 4.06 (t, J=5.3 Hz, 2H), 3.80 (t, J=12.8 Hz, 2H), 3.49 (t, J=5.4 Hz, 2H).

The following compounds were synthesised according to the general synthesis shown in scheme 10:

| No | Product [F10-6] | Characterisation |
|---|---|---|
| 400 | | RT 1.57 mins, MI 324/326 Method (4LCMS1) NMR (400 MHz, DMSO-$d_6$) δ 9.54 (s, 1H), 9.17 (s, $^1$H), 8.79 (d, J = 2.1 Hz, 1H), 8.62 (d, J = 4.9 Hz, 1H), 7.82 (t, J = 5.6 Hz, 1H), 4.60-4.48 (m, 1H), 4.04 (d, J = 14.6 Hz, 1H), 3.51-3.38 (m, 1H), 3.23 (d, J = 12.5 Hz, 1H), 3.20-3.12 (m, 2H), 3.11-2.96 (m, 1H), 1.41 (d, J = 7.0 Hz, 3H). |

| No | Product [F10-6] | Characterisation |
|---|---|---|
| 401 | 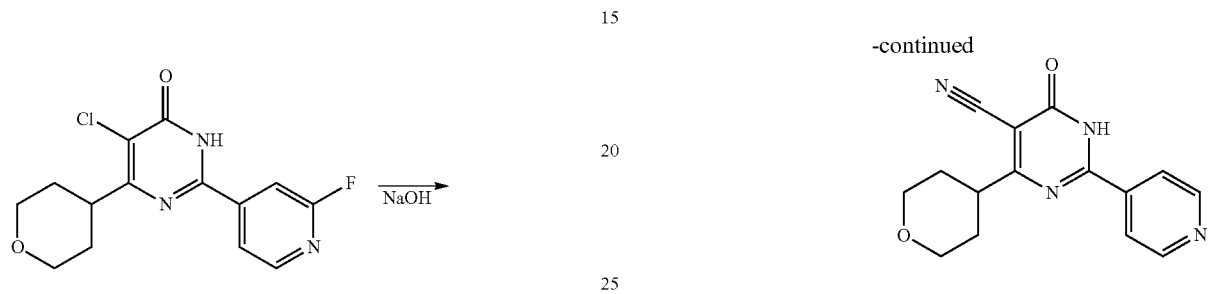 ·HCl | RT 1.98 mins, MI 376/378, Method (4LCMS1)<br>¹H NMR (400 MHz, DMSO-d6) δ 13.17 (br s, 1H), 10.12 (s, 2H), 8.63 (d, J = 5.2 Hz, 1H), 8.17 (d, J = 1.4 Hz, 1H), 8.08 (dd, J = 5.2, 1.5 Hz, 1H), 4.60 (t, J = 13.2 Hz, 2H), 4.12 (t, J = 5.2 Hz, 2H), 3.80 (t, J = 12.8 Hz, 2H), 3.51 (t, J = 5.2 Hz, 2H). |

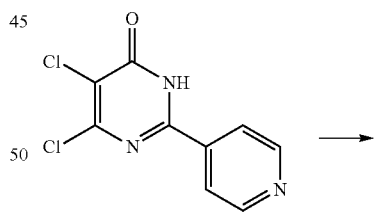

Synthesis of 5-chloro-2-(2-hydroxy-4-pyridyl)-4-tetrahydropyran-4-yl-1H-pyrimidin-6-one (402)

A mixture of 5-chloro-2-(2-fluoro-pyridin-4-yl)-6-(tetra-hydro-pyran-4-yl)-3H-pyrimidin-4-one (13) (0.155 g, 0.5 mmol) in aqueous sodium hydroxide (5 mL, 2 N) was heated at 120° C. for 20 min. The reaction mixture was cooled then neutralised by the addition of HCl. The mixture was extracted with DCM (2×15 mL), the extracts were combined and evaporated under reduced pressure. The crude reaction mixture was purified by HPLC (Method A) to give the title compound (10 mg, 7% yield). LCMS: RT 2.63, MI 308, Method (4LCMS1); ¹H NMR (400 MHz, d6-DMSO) δ 13.18 (1H, br s), 11.98 (1H, br s), 7.56 (1H, d), 7.21 (1H, s), 6.80 (1H, d), 3.92 (2H, dd), 3.45 (2H, t), 3.25 (1H, m), 1.89 (2H, m), 1.60 (2H, d).

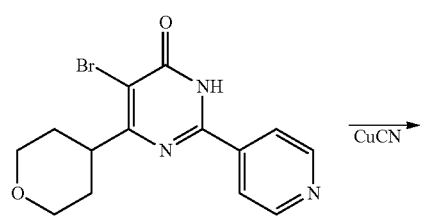

Synthesis of 6-oxo-2-(4-pyridyl)-4-tetrahydropyran-4-yl-1H-pyrimidine-5-carbonitrile (403)

A mixture of 5-bromo-2-(4-pyridyl)-4-tetrahydropyran-4-yl-1H-pyrimidin-6-one (3) (0.168 g, 0.5 mmol), N-methyl pyrrolidine (10 mL) and copper cyanide (89 mg, 1.0 mmol) was heated under microwave heating at 190° C. for 19 hours. Water (100 mL) was added and the mixture was extracted with DCM (2×250 mL), the extracts were combined and evaporated under reduced pressure. The crude reaction product was purified by column chromatography (100% DCM to 9:1 DCM:MeOH) followed by HPLC purification (Method A) to give the title compound (8 mg, 6% yield). LCMS: RT 2.58 min, MI 283, Method (4LCMS1); ¹H NMR (400 MHz, d6-DMSO) δ 8.85 (2H, s), 8.11 (2H, d), 3.98 (2H, dd), 3.48 (2H, t), 3.18 (1H, m), 1.97 (2H, dt), 1.69 (2H, d).

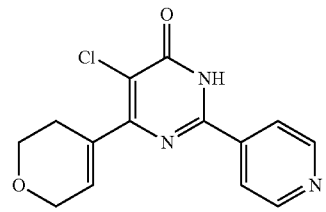

Synthesis of 5-chloro-4-(3,6-dihydro-2H-pyran-4-yl)-2-(4-pyridyl)-1H-pyrimidin-6-one (404)

A mixture of 4,6-dichloro-2-pyridin-4-yl-pyrimidine (4-002) (0.24 g, 1.0 mmol), 4-(4,4,5,5-tetramethyl-[1,3,2]

dioxaborolan-2-yl)-3,6-dihydro-2H-pyran (0.21 g, 1.0 mmol), (Ph₃P)₂PdCl₂ (0.21 g, 1.0 mmol), K₂CO₃ (0.07 g, 0.1 mmol), dioxane (10 mL) and water (2 mL) was heated under microwave heating at 150° C. for 55 min. The crude reaction mixture was diluted with DCM and extracted with water. The extracts were evaporated under reduced pressure and the crude reaction product was purified by HPLC (Method A) to give the title compound (0.01 g, 3% yield). LCMS: RT 2.55 min, MI 289, Method (4LCMS1); ¹H NMR (400 MHz, d6-DMSO) δ 13.50 (1H, s), 8.81 (2H, d), 8.05 (2H, d), 6.50 (1H, s), 4.26 (2H, m), 3.72 (2H, m), 2.51 (2H, m).

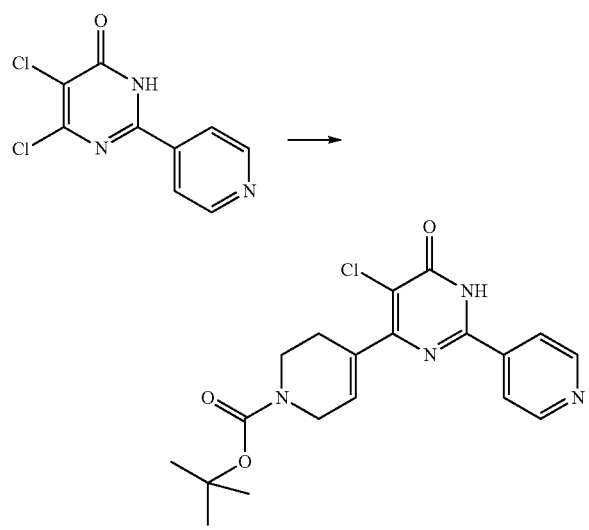

Synthesis of tert-butyl 4-[5-chloro-6-oxo-2-(4-pyridyl)-1H-pyrimidin-4-yl]-3,6-dihydro-2H-pyridine-1-carboxylate (405)

A mixture of 4,6-dichloro-2-pyridin-4-yl-pyrimidine (0.24 g, 1.0 mmol), tert-butyl-4-(4,4,5,5-tetramethyl-1,3,2-dioxaborolan-2-yl)-3,6-dihydro-2H-pyridine-1-carboxylate (4-002) (0.618 g, 2.0 mmol), (Ph₃P)₄Pd (0.115 g, 0.1 mmol), potassium phosphate (0.636 g, 3.0 mmol), dioxane (6 mL) and water (2 mL) was heated under microwave heating at 150° C. for 15 min. The crude reaction mixture was diluted with DCM and extracted with water. The extracts were evaporated under reduced pressure and the crude reaction product was purified by column chromatography (0% to 30% MeOH in DCM) to give the title compound (0.16 g, 41% yield). LCMS: RT 4.06 min, MI 389/391, Method (1LCMS1); ¹H NMR (400 MHz, d6-DMSO) δ 8.78 (2H, d), 8.05 (2H, d), 6.45 (1H, m), 4.07 (2H, m), 3.54 (2H, m), 2.48 (2H, m), 1.44 (9H, s).

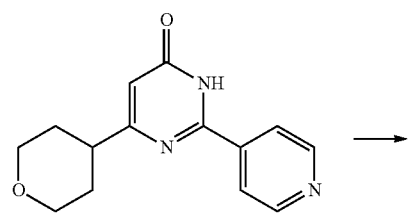

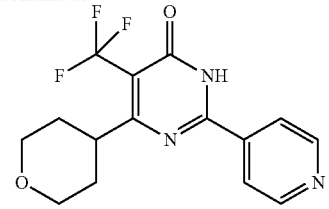

Synthesis of 2-(4-pyridyl)-4-tetrahydropyran-4-yl-5-(trifluoromethyl)-1H-pyrimidin-6-one (406)

5-Trifluoromethyldibenzothiopheniumtetrafluoroborate (0.51 g, 1.5 mmol) was added to a mixture of 2-(4-pyridyl)-4-tetrahydropyran-4-yl-1H-pyrimidin-6-one (1-002) (0.51 g, 1.5 mmol) in DMF (4 mL). The mixture was cooled to 0° C. and DBU (0.22 mL, 1.5 mmol) was added and the mixture was left to stir at room temperature for 3 hours. The mixture was evaporated under reduced pressure and the crude product was dissolved in DCM and washed with a saturated solution of sodium citrate then evaporated under reduced pressure and purified by HPLC (Method A) to give the title compound (0.01 g, 6% yield). LCMS: RT 3.19 min, MI 326, Method (4LCMS1); ¹H NMR (400 MHz, d6-DMSO) δ 13.66 (1H, s), 8.86 (2H, dd), 8.14 (2H, dd), 3.99 (2H, dd), 3.48 (2H, t), 3.29 (1H, t), 2.09 (2H, qd), 1.61 (2H, d).

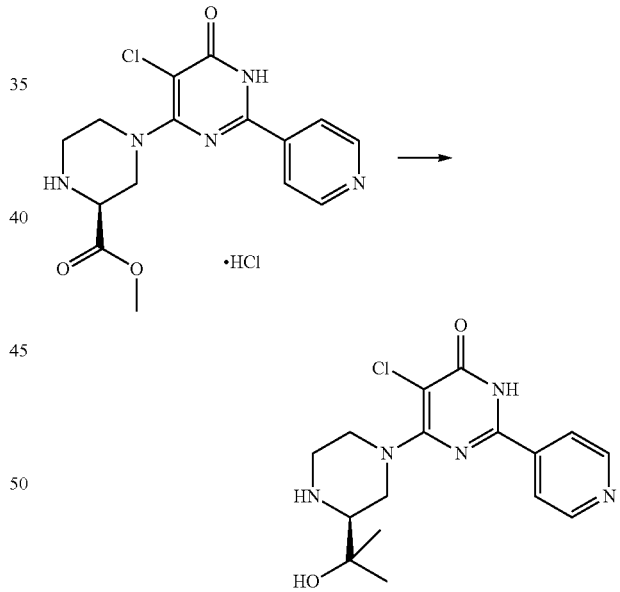

Synthesis of 5-chloro-4-[(3S)-3-(1-hydroxy-1-methyl-ethyl)piperazin-1-yl]-2-(4-pyridyl)-1H-pyrimidin-6-one (407)

A mixture of methyl (2S)-4-[5-chloro-6-oxo-2-(4-pyridyl)-1H-pyrimidin-4-yl]piperazine-2-carboxylate hydrochloride (163) (0.04 g, 0.104 mmol) in anhydrous THF (5 mL) was cooled to 0° C. Methyl magnesium bromide (104 μL, 0.312 mmol, of a 3 M solution in Et₂O) was added and the mixture was allowed to warm to room temperature then stirred for 18 hours. Further methyl magnesium bromide (104 µL, 0.312 mmol, of a 3 M solution in Et$_2$O) was added and the mixture allowed to stir at room temperature for 18 h. The reaction mixture was cooled to 0° C. then water (20 mL) was added slowly. The thick paste was sonicated with MeOH (20 mL), filtered and the filtrate evaporated under reduced pressure. The crude reaction mixture was purified by HPLC (Method A) to give the title compound (6 mg, 17% yield). LCMS: RT 0.63 min, MI 349, Method (1LCMS1); $^1$H NMR (500 MHz, MeOD) δ 8.73 (2H, d), 8.07 (2H, d), 4.69 (1H, m), 4.59 (1H, d), 3.47-3.34 (4H, m), 3.2-3.17 (1H, dd), 1.41 (3H, m), 1.34 (3H, m).

Synthesis of 5-bromo-4-[(3S)-3-isopropylpiperazin-1-yl]-2-(4-pyridyl)-1H-pyrimidin-6-one (408)

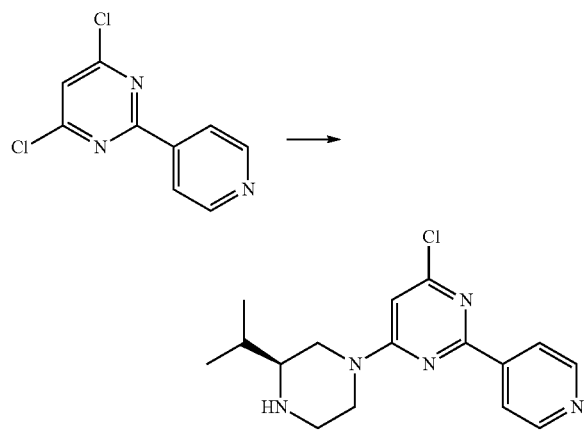

Synthesis of 4-chloro-6-[(3S)-3-isopropylpiperazin-1-yl]-2-(4-pyridyl)pyrimidine (11-001)

A mixture of 4,6-dichloro-2-pyridin-4-yl-pyrimidine (2-002) (0.35 g, 1.58 mmol), (S)-2-isopropyl piperazine.2HCl (0.34 g, 1.7 mmol), Et$_3$N (0.74 mL, 5.41 mmol) and isopropanol (20 mL) was stirred at room temperature for 18 hours. The reaction mixture was evaporated under reduced pressure and purified by column chromatography (DCM 100% to DCM:MeOH 95:5) to give the title compound (0.33 g, 68% yield). LCMS: RT 3.72 min, MI 318, Method (1LCMS1); $^1$H NMR (300 MHz, MeOD) δ 8.73-8.57 (m, 2H), 8.32-8.17 (m, 2H), 6.82 (s, 1H), 4.45 (br s, 2H), 3.18-2.94 (m, 2H), 2.85-2.70 (m, 2H), 2.40 (ddd, J=10.1, 6.8, 2.9 Hz, 1H), 1.71 (dq, J=13.5, 6.8 Hz, 1H), 1.05 (dd, J=6.7, 5.4 Hz, 6H).

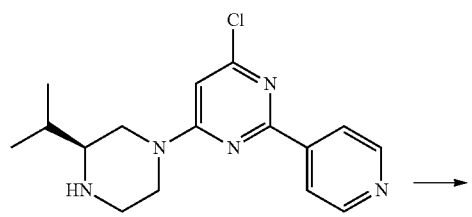

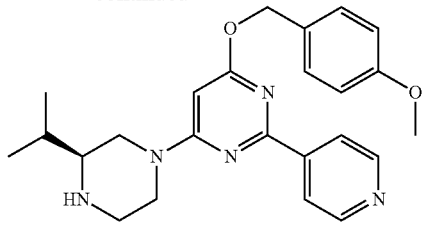

Synthesis of 4-((S)-3-Isopropyl-piperazin-1-yl)-6-(4-methoxy-benzyloxy)-2-pyridin-4-yl-pyrimidine (11-002)

A solution of 4-chloro-6-[(3S)-3-isopropylpiperazin-1-yl]-2-(4-pyridyl)pyrimidine (11-001) (0.32 g, 1.01 mmol) in anhydrous THF (2 mL) was cooled to 0° C. under a nitrogen atmosphere. Sodium hydride (61 mg, 1.5 mmol, 60% in oil) was added followed by the dropwise addition of 4-methoxybenzyl alcohol (190 µL, 1.5 mmol). The reaction mixture was allowed to warm to room temperature then left to stir for four days. The reaction mixture was cooled to 0° C. and a saturated solution of ammonium chloride (20 mL) was added, the mixture was extracted with EtOAc (2×30 mL). The extracts were combined, dried (MgSO$_4$), filtered and evaporated under reduced pressure to give a dark residue that was purified by column chromatography (100% cyclohexane to 100% EtOAc) to give the title compound (0.24 g, 58% yield). LCMS: RT 3.36 min, MI 419, Method (1LCMS1).

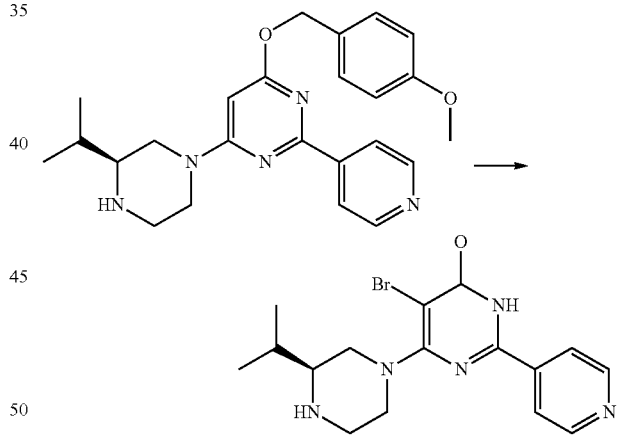

Synthesis of 5-bromo-4-[(3S)-3-isopropylpiperazin-1-yl]-2-(4-pyridyl)-1H-pyrimidin-6-one (408)

A mixture of 4-((S)-3-isopropyl-piperazin-1-yl)-6-(4-methoxy-benzyloxy)-2-pyridin-4-yl-pyrimidine (11-002) (0.24 g, 0.59 mmol) and NBS (116 mg, 0.65 mmol) in anhydrous DMF (1.18 mL) was stirred at room temperature for 24 hours. Water (40 mL) was added and the mixture was extracted with DCM (2×40 mL), the extracts were combined, dried (MgSO$_4$), filtered and evaporated under reduced pressure. The crude reaction mixture was purified by column chromatography (EtOAc:cyclohexane). The reaction intermediate was dissolved in DCM (2 mL) and TFA (0.5 mL) was added, the mixture was left to stir at room temperature overnight, then evaporated under reduced pressure and purified by HPLC (Method A) to give the title compound (0.013 g, 6% yield). LCMS: RT 1.81 min, MI 379, Method (1LCMS1); $^1$H NMR (400 MHz, CD$_3$OD) δ 8.72 (2H, d), 8.13 (2H, d), 4.61 (1H, d), 4.48 (1H, d), 3.50 (1H, d), 3.42 (1H, t), 3.33 (1H, m), 3.22 (1H, m), 3.12 (1H, m), 1.90 (1H, m), 1.14 (6H, t).

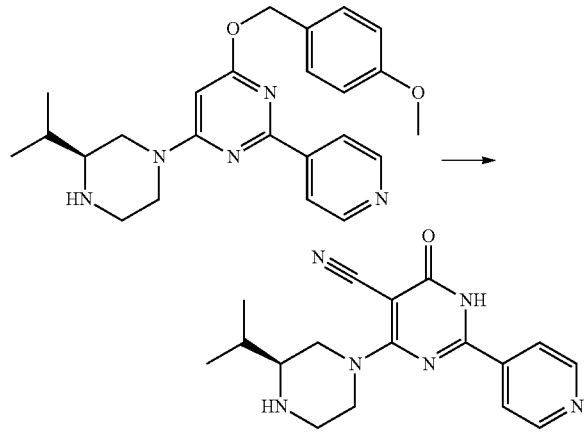

Synthesis of 4-[(3S)-3-isopropylpiperazin-1-yl]-6-oxo-2-(4-pyridyl)-1H-pyrimidine-5-carbonitrile (409)

A mixture of 4-((S)-3-isopropyl-piperazin-1-yl)-6-(4-methoxy-benzyloxy)-2-pyridin-4-yl-pyrimidine (11-002) (0.24 g, 0.59 mmol) and NBS (116 mg, 0.65 mmol) in anhydrous DMF (1.18 mL) was stirred at room temperature for 24 hours. Water (40 mL) was added and the mixture was extracted with DCM (2×40 mL), the extracts were combined, dried (MgSO$_4$), filtered and evaporated under reduced pressure. The crude reaction mixture was purified by column chromatography (EtOAc:cyclohexane). To the reaction intermediate (0.18 g, 0.37 mmol) was added Zn(CN)$_2$ (0.089 g, 0.755 mmol), Pd(PPh$_3$)$_4$ (0.145 g, 0.126 mmol), CuI (0.036 g, 0.18 mmol) in anhydrous DMF (1 mL) and the mixture heated under microwave heating at 100° C. for 30 min. Water (5 mL) was added and the mixture was extracted with DCM (2×10 mL), the extracts were combined, dried (MgSO$_4$), filtered and evaporated under reduced pressure. The crude reaction mixture was dissolved in DCM (2 mL) and TFA (0.5 mL) was added, the mixture was left to stir at room temperature overnight, then evaporated under reduced pressure and purified by HPLC (Method A) to give the title compound (2 mg, 2% yield). LCMS: RT 1.72 min, MI 324, Method (1LCMS1).

Synthesis of 5-bromo-4-[(3S)-3-tert-butylpiperazin-1-yl]-2-(4-pyridyl)-1H-pyrimidin-6-one (410)

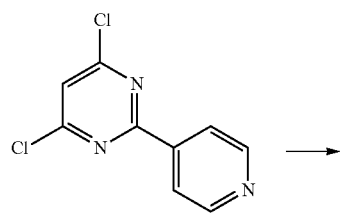

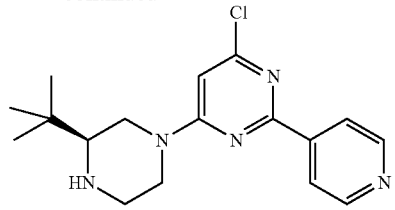

Synthesis of 4-[(3S)-3-tert-butylpiperazin-1-yl]-6-chloro-2-(4-pyridyl)pyrimidine (11-003)

A mixture of 4,6-dichloro-2-pyridin-4-yl-pyrimidine (2-002) (0.35 g, 1.58 mmol), (S)-2-tert-butyl piperazine.2HCl (0.366 g, 1.7 mmol), Et$_3$N (0.74 mL, 5.41 mmol) and isopropanol (20 mL) was stirred at room temperature for 18 hours. The reaction mixture was evaporated under reduced pressure and purified by column chromatography (DCM 100% to DCM:MeOH 95:5) to give the title compound (0.31 g, 61% yield). LCMS: RT 3.06 min, MI 331, Method (1LCMS1); $^1$H NMR (300 MHz, MeOD) δ 8.69-8.59 (m, 2H), 8.27-8.19 (m, 2H), 6.78 (s, 1H), 4.71-4.09 (m, 2H), 3.20-2.92 (m, 2H), 2.76 (td, J=11.9, 3.3 Hz, 2H), 2.35 (dd, J=10.9, 2.6 Hz, 1H), 1.03 (s, 9H).

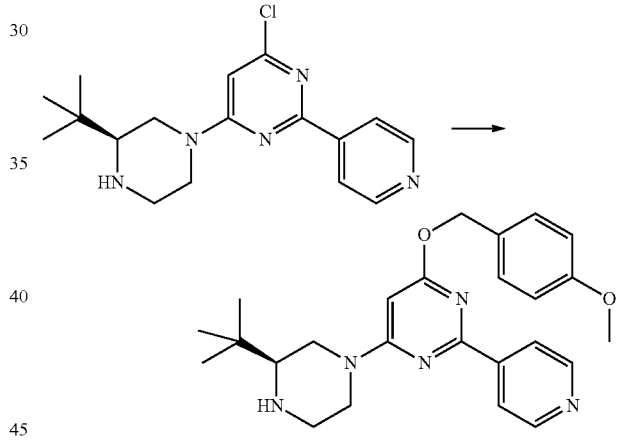

Synthesis of 4-((S)-3-tert-butyl-piperazin-1-yl)-6-(4-methoxy-benzyloxy)-2-pyridin-4-yl-pyrimidine (11-004)

A solution of 4-[(3S)-3-tert-butylpiperazin-1-yl]-6-chloro-2-(4-pyridyl)pyrimidine (0.29 g, 0.89 mmol) in anhydrous THF (2 mL) was cooled to 0° C. under a nitrogen atmosphere. Sodium hydride (54 mg, 1.33 mmol, 60% in oil) was added followed by the dropwise addition of 4-methoxybenzyl alcohol (167 μL, 133 mmol). The reaction mixture was allowed to warm to room temperature then left to stir for four days. The reaction mixture was cooled to 0° C. and a saturated solution of ammonium chloride (20 mL) was added, the mixture was extracted with EtOAc (2×30 mL). The extracts were combined, dried (MgSO$_4$), filtered and evaporated under reduced pressure to give a dark residue that was purified by column chromatography (100% cyclohexane to 100% EtOAc) to give the title compound (0.34 g, 89% yield). LCMS: RT 3.43 min, MI 433, Method (1LCMS1); $^1$H NMR (300 MHz, CDCl$_3$) δ 8.72 (d, J=6.1

Hz, 2H), 8.23 (d, J=6.1 Hz, 2H), 7.41 (d, J=8.7 Hz, 2H), 6.91 (d, J=8.7 Hz, 2H), 5.83 (s, 1H), 5.44 (s, 2H), 4.36 (br s, 2H), 3.81 (s, 3H), 3.20-3.10 (m, 1H), 2.99-2.76 (m, 2H), 2.68 (dd, J=12.5, 10.9 Hz, 1H), 2.37 (dd, J=10.8, 2.6 Hz, 1H), 1.01 (s, 9H).

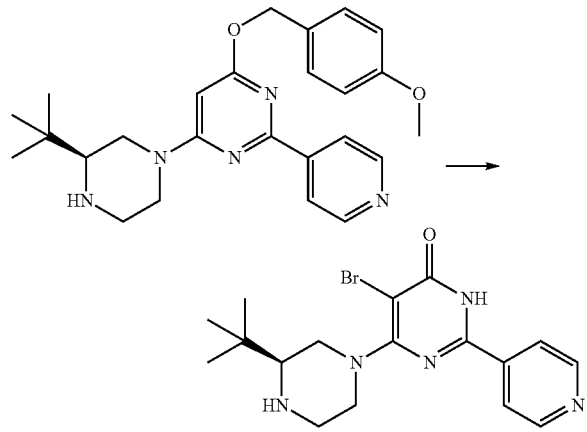

Synthesis of 5-bromo-4-[(3S)-3-tert-butylpiperazin-1-yl]-2-(4-pyridyl)-1H-pyrimidin-6-one (410)

A mixture of 4-((S)-3-tert-butyl-piperazin-1-yl)-6-(4-methoxy-benzyloxy)-2-pyridin-4-yl-pyrimidine (11-004) (0.29 g, 0.66 mmol), NBS (131 mg, 0.73 mmol) in anhydrous DMF (1.34 mL) was stirred at room temperature for 24 hours. Water (40 mL) was added and the mixture was extracted with DCM (2×40 mL), the extracts were combined, dried (MgSO$_4$), filtered and evaporated under reduced pressure. The crude reaction mixture was purified by column chromatography (EtOAc:cyclohexane). The reaction intermediate was dissolved in DCM (2 mL) and TFA (0.5 mL) was added, the mixture was left to stir at room temperature overnight, then evaporated under reduced pressure and purified by HPLC (Method A) to give the title compound (0.011 g, 4% yield). LCMS: RT 2.15 min, MI 393, Method (1LCMS1); $^1$H NMR (400 MHz, MeOD) δ 8.75 (2H, d), 8.10 (2H, d), 4.62 (1H, d), 4.45 (1H, d), 3.40 (2H, m), 2.30 (1H, m), 3.15 (2H, m), 1.20 (9H, s).

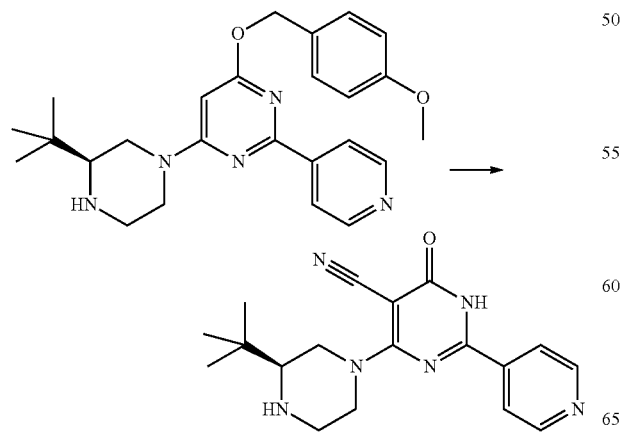

Synthesis of 4-[(3S)-3-tert-butylpiperazin-1-yl]-6-oxo-2-(4-pyridyl)-1H-pyrimidine-5-carbonitrile (411)

A mixture of 4-((S)-3-tert-butyl-piperazin-1-yl)-6-(4-methoxy-benzyloxy)-2-pyridin-4-yl-pyrimidine (11-004) (0.29 g, 0.66 mmol), NBS (131 mg, 0.73 mmol) in anhydrous DMF (1.34 mL) was stirred at room temperature for 24 hours. Water (40 mL) was added and the mixture was extracted with DCM (2×40 mL), the extracts were combined, dried (MgSO$_4$), filtered and evaporated under reduced pressure. The crude reaction mixture was purified by column chromatography (EtOAc:cyclohexane). To the reaction intermediate (0.15 g, 0.29 mmol) was added Zn(CN)$_2$ (0.069 g, 0.58 mmol), Pd(PPh$_3$)$_4$ (0.098 g, 0.113 mmol) and CuI (0.028 g, 0.15 mmol) in anhydrous DMF (1 mL). The mixture was heated under microwave heating at 100° C. for 30 min. Water (5 mL) was added and the mixture was extracted with DCM (2×10 mL), the extracts were combined, dried (MgSO$_4$), filtered and evaporated under reduced pressure. The crude reaction mixture was dissolved in DCM (2 mL) and TFA (0.5 mL) was added, the mixture was left to stir at room temperature overnight, then evaporated under reduced pressure and purified by HPLC (Method A) to give the title compound (2 mg, 2% yield). LCMS: RT 1.76 min, MI 339, Method (1LCMS1); $^1$H NMR (400 MHz, MeOD) δ 8.82 (2H, d), 8.03 (2H, d), 5.27 (1H, d), 5.18 (1H, d), 3.58 (2H, m), 3.39 (3H, m), 1.16 (9H, s).

Synthesis of 1-[5-chloro-2-(2-fluoro-4-pyridyl)-6-oxo-1H-pyrimidin-4-yl]-1,4-diazepan-6-one 2,2,2-trifluoroacetic acid (412)

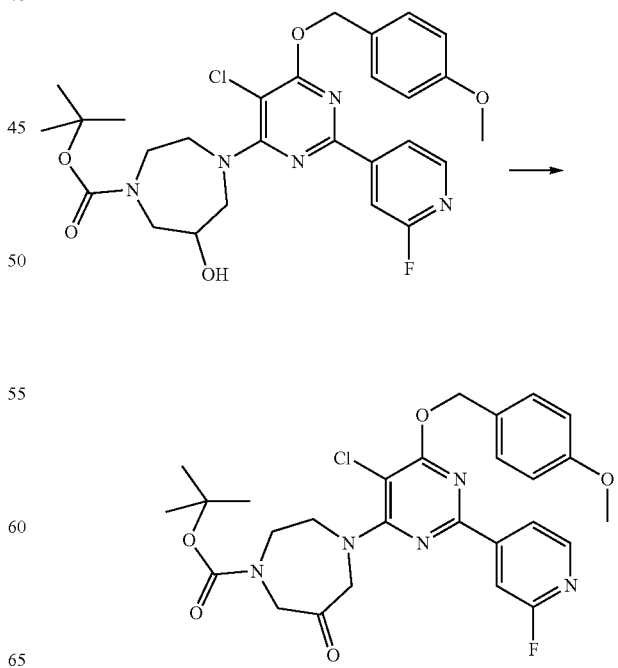

285

Synthesis of tert-butyl 4-[5-chloro-2-(2-fluoro-4-pyridyl)-6-[(4-methoxyphenyl)methoxy]pyrimidin-4-yl]-6-oxo-1,4-diazepane-1-carboxylate (11-005)

A solution of tert-butyl 4-[5-chloro-2-(2-fluoro-4-pyridyl)-6-[(4-methoxyphenyl)methoxy]pyrimidin-4-yl]-6-hydroxy-1,4-diazepane-1-carboxylate (0.45 g, 0.8 mmol) (prepared according to scheme 7) in DCM (4 mL) was stirred at room temperature. Dess Martin periodinane (0.38 g, 0.88 mmol) was added and the mixture was stirred at room temperature for 2 h. After this time a saturated solution of $Na_2S_2O_3$ was added and then a saturated solution of $NaHCO_3$. The mixture was extracted with EtOAc (2×10 mL), the extracts were combined, washed with a saturated solution of NaHCO3, dried ($Na_2SO_4$), filtered and then evaporated under reduced pressure. Purification by chromatography (cHex/EtOAc 1/0 to 50/50) gave the title compound (0.295 g, 66%) as a white solid. LCMS: RT 3.77 min, MI 558.1, Method (1LCMS13).

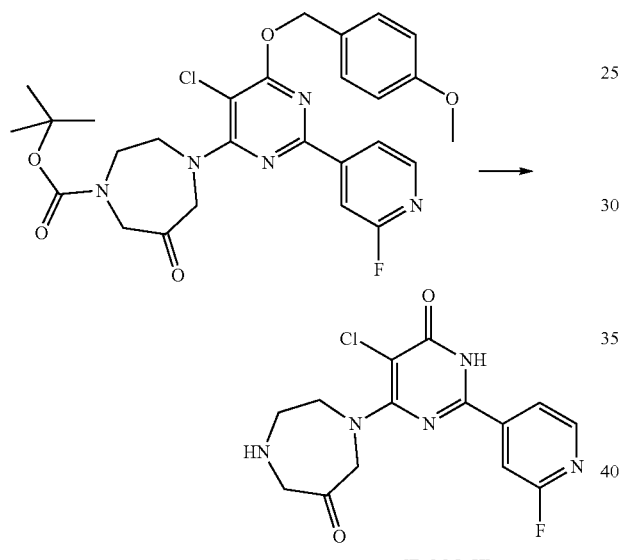

Synthesis of 1-[5-chloro-2-(2-fluoro-4-pyridyl)-6-oxo-1H-pyrimidin-4-yl]-1,4-diazepan-6-one 2,2,2-trifluoroacetic acid (412)

To a solution of tert-butyl 4-[5-chloro-2-(2-fluoro-4-pyridyl)-6-[(4-methoxyphenyl)methoxy]pyrimidin-4-yl]-6-oxo-1,4-diazepane-1-carboxylate (11-005) (0.1 g, 0.179 mmol) in chloroform (2 mL) was added trifluoroacetic acid (0.14 mL, 1.792 mmol) and the reaction mixture was stirred at room temperature for 6 h. The reaction mixture was concentrated under vacuum and the residue was dissolved in a minimum volume of MeOH. $Et_2O$ was then added dropwise under vigorous stirring until no further precipitation occurred. The yellow solid was collected by filtration to give the title compound (0.061 g, 75% yield). LCMS: RT 1.70, 1.89 min, (split peak) MI 356.1, Method (1LCMS12). $^1$H NMR (300 MHz, d6-DMSO, 80° C.) δ 8.42 (d, J=3.9 Hz, 1H), 7.92 (dt, J=3.9 and 1.2 Hz, 1H), 7.67 (s, 1H), 4.41 (m, 2H), 4.28 (t, J=3.6 Hz, 2H), 3.36 (t, J=3.6 Hz, 4H).

286

Synthesis of 5-chloro-2-(4-pyridyl)-4-(2,2,6,6-tetrafluoromorpholin-4-yl)-1H-pyrimidin-6-one (413)

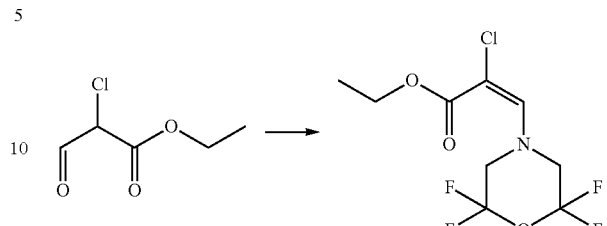

Synthesis of ethyl-2-chloro-3-(2,2,6,6-tetrafluoromorpholin-4-yl)prop-2-enoate (11-006)

A mixture of 2,2,6,6-tetrafluoromorpholine (0.41 g, 2.557 mmol) in DCM (12.8 mL) was stirred at room temperature, ethyl 2-chloro-3-oxo-propanoate (0.4 g, 2.684 mmol) was added and the reaction mixture was left to stir at room temperature for 24 h. The crude reaction mixture was evaporated under reduced pressure and the crude product was used in the next step without further purification. LCMS: RT 4.50 min, MI 292.6/294.6, Method (1LCMS12).

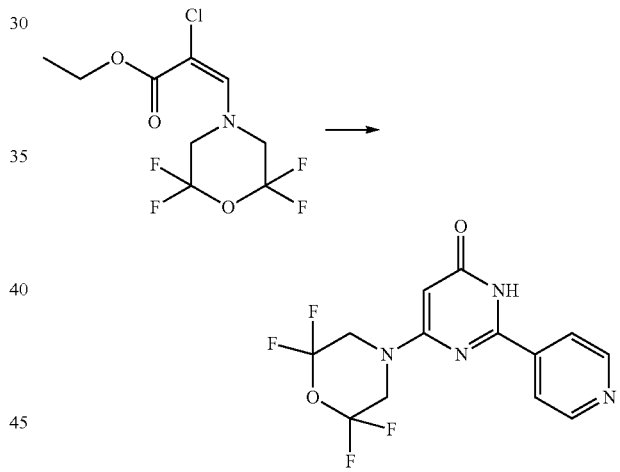

Synthesis of 2-(4-pyridyl)-4-(2,2,6,6-tetrafluoromorpholin-4-yl)-1H-pyrimidin-6-one (11-007)

1,8-Diazabicyclo[5.4.0]undec-7-ene (0.38 mL, 2.572 mmol) was added to a mixture of pyridine-4-carboximidamide hydrochloride (0.23 g, 1.44 mmol), ethyl (E)-2-chloro-3-(2,2,6,6-tetrafluoromorpholin-4-yl)prop-2-enoate (11-006) (0.25 g, 0.857 mmol) in methanol (2 mL). The reaction mixture was heated under microwave heating at 150° C. for 30 min. The mixture was cooled to room temperature and evaporated under reduced pressure. The resultant gum was acidified with 2 N HCl and extracted with DCM (3×10 mL). The aqueous phase was then neutralised with 2 N NaOH to give a precipitate that was collected by filtration. The solid was suspended in MeOH (10 mL), sonicated, then centrifuged for 15 min. The supernatant was discarded and the remaining solid was dried under vacuum to give the title compound (0.084 g, 29.7% yield) which was used in the next step without further purification. LCMS: RT 3.04 min, MI 331.7, Method (1LCMS12); ¹H NMR (600 MHz, DMSO-d6) δ 12.32 (s, 1H), 8.76 (d, 2H), 8.10-8.21 (m, 2H), 6.08 (s, 1H), 4.42-4.58 (m, 4H).

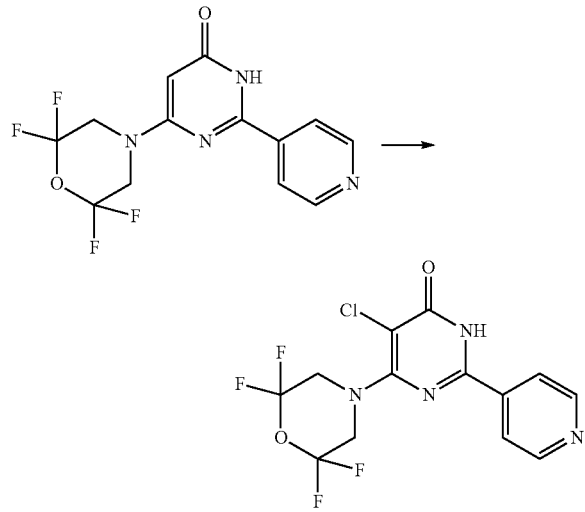

Synthesis of 5-chloro-2-(4-pyridyl)-4-(2,2,6,6-tetrafluoromorpholin-4-yl)-1H-pyrimidin-6-one (413)

To a solution of 2-(4-pyridyl)-4-(2,2,6,6-tetrafluoromorpholin-4-yl)-1H-pyrimidin-6-one (11-007) (0.07 g, 0.221 mmol) in DMA (2 mL) at 0° C. was added N-chlorosuccinimide (0.04 g, 0.265 mmol) and the reaction mixture was stirred at 0° C. for 6 h, then kept in the fridge overnight. The reaction mixture was partitioned between water (4 mL) and EtOAc (8 mL). The aqueous phase was further extracted with EtOAc (6 mL) and the combined organic phases washed with water (4 mL), brine (4 mL), dried (MgSO₄), filtered and concentrated under reduced pressure. The residue was purified by flash column chromatography on silica gel eluting with MeOH in DCM (0 to 5%) to give the title compound (0.01 g, 12.4% yield). LCMS: RT 3.47 min, MI 365.7, Method (1LCMS12); ¹H NMR (600 MHz, Methanol-d4) δ 8.68-8.80 (m, 2H), 8.01-8.16 (m, 2H), 4.36 (t, 4H).

Synthesis of 2-[4-[5-chloro-2-(2-fluoro-4-pyridyl)-6-oxo-1H-pyrimidin-4-yl]-6,6-difluoro-1,4-diazepan-1-yl]acetamide (414)

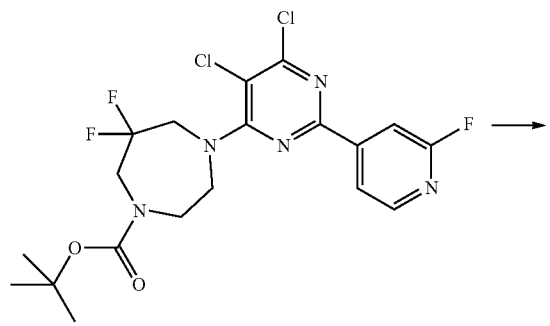

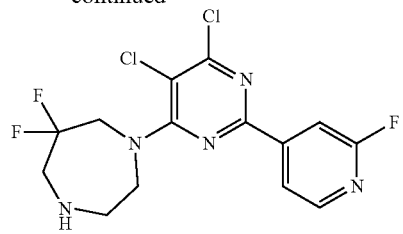

Synthesis of 1-[5,6-dichloro-2-(2-fluoro-4-pyridyl) pyrimidin-4-yl]-6,6-difluoro-1,4-diazepane (11-008)

To a solution of tert-butyl 4-[5,6-dichloro-2-(2-fluoro-4-pyridyl)pyrimidin-4-yl]-6,6-difluoro-1,4-diazepane-1-carboxylate (7-001) (0.36 g, 0.753 mmol) in chloroform (3 mL) was added TFA (0.58 mL, 7.527 mmol). The reaction mixture was allowed to stir at room temperature for 2 h. The reaction mixture was concentrated under reduced pressure and a saturated solution of NaHCO₃ was added to the residue. The precipitate was collected by filtration and the solid sonicated in MeOH, filtered and dried in a vacuum oven to give the title compound (0.165 g, 57.9% yield) as a white solid. LCMS: RT 2.18 min, MI 378.22, Method (1LCMS13); ¹H NMR (600 MHz, DMSO-d6) δ 8.41 (1H, m), 8.10 (1H, m), 7.78 (1H, m), 4.60 (2H, m), 3.91 (2H, m), 3.15 (2H, m), 3.06 (2H, m), 2.90 (1H, br s).

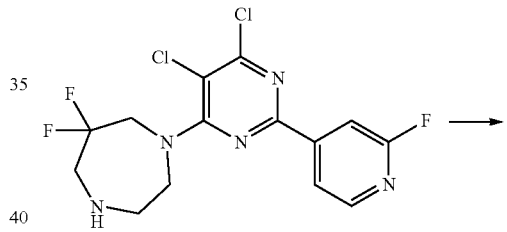

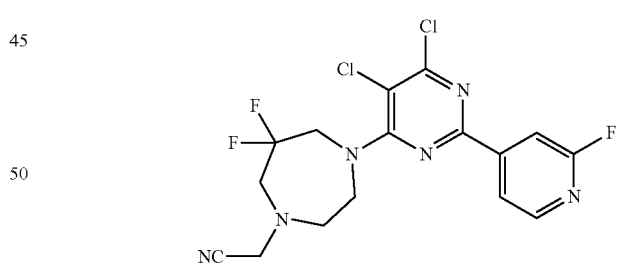

Synthesis of 2-[4-[5,6-dichloro-2-(2-fluoro-4-pyridyl)pyrimidin-4-yl]-6,6-difluoro-1,4-diazepan-1-yl]acetonitrile (11-009)

To a solution of chloroacetonitrile (0.02 g, 0.317 mmol) in chloroform (2 mL) was added 1-[5,6-dichloro-2-(2-fluoro-4-pyridyl)pyrimidin-4-yl]-6,6-difluoro-1,4-diazepane (11-008) (0.1 g, 0.264 mmol) and Et₃N (0.06 mL, 0.397 mmol). The reaction mixture was stirred at 50° C. overnight. Further chloroacetonitrile (0.02 g, 0.317 mmol) and Et₃N (0.06 mL, 0.397 mmol) were added and the mixture was left to stir at 50 C for 24 h at 50° C. The reaction mixture was cooled and evaporated under reduced pressure. The crude reaction mixture was purified by normal phase flash column chromatography on silica (eluting with EtOAc 0 to 100% in cyclohexane) to give the title compound (0.067 g, 60.7% yield) as white solid. LCMS: RT 5.16 min, MI 417.12, Method (1LCMS12); $^1$H NMR (600 MHz, DMSO-d6) δ 8.40 (1H, m), 8.10 (1H, m), 7.80 (1H, m), 4.60 (2H, m), 4.10 (2H, m), 3.91 (2H, m), 3.15 (2H, m), 3.09 (2H, m).

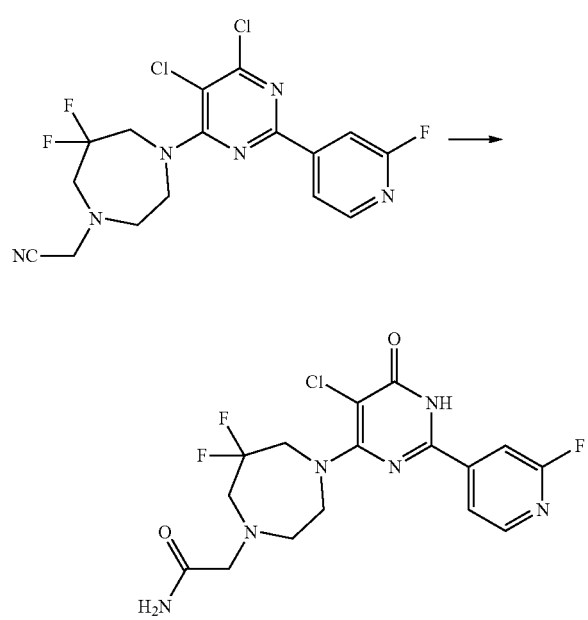 [SMILES: N#CCN1CCN(c2nc(-c3ccnc(F)c3)nc(Cl)c2Cl)CC(F)(F)C1 ; NC(=O)CN1CCN(c2nc(-c3ccnc(F)c3)[nH]c(=O)c2Cl)CC(F)(F)C1]

Synthesis of 2-[4-[5-chloro-2-(2-fluoro-4-pyridyl)-6-oxo-1H-pyrimidin-4-yl]-6,6-difluoro-1,4-diazepan-1-yl]acetamide (414)

To a solution of 2-[4-[5,6-dichloro-2-(2-fluoro-4-pyridyl)pyrimidin-4-yl]-6,6-difluoro-1,4-diazepan-1-yl]acetonitrile (11-009) (0.07 g, 0.161 mmol) in 1,4-dioxane (1 mL) was added NaOH (0.96 mL, 1.927 mmol of a 2N solution). The reaction mixture was refluxed for 3 h. The reaction mixture was cooled to room temperature and then acidified with 2 M aq HCl over an ice/bath. The yellow precipitate was removed by filtration and the supernatant was basified to pH 8-9 with NaHCO$_3$ then extracted with DCM/IPA (4/1) (3×30 mL). The combined organic phase was dried (MgSO$_4$) and filtered and concentrated under reduced pressure. The crude residue was purified by normal phase flash column chromatography on silica (eluting with EtOAc 0 to 100% in cyclohexane) followed by HPLC (Method A) to give the title compound (0.008 g, 11.9% yield) as a white solid. LCMS: RT 2.93 min, MI 417.0, Method (1LCMS12); $^1$H NMR (600 MHz, DMSO-d6) δ 13.06 (br s, 1H), 8.42 (d, J=5.6 Hz, 1H), 8.02 (d, J=4.8 Hz, 1H), 7.80 (s, 1H), 7.27 (br s, 1H), 7.16 (br s, 1H), 4.49 (m, 2H), 3.86 (m, 2H), 3.24 (s, 2H), 3.13 (t, J=13.9 Hz, 2H), 3.05 (t, J=4.9 Hz, 2H).

Synthesis of 5-chloro-4-(6,6-difluoro-4-methyl-1,4-diazepan-1-yl)-2-(2-fluoro-4-pyridyl)-1H-pyrimidin-6-one (415)

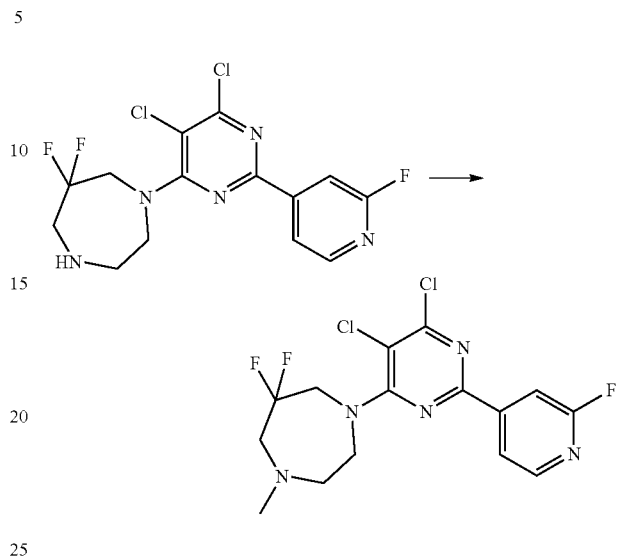

Synthesis of 1-[5,6-dichloro-2-(2-fluoro-4-pyridyl)pyrimidin-4-yl]-6,6-difluoro-4-methyl-1,4 diazepane (11-010)

A solution of 1-[5,6-dichloro-2-(2-fluoro-4-pyridyl)pyrimidin-4-yl]-6,6-difluoro-1,4-diazepane (11-008) (188 mg, 0.497 mmol), sodium triacetoxy borohydride (71 mg, 0.994 mmol) and paraformaldehyde aqueous solution (37%, 0.5 mL, 4.971 mmol) in THF (9 mL) was stirred for 3 h at room temperature. Further sodium triacetoxy borohydride (142 mg, 1.998 mmol) was added and the reaction mixture stirred for 24 h at room temperature. The reaction mixture was diluted with a saturated solution of sodium bicarbonate (aq) (100 mL) and extracted with EtOAc (100 mL). The organic extract was washed with a saturated solution of sodium bicarbonate (aq) (100 mL), brine, dried over MgSO$_4$, filtered and concentrated by rotary evaporation to give the title compound (183 mg, 94% yield) as an off-white solid. LCMS: RT 4.59 min, MI 392, Method (4LCMS1).

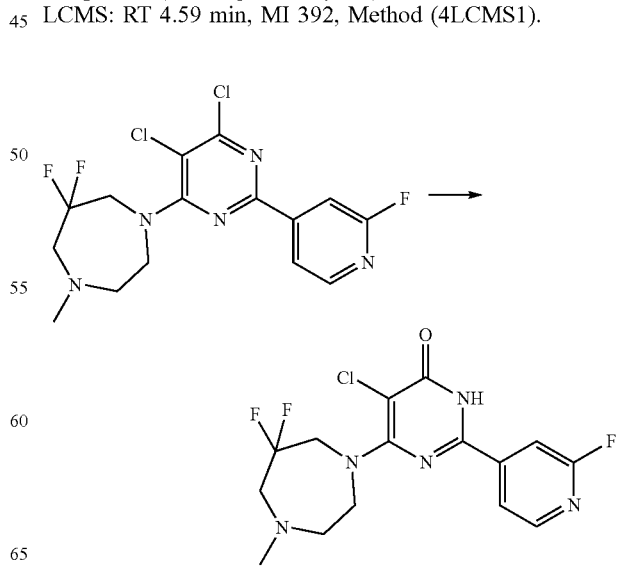

Preparation of 5-chloro-4-(6,6-difluoro-4-methyl-1,4-diazepan-1-yl)-2-(2-fluoro-4-pyridyl)-1H-pyrimidin-6-one (415)

To a solution of 1-[5,6-dichloro-2-(2-fluoro-4-pyridyl)pyrimidin-4-yl]-6,6-difluoro-4-methyl-1,4-diazepane (11-010) (280 mg, 0.714 mmol) in 1,4-dioxane (7 mL) was added NaOH (4.28 mL of a 2 M aq solution, 8.567 mmol). The reaction mixture was refluxed for 24 h. The reaction mixture was cooled to room temperature and the mixture adjusted to approx. pH 5 by addition of 2 M HCl (aq). The resulting solution was extracted with DCM (2×100 mL). The combined organic extracts were concentrated by rotary evaporation and the residue was purified by column chromatography on silica gel, eluting with cyclohexane containing 0-100% EtOAc. The appropriate fractions were combined and concentrated. The resulting solid was dried under vacuum at 40° C. for 5 days to give the title compound (13 mg, 5% yield) as an off-white solid. LCMS: RT 2.16 min, MI 374, Method (4LCMS1); $^1$H NMR (400 MHz, DMSO-d6) δ 13.04 (s, 1H), 8.45 (d, J=5.3 Hz, 1H), 8.03 (dt, J=5.3, 1.7 Hz, 1H), 7.82 (s, 1H), 4.45 (t, J=13.3 Hz, 2H), 3.93-3.81 (m, 2H), 3.00-2.87 (m, 4H), 2.43 (s, 3H).

Synthesis of 5-chloro-4-piperazin-1-yl-2-(4-pyridyl)-1H-pyrimidin-6-one hydrochloride (416)

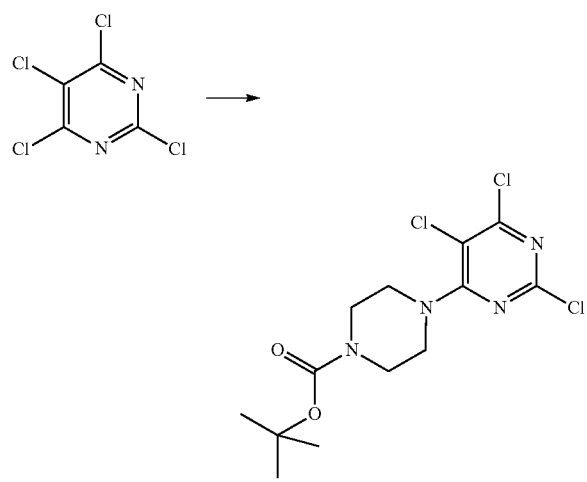

Synthesis of 4-(2,5,6-trichloro-pyrimidin-4-yl)-piperazine-1-carboxylic acid tert-butyl ester (11-011)

To a stirred clear brown solution of 2,4,5,6-tetrachloropyrimidine (23.0 mmol, 5.01 g) and boc-piperazine (23.08 mmol. 4.30 g) in ethanol (150 mL), at room temperature, was added triethylamine (31.7 mmol, 3.20 g). An exotherm was observed. The mixture was left to stir at room temperature overnight. The mixture was concentrated under reduced pressure to give a white solid. Water (300 mL) was poured into the mixture to dissolve the triethylamine hydrochloride and the mixture was stirred at room temperature for 30 min and the precipitate was collected by filtration to give the title compound (8.42 g, 100% yield).

LCMS: RT 5.74 min, MI 367, Method (4LCMS1); $^1$H NMR (400 MHz, CDCl$_3$) δ 3.75 (t, J=5.2 Hz, 4H), 3.59-3.54 (m, 4H), 1.48 (s, 9H).

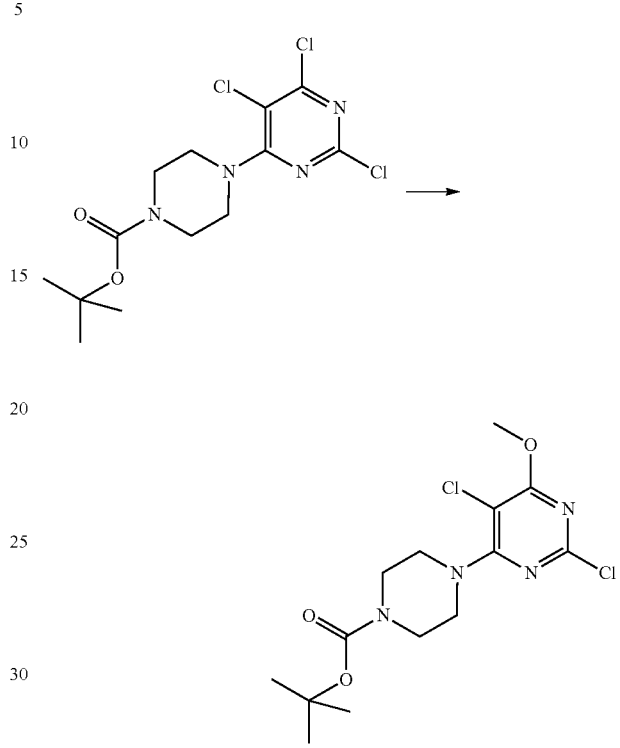

Synthesis of 4-(2,5-dichloro-6-methoxy-pyrimidin-4-yl)-piperazine-1-carboxylic acid tert-butyl ester (11-012)

A mixture of 4-(2,5,6-trichloro-pyrimidin-4-yl)-piperazine-1-carboxylic acid tert-butyl ester (11-011) (8.16 mmol, 3.00 g) and sodium methoxide (8.15 mmol, 0.44 g) in methanol (80 mL) was heated at reflux overnight. The mixture was concentrated under reduced pressure and the crude mixture adsorbed onto silica gel and purified by flash chromatography on silica gel (eluting with cyclohexane/ethyl acetate) to afford the title compound (1.4 g, 47% yield). LCMS: RT 5.57 min, MI 363, Method (4LCMS1); $^1$H NMR (400 MHz, CDCl$_3$) δ 4.03 (s, 3H), 3.64 (t, 4H), 3.55-3.52 (m, 4H), 1.54 (s, 9H).

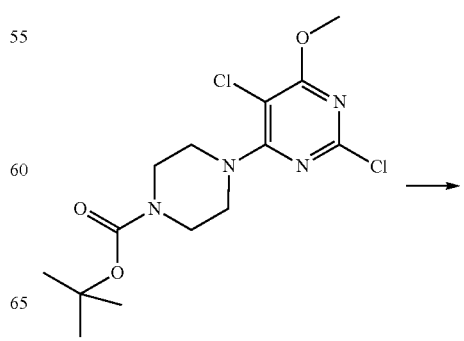

-continued

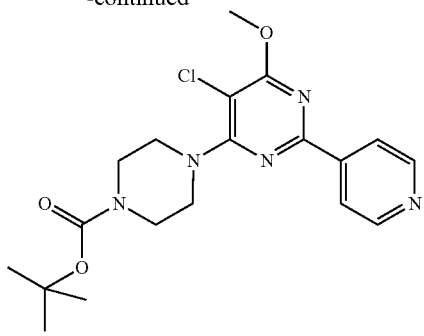

Synthesis of 4-(5-chloro-6-methoxy-2-pyridin-4-yl-pyrimidin-4-yl)-piperazine-1-carboxylic acid tert-butyl ester (11-013)

A mixture of 4-(2,5-dichloro-6-methoxy-pyrimidin-4-yl)-piperazine-1-carboxylic acid tert-butyl ester (11-012) (2.75 mmol, 0.999 g), pyridin-4-boronic acid (2.77 mmol, 0.34 g), (Ph$_3$P)$_2$PdCl$_2$ (0.142 mmol, 0.10 g) and potassium carbonate (7.97 mmol, 1.10 g) was combined in a 3:1 mixture of 1,-4-dioxane and water (20 mL) and irradiated with microwaves for 30 minutes at 130° C. The reaction mixture was concentrated under reduced pressure and the crude mixture was adsorbed onto silica gel and purified by flash chromatography on silica gel (eluting with cyclohexane/ethyl acetate) to afford the title compound (0.87 g, 78% yield) as a yellow solid. $^1$H NMR (400 MHz, CDCl$_3$) δ 8.78-8.69 (m, 2H), 8.19 (d, J=6.1 Hz, 2H), 4.15 (s, 3H), 3.70 (dd, J=6.6, 3.5 Hz, 4H), 3.65-3.58 (m, 4H), 1.50 (s, 9H).

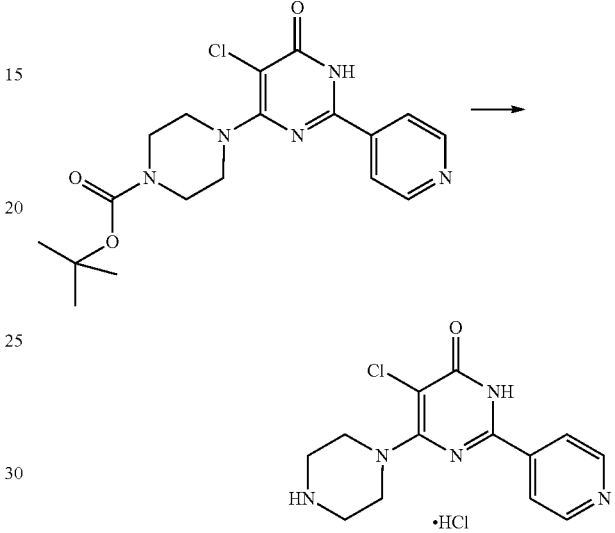

Synthesis of 4-(5-chloro-6-oxo-2-pyridin-4-yl-1,6-dihydro-pyrimidin-4-yl)-piperazine-1-carboxylic acid tert-butyl ester (11-014)

A mixture of 4-(5-chloro-6-methoxy-2-pyridin-4-yl-pyrimidin-4-yl)-piperazine-1-carboxylic acid tert-butyl ester (11-013) (3.37 mmol, 1.37 g) and sodium hydroxide pellets (33.7 mmol, 1.35 g) in 2-methoxyethanol (20 mL) was irradiated with microwaves at 150° C. for 30 min. The reaction mixture was concentrated under reduced pressure to give a black gum. This was adsorbed onto silica gel and purified by flash chromatography on silica gel (eluting with 5% methanol in dichloromethane, then 100% methanol) to afford the title compound (0.74 g, 56% yield). LCMS: RT 3.56 min, MI 392, Method (4LCMS1).

Synthesis of 5-chloro-4-piperazin-1-yl-2-(4-pyridyl)-1H-pyrimidin-6-one hydrochloride (416)

To a clear, yellow solution of 4-(5-chloro-6-oxo-2-pyridin-4-yl-1,6-dihydro-pyrimidin-4-yl)-piperazine-1-carboxylic acid tert-butyl ester (11-014) (0.740 mmol, 0.290 g) in 1,4-dioxane (20 mL), at room temperature, was added, dropwise over 2 minutes, hydrochloric acid in 1,4-dioxane (4 M, 1 mL) to give a light brown precipitate. The mixture was concentrated under reduced pressure. The residue was washed with diethyl ether and collected by filtration to afford the title compound (0.146 g, 54% yield) as a yellow solid. LCMS: RT 0.92 min, MI 292, Method (4LCMS5); $^1$H NMR (400 MHz, MeOD) δ 9.01-8.97 (m, 2H), 8.87-8.82 (m, 2H), 4.07-3.95 (m, 4H), 3.48-3.37 (m, 4H).

Assays and Model Systems and Methods

The compounds disclosed herein were tested for their ability to inhibit the activity of Cdc7 according to the methods described below. In general, the compounds of Formula I were found to effectively inhibit the activity of Cdc7.

Cdc7 Biochemical Assays

Method 1

This protocol describes a method for assaying Cdc7/ASK for activity. The assay is a 384 well ELISA assay, utilising a whole protein substrate (MCM2) and an antibody against Phospho MCM2 (S53). This site is thought to be specific to Cdc7/ASK phosphorylation and the assay has been validated using knockout mutants.

Reagents
TBS: 25 mM Tris pH 7.2, 150 mM NaCl. (Dilute 10× stock by 1:10).
Wash Buffer: TBS+0.05% Tween 20. (Add 100 mL 1 M Tris pH 7.2, 120 mL 5 M NaCl and 2 mL 100% Tween 20 per 4 L).
Kinase Reaction Buffer: 50 mM Tris-HCl pH 8.5, 10 mM $MgCl_2$, 1 mM DTT. (Dilute 10× stock by 1:10 and add 100 μL 1M DTT per 100 mL prior to assay).
Diethanolamine Buffer: 1 M diethanolamine pH 9.8, 0.5 mM $MgCl_2$.
Stop Solution: 1 M NaOH.
MCM2 was expressed and purified in-house and used in the assay at a final assay concentration of 436 ng/well.
Cdc7/ASK is purchased from commercial suppliers and used in the assay at a final assay concentration of 37.97 ng/well or 20.63 nM.
ATP used as a final assay concentration of 2 μM.
Primary Antibody: Rabbit anti-Phospho MCM2 (S53 Antibody (BL3353)), is purchased from commercial suppliers at 0.2 mg/mL and used at a final assay concentration by diluting 1:800 in TBS.
Secondary Antibody: Anti-Rabbit/AP Antibody is supplied is purchased from commercial suppliers at 1 mg/mL and used at a final assay concentration by diluting 1:2000 in TBS.
Development Reagent: Dissolve one 20 mg PNPP tablet (Sigma, product N2765, 20 mg per tablet) per 20 mL diethanolamine Buffer (or one 5 mg PNPP tablet per 5 mL diethanolamine buffer). Cover in foil and leave shaking on a roller shaker at room temperature for up to an hour to dissolve.

Methods
1. Add 20 μL 1× working stock of Substrate (MCM2) in TBS to all wells of a clear, 384 well, Nickel-chelate microplate to give a final concentration of 250 ng/well. Incubate at room temperature for at least 1 hour. Plates can be pre-coated for 1 hour and stored at 4° C. for up to 8 days.
2. Wash with TBS+0.05% Tween 20 (80 μL×3).
3. Add 2 μL 10× test compounds, including the positive control, in 40% DMSO/water to 'test' wells. Add 2 μL 40% DMSO/water to 'control' and 'blank' wells. The final DMSO concentration will be 4%.
4. Add 13 μL CDC7/ASK Kinase (1.5× stock) in Kinase Reaction Buffer to 'test' and 'control' wells to give a final concentration of 5 ng/well. Add 13 μL Kinase Reaction Buffer to 'blank' wells.
5. Add 5 μL ATP (4× stock) in Kinase Reaction Buffer to all wells to give a final concentration of 2 μM.
6. Incubate at room temperature for 90 minutes.
7. Wash with TBS+0.05% Tween 20 (80 μL×3).
8. Add 20 μL 1× working solution of Primary Antibody in TBS to all wells. Incubate at room temperature for 30 minutes.
9. Wash with TBS+0.05% Tween 20 (80 μL×3).
10. Add 20 μL 1× working solution of Secondary Antibody in TBS to all wells. Incubate at room temperature for 30 minutes.
11. Wash with TBS+0.05% Tween 20 (80 μL×3).
12. Add 20 μL 1× Development Reagent to all wells.
13. Incubate at room temperature for 2 hours. Stop the reaction by adding 20 μL Stop Solution to all wells and record Absorbance on a Pherastar plate reader.

Percentage inhibition values were calculated from absorbance values, using the no compound (DMSO) and no enzyme control values as 0% and 100% inhibition, respectively. $IC_{50}$ determination was performed with ExcelFit software (IDBS) using curve fit 205. Z' factors were determined for each plate tested and were all above 0.5.

Method 2

This protocol describes a method for assaying Cdc7/ASK for activity. The assay is a 384 well mobility shift assay (MSA) run on the EZ Reader II microfluidics plate reader (Caliper LifeSciences), utilising a peptide substrate based on the MCM2 sequence. The assay technology is based on the change in mobility between the peptide substrate and the phosphorylated product. A 10 nL volume of the reaction mixture is sipped onto the microfluidic chip where the substrate and product are separated by electrophoresis and detected via laser-induced fluorescence (488 nm LED). The reaction can be monitored in real-time for kinetic experiments or as an end-point for $IC_{50}$ determinations. The % conversion of substrate is calculated from peak heights of product (P) and substrate (S) peptides (% conversion=P/(P+S)*100).

Reagents
10× Assay Buffer: 200 mM HEPES pH 8, 100 mM $MgCl_2$, 0.1% v/v Triton X-100 and 15 mM DTT. Prepare fresh buffer from 1 M HEPES pH 8, 1 M $MgCl_2$, 1 M DTT and 10% Triton x-100 stocks for each experiment.
Cdc7/ASK is purchased from commercial suppliers and used in the assay at a final assay concentration of 0.847 ng/μL or 9.2 nM.
MCM2 peptide is purchased from commercial suppliers and used in the assay at a final assay concentration of 2.5 μM.
ATP used in the assay at a final assay concentration of 12.5 μM.

Methods
1. Prepare intermediate (daughter) compound plate by transferring 2 μL of compound from the mother plate to 18 μL of 33.3% DMSO in a clear polypropylene plate.
2. Dry-spot 1 μL of compound from the intermediate compound plate to empty assay plate.
3. Add 5 μL of 1.694 ng/μL CDC7/ASK working solution to 'test' and 'control' wells or 10 μL of 2× Assay Buffer to 'blank' wells.
4. Add 4 μL 2.5 μM peptide/12.5 μM ATP working solution to all wells.
5. Incubate at 37° C. for 1 hour then remove from the incubator and leave for a further 1 hour at room temperature.
6. Place plate into an EZReader II to read.

Percentage inhibition values were calculated from % of substrate conversion values, using the no compound (DMSO) and no enzyme control values as 0% and 100% inhibition, respectively. $IC_{50}$ determination was performed with ExcelFit software (IDBS) using curve fit 205. Z' factors were determined for each plate tested and were all above 0.5.

Method 3

This protocol describes a method for assaying a compounds' ability to inhibit Cdc7 activity by measuring pS40MCM2 levels in a Cdc7/Dbf4 Enzyme TR-FRET Assay.

2.5 nM Cdc7/Dbf4 was incubated with 100 nM of biotin-labelled peptide 35-TDALTS(pS)PGRDLP in the presence of 1 μM ATP at 25° C. for 120 minutes. The phosphorylation of the peptide was detected using TR-FRET. Anti-Mcm2 (pS40) antibody, Terbium anti-rabbit secondary antibody and Streptavidin-Alexa Fluor488 form the detection system.

Method 4
This protocol describes a method for assaying Cdc7/ASK for activity. The assay is an off-chip mobility shift assay (MSA) run at Carna Biosciences.
Materials and Methods
  1. Preparation of Test Compound Solution.
  The test compound was dissolved in and diluted with dimethylsulfoxide (DMSO) to achieve 100-fold higher concentration which was specified by the sponsor. Then the solution was further 25-fold diluted with assay buffer to make the final test compound solution. Reference compounds for assay control were prepared similarly.
  2. Kinase
  Cdc7/ASK: Full-length human Cdc7 [1-574(end) amino acids of accession number NP_003494.1] was co-expressed as N-terminal GST-fusion protein (92 kDa) with Dbf4(ASK) [1-674(end) amino acids of accession number NP_006707.1] using baculovirus expression system. GST-Cdc7 was purified by using glutathione sepharose chromatography.
  3. Assay Reagents and Procedures
  Off-chip Mobility Shift Assay (MSA)
  1) The 5 mL of ×4 compound solution, 5 mL of ×4 Substrate/ATP/Metal solution, and 10 mL of ×2 kinase solution were prepared with assay buffer (20 mM HEPES, 0.01% Triton X-100, 1 mM DTT, pH 7.5) and mixed and incubated in a well of polypropylene 384 well microplate for 5 hours at room temperature.
  2) 70 mL of Termination Buffer (QuickScout Screening Assist MSA; Carna Biosciences) was added to the well.
  3) The reaction mixture was applied to LabChip system (Perkin Elmer), and the product and substrate peptide peaks were separated and quantitated.
  4) The kinase reaction was evaluated by the product ratio calculated from peak heights of product (P) and substrate (S) peptides (P/(P+S)).
  4. Reaction Conditions

| Kinase | Platform | Substrate Name | (nM) | ATP ($\mu$M) Km | Assay | Metal Name | (mM) | Positive control |
|---|---|---|---|---|---|---|---|---|
| Cdc7/ASK | MSA | MCM2 peptide | 1000 | 2.8 | 5 | Mg | 10 | Staurosporine |

Reaction time is 5 hours.
5. Data Analysis
The readout value of reaction control (complete reaction mixture) was set as a 0% inhibition, and the readout value of background (Enzyme(−)) was set as a 100% inhibition, then the percent inhibition of each test solution was calculated.
$IC_{50}$ value was calculated from concentration vs. % Inhibition curves by fitting to a four parameter logistic curve.

| Product Number | Biochemical Method 1 ($pIC_{50}$) | Biochemical Method 2 ($pIC_{50}$) | Biochemical Method 3 ($pIC_{50}$) | Biochemical Method 4 ($pIC_{50}$) |
|---|---|---|---|---|
| 1 | 7.15 | | | |
| 2 | 8.76 | | | |
| 3 | 8.17 | | | |
| 4 | 6.48 | | | |
| 5 | 8.20 | | | |
| 6 | 8.84 | | | |
| 7 | 5.61 | | | |
| 8 | 8.44 | | | |
| 9 | 8.47 | | | |
| 10 | 8.52 | | | |
| 11 | 8.28 | | | |
| 12 | 7.70 | | | |
| 13 | 8.91 | | 9.12 | |
| 14 | 6.91 | | | |
| 15 | 6.08 | | | |
| 16 | 7.89 | | | |
| 17 | 8.63 | | | |
| 18 | 9.10 | | | |
| 19 | 8.47 | | | |
| 20 | 6.46 | | | |
| 21 | 8.82 | | | |
| 22 | 7.13 | | | |
| 23 | 7.72 | | | |
| 24 | 5.99 | | | |
| 25 | 7.63 | | | |
| 26 | 8.17 | | | |
| 27 | 7.67 | | | |
| 28 | 7.95 | | | |
| 29 | 5.90 | | | |
| 30 | 6.88 | | | |
| 31 | 7.40 | | | |
| 32 | 7.00 | | | |
| 33 | 7.89 | | | |
| 34 | 7.88 | | | |
| 35 | 7.64 | | | |
| 36 | 7.59 | | | |
| 37 | 7.52 | | | |
| 38 | 8.25 | | | |
| 39 | 8.08 | | 8.24 | |
| 40 | 8.09 | | | |
| 41 | 8.16 | | | |
| 42 | 8.29 | | | |
| 43 | 8.50 | | | |
| 44 | 7.20 | | | |
| 45 | 8.06 | | | |
| 46 | 8.85 | | | |
| 47 | 8.95 | | | |
| 48 | 8.59 | | | |
| 49 | 7.80 | | | |
| 50 | 8.51 | | | |
| 51 | 8.29 | | | |
| 52 | 8.58 | | | |
| 53 | 8.24 | | | |
| 54 | 9.06 | | | |
| 55 | 8.68 | | | |
| 56 | 8.79 | | | |
| 57 | 8.46 | | | |
| 58 | 9.04 | | | |
| 59 | 8.59 | | | |
| 60 | 8.72 | | | |
| 61 | 8.21 | | | |
| 62 | 7.92 | | | |
| 63 | 8.49 | | | |
| 64 | 8.40 | | | |
| 65 | 8.23 | | | |
| 66 | 7.83 | | | |

| Product Number | Biochemical Method 1 (pIC$_{50}$) | Biochemical Method 2 (pIC$_{50}$) | Biochemical Method 3 (pIC$_{50}$) | Biochemical Method 4 (pIC$_{50}$) |
|---|---|---|---|---|
| 67 | 8.81 | | | |
| 68 | 8.57 | | | |
| 69 | 8.45 | | | |
| 70 | 7.80 | | | |
| 71 | 7.84 | | | |
| 72 | 8.16 | | | |
| 73 | 8.29 | | | |
| 74 | 6.61 | | | |
| 75 | 8.04 | | | |
| 76 | 8.46 | | | |
| 77 | 8.53 | | | |
| 78 | 8.64 | | | |
| 79 | 7.99 | | | |
| 80 | 6.91 | | | |
| 81 | 8.03 | | | |
| 82 | 7.50 | | | |
| 83 | 6.78 | | | |
| 84 | 7.63 | | | |
| 85 | 7.32 | | | |
| 86 | 6.86 | | | |
| 87 | 8.52 | | | |
| 88 | 7.85 | | | |
| 89 | 8.64 | | | |
| 90 | 9.07 | | 9.45 | |
| 91 | 7.18 | | | |
| 92 | 7.08 | | | |
| 93 | 6.39 | | | |
| 94 | 8.16 | | | |
| 95 | 7.17 | | | |
| 96 | 7.37 | | | |
| 97 | 6.70 | | | |
| 98 | 7.07 | | | |
| 99 | 7.07 | | | |
| 100 | 7.92 | | | |
| 101 | 8.36 | | | |
| 102 | 7.28 | | | |
| 103 | 7.53 | | | |
| 104 | 8.42 | | | |
| 105 | 7.85 | | | |
| 106 | 8.12 | | | |
| 107 | 8.15 | | | |
| 108 | 6.76 | | | |
| 109 | 8.44 | | | |
| 110 | 6.18 | | | |
| 111 | 7.79 | | | |
| 112 | 8.21 | | | |
| 113 | 7.54 | | | |
| 114 | 7.72 | | | |
| 115 | 6.64 | | | |
| 116 | 7.90 | | | |
| 117 | 8.28 | | | |
| 118 | 6.42 | | | |
| 119 | 8.45 | | | |
| 120 | 6.61 | | | |
| 121 | 8.25 | | | |
| 122 | 8.18 | | | |
| 123 | 8.03 | | | |
| 124 | 6.58 | | | |
| 125 | 7.39 | | | |
| 126 | 7.27 | | | |
| 127 | 7.34 | | | |
| 128 | 8.59 | | | |
| 129 | 8.68 | | | |
| 130 | 8.59 | | 8.63 | |
| 131 | 8.09 | | | |
| 132 | 8.71 | | | |
| 133 | 7.25 | | | |
| 134 | 7.72 | | | |
| 135 | 7.63 | | | |
| 136 | 7.70 | | | |
| 137 | 6.23 | | | |
| 138 | 7.00 | | | |
| 139 | 8.02 | | 8.39 | |
| 140 | 8.22 | | | |
| 141 | 6.84 | | | |
| 142 | 7.81 | | | |
| 143 | 7.67 | | | |
| 144 | 8.03 | | | |
| 145 | 8.60 | | | |
| 146 | 8.14 | | | |
| 147 | 8.37 | | 8.81 | |
| 148 | 7.47 | | | |
| 149 | 7.88 | | | |
| 150 | 7.85 | | | |
| 151 | 7.46 | | | |
| 152 | 7.71 | | | |
| 153 | 8.75 | | | |
| 154 | 8.61 | | | |
| 155 | 6.01 | | | |
| 156 | 8.40 | | | |
| 157 | 8.53 | | | |
| 158 | 7.71 | | | |
| 159 | 8.18 | | | |
| 160 | 8.79 | | | |
| 161 | 7.50 | | 8.76 | |
| 162 | 6.81 | | | |
| 163 | 7.17 | | | |
| 164 | 7.68 | | | |
| 165 | 6.90 | | | |
| 166 | 7.45 | | | |
| 167 | 8.09 | | | |
| 168 | 8.03 | | 8.72 | |
| 169 | 7.52 | | | |
| 170 | 8.96 | 8.93 | 8.98 | |
| 171 | 8.93 | | | |
| 172 | 7.90 | | | |
| 173 | 7.07 | | | |
| 174 | 7.51 | | | |
| 175 | 7.24 | | | |
| 176 | 7.68 | | | |
| 177 | 8.29 | | | |
| 178 | 8.37 | | | |
| 179 | 7.63 | | | |
| 180 | 8.84 | | 8.86 | |
| 181 | 8.62 | | | |
| 182 | 8.66 | | | |
| 183 | | | 9.29 | |
| 184 | 6.36 | 6.77 | 6.99 | |
| 185 | 9.11 | 9.11 | 9.14 | |
| 186 | 8.51 | 8.41 | | |
| 187 | | | 8.73 | |
| 188 | | | 8.76 | |
| 189 | | | 8.79 | |
| 190 | | | 9.15 | |
| 191 | | | 8.43 | |
| 192 | | | 9.09 | |
| 193 | | | 8.54 | |
| 194 | | | 7.84 | |
| 195 | | | 8.88 | |
| 196 | | | 8.72 | |
| 197 | | | 8.62 | |
| 198 | | | 7.18 | |
| 199 | | | 6.41 | |
| 200 | | | 8.09 | |
| 201 | | | 8.38 | |
| 202 | | | 8.00 | |
| 203 | | | 8.53 | |
| 204 | | | 8.39 | |
| 205 | | | 8.85 | |
| 206 | | | 10.01 | |
| 207 | | | 8.89 | |
| 208 | | | 9.31 | |
| 209 | | | 7.07 | |
| 210 | | | 8.36 | |
| 211 | | | 7.76 | |
| 212 | | | 7.10 | |
| 213 | | | 7.27 | |
| 214 | | | 7.83 | |
| 215 | | | 7.85 | |
| 216 | | | 8.77 | |

301 -continued

| Product Number | Biochemical Method 1 (pIC$_{50}$) | Biochemical Method 2 (pIC$_{50}$) | Biochemical Method 3 (pIC$_{50}$) | Biochemical Method 4 (pIC$_{50}$) |
|---|---|---|---|---|
| 217 | | | 7.34 | |
| 218 | | | 8.09 | |
| 219 | | | 8.17 | |
| 220 | | | 7.81 | |
| 221 | | | 8.54 | |
| 222 | | | 7.87 | |
| 223 | | | 8.54 | |
| 224 | | | 6.14 | |
| 225 | | | 8.68 | |
| 226 | | | 8.52 | |
| 227 | | | 8.65 | |
| 228 | | | 7.27 | |
| 229 | | | 8.07 | |
| 230 | | | 8.18 | |
| 231 | | | 8.54 | |
| 232 | | | 8.99 | |
| 233 | | | 8.66 | |
| 234 | | | 8.86 | |
| 235 | | | 8.92 | |
| 236 | | | 7.84 | |
| 237 | | | 8.10 | |
| 238 | | | 8.28 | |
| 239 | | | 8.96 | |
| 240 | | | 8.43 | |
| 241 | | | 8.66 | |
| 242 | | | 8.94 | |
| 243 | | | 8.70 | |
| 244 | | | 8.36 | |
| 245 | | | 8.69 | |
| 246 | | | 6.00 | |
| 247 | | | 8.34 | |
| 248 | | | 7.37 | |
| 249 | | | 8.03 | |
| 250 | | | 8.01 | |
| 251 | | | 8.39 | |
| 252 | | | 9.21 | |
| 253 | | | 8.13 | |
| 254 | | | 8.62 | |
| 255 | | | 8.15 | |
| 256 | | | 8.70 | |
| 257 | | | 8.22 | |
| 258 | | | 9.08 | |
| 259 | | | 8.55 | |
| 260 | | | 8.85 | |
| 261 | | | 9.09 | |
| 262 | | | 9.07 | |
| 263 | | | 7.96 | |
| 264 | | | 8.80 | |
| 265 | | | 8.39 | |
| 266 | | | 7.44 | |
| 267 | | | 8.41 | |
| 268 | | | 8.37 | |
| 269 | | | 9.28 | |
| 270 | | | 7.68 | |
| 271 | | | 8.83 | |
| 272 | | | 8.26 | |
| 273 | | | 9.19 | |
| 274 | | | 8.30 | |
| 275 | | | 9.10 | |
| 276 | | | 8.20 | |
| 277 | | | 8.97 | |
| 278 | | | 7.83 | |
| 279 | | | 9.14 | |
| 280 | | | 9.06 | |
| 281 | | | 8.98 | |
| 282 | | | 8.58 | |
| 283 | | | 8.27 | |
| 284 | | | 8.68 | |
| 285 | | | 8.04 | |
| 286 | | | 9.64 | |
| 287 | | | 7.72 | |
| 288 | | | 9.03 | |
| 289 | | | 7.02 | |
| 290 | | | 6.45 | |
| 291 | | | 8.38 | |

302 -continued

| Product Number | Biochemical Method 1 (pIC$_{50}$) | Biochemical Method 2 (pIC$_{50}$) | Biochemical Method 3 (pIC$_{50}$) | Biochemical Method 4 (pIC$_{50}$) |
|---|---|---|---|---|
| 292 | | | 7.94 | |
| 293 | | | 9.44 | |
| 294 | | | 6.74 | |
| 295 | | | 9.05 | |
| 296 | | | 8.12 | |
| 297 | | | 8.49 | |
| 298 | | | 8.39 | |
| 299 | | | 8.19 | |
| 300 | | | 8.52 | |
| 301 | | | 7.98 | |
| 302 | | | 7.60 | |
| 303 | | | 8.68 | |
| 304 | | | 8.86 | |
| 305 | | | 8.70 | |
| 306 | | | 8.89 | |
| 307 | 8.44 | 8.64 | | |
| 308 | 9.10 | 9.04 | | |
| 309 | 8.70 | | | |
| 310 | 8.46 | | | |
| 311 | | | 8.68 | |
| 312 | | | 9.23 | 8.43 |
| 313 | | | | 8.07 |
| 314 | 8.95 | 9.24 | | |
| 315 | | 8.82 | | |
| 316 | 8.88 | | 9.28 | |
| 317 | | 8.99 | 9.17 | |
| 318 | | 7.85 | | |
| 319 | | 8.82 | 9.03 | |
| 320 | | 8.43 | 9.10 | |
| 321 | | 8.64 | | |
| 322 | | 8.86 | | |
| 323 | | 9.24 | 9.27 | 8.51 |
| 324 | | | 7.84 | |
| 325 | | | 7.95 | |
| 326 | | | 9.31 | |
| 327 | | | 8.18 | |
| 328 | | | 9.24 | |
| 329 | | | 9.21 | |
| 330 | | | 9.02 | |
| 331 | | | 8.02 | |
| 332 | | | 8.20 | |
| 333 | | | 8.91 | |
| 334 | | | 9.14 | |
| 335 | | | 8.96 | |
| 336 | | | 8.74 | |
| 337 | | | 8.95 | |
| 338 | | | 9.15 | |
| 339 | | | 9.32 | |
| 340 | | | 8.60 | |
| 341 | | | 8.18 | |
| 342 | | | 6.89 | |
| 343 | | | 8.17 | |
| 344 | | | 8.56 | |
| 345 | | | 8.89 | |
| 346 | | | 8.98 | |
| 347 | | | 8.44 | |
| 348 | | | 8.71 | |
| 349 | | | 7.08 | |
| 350 | | | 8.66 | |
| 351 | | | 8.87 | |
| 352 | | | 8.44 | |
| 353 | | | 8.79 | |
| 354 | | | 8.70 | |
| 355 | | | 8.57 | |
| 356 | | | 8.00 | |
| 357 | | | 8.68 | |
| 358 | | | 8.94 | |
| 359 | | | 8.70 | |
| 360 | 8.82 | | 9.06 | |
| 361 | 8.63 | | | |
| 362 | 8.78 | 9.13 | | |
| 363 | 8.33 | 8.75 | | |
| 364 | 9.41 | 9.30 | 8.85 | |
| 365 | | 8.15 | | |
| 366 | | 7.22 | | |

| Product Number | Biochemical Method 1 (pIC$_{50}$) | Biochemical Method 2 (pIC$_{50}$) | Biochemical Method 3 (pIC$_{50}$) | Biochemical Method 4 (pIC$_{50}$) |
|---|---|---|---|---|
| 367 | | 6.53 | | |
| 368 | | 9.22 | | |
| 369 | | 8.26 | | |
| 370 | | 7.92 | | |
| 371 | | 8.51 | | |
| 372 | | 6.58 | | |
| 373 | | | | 8.28 |
| 374 | | | | 8.24 |
| 375 | | | | 8.13 |
| 376 | | | | 8.26 |
| 377 | | | | 8.36 |
| 378 | | | 8.23 | |
| 379 | | | | 8.10 |
| 380 | | | | 8.40 |
| 381 | | | | 7.15 |
| 382 | | | | 7.93 |
| 383 | | | | 8.35 |
| 384 | | | | 7.37 |
| 385 | | | | 7.94 |
| 386 | | | | 8.25 |
| 387 | | | | 8.22 |
| 388 | | | | 7.04 |
| 389 | | | | 7.67 |
| 390 | | | | 8.37 |
| 391 | | | | 7.45 |
| 392 | | | | 7.41 |
| 393 | | | | 7.86 |
| 394 | | | | 7.15 |
| 395 | | | | 8.11 |
| 396 | | | | 6.87 |
| 397 | | | 6.66 | |
| 398 | | | 6.53 | |
| 399 | | | | 7.90 |
| 400 | | | | 8.24 |
| 401 | | | | 8.32 |
| 402 | 6.95 | | | |
| 403 | 7.59 | | | |
| 404 | 6.78 | | | |
| 405 | 6.25 | | | |
| 406 | 6.07 | | | |
| 407 | 7.22 | | | |
| 408 | | 8.28 | | |
| 409 | | 7.94 | | |
| 410 | | 8.04 | | |
| 411 | | 7.98 | | |
| 412 | | | 9.19 | |
| 413 | | | 8.86 | |
| 414 | | | 9.05 | |
| 415 | | | | 8.03 |
| 416 | 8.71 | | | |

Cdc7 Cell Pharmacodynamics Assays

Method 1

This protocol describes a method to investigate the inhibition of Cdc7 activity of compounds by measuring pS53MCM2 levels in cells after treatment.

Reagents

HCT116 cells (wild type P53 positive)
McCoys 5A media (PAA Laboratories Ltd, E15-022)
10% FCS (Sera Laboratories International Ltd, EU000F Batch:108005)
100× L-Glutamine (Invitrogen, 25030-024)
D-PBS without CaCl$_2$ and MgCl$_2$ (Invitrogen, ref 14190-094)
Trypsin/EDTA (Invitrogen 25300-054)
2% BSA in PBS
Cell Extraction Buffer (Invitrogen FNN0011)
Protease inhibitor cocktail (Sigma P-2714)
PMSF 0.3M stock in DMSO (Sigma P7626)
Antibody-rabbit pMCM2 Ser53 (Bethyl #A300-756A)
Antibody-goat MCM2 (Bethyl #A300-122A)
Antibody-goat Anti Rabbit IgG HRP (Perbio Science UK Ltd 31462)
1×PBS
FACE Wash buffer (0.02% Triton X100 in 1×PBS)
SuperSignal ELISA Pico Chemiluminescent Substrate (Perbio Science UK Ltd 37070)

Method 72 hours prior to the start of the experiment plate 1×10$^6$ HCT 116 cells in a 150 cm$^2$ flask in complete McCoys 5A media (+10% FCS+1× L-glutamine).

Plate 20,000 HCT116 cells per well in standard TC treated 96 well plate in 100 µL complete McCoys 5A media.

Allow cells to settle overnight in incubator set at 37° C. and 5% CO$_2$.

Remove intermediate plate from fridge and place at 37° C. overnight to allow to equilibrate.

Cell treatment: cell assay plate 100 µL; daughter to cell transfer volume 3.33 µL; daughter volume 45 µL; mother plate to daughter volume 5 µL.

Once all cells are treated remove the cells to the incubator and incubate for 6 hours.

Dilute the capture antibody (total MCM2#A300-122A) 1 in 250 in the required volume of PBS (5 mL per assay plate) and add 50 µL to each well of a Hybond plate excluding wells 12E to 12H. In these wells add 50 µL PBS. Seal the plate and incubate at room temperature for a minimum of 2 hours.

Defrost aliquot of Invitrogen Cell Extraction Buffer (FNN0011) on ice and supplement with appropriate volume of both Sigma protease inhibitor cocktail (P-2714) and PMSF (final conc 1 mM from a 1 M stock in DMSO).

After the 6 hour cell treatment time tap out the media from the assay plates and place them in the −70° C. freezer for at least 5 minutes.

Remove plates from freezer and add 20 µL of ice cold complete lysis buffer on ice. Incubate cells for 30 minutes at 4° C.

Add 80 µL per well 2% BSA.

Transfer 80 µL from the lysis plate to the same wells in the capture/ELISA plate. Cover with plate seal and incubate plates overnight at 4° C.

Wash plates with PBS, remove any residual remaining liquid and add 50 µL per well of pMCM2 Ser53 antibody (#A300-756A) diluted 1 in 100 in 2% BSA. Cover plate and incubate at room temperature for 2 hours with gentle shaking.

Wash plates with PBS, remove any residual remaining liquid and Incubate with 50 µL goat anti rabbit antibody (1 in 800 dilution in 2% BSA) for 1 hour at room temperature.

Wash plates with PBS, remove any residual remaining liquid and add 50 µL mixed SuperSignal Pico substrate.

Incubate each plate for 5 minutes at room temperature shielding the plates from direct light (with a cover plate). Read plates with the luminescent detection.

Method 2A and 2B

This protocol describes a method to investigate the inhibition of Cdc7 activity by measuring pS40MCM2 levels in cells, after treatment with compounds.

Reagents

HCT116 cells (ATCC, #CCL-247)
McCoys 5A with L-glutamine (Cellgro, #10-050-CV)
10% FCS (Cellgro, #35-010-CV)
D-PBS without CaCl$_2$ and MgCl$_2$ (Cellgro, #21-031-CV)
Trypsin/EDTA (Cellgro, #25-052-CL)
BSA (Calbiochem, 126593)

Cell Extraction Buffer (Invitrogen FNN0011)
Protease inhibitor cocktail (Sigma P-2714)
PMSF 0.3M stock in DMSO (Sigma P7626)
Antibody-rabbit pMCM2 Ser40 (Abcam, AB133243)
Antibody-goat MCM2 (Bethyl #A300-122A)
Antibody-goat Anti Rabbit IgG HRP (Thermo, 31462)
SuperSignal ELISA Pico Chemiluminescent Substrate (Perbio Science UK Ltd 37069)
10×PBS (Growcells, MRGF-6236)
Triton X100 (Sigma, P-T8787)
DMSO (Fisher, D128-1)
2-Propanol (J. T. Baker, 9095-03)

Method

Seed $1\times10^6$ HCT116 cells into each of two 175 cm² flask containing 30 mL Cell Growth Media and incubate at 37° C., 5% $CO_2$ for 3 days.

Harvest the cells from one T175 cm² flask and count.

Dilute with Cell Growth Media to a cell density of $2\times10^5$. Dispense 100 µL to each well (20,000 HCT116 cells/well) of TC treated 96-well plate(s).

Allow cells to settle overnight in incubator set at 37° C. and 5% $CO_2$.

Cell treatment: Transfer 0.25 µL/well from the compound plate to the wells of the cell plate(s). This is a 1:400 dilution of compound in the assay.

Once all cells are treated place the cells back to the incubator and incubate for either 6 hours (Method 2A) or 18 hours (Method 2B).

Dilute the capture antibody (total MCM2#A300-122A) 1 in 250 in the required volume of PBS (5 mL per assay plate, plus 5 mL for dead volume) and add 50 µL to each well of a Hybond plate except wells A12 & B12. Seal the plate and incubate at room temperature for a minimum of 2 hours.

Defrost aliquot of Invitrogen Cell Extraction Buffer (FNN0011) on ice and supplement with appropriate volume of both Sigma protease inhibitor cocktail (P-2714) and PMSF (final conc 1 mM from a 1 M stock in DMSO).

After the 6 hour or 18 hour cell treatment time, tap out the media from the assay plates and place them in the −70° C. freezer for at least 5 minutes.

Flick out the remaining liquid in the previously prepared capture Ab plate(s) and add 200 µL 2% BSA per well. Incubate for 1 hour at room temperature.

Remove plates from freezer and add 20 µL of ice cold complete lysis buffer. Incubate cells for 30 minutes at 4° C.

Add 30 µL per well 2% BSA

At the end of the 1 hour incubation, wash the Capture/ELISA plate(s) with Wash Buffer on the BioTek plate washer.

Transfer 40 µL per well of the lysis plate(s) to the same wells in the Capture/ELISA plate. Incubate cells overnight at 4° C.

At the end of the overnight incubation, wash the ELISA plate(s) with Wash Buffer on BioTek plate washer.

Prepare Detection Antibody Buffer and dispense 50 µL to all wells of ELISA plate(s) except wells G1 & H1. Cover plate and incubate at room temperature for 2 hours with gentle shaking.

At the end of the 2 hour incubation, wash the ELISA plate(s) with Wash Buffer on the BioTek plate washer.

Prepare the Conjugated Antibody Buffer and dispense 50 µL to all wells of ELISA plate(s).

Cover the plate and incubate at room temperature for 1 hour with gentle shaking.

At the end of the 1 hour incubation, wash the ELISA plate(s) with Wash Buffer on the BioTek plate washer.

Prepare Substrate Buffer and dispense 50 µL to all wells of ELISA plate(s).

Incubate for a minimum of 10 minutes and read plates on the EnVision 2100 Multilabel Reader (Mirror: Luminescence (404) & Luminescence 700 (212); Measurement Height: 6.5 mm; Measurement Time: 0.2 s).

Method 3

This protocol describes a method to investigate the inhibition of Cdc7 activity by measuring pS53MCM2 levels in cells, after treatment with compounds.

Reagents

SW48 cells
RPMI 1640 (Sigma, R5886)
10% FCS (Sera Laboratories International Ltd, EU000F Batch:108005)
100× L-Glutamine (Invitrogen, 25030-024)
D-Glucose Solution (10%) (Sigma, G8644)
HEPES Buffer Solution (Sigma, 83264)
Sodium Pyruvate (Sigma, S8636)
PBS (Fisger, BP399-4)
Trypsin/EDTA (Invitrogen 25300-054)
2% BSA in PBS
Cell Extraction Buffer (Invitrogen FNN0011)
Protease inhibitor cocktail (Sigma P-2714)
PMSF 0.3M stock in DMSO (Sigma P7626)
Antibody-rabbit pMCM2 Ser53 (Bethyl #A300-756A)
Antibody-goat MCM2 (Bethyl #A300-122A)
Antibody-goat Anti Rabbit IgG HRP (Perbio Science UK Ltd 31462)
SuperSignal ELISA Pico Chemiluminescent Substrate (Perbio Science UK Ltd 37070)

Method

Plate 30,000 SW48 cells per well in standard TC treated 96 well plate in 100 µL complete RPMI 1640 medium.

Allow cells to settle overnight in incubator set at 37° C. and 5% $CO_2$.

Cell treatment: prepare a 384 well plate containing 80 µl PBS/well. The PBS should be at room temperature—to be referred to as intermediate plate. Transfer 2 µL of compound from mother plate to intermediate (daughter plate) 1:40 dilution, then 5 µL intermediate to cell (daughter) plate.

Once all cells are treated place the cells back to the incubator and incubate for 6 hours.

Dilute the capture antibody (total MCM2#A300-122A) 1 in 250 in the required volume of PBS (5 mL per assay plate, plus 5 mL for dead volume) and add 50 µL to each well of a Hybond plate. Seal the plate and incubate at room temperature for a minimum of 2 hours.

Defrost aliquot of Invitrogen Cell Extraction Buffer (FNN0011) on ice and supplement with appropriate volume of both Sigma protease inhibitor cocktail (P-2714) and PMSF (final conc 1 mM from a 1 M stock in DMSO).

After the 6 hour cell treatment time, tap out the media from the assay plates and place them in the −80° C. freezer for at least 5 minutes.

Remove plates from freezer and add 20 µL of ice cold complete lysis buffer, with the multidrop. Incubate cells for 30 minutes at 4° C.

Add 80 µL per well 2% BSA.

Flick out the remaining liquid from the capture plate and transfer 80 µL from the lysis plate to the same wells in the capture/ELISA plate, using the Biomek. Cover with plate seal and incubate plates overnight at 4° C.

Wash plates with PBS, remove any residual remaining liquid and add 50 μL per well of pMCM2 Ser53 antibody (#A300-756A) diluted 1 in 100 in 2% BSA. Cover plate and incubate at room temperature for 2 hours with gentle shaking.

Wash plates with PBS, remove any residual remaining liquid and Incubate with 50 μL goat anti rabbit antibody (1 in 800 dilution in 2% BSA), for 1 hour at room temperature.

Wash plates with PBS, remove any residual remaining liquid and add 50 μL mixed SuperSignal Pico substrate.

Incubate each plate for 5 minutes at room temperature shielding the plates from direct light (with a cover plate). Read plates with the luminescent detection.

| Number | Biomarker Method 1 ($pEC_{50}$) | Biomarker Method 2A ($pEC_{50}$) | Biomarker Method 2B ($pEC_{50}$) | Biomarker Method 3 ($pEC_{50}$) |
|---|---|---|---|---|
| 28 | 6.72 | | | |
| 31 | 6.40 | | | |
| 76 | 6.74 | | | |
| 77 | 7.03 | | | |
| 78 | 6.33 | | | |
| 81 | 6.71 | | | |
| 82 | 6.01 | | | |
| 84 | 6.23 | | | |
| 85 | 6.05 | | | |
| 87 | 6.83 | | | |
| 88 | 6.97 | | | |
| 89 | 7.13 | | | |
| 90 | 7.48 | | 7.87 | 6.23 |
| 91 | 5.50 | | | |
| 94 | 6.12 | | | |
| 101 | 7.35 | | | |
| 103 | 5.94 | | | |
| 104 | 6.81 | | | |
| 105 | 6.37 | | | |
| 106 | 7.15 | | | |
| 107 | 6.44 | | | |
| 109 | 6.82 | | | |
| 111 | 6.12 | | | |
| 112 | 6.12 | | | |
| 114 | 5.81 | | | |
| 116 | 6.22 | | | |
| 121 | 6.93 | | | |
| 122 | 6.38 | | | |
| 123 | 6.65 | | | |
| 125 | 6.04 | | | |
| 127 | 6.65 | | | |
| 128 | 7.10 | | | |
| 129 | 6.06 | | | |
| 130 | 6.97 | 6.11 | | |
| 131 | 6.95 | | | |
| 132 | 7.47 | | | |
| 134 | 6.16 | | | |
| 135 | 6.18 | | | |
| 136 | 5.68 | | | |
| 139 | 6.49 | 6.07 | | 5.39 |
| 140 | 6.34 | | | |
| 142 | 6.18 | | | |
| 143 | 6.39 | | | |
| 144 | 6.23 | | | |
| 145 | 6.57 | | | |
| 146 | 6.64 | | | |
| 147 | 6.94 | 6.37 | | |
| 150 | 6.37 | | | |
| 151 | 6.30 | | | |
| 152 | 6.06 | | | |
| 153 | 6.90 | | | |
| 154 | 7.20 | | | |
| 156 | 7.18 | | | |
| 157 | 7.10 | | | |
| 158 | 5.76 | | | |
| 159 | 6.68 | | | |
| 160 | 7.50 | | | |
| 164 | 6.14 | | | |
| 166 | 5.55 | | | |
| 167 | 6.08 | | | |
| 169 | 6.25 | | | |
| 170 | 7.50 | 7.66 | | |
| 171 | 7.14 | | | |
| 176 | 5.56 | | | |
| 177 | 6.67 | | | |
| 180 | 7.57 | 7.43 | | 6.47 |
| 181 | 6.88 | | | |
| 182 | 5.88 | | | |
| 183 | | 6.83 | | |
| 185 | 7.07 | 7.07 | | |
| 186 | 6.46 | | | |
| 188 | | 6.77 | | |
| 190 | | 6.13 | | |
| 192 | | 7.05 | 7.31 | |
| 196 | | 7.14 | | |
| 197 | | 6.50 | | |
| 201 | | | 6.09 | |
| 203 | | 6.44 | | |
| 205 | | 6.56 | | |
| 206 | | | 7.40 | 6.25 |
| 208 | | | 7.19 | |
| 221 | | 5.79 | 6.25 | |
| 223 | | 7.25 | 7.32 | |
| 232 | | 5.70 | 6.01 | |
| 234 | | 7.41 | | |
| 235 | | 5.95 | | |
| 243 | | 6.54 | | |
| 244 | | | 6.40 | |
| 252 | | 7.42 | | |
| 258 | | | 6.25 | |
| 260 | | | 7.14 | |
| 261 | | | 6.27 | |
| 262 | | | 7.71 | 6.46 |
| 271 | | | 6.53 | |
| 272 | | | 6.30 | |
| 273 | | | 6.37 | |
| 275 | | | 5.68 | |
| 277 | | | 6.55 | |
| 279 | | | 7.24 | 5.88 |
| 281 | | | 6.34 | |
| 282 | | | 6.63 | |
| 284 | | | 6.41 | |
| 286 | | | 7.81 | 6.29 |
| 293 | | | 7.53 | |
| 296 | | | 5.99 | |
| 297 | | | 6.04 | |
| 298 | | | 6.48 | |
| 300 | | | 6.94 | |
| 301 | | | 5.72 | |
| 303 | | | 6.90 | |
| 304 | | | 6.67 | |
| 306 | | | 6.76 | |
| 308 | 6.75 | | | |
| 309 | 7.21 | | | |
| 310 | 7.23 | | | |
| 312 | | 7.94 | 8.12 | 6.84 |
| 313 | | | | 6.12 |
| 314 | 7.91 | | | |
| 315 | 7.20 | | | |
| 316 | 7.40 | 7.35 | | |
| 317 | 7.01 | 6.66 | | |
| 319 | 7.13 | 6.90 | | |
| 320 | | 6.50 | | |
| 321 | 6.34 | | | |
| 322 | 7.37 | | | |
| 323 | 7.65 | 7.92 | 8.25 | 7.10 |
| 326 | | 7.39 | | |
| 328 | | 8.41 | | |
| 333 | | 6.46 | 7.06 | |
| 334 | | 6.87 | 7.21 | |
| 335 | | | 6.34 | |
| 337 | | | 6.43 | |
| 338 | | | 6.75 | |

-continued

| Number | Biomarker Method 1 (pEC$_{50}$) | Biomarker Method 2A (pEC$_{50}$) | Biomarker Method 2B (pEC$_{50}$) | Biomarker Method 3 (pEC$_{50}$) |
|---|---|---|---|---|
| 339 | | | 7.97 | 6.96 |
| 340 | | | 6.76 | |
| 345 | | | 5.76 | |
| 347 | | | 6.50 | |
| 348 | | | 6.59 | |
| 350 | | | 6.81 | |
| 351 | | | 6.86 | |
| 352 | | | 6.36 | |
| 355 | | | 6.54 | |
| 357 | | | 6.70 | |
| 358 | | | 8.61 | 7.05 |
| 359 | | | 7.56 | |
| 360 | 7.24 | 7.08 | | |
| 361 | 5.62 | | | |
| 362 | 6.52 | | | |
| 363 | 6.10 | | | |
| 364 | 7.69 | 7.57 | | |
| 365 | 6.58 | | | |
| 368 | 7.81 | | | |
| 369 | 6.05 | | | |
| 370 | 5.99 | | | |
| 371 | 6.61 | | | |
| 373 | | | | 6.41 |
| 374 | | | | 6.36 |
| 375 | | | | 5.91 |
| 376 | | | | 6.85 |
| 377 | | | | 6.83 |
| 378 | | | 6.36 | 5.68 |
| 379 | | | | 5.88 |
| 380 | | | | 6.70 |
| 381 | | | | 5.32 |
| 382 | | | | 6.16 |
| 383 | | | | 6.67 |
| 384 | | | | 5.33 |
| 385 | | | | 5.87 |
| 386 | | | | 6.00 |
| 387 | | | | 6.51 |
| 388 | | | | 5.29 |
| 389 | | | | 5.68 |
| 390 | | | | 6.97 |
| 391 | | | | 5.45 |
| 392 | | | | 5.24 |
| 393 | | | | 5.90 |
| 394 | | | | 5.26 |
| 395 | | | | 5.67 |
| 396 | | | | 5.11 |
| 399 | | | | 5.78 |
| 400 | | | | 6.71 |
| 401 | | | | 6.36 |
| 408 | 6.59 | | | |
| 410 | 6.57 | | | |
| 412 | | 6.47 | | |
| 413 | | | 6.51 | |
| 415 | | | | 6.15 |
| 416 | 6.96 | | | |

REFERENCES

A number of scientific papers were referenced in this application so as to more fully describe the state of the art to which this application pertains. Full citations for these references are provided below.

Bonte, D., Lindvall, C., Liu, H., Dykema, K., Furge, K., Weinreich, M. (2008). Cdc7-Dbf4 Kinase Overexpression in Multiple Cancers and Tumor Cell Lines Is Correlated with p53 Inactivation. Neoplasia 10, 920-931

Bousset, K., and Diffley, J. F. X. (1998). The Cdc7 protein kinase is required for origin firing during S phase. Genes Dev. 12, 480-490

Bruck, I., and Kaplan, D. (2009). Dbf4-Cdc7 phosphorylation of Mcm2 is required for cell growth. J. Biol. Chem. 284, 28823-28831

Charych, D. H., Coyne, M., Yabannavar, A., Narberes, J., Chow, S., Wallroth, M., Shafer, C., and Walter, A. O. (2008). Inhibition of Cdc7/Dbf4 kinase activity affects specific phosphorylation sites on MCM2 in cancer cells. J. Cell. Biochem. 104, 1075-1086

Cheng, A. N., Jianga, S. S., Fanc, C.-C., Loa, Y.-K., Kuoa, C.-Y., Chena, C.-H., Liua, Y.-L., Leea, C.-C., Chene, W.-S., Huanga, T.-S., Wangf, T.-Y., Leea, A. Y.-L., (2013). Increased Cdc7 expression is a marker of oral squamous cell carcinoma and overexpression of Cdc7 contributes to the resistance to DNA-damaging agents. Cancer Let. 337, 218-225

Cho, W.-H., Lee, Y.-J., Kong, S.-I., Hurwitz, J., and Lee, J.-K. (2006). CDC7 kinase phosphorylates serine residues adjacent to acidic amino acids in the minichromosome maintenance 2 protein. Proc. Natl. Acad. Sci. U.S.A 103, 11521-11526

Choschzick, M., Lebeau, A., Marx, A. H., Tharun, L., Terracciano, L., Heilenkötter, U., Jaenicke, F., Bokemeyer, C., Simon, R., Sauter, G., et al. (2010). Overexpression of cell division cycle 7 homolog is associated with gene amplification frequency in breast cancer. Hum. Pathol. 41, 358-365

Donaldson, A. D., Fangman, W. L., and Brewer, B. J. (1998). Cdc7 is required throughout the yeast S phase to activate replication origins. Genes Dev., 491-501

Duncker, B. (2003). Cdc7 kinases (DDKs) and checkpoint responses: lessons from two yeasts. Mutation Research-Fundamental and Molecular Mechanisms of Mutagenesis 532, 21-27

Francis, L. I., Randell, J. C. W., Takara, T. J., Uchima, L., and Bell, S. P. (2009). Incorporation into the prereplicative complex activates the Mcm2-7 helicase for Cdc7-Dbf4 phosphorylation. Genes Dev. 23, 643-654

Im, J.-S., and Lee, J.-K. (2008). ATR-dependent activation of p38 MAP kinase is responsible for apoptotic cell death in cells depleted of Cdc7. J. Biol. Chem. 283, 25171-25177

Jiang, W., McDonald, D., Hope, T. J., and Hunter, T. (1999). Mammalian Cdc7-Dbf4 protein kinase complex is essential for initiation of DNA replication. EMBO J. 18, 5703-5713

Kim, J. (2003). Functions of mammalian Cdc7 kinase in initiation/monitoring of DNA replication and development. Mutation Research-Fundamental and Molecular Mechanisms of Mutagenesis 532, 29-40

Kulkarni, A. a., Kingsbury, S. R., Tudzarova, S., Hong, H.-K., Loddo, M., Rashid, M., Rodriguez-Acebes, S., Prevost, A. T., Ledermann, J. a., Stoeber, K., et al. (2009). Cdc7 kinase is a predictor of survival and a novel therapeutic target in epithelial ovarian carcinoma. Clin. Cancer Res. 15, 2417-2425

Kumagai, H., Sato, N., Yamada, M., Mahony, D., Seghezzi, W., Lees, E., Arai, K., and Masai, H. (1999). A novel growth- and cell cycle-regulated protein, ASK, activates human Cdc7-related kinase and is essential for G1/S transition in mammalian cells. Mol. Cell. Biol. 19, 5083-5095

Masai, H., and Arai, K.-I. (2002). Cdc7 kinase complex: a key regulator in the initiation of DNA replication. J. Cell. Physiol. 190, 287-296

Masai, H., Taniyama, C., Ogino, K., Matsui, E., Kakusho, N., Matsumoto, S., Kim, J.-M., Ishii, A., Tanaka, T., Kobayashi, T., et al. (2006). Phosphorylation of MCM4 by Cdc7 kinase facilitates its interaction with Cdc45 on the chromatin. J. Biol. Chem. 281, 39249-39261

Montagnoli, A., Tenca, P., Sola, F., Carpani, D., Brotherton, D., Albanese, C., and Santocanale, C. (2004). Cdc7 inhibition reveals a p53-dependent replication checkpoint that is defective in cancer cells. Cancer Res. 64, 7110-7116

Montagnoli, A., Valsasina, B., Brotherton, D., Troiani, S., Rainoldi, S., Tenca, P., Molinari, A., and Santocanale, C. (2006). Identification of Mcm2 phosphorylation sites by S-phase-regulating kinases. J. Biol. Chem. 281, 10281-10290

Montagnoli, A., Valsasina, B., Croci, V., Menichincheri, M., Rainoldi, S., Marchesi, V., Tibolla, M., Tenca, P., Brotherton, D., Albanese, C., et al. (2008). A Cdc7 kinase inhibitor restricts initiation of DNA replication and has antitumor activity. Nat. Chem. Biol. 4, 357-365

Pereverzeva, I., Whitmire, E., and Khan, B. (2000). Distinct Phosphoisoforms of the *Xenopus* Mcm4 Protein Regulate the Function of the Mcm Complex Mol. Cell. Biol. 20, 3667-3676

Rodriguez-Acebes, S., Proctor, I., Loddo, M., Wollenschlaeger, A., Rashid, M., Falzon, M., Prevost, a. T., Sainsbury, R., Stoeber, K., and Williams, G. H. (2010). Targeting DNA replication before it starts: Cdc7 as a therapeutic target in p53-mutant breast cancers. Am. J. Pathol. 177, 2034-2045

Shreeram, S., Sparks, A., Lane, D. P., and Blow, J. J. (2002). Cell type-specific responses of human cells to inhibition of replication licensing. Oncogene 21, 6624-6632

Sheu, Y.-J., and Stillman, B. (2006). Cdc7-Dbf4 phosphorylates MCM proteins via a docking site-mediated mechanism to promote S phase progression. Mol. Cell 24, 101-113

Sheu, Y.-J., and Stillman, B. (2010). The Dbf4-Cdc7 kinase promotes S phase by alleviating an inhibitory activity in Mcm4. Nature 463, 113-117; Woo, R. a., and Poon, R. Y. C. (2003). Cyclin-dependent kinases and S phase control in mammalian cells. Cell Cycle 2, 316-324

Takeda, T., Ogino, K., Tatebayashi, K., Ikeda, H., Ki, A., and Masai, H. (2001). Regulation of initiation of S phase, replication checkpoint signaling, and maintenance of mitotic chromosome structures during S phase by Hsk1 kinase in the fission yeast. Mol. Biol. Cell 12, 1257-1274

Tenca, P., Brotherton, D., Montagnoli, A., Rainoldi, S., Albanese, C., Santocanale, C. (2007). Cdc7 Is an Active Kinase in Human Cancer Cells Undergoing Replication Stress. J. Biol. Chem. 282, 208-215

Tsuji, T., Ficarro, S. B., and Jiang, W. (2006). Essential Role of Phosphorylation of MCM2 by Cdc7/Dbf4 in the Initiation of DNA Replication in Mammalian Cells. Mol. Biol. Cell 17, 4459-4472

Tudzarova, S., Trotter, M. W. B., Wollenschlaeger, A., Mulvey, C., Godovac-Zimmermann, J., Williams, G. H., and Stoeber, K. (2010). Molecular architecture of the DNA replication origin activation checkpoint. EMBO J. 29, 3381-3394

The invention claimed is:

1. A compound of Formula I

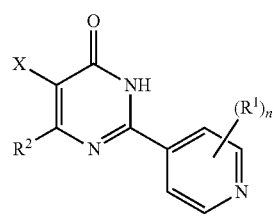

Formula I and/or a salt thereof wherein,

X is chosen from halogen, haloC$_1$-C$_2$alkyl, and CN;

Each R$^1$ is independently chosen from C$_1$-C$_2$alkyl, —CN, haloC$_1$-C$_4$alkyl, halogen, —NO$_2$, —NR$^3$R$^4$, and —C$_0$-C$_4$alkylOR$^3$ R$^2$ is:

i) a group A-B-C wherein:
A is a bond or is C$_1$-C$_{10}$alkyl;
B is absent or is chosen from S(O)$_p$, NR$^3$, O, C$_2$-C$_{10}$alkenyl, and C$_2$-C$_{10}$alkynyl; and
C is a 3 to 15 membered heterocycloalkyl or a 4 to 11 membered cycloalkyl either of which is optionally substituted with one or more R$^5$; or ii) a group D-E-F wherein:
D is chosen from NR$^3$ or;
E is a bond or is C$_1$-C$_{10}$alkyl; and
F is a 3 to 15 membered heterocycloalkyl or an aryl, each of which is optionally substituted with one or more groups chosen from C$_1$-C$_{10}$alkyl, halogen, amino or alkoxy;

R$^3$ and R$^4$ are each independently chosen from H, C$_1$-C$_{10}$alkyl, C$_2$-C$_{10}$alkenyl, C$_2$-C$_{10}$alkynyl, haloC$_1$-C$_6$alkyl, C$_0$-C$_6$alkylaryl, C$_0$-C$_6$alkylcycloalkyl, C$_0$-C$_6$alkylheteroaryl, C$_0$-C$_6$alkylheterocycloalkyl, wherein any of the foregoing, except for H, is optionally substituted with one or more R$^5$; or R$^3$ and R$^4$ may be taken together to form a 3 to 15 membered carbocyclic or heterocyclic ring system, wherein said ring system is optionally substituted with one or more R$^5$;

Each R$^5$ is independently chosen from C$_1$-C$_{10}$alkyl, C$_2$-C$_{10}$alkenyl, C$_2$-C$_{10}$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, —C$_0$-C$_6$alkylCN, —C$_0$-C$_6$alkylC(=O)C$_0$-C$_6$alkylR$^6$, —C$_0$-C$_6$alkyC(=O)C$_0$-C$_6$alkylOR$^6$, —C$_0$-C$_6$alkylC(=O)C$_0$-C$_6$alkylNR$^6$R$^6$, —C$_0$-C$_6$alkylC(=O)C$_0$-C$_6$alkylNR$^6$C(=O)OR$^6$, —C$_0$-C$_6$alkylC(=O)C$_0$-C$_6$alkylC(=O)R$^6$, haloC$_1$-C$_6$alkyl, halogen, —NO$_2$, —C$_0$-C$_6$alkyNR$^6$R$^6$, —C$_0$-C$_6$alkylNR$^6$NR$^6$R$^6$, —C$_0$-C$_6$alkylN=NR$^6$, —C$_0$-C$_6$alkyNR$^6$C$_0$-C$_6$alkylOR$^6$, —C$_0$-C$_6$alkylNR$^6$C$_0$-C$_6$alkylC(=O)R$^6$, —C$_0$-C$_6$alkylNR$^6$C(=O)C$_0$-C$_6$alkylC(=O)R$^6$, —C$_0$-C$_6$alkylNR$^6$C$_0$-C$_6$alkylC(=O)OR$^6$, —C$_0$-C$_6$alkylNR$^6$C$_0$-C$_6$alkylC(=O)NR$^6$R$^6$, —C$_0$-C$_6$alkyNR$^6$C(=O)C$_0$-C$_6$alkyNR$^6$C(=O)R$^6$, —C$_0$-C$_6$alkylNR$^6$C(=O)C$_0$-C$_6$alkylNR$^6$C(=O)OR$^6$, —C$_0$-C$_6$alkylNR$^6$C(=O)C$_0$-C$_6$alkylC(=O)NR$^6$R$^6$, —C$_0$-C$_6$alkyNR$^6$C$_0$-C$_6$alkyS(=O)$_2$R$^6$, —C$_0$-C$_6$alkylNR$^6$S(=O)$_2$C$_0$-C$_6$alkylNR$^6$R$^6$, —C$_0$-C$_6$alkylOR$^6$, (=O),—C$_0$-C$_6$alkylOC(=O)C$_0$-C$_6$alkyR$^6$, —C$_0$-C$_6$alkylOC(=O)C$_0$-C$_6$alkylNR$^6$R$^6$, —C$_0$-C$_6$alkylOC(=O)C$_0$-C$_6$alkylOR$^6$, —C$_0$-C$_6$alkylOS(=O)R$^6$, —C$_0$-C$_6$alkylOS(=O)$_2$R$^6$, —C$_0$-C$_6$alkylOS(=O)$_2$C$_0$-C$_6$alkylOR$^6$, —C$_0$-C$_6$alkylOS(=O)$_2$C$_0$-C$_6$alkylNR$^6$R$^6$, —C$_0$-C$_6$alkylOP(=O)R$^6$R$^6$, —C$_0$-C$_6$alkylOP(=O)(NR$^6$R$^6$)(NR$^6$R$^6$), —C$_0$-C$_6$alkylOP(=O)(OR$^6$)(OR$^6$), —C$_0$-C$_6$alkylOP(=O)(SR$^6$)(SR$^6$), —C$_0$-C$_6$alkyP(=O)R$^6$R$^6$, —C$_0$-C$_6$alkyP(=O)(NR$^6$R$^6$)(NR$^6$R$^6$), —C$_0$-C$_6$alkyIP(=O)(OR$^6$)(OR$^6$), —C$_0$-C$_6$alkyP(=O)(SR$^6$)(SR$^6$), —C$_0$-C$_6$alkyS(=O)$_p$R$^6$, —C$_0$-C$_6$alkylS(=O)$_2$C$_0$-C$_6$alkylNR$^6$R$^6$, —C$_0$-C$_6$alkylS(=O)C$_0$-C$_6$alkylNR$^6$R$^6$, and —C$_0$-C$_6$alkylSCN, wherein any of the foregoing is optionally substituted with one or more R7; or together with carbon atoms to which they are attached, two $R^5$ groups may be linked to form a fused aryl, heteroaryl, 3 to 6 membered heterocycloalkyl or a 3 to 6 membered cycloalkyl;

Each $R^6$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing except for H is optionally substituted with one or more $R^7$; or Two $R^6$ may be taken together to form a 3 to 15 membered carbocyclic or heterocyclic ring system, wherein said ring system is optionally substituted with one or more $R^7$;

Each $R^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR$^8$, —$C_0$-$C_6$alkylC(=O)$C_0$-$C_6$alkylOR$^8$, —$C_0$-$C_6$alkylC(=O)$C_0$-$C_6$alkylNR$^8$R$^8$, —$C_0$-$C_6$alkylC(=O)$C_0$-$C_6$alkylNR$^8$C(=O)OR$^8$, —$C_0$-$C_6$alkylC(=O)$C_0$-$C_6$alkylC(=O)R$^8$, halo$C_1$-$C_6$alkyl, halogen, —NO$_2$, —$C_0$-$C_6$alkylNR$^8$R$^8$, —$C_0$-$C_6$alkylNR$^8$NR$^8$R$^8$, —$C_0$-$C_6$alkylN=NR$^8$, —$C_0$-$C_6$alkyNR$^8$C$_0$-$C_6$alkylOR$^8$, —$C_0$-$C_6$alkylNR$^8$C$_0$-$C_6$alkylC(=O)R$^8$, —$C_0$-$C_6$alkylNR$^8$C(=O)$C_0$-$C_6$alkylC(=O)R$^8$, —$C_0$-$C_6$alkylNR$^8$C$_0$-$C_6$alkylC(=O)OR$^8$, —$C_0$-$C_6$alkylNR$^8$C$_0$-$C_6$alkylC(=O)C(=O)OR$^8$, —$C_0$-$C_6$alkylNR$^8$C$_0$-$C_6$alkylC(=O)NR$^8$R$^8$, —$C_0$-$C_6$alkylNR$^8$C(=O)$C_0$-$C_6$alkylNR$^8$C(=O)R$^8$, —$C_0$-$C_6$alkylNR$^8$C(=O)$C_0$-$C_6$alkylNR$^8$C(=O)OR$^8$, —$C_0$-$C_6$alkylNR$^8$C(=O)$C_0$-$C_6$alkylC(=O)NR'R'$, —$C_0$-$C_6$alkyNR$^8$C$_0$-$C_6$alkylS(=O)$_2$R$^8$, —$C_0$-$C_6$alkylNR$^8$S(=O)$_2$C$_0$-$C_6$alkylNR$^8$R$^8$, —$C_0$-$C_6$alkylOR$^8$, (=O), —$C_0$-$C_6$alkylOC(=O)$C_0$-$C_6$alkylR$^8$, —$C_0$-$C_6$alkylOC(=O)$C_0$-$C_6$alkyNR$^8$R$^8$, —$C_0$-$C_6$alkylOC(=O)$C_0$-$C_6$alkylOR$^8$, —$C_0$-$C_6$alkylOS(=O)R$^8$, —$C_0$-$C_6$alkylOS(=O)$_2$R$^8$, —$C_0$-$C_6$alkylOS(=O)$_2$C$_0$-$C_6$alkylOR$^8$, —$C_0$-$C_6$alkylOS(=O)$_2$C$_0$-$C_6$alkyNR$^8$R$^8$, —$C_0$-$C_6$alkylOP(=O)R$^8$R$^8$, —$C_0$-$C_6$alkylOP(=O)(NR$^8$R$^8$)(NR$^8$R$^8$), —$C_0$-$C_6$alkylOP(=O)(OR)(OR$^8$), —$C_0$-$C_6$alkylOP(=O)(SR$^8$)(SR$^8$), —$C_0$-$C_6$alkyP(=O)R$^8$R$^8$, —$C_0$-$C_6$alkyP(=O)(NR$^8$R$^8$)(NR$^8$R$^8$), —$C_0$-$C_6$alkylP(=O)(OR$^8$)(OR$^8$), —$C_0$-$C_6$alkylP(=O)(SR$^8$)(SR$^8$), —$C_0$-$C_6$alkyS(=O)$_p$R$^8$, —$C_0$-$C_6$alkylS(=O)$_2$C$_0$-$C_6$alkylNR$^8$R$^8$, —$C_0$-$C_6$alkylS(=O)$C_0$-$C_6$alkylNR$^8$R$^8$, and —$C_0$-$C_6$alkylSCN;

Each $R^8$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, and $C_0$-$C_6$alkylheterocycloalkyl;

Each p is independently 0, 1 or 2; and

Each n is independently 0, 1, 2, 3 or 4;

With the proviso that the compound is not one of the following:

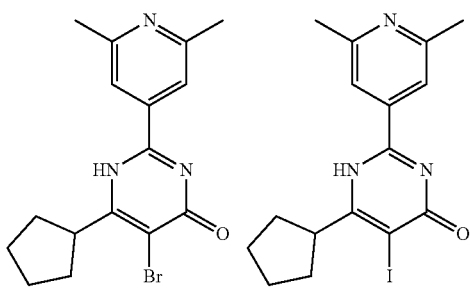

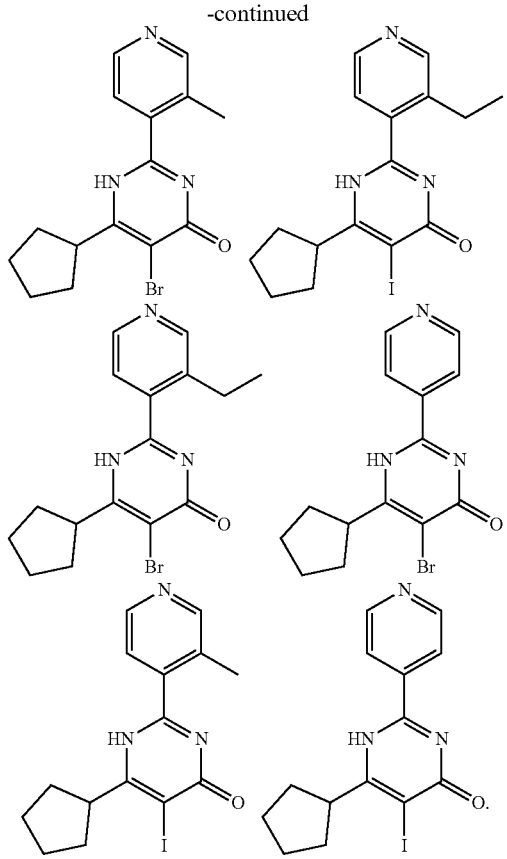

2. A compound according to claim 1, wherein X is halogen.

3. A compound according to claim 1, wherein R is selected from halogen, CF$_3$ or OH.

4. A compound according to claim 1, wherein $R^2$ is a group A-B-C wherein:
A is a bond or is $C_1$-$C_2$alkyl;
B is absent or is chosen from S, NR$^3$ or O; and
C is a 3 to 12 membered heterocycloalkyl or a 4 to 8 membered cycloalkyl either of which is optionally substituted with one or more $R^5$.

5. A compound according to claim 1 wherein $R^2$ is a 3 to 8 membered heterocycloalkyl optionally substituted with one or more $R^5$, wherein $R^5$ is selected from $C_1$-$C_4$alkyl, halo$C_1$-$C_4$alkyl or halogen.

6. A compound according to claim 1, wherein $R^3$ and $R^4$ are each independently chosen from H, $C_1$-$C_6$alkyl or halo$C_1$-$C_4$alkyl.

7. A compound according to claim 1, wherein each $R^5$ is independently chosen from $C_1$-$C_6$alkyl, $C_2$-$C_6$alkenyl, $C_2$-$C_6$alkynyl, $C_0$-$C_2$alkylaryl, $C_0$-$C_2$alkylcycloalkyl, $C_0$-$C_2$alkylheterocycloalkyl, $C_0$-$C_2$alkylheteroaryl, —$C_0$-$C_4$alkylCN, —$C_0$-$C_2$alkyC(=O)$C_0$-$C_6$alkyR$^6$, —$C_0$-$C_2$alkylC(=O)$C_0$-$C_6$alkylOR$^6$, —$C_0$-$C_2$alkyC(=O)$C_0$-$C_6$alkyNR$^6$R$^6$, —$C_0$-$C_4$alkylC(=O)$C_0$-$C_6$alkylNR$^6$C(=O)OR$^6$, halo$C_1$-$C_6$alkyl, halogen, —NO$_2$, —$C_0$-$C_4$alkyNR$^6$R$^6$, —$C_0$-$C_2$alkylNR$^6$C$_0$-$C_6$alkylC(=O)R$^6$, —$C_0$-$C_6$alkylNR$^6$C(=O)$C_0$-$C_6$alkylC(=O)R$^6$, —$C_0$-$C_6$alkylNR$^6$C$_0$-$C_6$alkylS(=O)$_2$R$^6$, —$C_0$-$C_6$alkylOR$^6$ and —$C_0$-$C_2$alkylS(=O)$_p$R$^6$, wherein any of the foregoing is optionally substituted with one or more $R^7$.

8. A compound according to claim 1, wherein each $R^6$ is independently chosen from H, $C_1$-$C_6$alkyl, halo$C_1$-$C_4$alkyl, $C_0$-$C_2$alkylaryl, $C_0$-$C_2$alkyl-5- or 6-membered cycloalkyl, $C_0$-$C_2$alkyl-5- or 6-membered heteroaryl, $C_0$-$C_2$alkyl-5- or 6-membered heterocycloalkyl, wherein any of the foregoing except for H is optionally substituted with one or more $R^7$.

9. A compound according to claim 1, wherein each $R^7$ is independently chosen from $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkyC(═O)$C_0$-$C_6$alkyl$R^8$, —$C_0$-$C_6$alkylC(═O)$C_0$-$C_6$alkylOR$^8$, —$C_0$-$C_6$alkyC(═O)$C_0$-$C_6$alkylNR$^8$R$^8$, —$C_0$-$C_6$alkylC(═O)$C_0$-$C_6$alkylNR$^8$C(═O)OR$^8$, halo$C_1$-$C_6$alkyl, halogen, —$C_0$-$C_6$alkylNR$^8$R$^8$, —$C_0$-$C_6$alkylNR$^8$$C_0$-$C_6$alkylC(═O)R$^8$, —$C_0$-$C_6$alkylNR$^8$C(═O)$C_0$-$C_6$alkylC(═O)R$^8$, —$C_0$-$C_6$alkylNR$^8$C(═O)$C_0$-$C_6$alkyl C(═O)OR$^8$, —$C_0$-$C_6$alkyNR$^8$$C_0$-$C_6$alkylS(═O)$_2$R$^8$, —$C_0$-$C_6$alkylOR$^8$, $C_0$-$C_6$alkylS(═O)$_p$R$^8$, —$C_0$-$C_6$alkylS(═O)$_2$$C_0$-$C_6$alkylNR$^8$R$^8$ and —$C_0$-$C_6$alkyS(═O)$C_0$-$C_6$alkyNR$^8$R$^8$.

10. A compound according to claim 1, wherein, each $R^7$ is independently chosen from $C_1$-$C_6$alkyl, —$C_0$-$C_4$alkylCN, —$C_0$-$C_2$alkylC(═O)$C_0$-$C_2$alkylR$^8$, —$C_0$-$C_2$alkylC(═O)$C_0$-$C_2$alkylOR$^8$, halo$C_1$-$C_4$alkyl, halogen, —$C_0$-$C_6$alkylNR$^8$R$^8$, —$C_0$-$C_2$alkylNR$^8$$C_0$-$C_2$alkylC(═O)R$^8$, —$C_0$-$C_2$alkylNR$^8$$C_0$-$C_2$alkylS(═O)$_2$R$^8$, —$C_0$-$C_4$alkylOR$^8$, $C_0$-$C_2$alkylS(═O)$_2$R$^8$ and —$C_0$-$C_2$alkyS(═O)$_2$$C_0$-$C_2$alkyNR$^8$R$^8$.

11. A compound according to claim 1, wherein each $R^8$ is independently chosen from H, $C_1$-$C_6$alkyl and halo$C_1$-$C_4$alkyl.

12. A compound according to claim 1, wherein n is 0 or 1.

13. A compound according to claim 1, wherein p is 2.

14. A compound according to claim 1 selected from one of the following:

tert-butyl 4-[5-chloro-6-oxo-2-(4-pyridyl)-1H-pyrimidin-4-yl]piperidine-1-carboxylate;
5-chloro-4-(4-piperidyl)-2-(4-pyridyl)-1H-pyrimidin-6-one;
5-bromo-2-(4-pyridyl)-4-tetrahydropyran-4-yl-1H-pyrimidin-6-one;
5-iodo-2-(4-pyridyl)-4-tetrahydropyran-4-yl-1H-pyrimidin-6-one;
5-fluoro-2-(4-pyridyl)-4-tetrahydropyran-4-yl-1H-pyrimidin-6-one;
5-chloro-2-(4-pyridyl)-4-tetrahydropyran-4-yl-1H-pyrimidin-6-one;
5-chloro-2-(4-pyridyl)-4-pyrrolidin-2-yl-1H-pyrimidin-6-one;
5-chloro-4-(3-piperidyl)-2-(4-pyridyl)-1H-pyrimidin-6-one;
5-chloro-4-(4-methyltetrahydropyran-4-yl)-2-(4-pyridyl)-1H-pyrimidin-6-one;
5-chloro-2-(2-fluoro-4-pyridyl)-4-(4-methyltetrahydropyran-4-yl)-1H-pyrimidin-6-one;
5-chloro-2-(4-pyridyl)-4-pyrrolidin-3-yl-1H-pyrimidin-6-one;
5-chloro-2-(4-pyridyl)-4-tetrahydrofuran-3-yl-1H-pyrimidin-6-one;
5-chloro-2-(2-fluoro-4-pyridyl)-4-tetrahydropyran-4-yl-1H-pyrimidin-6-one;
5-chloro-4-(2-isopropyltetrahydropyran-4-yl)-2-(4-pyridyl)-1H-pyrimidin-6-one;
5-chloro-2-(4-pyridyl)-4-tetrahydropyran-2-yl-1H-pyrimidin-6-one;
5-chloro-2-(4-pyridyl)-4-tetrahydropyran-3-yl-1H-pyrimidin-6-one;
5-fluoro-2-(2-fluoro-4-pyridyl)-4-tetrahydropyran-4-yl-1H-pyrimidin-6-one;
5-chloro-2-(2-fluoro-4-pyridyl)-4-(4-fluorotetrahydropyran-4-yl)-1H-pyrimidin-6-one;
5-chloro-4-(3-fluoro-3-piperidyl)-2-(4-pyridyl)-1H-pyrimidin-6-one;
5-chloro-4-morpholin-2-yl-2-(4-pyridyl)-1H-pyrimidin-6-one;
5-chloro-4-(4-fluoro-4-piperidyl)-2-(4-pyridyl)-1H-pyrimidin-6-one;
tert-butyl 4-[5-chloro-6-oxo-2-(4-pyridyl)-1H-pyrimidin-4-yl]-4-fluoro-piperidine-1-carboxylate;
5-chloro-2-(2-chloro-4-pyridyl)-4-tetrahydropyran-4-yl-1H-pyrimidin-6-one;
5-chloro-4-tetrahydropyran-4-yl-2-[2-(trifluoromethyl)-4-pyridyl]-1H-pyrimidin-6-one;
tert-butyl 4-[5-chloro-2-(2-fluoro-4-pyridyl)-6-oxo-1H-pyrimidin-4-yl]piperidine-1-carboxylate;
5-chloro-4-(1-piperidyl)-2-(4-pyridyl)-1H-pyrimidin-6-one;
5-chloro-4-(4-ethoxy-1-piperidyl)-2-(4-pyridyl)-1H-pyrimidin-6-one;
5-chloro-4-(3,4-dimethylpiperazin-1-yl)-2-(4-pyridyl)-1H-pyrimidin-6-one;
5-chloro-4-[3-(dimethylamino)pyrrolidin-1-yl]-2-(4-pyridyl)-1H-pyrimidin-6-one;
5-chloro-2-(4-pyridyl)-4-pyrrolidin-1-yl-1H-pyrimidin-6-one;
5-bromo-4-(4-ethylpiperazin-1-yl)-2-(4-pyridyl)-1H-pyrimidin-6-one;
tert-butyl 4-[5-chloro-6-oxo-2-(4-pyridyl)-1H-pyrimidin-4-yl]piperazine-1-carboxylate;
5-chloro-4-(3-oxopiperazin-1-yl)-2-(4-pyridyl)-1H-pyrimidin-6-one;
5-chloro-4-[1-(2-methylpropanoyl)-4-piperidyl]-2-(4-pyridyl)-1H-pyrimidin-6-one;
tert-butyl N-[2-[4-[5-chloro-6-oxo-2-(4-pyridyl)-1H-pyrimidin-4-yl]-1-piperidyl]-2-oxo-ethyl]carbamate;
4-[5-chloro-6-oxo-2-(4-pyridyl)-1H-pyrimidin-4-yl]-N-isopropyl-piperidine-1-carboxamide;
4-[1-(benzenesulfonyl)-4-piperidyl]-5-chloro-2-(4-pyridyl)-1H-pyrimidin-6-one;
5-chloro-2-(4-pyridyl)-4-[1-(2,2,2-trifluoroacetyl)-4-piperidyl]-1H-pyrimidin-6-one;
5-chloro-4-(1-isobutyl-4-piperidyl)-2-(4-pyridyl)-1H-pyrimidin-6-one;
4-(1-acetyl-4-piperidyl)-5-chloro-2-(4-pyridyl)-1H-pyrimidin-6-one;
4-(1-benzoyl-4-piperidyl)-5-chloro-2-(4-pyridyl)-1H-pyrimidin-6-one;
4-(4-acetylpiperazin-1-yl)-5-chloro-2-(4-pyridyl)-1H-pyrimidin-6-one;
5-chloro-4-(4-methylsulfonylpiperazin-1-yl)-2-(4-pyridyl)-1H-pyrimidin-6-one;
5-chloro-4-[1-(2,2-dimethylpropanoyl)-4-piperidyl]-2-(4-pyridyl)-1H-pyrimidin-6-one;
5-chloro-4-[1-(pyridine-2-carbonyl)-4-piperidyl]-2-(4-pyridyl)-1H-pyrimidin-6-one;
4-[4-[5-chloro-6-oxo-2-(4-pyridyl)-1H-pyrimidin-4-yl]piperidine-1-carbonyl]benzonitrile;
5-chloro-4-[1-(pyridazine-4-carbonyl)-4-piperidyl]-2-(4-pyridyl)-1H-pyrimidin-6-one;
3-[4-[5-chloro-6-oxo-2-(4-pyridyl)-1H-pyrimidin-4-yl]piperidine-1-carbonyl]benzonitrile;
5-chloro-4-[1-(2-iodobenzoyl)-4-piperidyl]-2-(4-pyridyl)-1H-pyrimidin-6-one;

5-chloro-4-[1-(3-hydroxybenzoyl)-4-piperidyl]-2-(4-pyridyl)-1H-pyrimidin-6-one;
5-chloro-4-[1-(furan-2-carbonyl)-4-piperidyl]-2-(4-pyridyl)-1H-pyrimidin-6-one;
5-chloro-4-[1-(3-methyl-1H-pyrazole-5-carbonyl)-4-piperidyl]-2-(4-pyridyl)-1H-pyrimidin-6-one;
5-chloro-4-[1-[2-(1H-imidazol-4-yl)acetyl]-4-piperidyl]-2-(4-pyridyl)-1H-pyrimidin-6-one;
5-chloro-4-[1-(2,4-dimethylthiazole-5-carbonyl)-4-piperidyl]-2-(4-pyridyl)-1H-pyrimidin-6-one;
5-chloro-4-[1-(1-methylimidazole-4-carbonyl)-4-piperidyl]-2-(4-pyridyl)-1H-pyrimidin-6-one;
5-chloro-4-[1-(2,5-dimethylpyrazole-3-carbonyl)-4-piperidyl]-2-(4-pyridyl)-1H-pyrimidin-6-one;
5-chloro-2-(4-pyridyl)-4-[1-(thiazole-4-carbonyl)-4-piperidyl]-1H-pyrimidin-6-one;
5-chloro-4-[1-(1,5-dimethylpyrazole-3-carbonyl)-4-piperidyl]-2-(4-pyridyl)-1H-pyrimidin-6-one;
5-chloro-2-(4-pyridyl)-4-[1-(thiadiazole-4-carbonyl)-4-piperidyl]-1H-pyrimidin-6-one;
4-[1-(4-acetylbenzoyl)-4-piperidyl]-5-chloro-2-(4-pyridyl)-1H-pyrimidin-6-one;
3-[4-[5-chloro-6-oxo-2-(4-pyridyl)-1H-pyrimidin-4-yl]piperidine-1-carbonyl]-4-methoxy-benzenesulfonamide;
N-[4-[4-[5-chloro-6-oxo-2-(4-pyridyl)-1H-pyrimidin-4-yl]piperidine-1-carbonyl]phenyl]acetamide;
5-chloro-4-[1-(4-isopropoxybenzoyl)-4-piperidyl]-2-(4-pyridyl)-1H-pyrimidin-6-one;
tert-butyl N-[(1S)-2-[4-[5-chloro-6-oxo-2-(4-pyridyl)-1H-pyrimidin-4-yl]-1-piperidyl]-1-methyl-2-oxo-ethyl]carbamate;
N-[4-[4-[5-chloro-6-oxo-2-(4-pyridyl)-1H-pyrimidin-4-yl]piperidine-1-carbonyl]phenyl]-N-methyl-methanesulfonamide;
5-chloro-4-[1-(2-chlorobenzoyl)-4-piperidyl]-2-(4-pyridyl)-1H-pyrimidin-6-one;
5-chloro-4-[1-(4-methylthiazole-5-carbonyl)-4-piperidyl]-2-(4-pyridyl)-1H-pyrimidin-6-one;
5-chloro-4-[1-(1H-pyrazole-4-carbonyl)-4-piperidyl]-2-(4-pyridyl)-1H-pyrimidin-6-one;
5-chloro-4-[1-(5-methylisoxazole-3-carbonyl)-4-piperidyl]-2-(4-pyridyl)-1H-pyrimidin-6-one;
5-chloro-4-[1-(2,2-difluorocyclopropanecarbonyl)-4-piperidyl]-2-(4-pyridyl)-1H-pyrimidin-6-one;
tert-butyl N-[(1R)-2-[4-[5-chloro-6-oxo-2-(4-pyridyl)-1H-pyrimidin-4-yl]-1-piperidyl]-1-methyl-2-oxo-ethyl]carbamate;
5-chloro-4-[1-(3-methylbenzoyl)-4-piperidyl]-2-(4-pyridyl)-1H-pyrimidin-6-one;
5-chloro-4-[1-[4-(methylsulfonylmethyl)benzoyl]-4-piperidyl]-2-(4-pyridyl)-1H-pyrimidin-6-one;
tert-butyl N-[1-[4-[5-chloro-6-oxo-2-(4-pyridyl)-1H-pyrimidin-4-yl]piperidine-1-carbonyl]butyl]carbamate;
4-[1-(2-aminopropanoyl)-4-piperidyl]-5-chloro-2-(4-pyridyl)-1H-pyrimidin-6-one;
5-chloro-2-(4-pyridyl)-4-[4-(2,2,2-trifluoroacetyl)piperazin-1-yl]-1H-pyrimidin-6-one;
5-chloro-4-[(3S)-3-methyl-4-(2,2,2-trifluoroacetyl)piperazin-1-yl]-2-(4-pyridyl)-1H-pyrimidin-6-one;
4-[(3S)-4-acetyl-3-methyl-piperazin-1-yl]-5-chloro-2-(4-pyridyl)-1H-pyrimidin-6-one;
5-chloro-4-(1-methyl-4-piperidyl)-2-(4-pyridyl)-1H-pyrimidin-6-one;
5-chloro-4-[4-[(3-chlorophenyl)methyl]piperazin-1-yl]-2-(4-pyridyl)-1H-pyrimidin-6-one;
5-chloro-4-(4-methylpiperazin-1-yl)-2-(4-pyridyl)-1H-pyrimidin-6-one;
5-chloro-4-(4-isobutylpiperazin-1-yl)-2-(4-pyridyl)-1H-pyrimidin-6-one;
5-chloro-4-(4-isopentylpiperazin-1-yl)-2-(4-pyridyl)-1H-pyrimidin-6-one;
5-chloro-4-[4-(cyclopentylmethyl)piperazin-1-yl]-2-(4-pyridyl)-1H-pyrimidin-6-one;
5-chloro-4-[4-(cyclohexylmethyl)piperazin-1-yl]-2-(4-pyridyl)-1H-pyrimidin-6-one;
5-chloro-4-(4-isopropylpiperazin-1-yl)-2-(4-pyridyl)-1H-pyrimidin-6-one;
5-chloro-2-(2-fluoro-4-pyridyl)-4-(1-isobutyl-4-piperidyl)-1H-pyrimidin-6-one;
5-chloro-4-[(3S)-3,4-dimethylpiperazin-1-yl]-2-(4-pyridyl)-1H-pyrimidin-6-one;
5-chloro-4-morpholino-2-(4-pyridyl)-1H-pyrimidin-6-one;
5-chloro-4-(3,3-difluoro-1-piperidyl)-2-(2-fluoro-4-pyridyl)-1H-pyrimidin-6-one;
5-chloro-4-(2-phenylmorpholin-4-yl)-2-(4-pyridyl)-1H-pyrimidin-6-one;
5-chloro-4-(2,6-dimethylmorpholin-4-yl)-2-(4-pyridyl)-1H-pyrimidin-6-one;
5-chloro-4-(2-isobutylmorpholin-4-yl)-2-(4-pyridyl)-1H-pyrimidin-6-one;
5-chloro-4-[2-(2-hydroxyethyl)morpholin-4-yl]-2-(4-pyridyl)-1H-pyrimidin-6-one;
5-chloro-4-(3-propylmorpholin-4-yl)-2-(4-pyridyl)-1H-pyrimidin-6-one;
4-[5-chloro-6-oxo-2-(4-pyridyl)-1H-pyrimidin-4-yl]morpholine-2-carboxamide;
4-[5-chloro-6-oxo-2-(4-pyridyl)-1H-pyrimidin-4-yl]-N,N-dimethyl-morpholine-2-carboxamide;
tert-butyl N-[[4-[5-chloro-6-oxo-2-(4-pyridyl)-1H-pyrimidin-4-yl]morpholin-2-yl]methyl]carbamate;
5-chloro-4-[2-(2-methoxyethyl)morpholin-4-yl]-2-(4-pyridyl)-1H-pyrimidin-6-one;
1-[5-chloro-6-oxo-2-(4-pyridyl)-1H-pyrimidin-4-yl]piperidine-4-carboxamide;
5-chloro-2-(4-pyridyl)-4-[3-(trifluoromethyl)piperazin-1-yl]-1H-pyrimidin-6-one;
4-(4-benzyl-1-piperidyl)-5-chloro-2-(4-pyridyl)-1H-pyrimidin-6-one;
5-chloro-4-(3,5-dimethyl-1-piperidyl)-2-(4-pyridyl)-1H-pyrimidin-6-one;
5-chloro-4-(4-hydroxy-1-piperidyl)-2-(4-pyridyl)-1H-pyrimidin-6-one;
5-chloro-4-(3-methyl-1-piperidyl)-2-(4-pyridyl)-1H-pyrimidin-6-one;
5-chloro-4-(4-fluoro-1-piperidyl)-2-(4-pyridyl)-1H-pyrimidin-6-one;
5-chloro-2-(4-pyridyl)-4-[3-(trifluoromethyl)-1-piperidyl]-1H-pyrimidin-6-one;
5-chloro-4-(3,5-dimethylpiperazin-1-yl)-2-(4-pyridyl)-1H-pyrimidin-6-one;
5-chloro-4-[4-(hydroxymethyl)-1-piperidyl]-2-(4-pyridyl)-1H-pyrimidin-6-one;
2-[4-[5-chloro-6-oxo-2-(4-pyridyl)-1H-pyrimidin-4-yl]piperazin-1-yl]-N,N-dimethyl-acetamide;
5-chloro-4-[4-(3-fluorophenyl)piperazin-1-yl]-2-(4-pyridyl)-1H-pyrimidin-6-one;
benzyl 4-[5-chloro-6-oxo-2-(4-pyridyl)-1H-pyrimidin-4-yl]piperazine-1-carboxylate;
5-chloro-4-[4-(3-methoxyphenyl)piperazin-1-yl]-2-(4-pyridyl)-1H-pyrimidin-6-one;

4-(azepan-1-yl)-5-chloro-2-(4-pyridyl)-1H-pyrimidin-6-one;

5-chloro-4-(1,4-diazepan-1-yl)-2-(4-pyridyl)-1H-pyrimidin-6-one;

5-chloro-2-(4-pyridyl)-4-[4-(3-pyridyl)piperazin-1-yl]-1H-pyrimidin-6-one;

1-[5-chloro-6-oxo-2-(4-pyridyl)-1H-pyrimidin-4-yl]-1,4-diazepan-5-one;

(2R)-1-[5-chloro-6-oxo-2-(4-pyridyl)-1H-pyrimidin-4-yl]pyrrolidine-2-carboxamide;

4-[5-chloro-6-oxo-2-(4-pyridyl)-1H-pyrimidin-4-yl]-1,4-diazepane-1-carbaldehyde;

4-[(9aS)-1,3,4,5,7,8,9,9a-octahydropyrrolo[1,2-a][1,4]diazepin-2-yl]-5-chloro-2-(4-pyridyl)-1H-pyrimidin-6-one;

5-chloro-4-(2,2-dimethylmorpholin-4-yl)-2-(4-pyridyl)-1H-pyrimidin-6-one;

5-chloro-4-(4-methyl-1-piperidyl)-2-(4-pyridyl)-1H-pyrimidin-6-one;

5-chloro-4-[3-(hydroxymethyl)-1-piperidyl]-2-(4-pyridyl)-1H-pyrimidin-6-one;

5-chloro-4-[3-(hydroxymethyl)azetidin-1-yl]-2-(4-pyridyl)-1H-pyrimidin-6-one;

5-chloro-4-[4-(2-hydroxyethyl)piperazin-1-yl]-2-(4-pyridyl)-1H-pyrimidin-6-one;

5-chloro-4-(2-oxa-7-azaspiro[3.4]octan-7-yl)-2-(4-pyridyl)-1H-pyrimidin-6-one;

5-chloro-4-(4,4-difluoro-1-piperidyl)-2-(4-pyridyl)-1H-pyrimidin-6-one;

5-chloro-2-(4-pyridyl)-4-thiomorpholino-1H-pyrimidin-6-one;

5-chloro-4-[(3R)-3-(hydroxymethyl)piperazin-1-yl]-2-(4-pyridyl)-1H-pyrimidin-6-one;

5-chloro-4-[(3S)-3-methylpiperazin-1-yl]-2-(4-pyridyl)-1H-pyrimidin-6-one;

5-chloro-4-(3-fluoro-1-piperidyl)-2-(4-pyridyl)-1H-pyrimidin-6-one;

5-chloro-4-(3,3-difluoro-1-piperidyl)-2-(4-pyridyl)-1H-pyrimidin-6-one;

5-chloro-4-[(3R)-3-fluoropyrrolidin-1-yl]-2-(4-pyridyl)-1H-pyrimidin-6-one;

5-chloro-4-(6,6-difluoro-3-azabicyclo[3.1.0]hexan-3-yl)-2-(4-pyridyl)-1H-pyrimidin-6-one;

5-chloro-2-(4-pyridyl)-4-[3-(trifluoromethyl)pyrrolidin-1-yl]-1H-pyrimidin-6-one;

5-chloro-4-[4-(2-hydroxyethyl)-1,4-diazepan-1-yl]-2-(4-pyridyl)-1H-pyrimidin-6-one;

4-(4-tert-butyl-1,4-diazepan-1-yl)-5-chloro-2-(4-pyridyl)-1H-pyrimidin-6-one;

5-chloro-4-(3-hydroxypyrrolidin-1-yl)-2-(4-pyridyl)-1H-pyrimidin-6-one;

5-chloro-2-(4-pyridyl)-4-[(3S)-3-(trifluoromethyl)piperazin-1-yl]-1H-pyrimidin-6-one;

5-chloro-4-[(3R)-3-methylpiperazin-1-yl]-2-(4-pyridyl)-1H-pyrimidin-6-one;

4-[5-chloro-6-oxo-2-(4-pyridyl)-1H-pyrimidin-4-yl]-1,4-diazepan-2-one;

5-chloro-2-(4-pyridyl)-4-[4-(2,2,2-trifluoroethyl)-1,4-diazepan-1-yl]-1H-pyrimidin-6-one;

5-chloro-4-(4-propyl-1,4-diazepan-1-yl)-2-(4-pyridyl)-1H-pyrimidin-6-one;

5-chloro-2-(4-pyridyl)-4-[4-(2,2,2-trifluoroacetyl)-1,4-diazepan-1-yl]-1H-pyrimidin-6-one;

5-chloro-4-(4-methylsulfonyl-1,4-diazepan-1-yl)-2-(4-pyridyl)-1H-pyrimidin-6-one;

5-chloro-2-(4-pyridyl)-4-[4-(2,2,2-trifluoroethyl)piperazin-1-yl]-1H-pyrimidin-6-one;

5-chloro-4-[4-(2,2-difluoroethyl)piperazin-1-yl]-2-(4-pyridyl)-1H-pyrimidin-6-one;

2-[4-[5-chloro-6-oxo-2-(4-pyridyl)-1H-pyrimidin-4-yl]piperazin-1-yl]acetonitrile;

4-[(8aS)-7,7-difluoro-1,3,4,6,8,8a-hexahydropyrrolo[1,2-a]pyrazin-2-yl]-5-chloro-2-(4-pyridyl)-1H-pyrimidin-6-one;

5-chloro-4-(4-prop-2-ynylpiperazin-1-yl)-2-(4-pyridyl)-1H-pyrimidin-6-one;

5-chloro-4-(2-oxa-7-azaspiro[3.5]nonan-7-yl)-2-(4-pyridyl)-1H-pyrimidin-6-one;

5-chloro-2-(4-pyridyl)-4-[4-(2,2,3,3-tetrafluoropropyl)piperazin-1-yl]-1H-pyrimidin-6-one;

1-[5-chloro-6-oxo-2-(4-pyridyl)-1H-pyrimidin-4-yl]piperidine-4-carbonitrile;

5-chloro-4-(3-oxa-9-azabicyclo[3.3.1]nonan-9-yl)-2-(4-pyridyl)-1H-pyrimidin-6-one;

4-(4-tert-butylpiperazin-1-yl)-5-chloro-2-(4-pyridyl)-1H-pyrimidin-6-one;

5-chloro-4-[3-(1,1-difluoroethyl)piperazin-1-yl]-2-(4-pyridyl)-1H-pyrimidin-6-one;

4-[(3S)-3-tert-butylpiperazin-1-yl]-5-chloro-2-(4-pyridyl)-1H-pyrimidin-6-one;

5-chloro-4-(5,8-diazaspiro[3.5]nonan-8-yl)-2-(4-pyridyl)-1H-pyrimidin-6-one;

5-chloro-2-(4-pyridyl)-4-[2-(trifluoromethyl)morpholin-4-yl]-1H-pyrimidin-6-one;

4-[(3S)-3-tert-butylpiperazin-1-yl]-5-chloro-2-(2-fluoro-4-pyridyl)-1H-pyrimidin-6-one;

5-chloro-4-[(1S,4S)-2,5-diazabicyclo[2.2.1]heptan-2-yl]-2-(4-pyridyl)-1H-pyrimidin-6-one;

O1-tert-butyl O2-methyl (2S)-4-[5-chloro-6-oxo-2-(4-pyridyl)-1H-pyrimidin-4-yl]piperazine-1,2-dicarboxylate;

methyl (2S)-4-[5-chloro-6-oxo-2-(4-pyridyl)-1H-pyrimidin-4-yl]piperazine-2-carboxylate;

4-[(3S)-3-benzylpiperazin-1-yl]-5-chloro-2-(4-pyridyl)-1H-pyrimidin-6-one;

4-[(3R)-3-benzylpiperazin-1-yl]-5-chloro-2-(4-pyridyl)-1H-pyrimidin-6-one;

5-chloro-4-[(2R,5R)-2,5-dimethylpiperazin-1-yl]-2-(4-pyridyl)-1H-pyrimidin-6-one;

5-chloro-4-(3-hydroxy-1-piperidyl)-2-(4-pyridyl)-1H-pyrimidin-6-one;

5-chloro-4-[3-(4-chlorophenyl)piperazin-1-yl]-2-(4-pyridyl)-1H-pyrimidin-6-one;

5-chloro-4-[3-(4-methoxyphenyl)piperazin-1-yl]-2-(4-pyridyl)-1H-pyrimidin-6-one;

5-chloro-2-(2-fluoro-4-pyridyl)-4-[(3S)-3-isopropylpiperazin-1-yl]-1H-pyrimidin-6-one;

5-chloro-2-(2-fluoro-4-pyridyl)-4-[(3S)-3-methylpiperazin-1-yl]-1H-pyrimidin-6-one;

5-chloro-4-[(2S,5S)-2,5-dimethylpiperazin-1-yl]-2-(4-pyridyl)-1H-pyrimidin-6-one;

5-chloro-4-[(2R,5S)-2,5-dimethylpiperazin-1-yl]-2-(4-pyridyl)-1H-pyrimidin-6-one;

5-chloro-4-[(3R)-3-(2-hydroxyethyl)piperazin-1-yl]-2-(4-pyridyl)-1H-pyrimidin-6-one;

5-chloro-4-[(3S)-3-(2-hydroxyethyl)piperazin-1-yl]-2-(4-pyridyl)-1H-pyrimidin-6-one;

5-chloro-2-(4-pyridyl)-4-[3-(trifluoromethyl)-1-piperidyl]-1H-pyrimidin-6-one;

5-chloro-2-(4-pyridyl)-4-[3-(2-thienyl)piperazin-1-yl]-1H-pyrimidin-6-one;

5-chloro-4-[3-(3-hydroxyphenyl)piperazin-1-yl]-2-(4-pyridyl)-1H-pyrimidin-6-one;

5-chloro-4-[3-(3-methoxyphenyl)piperazin-1-yl]-2-(4-pyridyl)-1H-pyrimidin-6-one;
5-chloro-2-(4-pyridyl)-4-[(3R)-3-(trifluoromethyl)piperazin-1-yl]-1H-pyrimidin-6-one;
5-chloro-4-[(3S)-3-methyl-4-(2,2,2-trifluoroethyl)piperazin-1-yl]-2-(4-pyridyl)-1H-pyrimidin-6-one;
5-chloro-2-(4-pyridyl)-4-[1-(2,2,2-trifluoroethyl)-4-piperidyl]-1H-pyrimidin-6-one;
4-[(3R)-3-aminoazepan-1-yl]-5-chloro-2-(2-fluoro-4-pyridyl)-1H-pyrimidin-6-one;
5-chloro-2-(4-pyridyl)-4-[rac-(3S,8aS)-3-isobutyl-3,4,6,7,8,8a-hexahydro-1H-pyrrolo[1,2-a]pyrazin-2-yl]-1H-pyrimidin-6-one;
4-[(3S)-3-tert-butylpiperazin-1-yl]-5-fluoro-2-(4-pyridyl)-1H-pyrimidin-6-one;
5-chloro-4-(1,4-oxazepan-4-yl)-2-(4-pyridyl)-1H-pyrimidin-6-one;
5-chloro-2-(2-fluoro-4-pyridyl)-4-[(3R)-3-(1-hydroxy-1-methyl-ethyl)piperazin-1-yl]-1H-pyrimidin-6-one;
4-[(3S)-3-aminoazepan-1-yl]-5-chloro-2-(2-fluoro-4-pyridyl)-1H-pyrimidin-6-one;
5-chloro-4-[(3S,5R)-3,5-dihydroxy-1-piperidyl]-2-(2-fluoro-4-pyridyl)-1H-pyrimidin-6-one;
5-chloro-2-(2-fluoro-4-pyridyl)-4-(6-hydroxy-1,4-diazepan-1-yl)-1H-pyrimidin-6-one;
5-chloro-2-(2-fluoro-4-pyridyl)-4-tetrahydropyran-4-ylsulfanyl-1H-pyrimidin-6-one;
5-chloro-2-(2-fluoro-4-pyridyl)-4-(3-oxa-8-azabicyclo[3.2.1]octan-8-yl)-1H-pyrimidin-6-one;
5-chloro-2-(2-fluoro-4-pyridyl)-4-(4-piperidylsulfanyl)-1H-pyrimidin-6-one;
4-(azetidin-3-yloxy)-5-chloro-2-(2-fluoro-4-pyridyl)-1H-pyrimidin-6-one;
4-[(1R,3 S)-3-aminocyclopentoxy]-5-chloro-2-(2-fluoro-4-pyridyl)-1H-pyrimidin-6-one;
5-chloro-2-(2-fluoro-4-pyridyl)-4-[(3R)-3-(methylamino)-1-piperidyl]-1H-pyrimidin-6-one;
5-chloro-2-(2-fluoro-4-pyridyl)-4-[(3S)-3-(methylamino)-1-piperidyl]-1H-pyrimidin-6-one;
5-chloro-4-(2,6-diazaspiro[3.3]heptan-2-yl)-2-(2-fluoro-4-pyridyl)-1H-pyrimidin-6-one;
5-chloro-2-(2-fluoro-4-pyridyl)-4-(oxetan-3-yloxy)-1H-pyrimidin-6-one;
5-chloro-2-(2-fluoro-4-pyridyl)-4-[(3S)-tetrahydrofuran-3-yl]oxy-1H-pyrimidin-6-one;
5-chloro-4-[(2S,6R)-2,6-dimethylmorpholin-4-yl]-2-(2-fluoro-4-pyridyl)-1H-pyrimidin-6-one;
5-chloro-2-(2-fluoro-4-pyridyl)-4-[2-(1-piperidylmethyl)morpholin-4-yl]-1H-pyrimidin-6-one;
1-[5-chloro-2-(2-fluoro-4-pyridyl)-6-oxo-1H-pyrimidin-4-yl]azepan-4-one;
5-chloro-4-(4,4-difluoroazepan-1-yl)-2-(2-fluoro-4-pyridyl)-1H-pyrimidin-6-one;
5-chloro-4-[(2R)-2-ethylmorpholin-4-yl]-2-(2-fluoro-4-pyridyl)-1H-pyrimidin-6-one;
5-chloro-4-(1,4-diazepan-1-yl)-2-(2-fluoro-4-pyridyl)-1H-pyrimidin-6-one;
5-chloro-2-(2-fluoro-4-pyridyl)-4-(6-hydroxy-1,4-oxazepan-4-yl)-1H-pyrimidin-6-one;
4-[5-chloro-2-(2-fluoro-4-pyridyl)-6-oxo-1H-pyrimidin-4-yl]-1,4-oxazepan-6-one;
4-[(3S)-3-anilino-1-piperidyl]-5-chloro-2-(2-fluoro-4-pyridyl)-1H-pyrimidin-6-one;
5-chloro-4-[[(3,3-dimethyl-4-piperidyl)-methyl-amino]-2-(2-fluoro-4-pyridyl)-1H-pyrimidin-6-one;
5-chloro-4-[(3,3-dimethyl-4-piperidyl)amino]-2-(2-fluoro-4-pyridyl)-1H-pyrimidin-6-one;
5-chloro-2-(2-fluoro-4-pyridyl)-4-[3-(morpholinomethyl)pyrrolidin-1-yl]-1H-pyrimidin-6-one;
5-chloro-4-(2,6-diazaspiro[4.5]decan-2-yl)-2-(2-fluoro-4-pyridyl)-1H-pyrimidin-6-one;
5-chloro-2-(2-fluoro-4-pyridyl)-4-[(3R)-3-hydroxypyrrolidin-1-yl]-1H-pyrimidin-6-one;
5-chloro-2-(2-fluoro-4-pyridyl)-4-[(3S)-3-hydroxypyrrolidin-1-yl]-1H-pyrimidin-6-one;
4-(3,4a,5,6,7,7a-hexahydro-2H-pyrrolo[3,4-b][1,4]oxazin-4-yl)-5-chloro-2-(2-fluoro-4-pyridyl)-1H-pyrimidin-6-one;
5-chloro-4-(1,7-diazaspiro[4.4]nonan-7-yl)-2-(2-fluoro-4-pyridyl)-1H-pyrimidin-6-one;
5-chloro-4-(2,7-diazaspiro[4.4]nonan-2-yl)-2-(2-fluoro-4-pyridyl)-1H-pyrimidin-6-one;
4-[(3R)-3-(aminomethyl)pyrrolidin-1-yl]-5-chloro-2-(2-fluoro-4-pyridyl)-1H-pyrimidin-6-one;
5-chloro-4-(2,9-diazaspiro[4.5]decan-2-yl)-2-(2-fluoro-4-pyridyl)-1H-pyrimidin-6-one;
4-(2,3,3a,4,5,6,7,7a-octahydropyrrolo[2,3-c]pyridin-1-yl)-5-chloro-2-(2-fluoro-4-pyridyl)-1H-pyrimidin-6-one;
5-chloro-2-(2-fluoro-4-pyridyl)-4-(4-piperidylamino)-1H-pyrimidin-6-one;
4-(2,3,3a,4,5,6,7,7a-octahydropyrrolo[3,2-b]pyridin-1-yl)-5-chloro-2-(2-fluoro-4-pyridyl)-1H-pyrimidin-6-one;
5-chloro-2-(2-fluoro-4-pyridyl)-4-(morpholin-3-ylmethylamino)-1H-pyrimidin-6-one;
4-(2,3,3a,4,5,6,7,7a-octahydropyrrolo[3,2-c]pyridin-1-yl)-5-chloro-2-(2-fluoro-4-pyridyl)-1H-pyrimidin-6-one;
4-(2,3,3a,4,6,6a-hexahydro-1H-pyrrolo[3,4-c]pyrrol-5-yl)-5-chloro-2-(2-fluoro-4-pyridyl)-1H-pyrimidin-6-one;
5-chloro-2-(2-fluoro-4-pyridyl)-4-(1-oxa-4,9-diazaspiro[5.5]undecan-4-yl)-1H-pyrimidin-6-one
5-chloro-2-(2-fluoro-4-pyridyl)-4-(3-tetrahydropyran-4-ylpyrrolidin-1-yl)-1H-pyrimidin-6-one;
5-chloro-2-(2-fluoro-4-pyridyl)-4-[methyl(tetrahydropyran-4-yl)amino]-1H-pyrimidin-6-one;
5-chloro-4-(2,8-diazaspiro[4.5]decan-2-yl)-2-(2-fluoro-4-pyridyl)-1H-pyrimidin-6-one;
1-[5-chloro-2-(2-fluoro-4-pyridyl)-6-oxo-1H-pyrimidin-4-yl]-N-methyl-piperidine-4-carboxamide;
N-[1-[5-chloro-2-(2-fluoro-4-pyridyl)-6-oxo-1H-pyrimidin-4-yl]-4-piperidyl]acetamide;
8-[5-chloro-2-(2-fluoro-4-pyridyl)-6-oxo-1H-pyrimidin-4-yl]-1,3,8-triazaspiro[4.5]decane-2,4-dione;
5-chloro-2-(2-fluoro-4-pyridyl)-4-(4-oxo-1-piperidyl)-1H-pyrimidin-6-one;
4-[(3R,4R)-3-amino-4-hydroxy-1-piperidyl]-5-chloro-2-(2-fluoro-4-pyridyl)-1H-pyrimidin-6-one;
5-chloro-4-(1,4-dioxa-8-azaspiro[4.5]decan-8-yl)-2-(2-fluoro-4-pyridyl)-1H-pyrimidin-6-one;
4-[(4aS,7aS)-3,4,4a,5,7,7a-hexahydro-2H-pyrrolo[3,4-b][1,4]oxazin-6-yl]-5-chloro-2-(2-fluoro-4-pyridyl)-1H-pyrimidin-6-one;
5-chloro-2-(2-fluoro-4-pyridyl)-4-(1-oxa-8-azaspiro[4.5]decan-8-yl)-1H-pyrimidin-6-one;
4-[5-chloro-2-(2-fluoro-4-pyridyl)-6-oxo-1H-pyrimidin-4-yl]piperazine-1-carboxamide;
4-[5-chloro-2-(2-fluoro-4-pyridyl)-6-oxo-1H-pyrimidin-4-yl]-N,N-dimethyl-piperazine-1-carboxamide;
5-chloro-4-(1,8-diazaspiro[4.5]decan-8-yl)-2-(2-fluoro-4-pyridyl)-1H-pyrimidin-6-one;

5-chloro-4-(2,8-diazaspiro[4.5]decan-8-yl)-2-(2-fluoro-4-pyridyl)-1H-pyrimidin-6-one;
4-(2,3,3a,5,6,6a-hexahydro-1H-pyrrolo[3,2-b]pyrrol-4-yl)-5-chloro-2-(2-fluoro-4-pyridyl)-1H-pyrimidin-6-one;
5-chloro-2-(2-fluoro-4-pyridyl)-4-(4-morpholino-1-piperidyl)-1H-pyrimidin-6-one;
5-chloro-4-(2,6-diazaspiro[3.4]octan-6-yl)-2-(2-fluoro-4-pyridyl)-1H-pyrimidin-6-one;
5-chloro-2-(2-fluoro-4-pyridyl)-4-[2-(morpholinomethyl)pyrrolidin-1-yl]-1H-pyrimidin-6-one;
(2R)-1-[5-chloro-2-(2-fluoro-4-pyridyl)-6-oxo-1H-pyrimidin-4-yl]pyrrolidine-2-carboxamide;
(2S)-1-[5-chloro-2-(2-fluoro-4-pyridyl)-6-oxo-1H-pyrimidin-4-yl]pyrrolidine-2-carboxamide;
(3R)-1-[5-chloro-2-(2-fluoro-4-pyridyl)-6-oxo-1H-pyrimidin-4-yl]pyrrolidine-3-carboxamide;
5-chloro-4-(1,9-diazaspiro[4.5]decan-9-yl)-2-(2-fluoro-4-pyridyl)-1H-pyrimidin-6-one;
(3S)-1-[5-chloro-2-(2-fluoro-4-pyridyl)-6-oxo-1H-pyrimidin-4-yl]pyrrolidine-3-carboxamide;
4-(3-amino-4-fluoro-1-piperidyl)-5-chloro-2-(2-fluoro-4-pyridyl)-1H-pyrimidin-6-one;
1-[5-chloro-2-(2-fluoro-4-pyridyl)-6-oxo-1H-pyrimidin-4-yl]-N-methyl-piperidine-3-carboxamide;
N-[1-[5-chloro-2-(2-fluoro-4-pyridyl)-6-oxo-1H-pyrimidin-4-yl]-4-piperidyl]-2-methyl-propanamide;
1-[5-chloro-2-(2-fluoro-4-pyridyl)-6-oxo-1H-pyrimidin-4-yl]-N-isopropyl-piperidine-4-carboxamide;
1-[5-chloro-2-(2-fluoro-4-pyridyl)-6-oxo-1H-pyrimidin-4-yl]-N-(2-hydroxyethyl)piperidine-4-carboxamide;
1-[5-chloro-2-(2-fluoro-4-pyridyl)-6-oxo-1H-pyrimidin-4-yl]-N-ethyl-piperidine-4-carboxamide;
5-chloro-4-(2,7-diazaspiro[4.5]decan-7-yl)-2-(2-fluoro-4-pyridyl)-1H-pyrimidin-6-one;
5-chloro-4-(1,7-diazaspiro[4.4]nonan-1-yl)-2-(2-fluoro-4-pyridyl)-1H-pyrimidin-6-one;
5-chloro-4-(1,9-diazaspiro[4.5]decan-1-yl)-2-(2-fluoro-4-pyridyl)-1H-pyrimidin-6-one;
4-[(3aS,6aS)-3,3a,4,5,6,6a-hexahydro-2H-pyrrolo[2,3-c]pyrrol-1-yl]-5-chloro-2-(2-fluoro-4-pyridyl)-1H-pyrimidin-6-one;
5-chloro-4-(3,8-diazabicyclo[3.2.1]octan-8-yl)-2-(2-fluoro-4-pyridyl)-1H-pyrimidin-6-one;
5-chloro-4-(1,8-diazaspiro[4.5]decan-1-yl)-2-(2-fluoro-4-pyridyl)-1H-pyrimidin-6-one;
4-(3,4,4a,5,6,7,8,8a-octahydro-2H-1,5-naphthyridin-1-yl)-5-chloro-2-(2-fluoro-4-pyridyl)-1H-pyrimidin-6-one;
5-chloro-2-(2-fluoro-4-pyridyl)-4-[4-(4-methylpiperazin-1-yl)-1-piperidyl]-1H-pyrimidin-6-one;
5-chloro-4-[ethyl(tetrahydropyran-4-yl)amino]-2-(2-fluoro-4-pyridyl)-1H-pyrimidin-6-one;
5-chloro-2-(2-fluoro-4-pyridyl)-4-[methyl-[(3S)-3-piperidyl]amino]-1H-pyrimidin-6-one;
5-chloro-2-(2-fluoro-4-pyridyl)-4-[methyl-[(3R)-3-piperidyl]amino]-1H-pyrimidin-6-one;
5-chloro-4-(6,8-dihydro-5H-[1,2,4]triazolo[4,3-a]pyrazin-7-yl)-2-(2-fluoro-4-pyridyl)-1H-pyrimidin-6-one;
5-chloro-2-(2-fluoro-4-pyridyl)-4-(3-isopropyl-6,8-dihydro-5H-[1,2,4]triazolo[4,3-a]pyrazin-7-yl)-1H-pyrimidin-6-one;
5-chloro-2-(2-fluoro-4-pyridyl)-4-[(3S)-3-(methylamino)pyrrolidin-1-yl]-1H-pyrimidin-6-one;
5-chloro-4-[(3S)-3-(dimethylamino)pyrrolidin-1-yl]-2-(2-fluoro-4-pyridyl)-1H-pyrimidin-6-one;
4-[(3S)-3-amino-3-methyl-pyrrolidin-1-yl]-5-chloro-2-(2-fluoro-4-pyridyl)-1H-pyrimidin-6-one;
N-[(3S)-1-[5-chloro-2-(2-fluoro-4-pyridyl)-6-oxo-1H-pyrimidin-4-yl]pyrrolidin-3-yl]acetamide;
4-(1,2,3,3a,5,6,7,7a-octahydropyrrolo[3,2-b]pyridin-4-yl)-5-chloro-2-(2-fluoro-4-pyridyl)-1H-pyrimidin-6-one;
5-chloro-2-(2-fluoro-4-pyridyl)-4-pyrrolidin-1-yl-1H-pyrimidin-6-one;
5-chloro-2-(2-fluoro-4-pyridyl)-4-(1-piperidyl)-1H-pyrimidin-6-one;
5-chloro-2-(2-fluoro-4-pyridyl)-4-[(2S)-2-methylpyrrolidin-1-yl]-1H-pyrimidin-6-one;
5-chloro-2-(2-fluoro-4-pyridyl)-4-[(2R)-2-methylpyrrolidin-1-yl]-1H-pyrimidin-6-one;
5-chloro-2-(2-fluoro-4-pyridyl)-4-[(2S)-2-methyl-1-piperidyl]-1H-pyrimidin-6-one;
5-chloro-2-(2-fluoro-4-pyridyl)-4-[(2R)-2-methyl-1-piperidyl]-1H-pyrimidin-6-one;
5-chloro-2-(2-fluoro-4-pyridyl)-4-[(3R)-3-methoxy-1-piperidyl]-1H-pyrimidin-6-one;
5-chloro-2-(2-fluoro-4-pyridyl)-4-[(3S)-3-methoxy-1-piperidyl]-1H-pyrimidin-6-one;
5-chloro-2-(2-fluoro-4-pyridyl)-4-(2-oxa-7-azaspiro[3.4]octan-7-yl)-1H-pyrimidin-6-one;
5-chloro-2-(2-fluoro-4-pyridyl)-4-[2-(phenoxymethyl)morpholin-4-yl]-1H-pyrimidin-6-one;
5-chloro-4-(6,6-difluoro-1,4-oxazepan-4-yl)-2-(2-fluoro-4-pyridyl)-1H-pyrimidin-6-one;
4-(4-aminophenoxy)-5-chloro-2-(2-fluoro-4-pyridyl)-1H-pyrimidin-6-one;
1-[5-chloro-2-(2-fluoro-4-pyridyl)-6-oxo-1H-pyrimidin-4-yl]-1,4-diazepan-5-one;
4-[benzyl(methyl)amino]-5-chloro-2-(2-fluoro-4-pyridyl)-1H-pyrimidin-6-one;
4-(benzylamino)-5-chloro-2-(2-fluoro-4-pyridyl)-1H-pyrimidin-6-one;
5-chloro-2-(2-fluoro-4-pyridyl)-4-[3-(trifluoromethyl)-6,8-dihydro-5H-[1,2,4]triazolo[4,3-a]pyrazin-7-yl]-1H-pyrimidin-6-one;
5-chloro-4-(1,9-dioxa-4-azaspiro[5.5]undecan-4-yl)-2-(2-fluoro-4-pyridyl)-1H-pyrimidin-6-one;
5-chloro-4-(1,4-diazabicyclo[3.2.2]nonan-4-yl)-2-(2-fluoro-4-pyridyl)-1H-pyrimidin-6-one;
4-benzyloxy-5-chloro-2-(2-fluoro-4-pyridyl)-1H-pyrimidin-6-one;
5-chloro-2-(2-fluoro-4-pyridyl)-4-[4-(1H-1,2,4-triazol-3-yl)piperazin-1-yl]-1H-pyrimidin-6-one;
5-chloro-2-(2-fluoro-4-pyridyl)-4-[5-(trifluoromethyl)-1,4-diazepan-1-yl]-1H-pyrimidin-6-one;
5-chloro-4-(3,3-dimethylpiperazin-1-yl)-2-(2-fluoro-4-pyridyl)-1H-pyrimidin-6-one;
5-chloro-2-(2-fluoro-4-pyridyl)-4-(4-methyl-1,4-diazepan-1-yl)-1H-pyrimidin-6-one;
5-chloro-2-(2-fluoro-4-pyridyl)-4-[4-(2,2,2-trifluoroethyl)-1,4-diazepan-1-yl]-1H-pyrimidin-6-one;
5-chloro-4-(2,2-dimethylmorpholin-4-yl)-2-(2-fluoro-4-pyridyl)-1H-pyrimidin-6-one;
5-chloro-4-(2,2-dimethyl-1,4-oxazepan-4-yl)-2-(2-fluoro-4-pyridyl)-1H-pyrimidin-6-one;
5-chloro-4-(2,4-dimethyl-1,4-diazepan-1-yl)-2-(2-fluoro-4-pyridyl)-1H-pyrimidin-6-one;
5-chloro-2-(2-fluoro-4-pyridyl)-4-(5-methyl-1,4-diazepan-1-yl)-1H-pyrimidin-6-one;
5-chloro-4-(6-fluoro-6-methyl-1,4-diazepan-1-yl)-2-(2-fluoro-4-pyridyl)-1H-pyrimidin-6-one;

5-chloro-2-(2-fluoro-4-pyridyl)-4-tetrahydropyran-4-yloxy-1H-pyrimidin-6-one;
2-[(2S)-4-[5-chloro-2-(2-fluoro-4-pyridyl)-6-oxo-1H-pyrimidin-4-yl]piperazin-2-yl]acetonitrile;
5-chloro-4-[(3R)-3-(1,1-difluoroethyl)piperazin-1-yl]-2-(4-pyridyl)-1H-pyrimidin-6-one;
5-fluoro-4-[(3S)-3-isopropylpiperazin-1-yl]-2-(4-pyridyl)-1H-pyrimidin-6-one;
5-chloro-4-[(3S)-3-isopropylpiperazin-1-yl]-2-(4-pyridyl)-1H-pyrimidin-6-one;
5-chloro-2-(2-fluoro-4-pyridyl)-4-(3-isopropylpiperazin-1-yl)-1H-pyrimidin-6-one;
5-chloro-2-(2-fluoro-4-pyridyl)-4-[(3S)-3-(1-hydroxycyclopropyl)piperazin-1-yl]-1H-pyrimidin-6-one;
5-chloro-4-(6,6-difluoro-1,4-diazepan-1-yl)-2-(2-fluoro-4-pyridyl)-1H-pyrimidin-6-one;
5-chloro-2-(2-fluoro-4-pyridyl)-4-[2-(trifluoromethyl)piperazin-1-yl]-1H-pyrimidin-6-one;
5-chloro-2-(2-fluoro-4-pyridyl)-4-[(3R)-3-(trifluoromethyl)piperazin-1-yl]-1H-pyrimidin-6-one;
5-chloro-4-[(3R)-3-(1,1-difluoroethyl)piperazin-1-yl]-2-(2-fluoro-4-pyridyl)-1H-pyrimidin-6-one;
5-chloro-2-(2-fluoro-4-pyridyl)-4-morpholino-1H-pyrimidin-6-one;
4-[(3S)-3-amino-1-piperidyl]-5-chloro-2-(2-fluoro-4-pyridyl)-1H-pyrimidin-6-one;
4-[(3S)-3-(aminomethyl)pyrrolidin-1-yl]-5-chloro-2-(2-fluoro-4-pyridyl)-1H-pyrimidin-6-one;
5-chloro-2-(2-fluoro-4-pyridyl)-4-[rac-(3R)-3-amino-1-piperidyl]-1H-pyrimidin-6-one;
4-[(3S)-3-aminopyrrolidin-1-yl]-5-chloro-2-(2-fluoro-4-pyridyl)-1H-pyrimidin-6-one;
4-(4-amino-1-piperidyl)-5-chloro-2-(2-fluoro-4-pyridyl)-1H-pyrimidin-6-one;
4-[(3S)-3-tert-butylpiperazin-1-yl]-5-fluoro-2-(2-fluoro-4-pyridyl)-1H-pyrimidin-6-one;
5-chloro-2-(2-fluoro-4-pyridyl)-4-[2-methylpiperazin-1-yl]-1H-pyrimidin-6-one;
5-chloro-2-(2-fluoro-4-pyridyl)-4-[rac-(2S)-2-methylpiperazin-1-yl]-1H-pyrimidin-6-one;
5-chloro-2-(2-fluoro-4-pyridyl)-4-[rac-(2R)-2-methylpiperazin-1-yl]-1H-pyrimidin-6-one;
4-[(3R)-3-aminopyrrolidin-1-yl]-5-chloro-2-(2-fluoro-4-pyridyl)-1H-pyrimidin-6-one;
4-(3-aminoazetidin-1-yl)-5-chloro-2-(2-fluoro-4-pyridyl)-1H-pyrimidin-6-one;
5-chloro-2-(2-fluoro-4-pyridyl)-4-[(2S)-2-methylpiperazin-1-yl]-1H-pyrimidin-6-one;
5-chloro-2-(2-fluoro-4-pyridyl)-4-[(3R)-3-isopropylpiperazin-1-yl]-1H-pyrimidin-6-one;
5-chloro-2-(2-fluoro-4-pyridyl)-4-[(3R)-3-methylmorpholin-4-yl]-1H-pyrimidin-6-one;
5-chloro-2-(2-fluoro-4-pyridyl)-4-(4-piperidyloxy)-1H-pyrimidin-6-one;
5-chloro-2-(2-fluoro-4-pyridyl)-4-[[(3R)-3-piperidyl]oxy]-1H-pyrimidin-6-one;
5-chloro-2-(2-fluoro-4-pyridyl)-4-[[(3S)-3-piperidyl]oxy]-1H-pyrimidin-6-one;
4-[(4aS,8aS)-2,3,4a,5,6,7,8,8a-octahydrobenzo[b][1,4]oxazin-4-yl]-5-chloro-2-(2-fluoro-4-pyridyl)-1H-pyrimidin-6-one;
5-chloro-2-(2-fluoro-4-pyridyl)-4-[(3S)-3-methylmorpholin-4-yl]-1H-pyrimidin-6-one;
5-chloro-2-(2-fluoro-4-pyridyl)-4-(3-oxa-9-azabicyclo[3.3.1]nonan-9-yl)-1H-pyrimidin-6-one;
5-chloro-4-[(3R)-3-ethylmorpholin-4-yl]-2-(2-fluoro-4-pyridyl)-1H-pyrimidin-6-one;
5-chloro-4-[(3S)-3-ethylmorpholin-4-yl]-2-(2-fluoro-4-pyridyl)-1H-pyrimidin-6-one;
5-chloro-2-(2-fluoro-4-pyridyl)-4-[(2R)-2-methylmorpholin-4-yl]-1H-pyrimidin-6-one;
5-chloro-2-(2-fluoro-4-pyridyl)-4-(1,4-oxazepan-4-yl)-1H-pyrimidin-6-one;
5-chloro-4-(3,3-dimethylmorpholin-4-yl)-2-(2-fluoro-4-pyridyl)-1H-pyrimidin-6-one;
5-chloro-4-(2,5-dimethylmorpholin-4-yl)-2-(2-fluoro-4-pyridyl)-1H-pyrimidin-6-one;
5-chloro-4-[(3R,5R)-3,5-dimethylmorpholin-4-yl]-2-(2-fluoro-4-pyridyl)-1H-pyrimidin-6-one;
5-chloro-4-[(3S,5S)-3,5-dimethylmorpholin-4-yl]-2-(2-fluoro-4-pyridyl)-1H-pyrimidin-6-one;
5-chloro-4-[(3S,5R)-3,5-dimethylmorpholin-4-yl]-2-(2-fluoro-4-pyridyl)-1H-pyrimidin-6-one;
(2R)-1-[5-chloro-2-(2-fluoro-4-pyridyl)-6-oxo-1H-pyrimidin-4-yl]piperazine-2-carbonitrile;
(2S)-1-[5-chloro-2-(2-fluoro-4-pyridyl)-6-oxo-1H-pyrimidin-4-yl]piperazine-2-carbonitrile;
5-chloro-4-(6,8-dihydro-5H-imidazo[1,5-a]pyrazin-7-yl)-2-(2-fluoro-4-pyridyl)-1H-pyrimidin-6-one;
4-[(8aS)-7,7-difluoro-1,3,4,6,8,8a-hexahydropyrrolo[1,2-a]pyrazin-2-yl]-5-chloro-2-(2-fluoro-4-pyridyl)-1H-pyrimidin-6-one;
4-[(8aS)-3,4,6,7,8,8a-hexahydro-1H-pyrrolo[1,2-a]pyrazin-2-yl]-5-chloro-2-(2-fluoro-4-pyridyl)-1H-pyrimidin-6-one;
4-[(3S,8aS)-3-isobutyl-3,4,6,7,8,8a-hexahydro-1H-pyrrolo[1,2-a]pyrazin-2-yl]-5-chloro-2-(2-fluoro-4-pyridyl)-1H-pyrimidin-6-one;
5-chloro-4-[4-(2,2-difluoroethyl)piperazin-1-yl]-2-(2-fluoro-4-pyridyl)-1H-pyrimidin-6-one;
5-chloro-2-(2-fluoro-4-pyridyl)-4-(7-methyl-1,4-diazepan-1-yl)-1H-pyrimidin-6-one;
5-chloro-2-(2-fluoro-4-pyridyl)-4-[(2R)-2-methyl-1,4-diazepan-1-yl]-1H-pyrimidin-6-one;
5-chloro-4-(6,8-dihydro-5H-imidazo[1,2-a]pyrazin-7-yl)-2-(2-fluoro-4-pyridyl)-1H-pyrimidin-6-one;
5-chloro-2-(2-fluoro-4-pyridyl)-4-(5,6,8,9-tetrahydro-[1,2,4]triazolo[4,3-d][1,4]diazepin-7-yl)-1H-pyrimidin-6-one;
5-chloro-2-(2-fluoro-4-pyridyl)-4-(3-methyl-1,4-oxazepan-4-yl)-1H-pyrimidin-6-one;
5-chloro-4-[5,8-dimethyl-3-(trifluoromethyl)-6,8-dihydro-5H-[1,2,4]triazolo[4,3-a]pyrazin-7-yl]-2-(2-fluoro-4-pyridyl)-1H-pyrimidin-6-one;
5-chloro-4-[(2R,5R)-2,5-dimethylmorpholin-4-yl]-2-(2-fluoro-4-pyridyl)-1H-pyrimidin-6-one;
5-chloro-4-(2,2-dimethylpiperazin-1-yl)-2-(2-fluoro-4-pyridyl)-1H-pyrimidin-6-one;
5-chloro-4-(2,3-dimethylmorpholin-4-yl)-2-(2-fluoro-4-pyridyl)-1H-pyrimidin-6-one;
5-chloro-2-(2-fluoro-4-pyridyl)-4-piperazin-1-yl-1H-pyrimidin-6-one;
5-chloro-4-(3,3-dimethylpiperazin-1-yl)-2-(4-pyridyl)-1H-pyrimidin-6-one;
4-[(3R)-3-(aminomethyl)-1-piperidyl]-5-chloro-2-(2-fluoro-4-pyridyl)-1H-pyrimidin-6-one;
4-[(3S)-3-(aminomethyl)-1-piperidyl]-5-chloro-2-(2-fluoro-4-pyridyl)-1H-pyrimidin-6-one;
5-chloro-4-[(2R)-2-methylpiperazin-1-yl]-2-(4-pyridyl)-1H-pyrimidin-6-one;
5-chloro-4-[(3S)-3-methylmorpholin-4-yl]-2-(4-pyridyl)-1H-pyrimidin-6-one;
5-chloro-4-(3-propylmorpholin-4-yl)-2-(4-pyridyl)-1H-pyrimidin-6-one;

5-chloro-4-(3-isobutylmorpholin-4-yl)-2-(4-pyridyl)-1H-pyrimidin-6-one;
5-chloro-4-(2-methylpiperazin-1-yl)-2-(4-pyridyl)-1H-pyrimidin-6-one;
5-chloro-4-[(2S)-2-ethylpiperazin-1-yl]-2-(4-pyridyl)-1H-pyrimidin-6-one;
5-chloro-2-(4-pyridyl)-4-[(2S)-2-isopropylpiperazin-1-yl]-1H-pyrimidin-6-one;
5-chloro-4-[(2R)-2-ethylpiperazin-1-yl]-2-(4-pyridyl)-1H-pyrimidin-6-one;
5-chloro-4-(3-phenylmorpholin-4-yl)-2-(4-pyridyl)-1H-pyrimidin-6-one;
5-chloro-4-(6-fluoro-1,4-diazepan-1-yl)-2-(2-fluoro-4-pyridyl)-1H-pyrimidin-6-one;
5-chloro-4-(6,6-difluoro-1,4-diazepan-1-yl)-2-(4-pyridyl)-1H-pyrimidin-6-one;
5-chloro-2-(2-fluoro-4-pyridyl)-4-[6-(trifluoromethyl)-1,4-diazepan-1-yl]-1H-pyrimidin-6-one;
5-chloro-4-[2-(difluoromethyl)piperazin-1-yl]-2-(2-fluoro-4-pyridyl)-1H-pyrimidin-6-one;
5-chloro-4-[2S-(difluoromethyl)piperazin-1-yl]-2-(2-fluoro-4-pyridyl)-1H-pyrimidin-6-one;
5-chloro-4-[2R-(difluoromethyl)piperazin-1-yl]-2-(2-fluoro-4-pyridyl)-1H-pyrimidin-6-one;
5-chloro-4-(4,7-diazaspiro[2.5]octan-4-yl)-2-(2-fluoro-4-pyridyl)-1H-pyrimidin-6-one;
cis-5-chloro-2-(2-fluoro-4-pyridyl)-4-[2-methyl-5-(trifluoromethyl)piperazin-1-yl]-1H-pyrimidin-6-one;
5-chloro-4-[6-fluoro-1,4-diazepan-1-yl]-2-(2-fluoro-4-pyridyl)-1H-pyrimidin-6-one;
5-chloro-4-[6S-fluoro-1,4-diazepan-1-yl]-2-(2-fluoro-4-pyridyl)-1H-pyrimidin-6-one;
5-chloro-4-[6R-fluoro-1,4-diazepan-1-yl]-2-(2-fluoro-4-pyridyl)-1H-pyrimidin-6-one;
5-chloro-4-[3-(1-fluoro-1-methyl-ethyl)piperazin-1-yl]-2-(2-fluoro-4-pyridyl)-1H-pyrimidin-6-one;
5-chloro-4-[3S-(1-fluoro-1-methyl-ethyl)piperazin-1-yl]-2-(2-fluoro-4-pyridyl)-1H-pyrimidin-6-one;
5-chloro-4-[3R-(1-fluoro-1-methyl-ethyl)piperazin-1-yl]-2-(2-fluoro-4-pyridyl)-1H-pyrimidin-6-one;
5-chloro-2-(2-fluoro-4-pyridyl)-4-[2-(trifluoromethyl)piperazin-1-yl]-1H-pyrimidin-6-one;
5-chloro-2-(2-fluoro-4-pyridyl)-4-[2S-(trifluoromethyl)piperazin-1-yl]-1H-pyrimidin-6-one;
5-chloro-2-(2-fluoro-4-pyridyl)-4-[2R-(trifluoromethyl)piperazin-1-yl]-1H-pyrimidin-6-one;
5-chloro-2-(2-fluoro-4-pyridyl)-4-[6-(trifluoromethyl)-1,4-diazepan-1-yl]-1H-pyrimidin-6-one;
5-chloro-2-(2-fluoro-4-pyridyl)-4-[6S-(trifluoromethyl)-1,4-diazepan-1-yl]-1H-pyrimidin-6-one;
5-chloro-2-(2-fluoro-4-pyridyl)-4-[6R-(trifluoromethyl)-1,4-diazepan-1-yl]-1H-pyrimidin-6-one;
5-chloro-2-(4-pyridyl)-4-[2-(trifluoromethyl)piperazin-1-yl]-1H-pyrimidin-6-one;
5-chloro-2-(4-pyridyl)-4-[2S-(trifluoromethyl)piperazin-1-yl]-1H-pyrimidin-6-one;
5-chloro-2-(4-pyridyl)-4-[2R-(trifluoromethyl)piperazin-1-yl]-1H-pyrimidin-6-one;
5-chloro-4-[2-(difluoromethyl)piperazin-1-yl]-2-(2-fluoro-4-pyridyl)-1H-pyrimidin-6-one;
5-chloro-4-[2S-(difluoromethyl)piperazin-1-yl]-2-(2-fluoro-4-pyridyl)-1H-pyrimidin-6-one;
5-chloro-4-[2R-(difluoromethyl)piperazin-1-yl]-2-(2-fluoro-4-pyridyl)-1H-pyrimidin-6-one;
5-chloro-4-[2-(difluoromethyl)piperazin-1-yl]-2-(4-pyridyl)-1H-pyrimidin-6-one;
5-chloro-4-[2R-(1,1-difluoroethyl)piperazin-1-yl]-2-(2-fluoro-4-pyridyl)-1H-pyrimidin-6-one;
5-chloro-4-[2S-(1,1-difluoroethyl)piperazin-1-yl]-2-(2-fluoro-4-pyridyl)-1H-pyrimidin-6-one;
5-chloro-4-[3-cyclopropylpiperazin-1-yl]-2-(2-fluoro-4-pyridyl)-1H-pyrimidin-6-one;
5-chloro-4-[3S-cyclopropylpiperazin-1-yl]-2-(2-fluoro-4-pyridyl)-1H-pyrimidin-6-one;
5-chloro-4-[3R-cyclopropylpiperazin-1-yl]-2-(2-fluoro-4-pyridyl)-1H-pyrimidin-6-one;
cis-5-chloro-2-(2-fluoro-4-pyridyl)-4-[2-methyl-5-(trifluoromethyl)piperazin-1-yl]-1H-pyrimidin-6-one;
cis-5-chloro-2-(2-fluoro-4-pyridyl)-4-[2R-methyl-5S-(trifluoromethyl)piperazin-1-yl]-1H-pyrimidin-6-one;
cis-5-chloro-2-(2-fluoro-4-pyridyl)-4-[2S-methyl-5R-(trifluoromethyl)piperazin-1-yl]-1H-pyrimidin-6-one;
5-chloro-2-(2-fluoro-4-pyridyl)-4-(morpholinomethyl)-1H-pyrimidin-6-one;
5-chloro-2-(2-fluoro-4-pyridyl)-4-(piperazin-1-ylmethyl)-1H-pyrimidin-6-one;
5-chloro-4-(6,6-difluoro-1,4-diazepan-1-yl)-2-(3-fluoro-4-pyridyl)-1H-pyrimidin-6-one;
5-chloro-2-(3-fluoro-4-pyridyl)-4-[(2R)-2-methylpiperazin-1-yl]-1H-pyrimidin-6-one;
5-chloro-2-(2-chloro-4-pyridyl)-4-(6,6-difluoro-1,4-diazepan-1-yl)-1H-pyrimidin-6-one;
5-chloro-2-(2-hydroxy-4-pyridyl)-4-tetrahydropyran-4-yl-1H-pyrimidin-6-one;
6-oxo-2-(4-pyridyl)-4-tetrahydropyran-4-yl-1H-pyrimidine-5-carbonitrile;
5-chloro-4-(3,6-dihydro-2H-pyran-4-yl)-2-(4-pyridyl)-1H-pyrimidin-6-one;
tert-butyl 4-[5-chloro-6-oxo-2-(4-pyridyl)-1H-pyrimidin-4-yl]-3,6-dihydro-2H-pyridine-1-carboxylate;
2-(4-pyridyl)-4-tetrahydropyran-4-yl-5-(trifluoromethyl)-1H-pyrimidin-6-one;
5-chloro-4-[(3S)-3-(1-hydroxy-1-methyl-ethyl)piperazin-1-yl]-2-(4-pyridyl)-1H-pyrimidin-6-one;
5-bromo-4-[(3S)-3-isopropylpiperazin-1-yl]-2-(4-pyridyl)-1H-pyrimidin-6-one;
4-[(3S)-3-isopropylpiperazin-1-yl]-6-oxo-2-(4-pyridyl)-1H-pyrimidine-5-carbonitrile;
5-bromo-4-[(3S)-3-tert-butylpiperazin-1-yl]-2-(4-pyridyl)-1H-pyrimidin-6-one;
4-[(3S)-3-tert-butylpiperazin-1-yl]-6-oxo-2-(4-pyridyl)-1H-pyrimidine-5-carbonitrile;
1-[5-chloro-2-(2-fluoro-4-pyridyl)-6-oxo-1H-pyrimidin-4-yl]-1,4-diazepan-6-one;
5-chloro-2-(4-pyridyl)-4-(2,2,6,6-tetrafluoromorpholin-4-yl)-1H-pyrimidin-6-one;
2-[4-[5-chloro-2-(2-fluoro-4-pyridyl)-6-oxo-1H-pyrimidin-4-yl]-6,6-difluoro-1,4-diazepan-1-yl]acetamide;
5-chloro-4-(6,6-difluoro-4-methyl-1,4-diazepan-1-yl)-2-(2-fluoro-4-pyridyl)-1H-pyrimidin-6-one;
5-chloro-4-piperazin-1-yl-2-(4-pyridyl)-1H-pyrimidin-6-one,
or pharmaceutically acceptable salts and/or solvates thereof.

15. A pharmaceutical composition comprising a compound according to claim 1, or a pharmaceutically acceptable salt or solvate thereof, in admixture with a pharmaceutically acceptable diluent or carrier, with the exception that the compounds identified in the proviso of claim 1 are not excluded.

16. A combination product comprising a compound, or a pharmaceutically acceptable salt or solvate thereof, as defined in claim 1, with one or more additional therapeutic agents, with the exception that the compounds identified in the proviso of claim 1 are not excluded.

17. A method of treating a proliferative disorder in a patient in need of such treatment, said method comprising administering to said patient a therapeutically effective amount of a compound according to claim 1, or a pharmaceutically acceptable salt or solvate thereof, with the exception that the compounds identified in the proviso of claim 1 are not excluded, wherein the proliferative disorder is a cancer selected from lung, colon, breast, ovarian, prostate, liver, pancreas, brain, and skin cancer.

* * * * *